US009492528B2

(12) United States Patent
D'Aoust et al.

(10) Patent No.: US 9,492,528 B2
(45) **Date of Patent: *Nov. 15, 2016**

(54) INFLUENZA VIRUS-LIKE PARTICLES (VLPS) COMPRISING HEMAGGLUTININ

(75) Inventors: Marc-Andre D'Aoust, Québec (CA); Manon Couture, St-Augustin-de-Desmaures (CA); Frédéric Ors, Québec (CA); Sonia Trepanier, St-Nicolas (CA); Pierre-Olivier Lavoie, Québec (CA); Michèle Dargis, Québec (CA); Louis-Philippe Vezina, Neuville (CA); Nathalie Landry, St-Romuald (CA)

(73) Assignee: MEDICAGO INC. (CA)

( * ) Notice: Subject to any disclaimer, the term of this patent is extended or adjusted under 35 U.S.C. 154(b) by 535 days.

This patent is subject to a terminal disclaimer.

(21) Appl. No.: 13/003,570

(22) PCT Filed: Jul. 2, 2009

(86) PCT No.: PCT/CA2009/000926

§ 371 (c)(1), (2), (4) Date: Apr. 26, 2011

(87) PCT Pub. No.: WO2010/003225

PCT Pub. Date: Jan. 14, 2010

(65) Prior Publication Data

US 2011/0293650 A1 Dec. 1, 2011

Related U.S. Application Data

(63) Continuation-in-part of application No. PCT/CA2009/000032, filed on Jan. 12, 2009, which is a continuation-in-part of application No. PCT/CA2008/001281, filed on Jul. 11, 2008.

(60) Provisional application No. 61/022,775, filed on Jan. 22, 2008, provisional application No. 60/959,414, filed on Jul. 13, 2007, provisional application No. 60/990,603, filed on Nov. 27, 2007, provisional application No. 61/013,272, filed on Dec. 12, 2007.

(30) Foreign Application Priority Data

Jan. 21, 2008 (CA) ..................................... 2615372

(51) Int. Cl.

| | |
|---|---|
| ***A61K 39/145*** | (2006.01) |
| ***C12N 15/82*** | (2006.01) |
| ***C12N 7/04*** | (2006.01) |
| ***C12N 15/44*** | (2006.01) |
| ***C07K 14/005*** | (2006.01) |
| ***C12N 7/00*** | (2006.01) |
| ***A61K 39/12*** | (2006.01) |
| *A61K 39/00* | (2006.01) |

(52) U.S. Cl.

CPC ............ *A61K 39/145* (2013.01); *A61K 39/12* (2013.01); *C07K 14/005* (2013.01); *C12N 7/00* (2013.01); *C12N 15/8257* (2013.01); *C12N 15/8258* (2013.01); *A61K 2039/517* (2013.01); *A61K 2039/5258* (2013.01); *A61K 2039/543* (2013.01); *A61K 2039/55505* (2013.01); *A61K 2039/55583* (2013.01); *A61K 2039/58* (2013.01); *C12N 2760/16122* (2013.01); *C12N 2760/16123* (2013.01); *C12N 2760/16134* (2013.01)

(58) Field of Classification Search

None

See application file for complete search history.

(56) References Cited

U.S. PATENT DOCUMENTS

| | | | | |
|---|---|---|---|---|
| 5,958,422 | A | 9/1999 | Lomonossoff | |
| 6,020,169 | A | 2/2000 | Lee et al. | |
| 6,042,832 | A | 3/2000 | Koprowski et al. | |
| 6,287,570 | B1 * | 9/2001 | Foley | 424/199.1 |
| 6,326,470 | B1 | 12/2001 | Cosgrove | |
| 6,489,537 | B1 | 12/2002 | Rea et al. | |
| 6,867,293 | B2 | 3/2005 | Andrews et al. | |
| 7,125,978 | B1 | 10/2006 | Vezina et al. | |

(Continued)

FOREIGN PATENT DOCUMENTS

| | | | |
|---|---|---|---|
| CA | 2615372 | A1 | 1/2009 |
| CA | 2693956 | A1 | 1/2009 |
| CA | 2707235 | A1 | 6/2009 |
| CN | 1861793 | A | 11/2006 |
| WO | WO 2000/56906 | A1 | 9/2000 |

(Continued)

OTHER PUBLICATIONS

Rivard et al (Plant Biotechnology Journal, 4, pp. 359-368, 2006).*
Ma et al (Nature Reviews, 4, 794-816, 2003).*
Kobayashi et al (JBC, 275(12), pp. 8772-8778, 2000).*
Whitelam (J Sci Food Agric, 68, pp. 1-9, 1995).*
Spitsin et al (Vaccine, 27, pp. 1289-1292, 2009).*

(Continued)

*Primary Examiner* — Anne Kubelik
*Assistant Examiner* — Stephen Uyeno
(74) *Attorney, Agent, or Firm* — Dawn C. Russell; Culhane Meadows PLLC

(57) ABSTRACT

A method for synthesizing influenza virus-like particles (VLPs) within a plant or a portion of a plant is provided. The method involves expression of influenza HA of type A/California/04/09 in plants and the purification by size exclusion chromatography. The invention is also directed towards a VLP comprising influenza HA protein of type A/California/04/09 and plants lipids. The invention is also directed to a nucleic acid encoding influenza HA of type A/California/04/09 as well as vectors. The VLPs may be used to formulate influenza vaccines, or may be used to enrich existing vaccines.

31 Claims, 119 Drawing Sheets

(56) References Cited

U.S. PATENT DOCUMENTS

| | | | | |
|---|---|---|---|---|
| 7,132,291 | B2 | 11/2006 | Cardineau et al. | |
| 7,763,450 | B2 | 7/2010 | Robinson et al. | |
| 8,771,703 | B2 | 7/2014 | Couture et al. | |
| 2001/0006950 | A1 | 7/2001 | Punnonen et al. | |
| 2005/0048074 | A1* | 3/2005 | Cardineau et al. | 424/186.1 |
| 2005/0223430 | A1 | 10/2005 | Bakker et al. | |
| 2006/0252132 | A1* | 11/2006 | Yang et al. | 435/91.1 |
| 2007/0207526 | A1 | 9/2007 | Coit et al. | |
| 2008/0008725 | A1 | 1/2008 | Weeks-Levy et al. | |
| 2009/0191309 | A1 | 7/2009 | Rastogi et al. | |
| 2010/0239610 | A1 | 9/2010 | D'Aoust et al. | |
| 2010/0310604 | A1 | 12/2010 | D'Aoust et al. | |
| 2011/0293650 | A1 | 12/2011 | D'Aoust et al. | |
| 2012/0189658 | A1 | 7/2012 | Couture et al. | |

FOREIGN PATENT DOCUMENTS

| | | | |
|---|---|---|---|
| WO | WO 2003/068923 | A2 | 8/2003 |
| WO | WO 2004/003207 | A1 | 1/2004 |
| WO | WO 2007/011904 | A2 | 1/2007 |
| WO | WO 2007/019094 | A2 | 2/2007 |
| WO | WO 2007/095318 | A2 | 8/2007 |
| WO | WO 2008/054540 | A2 | 5/2008 |
| WO | 2008/087391 | A1 | 7/2008 |
| WO | 2009/087391 | A | 7/2009 |
| WO | WO 2010/003225 | A1 | 1/2010 |
| WO | 2010/025285 | A1 | 3/2010 |
| WO | 2010/077712 | A1 | 7/2010 |
| WO | WO 2011/011390 | A1 | 1/2011 |
| WO | WO 2011/035422 | A1 | 3/2011 |
| WO | WO 2011/035423 | A1 | 3/2011 |
| WO | WO 2011/102900 | A1 | 8/2011 |
| WO | WO 2012/061815 | A2 | 5/2012 |
| WO | WO 2012/083445 | A1 | 6/2012 |

OTHER PUBLICATIONS

Sainsbury et al (Plant Biotechnology Journal (6, pp. 82-92, 2008).*
Wang et al (Trends in Plant Science, 9(5), pp. 244-252, 2004).*
Nutall et al (Eur J Biochem., 269(24), pp. 6042-6051, 2002).*
Sorensen et al (Journal of Biotechnology, 115(2), pp. 113-128, 2005).*
Yokoyama et al (BBA—Gene Structure and Expression, 1493(1-2), pp. 119-124, 2000).*
Office Action received for Canadian Patent Application No. 2,693,956, mailed on Sep. 22, 2011, 3 pages.
Office Action received for Canadian Patent Application No. 2,693,956, mailed on Jan. 20, 2012, 2 pages.
Office Action received for Canadian Patent Application No. 2,730,185, mailed on Jun. 28, 2011, 5 pages.
Office Action received for Canadian Patent Application No. 2,730,185, mailed on Nov. 30, 2011, 4 pages.
Office Action received for Canadian Patent Application No. 2,707,235, mailed on Oct. 28, 2011, 3 pages.
Office Action received for Canadian Patent Application No. 2,762,042, mailed on Feb. 16, 2012, 3 pages.
Office Action received for Chinese Patent Application No. 2008801070729, issued on Sep. 27, 2011, 13 pages. (8 pages of English Translation and 5 pages of Office Action).
Office Action received for Chinese Patent Application No. 200980109781.5, issued on Jan. 21, 2012, 13 pages (9 pages of English Translation and 4 pages of Office Action).
Office Action received for Eurasian Patent Application No. 201000195/28, mailed on Dec. 13, 2011, 4 pages (2 page of English Translation and 2 pages of Office Action).
Office Action received for Egyptian Patent Application No. 1222/2010, mailed on Nov. 18, 2011, 7 pages (See statement under 37 CFR 1.98(a)(3)).
Office Action received for European Patent Application No. 08783201.0 , mailed on May 26, 2011, 4 pages.
Extended European Search Report and European Search Opinion received for European Patent Application No. 09797336.6, mailed on Dec. 29, 2011, 7 pages.
Extended European Search Report and European Search Opinion received for European Patent Application No. 09793741.1, mailed on Aug. 9, 2011, 9 pages.
Extended European Search Report and European Search Opinion received for European Patent Application No. 09793751.0, mailed on Sep. 28, 2011, 10 pages.
Office Action received for Vietnam Patent Application No. 1-2012-00186, mailed on Mar. 8, 2011, 2 pages (1 page of English Translation and 1 page of Office Action).
Fischer et al., "Affinity-Purification of a TMV-Specific Recombinant Full-Size Antibody from a Transgenic Tobacco Suspension Culture", Journal of Immunological Methods, vol. 226, 1999, pp. 1-10.
Marozin et al., "Antigenic and Genetic Diversity among Swine Influenza A H1N1 and H1N2 viruses in Europe" Journal of General Virology, vol. 83, 2002, pp. 735-745.
Meshcheryakova et al., "Cowpea Mosaic Virus Chimeric Particles Bearing the Ectodomain of Matrix Protein 2 (M2E) of the Influenza A Virus: Production and Characterization", Molecular Biology, vol. 43, No. 4, 2009, pp. 685-694.
Nemchinov et al., "Transient Expression of the Ectodomain of Matrix Protein 2 (M2e) of Avian Influenza A Virus in Plants", Protein Expression and Purification, vol. 56, 2007, pp. 153-159.
Regnard et al., "High Level Protein Expression in Plants through the use of a Novel Autonomously Replicating Geminivirus Shuttle Vector," Plant Biotechnology Journal, vol. 8, 2010, pp. 38-46.
Weldon et al., "Enhanced Immunogenicity of Stabilized Trimeric Soluble Influenza Hemagglutinin", PLOS One, vol. 5, No. 9, e12466, Sep. 2010, pp. 1-8.
International Search Report and Written Opinion received for PCT Patent Application No. PCT/CA2011/001427 mailed on Mar. 20, 2012, 10 pages.
International Search Report and Written Opinion received for PCT Patent Application No. PCT/CA2011/001228 mailed on Jan. 18, 2012, 11 pages.
Anonymous: Protoplast preparation (from plant tissue), Dec. 1, 2006 (URL: http://www.ivaan.com/protocols/128.html.
Asahi-Ozaki et al. "Intranasal administration of adjuvant-combined recombinant influenza virus HA vaccine protects mice from the lethal H5N1 virus infection". Microbes and Infection 2006. vol. 8, pp. 2706-2714.
Bertioli, D J., et al. "Transgenic plants and insect cells expressing the coat protein of arabis mosaic virus produce empty virus-like particles". J. Gen Virol. 1991. vol. 72, pp. 1801-1809.
Bright, R.A., et al. "Impact of glycosylation on the immunogenicity of a DNA-based influenza H5 Ha vaccine". Virology, 2003, vol. 308, pp. 270-278.
Bright, R.A., et al. "Influenza virus-like particles elicit broader immune responses than whole virion inactivated influenza virus or recombinant hemagglutinin". Vaccine, 2007, vol. 25, pp. 3871-3878.
Doyle, C., et al. "Analysis of Progressive Deletions of the Transmembrane and Cytoplasmic Domains of Influenza Hemagglutinin". Journal of Cell Biology, vol. 103, pp. 1193-1204, 1986.
Eckert, D., et al. "Crystal Structure of GCN4-pIQI, a Trimeric Coiled Coil with Buried Polar Residues". Journal of Molecular Biology, 1998, vol. 284, pp. 859-865.
Firek, S. et al. "Secretion of a functional single-chain Fv protein in transgenic tobacco plants and cell suspension cultures". Plant Molecular Biology 1993, vol. 23, pp. 861-870.
Garten, et al. "Antigenic and genetic characteristics of swine-origin 2009 A(H1N1) Influenza viruses circulating in Humans". Science, Jul. 10, 2009, vol. 325, pp. 197-201.
Garten et al. "Emergence of a Novel Swine-Origin Influenza A (H1N1) Virus in Humans". New England Journal of Medicine, Jun. 18 2009, vol. 360, No. 25, pp. 2605-2616.
Genbank Accession AFU70328 Influenza ANietnam/1203/04 (H5N1) virus HA protein VN1203-ha-spc-opt.

(56) References Cited

OTHER PUBLICATIONS

Giddings, G., et al. "Transgenic plants as factories for biopharmaceuticals". Nature Biotech. vol. 18, pp. 1151-1155, Nov. 2000.
Gomord, V. et al. "Biopharmaceutical production in plants: problems, solutions and opportunities". *Trends in Biotechnol.* (2005) vol. 23, No. 11, pp. 559-565.
Houston, N., et al. "Phylogenetic Analyses Identify 10 Classes of the Protein Disulfide Isomerase Family in Plants, Including Single-Domain Protein Disulfide Isomerase-Related Proteins". Plant Physiology; Feb. 2005, vol. 137, pp. 762-778.
Influenza A virus (A/ New Caledonia/20/99(H1N1)) hemagglutinin (HA) gene, complete cds. Genbank Accession No. AY289929.1, 2003.
Hatta, M., et al. "Molecular Basis for High Virulence of Hong Kong H5N1 Influenza A Viruses". Science, Sep. 7, 2001, vol. 293, pp. 1840-1842.
Haynes, J. "Influenza virus-like particle vaccines". Expert Reviews Vaccines vol. 8(4), pp. 435-445 (2009).
Horimoto, T., et al. "The development and characterization of H5 influenza virus vaccines derived from a 2003 human isolate". Vaccine (2006) vol. 24, pp. 3669-3676.
Huang, Z. et al. "A DNA Replicon System for Rapid High-Level Production of Virus-Like Particles in Plants", Biotechnology and Bioengineering, Jul. 9, 2009, vol. 103:4, pp. 706-714.
Huang, Z.et al. "High-Level Rapid Production of Full-Size Monoclonal Antibodies in Plants by a Single-Vector DNA Replicon System", Biotechnology and Bioengineering, May 1, 2010 vol. 106:1, pp. 9-17.
Kaverin, N., et al. "Structural Differences among Hemagglutinins of Influenza A Virus Subtypes Are Reflected in Their Antigenic Architecture: Analysis of H9 Escape Mutants". J. Virol. vol. 78:1, pp. 240-249, 2004.
Klopfleisch, R., et al. "Neurotropism of Highly Pathogenic Avian Influenza Virus A/Chicken/Indonesia/2003 (H5N1) in Experimentally Infected Pigeons (Columbia livia f. domestica)". Vet Pathol. vol. 43, pp. 463-470, 2006.
Lelivelt, C., et al. "Stable Plastid Transformation in Lettuce (Lactuca sativa L.)". Plant Molecular Biology vol. 58, pp. 763-774, 2005.
Li, S. et al. "Influenza A Virus Transfectants with Chimeric Hemagglutinins Containing Epitopes from Different Subtypes". Journal of Virology, Jan. 1992, pp. 399-404.
Liu, L., et al. "Cowpea mosaic virus-based systems for the production of antigens and antibodies in plants". Vaccine 23 (2005) pp. 1788-1792.
Ma, J., et al. "The Production of Recombinant Pharmaceutical Proteins in Plants". Nature, Oct. 2003, vol. 4, pp. 794-805.
Mishin, V. et al. "Effect of Hemagglutinin Glycosylation on Influenza Virus Susceptibility to Neuraminidase Inhibitors". Journal of Virology 2005, pp. 12416-12424.
Mori, S.I., et al. "A Novel amino acid substitution at the receptor-binding site on the hemagglutinin of H3N2 influenza A viruses isolated from 6 cases with acute encephalopathy during the 1997-1998 season in Tokyo". Arch Virol, 1999, vol. 144, pp. 147-155.
Nobusawa, Ed. "Protective antigen of influenza virus". Dept. of Virology, Nippon Rinsho, vol. 55(1), 1997, pp. 2719-2724.
Paul, M., et al. "Mutational analysis of the human immunodeficiency virus type 1 VPU transmembrane domain that promotes the enhanced release of virus-like particles from the plasma membrane of mammalian cells". Journal of Virology, Feb. 1998, pp. 1270-1279.
Richter et al. "Production of hepatitis B surface antigen in transgenic plants for oral immunization". Nature Biotechnology vol. 18, Nov. 2000, pp. 1167-1171.
Shorrosh, B.S. "Molecular Cloning of a Putative Plant Endomembrane Protein Resembling Vertebrate Protein Disulfide-Isomerase and a Phosphatidylinositol-Specific Phospholipase C". Proceedings of the National Academy of Sciences, Dec. 1991, vol. 88, pp. 10941-10945.
Shorrosh, B. et al. "Sequence analysis and developmental expression of an alfalfa protein disulfide isomerase". Plant Molecular Biology, vol. 19, pp. 319-321, 1992.
Smith, C. "Accession Influenza A virus (A/Indonesia/05(H5N1) segment 4 hemagglut". GenBank: EF541394.1.
Spitsin, S. et al. "Immunological assessment of plant-derived avian flu H5/HA1 variants". Vaccine 27 (2009) 1289-1292.
Tatulian, S., et al. "Secondary Structure, Orientation, Oligomerization, and Lipid Interactions of the Transmembrane Domain of Influenza Hemagglutinin". Biochemistry, 2000, v. 39, pp. 496-507.
Van Ree, R. et al. "Beta (1,2)-Xylose and alpha (1,3)-fucose residues have a strong contribution in IgE binding to plant glycoallergens". Journal of Biological Chemistry, (2000) vol. 275:15, 11451-11458.
Wang, W. "Isolation, Identification and Molecular Analysis of the Main of Genes Avian Influenza Virus Isolates from Different Hosts". China Doctoral Dissertations Full-text Database, Agricultural Science and Technology (2008).
Warzecha, H. "Biopharmaceuticals from Plants: A multitude of Options for Posttranslational Modifications". Biotechnology and Genetic Engineering Reviews, vol. 25, pp. 315-330, 2008.
Weissenhorn et al. "Assembly of a rod-shaped chimera of a trimeric GCN4 zipper and the HIV-1 gp41 ectodomain expressed in *Escherichia coli*". Proc. Natl Acad. Sci USA, 1997, vol. 94, pp. 6065-6069.
Wiley, D.C., et al. "The Structure and Function of the Hemagglutinin Membrane Glycoprotein of Influenza Virus". Annual Review of Biochemistry, vol. 56(1), pp. 365-394, 1987.
Wilson, Iain, et al. "Core alpha 1,3-fucose is a key part of the epitope recognized by antibodies reacting against plant N-linked oligosaccharides and is present in a wide variety of plant extracts". Glycobiology (1998) vol. 8:7, 651-661.
Wydro, M. et al. "Optimization of transient Agrobacterium-mediated gene expression system in leaves of Nicotiana benthamiana". Acta Biochimica Polonica (2006) 53(2), 289-298.
Yang, Zhi-Yong et al. "Immunization by Avian H5 Influenza Hemagglutinin Mutants with Altered Receptor Binding Specificity". Science, vol. 317, Aug. 10, 2007, pp. 825-828.
Office Action dated May 21, 2013 re Australian application AU 2008278222.
Office Action dated Jun. 13, 2013 re Australian application AU 2009202819.
Office Action dated Mar. 26, 2014 re AU application 2009267769.
Office Action dated Dec. 18, 2013 re AU application 2010265766.
Exam Report dated Nov. 6, 2013 re Australian application AU 2010300034.
Office Action dated Sep. 6, 2012 re Canadian application CA 2,615,372.
Office Action dated Oct. 16, 2012 re Canadian application CA 2,693,956.
Office Action dated Mar. 1, 2013 re Canadian application CA 2,693,956.
Office Action dated Jun. 7, 2012 re Canadian application CA 2,707,235.
Office Action dated. Sep. 28 2012 re Canadian application CA 2,707,235.
Office Action dated Mar. 1, 2013 re Canadian application CA 2,707,235.
Notice of Allowance dated Aug. 14, 2013 re Canadian application CA 2,707,235.
Office Action dated Apr. 27, 2012 re Canadian application CA 2,730,185.
Office Action dated Sep. 6, 2012 re Canadian application CA 2,730,185.
Office Action dated Jun. 2 2014 re Canadian application CA 2,730,185.
Notice of Allowance dated Jun. 29, 2012 re Canadian application CA 2,762,042.
Office Action dated Jul. 9, 2012 re Canadian application CA 2,772,962.
Notice of Allowance dated Aug. 7, 2013 re Canadian application CA 2,815,887.

(56) References Cited

OTHER PUBLICATIONS

Office Action dated Nov. 27, 2012 re Chinese application CN 200980109781.5.
Office Action dated Apr. 6, 2012 re Chinese application CN 200980126670.5.
Office Action dated Nov. 5, 2012 re Chinese application CN 200980126670.5.
Office Action dated Mar. 15, 2013 re Chinese application CN 200980126670.5.
Office Action dated Jul. 23, 2013 re Chinese application CN 200980126670.5.
Office Action dated Jul. 24, 2012 re Chinese application CN 200880107072.9.
Office Action dated Feb. 21 2013 re Chinese application CN 200880107072.9.
Office Action dated Jul. 16, 2012 re Chinese application CN 200980134868.8.
Office Action dated Jan. 15, 2013 re Chinese application CN 200980134868.8.
Office Action dated May 30, 2013 re Chinese application CN 200980134868.8.
Decision on Rejection dated Feb. 20, 2014 re Chinese application CN 200980134868.8.
Office Action dated Mar. 4, 2014 re Chinese CN application 2011800641274.
Office Action dated Jun. 13, 2012 re Chinese application CN 200980136376.2.
Office Action dated Mar. 8 2013 re Chinese application CN 200980136376.2.
Office Action dated Oct. 10, 2013 re Chinese application CN 200980136376.2.
Office Action dated Jul. 1, 2014 re Chinese application CN 200980136376.2.
Office Action dated Jun. 28, 2013 re Chinese application CN 201080035066.4.
Office Action dated Feb. 19, 2014 re Chinese Application CN 201080035066.4.
Office Action dated Mar. 1, 2013 re Chinese application CN 201080042333.0.
Office Action dated Nov. 19, 2013 re Chinese application CN 201080042333.0.
Decision on Rejection May 28, 2014 re Chinese application CN 201080042333.0.
Office Action dated Jul. 29, 2013 re Chinese application CN 201080042336.4.
Office Action dated Jan. 13, 2014 re Chinese application CN 201310021693.8.
Office Action dated Jun. 13, 2012 re Eurasian application EA 20100195/28.
Notice of Allowance dated Aug. 28, 2012 re Eurasian application EA 201001198/28.
Office Action dated Apr. 24, 2013 re Eurasian application EA 201001198/28.
Office Action dated Dec. 26, 2013 re Eurasian application EA 201001198/28.
Office Action dated Sep. 3, 2014 re Eurasian App EA 201001198.
Office Action dated Aug. 27, 2013 re Egyptian application re EG PCT 61/2010.
Office Action dated Oct. 8, 2013 re European application re EP 10791119.0.
Office Action dated Oct. 26, 2012 re European application re EP 08783201.0.
Decision to Grant dated May 31, 2013 re European application re EP 08783201.0.
Decision to Grant Aug. 17, 2012 re European application re EP 09700061.6.
Exam Report dated Aug. 1, 2013 re European application re EP 09793751.0.
Supplemental European Search Report Apr. 10, 2014 re EP 11 83 7364.
Office Action Feb. 6, 2014 re European application No. 09797336.6.
Exam report dated Aug. 23, 2012 re European application EP 09793751.0.
European Office Action dated Jul. 4, 2014 re EP 10791119.0.
Supplementary Search Report dated Jan. 3, 2013; re EP 10818191.8.
Exam Report Oct. 23, 2013 re EP 10818191.8.
Exam Report dated Aug. 8, 2014 re EP 10818191.8.
Supplementary Search Report dated Jan. 28, 2013 re EP 10818190.0 ESR.
Exam Report dated Oct. 23, 2013 re EP 10818190.0.
Search Report dated Feb. 15, 2013 re European application EP 12181077.4.
Office Action dated Sep. 18, 2012 re Indonesian application ID W-00201002481.
Office Action dated May 10, 2013 re Indonesian application ID W-00201002481.
Office Action dated May 8, 2012 re Israeli application IL 203018.
Office Action dated Aug. 18, 2013 re Israeli application IL 203018.
Office Action dated May 9, 2012 re Israeli application IL 206967.
Office Action dated Oct. 25, 2012 re Israeli application IL 210215.
Office Action dated Mar. 30, 2014 re Israeli application 216937.
Office Action dated Jan. 15, 2014 re JP application 2011-516934.
Office Action dated Nov. 25, 2012 re Israeli application IL 210451 O.A.
IPRP PCT/CA2009/000032 dated Jul. 27, 2010.
IPRP PCT/CA2009/000941 dated Jan. 11, 2011.
IPRP PCT/CA2011/001228 dated Dec. 4, 2012.
IPRP PCT/CA2009/000926 dated Nov. 5, 2010.
ISR PCT/CA2012/050681 dated Jan. 3, 2013.
Office Action dated Jul. 9, 2013 re Japanese application JP 2010-516334.
Office Action dated Jan. 15, 2013 re Japanese application JP 2010-516334.
Office Action dated Aug. 30, 2013 re Japanese application JP 2010-542486.
Office Action dated Jan. 6, 2014 re Japanese application JP 2011-516935.
Office Action dated Feb. 13, 2014 re Japanese application JP 2011-517725.
Office Action dated May 28, 2013 re Japanese application JP 2012-516452.
Final Rejection dated Dec. 3, 2013 re Japanese application JP 2012-516452.
Reconsideration Report dated Jul. 18, 2014 re Japanese application JP 2012-516452.
Office Action dated Oct. 22, 2013 re Japanese application JP 2012-530059.
Office Action dated Jun. 11, 2013 re Japanese application JP 2012-530059.
Office Action dated Oct. 29, 2013 re Japanese application JP 2012-530060.
Japanese granted patent 5551780 (application 2012-530060) May 30, 2014.
Office Action dated Aug. 7, 2013 re Korean application KR 10-2012-7001798.
Office Action dated Mar. 6, 2013 re Mexican application MX/a/2010/000525.
Office Action dated Mar. 6, 2013 re Mexican application MX/a/2010/007962.
Office Action dated Nov. 7, 2013 re Mexican application MX/a/2010/007962.
Office Action dated Mar. 6, 2013 re Mexican application MX/a/2011/000459.
Office Action dated Sep. 19, 2012 re Mexican application MX/a/2011/000657.
Office Action dated May 13, 2013 re Mexican application MX/a/2011/000657.
Office Action dated Oct. 29, 2013 re Mexican application MX/a/2011/000657.
Office Action dated Jul. 2, 2014 re Mexican application MX/a/2011/000657.
Office Action dated Feb. 11, 2014 re Mexican application MX/a/2012/003372.

(56) References Cited

OTHER PUBLICATIONS

Office Action dated Aug. 27, 2014 re Mexican application MX/a/2012/003372.
Office Action Jul. 8, 2014 re Mexican application MX/a/2012/003373.
Letters Patent dated Aug. 6, 2012 re New Zealand application NZ 582360.
Office Action dated Jun. 27, 2012 re New Zealand application NZ 587108.
Office Action dated Jan. 28, 2013 re New Zealand application NZ 587108.
Office Action dated Jul. 9, 2012 re New Zealand application NZ 597401.
Exam Report dated Nov. 14, 2012 re NZ 598481.
NZ Letters Patent 598481.
Exam Report dated Nov. 15, 2012 re NZ 598508.
NZ Letters Patent 598508.
Office Action dated Apr. 5, 2013 re Russian application 2011105073/10.
Office Action dated Oct. 21, 2013 re Russian application 2011105073/10.
Office Action dated Aug. 1, 2013 re Russian application 2011105885/10.
Office Action dated Feb. 27, 2014 re Russian application 2011105885/10.
Office Action dated Jun. 19, 2014 re Russian application 2012115996/10.
Office Action dated Jun. 26, 2014 re Russian application 2012101946/10.
Granted Singapore Patent No. 158301 dated Apr. 30, 2012.
Written Opinion dated Mar. 12, 2012 re Singapore U.S. Pat. No. 201009568-5.
Search Report and Written Opinion dated Feb. 27, 2014 re Singapore U.S. Pat. No. 201201471-8.
South Africa Letters Patent 2010/05917.
Office Action dated Mar. 13, 2013 re Thailand application 1101003761.
Restriction Requirement dated Aug. 13, 2012 re U.S. Appl. No. 12/669,033.
Office Action dated Oct. 4, 2012 re U.S. Appl. No. 12/669,033.
Restriction Requirement dated Sep. 27, 2012 re U.S. Appl. No. 12/863,772.
Office Action dated Dec. 14, 2012 re U.S. Appl. No. 12/863,772.
Restriction Requirement dated Dec. 6, 2012 re U.S. Appl. No. 13/001,111.
Office Action dated Apr. 2, 2013 re U.S. Appl. No. 13/001,111.
Notice of Allowance dated Oct. 28, 2013 re U.S. Appl. No. 13/001,111.
Letters Patent dated Jul. 8, 2014 re U.S. Appl. No. 13/001,111 (no copy).
Office Action dated Jul. 12, 2013 re U.S. Appl. No. 13/054,452.
Final Office Action dated May 8, 2014 re U.S. Appl. No. 13/054,452.
Office Action dated Nov. 25, 2013 re U.S. Appl. No. 13/734,886.
Final Office Action dated Mar. 20, 2014 re U.S. Appl. No. 13/734,886.
Restriction Requirement dated Mar. 25, 2013 re U.S. Appl. No. 13/748,531.
Office Action dated Sep. 12, 2013 re U.S. Appl. No. 13/748,531.
Final Office Action dated Jun. 18, 2014 re U.S. Appl. No. 13/748,531.
Office Action dated Jan. 3, 2014 re U.S. Appl. No. 13/380,346.
Office Action dated May 21, 2014 re U.S. Appl. No. 13/380,346.
ZA South African granted Patent No. 2011/01231.
Abdel-Salam, A.M., et al. "Purification, serology and molecular detection of Egyptian isolates of banana bunchy top babuvirus and faba bean necrotic yellows nanovirus". Arab J. Biotech, 7(1), pp. 141-155, Jan. 2004.
Biemelt, Sophia, et al. "Production of Human Papillomavirus Type 16 Virus-Like particles in Transgenic Plants". J. of Virology, Sep. 2003, pp. 9211-9220.
Copeland, K.M., et al. "Functional Chimeras of Human Immunodeficiency Virus Type 1 gp 120 and Influenza A Virus (H3) Hemagglutinin". Journal of Virology, May 2005, pp. 6459-6471.
Davey, M.R., et al. "Plant protoplasts: status and biotechnological perspectives". Biotechnology Advances (2005) 23, pp. 131-171.
Ellis, R.J. "The molecular chaperone concept". Seminars in Cell Biology, Feb. 1990 (1):1-9.
Gomord, V., et al. "Plant-specific glycosylation patterns in the context of therapeutic protein productions". Plant Biotech Journal (2010) vol. 8, pp. 564-587.
Helenius, A., et al. Roles of N-Linked Glycans in the Endoplasmic Reticulum. Annu. Rev. Biochem. 2004, 73: pp. 1019-1049.
Novel Swine-Origin Influenza A (H1N1) Virus Investigation Team. "Emergence of a Novel Swine-Origin Influenza A (H1N1) Virus in Humans". The New England Journal of Medicine, Jun. 18, 2009, vol. 360:25. pp. 2605-2615.
Power, J.B., et al. "A Simple Method for the Isolation of Very Large Nos. of Leaf Protoplasts by using Mixtures of Cellulase and Pectinase". Biochem J., 111(5), 1969, 33P.
Santi, L., et al., "An efficient plant viral expression system generating orally immunogenic Norwalk virus-like particles". *Vaccine* (2008) 26, pp. 1846-1854.
Song, J., et al. "Influenza Virus-Like Particles Containing M2 Induce Broadly Cross Protective Immunity". PlosS One, Jan. 2011, vol. 6:1, pp. 1-11.
Takahashi, Y., et al. "A high-throughput screen of cell-death-inducing factors in Nicotiana benthamiana identifies a novel MAPKK that mediates INF1-induced cell death signaling and non-host resistance to Pseudomonas cichorii". The Plant Journal (2007) 49, pp. 1030-1040.
Twyman, M.R. et al. "Molecular farming in plants: host systems and expression technology". Trends in Biotechnology. vol. 21:12, Dec. 2003, pp. 570-578.
Wang, K., et al. "Viral proteins function as ion channels". Biochimica et Biophysica Acta. vol. 1808:2, Feb. 2011, pp. 510-515.
Webby, G.N., et al. Purification of the NY-RMV and NY-SGV Isolates of Varley Yellow Dwarf Virus and the Production and Properties of Their Antibodies. Plant Disease, Nov. 1992 pp. 1125-1132.
Wickramasinghe, S.R., et al. Tangential Flow Microfiltration and Ultrafiltration for Human Influenza A Virus Concentration and Purification. Biotechnology and Bioengineering, vol. 92:2, Oct. 20, 2005, pp. 199-208.
Yigzaw, Y., et al. "Exploitation of the Adsorptive Properties of Depth Filters for Host Cell Protein Removal during Monoclonal Antibody Purification". Biotechnol. Prog, 2006, vol. 22, pp. 288-296.
Notice of Acceptance re AU 2009267769 dated Jul. 2, 2015.
Exam Report dated Dec. 16, 2014 re AU 2009270404.
Exam Report dated May 7, 2015 re AU 2009270404.
Certificate of Grant 2010265766 dated Jul. 2, 2015.
Notice of Acceptance re AU 2010300033 dated Dec. 17, 2014.
Exam Report dated Dec. 24, 2014 re AU 2010300034.
Office Action dated May 4, 2015 re CA 2,730,171.
Notice of Allowance Jun. 1, 2015 re CA 2,730,185.
Office Action dated Apr. 14, 2015 re CA 2,730,668.
Office Action dated Jun. 1, 2015 re CA 2,850,407.
Office Action dated May 26, 2015 re CN 201310021693.8.
Notice of Re-Exam dated May 26, 2015 re CN 200980126670.5.
Office Action dated Nov. 26, 2014 re CN 2011800641274.
Office Action dated Mar. 25, 2015 re CN 200980136376.2.
Notice of Allowance dated Aug. 20, 2014 re CN 201080035066.4.
Office Action dated Nov. 15, 2014 re CN 201080042336.4.
Decision on Rejection dated May 28, 2015 re CN 201080042336.4.
Office Action dated Sep. 23, 2014 re CN application 201310021693.8.
Office Action Jun. 24, 2015 re CN 201280047819.2 (associate's translation).
Office Action dated Sep. 3, 2014 re EG application PCT 61/2010.

(56) References Cited

OTHER PUBLICATIONS

Decision to Grant dated Apr. 23, 2015 European application EP 09793751.0.
Office Action dated Mar. 27, 2015 re EP 11837364.6.
Intent to Grant EP 09793751.0 dated Dec. 10, 2014.
EP 10818190.0 Office Action dated Oct. 6, 2014.
Extended Search Report dated May 12, 2015 re EP 12836545.9.
Office Action dated Sep. 22, 2014 re ID W-0020102481.
Office Action dated Jan. 9, 2015 re ID W-0020102481.
Office Action dated Jan. 13, 2015 re JP app. 2011-516934.
Office Action dated Sep. 28, 2014 re Israeli app IL 218393.
Office Action dated Oct. 21, 2014 re IL 218422.
Exam Report dated Aug. 6, 2015 re 212/DELNP.2010.
Final Office Action dated Dec. 24 2014 re JP 2011-516935.
Office Action dated Jan. 26, 2015 re JP 2011-517725.
Office Action dated Jun. 16, 2015 re JP 2012-516452.
Office Action dated May 27, 2015 re JP 2014-039035.
Office Action dated Jun. 2, 2015 re JP 2014-076395.
Office Action dated Dec. 22, 2014 re KR 10-2010-7002538.
Decision to Grant re KR 10-2010-7002538 dated Jul. 20, 2015.
Office Action dated May 21, 2015 re KR 10-2010-7018343.
Office Action dated Sep. 15, 2014 re Malaysian app PI2010000142.
Office Action dated Jun. 15, 2015 re MX/a/2011/0-13517.
Office Action dated Feb. 16, 2015 re MX/a/2012/003373.
Exam Report dated Jan. 30, 2015 re NZ app 622731.
Decision of Grant dated Jan. 23, 2015 re RU 2011105885/10.
Office Action dated Sep. 29, 2014 re RU 2012115661/10.
Office Action dated Jun. 24, 2015 re RU 2012115661.
Office Action dated Nov. 12, 2014 re RU 2012115996/10.
Decision to Grant re RU 012115996 dated May 5, 2015.
Office Action dated Jan. 22, 2015 re RU app. 2012101946.
Decision to Grant dated Apr. 21, 2015 re RU 2012101946.
Certificate of Grant re SG 187500 dated Aug. 26, 2014.
Office Action dated Sep. 18, 2014 re Thailand app TH 1101003761.
Office Action dated Feb. 9, 2015 re U.S. Appl. No. 13/054,452.
Office Action dated Dec. 5, 2014 re U.S. Appl. No. 13/734,886.
Office Action dated Jun. 25, 2015 re U.S. Appl. No. 13/734,886.
Office Action dated Jan. 5, 2015 re U.S. Appl. No. 13/748,531.
Final Office Action dated Jun. 23, 2015 re U.S. Appl. No. 13/748,531.
Office Action dated Sep. 4, 2014 re U.S. Appl. No. 13/497,767.
Office Action dated Jun. 24, 2015 re U.S. Appl. No. 13/497,767.
Office Action dated Feb. 9, 2015 re U.S. Appl. No. 13/380,346.
Office Action dated Aug. 28 2014 re U.S. Appl. No. 13/497,757.
Office Action dated Jun. 25, 2015 re U.S. Appl. No. 13/497,757.
Denis, J. et al., "Immunogenicity of papaya mosaic virus-like particles fused to a hepatitis C virus epitope: Evidence for the critical function of multimerization." Virology 363 (2007) pp. 59-68.
Certificate of Grant dated Nov. 12, 2015 re AU 2010300034.
Office Action dated Sep. 7, 2015 re CN 201180064127.4 (translation).
Decision on Rejection dated Dec. 14, 2015 re CN 2009801363762 (translation).
Office Action dated Nov. 26, 2015 re CN 201310021693.8 (translation).
Office Action dated Aug. 12, 2015 re EP 097973366.
Intent to Grant dated Feb. 5, 2016 re EP 097973366.
Summons to Oral Proceedings dated Oct. 30, 2015 re EP 10791119.0.
Office Action dated Nov. 17, 2015 re EP 10818191.8.
Office Action dated Sep. 25, 2015 re EP 10818190.0.
Notice of Allowability dated Sep. 18, 2015 re W-00201002481 (translation).
Office Action dated Dec. 3, 2015 re W-00201201507 (translation).
Certificate of Grant dated May 27, 2015 re Israeli app. IL 203018.
Office Action dated Oct. 27, 2015 re JP 2013-536965 (translation).
Office Action dated Aug. 19, 2015 re KR 10-2011-7002827 (translation).
Final Rejection dated Jan. 22, 2016 re KR 10-2010-7018343 (translation).
Office Action dated Dec. 7, 2015 re MX/a/2011/013517 (translation).
Search Report dated Jul. 28, 2015 and Examination Report dated Aug. 14, 2015 re SG 2013053467.
Office Action dated Jan. 7, 2016 re U.S. Appl. No. 13/054,452.
Advisory Action dated Nov. 3, 2015 re U.S. Appl. No. 13/734,886.
Office Action dated Feb. 12, 2016 re U.S. Appl. No. 13/734,886.
Office Action dated Oct. 6, 2015 re U.S. Appl. No. 13/748,531.
Office Action dated Sep. 22, 2015 re U.S. Appl. No. 13/380,346.
Office Action dated Jan. 12, 2016 re U.S. Appl. No. 13/497,767.

* cited by examiner

*AGAGGTACCCCGGGCTGGTATATTTATATGTTGTCAAATAACTCAAAAACCATA*
*AAAGTTTAAGTTAGCAAGTGTGTACATTTTTACTTGAACAAAAATATTCACCTAC*
*TACTGTTATAAATCATTATTAAACATTAGAGTAAAGAAATATGGATGATAAGAAC*
*AAGAGTAGTGATATTTTGACAACAATTTTGTTGCAACATTTGAGAAAATTTTGTT*
*GTTCTCTCTTTTCATTGGTCAAAAACAATAGAGAGAGAAAAAGGAAGAGGGAG*
*AATAAAAACATAATGTGAGTATGAGAGAGAAAGTTGTACAAAAGTTGTACCAAA*
*ATAGTTGTACAAATATCATTGAGGAATTTGACAAAAGCTACACAAATAAGGGTT*
*AATTGCTGTAAATAAATAAGGATGACGCATTAGAGAGATGTACCATTAGAGAAT*
*TTTTGGCAAGTCATTAAAAAGAAAGAATAAATTATTTTTAAAATTAAAAGTTGAG*
*TCATTTGATTAAACATGTGATTATTTAATGAATTGATGAAAGAGTTGGATTAAAG*
*TTGTATTAGTAATTAGAATTTGGTGTCAAATTTAATTTGACATTTGATCTTTTCCT*
*ATATATTGCCCCATAGAGTCAGTTAACTCATTTTTTATATTTCATAGATCAAATAA*
*GAGAAATAACGGTATATTAATCCCTCCAAAAAAAAAAACGGTATATTTACTAAA*
*AAATCTAAGCCACGTAGGAGGATAACAGGATCCCCGTAGGAGGATAACATCCA*
*ATCCAACCAATCACAACAATCCTGATGAGATAACCCACTTTAAGCCCACGCATC*
*TGTGGCACATCTACATTATCTAAATCACACATTCTTCCACACATCTGAGCCACA*
*CAAAAACCAATCCACATCTTTATCACCCATTCTATAAAAAATCACACTTTGTGAG*
*TCTACACTTTGATTCCCTTCAAACACATACAAAGAGAAGAGACTAATTAATTAAT*
*TAATCATCTTGAGAGAAA*ATGGCGAAAAACGTTGCGATTTTCGGCTTATTGTTT
TCTCTTCTTGTGTTGGTTCCTTCTCAGATCT

GAGCTCTAAGTTAAAATGCTTCTTCGTCTCCTATTTATAATATGGTTTGTTATTG
TTAATTTTGTTCTTGTAGAAGAGCTTAATTAATCGTTGTTGTTATGAAATACTATT
TGTATGAGATGAACTGGTGTAATGTAATTCATTTACATAAGTGGAGTCAGAATC
AGAATGTTTCCTCCATAACTAACTAGACATGAAGACCTGCCGCGTACAATTGTC
TTATATTTGAACAACTAAAATTGAACATCTTTTGCCACAACTTTATAAGTGGTTA
ATATAGCTCAAATATATGGTCAAGTTCAATAGATTAATAATGGAAATATCAGTTA
TCGAAATTCATTAACAATCAACTTAACGTTATTAACTACTAATTTTATATCATCCC
CTTTGATAAATGATAGTACA

SEQ ID NO.1

AGATCTTCGCTGACACAATATGTATAGGCTACCATGCCAACAACTCAACCGACACTGTTGACACAGTAC
TTGAGAAGAATGTGACAGTGACACACTCTGTCAACCTACTTGAGGACAGTCACAATGGAAAACTATGTCT
ACTAAAAGGAATAGCCCCACTACAATTGGGTAATTGCAGCGTTGCCGGATGGATCTTAGGAAACCCAGA
ATGCGAATTACTGATTTCCAAGGAATCATGGTCCTACATTGTAGAAACACCAAATCCTGAGAATGGAACA
TGTTACCCAGGGTATTTCGCCGACTATGAGGAACTGAGGGAGCAATTGAGTTCAGTATCTTCATTTGAG
AGATTCGAAATATTCCCCAAAGAAAGCTCATGGCCCAACCACACCGTAACCGGAGTATCAGCATCATGC
TCCCATAATGGGAAAAGCAGTTTTTACAGAAATTTGCTATGGCTGACGGGGAAGAATGGTTTGTACCCA
AACCTGAGCAAGTCCTATGTAAACAACAAAGAGAAAGAAGTCCTTGTACTATGGGGTGTTCATCACCCG
CCTAACATAGGGAACCAAAGGGCACTCTATCATACAGAAAATGCTTATGTCTCTGTAGTGTCTTCACATT
ATAGCAGAAGATTCACCCCAGAAATAGCCAAAAGACCCAAAGTAAGAGATCAGGAAGGAAGAATCAACT
ACTACTGGACTCTGCTGGAACCTGGGGATACAATAATATTTGAGGCAAATGGAAATCTAATAGCGCCAT
GGTATGCTTTTGCACTGAGTAGAGGCTTTGGATCAGGAATCATCACCTCAAATGCACCAATGGATGAAT
GTGATGCGAAGTGTCAAACACCTCAGGGAGCTATAAACAGCAGTCTTCCTTTCCAGAATGTACACCCAG
TCACAATAGGAGAGTGTCCAAAGTATGTCAGGAGTGCAAAATTAAGGATGGTTACAGGACTAAGGAACA
TCCCATCCATTCAATCCAGAGGTTTGTTTGGAGCCATTGCCGGTTTCATTGAAGGGGGGTGGACTGGAA
TGGTAGATGGGTGGTATGGTTATCATCATCAGAATGAGCAAGGATCTGGCTATGCTGCAGATCAAAAAA
GTACACAAAATGCCATTAACGGGATTACAAACAAGGTCAATTCTGTAATTGAGAAAATGAACACTCAATT
CACAGCTGTGGGCAAAGAGTTCAACAAATTGGAAAGAAGGATGGAAAACTTAAATAAAAAAGTTGATGAT
GGGTTTCTAGACATTTGGACATATAATGCAGAATTGTTGGTTCTACTGGAAAATGAAAGGACTTTGGATT
TCCATGACTCCAATGTGAAGAATCTGTATGAGAAAGTAAAAAGCCAATTAAAGAATAATGCCAAAGAAAT
AGGAAACGGGTGTTTTGAGTTCTATCACAAGTGTAACAATGAATGCATGGAGAGTGTGAAAAATGGTAC
CTATGACTATCCAAAATATTCCGAAGAATCAAAGTTAAACAGGGAGAAAATTGATGGAGTGAAATTGGAA
TCAATGGGAGTATACTAAGAGCTCAGGCCT

Fig. 4B

SEQ ID NO. 2

GGTACCTATGACTATCCAAAATATTCCGAAGAATCAAAGTTAAACAGGGAGAAAATTGATGGAGTGAAAT
TGGAATCAATGGGAGTATACCAGATTCTGGCGATCTACTCAACTGTCGCCAGTTCCCTGGTTCTTTTGGT
CTCCCTGGGGGCAATCAGCTTCTGGATGTGTTCCAATGGGTCTTTGCAGTGTAGAATATGCATCTTAAGA
GCTCAGGCCT

Fig. 5

HA0 from H1 (SEQ ID NO:28)

AGATCTTCGCTGACACAATATGTATAGGCTACCATGCCAACAACTCAACCGACACTGTTGACA
CAGTACTTGAGAAGAATGTGACAGTGACACACTCTGTCAACCTACTTGAGGACAGTCACAATG
GAAAACTATGTCTACTAAAAGGAATAGCCCCACTACAATTGGGTAATTGCAGCGTTGCCGGAT
GGATCTTAGGAAACCCAGAATGCGAATTACTGATTTCCAAGGAATCATGGTCCTACATTGTAG
AAACACCAAATCCTGAGAATGGAACATGTTACCCAGGGTATTTCGCCGACTATGAGGAACTGA
GGGAGCAATTGAGTTCAGTATCTTCATTTGAGAGATTCGAAATATTCCCCAAAGAAAGCTCAT
GGCCCAACCACACCGTAACCGGAGTATCAGCATCATGCTCCCATAATGGGAAAAGCAGTTTTT
ACAGAAATTTGCTATGGCTGACGGGGAAGAATGGTTTGTACCCAAACCTGAGCAAGTCCTATG
TAAACAACAAAGAGAAAGAAGTCCTTGTACTATGGGGTGTTCATCACCCGCCTAACATAGGGA
ACCAAAGGGCACTCTATCATACAGAAAATGCTTATGTCTCTGTAGTGTCTTCACATTATAGCAG
AAGATTCACCCCAGAAATAGCCAAAAGACCCAAAGTAAGAGATCAGGAAGGAAGAATCAACTA
CTACTGGACTCTGCTGGAACCTGGGGATACAATAATATTTGAGGCAAATGGAAATCTAATAGC
GCCATGGTATGCTTTTGCACTGAGTAGAGGCTTTGGATCAGGAATCATCACCTCAAATGCACC
AATGGATGAATGTGATGCGAAGTGTCAAACACCTCAGGGAGCTATAAACAGCAGTCTTCCTTT
CCAGAATGTACACCCAGTCACAATAGGAGAGTGTCCAAAGTATGTCAGGAGTGCAAAATTAAG
GATGGTTACAGGACTAAGGAACATCCCATCCATTCAATCCAGAGGTTTGTTTGGAGCCATTGC
CGGTTTCATTGAAGGGGGGTGGACTGGAATGGTAGATGGGTGGTATGGTTATCATCATCAGA
ATGAGCAAGGATCTGGCTATGCTGCAGATCAAAAAAGTACACAAAATGCCATTAACGGGATTA
CAAACAAGGTCAATTCTGTAATTGAGAAAATGAACACTCAATTCACAGCTGTGGGCAAAGAGT
TCAACAAATTGGAAAGAAGGATGGAAAACTTAAATAAAAAAGTTGATGATGGGTTTCTAGACAT
TTGGACATATAATGCAGAATTGTTGGTTCTACTGGAAAATGAAAGGACTTTGGATTTCCATGAC
TCCAATGTGAAGAATCTGTATGAGAAAGTAAAAAGCCAATTAAAGAATAATGCCAAAGAAATAG
GAAACGGGTGTTTTGAGTTCTATCACAAGTGTAACAATGAATGCATGGAGAGTGTGAAAAATG
GTACCTATGACTATCCAAAATATTCCGAAGAATCAAAGTTAAACAGGGAGAAAATTGATGGAG
TGAAATTGGAATCAATGGGAGTATACCAGATTCTGGCGATCTACTCAACTGTCGCCAGTTCCC
TGGTTCTTTTGGTCTCCCTGGGGGCAATCAGCTTCTGGATGTGTTCCAATGGGTCTTTGCAGT
GTAGAATATGCATCTAAGAGCTCAGGCCT

Fig. 6

SEQ ID NO. 3

AAGCTTATGGAGAAAATAGTGCTTCTTCTTGCAATAGTCAGTCTTGTTAAAAGTGATCAGATTTGCATTGG
TTACCATGCAAACAATTCAACAGAGCAGGTTGACACAATCATGGAAAAGAACGTTACTGTTACACATGCC
CAAGACATACTGGAAAAGACACACAACGGGAAGCTCTGCGATCTAGATGGAGTGAAGCCTCTAATTTTA
AGAGATTGTAGTGTAGCTGGATGGCTCCTCGGGAACCCAATGTGTGACGAATTCATCAATGTACCGGAA
TGGTCTTACATAGTGGAGAAGGCCAATCCAACCAATGACCTCTGTTACCCAGGGAGTTTCAACGACTAT
GAAGAACTGAAACACCTATTGAGCAGAATAAACCATTTTGAGAAAATTCAAATCATCCCCAAAAGTTCTTG
GTCCGATCATGAAGCCTCATCAGGAGTTAGCTCAGCATGTCCATACCTGGGAAGTCCCTCCTTTTTTAGA
AATGTGGTATGGCTTATCAAAAAGAACAGTACATACCCAACAATAAAGAAAAGCTACAATAATACCAACCA
AGAGGATCTTTTGGTACTGTGGGGAATTCACCATCCTAATGATGCGGCAGAGCAGACAAGGCTATATCA
AAACCCAACCACCTATATTTCCATTGGGACATCAACACTAAACCAGAGATTGGTACCAAAAATAGCTACT
AGATCCAAAGTAAACGGGCAAAGTGGAAGGATGGAGTTCTTCTGGACAATTTTAAAACCTAATGATGCAA
TCAACTTCGAGAGTAATGGAAATTTCATTGCTCCAGAATATGCATACAAAATTGTCAAGAAAGGGGACTC
AGCAATTATGAAAAGTGAATTGGAATATGGTAACTGCAACACCAAGTGTCAAACTCCAATGGGGGCGATA
AACTCTAGTATGCCATTCCACAACATACACCCTCTCACCATCGGGGAATGCCCCAAATATGTGAAATCAA
ACAGATTAGTCCTTGCAACAGGGCTCAGAAATAGCCCTCAAAGAGAGAGCAGAAGAAAAAAGAGAGGAC
TATTTGGAGCTATAGCAGGTTTTATAGAGGGAGGATGGCAGGGAATGGTAGATGGTTGGTATGGGTACC
ACCATAGCAATGAGCAGGGGAGTGGGTACGCTGCAGACAAAGAATCCACTCAAAAGGCAATAGATGGA
GTCACCAATAAGGTCAACTCAATCATTGACAAAATGAACACTCAGTTTGAGGCCGTTGGAAGGGAATTTA
ATAACTTAGAAAGGAGAATAGAGAATTTAAACAAGAAGATGGAAGACGGGTTTCTAGATGTCTGGACTTA
TAATGCCGAACTTCTGGTTCTCATGGAAAATGAGAGAACTCTAGACTTTCATGACTCAAATGTTAAGAAC
CTCTACGACAAGGTCCGACTACAGCTTAGGGATAATGCAAAGGAGCTGGGTAACGGTTGTTTCGAGTTC
TATCACAAATGTGATAATGAATGTATGGAAAGTATAAGAAACGGAACGTACAACTATCCGCAGTATTCAG
AAGAAGCAAGATTAAAAAGAGAGGAAATAAGTGGGGTAAAATTGGAATCAATAGGAACTTACCAAATACT
GTCAATTTATTCAACAGTGGCGAGTTCCCTAGCACTGGCAATCATGATGGCTGGTCTATCTTTATGGATG
TGCTCCAATGGATCGTTACAATGCAGAATTTGCATTTAAGAGCTC

Fig. 7A

SEQ ID NO. 4

5'-GTATTAGTAATTAGAATTTGGTGTC-3'

Fig. 7B

SEQ ID NO. 5

5'-GCAAGAAGAAGCACTATTTTCTCCAT<u>TTTCTCTCAAGATGATTA</u>-3'

Fig. 7C

SEQ ID NO. 6

5'-<u>TTAATCATCTTGAGAGAAAA</u>TGGAGAAAATAGTGCTTCTTCTTGC-3'

Fig. 7D

SEQ ID NO. 7

5'-ACTTTGAGCTCTTAAATGCAAATTCTGCATTGTAACGA-3'

Fig. 8A

HA1 peptide sequence (SEQ ID NO:9)

MKAKLLVLLCTFTATYADTICIGYHANNSTDTVDTVLEKNVTVTHSVNLLEDSHNGKLCLLKGIAPLQ
LGNCSVAGWILGNPECELLISKESWSYIVETPNPENGTCYPGYFADYEELREQLSSVSSFERFEIFPK
ESSWPNHTVTGVSASCSHNGKSSFYRNLLWLTGKNGLYPNLSKSYVNNKEKEVLVLWGVHHPPNI
GNQRALYHTENAYVSVVSSHYSRRFTPEIAKRPKVRDQEGRINYYWTLLEPGDTIIFEANGNLIAPWY
AFALSRGFGSGIITSNAPMDECDAKCQTPQGAINSSLPFQNVHPVTIGECPKYVRSAKLRMVTGLRNI
PSIQSRGLFGAIAGFIEGGWTGMVDGWYGYHHQNEQGSGYAADQKSTQNAINGITNKVNSVIEKMN
TQFTAVGKEFNKLERRMENLNKKVDDGFLDIWTYNAELLVLLENERTLDFHDSNVKNLYEKVKSQLK
NNAKEIGNGCFEFYHKCNNECMESVKNGTYDYPKYSEESKLNREKIDGVKLESMGVYQILAIYSTVA
SSLVLLVSLGAISFWMCSNGSLQCRICI*

Fig. 8B

HA5 peptide sequence (SEQ ID No: 10)

MEKIVLLLAIVSLVKSDQICIGYHANNSTEQVDTIMEKNVTVTHAQDILEKTHNGKLCDLDGVKPLILR
DCSVAGWLLGNPMCDEFINVPEWSYIVEKANPTNDLCYPGSFNDYEELKHLLSRINHFEKIQIIPKSS
WSDHEASSGVSSACPYLGSPSFFRNVVWLIKKNSTYPTIKKSYNNTNQEDLLVLWGIHHPNDAAEQ
TRLYQNPTTYISIGTSTLNQRLVPKIATRSKVNGQSGRMEFFWTILKPNDAINFESNGNFIAPEYAYKI
VKKGDSAIMKSELEYGNCNTKCQTPMGAINSSMPFHNIHPLTIGECPKYVKSNRLVLATGLRNSPQR
ESRRKKRGLFGAIAGFIEGGWQGMVDGWYGYHHSNEQGSGYAADKESTQKAIDGVTNKVNSIIDK
MNTQFEAVGREFNNLERRIENLNKKMEDGFLDVWTYNAELLVLMENERTLDFHDSNVKNLYDKVRL
QLRDNAKELGNGCFEFYHKCDNECMESIRNGTYNYPQYSEEARLKREEISGVKLESIGTYQILSIYST
VASSLALAIMMAGLSLWMCSNGSLQCRICI*

Fig. 9

Subtype H7 (SEQ ID NO:11)

>BHB940420|gb:AF071776|Symbol:HA|Name:hemagglutinin precursor|Organism:Influenza A Virus A/chicken/New York/1995|Chromosome:4|Subtype:H7|Host:Avian GACAAAATATGTCTTGGGCACCATGCTGTGGCAAATGGAACAAAAGTGAACACATTAACAGAGAGGGGA
TTGAAGTAGTGAACGCCACAGAGACGGTGGAAACTGCGAATATCAAGAAAATATGTATTCAAGGGAAAAG
GCCAACAGATCTGGGACAATGTGGACTTCTAGGAACCCTAATAGGACCTCCCCAATGTGATCAATTCCTG
GAGTTTTACTCTGATTTGATAATTGAGCGAAGAGAAGGAACCGATGTGTGCTATCCCGGTAAATTCACAA
ATGAAGAATCACTGAGGCAGATCCTTCGAGGGTCAGGAGGAATTGATAAGGAGTCAATGGGTTTCACCTA
TAGTGGAATAAGAACCAATGGAGCGACAAGTGCCTGCAAAAGATCAGGTTCTTCTTTCTATGCAGAGATG
AAGTGGTTGCTGTCGAATTCAGACAATGCGGCATTCCCTCAAATGACAAAGTCGTATAGAAATCCCAGAA
ACAAACCAGCTCTGATAATTTGGGGAGTTCATCACTCTGGATCGGTTAGCGAGCAGACCAAACTCTATGG
AAGTGGAAACAAGTTGATAACAGTAGGAAGCTCAAAATACCAGCAATCATTCACCCCAAGTCCGGGAGCA
CGGCCACAAGTGAATGGACAATCAGGGAGAATCGATTTTCACTGGCTACTCCTTGATCCCAATGACACAG
TGACCTTCACTTTCAATGGGGCATTCATAGCCCCTGACAGGGCAAGTTTCTTTAGAGGAGAATCACTAGG
AGTCCAGAGTGATGTTCCTCTGGATTCTAGTTGTGGAGGGGATTGCTTTCACAGTGGGGGTACGATAGTC
AGTTCCCTGCCATTCCAAAACATCAACCCTAGAACTGTGGGGAGATGCCCTCGGTATGTCAAACAGACAA
GCCTCCTTTTGGCTACAGGAATGAGAAATGTTCCAGAGAATCCAAAGCCCAGAGGCCTTTTTGGAGCAAT
TGCTGGATTCATAGAGAATGGATGGGAGGGTCTCATCGATGGATGGTATGGTTTCAGACATCAAAATGCA
CAAGGGGAAGGAACTGCAGCTGACTACAAAAGCACCCAATCTGCAATAGATCAGATCACAGGCAAATTGA
ATCGTCTGATTGACAAAACAAATCAGCAGTTTGAGCTGATAGACAATGAGTTCAATGAGATAGAACAACA
AATAGGAAATGTCATTAATTGGACACGAGACGCAATGACTGAGGTATGGTCGTATAATGCTGAGCTGTTG
GTGGCAATGGAAAATCAGCATACAATAGATCTTGCGGACTCAGAAATGAACAAACTTTATGAGCGTGTCA
GAAAACAACTAAGGGAGAATGCTGAAGAAGATGGAACTGGATGTTTTGAGATATTCCATAAGTGTGATGA
TCAGTGCATGGAGAGCATAAGGAACAACACTTATGACCATACTCAATACAGAACAGAGTCATTGCAGAAT
AGAATACAGATAGACCCAGTGAAATTGAGTAGTGGATACAAAGACATAATCTTATGGTTTAGCTTCGGGG
CATCATGTTTTCTTCTTCTAGCCGTTGTAATGGGATTGGTTTTCATTTGCATAAAGAATGGAAACATGCG
GTGCACCATTTGTATATAA

Fig. 10A

Subtype H2 (SEQ ID NO:12)

>gi|408516|gb|L11132.1|FLADE88HA Influenza A virus (A/herring gull/DE/677/88 (H2N8)) hemagglutinin (HA) gene, complete cds AGCAAAAGCAGGGGTTATACCATAGACAACCAAAGGCAAGACAATGGCCATCATTTATCTAATTCTTCTG
TTCACAGCAGTGAGAGGGGACCAAATATGCATTGGATACCATTCCAACAATTCCACAGAAAAGGTTGACA
CAATCCTAGAGAGAAATGTCACTGTGACTCACGCTGAGGACATTCTTGAGAAGACTCACAATGGGAAGTT
ATGCAAACTAAATGGAATCCCTCCACTTGAATTAAGGGATTGCAGCATTGCCGGATGGCTCCTTGGGAAT
CCAGAATGTGATATACTTCTAACTGTGCCAGAATGGTCATACATAATAGAAAAAGAAAATCCAAGGAACG
GCTTGTGCTACCCAGGCAGTTTCAATGATTATGAAGAATTGAAGCATCTTATCAGCAGCGTGACACATTT
TGAGAAAGTAAAGATTCTGCCCAGAAATGAATGGACACAGCATACAACAACTGGAGGTTCACAGGCTTGC
GCAGACTATGGTGGTCCGTCATTCTTCCGGAACATGGTCTGGTTGACAAAGAAAGGGTCGAATTATCCAA
TTGCCAAAAGATCTTACAACAATACAAGTGGGGAACAAATGCTGATCATTTGGGGGATACATCACCCCAA
TGATGAAAGTGAACAAAGAGCATTGTATCAGAATGTGGGGACCTATGTGTCAGTAGGAACATCAACACTG
AACAAAAGATCATCCCCAGAAATAGCAACAAGACCTAAAGTGAATGGACAAGGAGGCAGAATGGAATTCT
CGTGGACTATCTTAGATATATGGGACACAATAAATTTTGAGAGTACTGGCAATCTAATTGCACCAGAATA
TGGTTTCAAAATATCCAAACGAGGTAGTTCAGGGATCATGAAAACAGAAGGAAAACTTGAAAACTGCGAG
ACCAAGTGCCAAACTCCTTTGGGAGCAATAAATACAACATTACCCTTTCACAATATCCACCCACTGACCA
TTGGTGAGTGCCCCAAATATGTAAAATCGGAAAGATTAGTCTTAGCAACAGGACTAAGAAACGTCCCTCA
GATTGAGTCAAGGGGATTGTTTGGGGCAATAGCTGGTTTTATAGAGGGTGGATGGCAAGGAATGGTTGAT
GGTTGGTATGGGTATCATCACAGCAATGACCAGGGATCTGGGTATGCAGCAGACAAAGAATCCACTCAAA
AGGCAATTGATGGAATCACCAACAAGGTAAATTCTGTGATCGAAAAGATGAACACCCAATTCGGAGCTGT
TGGAAAAGAATTCAGTAACTTGGAGAGAAGACTGGAGAACTTGAATAAAAAGATGGAGGACGGATTTCTA
GATGTGTGGACATACAATGCCGAGCTCCTAGTTCTAATGGAAAATGAGAGGACACTTGACTTTCATGATT
CTAATGTCAAGAATCTATATGATAAAGTCAGAATGCAACTGAGAGACAATGCAAAAGAACTAGGGAATGG
ATGTTTTGAATTTTATCACAAATGTGATGATGAATGCATGAACAGTGTGAAGAATGGGACATATGATTAT
TCCAAGTATGAAGAGGAGTCTAAACTAAACAGGACTGAAATCAAAGGGGTTAAATTGAGCAATATGGGGG
TTTATCAAATCCTTGCCATCTATGCTACAGTAGCAGGTTCCCTGTCACTGGCAATCATGATAGCTGGGAT
TTCTATATGGATGTGCTCCAACGGGTCTCTGCAATGCAGAATCTGCATATGATCATCAGTCATTTTGTAA
TTAAAAACACCCTTGTTTCTACT

Fig. 10B

Subtype H3 (SEQ ID NO:13)

>BHB2107299|gb:EF473574|Symbol:HA|Name:hemagglutinin|Organism:Influenza A Virus A/Texas/32/2003|Segment:4|Subtype:H3|Host:Human CAAAAACTTCCCGGAAATGACAACAGCACGGCAACGCTGTGCCTTGGGCACCATGCAGTACCAAACGGAA
CGATAGTGAAAACAATCACGAATGACCAAATTGAAGTTACTAATGCTACTGAGCTGGTACAGAGTTCCTC
AACAGGTGGAATATGCGACAGTCCTCATCAGATCCTTGATGGAGAAAACTGCACACTAATAGATGCTCTA
TTGGGAGACCCTCAGTGTGATGGCTTCCAAAATAAGAAATGGGACCTTTTTGTTGAACGCAGCAAAGCCT
ACAGCAACTGTTACCCTTATGATGTGCCGGATTATGCCTCCCTTAGGTCACTAGTTGCCTCATCCGGCAC
ACTGGAGTTTAACAATGAAAGCTTCGATTGGACTGGAGTCACTCAGAATGGAACAAGCTCTGCTTGCAAA
AGGAGATCTAATAAAAGTTTCTTTAGTAGATTGAATTGGTTGACCCACTTAAAATACAAATACCCAGCAT
TGAACGTGACTATGCCAAACAATGAAAAATTTGACAAATTGTACATTTGGGGGGTTCACCACCCGGGTAC
GGACAGTGACCAAATCAGCCTATATGCTCAAGCATCAGGAAGAATCACAGTCTCTACCAAAAGAAGCCAA
CAAACTGTAATCCCGAATATCGGATCTAGACCCAGGGTAAGGGATGTCTCCAGCCGAATAAGCATCTATT
GGACAATAGTAAAACCGGGAGACATACTTTTGATTAACAGCACAGGGAATCTAATTGCTCCTCGGGGTTA
CTTCAAAATACGAAGTGGGAAAAGCTCAATAATGAGATCAGATGCACCCATTGGCAAATGCAATTCCGAA
TGCATCACTCCAAATGGAAGCATTCCCAATGACAAACCATTTCAAAATGTAAACAGGATCACATATGGGG
CCTGTCCCAGATATGTTAAGCAAAACACTCTGAAATTGGCAACAGGGATGCGAAATGTACCAGAGAAACA
AACTAGAGGCATATTTGGCGCAATCGCGGGTTTCATAGAAAATGGTTGGGAGGGAATGGTGGACGGTTGG
TACGGTTTCAGGCATCAAAATTCTGAGGGCACAGGA

Fig. 10C

Subtype H4 (SEQ ID NO:14)

>BHB1050162|gb:DQ021859|Symbol:HA|Name:hemagglutinin|Organism:Influenza A Virus A/mallard/MN/33/00|Segment:4|Subtype:H4|Host:Avian ATGCTATCAATCACGATTCTGTTTCTGCTCATAGCAGAGGGTTCCTCTCAGAATTACACAGGCAATCCCG
TGATATGCCTGGGACATCATGCCGTATCCAATGGGACAATGGTGAAAACCCTGACTGATGACCAAGTAGA
AGTTGTCACTGCCCAAGAATTAGTGGAATCGCAACATCTACCGGAGTTGTGTCCTAGCCCTTTAAGATTA
GTAGATGGACAAACTTGTGACATCGTCAATGGTGCCTTGGGGAGTCCAGGCTGTGATCACTTGAATGGTG
CAGAATGGGATGTCTTCATAGAACGACCCACTGCTGTGGACACTTGTTATCCATTTGATGTGCCGGATTA
CCAGAGCCTACGGAGTATCCTAGCAAACAATGGGAAATTTGAGTTCATTGCTGAGGAATTCCAATGGAAC
ACAGTCAAACAAAATGGGAAATCCGGAGCATGCAAAAGAGCAAATGTGAATGACTTTTTCAACAGATTGA
ACTGGCTGACCAAATCTGATGGGAATGCATACCCACTTCAAAACCTGACAAAGGTTAACAACGGGGACTA
TGCAAGACTTTACATATGGGGAGTTCATCATCCTTCAACTGACACAGAACAAACCAACTTGTATAAGAAC
AACCCTGGGAGAGTAACTGTTTCCACCAAAACCAGTCAAACAAGTGTGGTACCAAACATTGGCAGTAGAC
CATGGGTAAGAGGCCAAAGCGGCAGGATTAGCTTCTATTGGACAATTGTGGAGCCAGGAGACCTCATAGT
CTTCAACACCATAGGGAATTTAATTGCTCCGAGAGGTCATTACAAGCTTAACAGTCAAAAGAAGAGCACA
ATTCTGAATACTGCAATTCCCATAGGATCTTGTGTTAGTAAATGTCACACAGATAGGGGTTCAATCTCTA
CAACCAAACCCTTTCAGAACATCTCAAGAATATCAATTGGGGACTGTCCCAAGTATGTCAAACAGGGATC
CTTGAAACTAGCTACAGGAATGAGGAATATCCCTGAGAAAGCAACCAGAGGCCTGTTTGGTGCAATTG

Fig. 10D

Subtype H5 (SEQ ID NO:15)

>BHB950029|gb:AF501235|Symbol:HA|Name:hemagglutinin|Organism:Influenza A Virus A/duck/Shanghai/1/2000|Segment:4|Subtype:H5|Host:Avian ATGGAGAAAATAGTGCTTCTTCTTGCAATAGTCACTCTTGTTAAAAGTGATCAGATTTGCATTGGTTACC
ATGCAAACAACTCGACAGAGCAGGTTGACACAATAATGGAAAAGAACGTTACTGTTACACATGCCCAAGA
CATACTGGAAAAGACACACAACGGGAAACTCTGCGATCTAGATGGAGTGAAGCCTCTAATTTTGAGAGAT
TGTAGTGTAGCTGGATGGCTCCTCGGAAACCCTATGTGTGACGAATTCATCAATGTGCCGGAATGGTCTT
ACATAGTGGAGAAGGCCAGTCCAGCCAATGACCTCTGTTACCCAGGGGATTTCAACGACTATGAAGAACT
GAAACACCTATTGAGCAGAATAAACCACTTTGAGAAAATTCAGATCATCCCCAAAAGTTCTTGGTCCAAT
CATGAAGCCTCATCAGGGGTGAGCGCAGCATGTCCATACCATGGGAAGCCCTCCTTTTTCAGAAATGTGG
TATGGCTTATCAAAAAGAACAGTGCATACCCAACAATAAAGAGGAGCTACAATAATACCAACCAAGAAGA
TCTTTTGGTACTGTGGGGGATTCACCATCCTAATGATGCGGCAGAGCAGACAAAGCTCTATCAAAACCCA
ACCACCTATATTTCCGTTGGAACATCAACACTAAACCAGAGATTGGTCCCAAAAATAGCTACTAGATCCA
AAGTAAACGGGCAAAGTGGAAGAATGGAGTTCTTCTGGACAATTTTAAAGCCGAATGATGCCATAAATTT
CGAGAGTAATGGAAATTTCATTGCTCCAGAATATGCATACAAAATTGTCAAGAAAGGGGACTCAGCAATT
ATGAAAAGTGAATTGGAATATGGTAACTGCAACACCAAGTGTCAAACTCCAATGGGGGCGATAAACTCTA
GTATGCCATTCCACAACATACACCCTCTCACAATCGGGGAATGCCCCAAATATGTGAAATCAAACAGATT
AGTCCTTGCGACTGGACTCAGAAATACCCCTCAAAGAGATAGAAGAAGAAAAAAGAGAGGACTATTTGGA
GCTATAGCAGGTTTTATAGAGGGAGGATGGCAAGGAATGGTAGATGGTTGGTATGGCTACCACCATAGCA
ATGAGCAGGGGAGTGGATACGCTGCAGACAAAGAATCCACTCAAAAGGCAATAGATGGAGTCACCAATAA
GGTCAACTCGATCATTGACAAAATGAACACTCAGTTTGAGGCCGTTGGAAGGGAATTTAATAACTTAGAA
AGGAGGATAGAAAATTTAAACAAGAAGATGGAAGACGGATTCCTAGATGTCTGGACTTATAATGCTGAAC
TTCTGGTTCTCATGGAAAATGAGAGAACTCTAGACTTTCATGATTCAAATGTCAAGAACCTTTACAACAA
GGTCCGACTACAGCTTAGGGATAATGCAAAGGAGCTGGGTAATGGTTGTTTCGAGTTCTATCACAAATGT
GATAATGAATGTATGGAAAGTGTAAAAAACGGGACGTATGACTACCCGCAGTATTCAGAAGAAGCAAGAC
TAAACAGAGAGGAAATAAGTGGAGTAAAATTGGAATCAATGGGAACTTACCAAATACTGTCAATTTATTC
AACAGTGGCGAGTTCCCTAGCACTGGCAATCATGGTAGCTGGTCTATCTTTATGGATGTGCTCCAATGGG
TCGTTACAATGCAGAATTTGCATTTAA

Fig. 10E

Subtype H6 (SEQ ID NO:16)

>BHB1049778|gb:DQ021667|Symbol:HA|Name:hemagglutinin|Organism:Influenza A Virus A/northern pintail/TX/828189/02|Segment:4|Subtype:H6|Host:Avian ATGATTGCAATCATTGTAATAGCGATACTGGCAGCAGCCGGAAAGTCAGACAAGATCTGCATTGGGTATC
ATGCCAACAATTCAACAACACAGGTGGATACGATACTTGAGAAGAATGTAACCGTCACACACTCAGTTGA
ATTGCTGGAGAATCAGAAGGAAGAAAGATTCTGCAAGATCTTGAACAAGGCCCCTCTCGACCTAAAGGGA
TGCACCATAGAGGGTTGGATCTTGGGGAATCCCCAATGCGATCTGTTGCTTGGTGACCAAAGCTGGTCAT
ATATAGTGGAAAGACCTACTGCCCAAAATGGGATATGCTACCCAGGAGCTTTGAATGAGGTAGAAGAACT
GAAAGCATTTATCGGATCAGGAGAAAGGGTAGAGAGATTTGAGATGTTTCCCAAAAGCACATGGGCAGGG
GTAGACACCAGCAGTGGGGTAACAAAAGCTTGTCCTTATAATAGTGGTTCATCTTTCTACAGAAACCTCC
TATGGATAATAAAGACCAAGTCAGCAGCGTATCCAGTAATTAAGGGAACTTACAGCAACACTGGAAACCA
GCCAATCCTCTATTTCTGGGGTGTGCACCATCCTCCTGACACCAATGAGCAAAATACTCTGTATGGCTCT
GGCGATCGGTATGTTAGGATGGGAACTGAGAGCATGAATTTTGCCAAGAGCCCAGAAATTGCGGCAAGAC
CCGCTGTGAATGGCCAAAGAGGTCGAATTGATTATTACTGGTCTGTTTTAAAACCAGGAGAAACCTTGAA
TGTGGAATCTAATGGAAATCTAATCGCTCCTTGGTATGCATACAAATTTGTCAACACAAATAATAAGGGA
GCCGTCTTCAAGTCAAATTTACCAATCGAGAATTGCGATGCCACATGCCAGACTATTGCAGGAGTCCTAA
GGACCAATAAAACATTTCAGAATGTGAGCCCTCTGTGGATAGGAGAATGCCCCAAGTATGTGAAAAGTGA
AAGTCTAAGGCTTGCTACTGGACTAAGAAATGTTCCACAGATTCAAACCAGAGGGCTTTTCGGAGCTATC

Fig. 10F

Subtype H8 (SEQ ID NO:17)

>gi|221317|dbj|D90304.1|FLAHAH8N4 Influenza A virus (A/Turkey/Ontario/6118/68(H8N4)) gene for hemagglutinin precursor, complete cds ATGGAAAAATTCATCGCAATAGCAACCTTGGCGAGCACAAATGCATACGATAGGATATGCATTGGGTACC
AATCAAACAACTCCACAGACACAGTGAACACTCTCATAGAACAGAATGTACCAGTCACCCAAACAATGGA
GCTCGTGGAAACAGAGAAACATCCCGCTTATTGTAACACTGATTTAGGTGCCCCATTGGAACTGCGAGAC
TGCAAGATTGAGGCAGTAATCTATGGGAACCCCAAGTGTGACATCCATCTGAAGGATCAAGGTTGGTCAT
ACATAGTGGAGAGGCCCAGCGCACCAGAAGGGATGTGTTACCCTGGATCTGTGGAAAATCTAGAAGAACT
GAGGTTTGTCTTCTCCAGTGCTGCATCTTACAAGAGAATAAGACTATTTGACTATTCCAGGTGGAATGTG
ACTAGATCTGGAACGAGTAAAGCATGCAATGCATCAACAGGTGGCCAATCCTTCTATAGGAGCATCAATT
GGTTGACCAAAAAGGAACCAGACACTTATGACTTCAATGAAGGAGCTTATGTTAATAATGAAGATGGAGA
CATCATTTTCTTATGGGGGATCCATCATCCGCCGGACACAAAAGAGCAGACAACACTATATAAAAATGCA
AACACTTTGAGTAGTGTTACTACTAACACTATAAACAGAAGCTTTCAACCAAATATTGGTCCCAGACCAT
TAGTAAGAGGACAGCAAGGGAGGATGGATTACTATTGGGGCATTCTGAAAAGAGGGGAGACTCTGAAGAT
CAGGACCAACGGAAATTTAATCGCACCTGAATTTGGCTATCTGCTCAAAGGTGAAAGCTACGGCAGAATA
ATTCAAAATGAGGATATACCCATCGGGAACTGTAACACAAAATGTCAAACATATGCGGGAGCAATCAATA
GCAGCAAACCCTTTCAGAATGCAAGTAGGCATTACATGGGAGAATGTCCCAAATATGTGAAGAAGGCAAG
CTTGCGACTTGCAGTTGGGCTTAGGAATACGCCTTCTGTTGAACCCAGAGGACTGTTTGGAGCCATTGCT
GGTTTCATTGAAGGAGGATGGTCTGGAATGATTGATGGGTGGTATGGATTTCATCACAGCAATTCAGAGG
GAACAGGAATGGCAGCTGACCAGAAATCAACACAAGAAGCCATCGATAAGATCACCAATAAAGTCAACAA
TATAGTTGACAAGATGAACAGGGAGTTTGAAGTTGTGAATCATGAGTTCTCTGAAGTTGAAAAAAGAATA
AACATGATAAACGATAAAATAGATGACCAAATTGAAGATCTTTGGGCTTACAATGCAGAGCTCCTTGTGC
TCTTAGAGAACCAGAAAACGCTAGACGAACATGATTCCAATGTCAAAAACCTTTTTGATGAAGTGAAAAG
GAGACTGTCAGCCAATGCAATAGATGCTGGGAACGGTTGCTTTGACATACTTCACAAATGCGACAATGAG
TGTATGGAAACTATAAAGAACGGAACTTACGATCATAAGGAATATGAAGAGGAGGCTAAACTAGAAAGGA
GCAAGATAAATGGAGTAAAACTAGAAGAGAACACCACTTACAAAATTCTTAGCATTTACAGTACAGTGGC
GGCCAGTCTTTGCTTGGCAATCCTGATTGCTGGAGGTTTAATCCTGGGCATGCAAAATGGATCTTGTAGA
TGCATGTTCTGTATTTGA

Fig. 10G

Subtype H9 (SEQ ID NO:18)

>BHB954830|gb:AM087218|Symbol:HA|Name:hemagglutinin|Organism:Influenza A Virus A/shoveler/Iran/G54/03|Segment:4|Subtype:H9|Host:Avian

ATGGAAACAGTATCACTAATGACTATACTACTAGTAGCAACAGCAAGCAATGCAGACAAAATCTGCATCG

GCCACCAGTCAACAAACTCCACAGAAACTGTGGACACGCTAACAGAAACCAATGTTCCTGTGACACATGC

CAAAGAATTGCTCCACACAGAGCACAATGGAATGCTGTGTGCAACAAATCTGGGACATCCCCTAATCTTA

GACACGTGCACTATTGAAGGACTGATCTATGGTAACCCTTCTTGTGACTTGCTGTTGGGAGGAAGAGAAT

GGTCCTACATCGTCGAAAGGTCATCAGCTGTAAATGGAACGTGTTACCCTGGGAATGTAGAGAACCTAGA

GGAACTCAGGACACTTTTTAGTTCCGCTAGTTCCTACCGAAGAATCCAAATCTTCCCAGACACAATCTGG

AATGTGACTTACACTGGAACAAGCAAAGCATGTTCAGATTCATTCTACAGGAGTATGAGATGGCTGACTC

AAAAAAGCGGGTCTTACCCTGTTCAAGACGCTCAATACACAAATAATATGGGAAAGAGCATTCTTTTCGT

GTGGGGCATACATCACCCACCCACTGAAGCTGCACAGACAAATTTGTACACAAGAACCGACACAACAACA

AGCGTGACAACAGAAGACTTAAATAGGATCTTCAAACCGATGGTAGGGCCAAGGCCCCTTGTCAATGGTC

TGCAGGGAAGAATTAATTATTATTGGTCGGTACTAAAACCAGGCCAGACACTGCGAGTAAGATCCAATGG

GAATCTAATTGCTCCATGGTATGGACACATTCTTTCGGGAGGGAGCCATGGAAGAATCCTGAAGACTGAT

TTAAAAAGTAGTAATTGCGTAGTGCAATGTCAGACTGAAAAAGGCGGCTTAAACAGTACATTGCCGTTCC

ACAATATCAGTAAATATGCATTTGGAAACTGTCCCAAATATGTTAGAGTTAAAAGTCTCAAACTGGCAGT

AGGGTTGAGGAACGTGCCTGCTAGATCAAGTAGAGGACTATTCGGAGCCATAGCTCCATTCATAGAAGGA

GGTTGGCCAGGACTAGTCGCTGGTTGGTATGGTTTCCAGCATTCAAATGATCAAGGGGTTGGTATTGCGG

CAGATAGGGATTCAACTCAAAAGGCAATTGATAGAATAACAACCAAGGTGAATAATATAGTCGACAAAAT

GAACAAACAATATGAAATAATTGATCATGAATTCAGTGAGGTTGAAACTAGGCTCAACATGATCAATAAT

AAGATTGATGACCAAATACAAGACATATGGGCATATAATGCAGAGTTGCTAGTACTACTTGAAAACCAGA

AAACACTCGATGAGCATGACGCAAATGTGAAGA

Fig. 10H

Subtype H10 (SEQ ID NO:19)

>gi|324365|gb|M21647.1|FLAMS84HA Influenza A virus (A/chicken/Germany/N/1949(H10N7)) hemagglutinin precursor, gene, complete cds AGCAAAAGCAGGGGTCACAATGTACAAAGTAGTAGTAATAATTGCGCTCCTTGGAGCAGTGAAAGGTCTT
GACAGAATCTGCCTAGGACACCATGCGGTTGCCAATGGAACCATTGTGAAGACCCTTACAAATGAACAAG
AGGAAGTGACCAATGCTACTGAGACGGTAGAGAGCACAAATTTGAATAAATTGTGTATGAAAGGAAGAAG
CTACAAGGACTTGGGCAATTGTCACCCGGTAGGAATGTTGATAGGAACACCTGTTTGTGATCCGCACTTG
ACCGGGACCTGGGACACTCTCATTGAGCGAGAGAATGCCATTGCCCACTGTTATCCAGGGGCAACCATAA
ATGAAGAAGCATTGAGGCAGAAAATAATGGAAAGTGGAGGAATCAGCAAGATGAGCACTGGCTTCACTTA
TGGGTCTTCCATCACCTCAGCTGGGACCACTAAGGCATGCATGAGAAATGGAGGAGATAGTTTCTATGCA
GAGCTCAAATGGCTAGTGTCAAAGACAAAGGGACAAAATTTCCCTCAGACAACAAACACCTATCGGAATA
CGGACACAGCAGAACATCTCATAATATGGGGAATTCATCACCCTTCCAGCACACAGGAAAAGAATGACTT
ATACGGAACTCAGTCACTATCTATATCAGTTGAGAGTTCTACATATCAGAACAACTTTGTTCCAGTTGTT
GGGGCAAGACCTCAGGTCAATGGACAAAGTGGGCGAATTGACTTTCACTGGACACTAGTACAGCCGGGTG
ACAACATAACCTTCTCAGACAATGGAGGTCTAATAGCACCAAGTCGAGTTAGCAAATTAACTGGAAGGGA
TTTGGGAATCCAATCAGAAGCGTTGATAGACAACAGTTGTGAATCCAAATGCTTTTGGAGAGGGGGTTCT
ATAAATACAAAGCTCCCTTTTCAAAATCTGTCACCCAGAACAGTAGGTCAATGCCCCAAATACGTAAATC
AGAGGAGTTTACTGCTTGCAACAGGGATGAGGAATGTGCCAGAAGTGGTGCAGGGAAGGGGTCTGTTTGG
TGCAATAGCAGGGTTCATAGAAAACGGATGGGAAGGAATGGTAGACGGCTGGTATGGTTTCAGACACCAA
AATGCCCAGGGCACAGGCCAAGCTGCTGATTACAAGAGTACTCAAGCAGCTATTGACCAAATCACAGGGA
AACTGAACAGGTTGATTGAGAAGACCAACACTGAGTTTGAGTCAATAGAATCTGAATTCAGTGAGACTGA
GCATCAAATTGGTAACGTCATTAATTGGACCAAAGATTCAATAACCGACATTTGGACTTACAACGCAGAG
CTATTAGTGGCAATGGAGAATCAGCACACAATTGACATGGCTGATTCAGAGATGCTAAATCTGTATGAAA
GGGTAAGAAAGCAACTCAGACAGAATGCAGAAGAAGACGGAAAGGCATGTTTTGAGATATATCATACTTG
TGATGATTCGTGCATGGAGAGTATAAGGAACAATACTTATGACCATTCACAATACAGAGAGGAGGCTCTT
CTGAATAGACTGAACATCAACCCAGTGAAACTTTCTTCGGGGTACAAAGACATCATACTTTGGTTTAGCT
TCGGGGAATCATGCTTTGTTCTTCTAGCCGTTGTTATGGGTCTTGTTTTCTTCTGCCTGAAAAATGGAAA
CATGCGATGCACAATCTGTATTTAGTTAAAAACACCTTGTTTCTACT

Fig. 10I

Subtype H11 (SEQ ID NO:20)

>gi|221307|dbj|D90306.1|FLAHAH11N Influenza A virus (A/duck/England/56(H11N6)) gene for hemagglutinin precursor, complete cds ATGGAGAAAACACTGCTATTTGCAGCTATTTTCCTTTGTGTGAAAGCAGATGAGATCTGTATCGGTATT
TAAGCAACAACTCGACAGACAAAGTTGACACAATAATTGAGAACAATGTCACGGTCACTAGCTCAGTGGA
ACTGGTTGAGACAGAACACACTGGATCATTCTGTTCAATCAATGGAAAACAACCAATAAGCCTTGGAGAT
TGTTCATTTGCTGGATGGATATTAGGAAACCCTATGTGTGATGAACTAATTGGAAAGACTTCATGGTCTT
ACATTGTGGAAAAACCCAATCCAACAAATGGAATCTGTTACCCAGGAACTTTAGAGAGTGAAGAAGAACT
AAGACTGAAATTCAGTGGAGTTTTAGAATTTAACAAATTCGAAGTATTCACATCAAATGGATGGGGTGCT
GTAAATTCAGGAGTAGGAGTAACCGCTGCATGCAAATTCGGGGGTTCTAATTCTTTCTTTCGAAACATGG
TATGGCTGATACACCAATCAGGAACATATCCTGTAATAAAGAGAACCTTTAACAACACCAAAGGCAGAGA
TGTACTGATTGTTTGGGGAATTCATCATCCTGCTACACTGACAGAACATCAAGATCTGTATAAAAAGGAC
AGCTCCTATGTAGCAGTGGGTTCAGAGACCTACAACAGAAGATTCACTCCAGAAATCAACACTAGGCCCA
GAGTCAATGGACAGGCCGGACGGATGACATTCTACTGGAAGATAGTCAAACCAGGAGAATCAATAACATT
CGAATCTAATGGGGCGTTCCTAGCTCCTAGATATGCTTTTGAGATTGTCTCTGTTGGAAATGGGAAACTG
TTCAGGAGCGAACTGAACATTGAATCATGCTCTACCAAATGTCAAACAGAAATAGGAGGAATTAATACGA
ACAAAAGCTTCCACAATGTTCACAGAAACACTATCGGGGATTGCCCCAAGTATGTGAATGTCAAATCCTT
AAAGCTTGCAACAGGACCTAGAAATGTCCCAGCAATAGCATCGAGAGGCTTGTTTGGAGCAATAGCTGGA
TTCATAGAAGGGGGATGGCCTGGACTGATCAATGGATGGTATGGGTTCCAACACAGGGACGAAGAAGGAA
CAGGCATTGCAGCAGACAAGGAGTCAACTCAAAAGGCAATAGACCAGATAACATCCAAGGTAAATAACAT
CGTTGACAGGATGAATACAAACTTTGAGTCTGTGCAACACGAATTCAGTGAAATAGAGGAAAGAATAAAT
CAATTATCAAAACACGTAGATGATTCTGTGGTTGACATCTGGTCATATAATGCACAGCTTCTCGTTTTAC
TTGAAAATGAGAAGACACTGGACCTCCATGACTCAAATGTCAGGAACCTCCATGAGAAAGTCAGAAGAAT
GCTAAAGGACAATGCCAAAGATGAGGGGAACGGATGCTTCACCTTTTACCATAAGTGTGACAATAAATGC
ATTGAACGAGTTAGAAACGGAACATATGATCATAAAGAATTCGAGGAGGAATCAAAAATCAATCGCCAGG
AGATTGAAGGGGTGAAACTAGATTCTAGTGGGAATGTGTATAAAATACTGTCAATTTACAGCTGCATTGC
AAGCAGTCTTGTATTGGCAGCACTCATCATGGGGTTCATGTTTTGGGCATGCAGTAATGGATCATGTAGA
TGTACCATTTGCATTTAG

Fig. 10J

Subtype H12 (SEQ ID NO:21)

>gi|221309|dbj|D90307.1|FLAHAH12N Influenza A virus (A/duck/Alberta/60/76(H12N5)) gene for hemagglutinin precursor, complete cds

ATGGAAAAATTCATCATTTTGAGTACTGTCTTGGCAGCAAGCTTTGCATATGACAAAATTTGCATTGGAT

ACCAAACAAACAACTCGACTGAAACGGTAAACACACTAAGTGAACAAAACGTTCCGGTGACGCAGGTGGA

AGAACTTGTACATCGTGGGATTGATCCGATCCTGTGTGGAACGGAACTAGGATCACCACTAGTGCTTGAT

GACTGTTCATTAGAGGCTCTAATCCTAGCCAATCCCAAATGTGATCTTTATTTGAATGGCAGGGAATGGT

CATACATAGTAGAGAGGCCCAAAGAGATGGAAGGAGTTTGCTATCCAGGGTCAATTGAAAACCAGGAAGA

GCTAAGATCTCTGTTTTCTTCCATCAAAAAATATGAAAGAGTGAAGATGTTTGATTTCACCAAATGGAAT

GTCACATACACTGGGACCAGCAAGGCCTGCAATAATACATCAAACCAAGGCTCATTCTATAGGAGCATGA

GATGGTTGACCTTAAAATCAGGACAATTTCCAGTCCAAACAGATGAGTACAAGAACACCAGAGATTCAGA

CATTGTATTCACCTGGGCCATTCACCACCCACCAACATCTGATGAACAAGTAAAATTATACAAAAATCCT

GATACTCTCTCTTCAGTCACCACCGTAGAAATCAATAGGAGCTTCAAGCCTAATATAGGGCCAAGACCAC

TCGTGAGAGGACAACAAGGGAGAATGGATTACTACTGGGCTGTTCTTAAACCTGGACAAACAGTCAAAAT

ACAAACCAATGGTAATCTTATTGCACCTGAATATGGTCACTTAATCACAGGGAAATCACATGGCAGGATA

CTCAAGAATAATTTGCCCATGGGACAGTGTGTGACTGAATGTCAATTGAACGAGGGTGTAATGAACACAA

GCAAACCTTTCCAGAACACTAGTAAGCACTATATTGGGAAATGCCCCAAATACATACCATCAGGGAGTTT

AAAATTGGCAATAGGGCTCAGGAATGTCCCACAAGTTCAAGATCGGGGGCTCTTTGGAGCAATTGCAGGT

TTCATAGAAGGCGGATGGCCAGGGCTAGTGGCTGGTTGGTACGGATTTCAGCATCAAAATGCGGAGGGGA

CAGGCATAGCTGCAGACAGAGACAGCACCCAAAGGGCAATAGACAATATGCAAAACAAACTCAACAATGT

CATCGACAAAATGAATAAACAATTTGAAGTGGTGAATCATGAGTTTTCAGAAGTGGAAAGCAGAATAAAC

ATGATTAATTCCAAAATTGATGATCAGATAACTGACATATGGGCATACAATGCTGAATTGCTTGTCCTAT

TGGAAAATCAGAAGACATTAGATGAGCATGACGCTAATGTAAGGAATCTACATGATCGGGTCAGAAGAGT

CCTGAGGGAAAATGCAATTGACACAGGAGACGGCTGCTTTGAGATTTTACATAAATGTGACAACAATTGT

ATGGACACGATTAGAAACGGGACATACAATCACAAAGAGTATGAGGAAGAAAGCAAAATCGAACGACAGA

AAGTCAATGGTGTGAAACTTGAGGAGAATTCTACATATAAAATTCTGAGCATCTACAGCAGTGTTGCCTC

AAGCTTAGTTCTACTGCTCATGATTATTGGGGGTTTCATTTTCGGGTGTCAAAATGGAAATGTTCGTTGT

ACTTTCTGTATTTAA

Fig. 10K

Subtype H13 (SEQ ID NO:22)

>gi|221311|dbj|D90308.1|FLAHAH13N Influenza A virus
(A/Gull/Maryland/704/77(H13N6)) gene for hemagglutinin precursor, complete cds ATGGCTCTAAATGTCATTGCAACTTTGACACTTATAAGTGTATGTGTACATGCAGACAGAATATGCGTGG
GGTATCTGAGCACCAATTCATCAGAAAGGGTCGACACGCTCCTTGAAAATGGGGTCCCAGTCACCAGCTC
CATTGATCTGATTGAGACAAACCACACAGGAACATACTGTTCTCTAAATGGAGTCAGTCCAGTGCATTTG
GGAGATTGCAGCTTTGAAGGATGGATTGTAGGAAACCCAGCCTGCACCAGCAACTTTGGGATCAGAGAGT
GGTCATACCTGATTGAGGACCCCGCGGCCCCTCATGGGCTTTGCTACCCTGGAGAATTAAACAACAATGG
TGAACTCAGACACTTGTTCAGTGGAATCAGGTCATTCAGTAGAACGGAATTGATCCCACCTACCTCCTGG
GGGGAAGTACTTGACGGTACAACATCTGCTTGCAGAGATAACACGGGAACCAACAGCTTCTATCGAAATT
TAGTTTGGTTTATAAAGAAGAATACTAGATATCCAGTTATCAGTAAGACCTACAACAATACAACGGGAAG
GGATGTTTTAGTTTTATGGGGAATACATCACCCAGTGTCTGTGGATGAGACAAAGACTCTGTATGTCAAT
AGTGATCCATACACACTGGTTTCCACCAAGTCTTGGAGCGAGAAATATAAACTAGAAACGGGAGTCCGAC
CTGGCTATAATGGACAGAGGAGCTGGATGAAAATTTATTGGTCTTTGATACATCCAGGGGAGATGATTAC
TTTCGAGAGTAATGGTGGATTTTTAGCCCCAAGATATGGGTACATAATTGAAGAATATGGAAAAGGAAGG
ATTTTCCAGAGTCGCATCAGAATGTCTAGGTGCAACACCAAGTGCCAGACTTCGGTTGGAGGGATAAACA
CAAACAGAACGTTCCAAAACATCGATAAGAATGCTCTTGGTGACTGTCCCAAATACATAAAGTCTGGCCA
ACTCAAGCTAGCCACTGGACTCAGAAATGTGCCAGCTATATCGAATAGAGGATTGTTCGGAGCAATTGCA
GGGTTCATAGAAGGAGGCTGGCCAGGTTTAATCAATGGTTGGTACGGTTTTCAGCATCAAAATGAACAGG
GAACAGGAATAGCTGCAGACAAAGAATCAACACAGAAAGCTATAGACCAGATAACAACCAAAATAAATAA
CATTATTGATAAAATGAATGGGAACTATGATTCAATTAGGGGTGAATTCAATCAAGTTGAGAAGCGTATA
AACATGCTTGCAGACAGAATAGATGATGCCGTGACGGACATTTGGTCATACAATGCCAAACTTCTTGTAT
TGCTGGAAAATGATAAAACTTTAGATATGCATGATGCTAATGTAAAGAATTTACATGAGCAAGTACGAAG
AGAATTGAAGGACAATGCAATTGACGAAGGAAATGGCTGTTTTGAACTCCTTCATAAATGCAATGACTCC
TGCATGGAAACTATAAGAAATGGAACGTATGACCACACTGAGTATGCAGAGGAGTCAAAGTTAAAGAGCC
AAGAAATCCATGGCATCAAACTCAAATCAGAAGACAACGTTTACAAAGCATTATCAATATACAGTTGCAT
TGCAAGTAGTGTTGTACTAGTAGGACTCATACTCTCTTTCATCATGTGGGCCTGTAGTAGTGGGAATTGC
CGATTCAATGTTTGTATATAA

Fig. 10L

Subtype H14 (SEQ ID NO:23)

>gi|324045|gb|M35997.1|FLAH1424 Influenza A/Mallard/Gurjev/263/82
hemagglutinin subtype H14 gene AGCAAAAGCAGGGGAAAATGATTGCACTCATATTGGTTGCACTGGCTCTGAGCCACACTGCTTATTCTCA
GATCACAAATGGGACAACAGGAAACCCCATTATATGCTTGGGGCATCATGCAGTGGAAAACGGCACATCT
GTTAAAACACTAACAGACAATCACGTAGAAGTTGTGTCAGCTAAAGAATTAGTTGAGACGAACCACACTG
ATGAACTGTGCCCAAGCCCCTTGAAGCTTGTCGACGGGCAAGACTGCCACCTCATCAATGGTGCATTGGG
GAGTCCAGGCTGTGACCGTTTGCAGGACACCACTTGGGATGTCTTCATTGAAAGGCCCACTGCAGTAGAC
ACATGTTATCCATTCGACGTCCCAGATTACCAGAGTCTCAGAAGCATCCTAGCAAGCAGTGGGAGTTTGG
AGTTCATCGCCGAACAATTCACCTGGAATGGTGTCAAAGTTGACGGATCAAGCAGTGCTTGTTTGAGGGG
CGGTCGCAACAGCTTCTTCTCCCGACTAAACTGGCTAACCAAAGCAACAAATGGAAACTATGGACCTATT
AACGTCACTAAAGAAAATACGGGCTCTTATGTCAGGCTCTATCTCTGGGGAGTGCATCACCCATCAAGCG
ATAATGAGCAAACGGATCTCTACAAGGTGGCAACAGGGAGAGTAACAGTATCTACCCGCTCGGACCAAAT
CAGTATTGTTCCCAATATAGGAAGTAGACCGAGGGTAAGGAATCAGAGCGGCAGGATAAGCATCTACTGG
ACCCTAGTAAACCCAGGGGACTCCATCATTTTCAACAGTATTGGGAATTTGATTGCACCAAGAGGCCACT
ACAAAATAAGCAAATCTACTAAGAGCACAGTGCTTAAAAGTGACAAAAGGATTGGGTCATGCACAAGCCC
TTGCTTAACTGATAAAGGTTCGATCCAAAGTGACAAACCTTTTCAGAATGTATCAAGGATTGCTATAGGA
AACTGCCCGAAATATGTAAAGCAAGGGTCCCTGATGTTAGCAACTGGAATGCGCAACATCCCTGGCAAAC
AGGCAAAGGGCTTATTTGGGGCAATTGCTGGATTCATTGAAAATGGTTGGCAAGGCCTGATTGATGGGTG
GTATGGATTCAGGCACCAAAATGCTGAAGGAACAGGAACTGCTGCAGACCTGAAGTCAACTCAGGCAGCC
ATTGATCAGATAAATGGCAAGCTGAACAGATTGATAGAGAAGACAAATGAAAAATATCACCAAATAGAAA
AGGAATTCGAACAGGTGGAAGGAAGAATACAAGACCTTGAGAAGTACGTTGAGGACACTAAGATTGATTT
GTGGTCATACAATGCTGAATTGCTAGTAGCACTAGACAATCAGCACACAATAGATGTCACAGACTCCGAA
ATGAACAAGCTTTTTGAAAGAGTAAGAAGGCAATTAAGAGAGAATGCAGAAGATCAAGGCAACGGTTGTT
TCGAGATATTCCATCAGTGTGACAACAATTGTATAGAAAGCATTAGAAACGGAACTTATGACCACAACAT
CTACAGGGATGAAGCCATCAACAATCGAATCAAAATAAATCCTGTCACTTTGACGATGGGGTACAAGGAC
ATAATCCTGTGGATTTCTTTCTCCATGTCATGCTTTGTCTTCGTGGCACTGATTCTGGGATTTGTTCTAT
GGGCTTGTCAAAACGGGAATATCCGATGCCAAATCTGTATATAAAGAAAAAACACCCTTGTTTCTACTC

Fig. 10M

Subtype H15 (SEQ ID NO:24)

>gi|1226068|gb|L43916.1|FLAHEMAC Influenza A/duck/Australia/341/83 (H15N8) hemagglutinin mRNA, complete cds AGCAAAAGCAGGGGATACAAAATGAACACTCAAATCATCGTCATTCTAGTCCTCGGACTGTCGATGGTGA
GATCTGACAAGATTTGTCTCGGGCACCATGCCGTAGCAAATGGGACAAAAGTCAACACACTAACTGAGAA
AGGAGTGGAAGTGGTCAATGCCACGGAGACAGTGGAGATTACAGGAATAAATAAAGTGTGCACAAAAGGG
AAGAAAGCGGTGGACTTGGGATCTTGTGGAATACTGGGAACTATCATTGGGCCTCCACAATGTGACTCTC
ATCTTAAATTCAAAGCTGATCTGATAATAGAAAGAAGAAATTCAAGTGACATCTGTTACCCAGGGAAATT
CACTAATGAGGAAGCACTGAGACAAATAATCAGAGAATCTGGTGGAATTGACAAAGAGCCAATGGGATTT
AGATATTCAGGAATAAAAACAGACGGGGCAACCAGTGCGTGTAAGAGAACAGTGTCCTCTTTCTACTCAG
AAATGAAATGGCTTTTATCCAGCAAGGCTAACCAGGTGTTCCCACAACTGAATCAGACATACAGGAACAA
CAGAAAAGAACCAGCCCTAATTGTTTGGGGAGTACATCATTCAAGTTCCTTGGATGAGCAAAATAAGCTA
TATGGAGCTGGGAACAAGCTGATAACAGTAGGAAGCTCAAAATACCAACAATCGTTTTCACCAAGTCCAG
GGGACAGGCCCAAAGTGAATGGTCAGGCCGGGAGGATCGACTTTCATTGGATGCTATTGGACCCAGGGGA
TACAGTCACTTTTACCTTCAATGGTGCATTCATAGCCCCAGATAGAGCCACCTTTCTCCGCTCTAATGCC
CCATCGGGAGTTGAGTACAATGGGAAGTCACTGGGAATACAGAGTGATGCACAAATTGATGAATCATGTG
AAGGGGAATGCTTCTACAGTGGAGGGACAATAAACAGCCCTTTGCCATTTCAAAACATCGATAGTTGGGC
TGTCGGAAGGTGCCCCAGATATGTAAAGCAATCAAGCCTGCCGCTGGCCTTAGGAATGAAAAATGTACCA
GAGAAAATACATACTAGGGGACTGTTCGGTGCAATTGCAGGATTCATCGAGAATGGATGGGAAGGACTCA
TTGATGGATGGTATGGATTTAGGCATCAAAATGCACAGGGGCAGGGAACAGCTGCTGACTACAAGAGTAC
TCAGGCTGCAATTGACCAGATAACAGGGAAACTTAATAGATTAATTGAAAAAACCAACACACAGTTTGAA
CTCATAGACAATGAGTTCACTGAAGTGGAGCAGCAGATAGGCAATGTAATAAACTGGACAAGGGACTCCT
TGACTGAGATCTGGTCATACAATGCTGAACTTCTAGTAGCAATGGAAAATCAGCATACAATTGACCTTGC
AGATTCTGAAATGAACAAACTCTATGAGAGAGTGAGAAGACAGCTAAGGGAGAATGCCGAGGAGGATGGA
ACTGGATGTTTTGAGATTTTCCACCGATGTGACGATCAATGTATGGAGAGCATACGAAATAATACTTACA
ATCACACTGAATATCGACAGGAAGCCTTACAGAATAGGATAATGATCAATCCGGTAAAGCTTAGTGGTGG
GTACAAAGATGTGATACTATGGTTTAGCTTCGGGGCATCATGTGTAATGCTTCTAGCCATTGCTATGGGT
CTTATTTTCATGTGTGTGAAAAACGGGAATCTGCGGTGCACTATCTGTATATAATTATTTGAAAAACACC
CTTGTTTCTACT

Fig. 10N

Subtype H16 (SEQ ID NO:25)

>gi|56425020|gb|AY684891.1| Influenza A virus (A/black-headed gull/Sweden/5/99(H16N3)) hemagglutinin (HA) gene, complete cds AGCAAAAGCAGGGGATATTGTCAAAACAACAGAATGGTGATCAAAGTGCTCTACTTTCTCATCGTATTGT
TAAGTAGGTATTCGAAAGCAGACAAAATATGCATAGGATATCTAAGCAACAACGCCACAGACACAGTAGA
CACACTGACAGAGAACGGAGTTCCAGTGACCAGCTCAGTTGATCTCGTTGAAACAAACCACACAGGAACA
TACTGCTCACTGAATGGAATCAGCCCAATTCATCTTGGTGACTGCAGCTTTGAGGGATGGATCGTAGGAA
ACCCTTCCTGTGCCACCAACATCAACATCAGAGAGTGGTCGTATCTAATTGAGGACCCCAATGCCCCCAA
CAAACTCTGCTTCCCAGGAGAGTTAGATAATAATGGAGAATTACGACATCTCTTCAGCGGAGTGAACTCT
TTTAGCAGAACAGAATTAATAAGTCCCAACAAATGGGGAGACATTCTGGATGGAGTCACCGCTTCTTGCC
GCGATAATGGGGCAAGCAGTTTTTACAGAAATTTGGTCTGGATAGTGAAGAATAAAAATGGAAAATACCC
TGTCATAAAGGGGGATTACAATAACACAACAGGCAGAGATGTTCTAGTACTCTGGGGCATTCACCATCCG
GATACAGAAACAACAGCCATAAACTTGTACGCAAGCAAAAACCCCTACACATTAGTATCAACAAAGGAAT
GGAGCAAAAGATATGAACTAGAAATTGGCACCAGAATAGGTGATGGACAGAGAAGTTGGATGAAACTATA
TTGGCACCTCATGCGCCCTGGAGAGAGGATAATGTTTGAAAGCAACGGGGGCCTTATAGCGCCCAGATAC
GGATACATCATTGAGAAGTACGGTACAGGACGAATTTTCCAAAGTGGAGTGAGAATGGCCAAATGCAACA
CAAAGTGTCAAACATCATTAGGTGGGATAAACACCAACAAAACTTTCCAAAACATAGAGAGAAATGCTCT
TGGAGATTGCCCAAAGTACATAAAGTCTGGACAGCTGAAGCTTGCAACTGGGCTGAGAAATGTCCCATCC
GTTGGTGAAAGAGGTTTGTTTGGTGCAATTGCAGGCTTCATAGAAGGAGGGTGGCCTGGGCTAATTAATG
GATGGTATGGTTTCCAGCATCAGAATGAACAGGGGACTGGCATTGCTGCAGACAAAGCCTCCACTCAGAA
AGCGATAGATGAAATAACAACAAAAATTAACAATATAATAGAGAAGATGAACGGAAACTATGATTCAATA
AGAGGGGAATTCAATCAAGTAGAAAAGAGGATCAACATGCTCGCTGATCGAGTTGATGATGCAGTAACTG
ACATATGGTCGTACAATGCTAAACTTCTTGTACTGCTTGAAAATGGGAGAACATTGGACTTACACGACGC
AAATGTCAGGAACTTACACGATCAGGTCAAGAGAATATTGAAAAGTAATGCTATTGATGAAGGAGATGGT
TGCTTCAATCTTCTTCACAAATGTAATGACTCATGCATGGAAACTATTAGAAATGGGACCTACAATCATG
AAGATTACAGGGAAGAATCACAACTGAAAAGGCAGGAAATTGAGGGAATAAAATTGAAGTCTGAAGACAA
TGTGTATAAAGTACTGTCGATTTATAGCTGCATTCCAAGCAGTATTGTGCTGGTAGGTCTCATACTTGCG
TTCATAATGTGGGCATGCAGCAATGGAAATTGCCGGTTTAATGTTTGTATATAGTCGGAAAAAATACCCT
TGTTTCTACT

Fig. 10O

Influenza B (SEQ ID NO:26)

>gi|325175|gb|K00423.1|FLBHAZO Influenza B/Lee/40, hemagglutinin (seg 4), complete segment AGCAGAAGCGTTGCATTTTCTAATATCCACAAAATGAAGGCAATAATTGTACTACTCATGGTAGTAACAT
CCAATGCAGATCGAATCTGCACTGGGATAACATCGTCAAACTCACCTCATGTGGTTAAAACTGCCACTCA
AGGGGAAGTCAATGTGACTGGTGTGATACCACTAACAACAACACCTACCAAATCTCATTTTGCAAATCTC
AAAGGAACACAGACCAGAGGAAAACTATGCCCAAACTGTTTTAACTGCACAGATCTGGACGTGGCCCTAG
GCAGACCAAAATGCATGGGGAACACACCCTCCGCAAAAGTCTCAATACTCCATGAAGTCAAACCTGCTAC
ATCTGGATGCTTTCCTATAATGCACGACAGAACAAAAATCAGACAACTACCTAATCTTCTCAGAGGATAT
GAAAACATCAGGTTATCAACCAGTAATGTTATCAATACAGAGACGGCACCAGGAGGACCCTACAAGGTGG
GGACCTCAGGATCTTGCCCTAACGTTGCTAATGGGAACGGCTTCTTCAACACAATGGCTTGGGTTATCCC
AAAAGACAACAACAAGACAGCAATAAATCCAGTAACAGTAGAAGTACCATACATTTGTTCAGAAGGGGAA
GACCAAATTACTGTTTGGGGGTTCCACTCTGATGACAAAACCCAAATGGAAAGACTCTATGGAGACTCAA
ATCCTCAAAAGTTCACCTCATCTGCCAATGGAGTAACCACACATTATGTTTCTCAGATTGGTGGCTTCCC
AAATCAAACAGAAGACGAAGGGCTAAAACAAAGCGGCAGAATTGTTGTTGATTACATGGTACAAAAACCT
GGAAAAACAGGAACAATTGTTTATCAAAGAGGCATTTTATTGCCTCAAAAAGTGTGGTGCGCAAGTGGCA
GGAGCAAGGTAATAAAAGGGTCCTTGCCTTTAATTGGTGAAGCAGATTGCCTCCACGAAAAGTACGGTGG
ATTAAATAAAAGCAAGCCTTACTACACAGGAGAGCATGCAAAGGCCATAGGAAATTGCCCAATATGGGTG
AAAACACCCTTGAAGCTGGCCAATGGAACCAAATATAGACCGCCTGCAAAACTATTAAAGGAAAGAGGTT
TCTTCGGAGCTATTGCTGGTTTCTTGGAAGGAGGATGGGAAGGAATGATTGCAGGTTGGCACGGATACAC
ATCTCATGGAGCACATGGAGTGGCAGTGGCAGCAGACCTTAAGAGTACACAAGAAGCTATAAACAAGATA
ACAAAAAATCTCAACTATTTAAGTGAGCTAGAAGTAAAAAACCTTCAAAGACTAAGCGGAGCAATGAATG
AGCTTCACGACGAAATACTCGAGCTAGACGAAAAAGTGGATGATCTAAGAGCTGATACAATAAGCTCACA
AATAGAGCTTGCAGTCTTGCTTTCCAACGAAGGGATAATAAACAGTGAAGATGAGCATCTCTTGGCACTT
GAAAGAAAACTGAAGAAAATGCTTGGCCCCTCTGCTGTAGAAATAGGGAATGGGTGCTTTGAAACCAAAC
ACAAATGCAACCAGACTTGCCTAGACAGGATAGCTGCTGGCACCTTTAATGCAGGAGATTTTTCTCTTCC
CACTTTTGATTCATTAAACATTACTGCTGCATCTTTAAATGATGATGGCTTGGATAATCATACTATACTG
CTCTACTACTCAACTGCTGCTTCTAGCTTGGCTGTAACATTAATGATAGCTATCTTCATTGTCTACATGG
TCTCCAGAGACAATGTTTCTTGTTCCATCTGTCTGTGAGGGAGATTAAGCCCTGTGTTTTCCTTTACTGT
AGTGCTCATTTGCTTGTCACCATTACAAAGAAACGTTATTGAAAAATGCTCTTGTTACTACT

Fig. 10P

Influenza C (SEQ ID NO:27)

>gi|325317|gb|M17868.1|FLCHAJO Influenza C/Johannesburg/66
hemagglutinin esterase RNA (seg 4), complete cds
AGCAGAAGCAGGGGGTTAATAATGTTTTTCTCATTACTCTTGGTGTTGGGCCTCACAGAGGCTGAAAAAA
TAAAGATATGCCTTCAAAAGCAAGTGAACAGTAGCTTCAGCCTACACAATGGCTTCGGAGGAAATTTGTA
TGCCACAGAAGAAAAAAGAATGTTTGAGCTTGTTAAGCCCAAAGCTGGAGCCTCTGTCTTGAATCAAAGT
ACATGGATTGGCTTTGGAGATTCAAGGACTGACAAAAGCAATTCAGCTTTTCCTAGGTCTGCTGATGTTT
CAGCAAAAACTGCTGATAAGTTTCGTTTTTTGTCTGGTGGATCCTTAATGTTGAGTATGTTTGGCCCACC
TGGGAAGGTAGACTACCTTTACCAAGGATGTGGAAAACATAAAGTTTTTTATGAAGGAGTTAACTGGAGT
CCACATGCTGCTATAAATTGTTACAGAAAAAATTGGACTGATATCAAACTGAATTTCCAGAAAAACATTT
ATGAATTGGCTTCACAATCACATTGCATGAGCTTGGTGAATGCCTTGGACAAAACTATTCCTTTACAAGT
GACTGCTGGGACTGCAGGAAATTGCAACAACAGCTTCTTAAAAAATCCAGCATTGTACACACAAGAAGTC
AAGCCTTCAGAAAACAAATGTGGGAAAGAAAATCTTGCTTTCTTCACACTTCCAACCCAATTTGGAACCT
ATGAGTGCAAACTGCATCTTGTGGCTTCTTGCTATTTCATCTATGATAGTAAAGAAGTGTACAATAAAAG
AGGATGTGACAACTACTTTCAAGTGATCTATGATTCATTTGCAAAAGTCGTTGGAGGACTAGATAACAGG
GTATCACCTTACACAGGGAATTCTGGAGACACCCCAACAATGCAATGTGACATGCTCCAGCTGAAACCTG
GAAGATATTCAGTAAGAAGCTCTCCAAGATTCCTTTTAATGCCTGAAAGAAGTTATTGCTTTGACATGAA
AGAAAAAGGACCAGTCACTGCTGTCCAATCCATTTGGGGAAAAGGCAGAGAATCTGACTATGCAGTGGAT
CAAGCTTGCTTGAGCACTCCAGGGTGCATGTTGATCCAAAAGCAAAAGCCATACATTGGAGAAGCTGATG
ATCACCATGGAGATCAAGAAATGAGGGAGTTGCTGTCAGGACTGGACTATGAAGCTAGATGCATATCACA
ATCAGGGTGGGTGAATGAAACCAGTCCTTTTACGGAGAAATACCTCCTTCCTCCCAAATTTGGAACATGC
CCTTTGGCTGCAAAGGAAGAATCCATTCCAAAAATCCCAGATGGCCTTCTAATTCCCACCAGTGGAACCG
ATACCACTGTAACCAAACCTAAGAGCAGAATTTTTGGAATCGATGACCTCATTATTGGTGTGCTCTTTGT
TGCAATCGTTGAAACAGGAATTGGAGGCTATCTGCTTGGAAGTAGAAAAGAATCAGGAGGAGGTGTGACA
AAAGAATCAGCTGAAAAAGGGTTTGAGAAAATTGGAAATGACATACAAATTTTAAAATCTTCTATAAATA
TCGCAATAGAAAAACTAAATGACAGAATTTCTCATGATGAGCAAGCCATCAGAGATCTAACTTTAGAAAT
TGAAAATGCAAGATCTGAAGCTTTATTGGGAGAATTGGGAATAATAAGAGCCTTATTGGTAGGAAATATA
AGCATAGGATTACAGGAATCTTTATGGGAACTAGCTTCAGAAATAACAAATAGAGCAGGAGATCTAGCAG
TTGAAGTCTCCCCAGGTTGCTGGATAATTGACAATAACATTTGTGATCAAAGCTGTCAAAATTTTATTTT
CAAGTTCAACGAAACTGCACCTGTTCCAACCATTCCCCCTCTTGACACAAAAATTGATCTGCAATCAGAT
CCTTTTTACTGGGGAAGCAGCTTGGGCTTAGCAATAACTGCTACTATTTCATTGGCAGCTTTGGTGATCT
CTGGGATCGCCATCTGCAGAACTAAATGATTGAGACAATTTTGAAAAATGGATAATGTGTTGGTCAATAT
TTTGTACAGTTTTATAAAAAACAAAAATCCCCTTGCTACTGCT

Fig. 10Q

SEQ ID NO: 29

5'-AGTTC<u>CCCGGG</u>CTGGTATATTTATATGTTGTC-3'

Fig. 10 R

SEQ ID NO: 30

5'-AATA<u>GAGCTC</u>CATTTTCTCTCAAGATGATTAATTAATTAATTAGTC-3

Fig. 10S

SEQ ID NO: 31

5'-AATA<u>GAGCTC</u>GTTAAAATGCTTCTTCGTCTCCTATTTATAATATGG-3'

Fig. 10T

SEQ ID NO: 32

5'-
TTAC<u>GAATTC</u>TCCTTCCTAATTGGTGTACTATCATTTATCAAAGGGGA-3'

1- Commercial H5 (A/Vietnam/1203/2004) (750 ng)

2- Leaf protein extract from mock (37.5 μg)

3- Leaf protein extract from R660-infiltrated plant (37.5 μg)

Fig. 16

SEQ ID NO: 33

ATGAAAGCAAAACTACTGGTCCTGTTATGTACATTTACAGCTACATATGCAGA
CACAATATGTATAGGCTACCATGCCAACAACTCAACCGACACTGTTGACACAG
TACTTGAGAAGAATGTGACAGTGACACACTCTGTCAACCTACTTGAGGACAGT
CACAATGGAAAACTATGTCTACTAAAAGGAATAGCCCCACTACAATTGGGTAA
TTGCAGCGTTGCCGGATGGATCTTAGGAAACCCAGAATGCGAATTACTGATTT
CCAAGGAATCATGGTCCTACATTGTAGAAACACCAAATCCTGAGAATGGAACA
TGTTACCCAGGGTATTTCGCCGACTATGAGGAACTGAGGGAGCAATTGAGTTC
AGTATCTTCATTTGAGAGATTCGAAATATTCCCCAAAGAAAGCTCATGGCCCA
ACCACACCGTAACCGGAGTATCAGCATCATGCTCCCATAATGGGAAAAGCAGT
TTTTACAGAAATTTGCTATGGCTGACGGGGAAGAATGGTTTGTACCCAAACCT
GAGCAAGTCCTATGTAAACAACAAAGAGAAAGAAGTCCTTGTACTATGGGGTG
TTCATCACCCGCCTAACATAGGGAACCAAAGGGCCCTCTATCATACAGAAAAT
GCTTATGTCTCTGTAGTGTCTTCACATTATAGCAGAAGATTCACCCCAGAAAT
AGCCAAAAGACCCAAAGTAAGAGATCAGGAAGGAAGAATCAACTACTACTGGA
CTCTGCTGGAACCTGGGGATACAATAATATTTGAGGCAAATGGAAATCTAATA
GCGCCATGGTATGCTTTTGCACTGAGTAGAGGCTTTGGATCAGGAATCATCAC
CTCAAATGCACCAATGGATGAATGTGATGCGAAGTGTCAAACACCTCAGGGAG
CTATAAACAGCAGTCTTCCTTTCCAGAATGTACACCCAGTCACAATAGGAGAG
TGTCCAAAGTATGTCAGGAGTGCAAAATTAAGGATGGTTACAGGACTAAGGAA
CATCCCATCCATTCAATCCAGAGGTTTGTTTGGAGCCATTGCCGGTTTCATTG
AAGGGGGGTGGACTGGAATGGTAGATGGGTGGTATGGTTATCATCATCAGAAT
GAGCAAGGATCTGGCTATGCTGCAGATCAAAAAAGTACACAAAATGCCATTAA
CGGGATTACAAACAAGGTGAATTCTGTAATTGAGAAAATGAACACTCAATTCA
CAGCTGTGGGCAAAGAATTCAACAAATTGGAAAGAAGGATGGAAAACTTAAAT
AAAAAAGTTGATGATGGGTTTCTAGACATTTGGACATATAATGCAGAATTGTT
GGTTCTACTGGAAAATGAAAGGACTTTGGATTTCCATGACTCCAATGTGAAGA
ATCTGTATGAGAAAGTAAAAAGCCAATTAAAGAATAATGCCAAAGAAATAGGA
AACGGGTGTTTTGAATTCTATCACAAGTGTAACAATGAATGCATGGAGAGTGT
GAAAAATGGAACTTATGACTATCCAAAATATTCCGAAGAATCAAAGTTAAACA
GGGAGAAAATTGATGGAGTGAAATTGGAATCAATGGGAGTCTATCAGATTCTG
GCGATCTACTCAACTGTCGCCAGTTCCCTGGTTCTTTTGGTCTCCCTGGGGGC
AATCAGCTTCTGGATGTGTTCCAATGGGTCTTTGCAGTGTAGAATATGCATCT
GAGACCAGAATTTCA

Fig. 17

SEQ ID NO: 34

CCAAATCCTTAACATTCTTTCAACACCAACAATGGCGAAAAACGTTGCGATT
TTCGGTTTATTGTTTTCTCTTCTTCTGTTGGTTCCTTCTCAGATCTTCGCTG
AGGAATCATCAACTGACGCTAAGGAATTTGTTCTTACATTGGATAACACTAA
TTTCCATGACACTGTTAAGAAGCACGATTTCATCGTCGTTGAATTCTACGCA
CCTTGGTGTGGACACTGTAAGAAGCTAGCCCCAGAGTATGAGAAGGCTGCTT
CTATCTTGAGCACTCACGAGCCACCAGTTGTTTTGGCTAAAGTTGATGCCAA
TGAGGAGCACAACAAAGACCTCGCATCGGAAAATGATGTTAAGGGATTCCCA
ACCATTAAGATTTTTAGGAATGGTGGAAAGAACATTCAAGAATACAAAGGTC
CCCGTGAAGCTGAAGGTATTGTTGAGTATTTGAAAAAACAAAGTGGCCCTGC
ATCCACAGAAATTAAATCTGCTGATGATGCGACCGCTTTTGTTGGTGACAAC
AAAGTTGTTATTGTCGGAGTTTTCCCTAAATTTTCTGGTGAGGAGTACGATA
ACTTCATTGCATTAGCAGAGAAGTTGCGTTCTGACTATGACTTTGCTCACAC
TTTGAATGCCAAACACCTTCCAAAGGGAGACTCATCAGTGTCTGGGCCTGTG
GTTAGGTTATTTAAGCCATTTGACGAGCTCTTTGTTGACTCAAAGGATTTCA
ATGTAGAAGCTCTAGAGAAATTCATTGAAGAATCCAGTACCCCAATTGTGAC
TGTCTTCAACAATGAGCCTAGCAATCACCCTTTTGTTGTCAAATTCTTTAAC
TCTCCCAACGCAAAGGCTATGTTGTTCATCAACTTTACTACCGAAGGTGCTG
AATCTTTCAAAACAAAATACCATGAAGTGGCTGAGCAATACAAACAACAGGG
AGTTAGCTTTCTTGTTGGAGATGTTGAGTCTAGTCAAGGTGCCTTCCAGTAT
TTTGGACTGAAGGAAGAACAAGTACCTCTAATTATTATTCAGCATAATGATG
GCAAGAAGTTTTTCAAACCCAATTTGGAACTTGATCAACTCCCAACTTGGTT
GAAGGCATACAAGGATGGCAAGGTTGAACCATTTGTCAAGTCTGAACCTATT
CCTGAAACTAACAACGAGCCTGTTAAAGTGGTGGTTGGGCAAACTCTTGAGG
ACGTTGTTTTCAAGTCTGGGAAGAATGTTTTGATAGAGTTTTATGCTCCTTG
GTGTGGTCACTGCAAGCAGTTGGCTCCAATCTTGGATGAAGTTGCTGTCTCA
TTCCAAAGCGATGCTGATGTTGTTATTGCAAAACTGGATGCAACTGCCAACG
ATATCCCAACCGACACCTTTGATGTCCAAGGCTATCCAACCTTGTACTTCAG
GTCAGCAAGTGGAAAACTATCACAATACGACGGTGGTAGGACAAAGGAAGAC
ATCATAGAATTCATTGAAAAGAACAAGGATAAAACTGGTGCTGCTCATCAAG
AAGTAGAACAACCAAAAGCTGCTGCTCAGCCAGAAGCAGAACAACCAAAAGA
TGAGCTTTGAAAAGTTCCGCTTGGAGGATATCGGCACACAGTCATCTGCGGG
CTTTACAACTCTTTTGTATCTCAGAATCAGAAGTTAGGAAATCTTAGTGCCA
ATCTATCTATTTTTGCGTTTCATTTTATCTTTTTGGTTTACTCTAATGTATT
ACTGAATAATGTGAGTTTTGGCGGAGTTTAGTACTGGAACTTTTGTTTCTGT
AAAAAAAAAAAAA

Fig. 18

SEQ ID NO: 35

AGCGAAAGCAGGTAGATATTGAAAGATGAGTCTTCTAACCGAGGTCGAAACGTAC
GTTCTCTCTATCATCCCGTCAGGCCCCCTCAAAGCCGAGATCGCACAGAGACTTG
AAGATGTCTTTGCAGGGAAGAACACCGATCTTGAGGTTCTCATGGAATGGCTAAA
GACAAGACCAATCCTGTCACCTCTGACTAAGGGGATTTTAGGATTTGTGTTCACG
CTCACCGTGCCCAGTGAGCGAGGACTGCAGCGTAGACGCTTTGTCCAAAATGCCC
TTAATGGGAACGGGGATCCAAATAACATGGACAAAGCAGTTAAACTGTATAGGAA
GCTCAAGAGGGAGATAACATTCCATGGGGCCAAAGAAATCTCACTCAGTTATTCT
GCTGGTGCACTTGCCAGTTGTATGGGCCTCATATACAACAGGATGGGGGCTGTGA
CCACTGAAGTGGCATTTGGCCTGGTATGTGCAACCTGTGAACAGATTGCTGACTC
CCAGCATCGGTCTCATAGGCAAATGGTGACAACAACCAACCCACTAATCAGACAT
GAGAACAGAATGGTTTTAGCCAGCACTACAGCTAAGGCTATGGAGCAAATGGCTG
GATCGAGTGAGCAAGCAGCAGAGGCCATGGAGGTTGCTAGTCAGGCTAGGCAAAT
GGTGCAAGCGATGAGAACCATTGGGACTCATCCTAGCTCCAGTGCTGGTCTGAAA
AATGATCTTCTTGAAAATTTGCAGGCCTATCAGAAACGAATGGGGGTGCAGATGC
AACGGTTCAAGTGATCCTCTCGCTATTGCCGCAAATATCATTGGGATCTTGCACT
TGATATTGTGGATTCTTGATCGTCTTTTTTTCAAATGCATTTACCGTCGCTTTAA
ATACGGACTGAAAGGAGGGCCTTCTACGGAAGGAGTGCCAAAGTCTATGAGGGAA
GAATATCGAAAGGAACAGCAGAGTGCTGTGGATGCTGACGATGGTCATTTTGTCA
GCATAGAGCTGGAGTAAAAAACTACCTTGTTTCTACT

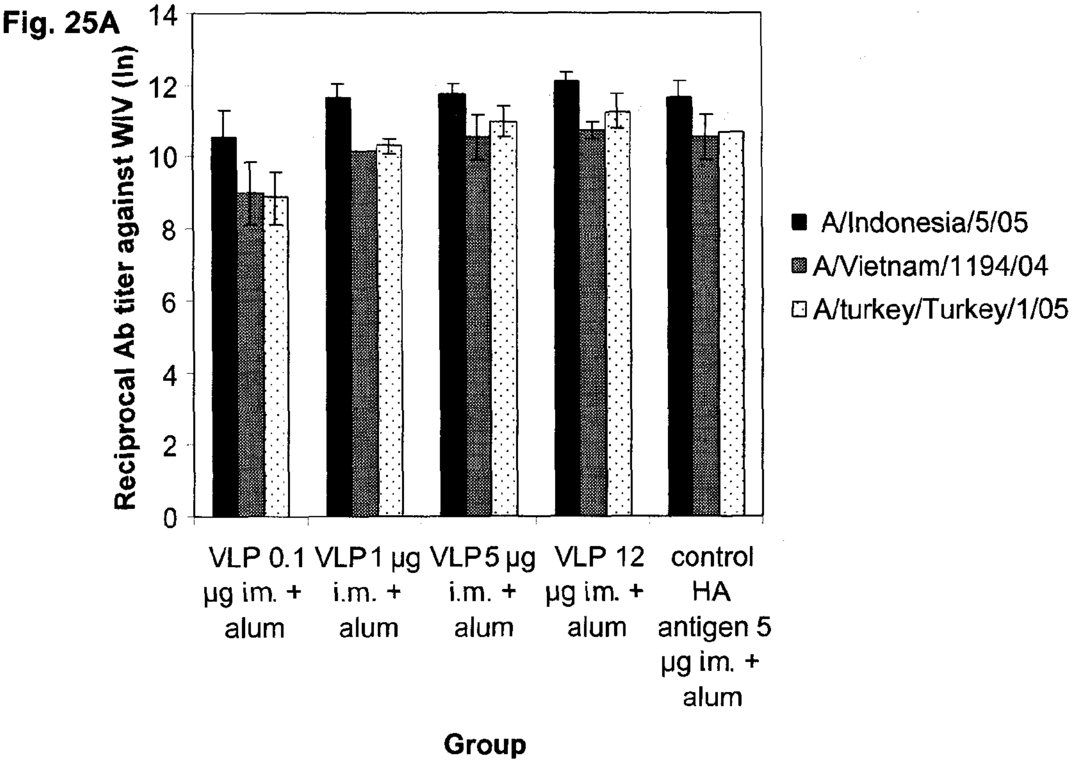

Fig. 25A

Bar chart: Reciprocal Ab titer against WIV (ln) vs Group

Groups: VLP 0.1 µg im. + alum, VLP 1 µg i.m. + alum, VLP 5 µg i.m. + alum, VLP 12 µg im. + alum, control HA antigen 5 µg im. + alum Legend:
- A/Indonesia/5/05
- A/Vietnam/1194/04
- A/turkey/Turkey/1/05

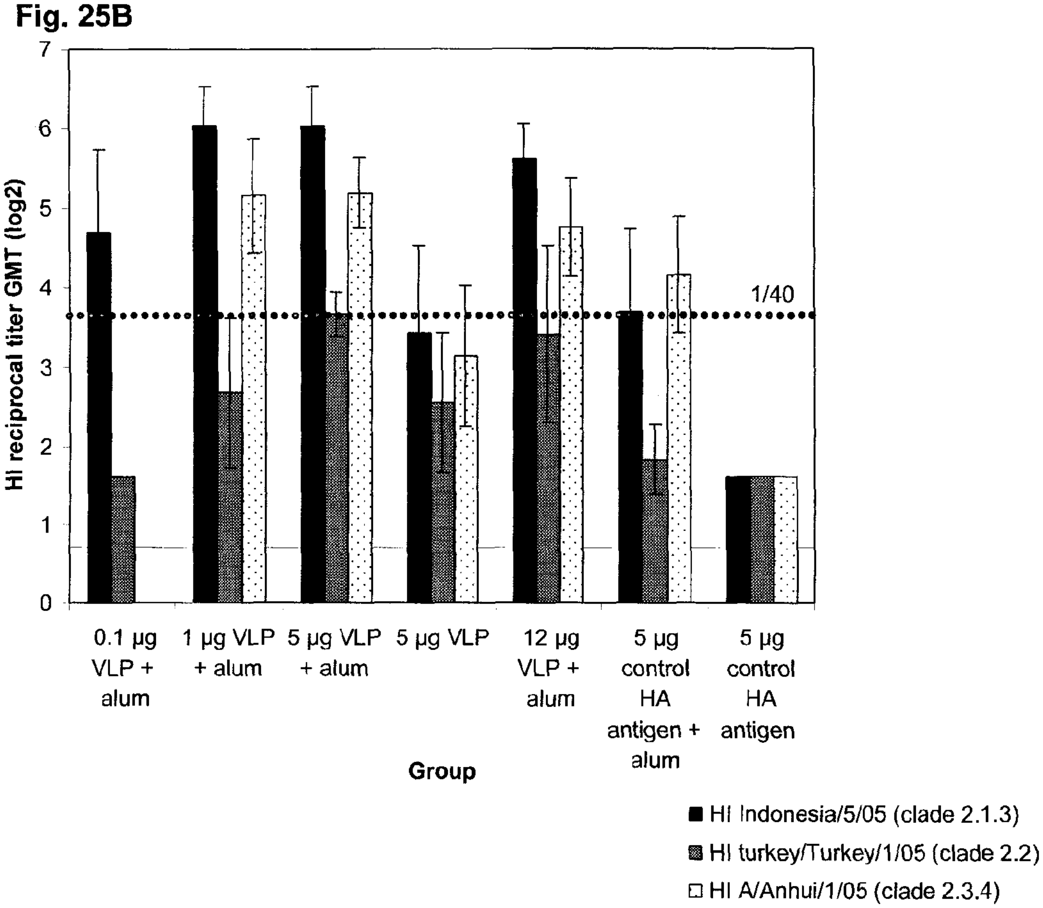

Fig. 25B

Bar chart: HI reciprocal titer GMT (log2) vs Group; dashed line at 1/40

Groups: 0.1 µg VLP + alum, 1 µg VLP + alum, 5 µg VLP + alum, 5 µg VLP, 12 µg VLP + alum, 5 µg control HA antigen + alum, 5 µg control HA antigen Legend:
- HI Indonesia/5/05 (clade 2.1.3)
- HI turkey/Turkey/1/05 (clade 2.2)
- HI A/Anhui/1/05 (clade 2.3.4)

Fig. 28

SEQ ID NO: 36

CACTTTGTGAGTCTACACTTTGATTCCCTTCAAACACATACAAAGAGAAGAGA
CTAATTAATTAATTAATCATCTTGAGAGAAAATGAAAGTAAAACTACTGGTCC
TGTTATGCACATTTACAGCTACATATGCAGACACAATATGTATAGGCTACCAT
GCTAACAACTCGACCGACACTGTTGACACAGTACTTGAAAAGAATGTGACAG
TGACACACTCTGTCAACCTGCTTGAGAACAGTCACAATGGAAAACTATGTCT
ATTAAAAGGAATAGCCCCACTACAATTGGGTAATTGCAGCGTTGCCGGGTG
GATCTTAGGAAACCCAGAATGCGAATTACTGATTTCCAAGGAGTCATGGTCC
TACATTGTAGAAAAACCAAATCCTGAGAATGGAACATGTTACCCAGGGCATT
TCGCTGACTATGAGGAACTGAGGGAGCAATTGAGTTCAGTATCTTCATTTGA
GAGGTTCGAAATATTCCCCAAAGAAAGCTCATGGCCCAACCACACCGTAACC
GGAGTGTCAGCATCATGCTCCCATAATGGGGAAAGCAGTTTTTACAGAAATT
TGCTATGGCTGACGGGGAAGAATGGTTTGTACCCAAACCTGAGCAAGTCCT
ATGCAAACAACAAAGAAAAAGAAGTCCTTGTACTATGGGGTGTTCATCACCC
GCCAAACATAGGTGACCAAAAGGCCCTCTATCATACAGAAAATGCTTATGTC
TCTGTAGTGTCTTCACATTATAGCAGAAAATTCACCCCAGAAATAGCCAAAAG
ACCCAAAGTAAGAGATCAAGAAGGAAGAATCAATTACTACTGGACTCTGCTT
GAACCCGGGGATACAATAATATTTGAGGCAAATGGAAATCTAATAGCGCCAA
GATATGCTTTCGCACTGAGTAGAGGCTTTGGATCAGGAATCATCAACTCAAA
TGCACCAATGGATAAATGTGATGCGAAGTGCCAAACACCTCAGGGAGCTATA
AACAGCAGTCTTCCTTTCCAGAACGTACACCCAGTCACAATAGGAGAGTGTC
CAAAGTATGTCAGGAGTGCAAAATTAAGGATGGTTACAGGACTAAGGAACAT
CCCATCCATTCAATCCAGAGGTTTGTTTGGAGCCATTGCCGGTTTCATTGAA
GGGGGGTGGACTGGAATGGTAGATGGTTGGTATGGTTATCATCATCAGAAT
GAGCAAGGATCTGGCTATGCTGCAGATCAAAAAAGCACACAAAATGCCATTA
ATGGGATTACAAACAAGGTCAATTCTGTAATTGAGAAAATGAACACTCAATTC
ACAGCAGTGGGCAAAGAGTTCAACAAATTGGAAAGAAGGATGGAAAACTTG
AATAAAAAAGTTGATGATGGGTTTATAGACATTTGGACATATAATGCAGAACT
GTTGGTTCTACTGGAAAATGAAAGGACTTTGGATTTCCATGACTCCAATGTG
AAGAATCTGTATGAGAAAGTAAAAAGCCAGTTAAAGAATAATGCTAAAGAAAT
AGGAAATGGGTGTTTTGAGTTCTATCACAAGTGTAACGATGAATGCATGGAG
AGTGTAAAGAATGGAACTTATGACTATCCAAAATATTCCGAAGAATCAAAGTT
AAACAGGGAGAAAATTGATGGAGTGAAATTGGAATCAATGGGAGTCTATCAG
ATTCTGGCGATCTACTCAACAGTCGCCAGTTCTCTGGTTCTTTTGGTCTCCC
TGGGGGCAATCAGCTTCTGGATGTGTTCCAATGGGTCTTTACAGTGTAGAAT
ATGCATCTAAGAGCTC

Fig. 29

SEQ ID NO: 37

CACTTTGTGAGTCTACACTTTGATTCCCTTCAAACACATACAAAGAGAAGAGACT
AATTAATTAATTAATCATCTTGAGAGAAAATGAAAGTAAAACTACTGGTCCTGTTA
TGCACATTTACAGCTACATATGCAGACACAATATGTATAGGCTACCATGCCAACA
ACTCAACCGACACTGTTGACACAGTACTTGAGAAGAATGTGACAGTGACACACT
CTGTCAACCTGCTTGAGGACAGTCACAATGGAAAATTATGTCTATTAAAAGGAAT
AGCCCCACTACAATTGGGTAATTGCAGCGTTGCCGGATGGATCTTAGGAAACCC
AGAATGCGAATTACTGATTTCCAGGGAATCATGGTCCTACATTGTAGAAAAACCA
AATCCTGAGAATGGAACATGTTACCCAGGGCATTTCGCCGACTATGAGGAACTG
AGGGAGCAATTGAGTTCAGTATCTTCATTTGAGAGATTCGAAATATTCCCCAAAG
AAAGCTCATGGCCCAACCACACCACAACCGGAGTATCAGCATCATGCTCCCATA
ATGGGGAAAGCAGTTTTTACAAAAATTTGCTATGGCTGACGGGGAAGAATGGTTT
GTACCCAAACCTGAGCAAGTCCTATGCAAACAACAAAGAGAAAGAAGTCCTTGTA
CTATGGGGTGTTCATCACCCGCCTAACATAGGTGACCAAAGGGCTCTCTATCAT
AAAGAAAATGCTTATGTCTCTGTAGTGTCTTCACATTATAGCAGAAAATTCACCCC
AGAAATAGCCAAAAGACCCAAAGTAAGAGATCAAGAAGGAAGAATCAACTACTAC
TGGACTCTACTTGAACCCGGGGATACAATAATATTTGAGGCAAATGGAAATCTAA
TAGCGCCAAGATATGCTTTCGCACTGAGTAGAGGCTTTGGATCAGGAATCATCA
ACTCAAATGCACCAATGGATGAATGTGATGCGAAGTGCCAAACACCTCAGGGAG
CTATAAACAGCAGTCTTCCTTTCCAGAATGTACACCCTGTCACAATAGGAGAGTG
TCCAAAGTATGTCAGGAGTGCAAAATTAAGGATGGTTACAGGACTAAGGAACAT
CCCATCCATTCAATCCAGAGGTTTGTTTGGAGCCATTGCCGGTTTCATTGAAGG
GGGGTGGACTGGAATGGTAGATGGTTGGTATGGTTATCATCATCAGAATGAGCA
AGGATCTGGCTATGCTGCAGATCAAAAAAGCACACAAAATGCCATTAATGGGATT
ACAAACAAGGTCAATTCTGTAATTGAGAAAATGAACACTCAATTCACAGCTGTGG
GCAAAGAGTTCAACAAATTGGAAAGAAGGATGGAAAACTTAAATAAAAAAGTTGA
TGATGGGTTTATAGACATTTGGACATATAATGCAGAATTGTTGGTTCTACTGGAA
AATGAAAGGACTTTGGATTTCCATGACTCCAATGTGAAGAATCTGTATGAGAAAG
TAAAAAGCCAATTAAAGAATAATGCCAAAGAAATAGGAAATGGGTGTTTTGAGTT
CTATCATAAGTGTAACGATGAATGCATGGAGAGTGTAAAAAATGGAACTTATGAC
TATCCAAAATATTCCGAAGAATCAAAGTTAAACAGGGAGAAAATTGATGGAGTGA
AATTGGAATCAATGGGAGTCTATCAGATTCTGGCGATCTACTCAACAGTCGCCAG
TTCTCTGGTTCTTTTGGTCTCCCTGGGGGCAATCAGCTTCTGGATGTGTTCCAAT
GGGTCTTTGCAGTGTAGAATATGCATCTGAGAGCTC

Fig. 30

SEQ ID NO: 38

CACTTTGTGAGTCTACACTTTGATTCCCTTCAAACACATACAAAGAGAAGAGA
CTAATTAATTAATTAATCATCTTGAGAGAAAATGAAGACTATCATTGCTTTGAG
CTACATTCTATGTCTGGTTTTCACTCAAAAACTTCCCGGAAATGACAACAGCA
CGGCAACGCTGTGCCTTGGGCACCATGCAGTACCAAACGGAACGATAGTGA
AAACAATCACGAATGACCAAATTGAAGTTACTAATGCTACTGAGCTGGTTCAG
AGTTCCTCAACAGGTGAAATATGCGACAGTCCTCATCAGATCCTTGATGGAG
AAAACTGCACACTAATAGATGCTCTATTGGGAGACCCTCAGTGTGATGGCTT
CCAAAATAAGAAATGGGACCTTTTTGTTGAACGCAGCAAAGCCTACAGCAACT
GTTACCCTTATGATGTGCCGGATTATGCCTCCCTTAGGTCACTAGTTGCCTCA
TCCGGCACACTGGAGTTTAACAATGAAAGTTTCAATTGGACTGGAGTCACTCA
AAACGGAACAAGCTCTGCTTGCATAAGGAGATCTAATAACAGTTTCTTTAGTA
GATTGAATTGGTTGACCCACTTAAAATTCAAATACCCAGCATTGAACGTGACT
ATGCCAAACAATGAAAAATTTGACAAATTGTACATTTGGGGGGTTCACCACCC
GGGTACGGACAATGACCAAATCTTCCTGTATGCTCAAGCATCAGGAAGAATC
ACAGTCTCTACCAAAAGAAGCCAACAAACTGTAATCCCGAATATCGGATCTAG
ACCCAGAGTAAGGAATATCCCCAGCAGAATAAGCATCTATTGGACAATAGTAA
AACCGGGAGACATACTTTTGATTAACAGCACAGGGAATCTAATTGCTCCTAG
GGGTTACTTCAAAATACGAAGTGGGAAAAGCTCAATAATGAGATCAGATGCA
CCCATTGGCAAATGCAATTCTGAATGCATCACTCCAAACGGAAGCATTCCCAA
TGACAAACCATTCCAAAATGTAAACAGGATCACATACGGGGCCTGTCCCAGA
TATGTTAAGCAAAACACTCTGAAATTGGCAACAGGGATGCGAAATGTACCAG
AGAAACAAACTAGAGGCATATTTGGCGCAATCGCGGGTTTCATAGAAAATGG
TTGGGAGGGAATGGTGGATGGTTGGTATGGTTTCAGGCATCAAAATTCTGAG
GGAATAGGACAAGCAGCAGATCTCAAAAGCACTCAAGCAGCAATCGATCAAA
TCAATGGGAAGCTGAATAGGTTGATCGGGAAAACCAACGAGAAATTCCATCA
GATTGAAAAAGAGTTCTCAGAAGTCGAAGGGAGAATCCAGGACCTTGAGAAA
TATGTTGAGGACACCAAAATAGATCTCTGGTCATACAACGCGGAGCTTCTTGT
TGCCCTGGAGAACCAACATACAATTGATCTAACTGACTCAGAAATGAACAAAC
TGTTTGAAAAAACAAAGAAGCAACTGAGGGAAAATGCTGAGGATATGGGCAA
TGGTTGTTTCAAAATATACCACAAATGTGACAATGCCTGCATAGGATCAATCA
GAAATGGAACTTATGACCACGATGTATACAGAGATGAAGCATTAAACAACCG
GTTCCAGATCAAGGGCGTTGAGCTGAAGTCAGGATACAAAGATTGGATACTA
TGGATTTCCTTTGCCATATCATGTTTTTGCTTTGTGTTGCTTTGTTGGGGTTC
ATCATGTGGGCCTGCCAAAAAGGCAACATTAGGTGCAACATTTGCATTTGAG
AGCTC

Fig. 31

SEQ ID NO: 39

CACTTTGTGAGTCTACACTTTGATTCCCTTCAAACACATACAAAGAGAAGAG
ACTAATTAATTAATTAATCATCTTGAGAGAAAATGAAGACTATCATTGCTTTG
AGCTACATTCTATGTCTGGTTTTCACTCAAAAACTTCCCGGAAATGACAACA
GCACGGCAACGCTGTGCCTTGGGCACCATGCAGTACCAAACGGAACGATA
GTGAAAACAATCACGAATGACCAAATTGAAGTTACTAATGCTACTGAGCTG
GTTCAGAGTTCCTCAACAGGTGGAATATGCGACAGTCCTCATCAGATCCTT
GATGGAGAAAACTGCACACTAATAGATGCTCTATTGGGAGACCCTCAGTGT
GATGGCTTCCAAAATAAGAAATGGGACCTTTTTGTTGAACGCAGCAAAGCC
TACAGCAACTGTTACCCTTATGATGTGCCGGATTATGCCTCCCTTAGGTCA
CTAGTTGCCTCATCCGGCACACTGGAGTTTAACGATGAAAGTTTCAATTGG
ACTGGAGTCACTCAAAATGGAACAAGCTCTGCTTGCAAAAGGAGATCTAAT
AACAGTTTCTTTAGTAGATTGAATTGGTTGACCCACTTAAAATTCAAATACC
CAGCATTGAACGTGACTATGCCAAACAATGAAAAATTTGACAAATTGTACAT
TTGGGGGGTTCACCACCCGGGTACGGACAATGACCAAATCTTCCTGCATG
CTCAAGCATCAGGAAGAATCACAGTCTCTACCAAAAGAAGCCAACAAACTG
TAATCCCGAATATCGGATCTAGACCCAGAATAAGGAATATCCCCAGCAGAA
TAAGCATCTATTGGACAATAGTAAAACCGGGAGACATACTTTTGATTAACAG
CACAGGGAATCTAATTGCTCCTAGGGGTTACTTCAAAATACGAAGTGGGAA
AAGCTCAATAATGAGATCAGATGCACCCATTGGCAAATGCAATTCTGAATG
CATCACTCCAAATGGAAGCATTCCCAATGACAAACCATTTCAAAATGTAAAC
AGGATCACATATGGGGCCTGTCCCAGATATGTTAAGCAAAACACTCTGAAA
TTGGCAACAGGGATGCGAAATGTACCAGAGAAACAAACTAGAGGCATATTT
GGCGCAATCGCGGGTTTCATAGAAAATGGTTGGGAGGGAATGGTGGATGG
TTGGTACGGTTTCAGGCATCAAAATTCTGAGGGAATAGGACAAGCAGCAGA
TCTCAAAAGCACTCAAGCAGCAATCAATCAAATCAATGGGAAGCTGAATAG
GTTGATCGGGAAAACCAACGAGAAATTCCATCAGATTGAAAAAGAGTTCTC
AGAAGTAGAAGGGAGAATCCAGGACCTCGAGAAATATGTTGAGGACACTAA
AATAGATCTCTGGTCATACAACGCGGAGCTTCTTGTTGCCCTGGAGAACCA
ACATACAATTGATCTAACTGACTCAGAAATGAACAAACTGTTTGAAAGAACA
AAGAAGCAACTGAGGGAAAATGCTGAGGATATGGGCAATGGTTGTTTCAAA
ATATACCACAAATGTGACAATGCCTGCATAGGATCAATCAGAAATGGAACTT
ATGACCATGATGTATACAGAGATGAAGCATTAAACAACCGGTTCCAGATCA
AAGGCGTTGAGCTGAAGTCAGGATACAAAGATTGGATACTATGGATTTCCT
TTGCCATATCATGTTTTTTGCTTTGTGTTGCTTTGTTGGGGTTCATCATGTG
GGCCTGCCAAAAAGGCAACATTAGGTGCAACATTTGCATTTGAGAGCTC

Fig. 32

SEQ ID NO: 40

CACTTTGTGAGTCTACACTTTGATTCCCTTCAAACACATACAAAGAGAAGA
GACTAATTAATTAATTAATCATCTTGAGAGAAAATGAAGGCAATAATTGTAC
TACTCATGGTAGTAACATCCAATGCAGATCGAATCTGCACTGGGATAACAT
CGTCAAACTCACCACATGTTGTCAAAACTGCTACTCAAGGGGAGGTCAAT
GTGACTGGTGTAATACCACTGACAACAACACCCACCAAATCTCATTTTGCA
AATCTCAAAGGAACAGAAACCAGAGGGAAACTATGCCCAAAATGCCTCAA
CTGCACAGATCTGGACGTGGCCTTGGGCAGACCAAAATGCACGGGGAAC
ATACCCTCGGCAAGAGTTTCAATACTCCATGAAGTCAGACCTGTTACATCT
GGGTGCTTTCCTATAATGCACGACAGAACAAAAATTAGACAGCTGCCTAAA
CTTCTCAGAGGATACGAACATATCAGGTTATCAACTCATAACGTTATCAAT
GCAGAAAATGCACCAGGAGGACCCTACAAAATTGGAACCTCAGGGTCTTG
CCCTAACGTTACCAATGGAAACGGATTTTTCGCAACAATGGCTTGGGCCG
TCCCAAAAAACGACAACAACAAAACAGCAACAAATTCATTAACAATAGAAG
TACCATACATTTGTACAGAAGGAGAAGACCAAATTACCGTTTGGGGGTTC
CACTCTGATAACGAAACCCAAATGGCAAAGCTCTATGGGGACTCAAAGCC
CCAGAAGTTCACCTCATCTGCCAACGGAGTGACCACACATTACGTTTCAC
AGATTGGTGGCTTCCCAAATCAAACAGAAGACGGAGGACTACCACAAAGC
GGTAGAATTGTTGTTGATTACATGGTGCAAAAATCTGGGAAAACAGGAAC
AATTACCTATCAAAGAGGTATTTTATTGCCTCAAAAAGTGTGGTGCGCAAG
TGGCAGGAGCAAGGTAATAAAAGGATCGTTGCCTTTAATTGGAGAAGCAG
ATTGCCTCCACGAAAAATACGGTGGATTAAACAAAAGCAAGCCTTACTACA
CAGGGGAACATGCAAAGGCCATAGGAAATTGCCCAATATGGGTGAAAACA
CCCTTGAAGCTGGCCAATGGAACCAAATATAGACCTCCTGCAAAACTATTA
AAGGAAAGGGGTTTCTTCGGAGCTATTGCTGGTTTCTTAGAAGGAGGATG
GGAAGGAATGATTGCAGGTTGGCACGGATACACATCCCATGGGGCACAT
GGAGTAGCGGTGGCAGCAGACCTTAAGAGCACTCAAGAGGCCATAAACA
AGATAACAAAAAATCTCAACTCTTTGAGTGAGCTGGAAGTAAAGAATCTTC
AAAGACTAAGCGGTGCCATGGATGAACTCCACAACGAAATACTAGAACTA
GACGAGAAAGTGGATGATCTCAGAGCTGATACAATAAGCTCACAAATAGA
ACTCGCAGTCCTGCTTTCCAATGAAGGAATAATAAACAGTGAAGATGAGC
ATCTCTTGGCGCTTGAAAGAAAGCTGAAGAAAATGCTGGGCCCCTCTGCT
GTAGAGATAGGGAATGGATGCTTTGAAACCAAACACAAGTGCAACCAGAC
CTGTCTCGACAGAATAGCTGCTGGTACCTTTGATGCAGGAGAATTTTCTCT
CCCCACTTTTGATTCACTGAATATTACTGCTGCATCTTTAAATGACGATGG
ATTGGATAATCATACTATACTGCTTTACTACTCAACTGCTGCCTCCAGTTT
GGCTGTAACATTGATGATAGCTATCTTTGTTGTTTATATGGTCTCCAGAGA
CAATGTTTCTTGCTCCATCTGTCTATAAGAGCTC

Fig. 33

SEQ ID NO: 41

CACTTTGTGAGTCTACACTTTGATTCCCTTCAAACACATACAAAGAGAA
GAGACTAATTAATTAATTAATCATCTTGAGAGAAAATGAAGGCAATAATT
GTACTACTCATGGTAGTAACATCCAATGCAGATCGAATCTGCACTGGAA
TAACATCTTCAAACTCACCTCATGTGGTCAAAACAGCCACTCAAGGGGA
GGTCAATGTGACTGGTGTGATACCACTAACAACAACACCAACAAAATCT
TATTTTGCAAATCTCAAAGGAACAAGGACCAGAGGGAAACTATGCCCA
GACTGTCTCAACTGCACAGATCTGGATGTGGCTTTGGGCAGACCAATG
TGTGTGGGGACCACACCTTCGGCGAAGGCTTCAATACTCCACGAAGTC
AAACCTGTTACATCCGGGTGCTTTCCTATAATGCACGACAGAACAAAAA
TCAGGCAACTACCCAATCTTCTCAGAGGATATGAAAATATCAGGCTATC
AACCCAAAACGTCATCGATGCGGAAAAGGCACCAGGAGGACCCTACA
GACTTGGAACCTCAGGATCTTGCCCTAACGCTACCAGTAAGAGCGGAT
TTTTCGCAACAATGGCTTGGGCTGTCCCAAAGGACAACAACAAAAATG
CAACGAACCCACTAACAGTAGAAGTACCATACATTTGTACAGAAGGGG
AAGACCAAATCACTGTTTGGGGGTTCCATTCAGATAACAAAACCCAAAT
GAAGAACCTCTATGGAGACTCAAATCCTCAAAAGTTCACCTCATCTGCT
AATGGAGTAACCACACACTATGTTTCTCAGATTGGCAGCTTCCCAGATC
AAACAGAAGACGGAGGACTACCACAAAGCGGCAGGATTGTTGTTGATT
ACATGATGCAAAAACCTGGGAAAACAGGAACAATTGTCTACCAAAGAG
GTGTTTTGTTGCCTCAAAAGGTGTGGTGCGCGAGTGGCAGGAGCAAA
GTAATAAAAGGGTCCTTGCCTTTAATTGGTGAAGCAGATTGCCTTCATG
AAAAATACGGTGGATTAAACAAAAGCAAGCCTTACTACACAGGAGAACA
TGCAAAAGCCATAGGAAATTGCCCAATATGGGTGAAAACACCTTTGAA
GCTCGCCAATGGAACCAAATATAGACCTCCTGCAAAACTATTAAAGGAA
AGGGGTTTCTTCGGAGCTATTGCTGGTTTCCTAGAAGGAGGATGGGAA
GGAATGATTGCAGGCTGGCACGGATACACATCTCACGGAGCACATGG
AGTGGCAGTGGCGGCGGACCTTAAGAGTACGCAAGAAGCTATAAACAA
GATAACAAAAAATCTCAATTCTTTGAGTGAGCTAGAAGTAAAGAATCTT
CAAAGACTAAGTGGTGCCATGGATGAACTCCACAACGAAATACTCGAG
CTGGATGAGAAAGTGGATGATCTCAGAGCTGACACTATAAGCTCGCAA
ATAGAACTTGCAGTCTTGCTTTCCAACGAAGGAATAATAAACAGTGAAG
ATGAGCATCTATTGGCACTTGAGAGAAAACTAAAGAAAATGCTGGGTC
CCTCTGCTGTAGAGATAGGAAATGGATGCTTCGAAACCAAACACAAGT
GCAACCAGACCTGCTTAGACAGGATAGCTGCTGGCACCTTTAATGCAG
GAGAATTTTCTCTCCCCACTTTTGATTCACTGAACATTACTGCTGCATCT
TTAAATGATGATGGATTGGATAACCATACTATACTGCTCTATTACTCAAC
TGCTGCTTCTAGTTTGGCTGTAACATTGATGCTAGCTATTTTTATTGTTT
ATATGGTCTCCAGAGACAACGTTTCATGCTCCATCTGTCTATAAGAGCT
C

Fig. 34

SEQ ID NO: 42

CACTTTGTGAGTCTACACTTTGATTCCCTTCAAACACATACAAAGAGAA
GAGACTAATTAATTAATTAATCATCTTGAGAGAAAATGGCCATCATTTA
TCTAATTCTCCTGTTCACAGCAGTGAGAGGGGACCAAATATGCATTGG
ATACCATGCCAATAATTCCACAGAGAAGGTCGACACAATTCTAGAGCG
GAACGTCACTGTGACTCATGCCAAGGACATTCTTGAGAAGACCCATAA
CGGAAAGTTATGCAAACTAAACGGAATCCCTCCACTTGAACTAGGGGA
CTGTAGCATTGCCGGATGGCTCCTTGGAAATCCAGAATGTGATAGGCT
TCTAAGTGTGCCAGAATGGTCCTATATAATGGAGAAAGAAAACCCGAG
AGACGGTTTGTGTTATCCAGGCAGCTTCAATGATTATGAAGAATTGAAA
CATCTCCTCAGCAGCGTGAAACATTTCGAGAAAGTAAAGATTCTGCCC
AAAGATAGATGGACACAGCATACAACAACTGGAGGTTCACGGGCCTG
CGCGGTGTCTGGTAATCCATCATTCTTCAGGAACATGGTCTGGCTGAC
AAAGAAAGAATCAAATTATCCGGTTGCCAAAGGATCGTACAACAATAC
AAGCGGAGAACAAATGCTAATAATTTGGGGGGTGCACCATCCCAATGA
TGAGACAGAACAAAGAACATTGTACCAGAATGTGGGAACCTATGTTTC
CGTAGGCACATCAACATTGAACAAAAGGTCAACCCCAGACATAGCAAC
AAGGCCTAAAGTGAATGGACTAGGAAGTAGAATGGAGTTCTCTTGGAC
CCTATTGGATATGTGGGACACCATAAATTTTGAGAGTACTGGTAATCTA
ATTGCACCAGAGTATGGATTCAAAATATCGAAAAGAGGTAGTTCAGGG
ATCATGAAAACAGAAGGAACACTTGAGAACTGTGAGACCAAATGCCAA
ACTCCTTTGGGAGCAATAAATACAACATTGCCTTTTCACAATGTCCACC
CACTGACAATAGGTGAGTGCCCCAAATATGTAAAATCGGAGAAGTTGG
TCTTAGCAACAGGACTAAGGAATGTTCCCCAGATTGAATCAAGAGGAT
TGTTTGGGGCAATAGCTGGTTTTATAGAAGGAGGATGGCAAGGAATG
GTTGATGGTTGGTATGGATACCATCACAGCAATGACCAGGGATCAGG
GTATGCAGCAGACAAAGAATCCACTCAAAAGGCATTTGATGGAATCAC
CAACAAGGTAAATTCTGTGATTGAAAAGATGAACACCCAATTTGAAGCT
GTTGGGAAAGAGTTCAGTAACTTAGAGAGAAGACTGGAGAACTTGAAC
AAAAAGATGGAAGACGGGTTTCTAGATGTGTGGACATACAATGCTGAG
CTTCTAGTTCTGATGGAAAATGAGAGGACACTTGACTTTCATGATTCTA
ATGTCAAGAATCTGTATGATAAAGTCAGAATGCAGCTGAGAGACAACG
TCAAAGAACTAGGAAATGGATGTTTTGAATTTTATCACAAATGTGATGA
TGAATGCATGAATAGTGTGAAAAACGGGACGTATGATTATCCCAAGTA
TGAAGAAGAGTCTAAACTAAATAGAAATGAAATCAAAGGGGTAAAATTG
AGCAGCATGGGGGTTTATCAAATCCTTGCCATTTATGCTACAGTAGCA
GGTTCTCTGTCACTGGCAATCATGATGGCTGGGATCTCTTTCTGGATG
TGCTCCAACGGGTCTCTGCAGTGCAGGATCTGCATATGAGAGCTC

Fig. 35

SEQ ID NO: 43

CACTTTGTGAGTCTACACTTTGATTCCCTTCAAACACATACAAAGAGAAG
AGACTAATTAATTAATTAATCATCTTGAGAGAAAATGGAGAAAATAGTGCT
TCTTCTTGCAATAGTCAGCCTTGTTAAAAGTGATCAGATTTGCATTGGTTA
CCATGCAAACAACTCGACAGAGCAGGTTGACACAATAATGGAAAAGAAC
GTTACTGTTACACATGCCCAAGACATACTGGAAAAGACACACAACGGGA
AGCTCTGCGATCTAGATGGAGTGAAGCCTCTGATTTTAAGAGATTGTAGT
GTAGCTGGATGGCTCCTCGGAAACCCAATGTGTGACGAGTTCATCAATG
TGCCGGAATGGTCTTACATAGTGGAGAAGGCCAACCCAGCCAATGACCT
CTGTTACCCAGGGAATTTCAACGACTATGAAGAACTGAAACACCTATTGA
GCAGAATAAACCATTTTGAGAAAATTCAGATCATCCCCAAAAGTTCTTGG
TCCGATCATGAAGCCTCATCAGGGGTCAGCTCAGCATGTCCATACCAGG
GAACGCCCTCCTTTTTCAGAAATGTGGTATGGCTTATCAAAAAGAACAAT
ACATACCCAACAATAAAGAGAAGCTACAATAATACCAACCAGGAAGATCT
TTTGATACTGTGGGGGATTCATCATTCTAATGATGCGGCAGAGCAGACAA
AGCTCTATCAAAACCCAACCACCTATATTTCCGTTGGGACATCAACACTA
AACCAGAGATTGGTACCAAAAATAGCTACTAGATCCAAAGTAAACGGGCA
AAGTGGAAGGATGGATTTCTTCTGGACAATTTTAAAACCGAATGATGCAA
TCAACTTCGAGAGTAATGGAAATTTCATTGCTCCAGAATATGCATACAAA
ATTGTCAAGAAAGGGGACTCAGCAATTGTTAAAAGTGAAGTGGAATATGG
TAACTGCAATACAAAGTGTCAAACTCCAATAGGGGCGATAAACTCTAGTA
TGCCATTCCACAACATACACCCTCTCACCATCGGGGAATGCCCCAAATAT
GTGAAATCAAACAAATTAGTCCTTGCGACTGGGCTCAGAAATAGTCCTCT
AAGAGAAAGAAGAAGAAAAAGAGGACTATTTGGAGCTATAGCAGGGTTT
ATAGAGGGAGGATGGCAGGGAATGGTAGATGGTTGGTATGGGTACCAC
CATAGCAATGAGCAGGGGAGTGGGTACGCTGCAGACAAAGAATCCACTC
AAAAGGCAATAGATGGAGTCACCAATAAGGTCAACTCGATCATTGACAAA
ATGAACACTCAGTTTGAGGCCGTTGGAAGGGAATTTAATAACTTAGAAAG
GAGAATAGAGAATTTAAACAAGAAAATGGAAGACGGATTCCTAGATGTCT
GGACTTATAATGCTGAACTTCTGGTTCTCATGGAAAATGAGAGAACTCTA
GACTTCCATGATTCAAATGTCAAGAACCTTTACGACAAGGTCCGACTACA
GCTTAGGGATAATGCAAAGGAGCTGGGTAACGGTTGTTTCGAGTTCTAT
CACAAATGTGATAATGAATGTATGGAAAGTGTAAGAAACGGAACGTATGA
CTACCCGCAGTATTCAGAAGAAGCAAGATTAAAAAGAGAGGAAATAAGT
GGAGTAAAATTGGAATCAATAGGAACTTACCAAATACTGTCAATTTATTCA
ACAGTTGCGAGTTCTCTAGCACTGGCAATCATGGTGGCTGGTCTATCTTT
GTGGATGTGCTCCAATGGGTCGTTACAATGCAGAATTTGCATTTAAGAGC
TC

Fig. 36

SEQ ID NO: 44

CACTTTGTGAGTCTACACTTTGATTCCCTTCAAACACATACAAAGAGAAGA
GACTAATTAATTAATTAATCATCTTGAGAGAAAATGGAGAAAATAGTGCTTC
TTTTTGCAATAGTCAGTCTTGTTAAAAGTGATCAGATTTGCATTGGTTACCA
TGCAAACAACTCGACAGAGCAGGTTGACACAATAATGGAAAAGAACGTTA
CTGTTACACATGCCCAAGACATACTGGAAAAGACACACAATGGGAAGCTC
TGCGATCTAGATGGAGTGAAGCCTCTAATTTTGAGAGATTGTAGTGTAGCT
GGATGGCTCCTCGGAAACCCAATGTGTGACGAGTTCATCAATGTGCCGGA
ATGGTCTTACATAGTGGAGAAGGCCAATCCAGTCAATGACCTCTGTTACC
CAGGGGATTTCAATGACTATGAAGAATTGAAACACCTATTGAGCAGAATAA
ACCATTTTGAGAAAATTCAGATCATCCCCAAAAGTTCTTGGTCCAGTCATG
AAGCCTCATTGGGGGTCAGCTCAGCATGTCCATACCAGGGAAAGTCCTCC
TTTTTCAGAAATGTGGTATGGCTTATCAAAAAGAACAGTACATACCCAACA
ATAAAGAGGAGCTACAATAATACCAACCAAGAAGATCTTTTGGTACTGTGG
GGGATTCACCATCCTAATGATGCGGCAGAGCAGACAAAGCTCTATCAAAA
CCCAACCACCTATATTTCCGTTGGGACATCTACACTAAACCAGAGATTGGT
ACCAAGAATAGCTACTAGATCCAAAGTAAACGGGCAAAGTGGAAGGATGG
AGTTCTTCTGGACAATTTTAAAACCGAATGATGCAATCAACTTCGAGAGTA
ATGGAAATTTCATTGCTCCAGAATATGCATACAAAATTGTCAAGAAAGGGG
ACTCAACAATTATGAAAAGTGAATTGGAATATGGTAACTGCAATACCAAGT
GTCAAACTCCAATGGGGGCGATAAACTCTAGCATGCCATTCCACAATATAC
ACCCTCTCACCATCGGGGAATGCCCCAAATATGTGAAATCAAACAGATTA
GTCCTTGCGACTGGGCTCAGAAATAGCCCTCAAAGAGAGAGAAGAAGAAA
AAAGAGAGGATTATTTGGAGCTATAGCAGGTTTTATAGAGGGAGGATGGC
AGGGAATGGTAGATGGTTGGTATGGGTACCACCATAGCAACGAGCAGGG
GAGTGGGTACGCTGCAGACAAAGAATCCACTCAAAAGGCAATAGATGGAG
TCACCAATAAGGTCAACTCGATTATTGACAAAATGAACACTCAGTTTGAGG
CCGTTGGAAGGGAATTTAACAACTTAGAAAGGAGAATAGAGAATTTAAACA
AGAAGATGGAAGACGGGTTCCTAGATGTCTGGACTTATAATGCTGAACTT
CTAGTTCTCATGGAAAACGAGAGAACTCTAGACTTTCATGACTCAAATGTC
AAGAACCTTTACGACAAGGTCCGACTACAGCTTAGGGATAATGCAAAGGA
GCTGGGTAACGGTTGTTTCGAGTTCTATCATAAATGTGATAATGAATGTAT
GGAAAGTGTAAGAAACGGAACGTATGACTACCCGCAGTATTCAGAAGAAG
CAAGACTAAAAAGAGAGGAAATAAGTGGAGTAAAATTGGAATCAATAGGA
ATTTACCAAATATTGTCAATTTATTCTACAGTGGCCAGCTCCCTAGCACTG
GCAATCATGGTAGCTGGTCTATCCTTATGGATGTGCTCCAATGGGTCGTT
ACAATGCAGAATTTGCATTTAAGAGCTC

Fig. 37

SEQ ID NO: 45

<u>CACTTTGTG</u>AGTCTACACTTTGATTCCCTTCAAACACATACAAAGAGAAGA
GACTAATTAATTAATTAATCATCTTGAGAGAAA<u>ATG</u>ATTGCAATCATTGTAA
TAGCAATACTGGCAGCAGCCGGAAAGTCAGACAAGATCTGCATTGGGTAT
CATGCCAACAATTCAACAACACAGGTAGATACGATACTTGAGAAGAATGT
GACTGTCACACACTCAATTGAATTGCTGGAAAATCAGAAGGAAGAAAGAT
TCTGCAAGATATTGAACAAGGCCCCTCTCGACTTAAGGGAATGTACCATA
GAGGGTTGGATCTTGGGGAATCCCCAATGCGACCTATTGCTTGGTGATCA
AAGCTGGTCATACATTGTGGAAAGACCTACTGCTCAAAACGGGATCTGCT
ACCCAGGAACCTTAAATGAGGTAGAAGAACTGAGGGCACTTATTGGATCA
GGAGAAAGGGTAGAGAGATTTGAGATGTTTCCCCAAAGCACCTGGCAAG
GAGTTGACACCAACAGTGGAACAACAAGATCCTGCCCTTATTCTACTGGT
GCGTCTTTCTACAGAAACCTCCTATGGATAATAAAAACCAAGACAGCAGA
ATATCCAGTAATTAAGGGAATTTACAACAACACTGGAACCCAGCCAATCCT
CTATTTCTGGGGTGTGCATCATCCTCCTAACACCGACGAGCAAGATACTC
TGTATGGCTCTGGTGATCGATACGTTAGAATGGGAACTGAAAGCATGAAT
TTTGCCAAGAGTCCGGAAATTGCGGCAAGGCCTGCTGTGAATGGACAAA
GAGGCAGAATTGATTATTATTGGTCGGTTTTAAAACCAGGGGAAACCTTG
AATGTGGAATCTAATGGAAATCTAATCGCCCCTTGGTATGCATACAAATTT
GTCAACACAAATAGTAAAGGAGCCGTCTTCAGGTCAGATTTACCAATCGA
GAACTGCGATGCCACATGCCAGACTATTGCAGGGGTTCTAAGGACCAATA
AAACATTTCAGAATGTGAGTCCCCTGTGGATAGGAGAATGTCCCAAATAC
GTGAAAAGTGAAAGTCTGAGGCTTGCAACTGGACTAAGAAATGTTCCACA
GATTGAAACTAGAGGACTCTTCGGAGCTATTGCAGGGTTTATTGAAGGAG
GATGGACTGGGATGATAGATGGGTGGTATGGCTATCACCATGAAAATTCT
CAAGGGTCAGGATATGCAGCAGACAGAGAAAGCACTCAAAAGGCTGTAA
ACAGAATTACAAATAAGGTCAATTCCATCATCAACAAAATGAACACACAAT
TTGAAGCTGTCGATCACGAATTTTCAAATCTGGAGAGGAGAATTGACAAT
CTGAACAAAAGAATGCAAGATGGATTTCTGGATGTTTGGACATACAATGC
TGAACTGTTGGTTCTTCTTGAAAACGAAAGAACACTAGACATGCATGACG
CAAATGTGAAGAACCTACATGAAAAGGTCAAATCACAACTAAGGGACAAT
GCTACGATCTTAGGGAATGGTTGCTTTGAATTTTGGCATAAGTGTGACAAT
GAATGCATAGAGTCTGTCAAAAATGGTACATATGACTATCCCAAATACCAG
ACTGAAAGCAAATTAAACAGGCTAAAAATAGAATCAGTAAAGCTAGAGAAC
CTTGGTGTGTATCAAATTCTTGCCATTTATAGTACGGTATCGAGCAGCCTA
GTGTTGGTAGGGCTGATCATGGCAATGGGTCTTTGGATGTGTTCAAATGG
TTCAATGCAGTGCAGGATATGTATATAA<u>GAGCTC</u>

Fig. 38

SEQ ID NO: 46

CACTTTGTGAGTCTACACTTTGATTCCCTTCAAACACATACAAAGAGAAGA
GACTAATTAATTAATTAATCATCTTGAGAGAAAATGAACACTCAAATTCTAA
TATTAGCCACTTCGGCATTCTTCTATGTACGTGCAGATAAAATCTGCCTAG
GACATCATGCTGTGTCTAATGGAACCAAAGTAGACACCCTTACTGAAAAA
GGAATAGAAGTTGTCAATGCAACAGAAACAGTTGAACAAACAAACATCCC
TAAGATCTGCTCAAAAGGAAAACAGACTGTTGACCTTGGTCAATGTGGAT
TACTAGGGACCGTTATTGGTCCTCCCCAATGTGACCAATTTCTTGAGTTCT
CTGCTAATTTAATAGTTGAAAGAAGGGAAGGTAATGACATTTGTTATCCAG
GCAAATTTGACAATGAAGAAACATTGAGAAAAATACTCAGAAAATCCGGA
GGAATTAAAAAGGAGAATATGGGATTCACATATACCGGAGTGAGAACCAA
TGGAGAGACTAGCGCATGTAGAAGGTCAAGATCTTCCTTTTATGCAGAGA
TGAAATGGCTTCTATCCAGCACAGACAATGGGACATTTCCACAAATGACA
AAGTCCTACAAGAACACTAAGAAGGTACCAGCTCTGATAATCTGGGGAAT
CCACCACTCAGGATCAACTACTGAACAGACTAGATTATATGGAAGTGGGA
ATAAATTGATAACAGTTTGGAGTTCCAAATACCAACAATCTTTTGTCCCAA
ATCCTGGACCAAGACCGCAAATGAATGGTCAATCAGGAAGAATTGACTTT
CACTGGCTGATGCTAGATCCCAATGATACTGTCACTTTCAGTTTTAATGGG
GCCTTTATAGCACCTGACCGCGCCAGTTTTCTAAGAGGTAAATCTCTAGG
AATCCAAAGTGATGCACAACTTGACAATAATTGTGAAGGTGAATGCTATCA
TATTGGAGGTACTATAATTAGCAACTTGCCCTTTCAAAACATTAATAGTAG
GGCAATCGGAAAATGCCCCAGATACGTGAAGCAGAAGAGCTTAATGCTA
GCAACAGGAATGAAAAATGTTCCTGAAGCTCCTGCACATAAACAACTAAC
TCATCACATGCGCAAAAAAAGAGGTTTATTTGGTGCAATAGCAGGATTCAT
TGAAAATGGGTGGGAAGGATTAATAGACGGATGGTATGGATATAAGCATC
AGAATGCACAAGGAGAAGGGACTGCTGCAGACTACAAAAGTACACAATCT
GCTATCAACCAAATAACCGGAAAATTGAACAGACTAATAGAAAAAACCAAC
CAGCAATTCGAACTAATAGATAATGAGTTCAATGAAATAGAAAAACAAATT
GGCAATGTTATTAACTGGACTAGAGATTCTATCATCGAAGTATGGTCATAT
AATGCAGAGTTCCTCGTAGCAGTGGAGAATCAACACACTATTGATTTAACT
GACTCAGAAATGAACAAACTATATGAAAAGGTAAGAAGACAACTGAGAGA
AAATGCTGAGGAAGATGGTAATGGCTGTTTTGAAATATTCCACCAATGTG
ACAATGATTGCATGGCCAGCATTAGAAACAACACATATGACCATAAAAAT
ACAGAAAAGAGGCAATACAAAACAGAATCCAGATTGACGCAGTAAAGTTG
AGCAGTGGTTACAAAGATATAATACTTTGGTTTAGCTTCGGGGCATCATG
TTTCTTATTTCTTGCCATTGCAATGGGTCTTGTTTTCATATGTATAAAAAT
GGAAACATGCGGTGCACTATTTGTATATAAGAGCTC

Fig. 39

SEQ ID NO: 47

CACTTTGTGAGTCTACACTTTGATTCCCTTCAAACACATACAAAGAGAAGA
GACTAATTAATTAATTAATCATCTTGAGAGAAAATGGAAACAATATCACTAA
TAACTATACTACTAGTAGTAACAGCAAGCAATGCAGATAAAATCTGCATCG
GCCACCAGTCAACAAACTCCACAGAAACTGTGGACACGCTAACAGAAACC
AATGTTCCTGTGACACATGCCAAAGAATTGCTCCACACAGAGCATAATGGA
ATGCTGTGTGCAACAAGCCTGGGACATCCCCTCATTCTAGACACATGCAC
TATTGAAGGACTAGTCTATGGCAACCCTTCTTGTGACCTGCTGTTGGGAG
GAAGAGAATGGTCCTACATCGTCGAAAGATCATCAGCTGTAAATGGAACG
TGTTACCCTGGGAATGTAGAAAACCTAGAGGAACTCAGGACACTTTTTAGT
TCCGCTAGTTCCTACCAAAGAATCCAAATCTTCCCAGACACAACCTGGAAT
GTGACTTACACTGGAACAAGCAGAGCATGTTCAGGTTCATTCTACAGGAG
TATGAGATGGCTGACTCAAAAGAGCGGTTTTTACCCTGTTCAAGACGCCC
AATACACAAATAACAGGGGAAAGAGCATTCTTTTCGTGTGGGGCATACAT
CACCCACCCACCTATACCGAGCAAACAAATTTGTACATAAGAAACGACACA
ACAACAAGCGTGACAACAGAAGATTTGAATAGGACCTTCAAACCAGTGATA
GGGCCAAGGCCCCTTGTCAATGGTCTGCAGGGAAGAATTGATTATTATTG
GTCGGTACTAAAACCAGGCCAAACATTGCGAGTACGATCCAATGGGAATC
TAATTGCTCCATGGTATGGACACGTTCTTTCAGGAGGGAGCCATGGAAGA
ATCCTGAAGACTGATTTAAAAGGTGGTAATTGTGTAGTGCAATGTCAGACT
GAAAAAGGTGGCTTAAACAGTACATTGCCATTCCACAATATCAGTAAATAT
GCATTTGGAACCTGCCCCAAATATGTAAGAGTTAATAGTCTCAAACTGGCA
GTCGGTCTGAGGAACGTGCCTGCTAGATCAAGTAGAGGACTATTTGGAGC
CATAGCTGGATTCATAGAAGGAGGTTGGCCAGGACTAGTCGCTGGCTGG
TATGGTTTCCAGCATTCAAATGATCAAGGGGTTGGTATGGCTGCAGATAG
GGATTCAACTCAAAAGGCAATTGATAAAATAACATCCAAGGTGAATAATAT
AGTCGACAAGATGAACAAGCAATATGAAATAATTGATCATGAATTTAGTGA
GGTTGAAACTAGACTCAATATGATCAATAATAAGATTGATGACCAAATACA
AGACGTATGGGCATATAATGCAGAATTGCTAGTACTACTTGAAAATCAAAA
AACACTCGATGAGCATGATGCGAACGTGAACAATCTATATAACAAGGTGA
AGAGGGCACTGGGCTCCAATGCTATGGAAGATGGGAAAGGCTGTTTCGA
GCTATACCATAAATGTGATGATCAGTGCATGGAAACAATTCGGAACGGGA
CCTATAATAGGAGAAAGTATAGAGAGGAATCAAGACTAGAAAGGCAGAAA
ATAGAGGGGGTTAAGCTGGAATCTGAGGGAACTTACAAAATCCTCACCAT
TTATTCGACTGTCGCCTCATCTCTTGTGCTTGCAATGGGGTTTGCTGCCTT
CCTGTTCTGGGCCATGTCCAATGGATCTTGCAGATGCAACATTTGTATATA
AGAGCTC

Fig. 40A

SEQ ID NO: 48

MKVKLLVLLCTFTATYADTICIGYHANNSTDTVDTVLEKNVTVTHSVNLLENSH
NGKLCLLKGIAPLQLGNCSVAGWILGNPECELLISKESWSYIVEKPNPENGTCY
PGHFADYEELREQLSSVSSFERFEIFPKESSWPNHTVTGVSASCSHNGESSF
YRNLLWLTGKNGLYPNLSKSYANNKEKEVLVLWGVHHPPNIGDQKALYHTEN
AYVSVVSSHYSRKFTPEIAKRPKVRDQEGRINYYWTLLEPGDTIIFEANGNLIAP
RYAFALSRGFGSGIINSNAPMDKCDAKCQTPQGAINSSLPFQNVHPVTIGECP
KYVRSAKLRMVTGLRNIPSIQSRGLFGAIAGFIEGGWTGMVDGWYGYHHQNE
QGSGYAADQKSTQNAINGITNKVNSVIEKMNTQFTAVGKEFNKLERRMENLNK
KVDDGFIDIWTYNAELLVLLENERTLDFHDSNVKNLYEKVKSQLKNNAKEIGNG
CFEFYHKCNDECMESVKNGTYDYPKYSEESKLNREKIDGVKLESMGVYQILAI
YSTVASSLVLLVSLGAISFWMCSNGSLQCRICI

Fig. 40B

SEQ ID NO: 49

MKVKLLVLLCTFTATYADTICIGYHANNSTDTVDTVLEKNVTVTHSVNLLEDSH
NGKLCLLKGIAPLQLGNCSVAGWILGNPECELLISRESWSYIVEKPNPENGTCY
PGHFADYEELREQLSSVSSFERFEIFPKESSWPNHTTTGVSASCSHNGESSFY
KNLLWLTGKNGLYPNLSKSYANNKEKEVLVLWGVHHPPNIGDQRALYHKENA
YVSVVSSHYSRKFTPEIAKRPKVRDQEGRINYYWTLLEPGDTIIFEANGNLIAPR
YAFALSRGFGSGIINSNAPMDECDAKCQTPQGAINSSLPFQNVHPVTIGECPK
YVRSAKLRMVTGLRNIPSIQSRGLFGAIAGFIEGGWTGMVDGWYGYHHQNEQ
GSGYAADQKSTQNAINGITNKVNSVIEKMNTQFTAVGKEFNKLERRMENLNKK
VDDGFIDIWTYNAELLVLLENERTLDFHDSNVKNLYEKVKSQLKNNAKEIGNGC
FEFYHKCNDECMESVKNGTYDYPKYSEESKLNREKIDGVKLESMGVYQILAIY
STVASSLVLLVSLGAISFWMCSNGSLQCRICI

Fig. 41A

SEQ ID NO: 50

MKTIIALSYILCLVFTQKLPGNDNSTATLCLGHHAVPNGTIVKTITNDQIEVTN
ATELVQSSSTGEICDSPHQILDGENCTLIDALLGDPQCDGFQNKKWDLFVE
RSKAYSNCYPYDVPDYASLRSLVASSGTLEFNNESFNWTGVTQNGTSSA
CIRRSNNSFFSRLNWLTHLKFKYPALNVTMPNNEKFDKLYIWGVHHPGTD
NDQIFLYAQASGRITVSTKRSQQTVIPNIGSRPRVRNIPSRISIYWTIVKPGDI
LLINSTGNLIAPRGYFKIRSGKSSIMRSDAPIGKCNSECITPNGSIPNDKPFQ
NVNRITYGACPRYVKQNTLKLATGMRNVPEKQTRGIFGAIAGFIENGWEG
MVDGWYGFRHQNSEGIGQAADLKSTQAAIDQINGKLNRLIGKTNEKFHQIE
KEFSEVEGRIQDLEKYVEDTKIDLWSYNAELLVALENQHTIDLTDSEMNKLF
EKTKKQLRENAEDMGNGCFKIYHKCDNACIGSIRNGTYDHDVYRDEALNN
RFQIKGVELKSGYKDWILWISFAISCFLLCVALLGFIMWACQKGNIRCNICI

Fig. 41B

SEQ ID NO: 51

MKTIIALSYILCLVFTQKLPGNDNSTATLCLGHHAVPNGTIVKTITNDQIEVTN
ATELVQSSSTGGICDSPHQILDGENCTLIDALLGDPQCDGFQNKKWDLFVE
RSKAYSNCYPYDVPDYASLRSLVASSGTLEFNDESFNWTGVTQNGTSSA
CKRRSNNSFFSRLNWLTHLKFKYPALNVTMPNNEKFDKLYIWGVHHPGTD
NDQIFLHAQASGRITVSTKRSQQTVIPNIGSRPRIRNIPSRISIYWTIVKPGDI
LLINSTGNLIAPRGYFKIRSGKSSIMRSDAPIGKCNSECITPNGSIPNDKPFQ
NVNRITYGACPRYVKQNTLKLATGMRNVPEKQTRGIFGAIAGFIENGWEG
MVDGWYGFRHQNSEGIGQAADLKSTQAAINQINGKLNRLIGKTNEKFHQIE
KEFSEVEGRIQDLEKYVEDTKIDLWSYNAELLVALENQHTIDLTDSEMNKLF
ERTKKQLRENAEDMGNGCFKIYHKCDNACIGSIRNGTYDHDVYRDEALNN
RFQIKGVELKSGYKDWILWISFAISCFLLCVALLGFIMWACQKGNIRCNICI

Fig. 42A

SEQ ID NO: 52

MKAIIVLLMVVTSNADRICTGITSSNSPHVVKTATQGEVNVTGVIPLTTTPTKS
HFANLKGTETRGKLCPKCLNCTDLDVALGRPKCTGNIPSARVSILHEVRPVT
SGCFPIMHDRTKIRQLPKLLRGYEHIRLSTHNVINAENAPGGPYKIGTSGSCP
NVTNGNGFFATMAWAVPKNDNNKTATNSLTIEVPYICTEGEDQITVWGFHS
DNETQMAKLYGDSKPQKFTSSANGVTTHYVSQIGGFPNQTEDGGLPQSGRI
VVDYMVQKSGKTGTITYQRGILLPQKVWCASGRSKVIKGSLPLIGEADCLHE
KYGGLNKSKPYYTGEHAKAIGNCPIWVKTPLKLANGTKYRPPAKLLKERGFF
GAIAGFLEGGWEGMIAGWHGYTSHGAHGVAVAADLKSTQEAINKITKNLNS
LSELEVKNLQRLSGAMDELHNEILELDEKVDDLRADTISSQIELAVLLSNEGIIN
SEDEHLLALERKLKKMLGPSAVEIGNGCFETKHKCNQTCLDRIAAGTFDAGE
FSLPTFDSLNITAASLNDDGLDNHTILLYYSTAASSLAVTLMIAIFVVYMVSRD
NVSCSICL

Fig. 42B

SEQ ID NO: 53

MKAIIVLLMVVTSNADRICTGITSSNSPHVVKTATQGEVNVTGVIPLTTTPTKS
YFANLKGTRTRGKLCPDCLNCTDLDVALGRPMCVGTTPSAKASILHEVKPVT
SGCFPIMHDRTKIRQLPNLLRGYENIRLSTQNVIDAEKAPGGPYRLGTSGSC
PNATSKSGFFATMAWAVPKDNNKNATNPLTVEVPYICTEGEDQITVWGFHS
DNKTQMKNLYGDSNPQKFTSSANGVTTHYVSQIGSFPDQTEDGGLPQSGRI
VVDYMMQKPGKTGTIVYQRGVLLPQKVWCASGRSKVIKGSLPLIGEADCLH
EKYGGLNKSKPYYTGEHAKAIGNCPIWVKTPLKLANGTKYRPPAKLLKERGF
FGAIAGFLEGGWEGMIAGWHGYTSHGAHGVAVAADLKSTQEAINKITKNLN
SLSELEVKNLQRLSGAMDELHNEILELDEKVDDLRADTISSQIELAVLLSNEGII
NSEDEHLLALERKLKKMLGPSAVEIGNGCFETKHKCNQTCLDRIAAGTFNAG
EFSLPTFDSLNITAASLNDDGLDNHTILLYYSTAASSLAVTLMLAIFIVYMVSRD
NVSCSICL

Fig. 43A

SEQ ID NO: 54

MAIIYLILLFTAVRGDQICIGYHANNSTEKVDTILERNVTVTHAKDILEKTHNGKLC
KLNGIPPLELGDCSIAGWLLGNPECDRLLSVPEWSYIMEKENPRDGLCYPGSF
NDYEELKHLLSSVKHFEKVKILPKDRWTQHTTTGGSRACAVSGNPSFFRNMV
WLTKKESNYPVAKGSYNNTSGEQMLIIWGVHHPNDETEQRTLYQNVGTYVSV
GTSTLNKRSTPDIATRPKVNGLGSRMEFSWTLLDMWDTINFESTGNLIAPEYGF
KISKRGSSGIMKTEGTLENCETKCQTPLGAINTTLPFHNVHPLTIGECPKYVKSE
KLVLATGLRNVPQIESRGLFGAIAGFIEGGWQGMVDGWYGYHHSNDQGSGYA
ADKESTQKAFDGITNKVNSVIEKMNTQFEAVGKEFSNLERRLENLNKKMEDGFL
DVWTYNAELLVLMENERTLDFHDSNVKNLYDKVRMQLRDNVKELGNGCFEFY
HKCDDECMNSVKNGTYDYPKYEEESKLNRNEIKGVKLSSMGVYQILAIYATVAG
SLSLAIMMAGISFWMCSNGSLQCRICI

Fig. 43B

SEQ ID NO: 55

MEKIVLLLAIVSLVKSDQICIGYHANNSTEQVDTIMEKNVTVTHAQDILEKTHNGK
LCDLDGVKPLILRDCSVAGWLLGNPMCDEFINVPEWSYIVEKANPANDLCYPG
NFNDYEELKHLLSRINHFEKIQIIPKSSWSDHEASSGVSSACPYQGTPSFFRNVV
WLIKKNNTYPTIKRSYNNTNQEDLLILWGIHHSNDAAEQTKLYQNPTTYISVGTS
TLNQRLVPKIATRSKVNGQSGRMDFFWTILKPNDAINFESNGNFIAPEYAYKIVK
KGDSAIVKSEVEYGNCNTKCQTPIGAINSSMPFHNIHPLTIGECPKYVKSNKLVL
ATGLRNSPLRERRRKRGLFGAIAGFIEGGWQGMVDGWYGYHHSNEQGSGYA
ADKESTQKAIDGVTNKVNSIIDKMNTQFEAVGREFNNLERRIENLNKKMEDGFL
DVWTYNAELLVLMENERTLDFHDSNVKNLYDKVRLQLRDNAKELGNGCFEFYH
KCDNECMESVRNGTYDYPQYSEEARLKREEISGVKLESIGTYQILSIYSTVASSL
ALAIMVAGLSLWMCSNGSLQCRICI

Fig. 44A

SEQ ID NO: 56

MEKIVLLFAIVSLVKSDQICIGYHANNSTEQVDTIMEKNVTVTHAQDILEKTHNGKL
CDLDGVKPLILRDCSVAGWLLGNPMCDEFINVPEWSYIVEKANPVNDLCYPGDF
NDYEELKHLLSRINHFEKIQIIPKSSWSSHEASLGVSSACPYQGKSSFFRNVVWLI
KKNSTYPTIKRSYNNTNQEDLLVLWGIHHPNDAAEQTKLYQNPTTYISVGTSTLN
QRLVPRIATRSKVNGQSGRMEFFWTILKPNDAINFESNGNFIAPEYAYKIVKKGD
STIMKSELEYGNCNTKCQTPMGAINSSMPFHNIHPLTIGECPKYVKSNRLVLATG
LRNSPQRERRRKKRGLFGAIAGFIEGGWQGMVDGWYGYHHSNEQGSGYAAD
KESTQKAIDGVTNKVNSIIDKMNTQFEAVGREFNNLERRIENLNKKMEDGFLDV
WTYNAELLVLMENERTLDFHDSNVKNLYDKVRLQLRDNAKELGNGCFEFYHKC
DNECMESVRNGTYDYPQYSEEARLKREEISGVKLESIGIYQILSIYSTVASSLALAI
MVAGLSLWMCSNGSLQCRICI

Fig. 44B

SEQ ID NO: 57

MIAIIVIAILAAAGKSDKICIGYHANNSTTQVDTILEKNVTVTHSIELLENQKEERFCK
ILNKAPLDLRECTIEGWILGNPQCDLLLGDQSWSYIVERPTAQNGICYPGTLNEV
EELRALIGSGERVERFEMFPQSTWQGVDTNSGTTRSCPYSTGASFYRNLLWIIK
TKTAEYPVIKGIYNNTGTQPILYFWGVHHPPNTDEQDTLYGSGDRYVRMGTESM
NFAKSPEIAARPAVNGQRGRIDYYWSVLKPGETLNVESNGNLIAPWYAYKFVNT
NSKGAVFRSDLPIENCDATCQTIAGVLRTNKTFQNVSPLWIGECPKYVKSESLRL
ATGLRNVPQIETRGLFGAIAGFIEGGWTGMIDGWYGYHHENSQGSGYAADRES
TQKAVNRITNKVNSIINKMNTQFEAVDHEFSNLERRIDNLNKRMQDGFLDVWTY
NAELLVLLENERTLDMHDANVKNLHEKVKSQLRDNATILGNGCFEFWHKCDNEC
IESVKNGTYDYPKYQTESKLNRLKIESVKLENLGVYQILAIYSTVSSSLVLVGLIMA
MGLWMCSNGSMQCRICI

Fig. 45A

SEQ ID NO: 58

MNTQILILATSAFFYVRADKICLGHHAVSNGTKVDTLTEKGIEVVNATETVEQT
NIPKICSKGKQTVDLGQCGLLGTVIGPPQCDQFLEFSANLIVERREGNDICYPG
KFDNEETLRKILRKSGGIKKENMGFTYTGVRTNGETSACRRSRSSFYAEMKW
LLSSTDNGTFPQMTKSYKNTKKVPALIIWGIHHSGSTTEQTRLYGSGNKLITV
WSSKYQQSFVPNPGPRPQMNGQSGRIDFHWLMLDPNDTVTFSFNGAFIAPD
RASFLRGKSLGIQSDAQLDNNCEGECYHIGGTIISNLPFQNINSRAIGKCPRYV
KQKSLMLATGMKNVPEAPAHKQLTHHMRKKRGLFGAIAGFIENGWEGLIDG
WYGYKHQNAQGEGTAADYKSTQSAINQITGKLNRLIEKTNQQFELIDNEFNEI
EKQIGNVINWTRDSIIEVWSYNAEFLVAVENQHTIDLTDSEMNKLYEKVRRQL
RENAEEDGNGCFEIFHQCDNDCMASIRNNTYDHKKYRKEAIQNRIQIDAVKLS
SGYKDIILWFSFGASCFLFLAIAMGLVFICIKNGNMRCTICI

Fig. 45B

SEQ ID NO: 59

METISLITILLVVTASNADKICIGHQSTNSTETVDTLTETNVPVTHAKELLHTEHN
GMLCATSLGHPLILDTCTIEGLVYGNPSCDLLLGGREWSYIVERSSAVNGTCY
PGNVENLEELRTLFSSASSYQRIQIFPDTTWNVTYTGTSRACSGSFYRSMRW
LTQKSGFYPVQDAQYTNNRGKSILFVWGIHHPPTYTEQTNLYIRNDTTTSVTT
EDLNRTFKPVIGPRPLVNGLQGRIDYYWSVLKPGQTLRVRSNGNLIAPWYGH
VLSGGSHGRILKTDLKGGNCVVQCQTEKGGLNSTLPFHNISKYAFGTCPKYV
RVNSLKLAVGLRNVPARSSRGLFGAIAGFIEGGWPGLVAGWYGFQHSNDQG
VGMAADRDSTQKAIDKITSKVNNIVDKMNKQYEIIDHEFSEVETRLNMINNKID
DQIQDVWAYNAELLVLLENQKTLDEHDANVNNLYNKVKRALGSNAMEDGKG
CFELYHKCDDQCMETIRNGTYNRRKYREESRLERQKIEGVKLESEGTYKILTI
YSTVASSLVLAMGFAAFLFWAMSNGSCRCNICI

Fig. 51

SEQ ID NO: 60
H5 from A/Indonesia/5/2005 (Construct # 660)
AGAGGTACCCCGGGCTGGTATATTTATATGTTGTCAAATAACTCAAAAACCATAAAAGTTTAAGTT
AGCAAGTGTGTACATTTTTACTTGAACAAAAATATTCACCTACTACTGTTATAAATCATTATTAAAC
ATTAGAGTAAAGAAATATGGATGATAAGAACAAGAGTAGTGATATTTTGACAACAATTTTGTTGCA
ACATTTGAGAAAATTTTGTTGTTCTCTCTTTTCATTGGTCAAAAACAATAGAGAGAGAAAAAGGAA
GAGGGAGAATAAAAACATAATGTGAGTATGAGAGAGAAAGTTGTACAAAAGTTGTACCAAAATAG
TTGTACAAATATCATTGAGGAATTTGACAAAAGCTACACAAATAAGGGTTAATTGCTGTAAATAAA
TAAGGATGACGCATTAGAGAGATGTACCATTAGAGAATTTTTGGCAAGTCATTAAAAAGAAAGAAT
AAATTATTTTTAAAATTAAAAGTTGAGTCATTTGATTAAACATGTGATTATTTAATGAATTGATGAAA
GAGTTGGATTAAAGTTGTATTAGTAATTAGAATTTGGTGTCAAATTTAATTTGACATTTGATCTTTT
CCTATATATTGCCCCATAGAGTCAGTTAACTCATTTTTATATTTCATAGATCAAATAAGAGAAATAA
CGGTATATTAATCCCTCCAAAAAAAAAAAACGGTATATTTACTAAAAAATCTAAGCCACGTAGGAG
GATAACAGGATCCCCGTAGGAGGATAACATCCAATCCAACCAATCACAACAATCCTGATGAGATA
ACCCACTTTAAGCCCACGCATCTGTGGCACATCTACATTATCTAAATCACACATTCTTCCACACAT
CTGAGCCACACAAAAACCAATCCACATCTTTATCACCCATTCTATAAAAAATCACACTTTGTGAGT
CTACACTTTGATTCCCTTCAAACACATACAAAGAGAAGAGACTAATTAATTAATTAATCATCTTGA
GAGAAAATGGAGAAAATAGTGCTTCTTCTTGCAATAGTCAGTCTTGTTAAAAGTGATCAGATTTGC
ATTGGTTACCATGCAAACAATTCAACAGAGCAGGTTGACACAATCATGGAAAAGAACGTTACTGT
TACACATGCCCAAGACATACTGGAAAAGACACACAACGGGAAGCTCTGCGATCTAGATGGAGTG
AAGCCTCTAATTTTAAGAGATTGTAGTGTAGCTGGATGGCTCCTCGGGAACCCAATGTGTGACGA
ATTCATCAATGTACCGGAATGGTCTTACATAGTGGAGAAGGCCAATCCAACCAATGACCTCTGTT
ACCCAGGGAGTTTCAACGACTATGAAGAACTGAAACACCTATTGAGCAGAATAAACCATTTTGAG
AAAATTCAAATCATCCCCAAAAGTTCTTGGTCCGATCATGAAGCCTCATCAGGAGTTAGCTCAGC
ATGTCCATACCTGGGAAGTCCCTCCTTTTTTAGAAATGTGGTATGGCTTATCAAAAAGAACAGTA
CATACCCAACAATAAAGAAAAGCTACAATAATACCAACCAAGAGGATCTTTTGGTACTGTGGGGA
ATTCACCATCCTAATGATGCGGCAGAGCAGACAAGGCTATATCAAAACCCAACCACCTATATTTC
CATTGGGACATCAACACTAAACCAGAGATTGGTACCAAAAATAGCTACTAGATCCAAAGTAAACG
GGCAAAGTGGAAGGATGGAGTTCTTCTGGACAATTTTAAAACCTAATGATGCAATCAACTTCGAG
AGTAATGGAAATTTCATTGCTCCAGAATATGCATACAAAATTGTCAAGAAAGGGGACTCAGCAATT
ATGAAAAGTGAATTGGAATATGGTAACTGCAACACCAAGTGTCAAACTCCAATGGGGGCGATAAA
CTCTAGTATGCCATTCCACAACATACACCCTCTCACCATCGGGGAATGCCCCAAATATGTGAAAT
CAAACAGATTAGTCCTTGCAACAGGGCTCAGAAATAGCCCTCAAAGAGAGAGCAGAAGAAAAAA
GAGAGGACTATTTGGAGCTATAGCAGGTTTTATAGAGGGAGGATGGCAGGGAATGGTAGATGGT
TGGTATGGGTACCACCATAGCAATGAGCAGGGGAGTGGGTACGCTGCAGACAAAGAATCCACTC
AAAAGGCAATAGATGGAGTCACCAATAAGGTCAACTCAATCATTGACAAAATGAACACTCAGTTT
GAGGCCGTTGGAAGGGAATTTAATAACTTAGAAAGGAGAATAGAGAATTTAAACAAGAAGATGGA
AGACGGGTTTCTAGATGTCTGGACTTATAATGCCGAACTTCTGGTTCTCATGGAAAATGAGAGAA
CTCTAGACTTTCATGACTCAAATGTTAAGAACCTCTACGACAAGGTCCGACTACAGCTTAGGGAT
AATGCAAAGGAGCTGGGTAACGGTTGTTTCGAGTTCTATCACAAATGTGATAATGAATGTATGGA
AAGTATAAGAAACGGAACGTACAACTATCCGCAGTATTCAGAAGAAGCAAGATTAAAAAGAGAGG
AAATAAGTGGGGTAAAATTGGAATCAATAGGAACTTACCAAATACTGTCAATTTATTCAACAGTGG
CGAGTTCCCTAGCACTGGCAATCATGATGGCTGGTCTATCTTTATGGATGTGCTCCAATGGATCG
TTACAATGCAGAATTTGCATTTAAGAGCTCTAAGTTAAAATGCTTCTTCGTCTCCTATTTATAATAT
GGTTTGTTATTGTTAATTTTGTTCTTGTAGAAGAGCTTAATTAATCGTTGTTGTTATGAAATACTAT
TTGTATGAGATGAACTGGTGTAATGTAATTCATTTACATAAGTGGAGTCAGAATCAGAATGTTTCC
TCCATAACTAACTAGACATGAAGACCTGCCGCGTACAATTGTCTTATATTTGAACAACTAAAATTG
AACATCTTTTGCCACAACTTTATAAGTGGTTAATATAGCTCAAATATATGGTCAAGTTCAATAGATT
AATAATGGAAATATCAGTTATCGAAATTCATTAACAATCAACTTAACGTTATTAACTACTAATTTTAT
ATCATCCCCTTTGATAAATGATAGTACA

Fig. 52

SEQ ID NO: 61

H1 from A/New Caledonia/20/1999 (Construct # 540)

AGAGGTACCCCGGGCTGGTATATTTATATGTTGTCAAATAACTCAAAAACCATAAAAGTTTAAGTT
AGCAAGTGTGTACATTTTTACTTGAACAAAAATATTCACCTACTACTGTTATAAATCATTATTAAAC
ATTAGAGTAAAGAAATATGGATGATAAGAACAAGAGTAGTGATATTTTGACAACAATTTTGTTGCA
ACATTTGAGAAAATTTTGTTGTTCTCTCTTTTCATTGGTCAAAAACAATAGAGAGAGAAAAAGGAA
GAGGGAGAATAAAAACATAATGTGAGTATGAGAGAGAAAGTTGTACAAAAGTTGTACCAAAATAG
TTGTACAAATATCATTGAGGAATTTGACAAAAGCTACACAAATAAGGGTTAATTGCTGTAAATAAA
TAAGGATGACGCATTAGAGAGATGTACCATTAGAGAATTTTTGGCAAGTCATTAAAAAGAAAGAA
TAAATTATTTTTAAAATTAAAAGTTGAGTCATTTGATTAAACATGTGATTATTTAATGAATTGATGAA
AGAGTTGGATTAAAGTTGTATTAGTAATTAGAATTTGGTGTCAAATTTAATTTGACATTTGATCTTT
TCCTATATATTGCCCCATAGAGTCAGTTAACTCATTTTTATATTTCATAGATCAAATAAGAGAAATA
ACGGTATATTAATCCCTCCAAAAAAAAAAAACGGTATATTTACTAAAAAATCTAAGCCACGTAGGA
GGATAACAGGATCCCCGTAGGAGGATAACATCCAATCCAACCAATCACAACAATCCTGATGAGA
TAACCCACTTTAAGCCCACGCATCTGTGGCACATCTACATTATCTAAATCACACATTCTTCCACAC
ATCTGAGCCACACAAAAACCAATCCACATCTTTATCACCCATTCTATAAAAAATCACACTTTGTGA
GTCTACACTTTGATTCCCTTCAAACACATACAAAGAGAAGAGACTAATTAATTAATTAATCATCTT
GAGAGAAAATGGCGAAAAACGTTGCGATTTTCGGCTTATTGTTTTCTCTTCTTGTGTTGGTTCCTT
CTCAGATCTTCGCTGACACAATATGTATAGGCTACCATGCCAACAACTCAACCGACACTGTTGAC
ACAGTACTTGAGAAGAATGTGACAGTGACACACTCTGTCAACCTACTTGAGGACAGTCACAATG
GAAAACTATGTCTACTAAAAGGAATAGCCCCACTACAATTGGGTAATTGCAGCGTTGCCGGATG
GATCTTAGGAAACCCAGAATGCGAATTACTGATTTCCAAGGAATCATGGTCCTACATTGTAGAAA
CACCAAATCCTGAGAATGGAACATGTTACCCAGGGTATTTCGCCGACTATGAGGAACTGAGGGA
GCAATTGAGTTCAGTATCTTCATTTGAGAGATTCGAAATATTCCCCAAAGAAAGCTCATGGCCCA
ACCACACCGTAACCGGAGTATCAGCATCATGCTCCCATAATGGGAAAAGCAGTTTTTACAGAAAT
TTGCTATGGCTGACGGGGAAGAATGGTTTGTACCCAAACCTGAGCAAGTCCTATGTAAACAACA
AAGAGAAAGAAGTCCTTGTACTATGGGGTGTTCATCACCCGCCTAACATAGGGAACCAAAGGGC
ACTCTATCATACAGAAAATGCTTATGTCTCTGTAGTGTCTTCACATTATAGCAGAAGATTCACCCC
AGAAATAGCCAAAAGACCCAAAGTAAGAGATCAGGAAGGAAGAATCAACTACTACTGGACTCTG
CTGGAACCTGGGGATACAATAATATTTGAGGCAAATGGAAATCTAATAGCGCCATGGTATGCTTT
TGCACTGAGTAGAGGCTTTGGATCAGGAATCATCACCTCAAATGCACCAATGGATGAATGTGAT
GCGAAGTGTCAAACACCTCAGGGAGCTATAAACAGCAGTCTTCCTTTCCAGAATGTACACCCAG
TCACAATAGGAGAGTGTCCAAAGTATGTCAGGAGTGCAAAATTAAGGATGGTTACAGGACTAAG
GAACATCCCATCCATTCAATCCAGAGGTTTGTTTGGAGCCATTGCCGGTTTCATTGAAGGGGGG
TGGACTGGAATGGTAGATGGGTGGTATGGTTATCATCATCAGAATGAGCAAGGATCTGGCTATG
CTGCAGATCAAAAAAGTACACAAAATGCCATTAACGGGATTACAAACAAGGTCAATTCTGTAATT
GAGAAAATGAACACTCAATTCACAGCTGTGGGCAAAGAGTTCAACAAATTGGAAAGAAGGATGG
AAAACTTAAATAAAAAAGTTGATGATGGGTTTCTAGACATTTGGACATATAATGCAGAATTGTTGG
TTCTACTGGAAAATGAAAGGACTTTGGATTTCCATGACTCCAATGTGAAGAATCTGTATGAGAAA
GTAAAAAGCCAATTAAAGAATAATGCCAAAGAAATAGGAAACGGGTGTTTTGAGTTCTATCACAA
GTGTAACAATGAATGCATGGAGAGTGTGAAAAATGGTACCTATGACTATCCAAAATATTCCGAAG
AATCAAAGTTAAACAGGGAGAAAATTGATGGAGTGAAATTGGAATCAATGGGAGTATACCAGATT
CTGGCGATCTACTCAACTGTCGCCAGTTCCCTGGTTCTTTTGGTCTCCCTGGGGGCAATCAGCT
TCTGGATGTGTTCCAATGGGTCTTTGCAGTGTAGAATATGCATCTAAGAGCTCTAAGTTAAAATG
CTTCTTCGTCTCCTATTTATAATATGGTTTGTTATTGTTAATTTTGTTCTTGTAGAAGAGCTTAATT
AATCGTTGTTGTTATGAAATACTATTTGTATGAGATGAACTGGTGTAATGTAATTCATTTACATAAG
TGGAGTCAGAATCAGAATGTTTCCTCCATAACTAACTAGACATGAAGACCTGCCGCGTACAATTG
TCTTATATTTGAACAACTAAAATTGAACATCTTTTGCCACAACTTTATAAGTGGTTAATATAGCTCA
AATATATGGTCAAGTTCAATAGATTAATAATGGAAATATCAGTTATCGAAATTCATTAACAATCAAC
TTAACGTTATTAACTACTAATTTTATATCATCCCCTTTGATAAATGATAGTACA

Fig. 53

SEQ ID NO: 62

H1 from A/Brisbane/59/2007 (construct #774)

CTGGTATATTTATATGTTGTCAAATAACTCAAAAACCATAAAAGTTTAAGTTAGCAAGTGTGTACAT
TTTTACTTGAACAAAAATATTCACCTACTACTGTTATAAATCATTATTAAACATTAGAGTAAAGAAAT
ATGGATGATAAGAACAAGAGTAGTGATATTTTGACAACAATTTTGTTGCAACATTTGAGAAAATTTT
GTTGTTCTCTCTTTTCATTGGTCAAAAACAATAGAGAGAGAAAAAGGAAGAGGGAGAATAAAAACA
TAATGTGAGTATGAGAGAGAAAGTTGTACAAAAGTTGTACCAAAATAGTTGTACAAATATCATTGA
GGAATTTGACAAAAGCTACACAAATAAGGGTTAATTGCTGTAAATAAATAAGGATGACGCATTAGA
GAGATGTACCATTAGAGAATTTTTGGCAAGTCATTAAAAAGAAAGAATAAATTATTTTTAAAATTAA
AAGTTGAGTCATTTGATTAAACATGTGATTATTTAATGAATTGATGAAAGAGTTGGATTAAAGTTGT
ATTAGTAATTAGAATTTGGTGTCAAATTTAATTTGACATTTGATCTTTTCCTATATATTGCCCCATA
GAGTCAGTTAACTCATTTTTATATTTCATAGATCAAATAAGAGAAATAACGGTATATTAATCCCTCC
AAAAAAAAAAAACGGTATATTTACTAAAAAATCTAAGCCACGTAGGAGGATAACAGGATCCCCGTA
GGAGGATAACATCCAATCCAACCAATCACAACAATCCTGATGAGATAACCCACTTTAAGCCCACG
CATCTGTGGCACATCTACATTATCTAAATCACACATTCTTCCACACATCTGAGCCACACAAAAACC
AATCCACATCTTTATCACCCATTCTATAAAAAATCACACTTTGTGAGTCTACACTTTGATTCCCTTC
AAACACATACAAAGAGAAGAGACTAATTAATTAATTAATCATCTTGAGAGAAAATGAAAGTAAAACT
ACTGGTCCTGTTATGCACATTTACAGCTACATATGCAGACACAATATGTATAGGCTACCATGCTAA
CAACTCGACCGACACTGTTGACACAGTACTTGAAAAGAATGTGACAGTGACACACTCTGTCAACC
TGCTTGAGAACAGTCACAATGGAAAACTATGTCTATTAAAAGGAATAGCCCCACTACAATTGGGT
AATTGCAGCGTTGCCGGGTGGATCTTAGGAAACCCAGAATGCGAATTACTGATTTCCAAGGAGTC
ATGGTCCTACATTGTAGAAAAACCAAATCCTGAGAATGGAACATGTTACCCAGGGCATTTCGCTG
ACTATGAGGAACTGAGGGAGCAATTGAGTTCAGTATCTTCATTTGAGAGGTTCGAAATATTCCCC
AAAGAAAGCTCATGGCCCAACCACACCGTAACCGGAGTGTCAGCATCATGCTCCCATAATGGGG
AAAGCAGTTTTTACAGAAATTTGCTATGGCTGACGGGGAAGAATGGTTTGTACCCAAACCTGAGC
AAGTCCTATGCAAACAACAAAGAAAAAGAAGTCCTTGTACTATGGGGTGTTCATCACCCGCCAAA
CATAGGTGACCAAAAGGCCCTCTATCATACAGAAAATGCTTATGTCTCTGTAGTGTCTTCACATTA
TAGCAGAAAATTCACCCCAGAAATAGCCAAAAGACCCAAAGTAAGAGATCAAGAAGGAAGAATCA
ATTACTACTGGACTCTGCTTGAACCCGGGGATACAATAATATTTGAGGCAAATGGAAATCTAATAG
CGCCAAGATATGCTTTCGCACTGAGTAGAGGCTTTGGATCAGGAATCATCAACTCAAATGCACCA
ATGGATAAATGTGATGCGAAGTGCCAAACACCTCAGGGAGCTATAAACAGCAGTCTTCCTTTCCA
GAACGTACACCCAGTCACAATAGGAGAGTGTCCAAAGTATGTCAGGAGTGCAAAATTAAGGATG
GTTACAGGACTAAGGAACATCCCATCCATTCAATCCAGAGGTTTGTTTGGAGCCATTGCCGGTTT
CATTGAAGGGGGGTGGACTGGAATGGTAGATGGTTGGTATGGTTATCATCATCAGAATGAGCAA
GGATCTGGCTATGCTGCAGATCAAAAAAGCACACAAAATGCCATTAATGGGATTACAAACAAGGT
CAATTCTGTAATTGAGAAAATGAACACTCAATTCACAGCAGTGGGCAAAGAGTTCAACAAATTGG
AAAGAAGGATGGAAAACTTGAATAAAAAAGTTGATGATGGGTTTATAGACATTTGGACATATAATG
CAGAACTGTTGGTTCTACTGGAAAATGAAAGGACTTTGGATTTCCATGACTCCAATGTGAAGAAT
CTGTATGAGAAAGTAAAAAGCCAGTTAAAGAATAATGCTAAAGAAATAGGAAATGGGTGTTTTGAG
TTCTATCACAAGTGTAACGATGAATGCATGGAGAGTGTAAAGAATGGAACTTATGACTATCCAAAA
TATTCCGAAGAATCAAAGTTAAACAGGGAGAAAATTGATGGAGTGAAATTGGAATCAATGGGAGT
CTATCAGATTCTGGCGATCTACTCAACAGTCGCCAGTTCTCTGGTTCTTTTGGTCTCCCTGGGGG
CAATCAGCTTCTGGATGTGTTCCAATGGGTCTTTACAGTGTAGAATATGCATCTAAGAGCTCTAA
GTTAAAATGCTTCTTCGTCTCCTATTTATAATATGGTTTGTTATTGTTAATTTTGTTCTTGTAGAAGA
GCTTAATTAATCGTTGTTGTTATGAAATACTATTTGTATGAGATGAACTGGTGTAATGTAATTCATT
TACATAAGTGGAGTCAGAATCAGAATGTTTCCTCCATAACTAACTAGACATGAAGACCTGCCGCG
TACAATTGTCTTATATTTGAACAACTAAAATTGAACATCTTTTGCCACAACTTTATAAGTGGTTAAT
ATAGCTCAAATATATGGTCAAGTTCAATAGATTAATAATGGAAATATCAGTTATCGAAATTCATTAA
CAATCAACTTAACGTTATTAACTACTAATTTTATATCATCCCCTTTGATAAATGATAGTACA

Fig. 54

SEQ ID NO: 63

H1 from A/Solomon Islands/3/2006 (H1N1) (Construct # 775)

AGAGGTACCCCGGGCTGGTATATTTATATGTTGTCAAATAACTCAAAAACCATAAAAGTTTA
AGTTAGCAAGTGTGTACATTTTTACTTGAACAAAAATATTCACCTACTACTGTTATAAATCAT
TATTAAACATTAGAGTAAAGAAATATGGATGATAAGAACAAGAGTAGTGATATTTTGACAAC
AATTTTGTTGCAACATTTGAGAAAATTTTGTTGTTCTCTCTTTTCATTGGTCAAAAACAATAG
AGAGAGAAAAAGGAAGAGGGAGAATAAAAACATAATGTGAGTATGAGAGAGAAAGTTGTAC
AAAAGTTGTACCAAAATAGTTGTACAAATATCATTGAGGAATTTGACAAAAGCTACACAAATA
AGGGTTAATTGCTGTAAATAAATAAGGATGACGCATTAGAGAGATGTACCATTAGAGAATTT
TTGGCAAGTCATTAAAAAGAAAGAATAAATTATTTTTAAAATTAAAAGTTGAGTCATTTGATTA
AACATGTGATTATTTAATGAATTGATGAAAGAGTTGGATTAAAGTTGTATTAGTAATTAGAAT
TTGGTGTCAAATTTAATTTGACATTTGATCTTTTCCTATATATTGCCCCATAGAGTCAGTTAA
CTCATTTTTATATTTCATAGATCAAATAAGAGAAATAACGGTATATTAATCCCTCCAAAAAAA
AAAAACGGTATATTTACTAAAAAATCTAAGCCACGTAGGAGGATAACAGGATCCCCGTAGG
AGGATAACATCCAATCCAACCAATCACAACAATCCTGATGAGATAACCCACTTTAAGCCCAC
GCATCTGTGGCACATCTACATTATCTAAATCACACATTCTTCCACACATCTGAGCCACACAA
AAACCAATCCACATCTTTATCACCCATTCTATAAAAAATCACACTTTGTGAGTCTACACTTTG
ATTCCCTTCAAACACATACAAAGAGAAGAGACTAATTAATTAATTAATCATCTTGAGAGAAAA
TGAAAGTAAAACTACTGGTCCTGTTATGCACATTTACAGCTACATATGCAGACACAATATGT
ATAGGCTACCATGCCAACAACTCAACCGACACTGTTGACACAGTACTTGAGAAGAATGTGA
CAGTGACACACTCTGTCAACCTGCTTGAGGACAGTCACAATGGAAAATTATGTCTATTAAAA
GGAATAGCCCCACTACAATTGGGTAATTGCAGCGTTGCCGGATGGATCTTAGGAAACCCA
GAATGCGAATTACTGATTTCCAGGGAATCATGGTCCTACATTGTAGAAAAACCAAATCCTGA
GAATGGAACATGTTACCCAGGGCATTTCGCCGACTATGAGGAACTGAGGGAGCAATTGAG
TTCAGTATCTTCATTTGAGAGATTCGAAATATTCCCCAAAGAAAGCTCATGGCCCAACCACA
CCACAACCGGAGTATCAGCATCATGCTCCCATAATGGGGAAAGCAGTTTTTACAAAAATTT
GCTATGGCTGACGGGGAAGAATGGTTTGTACCCAAACCTGAGCAAGTCCTATGCAAACAA
CAAAGAGAAAGAAGTCCTTGTACTATGGGGTGTTCATCACCCGCCTAACATAGGTGACCAA
AGGGCTCTCTATCATAAAGAAAATGCTTATGTCTCTGTAGTGTCTTCACATTATAGCAGAAA
ATTCACCCCAGAAATAGCCAAAAGACCCAAAGTAAGAGATCAAGAAGGAAGAATCAACTAC
TACTGGACTCTACTTGAACCCGGGGATACAATAATATTTGAGGCAAATGGAAATCTAATAGC
GCCAAGATATGCTTTCGCACTGAGTAGAGGCTTTGGATCAGGAATCATCAACTCAAATGCA
CCAATGGATGAATGTGATGCGAAGTGCCAAACACCTCAGGGAGCTATAAACAGCAGTCTTC
CTTTCCAGAATGTACACCCTGTCACAATAGGAGAGTGTCCAAAGTATGTCAGGAGTGCAAA
ATTAAGGATGGTTACAGGACTAAGGAACATCCCATCCATTCAATCCAGAGGTTTGTTTGGA
GCCATTGCCGGTTTCATTGAAGGGGGGTGGACTGGAATGGTAGATGGTTGGTATGGTTAT
CATCATCAGAATGAGCAAGGATCTGGCTATGCTGCAGATCAAAAAAGCACACAAAATGCCA
TTAATGGGATTACAAACAAGGTCAATTCTGTAATTGAGAAAATGAACACTCAATTCACAGCT
GTGGGCAAAGAGTTCAACAAATTGGAAAGAAGGATGGAAAACTTAAATAAAAAAGTTGATG
ATGGGTTTATAGACATTTGGACATATAATGCAGAATTGTTGGTTCTACTGGAAAATGAAAGG
ACTTTGGATTTCCATGACTCCAATGTGAAGAATCTGTATGAGAAAGTAAAAAGCCAATTAAA
GAATAATGCCAAAGAAATAGGAAATGGGTGTTTTGAGTTCTATCATAAGTGTAACGATGAAT
GCATGGAGAGTGTAAAAAATGGAACTTATGACTATCCAAAATATTCCGAAGAATCAAAGTTA
AACAGGGAGAAAATTGATGGAGTGAAATTGGAATCAATGGGAGTCTATCAGATTCTGGCGA
TCTACTCAACAGTCGCCAGTTCTCTGGTTCTTTTGGTCTCCCTGGGGGCAATCAGCTTCTG
GATGTGTTCCAATGGGTCTTTGCAGTGTAGAATATGCATCTGAGAGCTCTAAGTTAAAATGC
TTCTTCGTCTCCTATTTATAATATGGTTTGTTATTGTTAATTTTGTTCTTGTAGAAGAGCTTAA
TTAATCGTTGTTGTTATGAAATACTATTTGTATGAGATGAACTGGTGTAATGTAATTCATTTA
CATAAGTGGAGTCAGAATCAGAATGTTTCCTCCATAACTAACTAGACATGAAGACCTGCCG
CGTACAATTGTCTTATATTTGAACAACTAAAATTGAACATCTTTTGCCACAACTTTATAAGTG
GTTAATATAGCTCAAATATATGGTCAAGTTCAATAGATTAATAATGGAAATATCAGTTATCGA
AATTCATTAACAATCAACTTAACGTTATTAACTACTAATTTTATATCATCCCCTTTGATAAATG
ATAGTACA

Fig. 55

SEQ ID NO: 64

H2 from A/Singapore/1/57 (H2N2) (construct # 780)

AGAGGTACCCCGGGCTGGTATATTTATATGTTGTCAAATAACTCAAAAACCATAAAAGTTTAA
GTTAGCAAGTGTGTACATTTTTACTTGAACAAAAATATTCACCTACTACTGTTATAAATCATTAT
TAAACATTAGAGTAAAGAAATATGGATGATAAGAACAAGAGTAGTGATATTTTGACAACAATTT
TGTTGCAACATTTGAGAAAATTTTGTTGTTCTCTCTTTTCATTGGTCAAAAACAATAGAGAGAG
AAAAAGGAAGAGGGAGAATAAAAACATAATGTGAGTATGAGAGAGAAAGTTGTACAAAAGTTG
TACCAAAATAGTTGTACAAATATCATTGAGGAATTTGACAAAAGCTACACAAATAAGGGTTAAT
TGCTGTAAATAAATAAGGATGACGCATTAGAGAGATGTACCATTAGAGAATTTTTGGCAAGTC
ATTAAAAAGAAAGAATAAATTATTTTTAAAATTAAAAGTTGAGTCATTTGATTAAACATGTGATT
ATTTAATGAATTGATGAAAGAGTTGGATTAAAGTTGTATTAGTAATTAGAATTTGGTGTCAAAT
TTAATTTGACATTTGATCTTTTCCTATATATTGCCCCATAGAGTCAGTTAACTCATTTTTATATT
TCATAGATCAAATAAGAGAAATAACGGTATATTAATCCCTCCAAAAAAAAAAAACGGTATATTT
ACTAAAAAATCTAAGCCACGTAGGAGGATAACAGGATCCCCGTAGGAGGATAACATCCAATC
CAACCAATCACAACAATCCTGATGAGATAACCCACTTTAAGCCCACGCATCTGTGGCACATCT
ACATTATCTAAATCACACATTCTTCCACACATCTGAGCCACACAAAAACCAATCCACATCTTTA
TCACCCATTCTATAAAAAATCACACTTTGTGAGTCTACACTTTGATTCCCTTCAAACACATACA
AAGAGAAGAGACTAATTAATTAATTAATCATCTTGAGAGAAAATGGCCATCATTTATCTAATTC
TCCTGTTCACAGCAGTGAGAGGGGACCAAATATGCATTGGATACCATGCCAATAATTCCACA
GAGAAGGTCGACACAATTCTAGAGCGGAACGTCACTGTGACTCATGCCAAGGACATTCTTGA
GAAGACCCATAACGGAAAGTTATGCAAACTAAACGGAATCCCTCCACTTGAACTAGGGGACT
GTAGCATTGCCGGATGGCTCCTTGGAAATCCAGAATGTGATAGGCTTCTAAGTGTGCCAGAA
TGGTCCTATATAATGGAGAAAGAAAACCCGAGAGACGGTTTGTGTTATCCAGGCAGCTTCAA
TGATTATGAAGAATTGAAACATCTCCTCAGCAGCGTGAAACATTTCGAGAAAGTAAAGATTCT
GCCCAAAGATAGATGGACACAGCATACAACAACTGGAGGTTCACGGGCCTGCGCGGTGTCT
GGTAATCCATCATTCTTCAGGAACATGGTCTGGCTGACAAAGAAAGAATCAAATTATCCGGTT
GCCAAAGGATCGTACAACAATACAAGCGGAGAACAAATGCTAATAATTTGGGGGGTGCACCA
TCCCAATGATGAGACAGAACAAAGAACATTGTACCAGAATGTGGGAACCTATGTTTCCGTAG
GCACATCAACATTGAACAAAAGGTCAACCCCAGACATAGCAACAAGGCCTAAAGTGAATGGA
CTAGGAAGTAGAATGGAGTTCTCTTGGACCCTATTGGATATGTGGGACACCATAAATTTTGAG
AGTACTGGTAATCTAATTGCACCAGAGTATGGATTCAAAATATCGAAAAGAGGTAGTTCAGGG
ATCATGAAAACAGAAGGAACACTTGAGAACTGTGAGACCAAATGCCAAACTCCTTTGGGAGC
AATAAATACAACATTGCCTTTTCACAATGTCCACCCACTGACAATAGGTGAGTGCCCCAAATA
TGTAAAATCGGAGAAGTTGGTCTTAGCAACAGGACTAAGGAATGTTCCCCAGATTGAATCAA
GAGGATTGTTTGGGGCAATAGCTGGTTTTATAGAAGGAGGATGGCAAGGAATGGTTGATGGT
TGGTATGGATACCATCACAGCAATGACCAGGGATCAGGGTATGCAGCAGACAAAGAATCCAC
TCAAAAGGCATTTGATGGAATCACCAACAAGGTAAATTCTGTGATTGAAAAGATGAACACCCA
ATTTGAAGCTGTTGGGAAAGAGTTCAGTAACTTAGAGAGAAGACTGGAGAACTTGAACAAAAA
GATGGAAGACGGGTTTCTAGATGTGTGGACATACAATGCTGAGCTTCTAGTTCTGATGGAAA
ATGAGAGGACACTTGACTTTCATGATTCTAATGTCAAGAATCTGTATGATAAAGTCAGAATGC
AGCTGAGAGACAACGTCAAAGAACTAGGAAATGGATGTTTTGAATTTTATCACAAATGTGATG
ATGAATGCATGAATAGTGTGAAAAACGGGACGTATGATTATCCCAAGTATGAAGAAGAGTCTA
AACTAAATAGAAATGAAATCAAAGGGGTAAAATTGAGCAGCATGGGGGTTTATCAAATCCTTG
CCATTTATGCTACAGTAGCAGGTTCTCTGTCACTGGCAATCATGATGGCTGGGATCTCTTTCT
GGATGTGCTCCAACGGGTCTCTGCAGTGCAGGATCTGCATATGAGAGCTCTAAGTTAAAATG
CTTCTTCGTCTCCTATTTATAATATGGTTTGTTATTGTTAATTTTGTTCTTGTAGAAGAGCTTAA
TTAATCGTTGTTGTTATGAAATACTATTTGTATGAGATGAACTGGTGTAATGTAATTCATTTACA
TAAGTGGAGTCAGAATCAGAATGTTTCCTCCATAACTAACTAGACATGAAGACCTGCCGCGTA
CAATTGTCTTATATTTGAACAACTAAAATTGAACATCTTTTGCCACAACTTTATAAGTGGTTAAT
ATAGCTCAAATATATGGTCAAGTTCAATAGATTAATAATGGAAATATCAGTTATCGAAATTCAT
TAACAATCAACTTAACGTTATTAACTACTAATTTTATATCATCCCCTTTGATAAATGATAGTACA

Fig. 56

SEQ ID NO: 65

H5 from A/Anhui/1/2005 (H5N1) (Construct# 781)

AGAGGTACCCCGGGCTGGTATATTTATATGTTGTCAAATAACTCAAAAACCATAAAAGTTTAAG
TTAGCAAGTGTGTACATTTTTACTTGAACAAAAATATTCACCTACTACTGTTATAAATCATTATT
AAACATTAGAGTAAAGAAATATGGATGATAAGAACAAGAGTAGTGATATTTTGACAACAATTTT
GTTGCAACATTTGAGAAAATTTTGTTGTTCTCTCTTTTCATTGGTCAAAAACAATAGAGAGAGA
AAAAGGAAGAGGGAGAATAAAAACATAATGTGAGTATGAGAGAGAAAGTTGTACAAAAGTTGT
ACCAAAATAGTTGTACAAATATCATTGAGGAATTTGACAAAAGCTACACAAATAAGGGTTAATT
GCTGTAAATAAATAAGGATGACGCATTAGAGAGATGTACCATTAGAGAATTTTTGGCAAGTCA
TTAAAAAGAAAGAATAAATTATTTTTAAAATTAAAAGTTGAGTCATTTGATTAAACATGTGATTAT
TTAATGAATTGATGAAAGAGTTGGATTAAAGTTGTATTAGTAATTAGAATTTGGTGTCAAATTTA
ATTTGACATTTGATCTTTTCCTATATATTGCCCCATAGAGTCAGTTAACTCATTTTTATATTTCAT
AGATCAAATAAGAGAAATAACGGTATATTAATCCCTCCAAAAAAAAAAAACGGTATATTTACTA
AAAAATCTAAGCCACGTAGGAGGATAACAGGATCCCCGTAGGAGGATAACATCCAATCCAAC
CAATCACAACAATCCTGATGAGATAACCCACTTTAAGCCCACGCATCTGTGGCACATCTACAT
TATCTAAATCACACATTCTTCCACACATCTGAGCCACACAAAAACCAATCCACATCTTTATCAC
CCATTCTATAAAAAATCACACTTTGTGAGTCTACACTTTGATTCCCTTCAAACACATACAAAGA
GAAGAGACTAATTAATTAATTAATCATCTTGAGAGAAAATGGAGAAAATAGTGCTTCTTCTTGC
AATAGTCAGCCTTGTTAAAAGTGATCAGATTTGCATTGGTTACCATGCAAACAACTCGACAGA
GCAGGTTGACACAATAATGGAAAAGAACGTTACTGTTACACATGCCCAAGACATACTGGAAAA
GACACACAACGGGAAGCTCTGCGATCTAGATGGAGTGAAGCCTCTGATTTTAAGAGATTGTA
GTGTAGCTGGATGGCTCCTCGGAAACCCAATGTGTGACGAGTTCATCAATGTGCCGGAATGG
TCTTACATAGTGGAGAAGGCCAACCCAGCCAATGACCTCTGTTACCCAGGGAATTTCAACGA
CTATGAAGAACTGAAACACCTATTGAGCAGAATAAACCATTTTGAGAAAATTCAGATCATCCCC
AAAAGTTCTTGGTCCGATCATGAAGCCTCATCAGGGGTCAGCTCAGCATGTCCATACCAGGG
AACGCCCTCCTTTTTCAGAAATGTGGTATGGCTTATCAAAAAGAACAATACATACCCAACAATA
AAGAGAAGCTACAATAATACCAACCAGGAAGATCTTTTGATACTGTGGGGGATTCATCATTCT
AATGATGCGGCAGAGCAGACAAAGCTCTATCAAAACCCAACCACCTATATTTCCGTTGGGACA
TCAACACTAAACCAGAGATTGGTACCAAAAATAGCTACTAGATCCAAAGTAAACGGGCAAAGT
GGAAGGATGGATTTCTTCTGGACAATTTTAAAACCGAATGATGCAATCAACTTCGAGAGTAAT
GGAAATTTCATTGCTCCAGAATATGCATACAAAATTGTCAAGAAAGGGGACTCAGCAATTGTT
AAAAGTGAAGTGGAATATGGTAACTGCAATACAAAGTGTCAAACTCCAATAGGGGCGATAAAC
TCTAGTATGCCATTCCACAACATACACCCTCTCACCATCGGGGAATGCCCCAAATATGTGAAA
TCAAACAAATTAGTCCTTGCGACTGGGCTCAGAAATAGTCCTCTAAGAGAAAGAAGAAGAAAA
AGAGGACTATTTGGAGCTATAGCAGGGTTTATAGAGGGAGGATGGCAGGGAATGGTAGATGG
TTGGTATGGGTACCACCATAGCAATGAGCAGGGGAGTGGGTACGCTGCAGACAAAGAATCCA
CTCAAAAGGCAATAGATGGAGTCACCAATAAGGTCAACTCGATCATTGACAAAATGAACACTC
AGTTTGAGGCCGTTGGAAGGGAATTTAATAACTTAGAAAGGAGAATAGAGAATTTAAACAAGA
AAATGGAAGACGGATTCCTAGATGTCTGGACTTATAATGCTGAACTTCTGGTTCTCATGGAAA
ATGAGAGAACTCTAGACTTCCATGATTCAAATGTCAAGAACCTTTACGACAAGGTCCGACTAC
AGCTTAGGGATAATGCAAAGGAGCTGGGTAACGGTTGTTTCGAGTTCTATCACAAATGTGATA
ATGAATGTATGGAAAGTGTAAGAAACGGAACGTATGACTACCCGCAGTATTCAGAAGAAGCAA
GATTAAAAAGAGAGGAAATAAGTGGAGTAAAATTGGAATCAATAGGAACTTACCAAATACTGT
CAATTTATTCAACAGTTGCGAGTTCTCTAGCACTGGCAATCATGGTGGCTGGTCTATCTTTGT
GGATGTGCTCCAATGGGTCGTTACAATGCAGAATTTGCATTTAAGAGCTCTAAGTTAAAATGC
TTCTTCGTCTCCTATTTATAATATGGTTTGTTATTGTTAATTTTGTTCTTGTAGAAGAGCTTAATT
AATCGTTGTTGTTATGAAATACTATTTGTATGAGATGAACTGGTGTAATGTAATTCATTTACATA
AGTGGAGTCAGAATCAGAATGTTTCCTCCATAACTAACTAGACATGAAGACCTGCCGCGTACA
ATTGTCTTATATTTGAACAACTAAAATTGAACATCTTTTGCCACAACTTTATAAGTGGTTAATAT
AGCTCAAATATATGGTCAAGTTCAATAGATTAATAATGGAAATATCAGTTATCGAAATTCATTAA
CAATCAACTTAACGTTATTAACTACTAATTTTATATCATCCCCTTTGATAAATGATAGTACA

Fig. 57

SEQ ID NO: 66
H5 from A/Vietnam/1194/2004 (H5N1) (Construct # 782)
AGAGGTACCCCGGGCTGGTATATTTATATGTTGTCAAATAACTCAAAAACCATAAAAGTTTAAG
TTAGCAAGTGTGTACATTTTTACTTGAACAAAAATATTCACCTACTACTGTTATAAATCATTATT
AAACATTAGAGTAAAGAAATATGGATGATAAGAACAAGAGTAGTGATATTTTGACAACAATTTT
GTTGCAACATTTGAGAAAATTTTGTTGTTCTCTCTTTTCATTGGTCAAAAACAATAGAGAGAGA
AAAAGGAAGAGGGAGAATAAAAACATAATGTGAGTATGAGAGAGAAAGTTGTACAAAAGTTGT
ACCAAAATAGTTGTACAAATATCATTGAGGAATTTGACAAAAGCTACACAAATAAGGGTTAATT
GCTGTAAATAAATAAGGATGACGCATTAGAGAGATGTACCATTAGAGAATTTTTGGCAAGTCA
TTAAAAAGAAAGAATAAATTATTTTTAAAATTAAAAGTTGAGTCATTTGATTAAACATGTGATTAT
TTAATGAATTGATGAAAGAGTTGGATTAAAGTTGTATTAGTAATTAGAATTTGGTGTCAAATTTA
ATTTGACATTTGATCTTTTCCTATATATTGCCCCATAGAGTCAGTTAACTCATTTTTATATTTCAT
AGATCAAATAAGAGAAATAACGGTATATTAATCCCTCCAAAAAAAAAAAACGGTATATTTACTA
AAAAATCTAAGCCACGTAGGAGGATAACAGGATCCCCGTAGGAGGATAACATCCAATCCAAC
CAATCACAACAATCCTGATGAGATAACCCACTTTAAGCCCACGCATCTGTGGCACATCTACAT
TATCTAAATCACACATTCTTCCACACATCTGAGCCACACAAAAACCAATCCACATCTTTATCAC
CCATTCTATAAAAAATCACACTTTGTGAGTCTACACTTTGATTCCCTTCAAACACATACAAAGA
GAAGAGACTAATTAATTAATTAATCATCTTGAGAGAAAATGGAGAAAATAGTGCTTCTTTTTGC
AATAGTCAGTCTTGTTAAAAGTGATCAGATTTGCATTGGTTACCATGCAAACAACTCGACAGA
GCAGGTTGACACAATAATGGAAAAGAACGTTACTGTTACACATGCCCAAGACATACTGGAAAA
GACACACAATGGGAAGCTCTGCGATCTAGATGGAGTGAAGCCTCTAATTTTGAGAGATTGTAG
TGTAGCTGGATGGCTCCTCGGAAACCCAATGTGTGACGAGTTCATCAATGTGCCGGAATGGT
CTTACATAGTGGAGAAGGCCAATCCAGTCAATGACCTCTGTTACCCAGGGGATTTCAATGACT
ATGAAGAATTGAAACACCTATTGAGCAGAATAAACCATTTTGAGAAAATTCAGATCATCCCCAA
AAGTTCTTGGTCCAGTCATGAAGCCTCATTGGGGGTCAGCTCAGCATGTCCATACCAGGGAA
AGTCCTCCTTTTTCAGAAATGTGGTATGGCTTATCAAAAAGAACAGTACATACCCAACAATAAA
GAGGAGCTACAATAATACCAACCAAGAAGATCTTTTGGTACTGTGGGGGATTCACCATCCTAA
TGATGCGGCAGAGCAGACAAAGCTCTATCAAAACCCAACCACCTATATTTCCGTTGGGACATC
TACACTAAACCAGAGATTGGTACCAAGAATAGCTACTAGATCCAAAGTAAACGGGCAAAGTGG
AAGGATGGAGTTCTTCTGGACAATTTTAAAACCGAATGATGCAATCAACTTCGAGAGTAATGG
AAATTTCATTGCTCCAGAATATGCATACAAAATTGTCAAGAAAGGGGACTCAACAATTATGAAA
AGTGAATTGGAATATGGTAACTGCAATACCAAGTGTCAAACTCCAATGGGGGCGATAAACTCT
AGCATGCCATTCCACAATATACACCCTCTCACCATCGGGGAATGCCCCAAATATGTGAAATCA
AACAGATTAGTCCTTGCGACTGGGCTCAGAAATAGCCCTCAAAGAGAGAGAAGAAGAAAAAA
GAGAGGATTATTTGGAGCTATAGCAGGTTTTATAGAGGGAGGATGGCAGGGAATGGTAGATG
GTTGGTATGGGTACCACCATAGCAACGAGCAGGGGAGTGGGTACGCTGCAGACAAAGAATC
CACTCAAAAGGCAATAGATGGAGTCACCAATAAGGTCAACTCGATTATTGACAAAATGAACAC
TCAGTTTGAGGCCGTTGGAAGGGAATTTAACAACTTAGAAAGGAGAATAGAGAATTTAAACAA
GAAGATGGAAGACGGGTTCCTAGATGTCTGGACTTATAATGCTGAACTTCTAGTTCTCATGGA
AAACGAGAGAACTCTAGACTTTCATGACTCAAATGTCAAGAACCTTTACGACAAGGTCCGACT
ACAGCTTAGGGATAATGCAAAGGAGCTGGGTAACGGTTGTTTCGAGTTCTATCATAAATGTGA
TAATGAATGTATGGAAAGTGTAAGAAACGGAACGTATGACTACCCGCAGTATTCAGAAGAAGC
AAGACTAAAAAGAGAGGAAATAAGTGGAGTAAAATTGGAATCAATAGGAATTTACCAAATATTG
TCAATTTATTCTACAGTGGCCAGCTCCCTAGCACTGGCAATCATGGTAGCTGGTCTATCCTTA
TGGATGTGCTCCAATGGGTCGTTACAATGCAGAATTTGCATTTAAGAGCTCTAAGTTAAAATG
CTTCTTCGTCTCCTATTTATAATATGGTTTGTTATTGTTAATTTTGTTCTTGTAGAAGAGCTTAA
TTAATCGTTGTTGTTATGAAATACTATTTGTATGAGATGAACTGGTGTAATGTAATTCATTTACA
TAAGTGGAGTCAGAATCAGAATGTTTCCTCCATAACTAACTAGACATGAAGACCTGCCGCGTA
CAATTGTCTTATATTTGAACAACTAAAATTGAACATCTTTTGCCACAACTTTATAAGTGGTTAAT
ATAGCTCAAATATATGGTCAAGTTCAATAGATTAATAATGGAAATATCAGTTATCGAAATTCATT
AACAATCAACTTAACGTTATTAACTACTAATTTTATATCATCCCCTTTGATAAATGATAGTACA

Fig. 58

SEQ ID NO: 67

H6 from A/Teal/Hong Kong/W312/97 (H6N1) (Construct # 783)

AGAGGTACCCCGGGCTGGTATATTTATATGTTGTCAAATAACTCAAAAACCATAAAAGTTTA
AGTTAGCAAGTGTGTACATTTTTACTTGAACAAAAATATTCACCTACTACTGTTATAAATCAT
TATTAAACATTAGAGTAAAGAAATATGGATGATAAGAACAAGAGTAGTGATATTTTGACAACA
ATTTTGTTGCAACATTTGAGAAAATTTTGTTGTTCTCTCTTTTCATTGGTCAAAAACAATAGA
GAGAGAAAAAGGAAGAGGGAGAATAAAAACATAATGTGAGTATGAGAGAGAAAGTTGTACA
AAAGTTGTACCAAAATAGTTGTACAAATATCATTGAGGAATTTGACAAAAGCTACACAAATAA
GGGTTAATTGCTGTAAATAAATAAGGATGACGCATTAGAGAGATGTACCATTAGAGAATTTT
TGGCAAGTCATTAAAAAGAAAGAATAAATTATTTTTAAAATTAAAAGTTGAGTCATTTGATTAA
ACATGTGATTATTTAATGAATTGATGAAAGAGTTGGATTAAAGTTGTATTAGTAATTAGAATT
TGGTGTCAAATTTAATTTGACATTTGATCTTTTCCTATATATTGCCCCATAGAGTCAGTTAAC
TCATTTTTATATTTCATAGATCAAATAAGAGAAATAACGGTATATTAATCCCTCCAAAAAAAAA
AAACGGTATATTTACTAAAAAATCTAAGCCACGTAGGAGGATAACAGGATCCCCGTAGGAG
GATAACATCCAATCCAACCAATCACAACAATCCTGATGAGATAACCCACTTTAAGCCCACGC
ATCTGTGGCACATCTACATTATCTAAATCACACATTCTTCCACACATCTGAGCCACACAAAA
ACCAATCCACATCTTTATCACCCATTCTATAAAAAATCACACTTTGTGAGTCTACACTTTGAT
TCCCTTCAAACACATACAAAGAGAAGAGACTAATTAATTAATTAATCATCTTGAGAGAAAATG
ATTGCAATCATTGTAATAGCAATACTGGCAGCAGCCGGAAAGTCAGACAAGATCTGCATTG
GGTATCATGCCAACAATTCAACAACACAGGTAGATACGATACTTGAGAAGAATGTGACTGT
CACACACTCAATTGAATTGCTGGAAAATCAGAAGGAAGAAAGATTCTGCAAGATATTGAACA
AGGCCCCTCTCGACTTAAGGGAATGTACCATAGAGGGTTGGATCTTGGGGAATCCCCAAT
GCGACCTATTGCTTGGTGATCAAAGCTGGTCATACATTGTGGAAAGACCTACTGCTCAAAA
CGGGATCTGCTACCCAGGAACCTTAAATGAGGTAGAAGAACTGAGGGCACTTATTGGATCA
GGAGAAAGGGTAGAGAGATTTGAGATGTTTCCCCAAAGCACCTGGCAAGGAGTTGACACC
AACAGTGGAACAACAAGATCCTGCCCTTATTCTACTGGTGCGTCTTTCTACAGAAACCTCCT
ATGGATAATAAAAACCAAGACAGCAGAATATCCAGTAATTAAGGGAATTTACAACAACACTG
GAACCCAGCCAATCCTCTATTTCTGGGGTGTGCATCATCCTCCTAACACCGACGAGCAAGA
TACTCTGTATGGCTCTGGTGATCGATACGTTAGAATGGGAACTGAAAGCATGAATTTTGCCA
AGAGTCCGGAAATTGCGGCAAGGCCTGCTGTGAATGGACAAAGAGGCAGAATTGATTATTA
TTGGTCGGTTTTAAAACCAGGGGAAACCTTGAATGTGGAATCTAATGGAAATCTAATCGCC
CCTTGGTATGCATACAAATTTGTCAACACAAATAGTAAAGGAGCCGTCTTCAGGTCAGATTT
ACCAATCGAGAACTGCGATGCCACATGCCAGACTATTGCAGGGGTTCTAAGGACCAATAAA
ACATTTCAGAATGTGAGTCCCCTGTGGATAGGAGAATGTCCCAAATACGTGAAAAGTGAAA
GTCTGAGGCTTGCAACTGGACTAAGAAATGTTCCACAGATTGAAACTAGAGGACTCTTCGG
AGCTATTGCAGGGTTTATTGAAGGAGGATGGACTGGGATGATAGATGGGTGGTATGGCTAT
CACCATGAAAATTCTCAAGGGTCAGGATATGCAGCAGACAGAGAAAGCACTCAAAAGGCTG
TAAACAGAATTACAAATAAGGTCAATTCCATCATCAACAAAATGAACACACAATTTGAAGCTG
TCGATCACGAATTTTCAAATCTGGAGAGGAGAATTGACAATCTGAACAAAAGAATGCAAGAT
GGATTTCTGGATGTTTGGACATACAATGCTGAACTGTTGGTTCTTCTTGAAAACGAAAGAAC
ACTAGACATGCATGACGCAAATGTGAAGAACCTACATGAAAAGGTCAAATCACAACTAAGG
GACAATGCTACGATCTTAGGGAATGGTTGCTTTGAATTTTGGCATAAGTGTGACAATGAATG
CATAGAGTCTGTCAAAAATGGTACATATGACTATCCCAAATACCAGACTGAAAGCAAATTAA
ACAGGCTAAAAATAGAATCAGTAAAGCTAGAGAACCTTGGTGTGTATCAAATTCTTGCCATT
TATAGTACGGTATCGAGCAGCCTAGTGTTGGTAGGGCTGATCATGGCAATGGGTCTTTGGA
TGTGTTCAAATGGTTCAATGCAGTGCAGGATATGTATATAAGAGCTCTAAGTTAAAATGCTT
CTTCGTCTCCTATTTATAATATGGTTTGTTATTGTTAATTTTGTTCTTGTAGAAGAGCTTAATT
AATCGTTGTTGTTATGAAATACTATTTGTATGAGATGAACTGGTGTAATGTAATTCATTTACA
TAAGTGGAGTCAGAATCAGAATGTTTCCTCCATAACTAACTAGACATGAAGACCTGCCGCG
TACAATTGTCTTATATTTGAACAACTAAAATTGAACATCTTTTGCCACAACTTTATAAGTGGTT
AATATAGCTCAAATATATGGTCAAGTTCAATAGATTAATAATGGAAATATCAGTTATCGAAAT
TCATTAACAATCAACTTAACGTTATTAACTACTAATTTTATATCATCCCCTTTGATAAATGATA
GTACA

Fig. 59

SEQ ID NO: 68

H9 from A/Hong Kong/1073/99 (H9N2) (Construct # 785)

AGAGGTACCCCGGGCTGGTATATTTATATGTTGTCAAATAACTCAAAAACCATAAAAGTTTAA
GTTAGCAAGTGTGTACATTTTTACTTGAACAAAAATATTCACCTACTACTGTTATAAATCATTA
TTAAACATTAGAGTAAAGAAATATGGATGATAAGAACAAGAGTAGTGATATTTTGACAACAAT
TTTGTTGCAACATTTGAGAAAATTTTGTTGTTCTCTCTTTTCATTGGTCAAAAACAATAGAGAG
AGAAAAAGGAAGAGGGAGAATAAAAACATAATGTGAGTATGAGAGAGAAAGTTGTACAAAAG
TTGTACCAAAATAGTTGTACAAATATCATTGAGGAATTTGACAAAAGCTACACAAATAAGGGT
TAATTGCTGTAAATAAATAAGGATGACGCATTAGAGAGATGTACCATTAGAGAATTTTTGGCA
AGTCATTAAAAAGAAAGAATAAATTATTTTTAAAATTAAAAGTTGAGTCATTTGATTAAACATG
TGATTATTTAATGAATTGATGAAAGAGTTGGATTAAAGTTGTATTAGTAATTAGAATTTGGTGT
CAAATTTAATTTGACATTTGATCTTTTCCTATATATTGCCCCATAGAGTCAGTTAACTCATTTT
TATATTTCATAGATCAAATAAGAGAAATAACGGTATATTAATCCCTCCAAAAAAAAAAAACGG
TATATTTACTAAAAAATCTAAGCCACGTAGGAGGATAACAGGATCCCCGTAGGAGGATAACA
TCCAATCCAACCAATCACAACAATCCTGATGAGATAACCCACTTTAAGCCCACGCATCTGTG
GCACATCTACATTATCTAAATCACACATTCTTCCACACATCTGAGCCACACAAAAACCAATCC
ACATCTTTATCACCCATTCTATAAAAAATCACACTTTGTGAGTCTACACTTTGATTCCCTTCAA
ACACATACAAAGAGAAGAGACTAATTAATTAATTAATCATCTTGAGAGAAAATGGAAACAATA
TCACTAATAACTATACTACTAGTAGTAACAGCAAGCAATGCAGATAAAATCTGCATCGGCCA
CCAGTCAACAAACTCCACAGAAACTGTGGACACGCTAACAGAAACCAATGTTCCTGTGACAC
ATGCCAAAGAATTGCTCCACACAGAGCATAATGGAATGCTGTGTGCAACAAGCCTGGGACA
TCCCCTCATTCTAGACACATGCACTATTGAAGGACTAGTCTATGGCAACCCTTCTTGTGACC
TGCTGTTGGGAGGAAGAGAATGGTCCTACATCGTCGAAAGATCATCAGCTGTAAATGGAAC
GTGTTACCCTGGGAATGTAGAAAACCTAGAGGAACTCAGGACACTTTTTAGTTCCGCTAGTT
CCTACCAAAGAATCCAAATCTTCCCAGACACAACCTGGAATGTGACTTACACTGGAACAAGC
AGAGCATGTTCAGGTTCATTCTACAGGAGTATGAGATGGCTGACTCAAAAGAGCGGTTTTTA
CCCTGTTCAAGACGCCCAATACACAAATAACAGGGGAAAGAGCATTCTTTTCGTGTGGGGC
ATACATCACCCACCCACCTATACCGAGCAAACAAATTTGTACATAAGAAACGACACAACAAC
AAGCGTGACAACAGAAGATTTGAATAGGACCTTCAAACCAGTGATAGGGCCAAGGCCCCTT
GTCAATGGTCTGCAGGGAAGAATTGATTATTATTGGTCGGTACTAAAACCAGGCCAAACATT
GCGAGTACGATCCAATGGGAATCTAATTGCTCCATGGTATGGACACGTTCTTTCAGGAGGG
AGCCATGGAAGAATCCTGAAGACTGATTTAAAAGGTGGTAATTGTGTAGTGCAATGTCAGAC
TGAAAAAGGTGGCTTAAACAGTACATTGCCATTCCACAATATCAGTAAATATGCATTTGGAAC
CTGCCCCAAATATGTAAGAGTTAATAGTCTCAAACTGGCAGTCGGTCTGAGGAACGTGCCT
GCTAGATCAAGTAGAGGACTATTTGGAGCCATAGCTGGATTCATAGAAGGAGGTTGGCCAG
GACTAGTCGCTGGCTGGTATGGTTTCCAGCATTCAAATGATCAAGGGGTTGGTATGGCTGC
AGATAGGGATTCAACTCAAAAGGCAATTGATAAAATAACATCCAAGGTGAATAATATAGTCGA
CAAGATGAACAAGCAATATGAAATAATTGATCATGAATTTAGTGAGGTTGAAACTAGACTCAA
TATGATCAATAATAAGATTGATGACCAAATACAAGACGTATGGGCATATAATGCAGAATTGCT
AGTACTACTTGAAAATCAAAAAACACTCGATGAGCATGATGCGAACGTGAACAATCTATATAA
CAAGGTGAAGAGGGCACTGGGCTCCAATGCTATGGAAGATGGGAAAGGCTGTTTCGAGCTA
TACCATAAATGTGATGATCAGTGCATGGAAACAATTCGGAACGGGACCTATAATAGGAGAAA
GTATAGAGAGGAATCAAGACTAGAAAGGCAGAAAATAGAGGGGGTTAAGCTGGAATCTGAG
GGAACTTACAAAATCCTCACCATTTATTCGACTGTCGCCTCATCTCTTGTGCTTGCAATGGG
GTTTGCTGCCTTCCTGTTCTGGGCCATGTCCAATGGATCTTGCAGATGCAACATTTGTATAT
AAGAGCTCTAAGTTAAAATGCTTCTTCGTCTCCTATTTATAATATGGTTTGTTATTGTTAATTT
TGTTCTTGTAGAAGAGCTTAATTAATCGTTGTTGTTATGAAATACTATTTGTATGAGATGAACT
GGTGTAATGTAATTCATTTACATAAGTGGAGTCAGAATCAGAATGTTTCCTCCATAACTAACT
AGACATGAAGACCTGCCGCGTACAATTGTCTTATATTTGAACAACTAAAATTGAACATCTTTT
GCCACAACTTTATAAGTGGTTAATATAGCTCAAATATATGGTCAAGTTCAATAGATTAATAAT
GGAAATATCAGTTATCGAAATTCATTAACAATCAACTTAACGTTATTAACTACTAATTTTATAT
CATCCCCTTTGATAAATGATAGTACA

Fig. 60

SEQ ID NO: 69

H3 from A/Brisbane/10/2007 (H3N2)

AGAGGTACCCCGGGCTGGTATATTTATATGTTGTCAAATAACTCAAAAACCATAAAAGTTTAAGT
TAGCAAGTGTGTACATTTTTACTTGAACAAAAATATTCACCTACTACTGTTATAAATCATTATTAA
ACATTAGAGTAAAGAAATATGGATGATAAGAACAAGAGTAGTGATATTTTGACAACAATTTTGTT
GCAACATTTGAGAAAATTTTGTTGTTCTCTCTTTTCATTGGTCAAAAACAATAGAGAGAGAAAAA
GGAAGAGGGAGAATAAAAACATAATGTGAGTATGAGAGAGAAAGTTGTACAAAAGTTGTACCAA
AATAGTTGTACAAATATCATTGAGGAATTTGACAAAAGCTACACAAATAAGGGTTAATTGCTGTA
AATAAATAAGGATGACGCATTAGAGAGATGTACCATTAGAGAATTTTTGGCAAGTCATTAAAAAG
AAAGAATAAATTATTTTTAAAATTAAAAGTTGAGTCATTTGATTAAACATGTGATTATTTAATGAAT
TGATGAAAGAGTTGGATTAAAGTTGTATTAGTAATTAGAATTTGGTGTCAAATTTAATTTGACATT
TGATCTTTTCCTATATATTGCCCCATAGAGTCAGTTAACTCATTTTTATATTTCATAGATCAAATA
AGAGAAATAACGGTATATTAATCCCTCCAAAAAAAAAAAAACGGTATATTTACTAAAAAATCTAAG
CCACGTAGGAGGATAACAGGATCCCCGTAGGAGGATAACATCCAATCCAACCAATCACAACAA
TCCTGATGAGATAACCCACTTTAAGCCCACGCATCTGTGGCACATCTACATTATCTAAATCACA
CATTCTTCCACACATCTGAGCCACACAAAAACCAATCCACATCTTTATCACCCATTCTATAAAAA
ATCACACTTTGTGAGTCTACACTTTGATTCCCTTCAAACACATACAAAGAGAAGAGACTAATTAA
TTAATTAATCATCTTGAGAGAAAATGAAGACTATCATTGCTTTGAGCTACATTCTATGTCTGGTT
TTCACTCAAAAACTTCCCGGAAATGACAACAGCACGGCAACGCTGTGCCTTGGGCACCATGCA
GTACCAAACGGAACGATAGTGAAAACAATCACGAATGACCAAATTGAAGTTACTAATGCTACTG
AGCTGGTTCAGAGTTCCTCAACAGGTGAAATATGCGACAGTCCTCATCAGATCCTTGATGGAG
AAAACTGCACACTAATAGATGCTCTATTGGGAGACCCTCAGTGTGATGGCTTCCAAAATAAGAA
ATGGGACCTTTTTGTTGAACGCAGCAAAGCCTACAGCAACTGTTACCCTTATGATGTGCCGGAT
TATGCCTCCCTTAGGTCACTAGTTGCCTCATCCGGCACACTGGAGTTTAACAATGAAAGTTTCA
ATTGGACTGGAGTCACTCAAAACGGAACAAGCTCTGCTTGCATAAGGAGATCTAATAACAGTTT
CTTTAGTAGATTGAATTGGTTGACCCACTTAAAATTCAAATACCCAGCATTGAACGTGACTATGC
CAAACAATGAAAAATTTGACAAATTGTACATTTGGGGGGTTCACCACCCGGGTACGGACAATGA
CCAAATCTTCCTGTATGCTCAAGCATCAGGAAGAATCACAGTCTCTACCAAAAGAAGCCAACAA
ACTGTAATCCCGAATATCGGATCTAGACCCAGAGTAAGGAATATCCCCAGCAGAATAAGCATCT
ATTGGACAATAGTAAAACCGGGAGACATACTTTTGATTAACAGCACAGGGAATCTAATTGCTCC
TAGGGGTTACTTCAAAATACGAAGTGGGAAAAGCTCAATAATGAGATCAGATGCACCCATTGG
CAAATGCAATTCTGAATGCATCACTCCAAACGGAAGCATTCCCAATGACAAACCATTCCAAAAT
GTAAACAGGATCACATACGGGGCCTGTCCCAGATATGTTAAGCAAAACACTCTGAAATTGGCA
ACAGGGATGCGAAATGTACCAGAGAAACAAACTAGAGGCATATTTGGCGCAATCGCGGGTTTC
ATAGAAAATGGTTGGGAGGGAATGGTGGATGGTTGGTATGGTTTCAGGCATCAAAATTCTGAG
GGAATAGGACAAGCAGCAGATCTCAAAAGCACTCAAGCAGCAATCGATCAAATCAATGGGAAG
CTGAATAGGTTGATCGGGAAAACCAACGAGAAATTCCATCAGATTGAAAAAGAGTTCTCAGAAG
TCGAAGGGAGAATCCAGGACCTTGAGAAATATGTTGAGGACACCAAAATAGATCTCTGGTCAT
ACAACGCGGAGCTTCTTGTTGCCCTGGAGAACCAACATACAATTGATCTAACTGACTCAGAAAT
GAACAAACTGTTTGAAAAAACAAAGAAGCAACTGAGGGAAAATGCTGAGGATATGGGCAATGG
TTGTTTCAAAATATACCACAAATGTGACAATGCCTGCATAGGATCAATCAGAAATGGAACTTATG
ACCACGATGTATACAGAGATGAAGCATTAAACAACCGGTTCCAGATCAAGGGCGTTGAGCTGA
AGTCAGGATACAAAGATTGGATACTATGGATTTCCTTTGCCATATCATGTTTTTTGCTTTGTGTT
GCTTTGTTGGGGTTCATCATGTGGGCCTGCCAAAAAGGCAACATTAGGTGCAACATTTGCATTT
GAGAGCTCTAAGTTAAAATGCTTCTTCGTCTCCTATTTATAATATGGTTTGTTATTGTTAATTTTG
TTCTTGTAGAAGAGCTTAATTAATCGTTGTTGTTATGAAATACTATTTGTATGAGATGAACTGGT
GTAATGTAATTCATTTACATAAGTGGAGTCAGAATCAGAATGTTTCCTCCATAACTAACTAGACA
TGAAGACCTGCCGCGTACAATTGTCTTATATTTGAACAACTAAAATTGAACATCTTTTGCCACAA
CTTTATAAGTGGTTAATATAGCTCAAATATATGGTCAAGTTCAATAGATTAATAATGGAAATATCA
GTTATCGAAATTCATTAACAATCAACTTAACGTTATTAACTACTAATTTTATATCATCCCCTTTGA
TAAATGATAGTACA

Fig. 61

SEQ ID NO: 70

H3 from A/Wisconsin/67/2005 (H3N2)

AGAGGTACCCCGGGCTGGTATATTTATATGTTGTCAAATAACTCAAAAACCATAAAAGTTTAA
GTTAGCAAGTGTGTACATTTTTACTTGAACAAAAATATTCACCTACTACTGTTATAAATCATTA
TTAAACATTAGAGTAAAGAAATATGGATGATAAGAACAAGAGTAGTGATATTTTGACAACAAT
TTTGTTGCAACATTTGAGAAAATTTTGTTGTTCTCTCTTTTCATTGGTCAAAAACAATAGAGAG
AGAAAAAGGAAGAGGGAGAATAAAAACATAATGTGAGTATGAGAGAGAAAGTTGTACAAAAG
TTGTACCAAAATAGTTGTACAAATATCATTGAGGAATTTGACAAAAGCTACACAAATAAGGGT
TAATTGCTGTAAATAAATAAGGATGACGCATTAGAGAGATGTACCATTAGAGAATTTTTGGCA
AGTCATTAAAAAGAAAGAATAAATTATTTTTAAAATTAAAAGTTGAGTCATTTGATTAAACATGT
GATTATTTAATGAATTGATGAAAGAGTTGGATTAAAGTTGTATTAGTAATTAGAATTTGGTGTC
AAATTTAATTTGACATTTGATCTTTTCCTATATATTGCCCCATAGAGTCAGTTAACTCATTTTTA
TATTTCATAGATCAAATAAGAGAAATAACGGTATATTAATCCCTCCAAAAAAAAAAAAACGGTAT
ATTTACTAAAAAATCTAAGCCACGTAGGAGGATAACAGGATCCCCGTAGGAGGATAACATCC
AATCCAACCAATCACAACAATCCTGATGAGATAACCCACTTTAAGCCCACGCATCTGTGGCA
CATCTACATTATCTAAATCACACATTCTTCCACACATCTGAGCCACACAAAAACCAATCCACA
TCTTTATCACCCATTCTATAAAAAATCACACTTTGTGAGTCTACACTTTGATTCCCTTCAAACA
CATACAAAGAGAAGAGACTAATTAATTAATTAATCATCTTGAGAGAAAATGAAGACTATCATT
GCTTTGAGCTACATTCTATGTCTGGTTTTCACTCAAAAACTTCCCGGAAATGACAACAGCAC
GGCAACGCTGTGCCTTGGGCACCATGCAGTACCAAACGGAACGATAGTGAAAACAATCACG
AATGACCAAATTGAAGTTACTAATGCTACTGAGCTGGTTCAGAGTTCCTCAACAGGTGGAAT
ATGCGACAGTCCTCATCAGATCCTTGATGGAGAAAACTGCACACTAATAGATGCTCTATTGG
GAGACCCTCAGTGTGATGGCTTCCAAAATAAGAAATGGGACCTTTTTGTTGAACGCAGCAAA
GCCTACAGCAACTGTTACCCTTATGATGTGCCGGATTATGCCTCCCTTAGGTCACTAGTTGC
CTCATCCGGCACACTGGAGTTTAACGATGAAAGTTTCAATTGGACTGGAGTCACTCAAAATG
GAACAAGCTCTGCTTGCAAAAGGAGATCTAATAACAGTTTCTTTAGTAGATTGAATTGGTTGA
CCCACTTAAAATTCAAATACCCAGCATTGAACGTGACTATGCCAAACAATGAAAAATTTGACA
AATTGTACATTTGGGGGGTTCACCACCCGGGTACGGACAATGACCAAATCTTCCTGCATGCT
CAAGCATCAGGAAGAATCACAGTCTCTACCAAAAGAAGCCAACAAACTGTAATCCCGAATAT
CGGATCTAGACCCAGAATAAGGAATATCCCCAGCAGAATAAGCATCTATTGGACAATAGTAA
AACCGGGAGACATACTTTTGATTAACAGCACAGGGAATCTAATTGCTCCTAGGGGTTACTTC
AAAATACGAAGTGGGAAAAGCTCAATAATGAGATCAGATGCACCCATTGGCAAATGCAATTC
TGAATGCATCACTCCAAATGGAAGCATTCCCAATGACAAACCATTTCAAAATGTAAACAGGAT
CACATATGGGGCCTGTCCCAGATATGTTAAGCAAAACACTCTGAAATTGGCAACAGGGATGC
GAAATGTACCAGAGAAACAAACTAGAGGCATATTTGGCGCAATCGCGGGTTTCATAGAAAAT
GGTTGGGAGGGAATGGTGGATGGTTGGTACGGTTTCAGGCATCAAAATTCTGAGGGAATAG
GACAAGCAGCAGATCTCAAAAGCACTCAAGCAGCAATCAATCAAATCAATGGGAAGCTGAAT
AGGTTGATCGGGAAAACCAACGAGAAATTCCATCAGATTGAAAAAGAGTTCTCAGAAGTAGA
AGGGAGAATCCAGGACCTCGAGAAATATGTTGAGGACACTAAAATAGATCTCTGGTCATACA
ACGCGGAGCTTCTTGTTGCCCTGGAGAACCAACATACAATTGATCTAACTGACTCAGAAATG
AACAAACTGTTTGAAAGAACAAAGAAGCAACTGAGGGAAAATGCTGAGGATATGGGCAATGG
TTGTTTCAAAATATACCACAAATGTGACAATGCCTGCATAGGATCAATCAGAAATGGAACTTA
TGACCATGATGTATACAGAGATGAAGCATTAAACAACCGGTTCCAGATCAAAGGCGTTGAGC
TGAAGTCAGGATACAAAGATTGGATACTATGGATTTCCTTTGCCATATCATGTTTTTTGCTTT
GTGTTGCTTTGTTGGGGTTCATCATGTGGGCCTGCCAAAAAGGCAACATTAGGTGCAACATT
TGCATTTGAGAGCTCTAAGTTAAAATGCTTCTTCGTCTCCTATTTATAATATGGTTTGTTATTG
TTAATTTTGTTCTTGTAGAAGAGCTTAATTAATCGTTGTTGTTATGAAATACTATTTGTATGAG
ATGAACTGGTGTAATGTAATTCATTTACATAAGTGGAGTCAGAATCAGAATGTTTCCTCCATA
ACTAACTAGACATGAAGACCTGCCGCGTACAATTGTCTTATATTTGAACAACTAAAATTGAAC
ATCTTTTGCCACAACTTTATAAGTGGTTAATATAGCTCAAATATATGGTCAAGTTCAATAGATT
AATAATGGAAATATCAGTTATCGAAATTCATTAACAATCAACTTAACGTTATTAACTACTAATTT
TATATCATCCCCTTTGATAAATGATAGTACA

Fig. 62

SEQ ID NO: 71
H7 from A/Equine/Prague/56 (H7N7)
AGAGGTACCCCGGGCTGGTATATTTATATGTTGTCAAATAACTCAAAAACCATAAAAGTTTAAG
TTAGCAAGTGTGTACATTTTTACTTGAACAAAAATATTCACCTACTACTGTTATAAATCATTATT
AAACATTAGAGTAAAGAAATATGGATGATAAGAACAAGAGTAGTGATATTTTGACAACAATTTT
GTTGCAACATTTGAGAAAATTTTGTTGTTCTCTCTTTTCATTGGTCAAAAACAATAGAGAGAGA
AAAAGGAAGAGGGAGAATAAAAACATAATGTGAGTATGAGAGAGAAAGTTGTACAAAAGTTGT
ACCAAAATAGTTGTACAAATATCATTGAGGAATTTGACAAAAGCTACACAAATAAGGGTTAATT
GCTGTAAATAAATAAGGATGACGCATTAGAGAGATGTACCATTAGAGAATTTTTGGCAAGTCA
TTAAAAAGAAAGAATAAATTATTTTTAAAATTAAAAGTTGAGTCATTTGATTAAACATGTGATTAT
TTAATGAATTGATGAAAGAGTTGGATTAAAGTTGTATTAGTAATTAGAATTTGGTGTCAAATTTA
ATTTGACATTTGATCTTTTCCTATATATTGCCCCATAGAGTCAGTTAACTCATTTTTATATTTCA
TAGATCAAATAAGAGAAATAACGGTATATTAATCCCTCCAAAAAAAAAAAACGGTATATTTACT
AAAAAATCTAAGCCACGTAGGAGGATAACAGGATCCCCGTAGGAGGATAACATCCAATCCAA
CCAATCACAACAATCCTGATGAGATAACCCACTTTAAGCCCACGCATCTGTGGCACATCTACA
TTATCTAAATCACACATTCTTCCACACATCTGAGCCACACAAAAACCAATCCACATCTTTATCA
CCCATTCTATAAAAAATCACACTTTGTGAGTCTACACTTTGATTCCCTTCAAACACATACAAAG
AGAAGAGACTAATTAATTAATTAATCATCTTGAGAGAAAATGAACACTCAAATTCTAATATTAG
CCACTTCGGCATTCTTCTATGTACGTGCAGATAAAATCTGCCTAGGACATCATGCTGTGTCTA
ATGGAACCAAAGTAGACACCCTTACTGAAAAAGGAATAGAAGTTGTCAATGCAACAGAAACAG
TTGAACAAACAAACATCCCTAAGATCTGCTCAAAAGGAAAACAGACTGTTGACCTTGGTCAAT
GTGGATTACTAGGGACCGTTATTGGTCCTCCCCAATGTGACCAATTTCTTGAGTTCTCTGCTA
ATTTAATAGTTGAAAGAAGGGAAGGTAATGACATTTGTTATCCAGGCAAATTTGACAATGAAGA
AACATTGAGAAAAATACTCAGAAAATCCGGAGGAATTAAAAAGGAGAATATGGGATTCACATA
TACCGGAGTGAGAACCAATGGAGAGACTAGCGCATGTAGAAGGTCAAGATCTTCCTTTTATG
CAGAGATGAAATGGCTTCTATCCAGCACAGACAATGGGACATTTCCACAAATGACAAAGTCCT
ACAAGAACACTAAGAAGGTACCAGCTCTGATAATCTGGGGAATCCACCACTCAGGATCAACT
ACTGAACAGACTAGATTATATGGAAGTGGGAATAAATTGATAACAGTTTGGAGTTCCAAATAC
CAACAATCTTTTGTCCCAAATCCTGGACCAAGACCGCAAATGAATGGTCAATCAGGAAGAATT
GACTTTCACTGGCTGATGCTAGATCCCAATGATACTGTCACTTTCAGTTTTAATGGGGCCTTT
ATAGCACCTGACCGCGCCAGTTTTCTAAGAGGTAAATCTCTAGGAATCCAAAGTGATGCACAA
CTTGACAATAATTGTGAAGGTGAATGCTATCATATTGGAGGTACTATAATTAGCAACTTGCCCT
TTCAAAACATTAATAGTAGGGCAATCGGAAAATGCCCCAGATACGTGAAGCAGAAGAGCTTAA
TGCTAGCAACAGGAATGAAAAATGTTCCTGAAGCTCCTGCACATAAACAACTAACTCATCACA
TGCGCAAAAAAAGAGGTTTATTTGGTGCAATAGCAGGATTCATTGAAAATGGGTGGGAAGGAT
TAATAGACGGATGGTATGGATATAAGCATCAGAATGCACAAGGAGAAGGGACTGCTGCAGAC
TACAAAAGTACACAATCTGCTATCAACCAAATAACCGGAAAATTGAACAGACTAATAGAAAAAA
CCAACCAGCAATTCGAACTAATAGATAATGAGTTCAATGAAATAGAAAAACAAATTGGCAATGT
TATTAACTGGACTAGAGATTCTATCATCGAAGTATGGTCATATAATGCAGAGTTCCTCGTAGC
AGTGGAGAATCAACACACTATTGATTTAACTGACTCAGAAATGAACAAACTATATGAAAAGGTA
AGAAGACAACTGAGAGAAAATGCTGAGGAAGATGGTAATGGCTGTTTTGAAATATTCCACCAA
TGTGACAATGATTGCATGGCCAGCATTAGAAACAACACATATGACCATAAAAAATACAGAAAA
GAGGCAATACAAAACAGAATCCAGATTGACGCAGTAAAGTTGAGCAGTGGTTACAAAGATATA
ATACTTTGGTTTAGCTTCGGGGCATCATGTTTCTTATTTCTTGCCATTGCAATGGGTCTTGTTT
TCATATGTATAAAAAATGGAAACATGCGGTGCACTATTTGTATATAAGAGCTCTAAGTTAAAAT
GCTTCTTCGTCTCCTATTTATAATATGGTTTGTTATTGTTAATTTTGTTCTTGTAGAAGAGCTTA
ATTAATCGTTGTTGTTATGAAATACTATTTGTATGAGATGAACTGGTGTAATGTAATTCATTTAC
ATAAGTGGAGTCAGAATCAGAATGTTTCCTCCATAACTAACTAGACATGAAGACCTGCCGCGT
ACAATTGTCTTATATTTGAACAACTAAAATTGAACATCTTTTGCCACAACTTTATAAGTGGTTAA
TATAGCTCAAATATATGGTCAAGTTCAATAGATTAATAATGGAAATATCAGTTATCGAAATTCAT
TAACAATCAACTTAACGTTATTAACTACTAATTTTATATCATCCCCTTTGATAAATGATAGTACA

Fig. 63

SEQ ID NO: 72
HA from B/Malaysia/2506/2004
AGAGGTACCCCGGGCTGGTATATTTATATGTTGTCAAATAACTCAAAAACCATAAAAGTTTAAG
TTAGCAAGTGTGTACATTTTTACTTGAACAAAAATATTCACCTACTACTGTTATAAATCATTATTA
AACATTAGAGTAAAGAAATATGGATGATAAGAACAAGAGTAGTGATATTTTGACAACAATTTTGT
TGCAACATTTGAGAAAATTTTGTTGTTCTCTCTTTTCATTGGTCAAAAACAATAGAGAGAGAAAA
AGGAAGAGGGAGAATAAAAACATAATGTGAGTATGAGAGAGAAAGTTGTACAAAAGTTGTACC
AAAATAGTTGTACAAATATCATTGAGGAATTTGACAAAAGCTACACAAATAAGGGTTAATTGCTG
TAAATAAATAAGGATGACGCATTAGAGAGATGTACCATTAGAGAATTTTTGGCAAGTCATTAAA
AAGAAAGAATAAATTATTTTTAAAATTAAAAGTTGAGTCATTTGATTAAACATGTGATTATTTAAT
GAATTGATGAAAGAGTTGGATTAAAGTTGTATTAGTAATTAGAATTTGGTGTCAAATTTAATTTG
ACATTTGATCTTTTCCTATATATTGCCCCATAGAGTCAGTTAACTCATTTTTATATTTCATAGATC
AAATAAGAGAAATAACGGTATATTAATCCCTCCAAAAAAAAAAAACGGTATATTTACTAAAAAAT
CTAAGCCACGTAGGAGGATAACAGGATCCCCGTAGGAGGATAACATCCAATCCAACCAATCAC
AACAATCCTGATGAGATAACCCACTTTAAGCCCACGCATCTGTGGCACATCTACATTATCTAAA
TCACACATTCTTCCACACATCTGAGCCACACAAAAACCAATCCACATCTTTATCACCCATTCTAT
AAAAAATCACACTTTGTGAGTCTACACTTTGATTCCCTTCAAACACATACAAAGAGAAGAGACT
AATTAATTAATTAATCATCTTGAGAGAAAATGAAGGCAATAATTGTACTACTCATGGTAGTAACA
TCCAATGCAGATCGAATCTGCACTGGGATAACATCGTCAAACTCACCACATGTTGTCAAAACTG
CTACTCAAGGGGAGGTCAATGTGACTGGTGTAATACCACTGACAACAACACCCACCAAATCTC
ATTTTGCAAATCTCAAAGGAACAGAAACCAGAGGGAAACTATGCCCAAAATGCCTCAACTGCA
CAGATCTGGACGTGGCCTTGGGCAGACCAAAATGCACGGGGAACATACCCTCGGCAAGAGTT
TCAATACTCCATGAAGTCAGACCTGTTACATCTGGGTGCTTTCCTATAATGCACGACAGAACAA
AAATTAGACAGCTGCCTAAACTTCTCAGAGGATACGAACATATCAGGTTATCAACTCATAACGT
TATCAATGCAGAAAATGCACCAGGAGGACCCTACAAAATTGGAACCTCAGGGTCTTGCCCTAA
CGTTACCAATGGAAACGGATTTTTCGCAACAATGGCTTGGGCCGTCCCAAAAAACGACAACAA
CAAAACAGCAACAAATTCATTAACAATAGAAGTACCATACATTTGTACAGAAGGAGAAGACCAA
ATTACCGTTTGGGGGTTCCACTCTGATAACGAAACCCAAATGGCAAAGCTCTATGGGGACTCA
AAGCCCCAGAAGTTCACCTCATCTGCCAACGGAGTGACCACACATTACGTTTCACAGATTGGT
GGCTTCCCAAATCAAACAGAAGACGGAGGACTACCACAAAGCGGTAGAATTGTTGTTGATTAC
ATGGTGCAAAAATCTGGGAAAACAGGAACAATTACCTATCAAAGAGGTATTTTATTGCCTCAAA
AAGTGTGGTGCGCAAGTGGCAGGAGCAAGGTAATAAAAGGATCGTTGCCTTTAATTGGAGAAG
CAGATTGCCTCCACGAAAAATACGGTGGATTAAACAAAAGCAAGCCTTACTACACAGGGGAAC
ATGCAAAGGCCATAGGAAATTGCCCAATATGGGTGAAAACACCCTTGAAGCTGGCCAATGGAA
CCAAATATAGACCTCCTGCAAAACTATTAAAGGAAAGGGGTTTCTTCGGAGCTATTGCTGGTTT
CTTAGAAGGAGGATGGGAAGGAATGATTGCAGGTTGGCACGGATACACATCCCATGGGGCAC
ATGGAGTAGCGGTGGCAGCAGACCTTAAGAGCACTCAAGAGGCCATAAACAAGATAACAAAAA
ATCTCAACTCTTTGAGTGAGCTGGAAGTAAAGAATCTTCAAAGACTAAGCGGTGCCATGGATG
AACTCCACAACGAAATACTAGAACTAGACGAGAAAGTGGATGATCTCAGAGCTGATACAATAA
GCTCACAAATAGAACTCGCAGTCCTGCTTTCCAATGAAGGAATAATAAACAGTGAAGATGAGC
ATCTCTTGGCGCTTGAAAGAAAGCTGAAGAAAATGCTGGGCCCCTCTGCTGTAGAGATAGGGA
ATGGATGCTTTGAAACCAAACACAAGTGCAACCAGACCTGTCTCGACAGAATAGCTGCTGGTA
CCTTTGATGCAGGAGAATTTTCTCTCCCCACTTTTGATTCACTGAATATTACTGCTGCATCTTTA
AATGACGATGGATTGGATAATCATACTATACTGCTTTACTACTCAACTGCTGCCTCCAGTTTGG
CTGTAACATTGATGATAGCTATCTTTGTTGTTTATATGGTCTCCAGAGACAATGTTTCTTGCTCC
ATCTGTCTATAAGAGCTCTAAGTTAAAATGCTTCTTCGTCTCCTATTTATAATATGGTTTGTTATT
GTTAATTTTGTTCTTGTAGAAGAGCTTAATTAATCGTTGTTGTTATGAAATACTATTTGTATGAGA
TGAACTGGTGTAATGTAATTCATTTACATAAGTGGAGTCAGAATCAGAATGTTTCCTCCATAACT
AACTAGACATGAAGACCTGCCGCGTACAATTGTCTTATATTTGAACAACTAAAATTGAACATCTT
TTGCCACAACTTTATAAGTGGTTAATATAGCTCAAATATATGGTCAAGTTCAATAGATTAATAAT
GGAAATATCAGTTATCGAAATTCATTAACAATCAACTTAACGTTATTAACTACTAATTTTATATCA
TCCCCTTTGATAAATGATAGTACA

Fig. 64

SEQ ID NO: 73
HA from B/Florida/4/2006
AGAGGTACCCCGGGCTGGTATATTTATATGTTGTCAAATAACTCAAAAACCATAAAAGTTTAAGT
TAGCAAGTGTGTACATTTTTACTTGAACAAAAATATTCACCTACTACTGTTATAAATCATTATTAA
ACATTAGAGTAAAGAAATATGGATGATAAGAACAAGAGTAGTGATATTTTGACAACAATTTTGTT
GCAACATTTGAGAAAATTTTGTTGTTCTCTCTTTTCATTGGTCAAAAACAATAGAGAGAGAAAAA
GGAAGAGGGAGAATAAAAACATAATGTGAGTATGAGAGAGAAAGTTGTACAAAAGTTGTACCAA
AATAGTTGTACAAATATCATTGAGGAATTTGACAAAAGCTACACAAATAAGGGTTAATTGCTGTA
AATAAATAAGGATGACGCATTAGAGAGATGTACCATTAGAGAATTTTTGGCAAGTCATTAAAAAG
AAAGAATAAATTATTTTTAAAATTAAAAGTTGAGTCATTTGATTAAACATGTGATTATTTAATGAAT
TGATGAAAGAGTTGGATTAAAGTTGTATTAGTAATTAGAATTTGGTGTCAAATTTAATTTGACATT
TGATCTTTTCCTATATATTGCCCCATAGAGTCAGTTAACTCATTTTTATATTTCATAGATCAAATA
AGAGAAATAACGGTATATTAATCCCTCCAAAAAAAAAAAACGGTATATTTACTAAAAAATCTAAG
CCACGTAGGAGGATAACAGGATCCCCGTAGGAGGATAACATCCAATCCAACCAATCACAACAA
TCCTGATGAGATAACCCACTTTAAGCCCACGCATCTGTGGCACATCTACATTATCTAAATCACA
CATTCTTCCACACATCTGAGCCACACAAAAACCAATCCACATCTTTATCACCCATTCTATAAAAA
ATCACACTTTGTGAGTCTACACTTTGATTCCCTTCAAACACATACAAAGAGAAGAGACTAATTAA
TTAATTAATCATCTTGAGAGAAAATGAAGGCAATAATTGTACTACTCATGGTAGTAACATCCAAT
GCAGATCGAATCTGCACTGGAATAACATCTTCAAACTCACCTCATGTGGTCAAAACAGCCACTC
AAGGGGAGGTCAATGTGACTGGTGTGATACCACTAACAACAACACCAACAAAATCTTATTTTGC
AAATCTCAAAGGAACAAGGACCAGAGGGAAACTATGCCCAGACTGTCTCAACTGCACAGATCT
GGATGTGGCTTTGGGCAGACCAATGTGTGTGGGGACCACACCTTCGGCGAAGGCTTCAATAC
TCCACGAAGTCAAACCTGTTACATCCGGGTGCTTTCCTATAATGCACGACAGAACAAAAATCAG
GCAACTACCCAATCTTCTCAGAGGATATGAAAATATCAGGCTATCAACCCAAAACGTCATCGAT
GCGGAAAAGGCACCAGGAGGACCCTACAGACTTGGAACCTCAGGATCTTGCCCTAACGCTAC
CAGTAAGAGCGGATTTTTCGCAACAATGGCTTGGGCTGTCCCAAAGGACAACAACAAAAATGC
AACGAACCCACTAACAGTAGAAGTACCATACATTTGTACAGAAGGGGAAGACCAAATCACTGTT
TGGGGGTTCCATTCAGATAACAAAACCCAAATGAAGAACCTCTATGGAGACTCAAATCCTCAAA
AGTTCACCTCATCTGCTAATGGAGTAACCACACACTATGTTTCTCAGATTGGCAGCTTCCCAGA
TCAAACAGAAGACGGAGGACTACCACAAAGCGGCAGGATTGTTGTTGATTACATGATGCAAAA
ACCTGGGAAAACAGGAACAATTGTCTACCAAAGAGGTGTTTTGTTGCCTCAAAAGGTGTGGTG
CGCGAGTGGCAGGAGCAAAGTAATAAAAGGGTCCTTGCCTTTAATTGGTGAAGCAGATTGCCT
TCATGAAAAATACGGTGGATTAAACAAAAGCAAGCCTTACTACACAGGAGAACATGCAAAAGCC
ATAGGAAATTGCCCAATATGGGTGAAAACACCTTTGAAGCTCGCCAATGGAACCAAATATAGAC
CTCCTGCAAAACTATTAAAGGAAAGGGGTTTCTTCGGAGCTATTGCTGGTTTCCTAGAAGGAG
GATGGGAAGGAATGATTGCAGGCTGGCACGGATACACATCTCACGGAGCACATGGAGTGGCA
GTGGCGGCGGACCTTAAGAGTACGCAAGAAGCTATAAACAAGATAACAAAAAATCTCAATTCTT
TGAGTGAGCTAGAAGTAAAGAATCTTCAAAGACTAAGTGGTGCCATGGATGAACTCCACAACG
AAATACTCGAGCTGGATGAGAAAGTGGATGATCTCAGAGCTGACACTATAAGCTCGCAAATAG
AACTTGCAGTCTTGCTTTCCAACGAAGGAATAATAAACAGTGAAGATGAGCATCTATTGGCACT
TGAGAGAAAACTAAAGAAAATGCTGGGTCCCTCTGCTGTAGAGATAGGAAATGGATGCTTCGA
AACCAAACACAAGTGCAACCAGACCTGCTTAGACAGGATAGCTGCTGGCACCTTTAATGCAGG
AGAATTTTCTCTCCCCACTTTTGATTCACTGAACATTACTGCTGCATCTTTAAATGATGATGGAT
TGGATAACCATACTATACTGCTCTATTACTCAACTGCTGCTTCTAGTTTGGCTGTAACATTGATG
CTAGCTATTTTTATTGTTTATATGGTCTCCAGAGACAACGTTTCATGCTCCATCTGTCTATAAGA
GCTCTAAGTTAAAATGCTTCTTCGTCTCCTATTTATAATATGGTTTGTTATTGTTAATTTTGTTCT
TGTAGAAGAGCTTAATTAATCGTTGTTGTTATGAAATACTATTTGTATGAGATGAACTGGTGTAA
TGTAATTCATTTACATAAGTGGAGTCAGAATCAGAATGTTTCCTCCATAACTAACTAGACATGAA
GACCTGCCGCGTACAATTGTCTTATATTTGAACAACTAAAATTGAACATCTTTTGCCACAACTTT
ATAAGTGGTTAATATAGCTCAAATATATGGTCAAGTTCAATAGATTAATAATGGAAATATCAGTTA
TCGAAATTCATTAACAATCAACTTAACGTTATTAACTACTAATTTTATATCATCCCCTTTGATAAA
TGATAGTACA

Fig. 65

Consensus of SEQ ID NO: 49, 48, 33 and 9

SEQ ID NO: 74

MK($X_1$)KLLVLLCTFTATYADTICIGYHANNSTDTVDTVLEKNVTVTHSVNLL
E($X_2$)SHNGKLCLLKGIAPLQLGNCSVAGWILGNPECELLIS($X_3$)ESWSYIVE($X_4$)P
NPENGTCYPG($X_5$)FADYEELREQLSSVSSFERFEIFPKESSWPNHT($X_6$)TGVSA
SCSHNG($X_7$)SSFY($X_8$)NLLWLTGKNGLYPNLSKSY($X_9$)NNKEKEVLVLWGVHHPPN
IG($X_{10}$)Q ($X_{11}$)ALYH($X_{12}$)ENAYVSVVSSHYSR($X_{13}$)FTPEIAKRPKVRDQEGRINYYWTLL
EPGDTIIFEANGNLIAP($X_{14}$)YAFALSRGFGSGII($X_{15}$)SNAPMD($X_{16}$)CDAKCQTPQG
AINSSLPFQNVHPVTIGECPKYVRSAKLRMVTGLRNIPSIQSRGLFGAIA
GFIEGGWTGMVDGWYGYHHQNEQGSGYAADQKSTQNAINGITNKVNSVIE
KMNTQFTAVGKEFNKLERRMENLNKKVDDGF($X_{17}$)DIWTYNAELLVLLENERT
LDFHDSNVKNLYEKVKSQLKNNAKEIGNGCFEFYHKCN($X_{18}$)ECMESVKNGTY
DYPKYSEESKLNREKIDGVKLESMGVYQILAIYSTVASSLVLLVSLGAIS
FWMCSNGSLQCRICI

Fig. 66

SEQ ID NO: 75

MKAKLLVLLCTFTATYADTICIGYHANNSTDTVDTVLEKNVTVTHSVNLLEDSHNGKLCLLKGIA
PLQLG
NCSVAGWILGNPECELLISKESWSYIVETPNPENGTCYPGYFADYEELREQLSSVSSFERFEIF
PKESSW
PNHTVTGVSASCSHNGKSSFYRNLLWLTGKNGLYPNLSKSYVNNKEKEVLVLWGVHHPPNI
GNQRALYHT
ENAYVSVVSSHYSRRFTPEIAKRPKVRDQEGRINYYWTLLEPGDTIIFEANGNLIAPWYAFALS
RGFGSG
IITSNAPMDECDAKCQTPQGAINSSLPFQNVHPVTIGECPKYVRSAKLRMVTGLRNIPSIQSRG
LFGAIA
GFIEGGWTGMVDGWYGYHHQNEQGSGYAADQKSTQNAINGITNKVNSVIEKMNTQFTAVGK
EFNKLERRM
ENLNKKVDDGFLDIWTYNAELLVLLENERTLDFHDSNVKNLYEKVKSQLKNNAKEIGNGCFEF
YHKCNNE
CMESVKNGTYDYPKYSEESKLNREKIDGVKLESMGVYQILAIYSTVASSLVLLVSLGAISFWMC
SNGSLQ
CRICI

Fig. 67

SEQ ID NO: 76

MSLLTEVETYVLSIIPSGPLKAEIAQRLEDVFAGKNTDLEVLMEWLKTRPILSPLTKGILGFVFTLTVPS
ERGLQRRRFVQNALNGNGDPNNMDKAVKLYRKLKREITFHGAKEISLSYSAGALASCMGLIYNRMGAV
TT
EVAFGLVCATCEQIADSQHRSHRQMVTTTNPLIRHENRMVLASTTAKAMEQMAGSSEQAAEAMEVAS
QAR
QMVQAMRTIGTHPSSSAGLKNDLLENLQAYQKRMGVQMQRFK

Figure 68

TTAATTAAGAATTCGAGCTCCACCGCGGAAACCTCCTCGGATTCCATTGCCCAGCTATCTGTC
ACTTTATTGAGAAGATAGTGGAAAAGGAAGGTGGCTCCTACAAATGCCATCATTGCGATAAAG
GAAAGGCCATCGTTGAAGATGCCTCTGCCGACAGTGGTCCCAAAGATGGACCCCCACCCACG
AGGAGCATCGTGGAAAAAGAAGACGTTCCAACCACGTCTTCAAAGCAAGTGGATTGATGTGAT
ATCTCCACTGACGTAAGGGATGACGCACAATCCCACTATCCTTCGCAAGACCCTTCCTCTATA
TAAGGAAGTTCATTTCATTTGGAGAGGTATTAAAATCTTAATAGGTTTTGATAAAAGCGAACGT
GGGGAAACCCGAACCAAACCTTCTTCTAAACTCTCTCTCATCTCTCTTAAAGCAAACTTCTCTC
TTGTCTTTCTTGCGTGAGCGATCTTCAACGTTGTCAGATCGTGCTTCGGCACCAGTACAACGT
TTTCTTTCACTGAAGCGAAATCAAAGATCTCTTTGTGGACACGTAGTGCGGCGCCATTAAATAA
CGTGTACTTGTCCTATTCTTGTCGGTGTGGTCTTGGGAAAAGAAAGCTTGCTGGAGGCTGCTG
TTCAGCCCCATACATTACTTGTTACGATTCTGCTGACTTTCGGCGGGTGCAATATCTCTACTTC
TGCTTGACGAGGTATTGTTGCCTGTACTTCTTTCTTCTTCTTCTTGCTGATTGGTTCTATAAGAA
ATCTAGTATTTTCTTTGAAACAGAGTTTTCCCGTGGTTTTCGAACTTGGAGAAAGATTGTTAAGC
TTCTGTATATTCTGCCCAAATTTGTCGGGCCCATGGTTTTCACACCTCAGATACTTGGACTTAT
GCTTTTTTGGATTTCAGCCTCCAGAGGTGATATTGTGCTAACTCAGTCTCCAGCCACCCTGTCT
GTGACTCCAGGAGATAGTGTCAGTCTTTCCTGCAGGGCCAGCCAAAGTATTAGCAACAACCTA
CACTGGTTTCAACAAAAATCGCATGAGTCTCCAAGGCTTCTCATCAAGTATGCTTCCCAGTCCA
TATCTGGGATCCCCTCCAGGTTCAGTGGCAGTGGATCTGGGACAGATTTCACTCTCAGTATCA
ACAGTGTGAAGACTGAAGATTTTGGAATGTTTTTCTGTCAACAGAGTAACAGCTGGCCTCTCAC
GTTCGGTGATGGGACAAAGCTGGAGCTGAAACGGGCTGATGCTGCACCAACTGTATCCATCT
TCCCACCATCCAGTGAGCAGTTAACATCTGGAGGTGCCTCAGTCGTGTGCTTCTTGAACAACT
TCTACCCCAAAGACATCAATGTCAAGTGGAAGATTGATGGCAGTGAACGACAAAATGGCGTCC
TGAACAGTTGGACTGATCAGGACAGCAAAGACAGCACCTACAGCATGAGCAGCACCCTCACG
TTGACCAAGGACGAGTATGAACGACATAACAGCTATACCTGTGAGGCCACTCACAAGACATCA
ACTTCACCCATTGTCAAGAGCTTCAACAGGAATGAGTGTTAGAGGCCTATTTTCTTTAGTTTGA
ATTTACTGTTATTCGGTGTGCATTTCTATGTTTGGTGAGCGGTTTTCTGTGCTCAGAGTGTGTT
TATTTTATGTAATTTAATTTCTTTGTGAGCTCCTGTTTAGCAGGTCGTCCCTTCAGCAAGGACAC
AAAAAGATTTTAATTTTATTAAAAAAAAAAAAAAAAAAGACCGGGAATTCGATATCAAGCTTATC
GACCTGCAGATCGTTCAAACATTTGGCAATAAAGTTTCTTAAGATTGAATCCTGTTGCCGGTCT
TGCGATGATTATCATATAATTTCTGTTGAATTACGTTAAGCATGTAATAATTAACATGTAATGCA
TGACGTTATTTATGAGATGGGTTTTTATGATTAGAGTCCCGCAATTATACATTTAATACGCGATA
GAAAACAAAATATAGCGCGCAAACTAGGATAAATTATCGCGCGCGGTGTCATCTATGTTACTA
GATTCTAGAGTCTCAAGCTTCGGCGCGCC

Figure 69

AAGCTTGCTAGCGGCCTCAATGGCCCTGCAGGTCGACTCTAGAGGTACCCCGGGCTGGTAT
ATTTATATGTTGTCAAATAACTCAAAAACCATAAAAGTTTAAGTTAGCAAGTGTGTACATTTTTA
CTTGAACAAAAATATTCACCTACTACTGTTATAAATCATTATTAAACATTAGAGTAAAGAAATAT
GGATGATAAGAACAAGAGTAGTGATATTTTGACAACAATTTTGTTGCAACATTTGAGAAAATTT
TGTTGTTCTCTCTTTTCATTGGTCAAAAACAATAGAGAGAGAAAAAGGAAGAGGGAGAATAAA
AACATAATGTGAGTATGAGAGAGAAAGTTGTACAAAAGTTGTACCAAAATAGTTGTACAAATAT
CATTGAGGAATTTGACAAAAGCTACACAAATAAGGGTTAATTGCTGTAAATAAATAAGGATGAC
GCATTAGAGAGATGTACCATTAGAGAATTTTTGGCAAGTCATTAAAAAGAAAGAATAAATTATT
TTTAAAATTAAAAGTTGAGTCATTTGATTAAACATGTGATTATTTAATGAATTGATGAAAGAGTT
GGATTAAAGTTGTATTAGTAATTAGAATTTGGTGTCAAATTTAATTTGACATTTGATCTTTTCCT
ATATATTGCCCCATAGAGTCAGTTAACTCATTTTTATATTTCATAGATCAAATAAGAGAAATAAC
GGTATATTAATCCCTCCAAAAAAAAAAAACGGTATATTTACTAAAAAATCTAAGCCACGTAGGA
GGATAACAGGATCCCCGTAGGAGGATAACATCCAATCCAACCAATCACAACAATCCTGATGA
GATAACCCACTTTAAGCCCACGCATCTGTGGCACATCTACATTATCTAAATCACACATTCTTCC
ACACATCTGAGCCACACAAAAACCAATCCACATCTTTATCACCCATTCTATAAAAAATCACACT
TTGTGAGTCTACACTTTGATTCCCTTCAAACACATACAAAGAGAAGAGACTAATTAATTAATTA
ATCATCTTGAGAGAAAATGGCGAAAAACGTTGCGATTTTCGGCTTATTGTTTTCTCTTCTTGTG
TTGGTTCCTTCTCAGATCTTCGCTGATCAGATTTGCATTGGTTACCATGCAAACAATTCAACAG
AGCAGGTTGACACAATCATGGAAAAGAACGTTACTGTTACACATGCCCAAGACATACTGGAAA
AGACACACAACGGGAAGCTCTGCGATCTAGATGGAGTGAAGCCTCTAATTTTAAGAGATTGTA
GTGTAGCTGGATGGCTCCTCGGGAACCCAATGTGTGACGAATTCATCAATGTACCGGAATGG
TCTTACATAGTGGAGAAGGCCAATCCAACCAATGACCTCTGTTACCCAGGGAGTTTCAACGAC
TATGAAGAACTGAAACACCTATTGAGCAGAATAAACCATTTTGAGAAAATTCAAATCATCCCCA
AAAGTTCTTGGTCCGATCATGAAGCCTCATCAGGAGTTAGCTCAGCATGTCCATACCTGGGAA
GTCCCTCCTTTTTTAGAAATGTGGTATGGCTTATCAAAAAGAACAGTACATACCCAACAATAAA
GAAAAGCTACAATAATACCAACCAAGAGGATCTTTTGGTACTGTGGGGAATTCACCATCCTAA
TGATGCGGCAGAGCAGACAAGGCTATATCAAAACCCAACCACCTATATTTCCATTGGGACATC
AACACTAAACCAGAGATTGGTACCAAAAATAGCTACTAGATCCAAAGTAAACGGGCAAAGTGG
AAGGATGGAGTTCTTCTGGACAATTTTAAAACCTAATGATGCAATCAACTTCGAGAGTAATGG
AAATTTCATTGCTCCAGAATATGCATACAAAATTGTCAAGAAAGGGGACTCAGCAATTATGAAA
AGTGAATTGGAATATGGTAACTGCAACACCAAGTGTCAAACTCCAATGGGGGCGATAAACTCT
AGTATGCCATTCCACAACATACACCCTCTCACCATCGGGGAATGCCCCAAATATGTGAAATCA
AACAGATTAGTCCTTGCAACAGGGCTCAGAAATAGCCCTCAAAGAGAGAGCAGAAGAAAAAA
GAGAGGACTATTTGGAGCTATAGCAGGTTTTATAGAGGGAGGATGGCAGGGAATGGTAGATG
GTTGGTATGGGTACCACCATAGCAATGAGCAGGGGAGTGGGTACGCTGCAGACAAAGAATC
CACTCAAAAGGCAATAGATGGAGTCACCAATAAGGTCAACTCAATCATTGACAAAATGAACAC
TCAGTTTGAGGCCGTTGGAAGGGAATTTAATAACTTAGAAAGGAGAATAGAGAATTTAAACAA
GAAGATGGAAGACGGGTTTCTAGATGTCTGGACTTATAATGCCGAACTTCTGGTTCTCATGGA
AAATGAGAGAACTCTAGACTTTCATGACTCAAATGTTAAGAACCTCTACGACAAGGTCCGACT
ACAGCTTAGGGATAATGCAAAGGAGCTGGGTAACGGTTGTTTCGAGTTCTATCACAAATGTGA
TAATGAATGTATGGAAAGTATAAGAAACGGAACGTACAACTATCCGCAGTATTCAGAAGAAGC
AAGATTAAAAAGAGAGGAAATAAGTGGGGTAAAATTGGAATCAATAGGAACTTACCAAATACT
GTCAATTTATTCAACAGTGGCGAGTTCCCTAGCACTGGCAATCATGATGGCTGGTCTATCTTT
ATGGATGTGCTCCAATGGATCGTTACAATGCAGAATTTGCATTTAAGAGCTCTAAGTTAAAATG
CTTCTTCGTCTCCTATTTATAATATGGTTTGTTATTGTTAATTTTGTTCTTGTAGAAGAGCTTAA
TTAATCGTTGTTGTTATGAAATACTATTTGTATGAGATGAACTGGTGTAATGTAATTCATTTACA
TAAGTGGAGTCAGAATCAGAATGTTTCCTCCATAACTAACTAGACATGAAGACCTGCCGCGTA
CAATTGTCTTATATTTGAACAACTAAAATTGAACATCTTTTGCCACAACTTTATAAGTGGTTAAT
ATAGCTCAAATATATGGTCAAGTTCAATAGATTAATAATGGAAATATCAGTTATCGAAATTCATT
AACAATCAACTTAACGTTATTAACTACTAATTTTATATCATCCCCTTTGATAAATGATAGTACAC
CAATTAGGAAGGAGCATGCTCGAGGCCTGGCTGGCCGAATTC

Figure 70

AAGCTTGCTAGCGGCCTCAATGGCCCTGCAGGTCGACTCTAGAGGTACCCCGGGCTGGTATA
TTTATATGTTGTCAAATAACTCAAAAACCATAAAAGTTTAAGTTAGCAAGTGTGTACATTTTTACT
TGAACAAAAATATTCACCTACTACTGTTATAAATCATTATTAAACATTAGAGTAAAGAAATATGGA
TGATAAGAACAAGAGTAGTGATATTTTGACAACAATTTTGTTGCAACATTTGAGAAAATTTTGTT
GTTCTCTCTTTTCATTGGTCAAAAACAATAGAGAGAGAAAAAGGAAGAGGGAGAATAAAAACAT
AATGTGAGTATGAGAGAGAAAGTTGTACAAAAGTTGTACCAAAATAGTTGTACAAATATCATTGA
GGAATTTGACAAAAGCTACACAAATAAGGGTTAATTGCTGTAAATAAATAAGGATGACGCATTA
GAGAGATGTACCATTAGAGAATTTTTGGCAAGTCATTAAAAAGAAAGAATAAATTATTTTTAAAA
TTAAAAGTTGAGTCATTTGATTAAACATGTGATTATTTAATGAATTGATGAAAGAGTTGGATTAA
AGTTGTATTAGTAATTAGAATTTGGTGTCAAATTTAATTTGACATTTGATCTTTTCCTATATATTG
CCCCATAGAGTCAGTTAACTCATTTTTATATTTCATAGATCAAATAAGAGAAATAACGGTATATT
AATCCCTCCAAAAAAAAAAAAACGGTATATTTACTAAAAAATCTAAGCCACGTAGGAGGATAACA
GGATCCCCGTAGGAGGATAACATCCAATCCAACCAATCACAACAATCCTGATGAGATAACCCA
CTTTAAGCCCACGCATCTGTGGCACATCTACATTATCTAAATCACACATTCTTCCACACATCTG
AGCCACACAAAAACCAATCCACATCTTTATCACCCATTCTATAAAAAATCACACTTTGTGAGTCT
ACACTTTGATTCCCTTCAAACACATACAAAGAGAAGAGACTAATTAATTAATTAATCATCTTGAG
AGAAAATGGCGAAAAACGTTGCGATTTTCGGCTTATTGTTTTCTCTTCTTGTGTTGGTTCCTTCT
CAGATCTTCGCTGACACAATATGTATAGGCTACCATGCTAACAACTCGACCGACACTGTTGACA
CAGTACTTGAAAAGAATGTGACAGTGACACACTCTGTCAACCTGCTTGAGAACAGTCACAATG
GAAAACTATGTCTATTAAAAGGAATAGCCCCACTACAATTGGGTAATTGCAGCGTTGCCGGGT
GGATCTTAGGAAACCCAGAATGCGAATTACTGATTTCCAAGGAGTCATGGTCCTACATTGTAGA
AAAACCAAATCCTGAGAATGGAACATGTTACCCAGGGCATTTCGCTGACTATGAGGAACTGAG
GGAGCAATTGAGTTCAGTATCTTCATTTGAGAGGTTCGAAATATTCCCCAAAGAAAGCTCATGG
CCCAACCACACCGTAACCGGAGTGTCAGCATCATGCTCCCATAATGGGGAAAGCAGTTTTTAC
AGAAATTTGCTATGGCTGACGGGGAAGAATGGTTTGTACCCAAACCTGAGCAAGTCCTATGCA
AACAACAAAGAAAAAGAAGTCCTTGTACTATGGGGTGTTCATCACCCGCCAAACATAGGTGAC
CAAAAGGCCCTCTATCATACAGAAAATGCTTATGTCTCTGTAGTGTCTTCACATTATAGCAGAA
AATTCACCCCAGAAATAGCCAAAAGACCCAAAGTAAGAGATCAAGAAGGAAGAATCAATTACTA
CTGGACTCTGCTTGAACCCGGGGATACAATAATATTTGAGGCAAATGGAAATCTAATAGCGCC
AAGATATGCTTTCGCACTGAGTAGAGGCTTTGGATCAGGAATCATCAACTCAAATGCACCAATG
GATAAATGTGATGCGAAGTGCCAAACACCTCAGGGAGCTATAAACAGCAGTCTTCCTTTCCAG
AACGTACACCCAGTCACAATAGGAGAGTGTCCAAAGTATGTCAGGAGTGCAAAATTAAGGATG
GTTACAGGACTAAGGAACATCCCATCCATTCAATCCAGAGGTTTGTTTGGAGCCATTGCCGGT
TTCATTGAAGGGGGGTGGACTGGAATGGTAGATGGTTGGTATGGTTATCATCATCAGAATGAG
CAAGGATCTGGCTATGCTGCAGATCAAAAAAGCACACAAAATGCCATTAATGGGATTACAAACA
AGGTCAATTCTGTAATTGAGAAAATGAACACTCAATTCACAGCAGTGGGCAAAGAGTTCAACAA
ATTGGAAAGAAGGATGGAAAACTTGAATAAAAAAGTTGATGATGGGTTTATAGACATTTGGACA
TATAATGCAGAACTGTTGGTTCTACTGGAAAATGAAAGGACTTTGGATTTCCATGACTCCAATG
TGAAGAATCTGTATGAGAAAGTAAAAAGCCAGTTAAAGAATAATGCTAAAGAAATAGGAAATGG
GTGTTTTGAGTTCTATCACAAGTGTAACGATGAATGCATGGAGAGTGTAAAGAATGGAACTTAT
GACTATCCAAAATATTCCGAAGAATCAAAGTTAAACAGGGAGAAAATTGATGGAGTGAAATTGG
AATCAATGGGAGTCTATCAGATTCTGGCGATCTACTCAACAGTCGCCAGTTCTCTGGTTCTTTT
GGTCTCCCTGGGGGCAATCAGCTTCTGGATGTGTTCCAATGGGTCTTTACAGTGTAGAATATG
CATCTAAGAGCTCTAAGTTAAAATGCTTCTTCGTCTCCTATTTATAATATGGTTTGTTATTGTTAA
TTTTGTTCTTGTAGAAGAGCTTAATTAATCGTTGTTGTTATGAAATACTATTTGTATGAGATGAAC
TGGTGTAATGTAATTCATTTACATAAGTGGAGTCAGAATCAGAATGTTTCCTCCATAACTAACTA
GACATGAAGACCTGCCGCGTACAATTGTCTTATATTTGAACAACTAAAATTGAACATCTTTTGC
CACAACTTTATAAGTGGTTAATATAGCTCAAATATATGGTCAAGTTCAATAGATTAATAATGGAA
ATATCAGTTATCGAAATTCATTAACAATCAACTTAACGTTATTAACTACTAATTTTATATCATCCC
CTTTGATAAATGATAGTACACCAATTAGGAAGGAGCATGCTCGAGGCCTGGCTGGCCGAATTC

Figure 71

AAGCTTGCTAGCGGCCTCAATGGCCCTGCAGGTCGACTCTAGAGGTACCCCGGGCTGGTATAT
TTATATGTTGTCAAATAACTCAAAAACCATAAAAGTTTAAGTTAGCAAGTGTGTACATTTTTACTT
GAACAAAAATATTCACCTACTACTGTTATAAATCATTATTAAACATTAGAGTAAAGAAATATGGAT
GATAAGAACAAGAGTAGTGATATTTTGACAACAATTTTGTTGCAACATTTGAGAAAATTTTGTTGT
TCTCTCTTTTCATTGGTCAAAAACAATAGAGAGAGAAAAAGGAAGAGGGAGAATAAAAACATAAT
GTGAGTATGAGAGAGAAAGTTGTACAAAAGTTGTACCAAAATAGTTGTACAAATATCATTGAGG
AATTTGACAAAAGCTACACAAATAAGGGTTAATTGCTGTAAATAAATAAGGATGACGCATTAGAG
AGATGTACCATTAGAGAATTTTTGGCAAGTCATTAAAAAGAAAGAATAAATTATTTTTAAAATTAA
AAGTTGAGTCATTTGATTAAACATGTGATTATTTAATGAATTGATGAAAGAGTTGGATTAAAGTTG
TATTAGTAATTAGAATTTGGTGTCAAATTTAATTTGACATTTGATCTTTTCCTATATATTGCCCCAT
AGAGTCAGTTAACTCATTTTTATATTTCATAGATCAAATAAGAGAAATAACGGTATATTAATCCCT
CCAAAAAAAAAAAACGGTATATTTACTAAAAAATCTAAGCCACGTAGGAGGATAACAGGATCCC
CGTAGGAGGATAACATCCAATCCAACCAATCACAACAATCCTGATGAGATAACCCACTTTAAGC
CCACGCATCTGTGGCACATCTACATTATCTAAATCACACATTCTTCCACACATCTGAGCCACAC
AAAAACCAATCCACATCTTTATCACCCATTCTATAAAAAATCACACTTTGTGAGTCTACACTTTGA
TTCCCTTCAAACACATACAAAGAGAAGAGACTAATTAATTAATTAATCATCTTGAGAGAAAATGG
CGAAAAACGTTGCGATTTTCGGCTTATTGTTTTCTCTTCTTGTGTTGGTTCCTTCTCAGATCTTC
GCTCAAAAACTTCCCGGAAATGACAACAGCACGGCAACGCTGTGCCTTGGGCACCATGCAGTA
CCAAACGGAACGATAGTGAAAACAATCACGAATGACCAAATTGAAGTTACTAATGCTACTGAGC
TGGTTCAGAGTTCCTCAACAGGTGAAATATGCGACAGTCCTCATCAGATCCTTGATGGAGAAAA
CTGCACACTAATAGATGCTCTATTGGGAGACCCTCAGTGTGATGGCTTCCAAAATAAGAAATGG
GACCTTTTTGTTGAACGCAGCAAAGCCTACAGCAACTGTTACCCTTATGATGTGCCGGATTATG
CCTCCCTTAGGTCACTAGTTGCCTCATCCGGCACACTGGAGTTTAACAATGAAAGTTTCAATTG
GACTGGAGTCACTCAAAACGGAACAAGCTCTGCTTGCATAAGGAGATCTAATAACAGTTTCTTT
AGTAGATTGAATTGGTTGACCCACTTAAAATTCAAATACCCAGCATTGAACGTGACTATGCCAAA
CAATGAAAAATTTGACAAATTGTACATTTGGGGGGTTCACCACCCGGGTACGGACAATGACCAA
ATCTTCCTGTATGCTCAAGCATCAGGAAGAATCACAGTCTCTACCAAAAGAAGCCAACAAACTG
TAATCCCGAATATCGGATCTAGACCCAGAGTAAGGAATATCCCCAGCAGAATAAGCATCTATTG
GACAATAGTAAAACCGGGAGACATACTTTTGATTAACAGCACAGGGAATCTAATTGCTCCTAGG
GGTTACTTCAAAATACGAAGTGGGAAAAGCTCAATAATGAGATCAGATGCACCCATTGGCAAAT
GCAATTCTGAATGCATCACTCCAAACGGAAGCATTCCCAATGACAAACCATTCCAAAATGTAAA
CAGGATCACATACGGGGCCTGTCCCAGATATGTTAAGCAAAACACTCTGAAATTGGCAACAGG
GATGCGAAATGTACCAGAGAAACAAACTAGAGGCATATTTGGCGCAATCGCGGGTTTCATAGA
AAATGGTTGGGAGGGAATGGTGGATGGTTGGTATGGTTTCAGGCATCAAAATTCTGAGGGAAT
AGGACAAGCAGCAGATCTCAAAAGCACTCAAGCAGCAATCGATCAAATCAATGGGAAGCTGAA
TAGGTTGATCGGGAAAACCAACGAGAAATTCCATCAGATTGAAAAAGAGTTCTCAGAAGTCGAA
GGGAGAATCCAGGACCTTGAGAAATATGTTGAGGACACCAAAATAGATCTCTGGTCATACAACG
CGGAGCTTCTTGTTGCCCTGGAGAACCAACATACAATTGATCTAACTGACTCAGAAATGAACAA
ACTGTTTGAAAAAACAAAGAAGCAACTGAGGGAAAATGCTGAGGATATGGGCAATGGTTGTTTC
AAAATATACCACAAATGTGACAATGCCTGCATAGGATCAATCAGAAATGGAACTTATGACCACG
ATGTATACAGAGATGAAGCATTAAACAACCGGTTCCAGATCAAGGGCGTTGAGCTGAAGTCAG
GATACAAAGATTGGATACTATGGATTTCCTTTGCCATATCATGTTTTTTGCTTTGTGTTGCTTTGT
TGGGGTTCATCATGTGGGCCTGCCAAAAAGGCAACATTAGGTGCAACATTTGCATTTGAGAGC
TCTAAGTTAAAATGCTTCTTCGTCTCCTATTTATAATATGGTTTGTTATTGTTAATTTTGTTCTTGT
AGAAGAGCTTAATTAATCGTTGTTGTTATGAAATACTATTTGTATGAGATGAACTGGTGTAATGT
AATTCATTTACATAAGTGGAGTCAGAATCAGAATGTTTCCTCCATAACTAACTAGACATGAAGAC
CTGCCGCGTACAATTGTCTTATATTTGAACAACTAAAATTGAACATCTTTTGCCACAACTTTATAA
GTGGTTAATATAGCTCAAATATATGGTCAAGTTCAATAGATTAATAATGGAAATATCAGTTATCG
AAATTCATTAACAATCAACTTAACGTTATTAACTACTAATTTTATATCATCCCCTTTGATAAATGAT
AGTACACCAATTAGGAAGGAGCATGCTCGAGGCCTGGCTGGCCGAATTC

Figure 72

AAGCTTGCTAGCGGCCTCAATGGCCCTGCAGGTCGACTCTAGAGGTACCCCGGGCTGGTATATT
TATATGTTGTCAAATAACTCAAAAACCATAAAAGTTTAAGTTAGCAAGTGTGTACATTTTTACTTGA
ACAAAAATATTCACCTACTACTGTTATAAATCATTATTAAACATTAGAGTAAAGAAATATGGATGAT
AAGAACAAGAGTAGTGATATTTTGACAACAATTTTGTTGCAACATTTGAGAAAATTTTGTTGTTCTC
TCTTTTCATTGGTCAAAAACAATAGAGAGAGAAAAAGGAAGAGGGAGAATAAAAACATAATGTGA
GTATGAGAGAGAAAGTTGTACAAAAGTTGTACCAAAATAGTTGTACAAATATCATTGAGGAATTTG
ACAAAAGCTACACAAATAAGGGTTAATTGCTGTAAATAAATAAGGATGACGCATTAGAGAGATGTA
CCATTAGAGAATTTTTGGCAAGTCATTAAAAAGAAAGAATAAATTATTTTTAAAATTAAAAGTTGAG
TCATTTGATTAAACATGTGATTATTTAATGAATTGATGAAAGAGTTGGATTAAAGTTGTATTAGTAA
TTAGAATTTGGTGTCAAATTTAATTTGACATTTGATCTTTTCCTATATATTGCCCCATAGAGTCAGT
TAACTCATTTTTATATTTCATAGATCAAATAAGAGAAATAACGGTATATTAATCCCTCCAAAAAAAA
AAAACGGTATATTTACTAAAAAATCTAAGCCACGTAGGAGGATAACAGGATCCCCGTAGGAGGAT
AACATCCAATCCAACCAATCACAACAATCCTGATGAGATAACCCACTTTAAGCCCACGCATCTGT
GGCACATCTACATTATCTAAATCACACATTCTTCCACACATCTGAGCCACACAAAAACCAATCCAC
ATCTTTATCACCCATTCTATAAAAAATCACACTTTGTGAGTCTACACTTTGATTCCCTTCAAACACA
TACAAAGAGAAGAGACTAATTAATTAATTAATCATCTTGAGAGAAAATGGCGAAAAACGTTGCGAT
TTTCGGCTTATTGTTTTCTCTTCTTGTGTTGGTTCCTTCTCAGATCTTCGCTGATCGAATCTGCACT
GGAATAACATCTTCAAACTCACCTCATGTGGTCAAAACAGCCACTCAAGGGGAGGTCAATGTGAC
TGGTGTGATACCACTAACAACAACACCAACAAAATCTTATTTTGCAAATCTCAAAGGAACAAGGAC
CAGAGGGAAACTATGCCCAGACTGTCTCAACTGCACAGATCTGGATGTGGCTTTGGGCAGACCA
ATGTGTGTGGGGACCACACCTTCGGCGAAGGCTTCAATACTCCACGAAGTCAAACCTGTTACATC
CGGGTGCTTTCCTATAATGCACGACAGAACAAAAATCAGGCAACTACCCAATCTTCTCAGAGGAT
ATGAAAATATCAGGCTATCAACCCAAAACGTCATCGATGCGGAAAAGGCACCAGGAGGACCCTA
CAGACTTGGAACCTCAGGATCTTGCCCTAACGCTACCAGTAAGAGCGGATTTTTCGCAACAATGG
CTTGGGCTGTCCCAAAGGACAACAACAAAAATGCAACGAACCCACTAACAGTAGAAGTACCATAC
ATTTGTACAGAAGGGGAAGACCAAATCACTGTTTGGGGGTTCCATTCAGATAACAAAACCCAAAT
GAAGAACCTCTATGGAGACTCAAATCCTCAAAAGTTCACCTCATCTGCTAATGGAGTAACCACAC
ACTATGTTTCTCAGATTGGCAGCTTCCCAGATCAAACAGAAGACGGAGGACTACCACAAAGCGG
CAGGATTGTTGTTGATTACATGATGCAAAAACCTGGGAAAACAGGAACAATTGTCTACCAAAGAG
GTGTTTTGTTGCCTCAAAAGGTGTGGTGCGCGAGTGGCAGGAGCAAAGTAATAAAAGGGTCCTT
GCCTTTAATTGGTGAAGCAGATTGCCTTCATGAAAAATACGGTGGATTAAACAAAAGCAAGCCTTA
CTACACAGGAGAACATGCAAAAGCCATAGGAAATTGCCCAATATGGGTGAAAACACCTTTGAAGC
TCGCCAATGGAACCAAATATAGACCTCCTGCAAAACTATTAAAGGAAAGGGGTTTCTTCGGAGCT
ATTGCTGGTTTCCTAGAAGGAGGATGGGAAGGAATGATTGCAGGCTGGCACGGATACACATCTC
ACGGAGCACATGGAGTGGCAGTGGCGGCGGACCTTAAGAGTACGCAAGAAGCTATAAACAAGAT
AACAAAAAATCTCAATTCTTTGAGTGAGCTAGAAGTAAAGAATCTTCAAAGACTAAGTGGTGCCAT
GGATGAACTCCACAACGAAATACTCGAGCTGGATGAGAAAGTGGATGATCTCAGAGCTGACACT
ATAAGCTCGCAAATAGAACTTGCAGTCTTGCTTTCCAACGAAGGAATAATAAACAGTGAAGATGA
GCATCTATTGGCACTTGAGAGAAAACTAAAGAAAATGCTGGGTCCCTCTGCTGTAGAGATAGGAA
ATGGATGCTTCGAAACCAAACACAAGTGCAACCAGACCTGCTTAGACAGGATAGCTGCTGGCAC
CTTTAATGCAGGAGAATTTTCTCTCCCCACTTTTGATTCACTGAACATTACTGCTGCATCTTTAAAT
GATGATGGATTGGATAACCATACTATACTGCTCTATTACTCAACTGCTGCTTCTAGTTTGGCTGTA
ACATTGATGCTAGCTATTTTTATTGTTTATATGGTCTCCAGAGACAACGTTTCATGCTCCATCTGTC
TATAAGAGCTCTAAGTTAAAATGCTTCTTCGTCTCCTATTTATAATATGGTTTGTTATTGTTAATTTT
GTTCTTGTAGAAGAGCTTAATTAATCGTTGTTGTTATGAAATACTATTTGTATGAGATGAACTGGTG
TAATGTAATTCATTTACATAAGTGGAGTCAGAATCAGAATGTTTCCTCCATAACTAACTAGACATGA
AGACCTGCCGCGTACAATTGTCTTATATTTGAACAACTAAAATTGAACATCTTTTGCCACAACTTTA
TAAGTGGTTAATATAGCTCAAATATATGGTCAAGTTCAATAGATTAATAATGGAAATATCAGTTATC
GAAATTCATTAACAATCAACTTAACGTTATTAACTACTAATTTTATATCATCCCCTTTGATAAATGAT
AGTACACCAATTAGGAAGGAGCATGCTCGAGGCCTGGCTGGCCGAATTC

Figure 73

TTAATTAAGAATTCGAGCTCCACCGCGGAAACCTCCTCGGATTCCATTGCCCAGCTATCT
GTCACTTTATTGAGAAGATAGTGGAAAAGGAAGGTGGCTCCTACAAATGCCATCATTGCG
ATAAAGGAAAGGCCATCGTTGAAGATGCCTCTGCCGACAGTGGTCCCAAAGATGGACCC
CCACCCACGAGGAGCATCGTGGAAAAAGAAGACGTTCCAACCACGTCTTCAAAGCAAGT
GGATTGATGTGATATCTCCACTGACGTAAGGGATGACGCACAATCCCACTATCCTTCGCA
AGACCCTTCCTCTATATAAGGAAGTTCATTTCATTTGGAGAGGTATTAAAATCTTAATAGGT
TTTGATAAAAGCGAACGTGGGGAAACCCGAACCAAACCTTCTTCTAAACTCTCTCTCATCT
CTCTTAAAGCAAACTTCTCTCTTGTCTTTCTTGCGTGAGCGATCTTCAACGTTGTCAGATC
GTGCTTCGGCACCAGTACAACGTTTTCTTTCACTGAAGCGAAATCAAAGATCTCTTTGTGG
ACACGTAGTGCGGCGCCATTAAATAACGTGTACTTGTCCTATTCTTGTCGGTGTGGTCTT
GGGAAAAGAAAGCTTGCTGGAGGCTGCTGTTCAGCCCCATACATTACTTGTTACGATTCT
GCTGACTTTCGGCGGGTGCAATATCTCTACTTCTGCTTGACGAGGTATTGTTGCCTGTAC
TTCTTTCTTCTTCTTCTTGCTGATTGGTTCTATAAGAAATCTAGTATTTTCTTTGAAACAGA
GTTTTCCCGTGGTTTTCGAACTTGGAGAAAGATTGTTAAGCTTCTGTATATTCTGCCCAAA
TTTGTCGGGCCCATGGCGAAAAACGTTGCGATTTTCGGCTTATTGTTTTCTCTTCTTGTGT
TGGTTCCTTCTCAGATCTTCGCTGACACAATATGTATAGGCTACCATGCCAACAACTCAAC
CGACACTGTTGACACAGTACTTGAGAAGAATGTGACAGTGACACACTCTGTCAACCTACT
TGAGGACAGTCACAATGGAAAACTATGTCTACTAAAAGGAATAGCCCCACTACAATTGGG
TAATTGCAGCGTTGCCGGATGGATCTTAGGAAACCCAGAATGCGAATTACTGATTTCCAA
GGAATCATGGTCCTACATTGTAGAAACACCAAATCCTGAGAATGGAACATGTTACCCAGG
GTATTTCGCCGACTATGAGGAACTGAGGGAGCAATTGAGTTCAGTATCTTCATTTGAGAG
ATTCGAAATATTCCCCAAAGAAAGCTCATGGCCCAACCACACCGTAACCGGAGTATCAGC
ATCATGCTCCCATAATGGGAAAAGCAGTTTTTACAGAAATTTGCTATGGCTGACGGGGAA
GAATGGTTTGTACCCAAACCTGAGCAAGTCCTATGTAAACAACAAAGAGAAAGAAGTCCTT
GTACTATGGGGTGTTCATCACCCGCCTAACATAGGGAACCAAAGGGCACTCTATCATACA
GAAAATGCTTATGTCTCTGTAGTGTCTTCACATTATAGCAGAAGATTCACCCCAGAAATAG
CCAAAAGACCCAAAGTAAGAGATCAGGAAGGAAGAATCAACTACTACTGGACTCTGCTGG
AACCTGGGGATACAATAATATTTGAGGCAAATGGAAATCTAATAGCGCCATGGTATGCTTT
TGCACTGAGTAGAGGCTTTGGATCAGGAATCATCACCTCAAATGCACCAATGGATGAATG
TGATGCGAAGTGTCAAACACCTCAGGGAGCTATAAACAGCAGTCTTCCTTTCCAGAATGT
ACACCCAGTCACAATAGGAGAGTGTCCAAAGTATGTCAGGAGTGCAAAATTAAGGATGGT
TACAGGACTAAGGAACATCCCATCCATTCAATCCAGAGGTTTGTTTGGAGCCATTGCCGG
TTTCATTGAAGGGGGGTGGACTGGAATGGTAGATGGGTGGTATGGTTATCATCATCAGAA
TGAGCAAGGATCTGGCTATGCTGCAGATCAAAAAAGTACACAAAATGCCATTAACGGGAT
TACAAACAAGGTCAATTCTGTAATTGAGAAAATGAACACTCAATTCACAGCTGTGGGCAAA
GAGTTCAACAAATTGGAAAGAAGGATGGAAAACTTAAATAAAAAAGTTGATGATGGGTTTC
TAGACATTTGGACATATAATGCAGAATTGTTGGTTCTACTGGAAAATGAAAGGACTTTGGA
TTTCCATGACTCCAATGTGAAGAATCTGTATGAGAAAGTAAAAAGCCAATTAAAGAATAAT
GCCAAAGAAATAGGAAACGGGTGTTTTGAGTTCTATCACAAGTGTAACAATGAATGCATG
GAGAGTGTGAAAAATGGTACCTATGACTATCCAAAATATTCCGAAGAATCAAAGTTAAACA
GGGAGAAAATTGATGGAGTGAAATTGGAATCAATGGGAGTATACCAGATTCTGGCGATCT
ACTCAACTGTCGCCAGTTCCCTGGTTCTTTTGGTCTCCCTGGGGGCAATCAGCTTCTGGA
TGTGTTCCAATGGGTCTTTGCAGTGTAGAATATGCATCTAAAGGCCTATTTTCTTTAGTTT
GAATTTACTGTTATTCGGTGTGCATTTCTATGTTTGGTGAGCGGTTTTCTGTGCTCAGAGT
GTGTTTATTTTATGTAATTTAATTTCTTTGTGAGCTCCTGTTTAGCAGGTCGTCCCTTCAGC
AAGGACACAAAAAGATTTTAATTTTATTAAAAAAAAAAAAAAAAAAAGACCGGGAATTCGATA
TCAAGCTTATCGACCTGCAGATCGTTCAAACATTTGGCAATAAAGTTTCTTAAGATTGAAT
CCTGTTGCCGGTCTTGCGATGATTATCATATAATTTCTGTTGAATTACGTTAAGCATGTAAT
AATTAACATGTAATGCATGACGTTATTTATGAGATGGGTTTTTATGATTAGAGTCCCGCAAT
TATACATTTAATACGCGATAGAAAACAAAATATAGCGCGCAAACTAGGATAAATTATCGCG
CGCGGTGTCATCTATGTTACTAGATTCTAGAGTCTCAAGCTTCGGCGCGCC

Figure 74

TTAATTAAGAATTCGAGCTCCACCGCGGAAACCTCCTCGGATTCCATTGCCCAGCTATCT
GTCACTTTATTGAGAAGATAGTGGAAAAGGAAGGTGGCTCCTACAAATGCCATCATTGCG
ATAAAGGAAAGGCCATCGTTGAAGATGCCTCTGCCGACAGTGGTCCCAAAGATGGACCC
CCACCCACGAGGAGCATCGTGGAAAAAGAAGACGTTCCAACCACGTCTTCAAAGCAAGT
GGATTGATGTGATATCTCCACTGACGTAAGGGATGACGCACAATCCCACTATCCTTCGCA
AGACCCTTCCTCTATATAAGGAAGTTCATTTCATTTGGAGAGGTATTAAAATCTTAATAGGT
TTTGATAAAAGCGAACGTGGGGAAACCCGAACCAAACCTTCTTCTAAACTCTCTCTCATCT
CTCTTAAAGCAAACTTCTCTCTTGTCTTTCTTGCGTGAGCGATCTTCAACGTTGTCAGATC
GTGCTTCGGCACCAGTACAACGTTTTCTTTCACTGAAGCGAAATCAAAGATCTCTTTGTGG
ACACGTAGTGCGGCGCCATTAAATAACGTGTACTTGTCCTATTCTTGTCGGTGTGGTCTT
GGGAAAAGAAAGCTTGCTGGAGGCTGCTGTTCAGCCCCATACATTACTTGTTACGATTCT
GCTGACTTTCGGCGGGTGCAATATCTCTACTTCTGCTTGACGAGGTATTGTTGCCTGTAC
TTCTTTCTTCTTCTTCTTGCTGATTGGTTCTATAAGAAATCTAGTATTTTCTTTGAAACAGA
GTTTTCCCGTGGTTTTCGAACTTGGAGAAAGATTGTTAAGCTTCTGTATATTCTGCCCAAA
TTTGTCGGGCCCATGGAGAAAATAGTGCTTCTTCTTGCAATAGTCAGTCTTGTTAAAAGTG
ATCAGATTTGCATTGGTTACCATGCAAACAATTCAACAGAGCAGGTTGACACAATCATGGA
AAAGAACGTTACTGTTACACATGCCCAAGACATACTGGAAAAGACACACAACGGGAAGCT
CTGCGATCTAGATGGAGTGAAGCCTCTAATTTTAAGAGATTGTAGTGTAGCTGGATGGCT
CCTCGGGAACCCAATGTGTGACGAATTCATCAATGTACCGGAATGGTCTTACATAGTGGA
GAAGGCCAATCCAACCAATGACCTCTGTTACCCAGGGAGTTTCAACGACTATGAAGAACT
GAAACACCTATTGAGCAGAATAAACCATTTTGAGAAAATTCAAATCATCCCCAAAAGTTCT
TGGTCCGATCATGAAGCCTCATCAGGAGTTAGCTCAGCATGTCCATACCTGGGAAGTCCC
TCCTTTTTTAGAAATGTGGTATGGCTTATCAAAAAGAACAGTACATACCCAACAATAAAGA
AAAGCTACAATAATACCAACCAAGAGGATCTTTTGGTACTGTGGGGAATTCACCATCCTAA
TGATGCGGCAGAGCAGACAAGGCTATATCAAAACCCAACCACCTATATTTCCATTGGGAC
ATCAACACTAAACCAGAGATTGGTACCAAAAATAGCTACTAGATCCAAAGTAAACGGGCAA
AGTGGAAGGATGGAGTTCTTCTGGACAATTTTAAAACCTAATGATGCAATCAACTTCGAGA
GTAATGGAAATTTCATTGCTCCAGAATATGCATACAAAATTGTCAAGAAAGGGGACTCAGC
AATTATGAAAAGTGAATTGGAATATGGTAACTGCAACACCAAGTGTCAAACTCCAATGGGG
GCGATAAACTCTAGTATGCCATTCCACAACATACACCCTCTCACCATCGGGGAATGCCCC
AAATATGTGAAATCAAACAGATTAGTCCTTGCAACAGGGCTCAGAAATAGCCCTCAAAGA
GAGAGCAGAAGAAAAAAGAGAGGACTATTTGGAGCTATAGCAGGTTTTATAGAGGGAGGA
TGGCAGGGAATGGTAGATGGTTGGTATGGGTACCACCATAGCAATGAGCAGGGGAGTGG
GTACGCTGCAGACAAAGAATCCACTCAAAAGGCAATAGATGGAGTCACCAATAAGGTCAA
CTCAATCATTGACAAAATGAACACTCAGTTTGAGGCCGTTGGAAGGGAATTTAATAACTTA
GAAAGGAGAATAGAGAATTTAAACAAGAAGATGGAAGACGGGTTTCTAGATGTCTGGACT
TATAATGCCGAACTTCTGGTTCTCATGGAAAATGAGAGAACTCTAGACTTTCATGACTCAA
ATGTTAAGAACCTCTACGACAAGGTCCGACTACAGCTTAGGGATAATGCAAAGGAGCTGG
GTAACGGTTGTTTCGAGTTCTATCACAAATGTGATAATGAATGTATGGAAAGTATAAGAAA
CGGAACGTACAACTATCCGCAGTATTCAGAAGAAGCAAGATTAAAAAGAGAGGAAATAAG
TGGGGTAAAATTGGAATCAATAGGAACTTACCAAATACTGTCAATTTATTCAACAGTGGCG
AGTTCCCTAGCACTGGCAATCATGATGGCTGGTCTATCTTTATGGATGTGCTCCAATGGA
TCGTTACAATGCAGAATTTGCATTTAAAGGCCTATTTTCTTTAGTTTGAATTTACTGTTATT
CGGTGTGCATTTCTATGTTTGGTGAGCGGTTTTCTGTGCTCAGAGTGTGTTTATTTTATGT
AATTTAATTTCTTTGTGAGCTCCTGTTTAGCAGGTCGTCCCTTCAGCAAGGACACAAAAAG
ATTTTAATTTTATTAAAAAAAAAAAAAAAAAAAGACCGGGAATTCGATATCAAGCTTATCGAC
CTGCAGATCGTTCAAACATTTGGCAATAAAGTTTCTTAAGATTGAATCCTGTTGCCGGTCT
TGCGATGATTATCATATAATTTCTGTTGAATTACGTTAAGCATGTAATAATTAACATGTAAT
GCATGACGTTATTTATGAGATGGGTTTTTATGATTAGAGTCCCGCAATTATACATTTAATAC
GCGATAGAAAACAAAATATAGCGCGCAAACTAGGATAAATTATCGCGCGCGGTGTCATCT
ATGTTACTAGATTCTAGAGTCTCAAGCTTCGGCGCGCC

Figure 75

TTAATTAAGAATTCGAGCTCCACCGCGGAAACCTCCTCGGATTCCATTGCCCAGCTATCT
GTCACTTTATTGAGAAGATAGTGGAAAAGGAAGGTGGCTCCTACAAATGCCATCATTGCG
ATAAAGGAAAGGCCATCGTTGAAGATGCCTCTGCCGACAGTGGTCCCAAAGATGGACCC
CCACCCACGAGGAGCATCGTGGAAAAAGAAGACGTTCCAACCACGTCTTCAAAGCAAGT
GGATTGATGTGATATCTCCACTGACGTAAGGGATGACGCACAATCCCACTATCCTTCGCA
AGACCCTTCCTCTATATAAGGAAGTTCATTTCATTTGGAGAGGTATTAAAATCTTAATAGG
TTTTGATAAAAGCGAACGTGGGGAAACCCGAACCAAACCTTCTTCTAAACTCTCTCTCAT
CTCTCTTAAAGCAAACTTCTCTCTTGTCTTTCTTGCGTGAGCGATCTTCAACGTTGTCAGA
TCGTGCTTCGGCACCAGTACAACGTTTTCTTTCACTGAAGCGAAATCAAAGATCTCTTTGT
GGACACGTAGTGCGGCGCCATTAAATAACGTGTACTTGTCCTATTCTTGTCGGTGTGGTC
TTGGGAAAAGAAAGCTTGCTGGAGGCTGCTGTTCAGCCCCATACATTACTTGTTACGATT
CTGCTGACTTTCGGCGGGTGCAATATCTCTACTTCTGCTTGACGAGGTATTGTTGCCTGT
ACTTCTTTCTTCTTCTTCTTGCTGATTGGTTCTATAAGAAATCTAGTATTTTCTTTGAAACA
GAGTTTTCCCGTGGTTTTCGAACTTGGAGAAAGATTGTTAAGCTTCTGTATATTCTGCCCA
AATTTGTCGGGCCCATGGCGAAAAACGTTGCGATTTTCGGCTTATTGTTTTCTCTTCTTGT
GTTGGTTCCTTCTCAGATCTTCGCTGATCAGATTTGCATTGGTTACCATGCAAACAATTCA
ACAGAGCAGGTTGACACAATCATGGAAAAGAACGTTACTGTTACACATGCCCAAGACATA
CTGGAAAAGACACACAACGGGAAGCTCTGCGATCTAGATGGAGTGAAGCCTCTAATTTTA
AGAGATTGTAGTGTAGCTGGATGGCTCCTCGGGAACCCAATGTGTGACGAATTCATCAAT
GTACCGGAATGGTCTTACATAGTGGAGAAGGCCAATCCAACCAATGACCTCTGTTACCCA
GGGAGTTTCAACGACTATGAAGAACTGAAACACCTATTGAGCAGAATAAACCATTTTGAG
AAAATTCAAATCATCCCCAAAAGTTCTTGGTCCGATCATGAAGCCTCATCAGGAGTTAGC
TCAGCATGTCCATACCTGGGAAGTCCCTCCTTTTTTAGAAATGTGGTATGGCTTATCAAAA
AGAACAGTACATACCCAACAATAAAGAAAAGCTACAATAATACCAACCAAGAGGATCTTTT
GGTACTGTGGGGAATTCACCATCCTAATGATGCGGCAGAGCAGACAAGGCTATATCAAA
ACCCAACCACCTATATTTCCATTGGGACATCAACACTAAACCAGAGATTGGTACCAAAAAT
AGCTACTAGATCCAAAGTAAACGGGCAAAGTGGAAGGATGGAGTTCTTCTGGACAATTTT
AAAACCTAATGATGCAATCAACTTCGAGAGTAATGGAAATTTCATTGCTCCAGAATATGCA
TACAAAATTGTCAAGAAAGGGGACTCAGCAATTATGAAAAGTGAATTGGAATATGGTAACT
GCAACACCAAGTGTCAAACTCCAATGGGGGCGATAAACTCTAGTATGCCATTCCACAACA
TACACCCTCTCACCATCGGGGAATGCCCCAAATATGTGAAATCAAACAGATTAGTCCTTG
CAACAGGGCTCAGAAATAGCCCTCAAAGAGAGAGCAGAAGAAAAAAGAGAGGACTATTT
GGAGCTATAGCAGGTTTTATAGAGGGAGGATGGCAGGGAATGGTAGATGGTTGGTATGG
GTACCACCATAGCAATGAGCAGGGGAGTGGGTACGCTGCAGACAAAGAATCCACTCAAA
AGGCAATAGATGGAGTCACCAATAAGGTCAACTCAATCATTGACAAAATGAACACTCAGT
TTGAGGCCGTTGGAAGGGAATTTAATAACTTAGAAAGGAGAATAGAGAATTTAAACAAGA
AGATGGAAGACGGGTTTCTAGATGTCTGGACTTATAATGCCGAACTTCTGGTTCTCATGG
AAAATGAGAGAACTCTAGACTTTCATGACTCAAATGTTAAGAACCTCTACGACAAGGTCC
GACTACAGCTTAGGGATAATGCAAAGGAGCTGGGTAACGGTTGTTTCGAGTTCTATCACA
AATGTGATAATGAATGTATGGAAAGTATAAGAAACGGAACGTACAACTATCCGCAGTATTC
AGAAGAAGCAAGATTAAAAAGAGAGGAAATAAGTGGGGTAAAATTGGAATCAATAGGAAC
TTACCAAATACTGTCAATTTATTCAACAGTGGCGAGTTCCCTAGCACTGGCAATCATGATG
GCTGGTCTATCTTTATGGATGTGCTCCAATGGATCGTTACAATGCAGAATTTGCATTTAAA
GGCCTATTTTCTTTAGTTTGAATTTACTGTTATTCGGTGTGCATTTCTATGTTTGGTGAGC
GGTTTTCTGTGCTCAGAGTGTGTTTATTTTATGTAATTTAATTTCTTTGTGAGCTCCTGTTT
AGCAGGTCGTCCCTTCAGCAAGGACACAAAAAGATTTTAATTTTATTAAAAAAAAAAAAAA
AAAAGACCGGGAATTCGATATCAAGCTTATCGACCTGCAGATCGTTCAAACATTTGGCAA
TAAAGTTTCTTAAGATTGAATCCTGTTGCCGGTCTTGCGATGATTATCATATAATTTCTGTT
GAATTACGTTAAGCATGTAATAATTAACATGTAATGCATGACGTTATTTATGAGATGGGTT
TTTATGATTAGAGTCCCGCAATTATACATTTAATACGCGATAGAAAACAAAATATAGCGCG
CAAACTAGGATAAATTATCGCGCGCGGTGTCATCTATGTTACTAGATTCTAGAGTCTCAA
GCTTCGGCGCGCC

Figure 76

TTAATTAAGAATTCGAGCTCCACCGCGGAAACCTCCTCGGATTCCATTGCCCAGCTAT
CTGTCACTTTATTGAGAAGATAGTGGAAAAGGAAGGTGGCTCCTACAAATGCCATCAT
TGCGATAAAGGAAAGGCCATCGTTGAAGATGCCTCTGCCGACAGTGGTCCCAAAGAT
GGACCCCCACCCACGAGGAGCATCGTGGAAAAAGAAGACGTTCCAACCACGTCTTCA
AAGCAAGTGGATTGATGTGATATCTCCACTGACGTAAGGGATGACGCACAATCCCACT
ATCCTTCGCAAGACCCTTCCTCTATATAAGGAAGTTCATTTCATTTGGAGAGGTATTAA
AATCTTAATAGGTTTTGATAAAAGCGAACGTGGGGAAACCCGAACCAAACCTTCTTCTA
AACTCTCTCTCATCTCTCTTAAAGCAAACTTCTCTCTTGTCTTTCTTGCGTGAGCGATC
TTCAACGTTGTCAGATCGTGCTTCGGCACCAGTACAACGTTTTCTTTCACTGAAGCGA
AATCAAAGATCTCTTTGTGGACACGTAGTGCGGCGCCATTAAATAACGTGTACTTGTC
CTATTCTTGTCGGTGTGGTCTTGGGAAAAGAAAGCTTGCTGGAGGCTGCTGTTCAGCC
CCATACATTACTTGTTACGATTCTGCTGACTTTCGGCGGGTGCAATATCTCTACTTCTG
CTTGACGAGGTATTGTTGCCTGTACTTCTTTCTTCTTCTTCTTGCTGATTGGTTCTATAA
GAAATCTAGTATTTTCTTTGAAACAGAGTTTTCCCGTGGTTTTCGAACTTGGAGAAAGA
TTGTTAAGCTTCTGTATATTCTGCCCAAATTTGTCGGGCCCATGAAAGTAAAACTACTG
GTCCTGTTATGCACATTTACAGCTACATATGCAGACACAATATGTATAGGCTACCATGC
TAACAACTCGACCGACACTGTTGACACAGTACTTGAAAAGAATGTGACAGTGACACAC
TCTGTCAACCTGCTTGAGAACAGTCACAATGGAAAACTATGTCTATTAAAAGGAATAGC
CCCACTACAATTGGGTAATTGCAGCGTTGCCGGGTGGATCTTAGGAAACCCAGAATG
CGAATTACTGATTTCCAAGGAGTCATGGTCCTACATTGTAGAAAAACCAAATCCTGAGA
ATGGAACATGTTACCCAGGGCATTTCGCTGACTATGAGGAACTGAGGGAGCAATTGA
GTTCAGTATCTTCATTTGAGAGGTTCGAAATATTCCCCAAAGAAAGCTCATGGCCCAA
CCACACCGTAACCGGAGTGTCAGCATCATGCTCCCATAATGGGGAAAGCAGTTTTTAC
AGAAATTTGCTATGGCTGACGGGGAAGAATGGTTTGTACCCAAACCTGAGCAAGTCCT
ATGCAAACAACAAAGAAAAAGAAGTCCTTGTACTATGGGGTGTTCATCACCCGCCAAA
CATAGGTGACCAAAAGGCCCTCTATCATACAGAAAATGCTTATGTCTCTGTAGTGTCTT
CACATTATAGCAGAAAATTCACCCCAGAAATAGCCAAAAGACCCAAAGTAAGAGATCA
AGAAGGAAGAATCAATTACTACTGGACTCTGCTTGAACCCGGGGATACAATAATATTT
GAGGCAAATGGAAATCTAATAGCGCCAAGATATGCTTTCGCACTGAGTAGAGGCTTTG
GATCAGGAATCATCAACTCAAATGCACCAATGGATAAATGTGATGCGAAGTGCCAAAC
ACCTCAGGGAGCTATAAACAGCAGTCTTCCTTTCCAGAACGTACACCCAGTCACAATA
GGAGAGTGTCCAAAGTATGTCAGGAGTGCAAAATTAAGGATGGTTACAGGACTAAGGA
ACATCCCATCCATTCAATCCAGAGGTTTGTTTGGAGCCATTGCCGGTTTCATTGAAGG
GGGGTGGACTGGAATGGTAGATGGTTGGTATGGTTATCATCATCAGAATGAGCAAGG
ATCTGGCTATGCTGCAGATCAAAAAAGCACACAAAATGCCATTAATGGGATTACAAACA
AGGTCAATTCTGTAATTGAGAAAATGAACACTCAATTCACAGCAGTGGGCAAAGAGTT
CAACAAATTGGAAAGAAGGATGGAAAACTTGAATAAAAAAGTTGATGATGGGTTTATAG
ACATTTGGACATATAATGCAGAACTGTTGGTTCTACTGGAAAATGAAAGGACTTTGGAT
TTCCATGACTCCAATGTGAAGAATCTGTATGAGAAAGTAAAAAGCCAGTTAAAGAATAA
TGCTAAAGAAATAGGAAATGGGTGTTTTGAGTTCTATCACAAGTGTAACGATGAATGCA
TGGAGAGTGTAAAGAATGGAACTTATGACTATCCAAAATATTCCGAAGAATCAAAGTTA
AACAGGGAGAAAATTGATGGAGTGAAATTGGAATCAATGGGAGTCTATCAGATTCTGG
CGATCTACTCAACAGTCGCCAGTTCTCTGGTTCTTTTGGTCTCCCTGGGGGCAATCAG
CTTCTGGATGTGTTCCAATGGGTCTTTACAGTGTAGAATATGCATCTAAAGGCCTATTT
TCTTTAGTTTGAATTTACTGTTATTCGGTGTGCATTTCTATGTTTGGTGAGCGGTTTTCT
GTGCTCAGAGTGTGTTTATTTTATGTAATTTAATTTCTTTGTGAGCTCCTGTTTAGCAGG
TCGTCCCTTCAGCAAGGACACAAAAAGATTTTAATTTTATTAAAAAAAAAAAAAAAAAAG
ACCGGGAATTCGATATCAAGCTTATCGACCTGCAGATCGTTCAAACATTTGGCAATAAA
GTTTCTTAAGATTGAATCCTGTTGCCGGTCTTGCGATGATTATCATATAATTTCTGTTGA
ATTACGTTAAGCATGTAATAATTAACATGTAATGCATGACGTTATTTATGAGATGGGTTT
TTATGATTAGAGTCCCGCAATTATACATTTAATACGCGATAGAAAACAAAATATAGCGC
GCAAACTAGGATAAATTATCGCGCGCGGTGTCATCTATGTTACTAGATTCTAGAGTCT
CAAGCTTCGGCGCGCC

Figure 77

TTAATTAAGAATTCGAGCTCCACCGCGGAAACCTCCTCGGATTCCATTGCCCAGCTATCT
GTCACTTTATTGAGAAGATAGTGGAAAAGGAAGGTGGCTCCTACAAATGCCATCATTGC
GATAAAGGAAAGGCCATCGTTGAAGATGCCTCTGCCGACAGTGGTCCCAAAGATGGAC
CCCCACCCACGAGGAGCATCGTGGAAAAAGAAGACGTTCCAACCACGTCTTCAAAGCAA
GTGGATTGATGTGATATCTCCACTGACGTAAGGGATGACGCACAATCCCACTATCCTTC
GCAAGACCCTTCCTCTATATAAGGAAGTTCATTTCATTTGGAGAGGTATTAAAATCTTAAT
AGGTTTTGATAAAAGCGAACGTGGGGAAACCCGAACCAAACCTTCTTCTAAACTCTCTCT
CATCTCTCTTAAAGCAAACTTCTCTCTTGTCTTTCTTGCGTGAGCGATCTTCAACGTTGTC
AGATCGTGCTTCGGCACCAGTACAACGTTTTCTTTCACTGAAGCGAAATCAAAGATCTCT
TTGTGGACACGTAGTGCGGCGCCATTAAATAACGTGTACTTGTCCTATTCTTGTCGGTGT
GGTCTTGGGAAAAGAAAGCTTGCTGGAGGCTGCTGTTCAGCCCCATACATTACTTGTTA
CGATTCTGCTGACTTTCGGCGGGTGCAATATCTCTACTTCTGCTTGACGAGGTATTGTTG
CCTGTACTTCTTTCTTCTTCTTCTTGCTGATTGGTTCTATAAGAAATCTAGTATTTTCTTTG
AAACAGAGTTTTCCCGTGGTTTTCGAACTTGGAGAAAGATTGTTAAGCTTCTGTATATTCT
GCCCAAATTTGTCGGGCCCATGGCGAAAAACGTTGCGATTTTCGGCTTATTGTTTTCTCT
TCTTGTGTTGGTTCCTTCTCAGATCTTCGCTGACACAATATGTATAGGCTACCATGCTAA
CAACTCGACCGACACTGTTGACACAGTACTTGAAAAGAATGTGACAGTGACACACTCTG
TCAACCTGCTTGAGAACAGTCACAATGGAAAACTATGTCTATTAAAAGGAATAGCCCCAC
TACAATTGGGTAATTGCAGCGTTGCCGGGTGGATCTTAGGAAACCCAGAATGCGAATTA
CTGATTTCCAAGGAGTCATGGTCCTACATTGTAGAAAAACCAAATCCTGAGAATGGAACA
TGTTACCCAGGGCATTTCGCTGACTATGAGGAACTGAGGGAGCAATTGAGTTCAGTATC
TTCATTTGAGAGGTTCGAAATATTCCCCAAAGAAAGCTCATGGCCCAACCACACCGTAAC
CGGAGTGTCAGCATCATGCTCCCATAATGGGGAAAGCAGTTTTTACAGAAATTTGCTATG
GCTGACGGGGAAGAATGGTTTGTACCCAAACCTGAGCAAGTCCTATGCAAACAACAAAG
AAAAAGAAGTCCTTGTACTATGGGGTGTTCATCACCCGCCAAACATAGGTGACCAAAAG
GCCCTCTATCATACAGAAAATGCTTATGTCTCTGTAGTGTCTTCACATTATAGCAGAAAAT
TCACCCCAGAAATAGCCAAAAGACCCAAAGTAAGAGATCAAGAAGGAAGAATCAATTACT
ACTGGACTCTGCTTGAACCCGGGGATACAATAATATTTGAGGCAAATGGAAATCTAATAG
CGCCAAGATATGCTTTCGCACTGAGTAGAGGCTTTGGATCAGGAATCATCAACTCAAAT
GCACCAATGGATAAATGTGATGCGAAGTGCCAAACACCTCAGGGAGCTATAAACAGCAG
TCTTCCTTTCCAGAACGTACACCCAGTCACAATAGGAGAGTGTCCAAAGTATGTCAGGA
GTGCAAAATTAAGGATGGTTACAGGACTAAGGAACATCCCATCCATTCAATCCAGAGGTT
TGTTTGGAGCCATTGCCGGTTTCATTGAAGGGGGGTGGACTGGAATGGTAGATGGTTG
GTATGGTTATCATCATCAGAATGAGCAAGGATCTGGCTATGCTGCAGATCAAAAAAGCAC
ACAAAATGCCATTAATGGGATTACAAACAAGGTCAATTCTGTAATTGAGAAAATGAACAC
TCAATTCACAGCAGTGGGCAAAGAGTTCAACAAATTGGAAAGAAGGATGGAAAACTTGA
ATAAAAAAGTTGATGATGGGTTTATAGACATTTGGACATATAATGCAGAACTGTTGGTTCT
ACTGGAAAATGAAAGGACTTTGGATTTCCATGACTCCAATGTGAAGAATCTGTATGAGAA
AGTAAAAAGCCAGTTAAAGAATAATGCTAAAGAAATAGGAAATGGGTGTTTTGAGTTCTA
TCACAAGTGTAACGATGAATGCATGGAGAGTGTAAAGAATGGAACTTATGACTATCCAAA
ATATTCCGAAGAATCAAAGTTAAACAGGGAGAAAATTGATGGAGTGAAATTGGAATCAAT
GGGAGTCTATCAGATTCTGGCGATCTACTCAACAGTCGCCAGTTCTCTGGTTCTTTTGGT
CTCCCTGGGGGCAATCAGCTTCTGGATGTGTTCCAATGGGTCTTTACAGTGTAGAATAT
GCATCTAAAGGCCTATTTTCTTTAGTTTGAATTTACTGTTATTCGGTGTGCATTTCTATGT
TTGGTGAGCGGTTTTCTGTGCTCAGAGTGTGTTTATTTTATGTAATTTAATTTCTTTGTGA
GCTCCTGTTTAGCAGGTCGTCCCTTCAGCAAGGACACAAAAAGATTTTAATTTTATTAAA
AAAAAAAAAAAAAAAGACCGGGAATTCGATATCAAGCTTATCGACCTGCAGATCGTTCAA
ACATTTGGCAATAAAGTTTCTTAAGATTGAATCCTGTTGCCGGTCTTGCGATGATTATCAT
ATAATTTCTGTTGAATTACGTTAAGCATGTAATAATTAACATGTAATGCATGACGTTATTTA
TGAGATGGGTTTTTATGATTAGAGTCCCGCAATTATACATTTAATACGCGATAGAAAACAA
AATATAGCGCGCAAACTAGGATAAATTATCGCGCGCGGTGTCATCTATGTTACTAGATTC
TAGAGTCTCAAGCTTCGGCGCGCC

Figure 78

TTAATTAAGAATTCGAGCTCCACCGCGGAAACCTCCTCGGATTCCATTGCCCAGCTAT
CTGTCACTTTATTGAGAAGATAGTGGAAAAGGAAGGTGGCTCCTACAAATGCCATCATT
GCGATAAAGGAAAGGCCATCGTTGAAGATGCCTCTGCCGACAGTGGTCCCAAAGATG
GACCCCCACCCACGAGGAGCATCGTGGAAAAAGAAGACGTTCCAACCACGTCTTCAA
AGCAAGTGGATTGATGTGATATCTCCACTGACGTAAGGGATGACGCACAATCCCACTA
TCCTTCGCAAGACCCTTCCTCTATATAAGGAAGTTCATTTCATTTGGAGAGGTATTAAA
ATCTTAATAGGTTTTGATAAAAGCGAACGTGGGGAAACCCGAACCAAACCTTCTTCTAA
ACTCTCTCTCATCTCTCTTAAAGCAAACTTCTCTCTTGTCTTTCTTGCGTGAGCGATCTT
CAACGTTGTCAGATCGTGCTTCGGCACCAGTACAACGTTTTCTTTCACTGAAGCGAAAT
CAAAGATCTCTTTGTGGACACGTAGTGCGGCGCCATTAAATAACGTGTACTTGTCCTAT
TCTTGTCGGTGTGGTCTTGGGAAAAGAAAGCTTGCTGGAGGCTGCTGTTCAGCCCCAT
ACATTACTTGTTACGATTCTGCTGACTTTCGGCGGGTGCAATATCTCTACTTCTGCTTG
ACGAGGTATTGTTGCCTGTACTTCTTTCTTCTTCTTCTTGCTGATTGGTTCTATAAGAAA
TCTAGTATTTTCTTTGAAACAGAGTTTTCCCGTGGTTTTCGAACTTGGAGAAAGATTGTT
AAGCTTCTGTATATTCTGCCCAAATTTGTCGGGCCCATGAAGACTATCATTGCTTTGAG
CTACATTCTATGTCTGGTTTTCACTCAAAAACTTCCCGGAAATGACAACAGCACGGCAA
CGCTGTGCCTTGGGCACCATGCAGTACCAAACGGAACGATAGTGAAAACAATCACGAA
TGACCAAATTGAAGTTACTAATGCTACTGAGCTGGTTCAGAGTTCCTCAACAGGTGAAA
TATGCGACAGTCCTCATCAGATCCTTGATGGAGAAAACTGCACACTAATAGATGCTCTA
TTGGGAGACCCTCAGTGTGATGGCTTCCAAAATAAGAAATGGGACCTTTTTGTTGAAC
GCAGCAAAGCCTACAGCAACTGTTACCCTTATGATGTGCCGGATTATGCCTCCCTTAG
GTCACTAGTTGCCTCATCCGGCACACTGGAGTTTAACAATGAAAGTTTCAATTGGACTG
GAGTCACTCAAAACGGAACAAGCTCTGCTTGCATAAGGAGATCTAATAACAGTTTCTTT
AGTAGATTGAATTGGTTGACCCACTTAAAATTCAAATACCCAGCATTGAACGTGACTAT
GCCAAACAATGAAAAATTTGACAAATTGTACATTTGGGGGGTTCACCACCCGGGTACG
GACAATGACCAAATCTTCCTGTATGCTCAAGCATCAGGAAGAATCACAGTCTCTACCAA
AAGAAGCCAACAAACTGTAATCCCGAATATCGGATCTAGACCCAGAGTAAGGAATATC
CCCAGCAGAATAAGCATCTATTGGACAATAGTAAAACCGGGAGACATACTTTTGATTAA
CAGCACAGGGAATCTAATTGCTCCTAGGGGTTACTTCAAAATACGAAGTGGGAAAAGC
TCAATAATGAGATCAGATGCACCCATTGGCAAATGCAATTCTGAATGCATCACTCCAAA
CGGAAGCATTCCCAATGACAAACCATTCCAAAATGTAAACAGGATCACATACGGGGCC
TGTCCCAGATATGTTAAGCAAAACACTCTGAAATTGGCAACAGGGATGCGAAATGTAC
CAGAGAAACAAACTAGAGGCATATTTGGCGCAATCGCGGGTTTCATAGAAAATGGTTG
GGAGGGAATGGTGGATGGTTGGTATGGTTTCAGGCATCAAAATTCTGAGGGAATAGGA
CAAGCAGCAGATCTCAAAAGCACTCAAGCAGCAATCGATCAAATCAATGGGAAGCTGA
ATAGGTTGATCGGGAAAACCAACGAGAAATTCCATCAGATTGAAAAAGAGTTCTCAGAA
GTCGAAGGGAGAATCCAGGACCTTGAGAAATATGTTGAGGACACCAAAATAGATCTCT
GGTCATACAACGCGGAGCTTCTTGTTGCCCTGGAGAACCAACATACAATTGATCTAAC
TGACTCAGAAATGAACAAACTGTTTGAAAAAACAAAGAAGCAACTGAGGGAAAATGCTG
AGGATATGGGCAATGGTTGTTTCAAAATATACCACAAATGTGACAATGCCTGCATAGGA
TCAATCAGAAATGGAACTTATGACCACGATGTATACAGAGATGAAGCATTAAACAACCG
GTTCCAGATCAAGGGCGTTGAGCTGAAGTCAGGATACAAAGATTGGATACTATGGATT
TCCTTTGCCATATCATGTTTTTTGCTTTGTGTTGCTTTGTTGGGGTTCATCATGTGGGC
CTGCCAAAAAGGCAACATTAGGTGCAACATTTGCATTTGAAGGCCTATTTTCTTTAGTT
TGAATTTACTGTTATTCGGTGTGCATTTCTATGTTTGGTGAGCGGTTTTCTGTGCTCAG
AGTGTGTTTATTTTATGTAATTTAATTTCTTTGTGAGCTCCTGTTTAGCAGGTCGTCCCT
TCAGCAAGGACACAAAAAGATTTTAATTTTATTAAAAAAAAAAAAAAAAAAAGACCGGGAA
TTCGATATCAAGCTTATCGACCTGCAGATCGTTCAAACATTTGGCAATAAAGTTTCTTAA
GATTGAATCCTGTTGCCGGTCTTGCGATGATTATCATATAATTTCTGTTGAATTACGTTA
AGCATGTAATAATTAACATGTAATGCATGACGTTATTTATGAGATGGGTTTTTATGATTA
GAGTCCCGCAATTATACATTTAATACGCGATAGAAAACAAAATATAGCGCGCAAACTAG
GATAAATTATCGCGCGCGGTGTCATCTATGTTACTAGATTCTAGAGTCTCAAGCTTCGG
CGCGCC

Figure 79

TTAATTAAGAATTCGAGCTCCACCGCGGAAACCTCCTCGGATTCCATTGCCCAGCTATC
TGTCACTTTATTGAGAAGATAGTGGAAAAGGAAGGTGGCTCCTACAAATGCCATCATTG
CGATAAAGGAAAGGCCATCGTTGAAGATGCCTCTGCCGACAGTGGTCCCAAAGATGGA
CCCCCACCCACGAGGAGCATCGTGGAAAAAGAAGACGTTCCAACCACGTCTTCAAAGC
AAGTGGATTGATGTGATATCTCCACTGACGTAAGGGATGACGCACAATCCCACTATCCT
TCGCAAGACCCTTCCTCTATATAAGGAAGTTCATTTCATTTGGAGAGGTATTAAAATCTT
AATAGGTTTTGATAAAAGCGAACGTGGGGAAACCCGAACCAAACCTTCTTCTAAACTCT
CTCTCATCTCTCTTAAAGCAAACTTCTCTCTTGTCTTTCTTGCGTGAGCGATCTTCAACG
TTGTCAGATCGTGCTTCGGCACCAGTACAACGTTTTCTTTCACTGAAGCGAAATCAAAG
ATCTCTTTGTGGACACGTAGTGCGGCGCCATTAAATAACGTGTACTTGTCCTATTCTTG
TCGGTGTGGTCTTGGGAAAAGAAAGCTTGCTGGAGGCTGCTGTTCAGCCCCATACATT
ACTTGTTACGATTCTGCTGACTTTCGGCGGGTGCAATATCTCTACTTCTGCTTGACGAG
GTATTGTTGCCTGTACTTCTTTCTTCTTCTTCTTGCTGATTGGTTCTATAAGAAATCTAGT
ATTTTCTTTGAAACAGAGTTTTCCCGTGGTTTTCGAACTTGGAGAAAGATTGTTAAGCTT
CTGTATATTCTGCCCAAATTTGTCGGGCCCATGGCGAAAAACGTTGCGATTTTCGGCTT
ATTGTTTTCTCTTCTTGTGTTGGTTCCTTCTCAGATCTTCGCTCAAAAACTTCCCGGAAA
TGACAACAGCACGGCAACGCTGTGCCTTGGGCACCATGCAGTACCAAACGGAACGATA
GTGAAAACAATCACGAATGACCAAATTGAAGTTACTAATGCTACTGAGCTGGTTCAGAG
TTCCTCAACAGGTGAAATATGCGACAGTCCTCATCAGATCCTTGATGGAGAAAACTGCA
CACTAATAGATGCTCTATTGGGAGACCCTCAGTGTGATGGCTTCCAAAATAAGAAATGG
GACCTTTTTGTTGAACGCAGCAAAGCCTACAGCAACTGTTACCCTTATGATGTGCCGGA
TTATGCCTCCCTTAGGTCACTAGTTGCCTCATCCGGCACACTGGAGTTTAACAATGAAA
GTTTCAATTGGACTGGAGTCACTCAAAACGGAACAAGCTCTGCTTGCATAAGGAGATCT
AATAACAGTTTCTTTAGTAGATTGAATTGGTTGACCCACTTAAAATTCAAATACCCAGCA
TTGAACGTGACTATGCCAAACAATGAAAAATTTGACAAATTGTACATTTGGGGGGTTCA
CCACCCGGGTACGGACAATGACCAAATCTTCCTGTATGCTCAAGCATCAGGAAGAATC
ACAGTCTCTACCAAAAGAAGCCAACAAACTGTAATCCCGAATATCGGATCTAGACCCAG
AGTAAGGAATATCCCCAGCAGAATAAGCATCTATTGGACAATAGTAAAACCGGGAGACA
TACTTTTGATTAACAGCACAGGGAATCTAATTGCTCCTAGGGGTTACTTCAAAATACGAA
GTGGGAAAAGCTCAATAATGAGATCAGATGCACCCATTGGCAAATGCAATTCTGAATGC
ATCACTCCAAACGGAAGCATTCCCAATGACAAACCATTCCAAAATGTAAACAGGATCAC
ATACGGGGCCTGTCCCAGATATGTTAAGCAAAACACTCTGAAATTGGCAACAGGGATG
CGAAATGTACCAGAGAAACAAACTAGAGGCATATTTGGCGCAATCGCGGGTTTCATAG
AAAATGGTTGGGAGGGAATGGTGGATGGTTGGTATGGTTTCAGGCATCAAAATTCTGA
GGGAATAGGACAAGCAGCAGATCTCAAAAGCACTCAAGCAGCAATCGATCAAATCAAT
GGGAAGCTGAATAGGTTGATCGGGAAAACCAACGAGAAATTCCATCAGATTGAAAAAG
AGTTCTCAGAAGTCGAAGGGAGAATCCAGGACCTTGAGAAATATGTTGAGGACACCAA
AATAGATCTCTGGTCATACAACGCGGAGCTTCTTGTTGCCCTGGAGAACCAACATACAA
TTGATCTAACTGACTCAGAAATGAACAAACTGTTTGAAAAAACAAAGAAGCAACTGAGG
GAAAATGCTGAGGATATGGGCAATGGTTGTTTCAAAATATACCACAAATGTGACAATGC
CTGCATAGGATCAATCAGAAATGGAACTTATGACCACGATGTATACAGAGATGAAGCAT
TAAACAACCGGTTCCAGATCAAGGGCGTTGAGCTGAAGTCAGGATACAAAGATTGGAT
ACTATGGATTTCCTTTGCCATATCATGTTTTTTGCTTTGTGTTGCTTTGTTGGGGTTCAT
CATGTGGGCCTGCCAAAAAGGCAACATTAGGTGCAACATTTGCATTTGAAGGCCTATTT
TCTTTAGTTTGAATTTACTGTTATTCGGTGTGCATTTCTATGTTTGGTGAGCGGTTTTCT
GTGCTCAGAGTGTGTTTATTTTATGTAATTTAATTTCTTTGTGAGCTCCTGTTTAGCAGG
TCGTCCCTTCAGCAAGGACACAAAAAGATTTTAATTTTATTAAAAAAAAAAAAAAAAAAG
ACCGGGAATTCGATATCAAGCTTATCGACCTGCAGATCGTTCAAACATTTGGCAATAAA
GTTTCTTAAGATTGAATCCTGTTGCCGGTCTTGCGATGATTATCATATAATTTCTGTTGA
ATTACGTTAAGCATGTAATAATTAACATGTAATGCATGACGTTATTTATGAGATGGGTTT
TTATGATTAGAGTCCCGCAATTATACATTTAATACGCGATAGAAAACAAAATATAGCGCG
CAAACTAGGATAAATTATCGCGCGCGGTGTCATCTATGTTACTAGATTCTAGAGTCTCA
AGCTTCGGCGCGCC

Figure 80

TTAATTAAGAATTCGAGCTCCACCGCGGAAACCTCCTCGGATTCCATTGCCCAGCTAT
CTGTCACTTTATTGAGAAGATAGTGGAAAAGGAAGGTGGCTCCTACAAATGCCATCAT
TGCGATAAAGGAAAGGCCATCGTTGAAGATGCCTCTGCCGACAGTGGTCCCAAAGAT
GGACCCCCACCCACGAGGAGCATCGTGGAAAAAGAAGACGTTCCAACCACGTCTTCA
AAGCAAGTGGATTGATGTGATATCTCCACTGACGTAAGGGATGACGCACAATCCCACT
ATCCTTCGCAAGACCCTTCCTCTATATAAGGAAGTTCATTTCATTTGGAGAGGTATTAA
AATCTTAATAGGTTTTGATAAAAGCGAACGTGGGGAAACCCGAACCAAACCTTCTTCT
AAACTCTCTCTCATCTCTCTTAAAGCAAACTTCTCTCTTGTCTTTCTTGCGTGAGCGAT
CTTCAACGTTGTCAGATCGTGCTTCGGCACCAGTACAACGTTTTCTTTCACTGAAGCG
AAATCAAAGATCTCTTTGTGGACACGTAGTGCGGCGCCATTAAATAACGTGTACTTGT
CCTATTCTTGTCGGTGTGGTCTTGGGAAAAGAAAGCTTGCTGGAGGCTGCTGTTCAG
CCCCATACATTACTTGTTACGATTCTGCTGACTTTCGGCGGGTGCAATATCTCTACTTC
TGCTTGACGAGGTATTGTTGCCTGTACTTCTTTCTTCTTCTTCTTGCTGATTGGTTCTA
TAAGAAATCTAGTATTTTCTTTGAAACAGAGTTTTCCCGTGGTTTTCGAACTTGGAGAA
AGATTGTTAAGCTTCTGTATATTCTGCCCAAATTTGTCGGGCCCATGAAGGCAATAATT
GTACTACTCATGGTAGTAACATCCAATGCAGATCGAATCTGCACTGGAATAACATCTT
CAAACTCACCTCATGTGGTCAAAACAGCCACTCAAGGGGAGGTCAATGTGACTGGTG
TGATACCACTAACAACAACACCAACAAAATCTTATTTTGCAAATCTCAAAGGAACAAGG
ACCAGAGGGAAACTATGCCCAGACTGTCTCAACTGCACAGATCTGGATGTGGCTTTG
GGCAGACCAATGTGTGTGGGGACCACACCTTCGGCGAAGGCTTCAATACTCCACGAA
GTCAAACCTGTTACATCCGGGTGCTTTCCTATAATGCACGACAGAACAAAAATCAGGC
AACTACCCAATCTTCTCAGAGGATATGAAAATATCAGGCTATCAACCCAAAACGTCATC
GATGCGGAAAAGGCACCAGGAGGACCCTACAGACTTGGAACCTCAGGATCTTGCCCT
AACGCTACCAGTAAGAGCGGATTTTTCGCAACAATGGCTTGGGCTGTCCCAAAGGAC
AACAACAAAAATGCAACGAACCCACTAACAGTAGAAGTACCATACATTTGTACAGAAG
GGGAAGACCAAATCACTGTTTGGGGGTTCCATTCAGATAACAAAACCCAAATGAAGAA
CCTCTATGGAGACTCAAATCCTCAAAAGTTCACCTCATCTGCTAATGGAGTAACCACA
CACTATGTTTCTCAGATTGGCAGCTTCCCAGATCAAACAGAAGACGGAGGACTACCAC
AAAGCGGCAGGATTGTTGTTGATTACATGATGCAAAAACCTGGGAAAACAGGAACAAT
TGTCTACCAAAGAGGTGTTTTGTTGCCTCAAAAGGTGTGGTGCGCGAGTGGCAGGAG
CAAAGTAATAAAAGGGTCCTTGCCTTTAATTGGTGAAGCAGATTGCCTTCATGAAAAAT
ACGGTGGATTAAACAAAAGCAAGCCTTACTACACAGGAGAACATGCAAAAGCCATAGG
AAATTGCCCAATATGGGTGAAAACACCTTTGAAGCTCGCCAATGGAACCAAATATAGA
CCTCCTGCAAAACTATTAAAGGAAAGGGGTTTCTTCGGAGCTATTGCTGGTTTCCTAG
AAGGAGGATGGGAAGGAATGATTGCAGGCTGGCACGGATACACATCTCACGGAGCA
CATGGAGTGGCAGTGGCGGCGGACCTTAAGAGTACGCAAGAAGCTATAAACAAGATA
ACAAAAAATCTCAATTCTTTGAGTGAGCTAGAAGTAAAGAATCTTCAAAGACTAAGTGG
TGCCATGGATGAACTCCACAACGAAATACTCGAGCTGGATGAGAAAGTGGATGATCTC
AGAGCTGACACTATAAGCTCGCAAATAGAACTTGCAGTCTTGCTTTCCAACGAAGGAA
TAATAAACAGTGAAGATGAGCATCTATTGGCACTTGAGAGAAAACTAAAGAAAATGCT
GGGTCCCTCTGCTGTAGAGATAGGAAATGGATGCTTCGAAACCAAACACAAGTGCAA
CCAGACCTGCTTAGACAGGATAGCTGCTGGCACCTTTAATGCAGGAGAATTTTCTCTC
CCCACTTTTGATTCACTGAACATTACTGCTGCATCTTTAAATGATGATGGATTGGATAA
CCATACTATACTGCTCTATTACTCAACTGCTGCTTCTAGTTTGGCTGTAACATTGATGC
TAGCTATTTTTATTGTTTATATGGTCTCCAGAGACAACGTTTCATGCTCCATCTGTCTAT
AAAGGCCTATTTTCTTTAGTTTGAATTTACTGTTATTCGGTGTGCATTTCTATGTTTGGT
GAGCGGTTTTCTGTGCTCAGAGTGTGTTTATTTTATGTAATTTAATTTCTTTGTGAGCT
CCTGTTTAGCAGGTCGTCCCTTCAGCAAGGACACAAAAAGATTTTAATTTTATTAAAAA
AAAAAAAAAAAAAGACCGGGAATTCGATATCAAGCTTATCGACCTGCAGATCGTTCAA
ACATTTGGCAATAAAGTTTCTTAAGATTGAATCCTGTTGCCGGTCTTGCGATGATTATC
ATATAATTTCTGTTGAATTACGTTAAGCATGTAATAATTAACATGTAATGCATGACGTTA
TTTATGAGATGGGTTTTTATGATTAGAGTCCCGCAATTATACATTTAATACGCGATAGA
AAACAAAATATAGCGCGCAAACTAGGATAAATTATCGCGCGCGGTGTCATCTATGTTA
CTAGATTCTAGAGTCTCAAGCTTCGGCGCGCC

Figure 81

TTAATTAAGAATTCGAGCTCCACCGCGGAAACCTCCTCGGATTCCATTGCCCAGCTATCTGTC
ACTTTATTGAGAAGATAGTGGAAAAGGAAGGTGGCTCCTACAAATGCCATCATTGCGATAAAG
GAAAGGCCATCGTTGAAGATGCCTCTGCCGACAGTGGTCCCAAAGATGGACCCCCACCCAC
GAGGAGCATCGTGGAAAAAGAAGACGTTCCAACCACGTCTTCAAAGCAAGTGGATTGATGTG
ATATCTCCACTGACGTAAGGGATGACGCACAATCCCACTATCCTTCGCAAGACCCTTCCTCTA
TATAAGGAAGTTCATTTCATTTGGAGAGGTATTAAAATCTTAATAGGTTTTGATAAAAGCGAAC
GTGGGGAAACCCGAACCAAACCTTCTTCTAAACTCTCTCTCATCTCTCTTAAAGCAAACTTCTC
TCTTGTCTTTCTTGCGTGAGCGATCTTCAACGTTGTCAGATCGTGCTTCGGCACCAGTACAAC
GTTTTCTTTCACTGAAGCGAAATCAAAGATCTCTTTGTGGACACGTAGTGCGGCGCCATTAAA
TAACGTGTACTTGTCCTATTCTTGTCGGTGTGGTCTTGGGAAAAGAAAGCTTGCTGGAGGCTG
CTGTTCAGCCCCATACATTACTTGTTACGATTCTGCTGACTTTCGGCGGGTGCAATATCTCTA
CTTCTGCTTGACGAGGTATTGTTGCCTGTACTTCTTTCTTCTTCTTCTTGCTGATTGGTTCTAT
AAGAAATCTAGTATTTTCTTTGAAACAGAGTTTTCCCGTGGTTTTCGAACTTGGAGAAAGATTG
TTAAGCTTCTGTATATTCTGCCCAAATTTGTCGGGCCCATGGCGAAAAACGTTGCGATTTTCG
GCTTATTGTTTTCTCTTCTTGTGTTGGTTCCTTCTCAGATCTTCGCTGATCGAATCTGCACTGG
AATAACATCTTCAAACTCACCTCATGTGGTCAAAACAGCCACTCAAGGGGAGGTCAATGTGAC
TGGTGTGATACCACTAACAACAACACCAACAAAATCTTATTTTGCAAATCTCAAAGGAACAAGG
ACCAGAGGGAAACTATGCCCAGACTGTCTCAACTGCACAGATCTGGATGTGGCTTTGGGCAG
ACCAATGTGTGTGGGGACCACACCTTCGGCGAAGGCTTCAATACTCCACGAAGTCAAACCTG
TTACATCCGGGTGCTTTCCTATAATGCACGACAGAACAAAAATCAGGCAACTACCCAATCTTC
TCAGAGGATATGAAAATATCAGGCTATCAACCCAAAACGTCATCGATGCGGAAAAGGCACCA
GGAGGACCCTACAGACTTGGAACCTCAGGATCTTGCCCTAACGCTACCAGTAAGAGCGGATT
TTTCGCAACAATGGCTTGGGCTGTCCCAAAGGACAACAACAAAAATGCAACGAACCCACTAAC
AGTAGAAGTACCATACATTTGTACAGAAGGGGAAGACCAAATCACTGTTTGGGGGTTCCATTC
AGATAACAAAACCCAAATGAAGAACCTCTATGGAGACTCAAATCCTCAAAAGTTCACCTCATCT
GCTAATGGAGTAACCACACACTATGTTTCTCAGATTGGCAGCTTCCCAGATCAAACAGAAGAC
GGAGGACTACCACAAAGCGGCAGGATTGTTGTTGATTACATGATGCAAAAACCTGGGAAAAC
AGGAACAATTGTCTACCAAAGAGGTGTTTTGTTGCCTCAAAAGGTGTGGTGCGCGAGTGGCA
GGAGCAAAGTAATAAAAGGGTCCTTGCCTTTAATTGGTGAAGCAGATTGCCTTCATGAAAAAT
ACGGTGGATTAAACAAAAGCAAGCCTTACTACACAGGAGAACATGCAAAAGCCATAGGAAATT
GCCCAATATGGGTGAAAACACCTTTGAAGCTCGCCAATGGAACCAAATATAGACCTCCTGCAA
AACTATTAAAGGAAAGGGGTTTCTTCGGAGCTATTGCTGGTTTCCTAGAAGGAGGATGGGAA
GGAATGATTGCAGGCTGGCACGGATACACATCTCACGGAGCACATGGAGTGGCAGTGGCGG
CGGACCTTAAGAGTACGCAAGAAGCTATAAACAAGATAACAAAAAATCTCAATTCTTTGAGTGA
GCTAGAAGTAAAGAATCTTCAAAGACTAAGTGGTGCCATGGATGAACTCCACAACGAAATACT
CGAGCTGGATGAGAAAGTGGATGATCTCAGAGCTGACACTATAAGCTCGCAAATAGAACTTG
CAGTCTTGCTTTCCAACGAAGGAATAATAAACAGTGAAGATGAGCATCTATTGGCACTTGAGA
GAAAACTAAAGAAAATGCTGGGTCCCTCTGCTGTAGAGATAGGAAATGGATGCTTCGAAACCA
AACACAAGTGCAACCAGACCTGCTTAGACAGGATAGCTGCTGGCACCTTTAATGCAGGAGAA
TTTTCTCTCCCCACTTTTGATTCACTGAACATTACTGCTGCATCTTTAAATGATGATGGATTGG
ATAACCATACTATACTGCTCTATTACTCAACTGCTGCTTCTAGTTTGGCTGTAACATTGATGCT
AGCTATTTTTATTGTTTATATGGTCTCCAGAGACAACGTTTCATGCTCCATCTGTCTATAAAGG
CCTATTTTCTTTAGTTTGAATTTACTGTTATTCGGTGTGCATTTCTATGTTTGGTGAGCGGTTTT
CTGTGCTCAGAGTGTGTTTATTTTATGTAATTTAATTTCTTTGTGAGCTCCTGTTTAGCAGGTC
GTCCCTTCAGCAAGGACACAAAAAGATTTTAATTTTATTAAAAAAAAAAAAAAAAAAAGACCGGG
AATTCGATATCAAGCTTATCGACCTGCAGATCGTTCAAACATTTGGCAATAAAGTTTCTTAAGA
TTGAATCCTGTTGCCGGTCTTGCGATGATTATCATATAATTTCTGTTGAATTACGTTAAGCATG
TAATAATTAACATGTAATGCATGACGTTATTTATGAGATGGGTTTTTATGATTAGAGTCCCGCA
ATTATACATTTAATACGCGATAGAAAACAAAATATAGCGCGCAAACTAGGATAAATTATCGCGC
GCGGTGTCATCTATGTTACTAGATTCTAGAGTCTCAAGCTTCGGCGCGCC

Figure 82

ATGTTTGGGCGCGGACCAACAAGGAAGAGTGATAACACCAAATATTACGATATTCT
TGGTGTTTCAAAAAGTGCTAGTGAAGATGAAATCAAGAAAGCCTATAGAAAGGCAG
CGATGAAGAACCATCCAGATAAGGGTGGGGATCCTGAGAAGTTCAAGGAGTTGGG
CCAAGCATATGAAGTGTTGAGCGATCCTGAAAAGAAAGAACTGTATGATCAATATG
GTGAAGATGCCCTTAAAGAAGGAATGGGGGGAGGCGCAGGAAGCTCATTTCATAA
TCCGTTTGATATTTTCGAATCATTTTTTGGTGCAGGCTTTGGTGGTGGTGGTCCTT
CACGCGCAAGAAGACAGAAGCAAGGAGAAGATGTGGTGCATTCTATAAAGGTTTC
CTTGGAGGATGTGTATAACGGCACTACAAAGAAGCTATCACTTTCTAGGAATGCAC
TGTGCTCAAAATGTAAAGGGAAAGGTTCAAAAAGTGGAACTGCTGGAAGGTGTTTT
GGATGCCAGGGCACAGGTATGAAGATTACCAGAAGGCAAATTGGACTGGGCATGA
TTCAACAAATGCAACACGTCTGTCCTGACTGCAAAGGAACAGGCGAGGTCATTAG
TGAGAGAGATAGATGCCCTCAATGCAAGGGAAACAAGATTACTCAAGAAAAGAAG
GTGCTGGAGGTGCATGTGGAAAAGGGGATGCAGCAGGGTCACAAGATTGTATTCG
AAGGACAAGCTGATGAAGCTCCTGATACAATCACAGGAGACATAGTTTTTGTCTTG
CAAGTAAAGGGACATCCGAAGTTTCGGAGGGAGCGTGATGACCTCCACATTGAAC
ACAATTTGAGCTTAACTGAGGCTCTCTGTGGCTTCCAGTTTAATGTCACACATCTT
GATGGAAGGCAACTATTGGTCAAATCGAACCCCGGCGAAGTCATCAAGCCAGGTC
AACATAAAGCTATAAATGATGAGGGAATGCCACAACATGGTAGGCCGTTCATGAAG
GGACGCCTATACATCAAGTTTAGTGTTGATTTCCCGGATTCGGGTTTTCTTTCCCC
AAGCCAAAGCCTGGAATTAGAAAAGATATTACCTCAAAAGACAAGCAAGAACTTGT
CCCAAAAGGAGGTAGATGATTGTGAGGAGACCACCCTGCATGATGTCAATATTGC
AGAGGAGATGAGTCGAAAGAAGCAACAATACCGTGAGGCATATGATGACGATGAT
GATGAAGATGATGAGCACTCGCAGCCTCGGGTGCAATGCGCTCAACAGTAG

Figure 83

AAGCTTGCATGCCTGCAGGTCGACTCTAGAGGATCCCCGGGCTGGTCTGTACATTCATCTTGCCGCCTTTGCA
TTCACTTGGCCACAAAGAGTAGAGAGAAGGAAGAGAAGAGCCCAGACTTCAAGAAGCGACCTTGCAAGTGCAC
TCGAGGGTCAGAAACTGTATATCATATCTATGTGAGAGAAAGGGGAACATTTGAGATGGAGTCCATTTACTTGA
GGTATACTTATTATTTTGATCAATAAATTTGTATACTTCTTATTTAGATCAATAAATTTGTCATTAAGCTATAATCCA
AAATAAATTACGATCAAATATGCAAATGTTAGCCAGTACTTGTGTTAAACTTGATGGCATCTCTTGGTTTCTTTGG
CAATCACATGCCTAAGAAATAAATAGTATCATATGATTGTGTTTGGTCAGACTTCAGAGTCAGATGACTCTGTTT
GGATAAACAGCTTAATTAAGCGCTTATAGAATATCATATGATTGTGTTTGGTCAGACTTCAGAGCATCTCTTGGT
TTCTCTGGCAATCATATGCCTAAGAAATAAATAGTATCATATGATTGTGTTTGGTCAGACTTCAGAGTCAGATGA
CCCTGTTTGGGTAAACAGCTTAATTAAGTGCTTATAGAATAAGCGCTTATCATATAAGTGCTTTTGTACAGTTATT
TCTATGAAAGTAGAAGAAATAGTCATATTGTTTTAATATAAGCTATCCTGGAGAGCTTGTGGAAATAACCAGAAA
AGAACTTATGGACACGTCATGAGCTGTTTACATAAGATCTCCCTAACAGTCTCAAAAGTGTTTATGCCAGTAGAT
AAATTCAAATAAGTCAATCTAAACAGACCCTAAATCCATTATGGTACCTATCATTTTAGCTTATTCCATCTTTATTA
AGAATGTCATGAGATAACATAATGATAACACATTATTTTGACACAAATGGGCAGATCTAGCAATTTAACTCTGGA
GTCCTTCAAGACTGCTGTTCTTACGAAGTTCACGTCCCTGAATCATGTTCCTGTATGGAAGCCTGAAAGACCTC
AAATTCTAAAAGGTGGCGATAAATTGAAGGTTTACAAAATATACCCTGCGGGCTTGACACAGAGGCAAGCTCTT
TATACCTTCCAGTTCAACGGGGATGTTGATTTCAGAAGTCACTTGGAGAGCAATCCTTGTGCCAAGTTTGAAGT
AATTTTTGTGTAGCATATGTTGAGCTACCTACAATTTACATGATCACCTAGCATTAGCTCTTTCACTTAACTGAGA
GAATGAAGTTTTAGGAATGAGTATGACCATGGAGTCGGCATGGCTTTGTAATGCCTACCCTACTTTGGCCAACT
CATCGGGGATTTACATTCAGAAAATATACATGACTTCAACCATACTTAAACCCCTTTTTGTAAGATAACTGAATGT
TCATATTTAATGTTGGGTTGTAGTGTTTTTACTTGATTATATCCAGACAGTTACAAGTTGGACAACAAGATTGTG
GGTCTGTACTGTTATTTATTTATTTTTTTTTTAGCAGAAACACCTTATCTTTTGTTTCGTTTGAATGTAGAATGAAA
ATAAAAGAAAGAAAATATAACATCATCGGCCGCGCTTGTCTAATTTCGGGCAGTTAGGATCCTCTCCGGTCACC
GGAAAGTTTCAGTAGAAGAAACAAAACACCGTGACTAAAATGATACTATTATTTTATTTATTGTGTTTTTCTTTTTT
CTACCGGAACTTTTTAGAACGGATCCCAACTCGTTCCGGGGCCGCTACAACTGAAACAAAAGAAGATATTTTCT
CTCTCTTCAGAAATGTAAGTTTTCCTTTACAGATACCCATTCACCATTTGATTCAGATGTGGTGACTAGAGATAA
AGCATACTAATTTGACTCTTGGAAACCCATAAAGTTTATGTTATCCGTGTTCTGGACCAATCCACTTGGGGGCAT
AACCTGTGTCTATGTGTGGTTTGGTTTCCATTCTGATTTATGCGGCGACTTGTAATTTAAAATCTAGGAGGGGCA
GACATTGAACAATCCCAATATTTTAATAACTTATGCAAGATTTTTTTTATTAATGAGATGATGTGTTTGTGACTGA
GATTGAGTCATACATTTCACTAAGAAATGGTTCCAAGTACCAAACTATCATGACCCAGTTGCAAACATGACGTTC
GGGAGTGGTCACTTTGATAGTTCAATTTCATCTTGGCTTCTTATTCCTTTTATAATTCTAATTCTTCTTGTGTAAAC
TATTTCATGTATTATTTTTCTTTAAAATTTACATGTCATTTATTTTGCCTCACTAACTCAATTTTGCATATAACAATG
ATAAGTGATATTTTGACTCACAAAATTTACATCAAATTTCGACATCGTTTATTATGTTCATTGGATGATTAACAAAT
ATAACAAACTTTGCAACTAATTAACCACCAACTGAATATAATTAACTATAACTGTGAAAGTAGTTAACTCATTTTT
ATATTTCATAGATCAAATAAGAGAAATAACGGTATATTAATCCCTCCAAAAAAAAAAAACGGTATATTTACTAAAA
AATCTAAGCCACGTAGGAGGATAACAGGATCCCCGTAGGAGGATAACATCCAATCCAACCAATCACAACAATC
CTGATGAGATAACCCACTTTAAGCCCACGCATCTGTGGCACATCTACATTATCTAAATCACACATTCTTCCACAC
ATCTGAGCCACACAAAAACCAATCCACATCTTTATCACCCATTCTATAAAAAATCACACTTTGTGAGTCTACACTT
TGATTCCCTTCAAACACATACAAAGAGAAGAGACTAATTAATTAATTAATCATCTTGAGAGAAAATGTTTGGGCG
CGGACCAACAAGGAAGAGTGATAACACCAAATATTACGATATTCTTGGTGTTTCAAAAAGTGCTAGTGAAGATG
AAATCAAGAAAGCCTATAGAAAGGCAGCGATGAAGAACCATCCAGATAAGGGTGGGGATCCTGAGAAGTTCAA
GGAGTTGGGCCAAGCATATGAAGTGTTGAGCGATCCTGAAAAGAAAGAACTGTATGATCAATATGGTGAAGAT
GCCCTTAAAGAAGGAATGGGGGGAGGCGCAGGAAGCTCATTTCATAATCCGTTTGATATTTTCGAATCATTTTT
TGGTGCAGGCTTTGGTGGTGGTGGTCCTTCACGCGCAAGAAGACAGAAGCAAGGAGAAGATGTGGTGCATTC
TATAAAGGTTTCCTTGGAGGATGTGTATAACGGCACTACAAAGAAGCTATCACTTTCTAGGAATGCACTGTGCT
CAAAATGTAAAGGGAAAGGTTCAAAAAGTGGAACTGCTGGAAGGTGTTTTGGATGCCAGGGCACAGGTATGAA
GATTACCAGAAGGCAAATTGGACTGGGCATGATTCAACAAATGCAACACGTCTGTCCTGACTGCAAAGGAACA
GGCGAGGTCATTAGTGAGAGAGATAGATGCCCTCAATGCAAGGGAAACAAGATTACTCAAGAAAAGAAGGTGC
TGGAGGTGCATGTGGAAAAGGGGATGCAGCAGGGTCACAAGATTGTATTCGAAGGACAAGCTGATGAAGCTC
CTGATACAATCACAGGAGACATAGTTTTTGTCTTGCAAGTAAAGGGACATCCGAAGTTTCGGAGGGAGCGTGAT
GACCTCCACATTGAACACAATTTGAGCTTAACTGAGGCTCTCTGTGGCTTCCAGTTTAATGTCACACATCTTGAT
GGAAGGCAACTATTGGTCAAATCGAACCCCGGCGAAGTCATCAAGCCAGGTCAACATAAAGCTATAAATGATG
AGGGAATGCCACAACATGGTAGGCCGTTCATGAAGGGACGCCTATACATCAAGTTTAGTGTTGATTTCCCGGA
TTCGGGTTTTCTTTCCCCAAGCCAAAGCCTGGAATTAGAAAAGATATTACCTCAAAAGACAAGCAAGAACTTGT
CCCAAAAGGAGGTAGATGATTGTGAGGAGACCACCCTGCATGATGTCAATATTGCAGAGGAGATGAGTCGAAA
GAAGCAACAATACCGTGAGGCATATGATGACGATGATGATGAAGATGATGAGCACTCGCAGCCTCGGGTGCAA
TGCGCTCAACAGTAGGAGCTCAGCTCGAATTTCCCCGATCGTTCAAACATTTGGCAATAAAGTTTCTTAAGATT
GAATCCTGTTGCCGGTCTTGCGATGATTATCATATAATTTCTGTTGAATTACGTTAAGCATGTAATAATTAACATG
TAATGCATGACGTTATTTATGAGATGGGTTTTTATGATTAGAGTCCCGCAATTATACATTTAATACGCGATAGAA
AACAAAATATAGCGCGCAAACTAGGATAAATTATCGCGCGCGGTGTCATCTATGTTACTAGATCGAATTC

Figure 84

AAGCTTGCATGCCTGCAGGTCGACTCTAGAGGATCCCCGGGCTGGTCTGTACATTCATCTTGCCGCCTTTGCATTCAC
TTGGCCACAAAGAGTAGAGAGAAGGAAGAGAAGAGCCCAGACTTCAAGAAGCGACCTTGCAAGTGCACTCGAGGGT
CAGAAACTGTATATCATATCTATGTGAGAGAAAGGGGAACATTTGAGATGGAGTCCATTTACTTGAGGTATACTTATTA
TTTTGATCAATAAATTTGTATACTTCTTATTTAGATCAATAAATTTGTCATTAAGCTATAATCCAAAATAAATTACGATCAA
ATATGCAAATGTTAGCCAGTACTTGTGTTAAACTTGATGGCATCTCTTGGTTTCTTTGGCAATCACATGCCTAAGAAAT
AAATAGTATCATATGATTGTGTTTGGTCAGACTTCAGAGTCAGATGACTCTGTTTGGATAAACAGCTTAATTAAGCGCT
TATAGAATATCATATGATTGTGTTTGGTCAGACTTCAGAGCATCTCTTGGTTTCTCTGGCAATCATATGCCTAAGAAATA
AATAGTATCATATGATTGTGTTTGGTCAGACTTCAGAGTCAGATGACCCTGTTTGGGTAAACAGCTTAATTAAGTGCTT
ATAGAATAAGCGCTTATCATATAAGTGCTTTTGTACAGTTATTTCTATGAAAGTAGAAGAAATAGTCATATTGTTTTAATA
TAAGCTATCCTGGAGAGCTTGTGGAAATAACCAGAAAAGAACTTATGGACACGTCATGAGCTGTTTACATAAGATCTC
CCTAACAGTCTCAAAAGTGTTTATGCCAGTAGATAAATTCAAATAAGTCAATCTAAACAGACCCTAAATCCATTATGGTA
CCTATCATTTTAGCTTATTCCATCTTTATTAAGAATGTCATGAGATAACATAATGATAACACATTATTTTGACACAAATGG
GCAGATCTAGCAATTTAACTCTGGAGTCCTTCAAGACTGCTGTTCTTACGAAGTTCACGTCCCTGAATCATGTTCCTGT
ATGGAAGCCTGAAAGACCTCAAATTCTAAAAGGTGGCGATAAATTGAAGGTTTACAAAATATACCCTGCGGGCTTGAC
ACAGAGGCAAGCTCTTTATACCTTCCAGTTCAACGGGGATGTTGATTTCAGAAGTCACTTGGAGAGCAATCCTTGTGC
CAAGTTTGAAGTAATTTTTGTGTAGCATATGTTGAGCTACCTACAATTTACATGATCACCTAGCATTAGCTCTTTCACTT
AACTGAGAGAATGAAGTTTTAGGAATGAGTATGACCATGGAGTCGGCATGGCTTTGTAATGCCTACCCTACTTTGGCC
AACTCATCGGGGATTTACATTCAGAAAATATACATGACTTCAACCATACTTAAACCCCTTTTTGTAAGATAACTGAATGT
TCATATTTAATGTTGGGTTGTAGTGTTTTTACTTGATTATATCCAGACAGTTACAAGTTGGACAACAAGATTGTGGGTCT
GTACTGTTATTTATTTATTTTTTTTTTAGCAGAAACACCTTATCTTTTGTTTCGTTTGAATGTAGAATGAAAATAAAAGAA
AGAAAATATAACATCATCGGCCGCGCTTGTCTAATTTCGGGCAGTTAGGATCCTCTCCGGTCACCGGAAAGTTTCAGT
AGAAGAAACAAAACACCGTGACTAAAATGATACTATTATTTTATTTATTGTGTTTTTCTTTTTTCTACCGGAACTTTTTAG
AACGGATCCCAACTCGTTCCGGGGCCGCTACAACTGAAACAAAAGAAGATATTTTCTCTCTCTTCAGAAATGTAAGTTT
TCCTTTACAGATACCCATTCACCATTTGATTCAGATGTGGTGACTAGAGATAAAGCATACTAATTTGACTCTTGGAAAC
CCATAAAGTTTATGTTATCCGTGTTCTGGACCAATCCACTTGGGGGCATAACCTGTGTCTATGTGTGGTTTGGTTTCCA
TTCTGATTTATGCGGCGACTTGTAATTTAAAATCTAGGAGGGGCAGACATTGAACAATCCCAATATTTTAATAACTTATG
CAAGATTTTTTTTATTAATGAGATGATGTGTTTGTGACTGAGATTGAGTCATACATTTCACTAAGAAATGGTTCCAAGTA
CCAAACTATCATGACCCAGTTGCAAACATGACGTTCGGGAGTGGTCACTTTGATAGTTCAATTTCATCTTGGCTTCTTA
TTCCTTTTATAATTCTAATTCTTCTTGTGTAAACTATTTCATGTATTATTTTTCTTTAAAATTTACATGTCATTTATTTTGCC
TCACTAACTCAATTTTGCATATAACAATGATAAGTGATATTTTGACTCACAAAATTTACATCAAATTTCGACATCGTTTAT
TATGTTCATTGGATGATTAACAAATATAACAAACTTTGCAACTAATTAACCACCAACTGAATATAATTAACTATAACTGTG
AAAGTAGTTAACTCATTTTTATATTTCATAGATCAAATAAGAGAAATAACGGTATATTAATCCCTCCAAAAAAAAAAAAC
GGTATATTTACTAAAAAATCTAAGCCACGTAGGAGGATAACAGGATCCCCGTAGGAGGATAACATCCAATCCAACCAA
TCACAACAATCCTGATGAGATAACCCACTTTAAGCCCACGCATCTGTGGCACATCTACATTATCTAAATCACACATTCT
TCCACACATCTGAGCCACACAAAAACCAATCCACATCTTTATCACCCATTCTATAAAAAATCACACTTTGTGAGTCTACA
CTTTGATTCCCTTCAAACACATACAAAGAGAAGAGACTAATTAATTAATTAATCATCTTGAGAGAAAATGTCGGGTAAA
GGAGAAGGACCAGCTATCGGTATCGATCTTGGTACCACTTACTCTTGCGTCGGAGTATGGCAACACGACCGTGTTGA
GATCATTGCTAATGATCAAGGAAACAGAACCACGCCATCTTACGTTGCTTTCACCGACTCCGAGAGGTTGATCGGTGA
CGCAGCTAAGAATCAGGTCGCCATGAACCCCGTTAACACCGTTTTCGACGCTAAGAGGTTGATCGGTCGTCGTTTCTC
TGACAGCTCTGTTCAGAGTGACATGAAATTGTGGCCATTCAAGATTCAAGCCGGACCTGCCGATAAGCCAATGATCTA
CGTCGAATACAAGGGTGAAGAGAAAGAGTTCGCAGCTGAGGAGATTTCTTCCATGGTTCTTATTAAGATGCGTGAGAT
TGCTGAGGCTTACCTTGGTGTCACAATCAAGAACGCCGTTGTTACCGTTCCAGCTTACTTCAACGACTCTCAGCGTCA
GGCTACAAAGGATGCTGGTGTCATCGCTGGTTTGAACGTTATGCGAATCATCAACGAGCCTACAGCCGCCGCTATTG
CCTACGGTCTTGACAAAAAGGCTACCAGCGTTGGAGAGAAGAATGTTCTTATCTTCGATCTTGGTGGTGGCACTTTTG
ATGTCTCTCTTCTTACCATTGAAGAGGGTATCTTTGAGGTGAAGGCAACTGCTGGTGACACCCATCTTGGTGGGGAAG
ATTTTGACAACAGAATGGTTAACCACTTTGTCCAAGAGTTCAAGAGGAAGAGTAAGAAGGATATCACCGGTAACCCAA
GAGCTCTTAGGAGGTTGAGAACTTCCTGTGAGAGAGCGAAGAGGACTCTTTCTTCCACTGCTCAGACCACCATCGAG
ATTGACTCTCTATACGAGGGTATCGACTTCTACTCCACCATCACCCGTGCTAGATTTGAGGAGCTCAACATGGATCTC
TTCAGGAAGTGTATGGAGCCAGTTGAGAAGTGTCTTCGTGATGCTAAGATGGACAAGAGCACTGTTCATGATGTTGTC
CTTGTTGGTGGTTCTACCCGTATCCCTAAGGTTCAGCAATTGCTCCAGGACTTCTTCAACGGCAAAGAGCTTTGCAAG
TCTATTAACCCTGATGAGGCTGTTGCCTACGGTGCTGCTGTCCAGGGAGCTATTCTCAGCGGTGAAGGAAACGAGAA
GGTTCAAGATCTTCTATTGCTCGATGTCACTCCTCTCTCCCTTGGTTTGGAAACTGCCGGTGGTGTCATGACCACTTTG
ATCCCAAGGAACACAACCATCCCAACCAAGAAGGAACAAGTCTTCTCCACCTACTCAGACAACCAACCCGGTGTGTTG
ATCCAGGTGTACGAAGGAGAGAGAGCCAGAACCAAGGACAACAACCTTCTTGGTAAATTTGAGCTCTCCGGAATTCC
TCCAGCTCCTCGTGGTGTCCCCCAGATCACAGTCTGCTTTGACATTGATGCCAATGGTATCCTCAATGTCTCTGCTGA
GGACAAGACCACCGGACAGAAGAACAAGATCACCATCACCAATGACAAGGGTCGTCTCTCCAAGGATGAGATTGAGA
AGATGGTTCAAGAGGCTGAGAAGTACAAGTCCGAAGACGAGGAGCACAAGAAGAAGGTTGAAGCCAAGAACGCTCT
CGAGAACTACGCTTACAACATGAGGAACACCATCCAAGACGAGAAGATTGGTGAGAAGCTCCCGGCTGCAGACAAGA
AGAAGATCGAGGATTCTATTGAGCAGGCGATTCAATGGCTCGAGGGTAACCAGTTGGCTGAGGCTGATGAGTTCGAA
GACAAGATGAAGGAATTGGAGAGCATCTGCAACCCAATCATTGCCAAGATGTACCAAGGAGCTGGTGGTGAAGCCGG
TGGTCCAGGTGCCTCTGGTATGGACGATGATGCTCCCCCTGCTTCAGGCGGTGCTGGACCTAAGATCGAGGAGGTC
GACTAAGAGCTCAGCTCGAATTTCCCCGATCGTTCAAACATTTGGCAATAAAGTTTCTTAAGATTGAATCCTGTTGCCG
GTCTTGCGATGATTATCATATAATTTCTGTTGAATTACGTTAAGCATGTAATAATTAACATGTAATGCATGACGTTATTTA
TGAGATGGGTTTTTATGATTAGAGTCCCGCAATTATACATTTAATACGCGATAGAAAACAAAATATAGCGCGCAAACTA
GGATAAATTATCGCGCGCGGTGTCATCTATGTTACTAGATCGAATTC

Figure 85A

AAGCTTGCATGCCTGCAGGTCGACTCTAGAGGATCCCCGGGCTGGTCTGTACATTCATCTTGCCGCCTTTGCATTCA
CTTGGCCACAAAGAGTAGAGAGAAGGAAGAGAAGAGCCCAGACTTCAAGAAGCGACCTTGCAAGTGCACTCGAGGG
TCAGAAACTGTATATCATATCTATGTGAGAGAAAGGGGAACATTTGAGATGGAGTCCATTTACTTGAGGTATACTTATT
ATTTTGATCAATAAATTTGTATACTTCTTATTTAGATCAATAAATTTGTCATTAAGCTATAATCCAAAATAAATTACGATC
AAATATGCAAATGTTAGCCAGTACTTGTGTTAAACTTGATGGCATCTCTTGGTTTCTTTGGCAATCACATGCCTAAGAA
ATAAATAGTATCATATGATTGTGTTTGGTCAGACTTCAGAGTCAGATGACTCTGTTTGGATAAACAGCTTAATTAAGCG
CTTATAGAATATCATATGATTGTGTTTGGTCAGACTTCAGAGCATCTCTTGGTTTCTCTGGCAATCATATGCCTAAGAA
ATAAATAGTATCATATGATTGTGTTTGGTCAGACTTCAGAGTCAGATGACCCTGTTTGGGTAAACAGCTTAATTAAGTG
CTTATAGAATAAGCGCTTATCATATAAGTGCTTTTGTACAGTTATTTCTATGAAAGTAGAAGAAATAGTCATATTGTTTT
AATATAAGCTATCCTGGAGAGCTTGTGGAAATAACCAGAAAAGAACTTATGGACACGTCATGAGCTGTTTACATAAGA
TCTCCCTAACAGTCTCAAAAGTGTTTATGCCAGTAGATAAATTCAAATAAGTCAATCTAAACAGACCCTAAATCCATTA
TGGTACCTATCATTTTAGCTTATTCCATCTTTATTAAGAATGTCATGAGATAACATAATGATAACACATTATTTTGACAC
AAATGGGCAGATCTAGCAATTTAACTCTGGAGTCCTTCAAGACTGCTGTTCTTACGAAGTTCACGTCCCTGAATCATG
TTCCTGTATGGAAGCCTGAAAGACCTCAAATTCTAAAAGGTGGCGATAAATTGAAGGTTTACAAAATATACCCTGCGG
GCTTGACACAGAGGCAAGCTCTTTATACCTTCCAGTTCAACGGGGATGTTGATTTCAGAAGTCACTTGGAGAGCAAT
CCTTGTGCCAAGTTTGAAGTAATTTTTGTGTAGCATATGTTGAGCTACCTACAATTTACATGATCACCTAGCATTAGCT
CTTTCACTTAACTGAGAGAATGAAGTTTTAGGAATGAGTATGACCATGGAGTCGGCATGGCTTTGTAATGCCTACCCT
ACTTTGGCCAACTCATCGGGGATTTACATTCAGAAAATATACATGACTTCAACCATACTTAAACCCCTTTTTGTAAGAT
AACTGAATGTTCATATTTAATGTTGGGTTGTAGTGTTTTTACTTGATTATATCCAGACAGTTACAAGTTGGACAACAAG
ATTGTGGGTCTGTACTGTTATTTATTTATTTTTTTTTTAGCAGAAACACCTTATCTTTTGTTTCGTTTGAATGTAGAATGA
AAATAAAAGAAAGAAAATATAACATCATCGGCCGCGCTTGTCTAATTTCGGGCAGTTAGGATCCTCTCCGGTCACCG
GAAAGTTTCAGTAGAAGAAACAAAACACCGTGACTAAAATGATACTATTATTTTATTTATTGTGTTTTTCTTTTTTCTAC
CGGAACTTTTTAGAACGGATCCCAACTCGTTCCGGGGCCGCTACAACTGAAACAAAAGAAGATATTTTCTCTCTCTTC
AGAAATGTAAGTTTTCCTTTACAGATACCCATTCACCATTTGATTCAGATGTGGTGACTAGAGATAAAGCATACTAATT
TGACTCTTGGAAACCCATAAAGTTTATGTTATCCGTGTTCTGGACCAATCCACTTGGGGGCATAACCTGTGTCTATGT
GTGGTTTGGTTTCCATTCTGATTTATGCGGCGACTTGTAATTTAAAATCTAGGAGGGGCAGACATTGAACAATCCCAA
TATTTTAATAACTTATGCAAGATTTTTTTATTAATGAGATGATGTGTTTGTGACTGAGATTGAGTCATACATTTCACTA
AGAAATGGTTCCAAGTACCAAACTATCATGACCCAGTTGCAAACATGACGTTCGGGAGTGGTCACTTTGATAGTTCAA
TTTCATCTTGGCTTCTTATTCCTTTTATAATTCTAATTCTTCTTGTGTAAACTATTTCATGTATTATTTTTCTTTAAAATTT
ACATGTCATTTATTTTGCCTCACTAACTCAATTTTGCATATAACAATGATAAGTGATATTTTGACTCACAAAATTTACAT
CAAATTTCGACATCGTTTATTATGTTCATTGGATGATTAACAAATATAACAAACTTTGCAACTAATTAACCACCAACTGA
ATATAATTAACTATAACTGTGAAAGTAGTTAACTCATTTTTATATTTCATAGATCAAATAAGAGAAATAACGGTATATTA
ATCCCTCCAAAAAAAAAAAACGGTATATTTACTAAAAAATCTAAGCCACGTAGGAGGATAACAGGATCCCCGTAGGAG
GATAACATCCAATCCAACCAATCACAACAATCCTGATGAGATAACCCACTTTAAGCCCACGCATCTGTGGCACATCTA
CATTATCTAAATCACACATTCTTCCACACATCTGAGCCACACAAAAACCAATCCACATCTTTATCACCCATTCTATAAAA
AATCACACTTTGTGAGTCTACACTTTGATTCCCTTCAAACACATACAAAGAGAAGAGACTAATTAATTAATTAATCATCT
TGAGAGAAAATGTCGGGTAAAGGAGAAGGACCAGCTATCGGTATCGATCTTGGTACCACTTACTCTTGCGTCGGAGT
ATGGCAACACGACCGTGTTGAGATCATTGCTAATGATCAAGGAAACAGAACCACGCCATCTTACGTTGCTTTCACCG
ACTCCGAGAGGTTGATCGGTGACGCAGCTAAGAATCAGGTCGCCATGAACCCCGTTAACACCGTTTTCGACGCTAAG
AGGTTGATCGGTCGTCGTTTCTCTGACAGCTCTGTTCAGAGTGACATGAAATTGTGGCCATTCAAGATTCAAGCCGG
ACCTGCCGATAAGCCAATGATCTACGTCGAATACAAGGGTGAAGAGAAAGAGTTCGCAGCTGAGGAGATTTCTTCCA
TGGTTCTTATTAAGATGCGTGAGATTGCTGAGGCTTACCTTGGTGTCACAATCAAGAACGCCGTTGTTACCGTTCCAG
CTTACTTCAACGACTCTCAGCGTCAGGCTACAAAGGATGCTGGTGTCATCGCTGGTTTGAACGTTATGCGAATCATCA
ACGAGCCTACAGCCGCCGCTATTGCCTACGGTCTTGACAAAAAGGCTACCAGCGTTGGAGAGAAGAATGTTCTTATC
TTCGATCTTGGTGGTGGCACTTTTGATGTCTCTCTTCTTACCATTGAAGAGGGTATCTTTGAGGTGAAGGCAACTGCT
GGTGACACCCATCTTGGTGGGGAAGATTTTGACAACAGAATGGTTAACCACTTTGTCCAAGAGTTCAAGAGGAAGAG
TAAGAAGGATATCACCGGTAACCCAAGAGCTCTTAGGAGGTTGAGAACTTCCTGTGAGAGAGCGAAGAGGACTCTTT
CTTCCACTGCTCAGACCACCATCGAGATTGACTCTCTATACGAGGGTATCGACTTCTACTCCACCATCACCCGTGCTA
GATTTGAGGAGCTCAACATGGATCTCTTCAGGAAGTGTATGGAGCCAGTTGAGAAGTGTCTTCGTGATGCTAAGATG
GACAAGAGCACTGTTCATGATGTTGTCCTTGTTGGTGGTTCTACCCGTATCCCTAAGGTTCAGCAATTGCTCCAGGAC
TTCTTCAACGGCAAAGAGCTTTGCAAGTCTATTAACCCTGATGAGGCTGTTGCCTACGGTGCTGCTGTCCAGGGAGC
TATTCTCAGCGGTGAAGGAAACGAGAAGGTTCAAGATCTTCTATTGCTCGATGTCACTCCTCTCTCCCTTGGTTTGGA
AACTGCCGGTGGTGTCATGACCACTTTGATCCCAAGGAACACAACCATCCCAACCAAGAAGGAACAAGTCTTCTCCA
CCTACTCAGACAACCAACCCGGTGTGTTGATCCAGGTGTACGAAGGAGAGAGAGCCAGAACCAAGGACAACAACCT
TCTTGGTAAATTTGAGCTCTCCGGAATTCCTCCAGCTCCTCGTGGTGTCCCCCAGATCACAGTCTGCTTTGACATTGA
TGCCAATGGTATCCTCAATGTCTCTGCTGAGGACAAGACCACCGGACAGAAGAACAAGATCACCATCACCAATGACA
AGGGTCGTCTCTCCAAGGATGAGATTGAGAAGATGGTTCAAGAGGCTGAGAAGTACAAGTCCGAAGACGAGGAGCA
CAAGAAGAAGGTTGAAGCCAAGAACGCTCTCGAGAACTACGCTTACAACATGAGGAACACCATCCAAGACGAGAAG
ATTGGTGAGAAGCTCCCGGCTGCAGACAAGAAGAAGATCGAGGATTCTATTGAGCAGGCGATTCAATGGCTCGAGG
GTAACCAGTTGGCTGAGGCTGATGAGTTCGAAGACAAGATGAAGGAATTGGAGAGCATCTGCAACCCAATCATTGCC
AAGATGTACCAAGGAGCTGGTGGTGAAGCCGGTGGTCCAGGTGCCTCTGGTATGGACGATGATGCTCCCCCTGCTT
CAGGCGGTGCTGGACCTAAGATCGAGGAGGTCGACTAAGAGCTCAGCTCGAATTTCCCCGATCGTTCAAACATTTG
GCAATAAAGTTTCTTAAGATTGAATCCTGTTGCCGGTCTTGCGATGATTATCATATAATTTCTGTTGAATTACGTTAAG
CATGTAATAATTAACATGTAATGCATGACGTTATTTATGAGATGGGTTTTTATGATTAGAGTCCCGCAATTATACATTTA

Figure 85B

ATACGCGATAGAAAACAAAATATAGCGCGCAAACTAGGATAAATTATCGCGCGCGGTGTCATCTATGTTACTAG
ATCGAATTCGTAATCATGGTCATAGCTGTTTCCTGTGTGAAATTGTTATCCGGGGCTGGTCTGTACATTCATCTT
GCCGCCTTTGCATTCACTTGGCCACAAAGAGTAGAGAGAAGGAAGAGAAGAGCCCAGACTTCAAGAAGCGAC
CTTGCAAGTGCACTCGAGGGTCAGAAACTGTATATCATATCTATGTGAGAGAAAGGGGAACATTTGAGATGGA
GTCCATTTACTTGAGGTATACTTATTATTTTGATCAATAAATTTGTATACTTCTTATTTAGATCAATAAATTTGTCA
TTAAGCTATAATCCAAAATAAATTACGATCAAATATGCAAATGTTAGCCAGTACTTGTGTTAAACTTGATGGCAT
CTCTTGGTTTCTTTGGCAATCACATGCCTAAGAAATAAATAGTATCATATGATTGTGTTTGGTCAGACTTCAGAG
TCAGATGACTCTGTTTGGATAAACAGCTTAATTAAGCGCTTATAGAATATCATATGATTGTGTTTGGTCAGACTT
CAGAGCATCTCTTGGTTTCTCTGGCAATCATATGCCTAAGAAATAAATAGTATCATATGATTGTGTTTGGTCAGA
CTTCAGAGTCAGATGACCCTGTTTGGGTAAACAGCTTAATTAAGTGCTTATAGAATAAGCGCTTATCATATAAGT
GCTTTTGTACAGTTATTTCTATGAAAGTAGAAGAAATAGTCATATTGTTTTAATATAAGCTATCCTGGAGAGCTTG
TGGAAATAACCAGAAAAGAACTTATGGACACGTCATGAGCTGTTTACATAAGATCTCCCTAACAGTCTCAAAAG
TGTTTATGCCAGTAGATAAATTCAAATAAGTCAATCTAAACAGACCCTAAATCCATTATGGTACCTATCATTTTAG
CTTATTCCATCTTTATTAAGAATGTCATGAGATAACATAATGATAACACATTATTTTGACACAAATGGGCAGATCT
AGCAATTTAACTCTGGAGTCCTTCAAGACTGCTGTTCTTACGAAGTTCACGTCCCTGAATCATGTTCCTGTATGG
AAGCCTGAAAGACCTCAAATTCTAAAAGGTGGCGATAAATTGAAGGTTTACAAAATATACCCTGCGGGCTTGAC
ACAGAGGCAAGCTCTTTATACCTTCCAGTTCAACGGGGATGTTGATTTCAGAAGTCACTTGGAGAGCAATCCTT
GTGCCAAGTTTGAAGTAATTTTTGTGTAGCATATGTTGAGCTACCTACAATTTACATGATCACCTAGCATTAGCT
CTTTCACTTAACTGAGAGAATGAAGTTTTAGGAATGAGTATGACCATGGAGTCGGCATGGCTTTGTAATGCCTA
CCCTACTTTGGCCAACTCATCGGGGATTTACATTCAGAAAATATACATGACTTCAACCATACTTAAACCCCTTTT
TGTAAGATAACTGAATGTTCATATTTAATGTTGGGTTGTAGTGTTTTTACTTGATTATATCCAGACAGTTACAAGT
TGGACAACAAGATTGTGGGTCTGTACTGTTATTTATTTATTTTTTTTTTAGCAGAAACACCTTATCTTTTGTTTCGT
TTGAATGTAGAATGAAAATAAAAGAAAGAAAATATAACATCATCGGCCGCGCTTGTCTAATTTCGGGCAGTTAG
GATCCTCTCCGGTCACCGGAAAGTTTCAGTAGAAGAAACAAAACACCGTGACTAAAATGATACTATTATTTTATT
TATTGTGTTTTTCTTTTTTCTACCGGAACTTTTTAGAACGGATCCCAACTCGTTCCGGGGCCGCTACAACTGAAA
CAAAAGAAGATATTTTCTCTCTCTTCAGAAATGTAAGTTTTCCTTTACAGATACCCATTCACCATTTGATTCAGAT
GTGGTGACTAGAGATAAAGCATACTAATTTGACTCTTGGAAACCCATAAAGTTTATGTTATCCGTGTTCTGGACC
AATCCACTTGGGGGCATAACCTGTGTCTATGTGTGGTTTGGTTTCCATTCTGATTTATGCGGCGACTTGTAATTT
AAAATCTAGGAGGGGCAGACATTGAACAATCCCAATATTTTAATAACTTATGCAAGATTTTTTTTATTAATGAGAT
GATGTGTTTGTGACTGAGATTGAGTCATACATTTCACTAAGAAATGGTTCCAAGTACCAAACTATCATGACCCAG
TTGCAAACATGACGTTCGGGAGTGGTCACTTTGATAGTTCAATTTCATCTTGGCTTCTTATTCCTTTTATAATTCT
AATTCTTCTTGTGTAAACTATTTCATGTATTATTTTTCTTTAAAATTTACATGTCATTTATTTTGCCTCACTAACTCA
ATTTTGCATATAACAATGATAAGTGATATTTTGACTCACAAAATTTACATCAAATTTCGACATCGTTTATTATGTTC
ATTGGATGATTAACAAATATAACAAACTTTGCAACTAATTAACCACCAACTGAATATAATTAACTATAACTGTGAA
AGTAGTTAACTCATTTTTATATTTCATAGATCAAATAAGAGAAATAACGGTATATTAATCCCTCCAAAAAAAAAAA
ACGGTATATTTACTAAAAAATCTAAGCCACGTAGGAGGATAACAGGATCCCCGTAGGAGGATAACATCCAATCC
AACCAATCACAACAATCCTGATGAGATAACCCACTTTAAGCCCACGCATCTGTGGCACATCTACATTATCTAAAT
CACACATTCTTCCACACATCTGAGCCACACAAAAACCAATCCACATCTTTATCACCCATTCTATAAAAAATCACA
CTTTGTGAGTCTACACTTTGATTCCCTTCAAACACATACAAAGAGAAGAGACTAATTAATTAATTAATCATCTTGA
GAGAAA*ATGTTTGGGCGCGGACCAACAAGGAAGAGTGATAACACCAAATATTACGATATTCTTGGTGTTTCAAA*
*AAGTGCTAGTGAAGATGAAATCAAGAAAGCCTATAGAAAGGCAGCGATGAAGAACCATCCAGATAAGGGTGGG*
*GATCCTGAGAAGTTCAAGGAGTTGGGCCAAGCATATGAAGTGTTGAGCGATCCTGAAAAGAAAGAACTGTATG*
*ATCAATATGGTGAAGATGCCCTTAAAGAAGGAATGGGGGGAGGCGCAGGAAGCTCATTTCATAATCCGTTTGA*
*TATTTTCGAATCATTTTTTGGTGCAGGCTTTGGTGGTGGTGGTCCTTCACGCGCAAGAAGACAGAAGCAAGGA*
*GAAGATGTGGTGCATTCTATAAAGGTTTCCTTGGAGGATGTGTATAACGGCACTACAAAGAAGCTATCACTTTC*
*TAGGAATGCACTGTGCTCAAAATGTAAAGGGAAAGGTTCAAAAAGTGGAACTGCTGGAAGGTGTTTTGGATGC*
*CAGGGCACAGGTATGAAGATTACCAGAAGGCAAATTGGACTGGGCATGATTCAACAAATGCAACACGTCTGTC*
*CTGACTGCAAAGGAACAGGCGAGGTCATTAGTGAGAGAGATAGATGCCCTCAATGCAAGGGAAACAAGATTAC*
*TCAAGAAAAGAAGGTGCTGGAGGTGCATGTGGAAAAGGGGATGCAGCAGGGTCACAAGATTGTATTCGAAGG*
*ACAAGCTGATGAAGCTCCTGATACAATCACAGGAGACATAGTTTTTGTCTTGCAAGTAAAGGGACATCCGAAGT*
*TTCGGAGGGAGCGTGATGACCTCCACATTGAACACAATTTGAGCTTAACTGAGGCTCTCTGTGGCTTCCAGTTT*
*AATGTCACACATCTTGATGGAAGGCAACTATTGGTCAAATCGAACCCCGGCGAAGTCATCAAGCCAGGTCAAC*
*ATAAAGCTATAAATGATGAGGGAATGCCACAACATGGTAGGCCGTTCATGAAGGGACGCCTATACATCAAGTTT*
*AGTGTTGATTTCCCGGATTCGGGTTTTCTTTCCCCAAGCCAAAGCCTGGAATTAGAAAAGATATTACCTCAAAA*
*GACAAGCAAGAACTTGTCCCAAAAGGAGGTAGATGATTGTGAGGAGACCACCCTGCATGATGTCAATATTGCA*
*GAGGAGATGAGTCGAAAGAAGCAACAATACCGTGAGGCATATGATGACGATGATGATGAAGATGATGAGCACT*
*CGCAGCCTCGGGTGCAATGCGCTCAACAGTAG*GAGCTCAGCTCGAATTTCCCCGATCGTTCAAACATTTGGCA
ATAAAGTTTCTTAAGATTGAATCCTGTTGCCGGTCTTGCGATGATTATCATATAATTTCTGTTGAATTACGTTAAG
CATGTAATAATTAACATGTAATGCATGACGTTATTTATGAGATGGGTTTTTATGATTAGAGTCCCGCAATTATACA
TTTAATACGCGATAGAAAACAAAATATAGCGCGCAAACTAGGATAAATTATCGCGCGCGGTGTCATCTATGTTA
CTAGATCGAATTC

Fig. 87
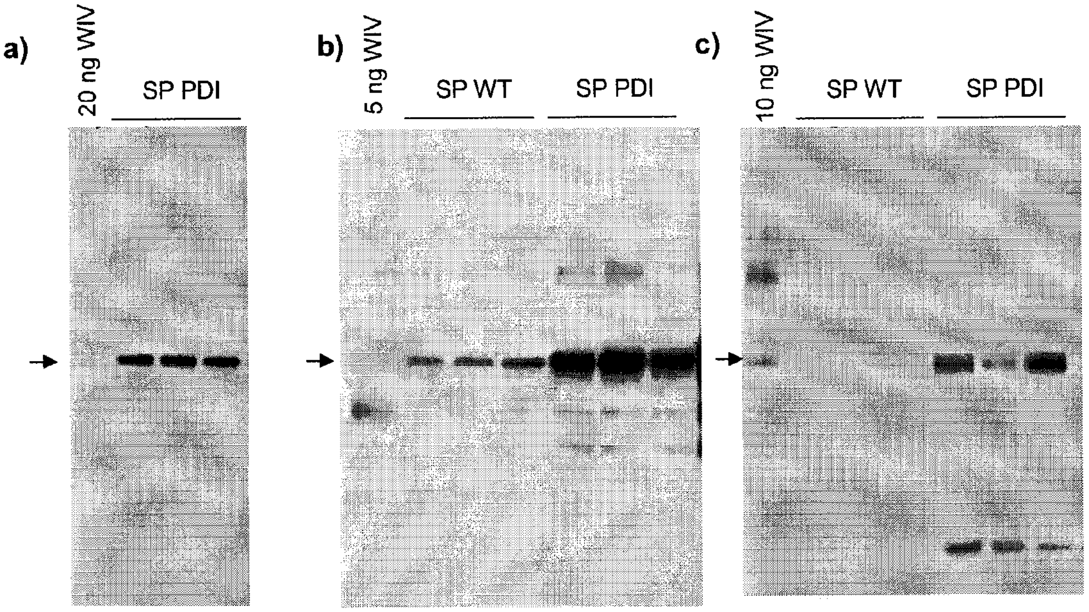
H1 (A/New Caledonia/20/99)
H1 (A/Brisbane/59/2007)
H3 (A/Brisbane/10/2007)
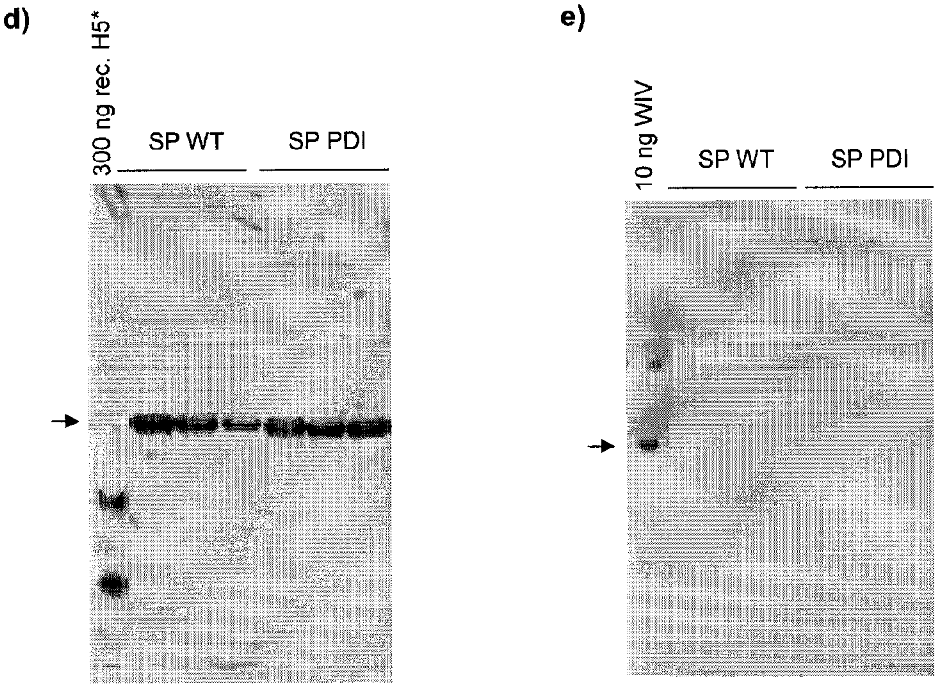
H5 (A/Indonesia/5/2005)
H1 (B/Florida/4/2006)
* Recombinant H5 (A/Vietnam/1203/2004) (from Protein Science Corporation)

Fig. 92 A

GTCAACATGGTGGAGCACGACACACTTGTCTACTCCAAAAATATCAAAGATACAGTCTCAGAAGACCAAAGGGCAATT
GAGACTTTTCAACAAAGGGTAATATCCGGAAACCTCCTCGGATTCCATTGCCCAGCTATCTGTCACTTTATTGTGAAG
ATAGTGGAAAAGGAAGGTGGCTCCTACAAATGCCATCATTGCGATAAAGGAAAGGCCATCGTTGAAGATGCCTCTGC
CGACAGTGGTCCCAAAGATGGACCCCCACCCACGAGGAGCATCGTGGAAAAAGAAGACGTTCCAACCACGTCTTCA
AAGCAAGTGGATTGATGTGATAACATGGTGGAGCACGACACACTTGTCTACTCCAAAAATATCAAAGATACAGTCTCA
GAAGACCAAAGGGCAATTGAGACTTTTCAACAAAGGGTAATATCCGGAAACCTCCTCGGATTCCATTGCCCAGCTATC
TGTCACTTTATTGTGAAGATAGTGGAAAAGGAAGGTGGCTCCTACAAATGCCATCATTGCGATAAAGGAAAGGCCATC
GTTGAAGATGCCTCTGCCGACAGTGGTCCCAAAGATGGACCCCCACCCACGAGGAGCATCGTGGAAAAAGAAGACG
TTCCAACCACGTCTTCAAAGCAAGTGGATTGATGTGATATCTCCACTGACGTAAGGGATGACGCACAATCCCACTATC
CTTCGCAAGACCCTTCCTCTATATAAGGAAGTTCATTTCATTTGGAGAGGTATTAAAATCTTAATAGGTTTTGATAAAA
GCGAACGTGGGGAAACCCGAACCAAACCTTCTTCTAAACTCTCTCTCATCTCTCTTAAAGCAAACTTCTCTCTTGTCTT
TCTTGCGTGAGCGATCTTCAACGTTGTCAGATCGTGCTTCGGCACCAGTACAACGTTTTCTTTCACTGAAGCGAAATC
AAAGATCTCTTTGTGGACACGTAGTGCGGCGCCATTAAATAACGTGTACTTGTCCTATTCTTGTCGGTGTGGTCTTGG
GAAAAGAAAGCTTGCTGGAGGCTGCTGTTCAGCCCCATACATTACTTGTTACGATTCTGCTGACTTTCGGCGGGTGC
AATATCTCTACTTCTGCTTGACGAGGTATTGTTGCCTGTACTTCTTTCTTCTTCTTCTTGCTGATTGGTTCTATAAGAAA
TCTAGTATTTTCTTTGAAACAGAGTTTTCCCGTGGTTTTCGAACTTGGAGAAAGATTGTTAAGCTTCTGTATATTCTGC
CCAAATTTGTCGGGCCCATGGCGAAAAACGTTGCGATTTTCGGCTTATTGTTTTCTCTTCTTGTGTTGGTTCCTTCTCA
GATCTTCGCTGACACATTATGTATAGGTTATCATGCGAACAATTCAACAGACACTGTAGACACAGTACTAGAAAAG
AATGTAACAGTAACACACTCTGTTAACCTTCTAGAAGACAAGCATAACGGGAAACTATGCAAACTAAGAGGGGTA
GCCCCATTGCATTTGGGTAAATGTAACATTGCTGGCTGGATCCTGGGAAATCCAGAGTGTGAATCACTCTCCACAG
CAAGCTCATGGTCCTACATTGTGGAAACACCTAGTTCAGACAATGGAACGTGTTACCCAGGAGATTTCATCGATTA
TGAGGAGCTAAGAGAGCAATTAAGCTCAGTGTCATCATTTGAAAGGTTTGAGATATTCCCCAAGACAAGTTCATGG
CCCAATCATGACTCGAACAAAGGTGTAACGGCAGCATGTCCTCATGCTGGAGCAAAAAGCTTCTACAAAAATTTAA
TATGGCTAGTTAAAAAAGGAAATTCATACCCAAAGCTCAGCAAATCCTACATTAATGATAAAGGGAAAGAAGTCCT
CGTGCTATGGGGCATTCACCATCCATCTACTAGTGCTGACCAACAAAGTCTCTATCAGAATGCAGATACATATGTTT
TTGTGGGGTCATCAAGATACAGCAAGAAGTTCAAGCCGGAAATAGCAATAAGACCCAAAGTGAGGGATCAAGAA
GGGAGAATGAACTATTACTGGACACTAGTAGAGCCGGGAGACAAAATAACATTCGAAGCAACTGGAAATCTAGTG
GTACCGAGATATGCATTCGCAATGGAAAGAAATGCTGGATCTGGTATTATCATTTCAGATACACCAGTCCACGATT
GCAATACAACTTGTCAAACACCCAAGGGTGCTATAAACACCAGCCTCCCATTTCAGAATATACATCCGATCACAAT
TGGAAAATGTCCAAAATATGTAAAAAGCACAAAATTGAGACTGGCCACAGGATTGAGGAATATCCCGTCTATTCAA
TCTAGAGGACTATTTGGGGCCATTGCCGGTTTCATTGAAGGGGGGTGGACAGGGATGGTAGATGGATGGTACGGT
TATCACCATCAAAATGAGCAGGGGTCAGGATATGCAGCCGACCTGAAGAGCACACAGAATGCCATTGACGAGATT
ACTAACAAAGTAAATTCTGTTATTGAAAAGATGAATACACAGTTCACAGCAGTAGGTAAAGAGTTCAACCACCTGG
AAAAAAGAATAGAGAATTTAAATAAAAAAGTTGATGATGGTTTCCTGGACATTTGGACTTACAATGCCGAACTGTT
GGTTCTATTGGAAAATGAAAGAACTTTGGACTACCACGATTCAAATGTGAAGAACTTATATGAAAAGGTAAGAAGC
CAGCTAAAAAACAATGCCAAGGAAATTGGAAACGGCTGCTTTGAATTTTACCACAAATGCGATAACACGTGCATG
GAAAGTGTCAAAAATGGGACTTATGACTACCCAAAATACTCAGAGGAAGCAAAATTAAACAGAGAAGAAATAGAT
GGGGTAAAGCTGGAATCAACAAGGATTTACCAGATTTTGGCGATCTATTCAACTGTCGCCAGTTCATTGGTACTGG
TAGTCTCCCTGGGGGCAATCAGTTTCTGGATGTGCTCTAATGGGTCTCTACAGTGTAGAATATGTATTTAAAGGCCT
ATTTTCTTTAGTTTGAATTTACTGTTATTCGGTGTGCATTTCTATGTTTGGTGAGCGGTTTTCTGTGCTCAGAGTGTGTT
TATTTTATGTAATTTAATTTCTTTGTGAGCTCCTGTTTAGCAGGTCGTCCCTTCAGCAAGGACACAAAAAGATTTTAATT
TTATTAAAAAAAAAAAAAAAAAAAGACCGGGAATTCGATATCAAGCTTATCGACCTGCAGATCGTTCAAACATTTGGCAA
TAAAGTTTCTTAAGATTGAATCCTGTTGCCGGTCTTGCGATGATTATCATATAATTTCTGTTGAATTACGTTAAGCATGT
AATAATTAACATGTAATGCATGACGTTATTTATGAGATGGGTTTTTATGATTAGAGTCCCGCAATTATACATTTAATACG
CGATAGAAAACAAAATATAGCGCGCAAACTAGGATAAATTATCGCGCGCGGTGTCATCTATGTTACTAGAT

Fig. 92 B

MAKNVAIFGLLFSLLVLVPSQIFADTLCIGYHANNSTDTVDTVLEKNVTVTHSVNLLEDKHNGKLCKLRGVAPL
HLGKCNIAGWILGNPECESLSTASSWSYIVETPSSDNGTCYPGDFIDYEELREQLSSVSSFERFEIFPKTSSWP
NHDSNKGVTAACPHAGAKSFYKNLIWLVKKGNSYPKLSKSYINDKGKEVLVLWGIHHPSTSADQQSLYQNAD
TYVFVGSSRYSKKFKPEIAIRPKVRDQEGRMNYYWTLVEPGDKITFEATGNLVVPRYAFAMERNAGSGIIISDT
PVHDCNTTCQTPKGAINTSLPFQNIHPITIGKCPKYVKSTKLRLATGLRNIPSIQSRGLFGAIAGFIEGGWTGMV
DGWYGYHHQNEQGSGYAADLKSTQNAIDEITNKVNSVIEKMNTQFTAVGKEFNHLEKRIENLNKKVDDGFLDI
WTYNAELLVLLENERTLDYHDSNVKNLYEKVRSQLKNNAKEIGNGCFEFYHKCDNTCMESVKNGTYDYPKYS
EEAKLNREEIDGVKLESTRIYQILAIYSTVASSLVLVVSLGAISFWMCSNGSLQCRICI

Fig. 93

2X35S promoter sequence (SEQ ID NO:129)

GTCAACATGGTGGAGCACGACACACTTGTCTACTCCAAAAATATCAAAGATACAGTC
TCAGAAGACCAAAGGGCAATTGAGACTTTTCAACAAAGGGTAATATCCGGAAACCT
CCTCGGATTCCATTGCCCAGCTATCTGTCACTTTATTGTGAAGATAGTGGAAAAGGA
AGGTGGCTCCTACAAATGCCATCATTGCGATAAAGGAAAGGCCATCGTTGAAGATG
CCTCTGCCGACAGTGGTCCCAAAGATGGACCCCCACCCACGAGGAGCATCGTGGA
AAAAGAAGACGTTCCAACCACGTCTTCAAAGCAAGTGGATTGATGTGATAACATGG
TGGAGCACGACACACTTGTCTACTCCAAAAATATCAAAGATACAGTCTCAGAAGACC
AAAGGGCAATTGAGACTTTTCAACAAAGGGTAATATCCGGAAACCTCCTCGGATTC
CATTGCCCAGCTATCTGTCACTTTATTGTGAAGATAGTGGAAAAGGAAGGTGGCTC
CTACAAATGCCATCATTGCGATAAAGGAAAGGCCATCGTTGAAGATGCCTCTGCCG
ACAGTGGTCCCAAAGATGGACCCCCACCCACGAGGAGCATCGTGGAAAAAGAAGA
CGTTCCAACCACGTCTTCAAAGCAAGTGGATTGATGTGATATCTCCACTGACGTAA
GGGATGACGCACAATCCCACTATCCTTCGCAAGACCCTTCCTCTATATAAGGAAGT
TCATTTCATTTGGAGAGG

Fig. 94

Intermediary expression cassette number 972, from PacI (upstream promoter) to AscI (immediately downstream NOS terminator). 2X35S promoter sequence is underlined. Mutated ATG are boxed. ApaI restriction site (immediately downstream ATG for protein coding sequence to be express, in this case HA0 of H5 A/Indonesia), is shaded. (SEQ ID NO:134)

TTAATTAAGTCGACAAGCTTGCATGCCTGCAGGTCAACATGGTGGAGCACGACACACTTGTCTACTCCA
AAAATATCAAAGATACAGTCTCAGAAGACCAAAGGGCAATTGAGACTTTTCAACAAAGGGTAATATCCGG
AAACCTCCTCGGATTCCATTGCCCAGCTATCTGTCACTTTATTGTGAAGATAGTGGAAAAGGAAGGTGGC
TCCTACAAATGCCATCATTGCGATAAAGGAAAGGCCATCGTTGAAGATGCCTCTGCCGACAGTGGTCCC
AAAGATGGACCCCCACCCACGAGGAGCATCGTGGAAAAAGAAGACGTTCCAACCACGTCTTCAAAGCAA
GTGGATTGATGTGATAACATGGTGGAGCACGACACACTTGTCTACTCCAAAAATATCAAAGATACAGTCT
CAGAAGACCAAAGGGCAATTGAGACTTTTCAACAAAGGGTAATATCCGGAAACCTCCTCGGATTCCATT
GCCCAGCTATCTGTCACTTTATTGTGAAGATAGTGGAAAAGGAAGGTGGCTCCTACAAATGCCATCATTG
CGATAAAGGAAAGGCCATCGTTGAAGATGCCTCTGCCGACAGTGGTCCCAAAGATGGACCCCCACCCA
CGAGGAGCATCGTGGAAAAAGAAGACGTTCCAACCACGTCTTCAAAGCAAGTGGATTGATGTGATATCT
CCACTGACGTAAGGGATGACGCACAATCCCACTATCCTTCGCAAGACCCTTCCTCTATATAAGGAAGTTC
ATTTCATTTGGAGAGGTATTAAAATCTTAATAGGTTTTGATAAAAGCGAACGTGGGGAAACCCGAACCAA
ACCTTCTTCTAAACTCTCTCTCATCTCTCTTAAAGCAAACTTCTCTCTTGTCTTTCTTGCGTGAGCGATCT
TCAACGTTGTCAGATCGTGCTTCGGCACCAGTACAACGTTTTCTTTCACTGAAGCGAAATCAAAGATCTC
TTTGTGGACACGTAGTGCGGCGCCATTAAATAACGTGTACTTGTCCTATTCTTGTCGGTGTGGTCTTGGG
AAAAGAAAGCTTGCTGGAGGCTGCTGTTCAGCCCCATACATTACTTGTTACGATTCTGCTGACTTTCGGC
GGGTGCAATATCTCTACTTCTGCTTGACGAGGTATTGTTGCCTGTACTTCTTTCTTCTTCTTCTTGCTGAT
TGGTTCTATAAGAAATCTAGTATTTTCTTTGAAACAGAGTTTTCCCGTGGTTTTCGAACTTGGAGAAAGAT
TGTTAAGCTTCTGTATATTCTGCCCAAATTTGTCGGGCCCATGGAGAAAATAGTGCTTCTTCTTGCAATA
GTCAGTCTTGTTAAAAGTGATCAGATTTGCATTGGTTACCATGCAAACAATTCAACAGAGCAGGTTGACA
CAATCATGGAAAAGAACGTTACTGTTACACATGCCCAAGACATACTGGAAAAGACACACAACGGGAAGC
TCTGCGATCTAGATGGAGTGAAGCCTCTAATTTTAAGAGATTGTAGTGTAGCTGGATGGCTCCTCGGGA
ACCCAATGTGTGACGAATTCATCAATGTACCGGAATGGTCTTACATAGTGGAGAAGGCCAATCCAACCA
ATGACCTCTGTTACCCAGGGAGTTTCAACGACTATGAAGAACTGAAACACCTATTGAGCAGAATAAACCA
TTTTGAGAAAATTCAAATCATCCCCAAAAGTTCTTGGTCCGATCATGAAGCCTCATCAGGAGTTAGCTCA
GCATGTCCATACCTGGGAAGTCCCTCCTTTTTTAGAAATGTGGTATGGCTTATCAAAAAGAACAGTACAT
ACCCAACAATAAAGAAAAGCTACAATAATACCAACCAAGAGGATCTTTTGGTACTGTGGGGAATTCACCA
TCCTAATGATGCGGCAGAGCAGACAAGGCTATATCAAAACCCAACCACCTATATTTCCATTGGGACATCA
ACACTAAACCAGAGATTGGTACCAAAAATAGCTACTAGATCCAAAGTAAACGGGCAAAGTGGAAGGATG
GAGTTCTTCTGGACAATTTTAAAACCTAATGATGCAATCAACTTCGAGAGTAATGGAAATTTCATTGCTCC
AGAATATGCATACAAAATTGTCAAGAAAGGGGACTCAGCAATTATGAAAAGTGAATTGGAATATGGTAAC
TGCAACACCAAGTGTCAAACTCCAATGGGGGCGATAAACTCTAGTATGCCATTCCACAACATACACCCTC
TCACCATCGGGGAATGCCCCAAATATGTGAAATCAAACAGATTAGTCCTTGCAACAGGGCTCAGAAATA
GCCCTCAAAGAGAGAGCAGAAGAAAAAAGAGAGGACTATTTGGAGCTATAGCAGGTTTTATAGAGGGAG
GATGGCAGGGAATGGTAGATGGTTGGTATGGGTACCACCATAGCAATGAGCAGGGGAGTGGGTACGCT
GCAGACAAAGAATCCACTCAAAAGGCAATAGATGGAGTCACCAATAAGGTCAACTCAATCATTGACAAAA
TGAACACTCAGTTTGAGGCCGTTGGAAGGGAATTTAATAACTTAGAAAGGAGAATAGAGAATTTAAACAA
GAAGATGGAAGACGGGTTTCTAGATGTCTGGACTTATAATGCCGAACTTCTGGTTCTCATGGAAAATGAG
AGAACTCTAGACTTTCATGACTCAAATGTTAAGAACCTCTACGACAAGGTCCGACTACAGCTTAGGGATA
ATGCAAAGGAGCTGGGTAACGGTTGTTTCGAGTTCTATCACAAATGTGATAATGAATGTATGGAAAGTAT
AAGAAACGGAACGTACAACTATCCGCAGTATTCAGAAGAAGCAAGATTAAAAAGAGAGGAAATAAGTGG
GGTAAAATTGGAATCAATAGGAACTTACCAAATACTGTCAATTTATTCAACAGTGGCGAGTTCCCTAGCA
CTGGCAATCATGATGGCTGGTCTATCTTTATGGATGTGCTCCAATGGATCGTTACAATGCAGAATTTGCA
TTTAAAGGCCTATTTTCTTTAGTTTGAATTTACTGTTATTCGGTGTGCATTTCTATGTTTGGTGAGCGGTTT
TCTGTGCTCAGAGTGTGTTTATTTTATGTAATTTAATTTCTTTGTGAGCTCCTGTTTAGCAGGTCGTCCCT
TCAGCAAGGACACAAAAAGATTTTAATTTTATTAAAAAAAAAAAAAAAAAGACCGGGAATTCGATATCAA
GCTTATCGACCTGCAGATCGTTCAAACATTTGGCAATAAAGTTTCTTAAGATTGAATCCTGTTGCCGGTC
TTGCGATGATTATCATATAATTTCTGTTGAATTACGTTAAGCATGTAATAATTAACATGTAATGCATGACGT
TATTTATGAGATGGGTTTTTATGATTAGAGTCCCGCAATTATACATTTAATACGCGATAGAAAACAAAATAT
AGCGCGCAAACTAGGATAAATTATCGCGCGCGGTGTCATCTATGTTACTAGATTCTAGAGTCTCAAGCTT
CGGCGCGCC

Fig. 95

Native H1 A/California/4/2009 sequence. Native H1 A/California/4/2009 signal peptide is underlined. SacI and StuI restriction sites are boxed. (SEQ ID NO:135)

ATGAAGGCAATACTAGTAGTTCTGCTATATACATTTGCAACCGCAAATG
CAGACACATTATGTATAGGTTATCATGCGAACAATTCAACAGACACTGT
AGACACAGTACTAGAAAAGAATGTAACAGTAACACACTCTGTTAACCTT
CTAGAAGACAAGCATAACGGGAAACTATGCAAACTAAGAGGGGTAGCC
CCATTGCATTTGGGTAAATGTAACATTGCTGGCTGGATCCTGGGAAAT
CCAGAGTGTGAATCACTCTCCACAGCAAGCTCATGGTCCTACATTGTG
GAAACACCTAGTTCAGACAATGGAACGTGTTACCCAGGAGATTTCATC
GATTATGAGGAGCTAAGAGAGCAATTGAGCTCAGTGTCATCATTTGAA
AGGTTTGAGATATTCCCCAAGACAAGTTCATGGCCCAATCATGACTCG
AACAAAGGTGTAACGGCAGCATGTCCTCATGCTGGAGCAAAAAGCTTC
TACAAAAATTTAATATGGCTAGTTAAAAAAGGAAATTCATACCCAAAGC
TCAGCAAATCCTACATTAATGATAAAGGGAAAGAAGTCCTCGTGCTATG
GGGCATTCACCATCCATCTACTAGTGCTGACCAACAAAGTCTCTATCA
GAATGCAGATACATATGTTTTTGTGGGGTCATCAAGATACAGCAAGAA
GTTCAAGCCGGAAATAGCAATAAGACCCAAAGTGAGGGATCAAGAAG
GGAGAATGAACTATTACTGGACACTAGTAGAGCCGGGAGACAAAATAA
CATTCGAAGCAACTGGAAATCTAGTGGTACCGAGATATGCATTCGCAA
TGGAAAGAAATGCTGGATCTGGTATTATCATTTCAGATACACCAGTCCA
CGATTGCAATACAACTTGTCAAACACCCAAGGGTGCTATAAACACCAG
CCTCCCATTTCAGAATATACATCCGATCACAATTGGAAAATGTCCAAAA
TATGTAAAAAGCACAAAATTGAGACTGGCCACAGGATTGAGGAATATC
CCGTCTATTCAATCTAGAGGCCTATTTGGGGCCATTGCCGGTTTCATTG
AAGGGGGGTGGACAGGGATGGTAGATGGATGGTACGGTTATCACCAT
CAAAATGAGCAGGGGTCAGGATATGCAGCCGACCTGAAGAGCACACA
GAATGCCATTGACGAGATTACTAACAAAGTAAATTCTGTTATTGAAAAG
ATGAATACACAGTTCACAGCAGTAGGTAAAGAGTTCAACCACCTGGAA
AAAAGAATAGAGAATTTAAATAAAAAAGTTGATGATGGTTTCCTGGACA
TTTGGACTTACAATGCCGAACTGTTGGTTCTATTGGAAAATGAAAGAAC
TTTGGACTACCACGATTCAAATGTGAAGAACTTATATGAAAAGGTAAGA
AGCCAGCTAAAAAACAATGCCAAGGAAATTGGAAACGGCTGCTTTGAA
TTTTACCACAAATGCGATAACACGTGCATGGAAAGTGTCAAAAATGGG
ACTTATGACTACCCAAAATACTCAGAGGAAGCAAAATTAAACAGAGAAG
AAATAGATGGGGTAAAGCTGGAATCAACAAGGATTTACCAGATTTTGG
CGATCTATTCAACTGTCGCCAGTTCATTGGTACTGGTAGTCTCCCTGG
GGGCAATCAGTTTCTGGATGTGCTCTAATGGGTCTCTACAGTGTAGAA
TATGTATTTAA

Fig. 96

Final sequence to be synthesized containing the H1 A/California/4/2009 sequence. M protein portion from DraIII to ApaI restriction site is underlined. PDISP is in bold. Mutated SacI and StuI restriction sites are boxed. (SEQ ID NO:136)

ATGCTAATATCACGTAGTGCGGCGCCATTAAATAACGTGTACTTGTCCTATTCTTGT
CGGTGTGGTCTTGGGAAAAGAAAGCTTGCTGGAGGCTGCTGTTCAGCCCCATACAT
TACTTGTTACGATTCTGCTGACTTTCGGCGGGTGCAATATCTCTACTTCTGCTTGAC
GAGGTATTGTTGCCTGTACTTCTTTCTTCTTCTTCTTGCTGATTGGTTCTATAAGAAA
TCTAGTATTTTCTTTGAAACAGAGTTTTCCCGTGGTTTTCGAACTTGGAGAAAGATT
GTTAAGCTTCTGTATATTCTGCCCAAATTTGTCGGGCCCATGGCGAAAAACGTTGC
GATTTTCGGCTTATTGTTTTCTCTTCTTGTGTTGGTTCCTTCTCAGATCTTCGCTGA
CACATTATGTATAGGTTATCATGCGAACAATTCAACAGACACTGTAGACACAGTACT
AGAAAAGAATGTAACAGTAACACACTCTGTTAACCTTCTAGAAGACAAGCATAACGG
GAAACTATGCAAACTAAGAGGGGTAGCCCCATTGCATTTGGGTAAATGTAACATTG
CTGGCTGGATCCTGGGAAATCCAGAGTGTGAATCACTCTCCACAGCAAGCTCATGG
TCCTACATTGTGGAAACACCTAGTTCAGACAATGGAACGTGTTACCCAGGAGATTTC
ATCGATTATGAGGAGCTAAGAGAGCAATTAAGCTCAGTGTCATCATTTGAAAGGTTT
GAGATATTCCCCAAGACAAGTTCATGGCCCAATCATGACTCGAACAAAGGTGTAAC
GGCAGCATGTCCTCATGCTGGAGCAAAAAGCTTCTACAAAAATTTAATATGGCTAGT
TAAAAAAGGAAATTCATACCCAAAGCTCAGCAAATCCTACATTAATGATAAAGGGAA
AGAAGTCCTCGTGCTATGGGGCATTCACCATCCATCTACTAGTGCTGACCAACAAA
GTCTCTATCAGAATGCAGATACATATGTTTTTGTGGGGTCATCAAGATACAGCAAGA
AGTTCAAGCCGGAAATAGCAATAAGACCCAAAGTGAGGGATCAAGAAGGGAGAAT
GAACTATTACTGGACACTAGTAGAGCCGGGAGACAAAATAACATTCGAAGCAACTG
GAAATCTAGTGGTACCGAGATATGCATTCGCAATGGAAAGAAATGCTGGATCTGGT
ATTATCATTTCAGATACACCAGTCCACGATTGCAATACAACTTGTCAAACACCCAAG
GGTGCTATAAACACCAGCCTCCCATTTCAGAATATACATCCGATCACAATTGGAAAA
TGTCCAAAATATGTAAAAAGCACAAAATTGAGACTGGCCACAGGATTGAGGAATATC
CCGTCTATTCAATCTAGAGGACTATTTGGGGCCATTGCCGGTTTCATTGAAGGGGG
GTGGACAGGGATGGTAGATGGATGGTACGGTTATCACCATCAAAATGAGCAGGGG
TCAGGATATGCAGCCGACCTGAAGAGCACACAGAATGCCATTGACGAGATTACTAA
CAAAGTAAATTCTGTTATTGAAAAGATGAATACACAGTTCACAGCAGTAGGTAAAGA
GTTCAACCACCTGGAAAAAAGAATAGAGAATTTAAATAAAAAAGTTGATGATGGTTT
CCTGGACATTTGGACTTACAATGCCGAACTGTTGGTTCTATTGGAAAATGAAAGAAC
TTTGGACTACCACGATTCAAATGTGAAGAACTTATATGAAAAGGTAAGAAGCCAGCT
AAAAAACAATGCCAAGGAAATTGGAAACGGCTGCTTTGAATTTTACCACAAATGCGA
TAACACGTGCATGGAAAGTGTCAAAAATGGGACTTATGACTACCCAAAATACTCAGA
GGAAGCAAAATTAAACAGAGAAGAAATAGATGGGGTAAAGCTGGAATCAACAAGGA
TTTACCAGATTTTGGCGATCTATTCAACTGTCGCCAGTTCATTGGTACTGGTAGTCT
CCCTGGGGGCAATCAGTTTCTGGATGTGCTCTAATGGGTCTCTACAGTGTAGAATA
TGTATTTAAAGGCCTAATA

Fig. 97

Synthesized fragment 1 (SEQ ID NO:137)

ATGCTAATATCACGTAGTGCGGCGCCATTAAATAACGTGTACTTGTCCTATTCTTGTCGGTGTGGTCTT
GGGAAAAGAAAGCTTGCTGGAGGCTGCTGTTCAGCCCCATACATTACTTGTTACGATTCTGCTGACTT
TCGGCGGGTGCAATATCTCTACTTCTGCTTGACGAGGTATTGTTGCCTGTACTTCTTTCTTCTTCTTCT
TGCTGATTGGTTCTATAAGAAATCTAGTATTTTCTTTGAAACAGAGTTTTCCCGTGGTTTTCGAACTTG
GAGAAAGATTGTTAAGCTTCTGTATATTCTGCCCAAATTTGTCGGGCCCATGGCGAAAAACGTTGCGA
TTTTCGGCTTATTGTTTTCTCTTCTTGTGTTGGTTCCTTCTCAGATCTTCGCTGACACATTATGTATAGG
TTATCATGCGAACAATTCAACAGACACTGTAGACACAGTACTAGAAAAGAATGTAACAGTAACACACTC
TGTTAACCTTCTAGAAGACAAGCATAACGGGAAACTATGCAAACTAAGAGGGGTAGCCCCATTGCATT
TGGGTAAATGTAACATTGCTGGCTGGATCCTGGGAAATCCAGAGTGTGAATCACTCTCCACAGCAAG
CTCATGGTCCTACATTGTGGAAACACCTAGTTCAGACAATGGAACGTGTTACCCAGGAGATTTCATCG
ATTATGAGGAGCTAAGAGAGCAATTAAGC

Synthesized fragment 2 (SEQ ID NO:138)

TGGAAACACCTAGTTCAGACAATGGAACGTGTTACCCAGGAGATTTCATCGATTATGAGGAGCTAAGA
GAGCAATTAAGCTCAGTGTCATCATTTGAAAGGTTTGAGATATTCCCCAAGACAAGTTCATGGCCCAA
TCATGACTCGAACAAAGGTGTAACGGCAGCATGTCCTCATGCTGGAGCAAAAAGCTTCTACAAAAATT
TAATATGGCTAGTTAAAAAAGGAAATTCATACCCAAAGCTCAGCAAATCCTACATTAATGATAAAGGGA
AAGAAGTCCTCGTGCTATGGGGCATTCACCATCCATCTACTAGTGCTGACCAACAAAGTCTCTATCAG
AATGCAGATACATATGTTTTTGTGGGGTCATCAAGATACAGCAAGAAGTTCAAGCCGGAAATAGCAAT
AAGACCCAAAGTGAGGGATCAAGAAGGGAGAATGAACTATTACTGGACACTAGTAGAGCCGGGAGAC
AAAATAACATTCGAAGCAACTGGAAATCTAGTGGTACCGAGATATGCATTCGCAATGGAAAGAAATGC
TGGATCTGGTATTATCATTTCAGATACACCAGTCCACGATTGCAATACAACTTGTCAAACACCCAAGG
GTGCTATAAACACCAGCCTCCCATTTCAGAATATACATCCGATCACAATTGGAAAATGTCCAAAATATG
TAAAAAGCACAAAATTGAGACTGGCCACAGGATTGAGGAATATCCCGTCTATTCAATCTAGAGGACTA
TTTGGGGCCATTGCCGGTTTCATTGAAGGGGGGTGGACAGGGATGGTAGATGGATGGTACGGTTATC
ACCATCAAAATGAGCAGGGGTCAGGATATGCAG

Synthesized fragment 3 (SEQ ID NO:139)

TTGAAGGGGGGTGGACAGGGATGGTAGATGGATGGTACGGTTATCACCATCAAAATGAGCAGGGGT
CAGGATATGCAGCCGACCTGAAGAGCACACAGAATGCCATTGACGAGATTACTAACAAAGTAAATTCT
GTTATTGAAAAGATGAATACACAGTTCACAGCAGTAGGTAAAGAGTTCAACCACCTGGAAAAAAGAAT
AGAGAATTTAAATAAAAAAGTTGATGATGGTTTCCTGGACATTTGGACTTACAATGCCGAACTGTTGGT
TCTATTGGAAAATGAAAGAACTTTGGACTACCACGATTCAAATGTGAAGAACTTATATGAAAAGGTAAG
AAGCCAGCTAAAAAACAATGCCAAGGAAATTGGAAACGGCTGCTTTGAATTTTACCACAAATGCGATA
ACACGTGCATGGAAAGTGTCAAAAATGGGACTTATGACTACCCAAAATACTCAGAGGAAGCAAAATTA
AACAGAGAAGAAATAGATGGGGTAAAGCTGGAATCAACAAGGATTTACCAGATTTTGGCGATCTATTC
AACTGTCGCCAGTTCATTGGTACTGGTAGTCTCCCTGGGGGCAATCAGTTTCTGGATGTGCTCTAATG
GGTCTCTACAGTGTAGAATATGTATTTAAAGGCCTAATA

Fig. 98

Expression cassette number 560, from PacI (upstream promoter) to AscI (immediately downstream NOS terminator). PDISP-HA0 H1 A/California/4/2009 sequence is underlined. (SEQ ID NO:146)

TTAATTAAGTCGACAAGCTTGCATGCCTGCAGGTCAACATGGTGGAGCACGACACACTTGTCTACTCCAAAAATA
TCAAAGATACAGTCTCAGAAGACCAAAGGGCAATTGAGACTTTTCAACAAAGGGTAATATCCGGAAACCTCCTCG
GATTCCATTGCCCAGCTATCTGTCACTTTATTGTGAAGATAGTGGAAAAGGAAGGTGGCTCCTACAAATGCCATCA
TTGCGATAAAGGAAAGGCCATCGTTGAAGATGCCTCTGCCGACAGTGGTCCCAAAGATGGACCCCCACCCACGA
GGAGCATCGTGGAAAAAGAAGACGTTCCAACCACGTCTTCAAAGCAAGTGGATTGATGTGATAACATGGTGGAGC
ACGACACACTTGTCTACTCCAAAAATATCAAAGATACAGTCTCAGAAGACCAAAGGGCAATTGAGACTTTTCAACA
AAGGGTAATATCCGGAAACCTCCTCGGATTCCATTGCCCAGCTATCTGTCACTTTATTGTGAAGATAGTGGAAAAG
GAAGGTGGCTCCTACAAATGCCATCATTGCGATAAAGGAAAGGCCATCGTTGAAGATGCCTCTGCCGACAGTGGT
CCCAAAGATGGACCCCCACCCACGAGGAGCATCGTGGAAAAAGAAGACGTTCCAACCACGTCTTCAAAGCAAGT
GGATTGATGTGATATCTCCACTGACGTAAGGGATGACGCACAATCCCACTATCCTTCGCAAGACCCTTCCTCTATA
TAAGGAAGTTCATTTCATTTGGAGAGGTATTAAAATCTTAATAGGTTTTGATAAAAGCGAACGTGGGGAAACCCGA
ACCAAACCTTCTTCTAAACTCTCTCTCATCTCTCTTAAAGCAAACTTCTCTCTTGTCTTTCTTGCGTGAGCGATCTT
CAACGTTGTCAGATCGTGCTTCGGCACCAGTACAACGTTTTCTTTCACTGAAGCGAAATCAAAGATCTCTTTGTGG
ACACGTAGTGCGGCGCCATTAAATAACGTGTACTTGTCCTATTCTTGTCGGTGTGGTCTTGGGAAAAGAAAGCTT
GCTGGAGGCTGCTGTTCAGCCCCATACATTACTTGTTACGATTCTGCTGACTTTCGGCGGGTGCAATATCTCTACT
TCTGCTTGACGAGGTATTGTTGCCTGTACTTCTTTCTTCTTCTTCTTGCTGATTGGTTCTATAAGAAATCTAGTATTT
TCTTTGAAACAGAGTTTTCCCGTGGTTTTCGAACTTGGAGAAAGATTGTTAAGCTTCTGTATATTCTGCCCAAATTT
GTCGGGCCCATGGCGAAAAACGTTGCGATTTTCGGCTTATTGTTTTCTCTTCTTGTGTTGGTTCCTTCTCAGATCT
TCGCTGACACATTATGTATAGGTTATCATGCGAACAATTCAACAGACACTGTAGACACAGTACTAGAAAAGAATGT
AACAGTAACACACTCTGTTAACCTTCTAGAAGACAAGCATAACGGGAAACTATGCAAACTAAGAGGGGTAGCCCC
ATTGCATTTGGGTAAATGTAACATTGCTGGCTGGATCCTGGGAAATCCAGAGTGTGAATCACTCTCCACAGCAAG
CTCATGGTCCTACATTGTGGAAACACCTAGTTCAGACAATGGAACGTGTTACCCAGGAGATTTCATCGATTATGAG
GAGCTAAGAGAGCAATTAAGCTCAGTGTCATCATTTGAAAGGTTTGAGATATTCCCCAAGACAAGTTCATGGCCCA
ATCATGACTCGAACAAAGGTGTAACGGCAGCATGTCCTCATGCTGGAGCAAAAAGCTTCTACAAAAATTTAATATG
GCTAGTTAAAAAAGGAAATTCATACCCAAAGCTCAGCAAATCCTACATTAATGATAAAGGGAAAGAAGTCCTCGTG
CTATGGGGCATTCACCATCCATCTACTAGTGCTGACCAACAAAGTCTCTATCAGAATGCAGATACATATGTTTTTG
TGGGGTCATCAAGATACAGCAAGAAGTTCAAGCCGGAAATAGCAATAAGACCCAAAGTGAGGGATCAAGAAGGG
AGAATGAACTATTACTGGACACTAGTAGAGCCGGGAGACAAAATAACATTCGAAGCAACTGGAAATCTAGTGGTA
CCGAGATATGCATTCGCAATGGAAAGAAATGCTGGATCTGGTATTATCATTTCAGATACACCAGTCCACGATTGCA
ATACAACTTGTCAAACACCCAAGGGTGCTATAAACACCAGCCTCCCATTTCAGAATATACATCCGATCACAATTGG
AAAATGTCCAAAATATGTAAAAAGCACAAAATTGAGACTGGCCACAGGATTGAGGAATATCCCGTCTATTCAATCT
AGAGGACTATTTGGGGCCATTGCCGGTTTCATTGAAGGGGGGTGGACAGGGATGGTAGATGGATGGTACGGTTA
TCACCATCAAAATGAGCAGGGGTCAGGATATGCAGCCGACCTGAAGAGCACACAGAATGCCATTGACGAGATTA
CTAACAAAGTAAATTCTGTTATTGAAAAGATGAATACACAGTTCACAGCAGTAGGTAAAGAGTTCAACCACCTGGA
AAAAAGAATAGAGAATTTAAATAAAAAAGTTGATGATGGTTTCCTGGACATTTGGACTTACAATGCCGAACTGTTG
GTTCTATTGGAAAATGAAAGAACTTTGGACTACCACGATTCAAATGTGAAGAACTTATATGAAAAGGTAAGAAGCC
AGCTAAAAAACAATGCCAAGGAAATTGGAAACGGCTGCTTTGAATTTTACCACAAATGCGATAACACGTGCATGGA
AAGTGTCAAAAATGGGACTTATGACTACCCAAAATACTCAGAGGAAGCAAAATTAAACAGAGAAGAAATAGATGGG
GTAAAGCTGGAATCAACAAGGATTTACCAGATTTTGGCGATCTATTCAACTGTCGCCAGTTCATTGGTACTGGTAG
TCTCCCTGGGGGCAATCAGTTTCTGGATGTGCTCTAATGGGTCTCTACAGTGTAGAATATGTATTTAAAGGCCTAT
TTTCTTTAGTTTGAATTTACTGTTATTCGGTGTGCATTTCTATGTTTGGTGAGCGGTTTTCTGTGCTCAGAGTGTGT
TTATTTTATGTAATTTAATTTCTTTGTGAGCTCCTGTTTAGCAGGTCGTCCCTTCAGCAAGGACACAAAAAGATTTT
AATTTTATTAAAAAAAAAAAAAAAAAAAGACCGGGAATTCGATATCAAGCTTATCGACCTGCAGATCGTTCAAACATT
TGGCAATAAAGTTTCTTAAGATTGAATCCTGTTGCCGGTCTTGCGATGATTATCATATAATTTCTGTTGAATTACGT
TAAGCATGTAATAATTAACATGTAATGCATGACGTTATTTATGAGATGGGTTTTTATGATTAGAGTCCCGCAATTAT
ACATTTAATACGCGATAGAAAACAAAATATAGCGCGCAAACTAGGATAAATTATCGCGCGCGGTGTCATCTATGTT
ACTAGATCTCTAGAGTCTCAAGCTTGGCGCGCC

INFLUENZA VIRUS-LIKE PARTICLES (VLPS) COMPRISING HEMAGGLUTININ

CROSS REFERENCE TO RELATED APPLICATIONS

This is a U.S. National Phase patent application of PCT/CA2009/000926 filed Jul. 2, 2009, which is a continuation-in-part of PCT/CA2009/000032 filed Jan. 12, 2009, which is a continuation-in-part of, and clams priority from Canadian patent application Serial No. 2,615,372 filed Jan. 21, 2008; U.S. provisional application Ser. No. 61/022,775 filed Jan. 22, 2008; U.S. provisional application Ser. No. 60/959,414 filed Jul. 13, 2007; U.S. provisional application Ser. No. 60/990,603 filed Nov. 27, 2007; U.S. provisional application Ser. No. 61/013,272 filed Dec. 12, 2007, all of which are hereby incorporated by reference in the present disclosure in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 267342001200SeqList.txt, date recorded: Jan. 7, 2011, size: 335 KB).

FIELD OF INVENTION

The present invention relates to the production of virus-like particles. More specifically, the present invention is directed to the production of virus-like particles comprising influenza antigens.

BACKGROUND OF THE INVENTION

Influenza is the leading cause of death in humans due to a respiratory virus. Common symptoms include fever, sore throat, shortness of breath, and muscle soreness, among others. During flu season, influenza viruses infect 10-20% of the population worldwide, leading to 250-500,000 deaths annually Influenza viruses are enveloped viruses that bud from the plasma membrane of infected mammalian and avian cells. They are classified into types A, B, or C, based on the nucleoproteins and matrix protein antigens present. Influenza type A viruses may be further divided into subtypes according to the combination of hemagglutinin (HA) and neuraminidase (NA) surface glycoproteins presented. HA governs the ability of the virus to bind to and penetrate the host cell. NA removes terminal sialic acid residues from glycan chains on host cell and viral surface proteins, which prevents viral aggregation and facilitates virus mobility. Currently, 16 HA (H1-H16) and 9 NA (N1-N9) subtypes are recognized. Each type A influenza virus presents one type of HA and one type of NA glycoprotein. Generally, each subtype exhibits species specificity; for example, all HA and NA subtypes are known to infect birds, while only subtypes H1, H2, H3, H5, H7, H9, H10, N1, N2, N3 and N7 have been shown to infect humans (Horimoto 2006; Suzuki 2005). Influenza viruses comprising H5, H7 and H9 are considered the most highly pathogenic forms of influenza A viruses, and are most likely to cause future pandemics.

Influenza pandemics are usually caused by highly transmittable and virulent influenza viruses, and can lead to elevated levels of illness and death globally. The emergence of new influenza A subtypes resulted in 4 major pandemics in the $20^{th}$ century. The Spanish flu, caused by an H1N1 virus, in 1918-1919 led to the deaths of over 50 million people worldwide between 1917 and 1920. Presently, the risk of the emergence of a new subtype, or of the transmission to humans of a subtype endemic in animals, is always present. Of particular concern is a highly virulent form of avian influenza (also called "bird flu"), outbreaks of which have been reported in several countries around the world. In many cases, this bird flu can result in mortality rates approaching 100% within 48 hours. The spread of the avian influenza virus (H5N1), first identified in Hong Kong in 1997, to other Asian countries and Europe has been postulated to be linked to the migratory patterns of wild birds.

The current method of combating influenza in humans is by annual vaccination. The vaccine is usually a combination of several strains that are predicted to be the dominant strains for the coming "flu-season". The prediction is coordinated by the World Health Organization. Generally, the number of vaccine doses produced each year is not sufficient to vaccinate the world's population. For example, Canada and the United-States obtain enough vaccines doses to immunize about one third of their population, while only 17% of the population of the European Union can be vaccinated. It is evident that current worldwide production of influenza vaccine would be insufficient in the face of a worldwide flu pandemic. Even if the necessary annual production could somehow be met in a given year, the dominant strains change from year to year, thus stockpiling at low-need times in the year is not practical. Economical, large scale production of an effective influenza vaccine is of significant interest to government and private industry alike.

The viral stocks for use in vaccines are produced in fertilized eggs. The virus particles are harvested, and for an inactivated viral vaccine, disrupted by detergent to inactivate. Live attenuated vaccines are made of influenza viruses that were adapted for growth at low temperature which means that at normal body temperature, the vaccine is attenuated. Such a vaccine is licensed in USA for use in individuals from 5 to 49 years of age. Inactivated whole virus vaccines are rendered harmless by inactivation with chemical agents and they have been produced in embryonic eggs or mammalian cell culture. All these types of vaccine show some specific advantages and disadvantages. One advantage of vaccines derived from whole viruses is the type of immunity induced by such vaccines. In general, split vaccines induce a strong antibody response while vaccines made of whole viruses induce both an antibody (humoral) and cellular response. Even though a functional antibody response is a criterion for licensure that correlates with protection induced by a vaccine, there is increasing evidence that a T-cell response is also important in influenza immunity—this may also provide better protection in the elderly.

In order to induce a cellular immune response, vaccines made of whole viruses were developed. Due to the high pathogenicity of the influenza strain (e.g. H5N1), these vaccines are produced in BL3+ facility. For highly pathogenic influenza strains such as H5N1, some manufacturers have modified the hemagglutinin gene sequence in order to reduce the pathogenicity of the influenza strain and to make it avirulent and more easily produced in embryonic eggs or mammalian cell culture. Others also use reassortant influenza strains in which the genetic sequences for the hemagglutinin and neuraminidase proteins are cloned in a high-yielding low pathogenic influenza donor strain (A/PR/8/34; Quan F-S et al, 2007). While these methods may produce useful vaccines, they do not provide a solution to the need for high-volume, low cost and fast production of vaccines in the scale necessary to meet the global need in a normal year, and would almost certainly be insufficient in the face of a pandemic.

Using this reverse genetic technology, one might also need to mutate the genetic sequence of the HA protein to make it avirulent. For highly pathogenic influenza strains, the production of whole virus vaccines either requires confinement procedures or the resulting vaccines do not exactly match the genetic sequence of the circulating virus. In the case of live-attenuated vaccines, there is still a risk that the administered vaccine can recombine with an influenza virus from the host, leading to a new influenza virus.

While this method maintains the antigenic epitope and post-translational modifications, there are a number of drawbacks to this method, including the risk of contamination due to the use of whole virus and variable yields depending on virus strain. Sub-optimal levels of protection may result from genetic heterogeneity in the virus due to its introduction into eggs. Other disadvantages includes extensive planning for obtaining eggs, contamination risks due to chemicals used in purification, and long production times. Also, persons hypersensitive to egg proteins may not be eligible candidates for receiving the vaccine.

In the case of a pandemic, split vaccine production is limited by the need to adapt the strain for growth in eggs and the variable production yields achieved. Although this technology has been used for years for the production of seasonal vaccines, it can hardly respond in a reasonable timeframe to a pandemic and worldwide manufacturing capacity is limited.

To avoid the use of eggs, influenza viruses have also been produced in mammalian cell culture, for example in MDCK or PERC.6 cells, or the like. Another approach is reverse genetics, in which viruses are produced by cell transformation with viral genes. These methods, however, also requires the use of whole virus as well as elaborate methods and specific culture environments.

Several recombinant products have been developed as recombinant influenza vaccine candidates. These approaches have focused on the expression, production, and purification of influenza type A HA and NA proteins, including expression of these proteins using baculovirus infected insect cells (Crawford et al, 1999; Johansson, 1999), viral vectors, and DNA vaccine constructs (Olsen et al., 1997).

Of recent concern is the outbreak of "swine flu" (strain A/California/04/09). An initial outbreak in Mexico brought this viral strain to the world attention in a few days, and has been detected in countries around the world, as a testament to the rapidity by which influenza may be transmitted, as well as a test for quarantine, antiviral production, infection control and ultimately, vaccine production.

Specifics of an influenza virus infection are well known. Briefly, the infectious cycle is initiated by the attachment of the virion surface HA protein to a sialic acid-containing cellular receptor (glycoproteins and glycolipids). The NA protein mediates processing of the sialic acid receptor, and virus penetration into the cell depends on HA-dependent receptor-mediated endocytosis. In the acidic confines of internalized endosomes containing an influenza virion, the HA protein undergoes conformational changes that lead to fusion of viral and cell membranes and virus uncoating and M2-mediated release of MI proteins from nucleocapsid-associated ribonucleoproteins (RNPs), which migrate into the cell nucleus for viral RNA synthesis. Antibodies to HA proteins prevent virus infection by neutralizing virus infectivity, whereas antibodies to NA proteins mediate their effect on the early steps of viral replication.

Crawford et al. (1999) disclose expression of influenza HA in baculovirus infected insect cells. The expressed proteins are described as being capable of preventing lethal influenza disease caused by avian H5 and H7 influenza subtypes. Johansson et al. (1999) teach that baculovirus-expressed influenza HA and NA proteins induce immune responses in animals superior to those induced by a conventional vaccine. Immunogenicity and efficacy of baculovirus-expressed hemagglutinin of equine influenza virus was compared to a homologous DNA vaccine candidate (Olsen et al., 1997). Collectively, these data demonstrate that a high degree of protection against influenza virus challenge can be induced with recombinant HA or NA proteins, using various experimental approaches and in different animal models.

Since previous research has shown that the surface influenza glycoproteins, HA and NA, are the primary targets for elicitation of protective immunity against influenza virus and that M1 provides a conserved target for cellular immunity to influenza, a new vaccine candidate may include these viral antigens as a protein macromolecular particle, such as virus-like particles (VLPs). As vaccine products, VLPs offer the advantage of being more immunogenic than subunit or recombinant antigens and are able to stimulate both humoral and cellular immune response (Grgacic and Anderson, 2006). Further, the particle with these influenza antigens may display conformational epitopes that elicit neutralizing antibodies to multiple strains of influenza viruses.

Production of a non-infectious influenza virus strain for vaccine purposes is one way to avoid inadvertent infection. Alternatively, virus-like particles (VLPs) as substitutes for the cultured virus have been investigated. VLPs mimic the structure of the viral capsid, but lack a genome, and thus cannot replicate or provide a means for a secondary infection.

Several studies have demonstrated that recombinant influenza proteins self-assemble into VLPs in cell culture using mammalian expression plasmids or baculovirus vectors (Gomez-Puertas et al., 1999; Neumann et al., 2000; Latham and Galarza, 2001). Gomez-Puertas et al. (1999) discloses that efficient formation of influenza VLP depends on the expression levels of several viral proteins. Neumann et al. (2000) established a mammalian expression plasmid-based system for generating infectious influenza virus-like particles entirely from cloned cDNAs. Latham and Galarza (2001) reported the formation of influenza VLPs in insect cells infected with recombinant baculovirus co-expressing HA, NA, M1, and M2 genes. These studies demonstrated that influenza virion proteins may self-assemble upon co-expression in eukaryotic cells.

Gomez-Puertas et al. (2000) teach that, in addition to the hemagglutinin (HA), the matrix protein (M1) of the influenza virus is essential for VLP budding from insect cells. However, Chen et al. (2007) teach that M1 might not be required for VLP formation, and observed that efficient release of M1 and VLPs required the presence of HA and sialidase activity provided by NA. The NA cleaves the sialic acids of the glycoproteins at the surface of the cells producing the VLPs, and releasing the VLPs in the medium.

Quan et al 2007 teaches that a VLP vaccine produced in a baculovirus expression system (insect cell) induces a protective immunity against some strains of influenza virus (A/PR8/34 (H1N1)). The VLPs studied by Quan were observed to bud from the plasma membrane, and were considered to be of the correct size and morphology, similar to those obtained in a mammalian system (MDCK cells).

PCT Publications WO 2004/098530 and WO 2004/098533 teach expression of Newcastle Disease Virus HN or Avian Influenza A/turkey/Wisconsin/68 (H5N9) in transformed NT-1 (tobacco) cells in culture. Compositions comprising the plant cell culture-expressed polypeptides elicit varying immune responses in rabbits and chickens.

Enveloped viruses may obtain their lipid envelope when 'budding' out of the infected cell and obtain the membrane from the plasma membrane, or from that of an internal organelle. Influenza virus particles and VLPs bud from the plasma membrane of the host cell. In mammalian or baculovirus cell systems, for example, influenza buds from the plasma membrane (Quan et al 2007). Only a few enveloped viruses are known to infect plants (for example, members of the Topoviruses and Rhabdoviruses). Of the known plant enveloped viruses, they are characterized by budding from internal membranes of the host cell, and not from the plasma membrane. Although a small number of recombinant VLPs have been produced in plant hosts, none were derived from the plasma membrane, raising the question whether plasma membrane-derived VLPs, including influenza VLPs can be produced in plants.

Current influenza VLP production technologies rely on the co-expression of multiple viral proteins, and this dependence represents a drawback of these technologies since in case of a pandemic and of yearly epidemics, response time is crucial for vaccination. A simpler VLP production system, for example, one that relies on the expression of only one or a few viral proteins without requiring expression of non-structural viral proteins is desirable to accelerate the development of vaccines.

In order to protect the world population from influenza and to stave off future pandemics, vaccine manufacturers will need to develop effective, rapid methods producing vaccine doses. The current use of fertilized eggs to produce vaccines is insufficient and involves a lengthy process.

SUMMARY OF THE INVENTION

It is an object of the invention to provide improved influenza virus like particles (VLPs).

According to the present invention there is provided a nucleic acid comprising a nucleotide sequence encoding an antigen from an enveloped virus operatively linked to a regulatory region active in a plant, the antigen is an influenza hemagglutinin (HA). Preferably, the antigen is an HA from influenza A/California/04/09.

The HA may comprise a native, or a non-native signal peptide; the non-native signal peptide may be a protein disulfide isomerase signal peptide.

The HA encoded by the nucleic acid may be a type A influenza, a type B influenza, or is a subtype of type A influenza, selected from the group comprising H1, H2, H3, H4, H5, H6, H7, H8, H9, H10, H11, H12, H13, H14, H15, and H16. In some aspects of the invention, the HA encoded by the nucleic acid may be from a type A influenza, and selected from the group comprising H1, H2, H3, H5, H6, H7 and H9. Preferably, the influenza HA is from strain A/California/04/09.

The present invention also provides a method of producing influenza virus like particles (VLPs) in a plant comprising:

a) introducing a nucleic acid encoding an antigen from an enveloped virus, for example an influenza hemagglutinin (HA) from strain A/California/04/09, operatively linked to a regulatory region active in the plant, into the plant, or portion thereof, and
b) incubating the plant or a portion therefore under conditions that permit the expression of the nucleic acid, thereby producing the VLPs.

The method may further comprise the steps of harvesting the plant and purifying or separating the VLPs from the plant tissue.

The method may further comprise, in the step of introducing (step a), a nucleic acid comprising a nucleotide sequence encoding one or more than one chaperon protein.

The one or more than one chaperone proteins may be selected from the group comprising Hsp40 and Hsp70.

The present invention includes the above method wherein, in the step of introducing (step a), the nucleic acid may be either transiently expressed in the plant, or stably expressed in the plant. Furthermore, the VLPs may be purified using size exclusion chromatography.

According to another aspect of the present invention, there is provided a method of producing influenza virus like particles (VLPs) in a plant comprising providing a plant, or a portion of a plant, comprising a nucleic acid comprising a nucleotide sequence encoding an HA from influenza A/California/04/09 operatively linked to a regulatory region active in a plant, and incubating the plant or portion of the plant under conditions that permit the expression of the nucleic acid, thereby producing the VLPs.

The method may further comprise the steps of harvesting the plant and purifying or separating the VLPs from the plant tissue.

The present invention includes the above method, wherein following the step of providing, a nucleic acid comprising a nucleotide sequence encoding one or more than one chaperone protein operatively linked to a regulatory region active in a plant is introduced, and the plant or portion of the plant incubated under conditions that permit expression of the nucleic acid, thereby producing the VLPs.

The one or more than one chaperone proteins may be selected from the group comprising Hsp40 and Hsp70.

The present invention includes the above method wherein, in the step of introducing (step a), the nucleic acid encoding the HA from influenza A/California/04/09 is stably expressed in the plant. Furthermore, the VLPs may be purified using size exclusion chromatography.

The present invention also provides a virus like particle (VLP) comprising an influenza virus HA protein, from strain A/California/04/09, and one or more than one lipid derived from a plant.

The HA protein of the VLP may be of a type A influenza, a type B influenza, or is a subtype of type A influenza HA selected from the group consisting of H1, H2, H3, H4, H5, H6, H7, H8, H9, H10, H11, H12, H13, H14, H15, and H16. In some aspects of the invention, the HA is from a type A influenza, selected from the group comprising H1, H2, H3, H5, H6, H7 and H9.

Also included in the present invention is a composition comprising an effective dose of a VLP, the VLP comprising an influenza virus HA protein, one or more than one plant lipid, and a pharmaceutically acceptable carrier.

The present invention also contemplates fragments or portions of HA proteins that form VLPs in a plant.

The present invention also pertains to a VLP comprising an influenza virus HA bearing plant-specific N-glycans, or modified N-glycans. The HA protein of the VLP may be of a type A influenza, a type B influenza, or is a subtype of type A influenza HA selected from the group consisting of H1, H2, H3, H4, H5, H6, H7, H8, H9, H10, H11, H12, H13, H14, H15, and H16. In some aspects of the invention, the HA is from a type A influenza, selected from the group comprising H1, H2, H3, H5, H6, H7 and H9.

The VLP may comprise an HA protein of one, or more than one subtype, including H1, H2, H3, H4, H5, H6, H7, H8, H9, H10, H11, H12, H13, H14, H15 or H16 or fragment or portion thereof. Examples of subtypes comprising such HA proteins include A/New Caledonia/20/99 (H1N1)A/Indonesia/5/2006 (H5N1), A/chicken/New York/1995, A/herring gull/DE/677/88 (H2N8), A/Texas/32/2003, A/mallard/MN/33/00, A/duck/Shanghai/1/2000, A/northern pintail/TX/828189/02, A/Turkey/Ontario/6118/68(H8N4), A/shoveler/Iran/G54/03, A/chicken/Germany/N/1949 (H10N7), A/duck/England/56(H11N6), A/duck/Alberta/60/76(H12N5), A/Gull/Maryland/704/77(H13N6), A/Mallard/Gurjev/263/82, A/duck/Australia/341/83 (H15N8), A/black-headed gull/Sweden/5/99(H16N3), B/Lee/40, C/Johannesburg/66, A/PuertoRico/8/34 (H1N1), A/Brisbane/59/2007 (H1N1), A/Solomon Islands 3/2006 (H1N1), A/Brisbane 10/2007 (H3N2), A/Wisconsin/67/2005 (H3N2), B/Malaysia/2506/2004, B/Florida/4/2006, A/Singapore/1/57 (H2N2), A/Anhui/1/2005 (H5N1), A/Vietnam/1194/2004 (H5N1), A/Teal/HongKong/W312/97 (H6N1), A/Equine/Prague/56 (H7N7), A/HongKong/1073/99 (H9N2), A/California/04/09 (H1N1).

In an aspect of the invention, the HA protein may be an H1, H2, H3, H5, H6, H7 or H9 subtype. In an another aspect, the H1 protein may be from the A/New Caledonia/20/99 (H1N1), A/PuertoRico/8/34 (H1N1), A/Brisbane/59/2007 (H1N1), A/Solomon Islands 3/2006 (H1N1) or A/California/04/09 (H1N1) strain. The H3 protein may also be from the A/Brisbane 10/2007 (H3N2) or A/Wisconsin/67/2005 (H3N2) strain. In a further aspect of the invention, the H2 protein may be from the A/Singapore/1/57 (H2N2) strain. The H5 protein may be from the A/Anhui/1/2005 (H5N1), A/Vietnam/1194/2004 (H5N1), or A/Indonesia/5/2005 strain. In an aspect of the invention, the H6 protein may be from the A/Teal/HongKong/W312/97 (H6N1) strain. The H7 protein may be from the A/Equine/Prague/56 (H7N7) strain. In an aspect of the invention, the H9 protein is from the A/HongKong/1073/99 (H9N2) strain. In a further aspect of the invention, the HA protein may be from an influenza virus may be a type B virus, including B/Malaysia/2506/2004 or B/Florida/4/2006. Examples of amino acid sequences of the HA proteins from H1, H2, H3, H5, H6, H7, H9 or B subtypes include SEQ ID NOs: 48-59 and 128.

The influenza virus HA protein may be H5 from strain A/Indonesia/05/05 (H5N1) or H1 from strain A/California/04/09 (H1N1).

The present invention also provides nucleic acid molecules comprising sequences encoding an HA protein. The nucleic acid molecules may further comprise one or more regulatory regions operatively linked to the sequence encoding an HA protein. The nucleic acid molecules may comprise a sequence encoding an H1, H2, H3, H4, H5, H6, H7, H8, H9, H10, H11, H12, H13, H14, H15, H16, B or C. In another aspect of the invention, the HA protein encoded by the nucleic acid molecule may be an H1, H2, H3, H5, H6, H7, H9, or B subtype. The H1 protein encoded by the nucleic acid molecule is from the A/New Caledonia/20/99 (H1N1), A/PuertoRico/8/34 (H1N1), A/Brisbane/59/2007 (H1N1), A/Solomon Islands 3/2006 (H1N1) or A/California/04/09 (H1N1) strain. In an aspect of the invention, the H3 protein encoded by the nucleic acid molecule may be from the A/Brisbane 10/2007 (H3N2), or A/Wisconsin/67/2005 (H3N2) strain. In a further aspect of the invention, the H2 protein encoded by the nucleic acid molecule may be from the A/Singapore/1/57 (H2N2) strain. The H5 protein encoded by the nucleic acid molecule may also be from the A/Anhui/1/2005 (H5N1), A/Vietnam/1194/2004 (H5N1), or A/Indonesia/5/2005 strain. In an aspect of the invention, the H6 protein encoded by the nucleic acid molecule may be from the A/Teal/HongKong/W312/97 (H6N1) strain. The H7 protein encoded by the nucleic acid molecule may also be from the A/Equine/Prague/56 (H7N7) strain. Additionally, the H9 protein encoded by the nucleic acid molecule may be from the A/HongKong/1073/99 (H9N2) strain. The HA protein from B subtype encoded by the nucleic acid may be from the B/Florida/4/2006, or B/Malaysia/2506/2004 strain. Examples of sequences of nucleic acid molecules encoding such HA proteins from H1, H2, H3, H5, H6, H7, H9 or B subtypes include SEQ ID NOs: 36-47 and 60-73 and 127.

The nucleic acid sequence may encode the influenza virus HA protein from strain A/Indonesia/05/05 (H5N1) or from strain A/California/04/09 (H1N1).

Regulatory regions that may be operatively linked to a sequence encoding an HA protein include those that are operative in a plant cell, an insect cell or a yeast cell. Such regulatory regions may include a plastocyanin regulatory region, a regulatory region of Ribulose 1,5-bisphosphate carboxylase/oxygenase (RuBisCO), chlorophyll a/b binding protein (CAB), ST-LS1, a polyhedrin regulatory region, or a gp64 regulatory region. Other regulatory regions include a 5' UTR, 3' UTR or terminator sequences. The plastocyanin regulatory region may be an alfalfa plastocyanin regulatory region; the 5' UTR, 3'UTR or terminator sequences may also be alfalfa sequences.

A method of inducing immunity to an influenza virus infection in a subject, is also provided, the method comprising administering the virus like particle comprising an influenza virus HA protein, one or more than one plant lipid, and a pharmaceutically acceptable carrier. The virus like particle may be administered to a subject orally, intradermally, intranasally, intramuscularly, intraperitoneally, intravenously, or subcutaneously.

The present invention also pertains to a virus like particle (VLP) comprising one or more than one protein derived from a virus selected from the group consisting of Influenza, Measles, Ebola, Marburg, and HIV, and one or more than one lipid derived from a non-sialylating host production cell. The HIV protein may be p24, gp120 or gp41; the Ebolavirus protein may be VP30 or VP35; the Marburg virus protein may be Gp/SGP; the Measles virus protein may be H-protein or F-protein.

Additionally the present invention relates to a virus like particle (VLP) comprising an influenza virus HA protein and one or more than one host lipid. For example if the host is insect, then the virus like particle (VLP) may comprise an influenza virus HA protein and one or more than one insect lipid, or if the host is a yeast, then the virus like particle (VLP) may comprise an influenza virus HA protein and one or more than one yeast lipid.

The present invention also relates to compositions comprising VLPs of two or more strains or subtypes of influenza. The two or more subtypes or strains may be selected from the group comprising: A/New Caledonia/20/99 (H1N1)A/Indonesia/5/2006 (H5N1), A/chicken/New York/1995, A/herring gull/DE/677/88 (H2N8), A/Texas/32/2003, A/mallard/MN/33/00, A/duck/Shanghai/1/2000, A/northern pintail/TX/828189/02, A/Turkey/Ontario/6118/68(H8N4), A/shoveler/Iran/G54/03, A/chicken/Germany/N/1949 (H10N7), A/duck/England/56(H11N6), A/duck/Alberta/60/76(H12N5), A/Gull/Maryland/704/77(H13N6), A/Mallard/Gurjev/263/82, A/duck/Australia/341/83 (H15N8), A/black-headed gull/Sweden/5/99(H16N3), B/Lee/40, C/Johannesburg/66, A/PuertoRico/8/34 (H1N1), A/Brisbane/59/2007 (H1N1), A/Solomon Islands 3/2006 (H1N1), A/Brisbane 10/2007 (H3N2), A/Wisconsin/67/2005 (H3N2), B/Malaysia/2506/2004, B/Florida/4/2006, A/Singapore/1/57 (H2N2), A/Anhui/1/2005 (H5N1), A/Vietnam/1194/2004 (H5N1), A/Teal/HongKong/W312/97 (H6N1), A/Equine/Prague/56 (H7N7), A/HongKong/1073/99 (H9N2), or A/California/04/09 (H1N1). The two or more subtypes or strains of VLPs may be present in about equivalent quantities; alternately one or more of the subtypes or strains may be the majority of the strains or subtypes represented.

The present invention pertains to a method for inducing immunity to influenza virus infection in an animal or target organism comprising administering an effective dose of a vaccine comprising one or more than one VLP, the VLP produced using a non-sialyating host, for example a plant host, an insect host, or a yeast host. The vaccine may be administered orally, intradermally, intranasally, intramusclarly, intraperitoneally, intravenously, or subcutaneously. The target organism may be selected from the group comprising humans, primates, horses, pigs, birds (avian) water fowl, migratory birds, quail, duck, geese, poultry, chicken, camel, canine, dogs, feline, cats, tiger, leopard, civet, mink, stone marten, ferrets, house pets, livestock, mice, rats, seal, whales and the like.

The present invention provides a method for producing VLPs containing hemagglutinin (HA) from different influenza strains in a suitable host capable of producing a VLP, for example, a plant, insect, or yeast. VLPs that are produced in plants contain lipids of plant origin, VLPs produced in insect cells comprise lipids from the plasma membrane of insect cells (generally referred to as “insect lipids”), and VLPs produced in yeast comprise lipids from the plasma membrane of yeast cells (generally referred to as “yeast lipids”).

The present invention also pertains to a plant, plant tissue or plant cell comprising a nucleic acid comprising a nucleotide sequence encoding an antigen from an enveloped virus operatively linked to a regulatory region active in a plant. The antigen may be an influenza hemagglutinin (HA). Preferably, the antigen is an HA from influenza A/California/04/09.

The plant may further comprise a nucleic acid comprising a nucleotide sequence encoding one or more than one chaperone proteins operatively linked to a regulatory region active in a plant. The one or more than one chaperon proteins may be selected from the group comprising Hsp40 and Hsp70.

The production of VLPs in plants presents several advantages over the production of these particles in insect cell culture. Plant lipids can stimulate specific immune cells and enhance the immune response induced. Plant membranes are made of lipids, phosphatidylcholine (PC) and phosphatidylethanolamine (PE), and also contain glycosphingolipids that are unique to plants and some bacteria and protozoa. Sphingolipids are unusual in that they are not esters of glycerol like PC or PE but rather consist of a long chain amino alcohol that forms an amide linkage to a fatty acid chain containing more than 18 carbons. PC and PE as well as glycosphingolipids can bind to CD1 molecules expressed by mammalian immune cells such as antigen-presenting cells (APCs) like dentritic cells and macrophages and other cells including B and T lymphocytes in the thymus and liver (Tsuji M., 2006). Furthermore, in addition to the potential adjuvant effect of the presence of plant lipids, the ability of plant N-glycans to facilitate the capture of glycoprotein antigens by antigen presenting cells (Saint-Jore-Dupas, 2007), may be advantageous of the production of VLPs in plants.

Without wishing to be bound by theory, it is anticipated that plant-made VLPs will induce a stronger immune reaction than VLPs made in other manufacturing systems and that the immune reaction induced by these plant-made VLPs will be stronger when compared to the immune reaction induced by live or attenuated whole virus vaccines.

Contrary to vaccines made of whole viruses, VLPs provide the advantage as they are non-infectious, thus restrictive biological containment is not as significant an issue as it would be working with a whole, infectious virus, and is not required for production. Plant-made VLPs provide a further advantage again by allowing the expression system to be grown in a greenhouse or field, thus being significantly more economical and suitable for scale-up.

Additionally, plants do not comprise the enzymes involved in synthesizing and adding sialic acid residues to proteins. VLPs may be produced in the absence of neuraminidase (NA), and there is no need to co-express NA, or to treat the producing cells or extract with sialidase (neuraminidase), to ensure VLP production in plants.

The VLPs produced in accordance with the present invention do not comprise M1 protein which is known to bind RNA. RNA is a contaminant of the VLP preparation and is undesired when obtaining regulatory approval for the VLP product.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1A shows a sequence of an alfalfa plastocyanin-based expression cassette used for the expression of H1 from strain A/New Caledonia/20/99 (H1N1) in accordance with an embodiment of the present invention (SEQ ID NO:8). Protein disulfide isomerase (PDI) signal peptide is underlined. BglII (AGATCT) and SacI (GAGCTC) restriction sites used for cloning are shown in bold.

FIG. 3 shows a size exclusion chromatography of protein extracts from leaves producing hemagglutinin H1 or H5.

FIG. 4A shows the sequence encoding the N terminal fragment of H1 (A/New Caledonia/20/99 (H1N1)) (SEQ ID NO:1). FIG. 4B shows the sequence encoding the C terminal fragment of H1 (A/New Caledonia/20/99 (H1N1)) (SEQ ID NO:2).

FIG. 5 shows the complete sequence encoding HA0 of H1 (A/New Caledonia/20/99 (H1N1)) (SEQ ID NO:28).

FIG. 6 shows the sequence encoding H5 (A/Indonesia/5/2005 (H5N1)) flanked by a HindIII site immediately upstream of the initial ATG, and a SacI site immediately downstream of the stop (TAA) codon (SEQ ID NO:3)

FIG. 7A shows the sequence of the primer Plasto-443c (SEQ ID NO:4). FIG. 7B shows the sequence of primer SpHA(Ind)-Plasto.r (SEQ ID NO:5). FIG. 7C shows the sequence of primer SpHA(Ind)-Plasto.r (SEQ ID NO:6). FIG. 7D shows the sequence of primer HA(Ind)-Sac.r (SEQ ID NO:7).

FIG. 8A shows the amino acid sequence of the H1 (A/New Caledonia/20/99 (H1N1); SEQ ID NO:9). FIG. 8B shows the amino acid sequence of H5 (A/Indonesia/5/2005 (H5N1); SEQ ID NO:10). Native signal peptide is indicated in bold.

FIG. 9 shows the nucleotide sequence of HA of influenza A subtype H7 (SEQ ID No: 11).

FIG. 10A shows the nucleotide sequence of Influenza A HA, subtype H2 (SEQ ID NO:12). FIG. 10B shows the nucleotide sequence of Influenza A HA subtype H3 (SEQ ID NO:13). FIG. 10C shows the nucleotide sequence of Influenza A HA subtype H4 (SEQ ID NO:14). FIG. 10D shows the nucleotide sequence of Influenza A HA subtype H5 (SEQ ID NO:15). FIG. 10E shows the nucleotide sequence of Influenza A HA subtype H6 (SEQ ID NO:16). FIG. 10F shows the nucleotide sequence of Influenza A HA subtype H8 (SEQ ID NO:17). FIG. 10G shows the nucleotide sequence of Influenza A HA subtype H9 (SEQ ID NO:18). FIG. 10H shows the nucleotide sequence of Influenza A HA subtype H10 (SEQ ID NO:19). FIG. 10I shows the nucleotide sequence of Influenza A HA subtype H11 (SEQ ID NO:20). FIG. 10J shows the nucleotide sequence of Influenza A HA subtype H12 (SEQ ID NO:21). FIG. 10K shows the nucleotide sequence of Influenza A HA subtype H13 (SEQ ID NO:22). FIG. 10L shows the nucleotide sequence of Influenza A HA subtype H14 (SEQ ID NO:23). FIG. 10M shows the nucleotide sequence of Influenza A HA subtype H15 (SEQ ID NO:24). FIG. 10N shows the nucleotide sequence of Influenza A HA subtype H16 (SEQ ID NO:25). FIG. 10O shows the nucleotide sequence of Influenza B HA (SEQ ID NO:26). FIG. 10P shows the nucleotide sequence of Influenza C HA (SEQ ID NO:27). FIG. 10Q shows the nucleotide sequence of primer XmaI-pPlas.c (SEQ ID NO: 29). FIG. 10R shows the nucleotide sequence of primer SacI-ATG-pPlas.r (SEQ ID NO: 30). FIG. 10S shows the nucleotide sequence of primer SacI-PlasTer.c (SEQ ID NO: 31). FIG. 10T shows the nucleotide sequence of primer EcoRI-PlasTer.r (SEQ ID NO: 32).

FIG. 13 shows characterization of hemagglutinin structures by size exclusion chromatography. Protein extract from separate biomasses producing H5 (A/Indonesia/5/2005 (H5N1)), H1 (A/New Caledonia/20/99 (H1N1)), soluble H1, or H1 and M1 were separated by gel filtration on S-500 HR. Commercial H1 (A/New Caledonia/20/99 (H1N1)) in the form of rosettes was also fractionated (H1 rosette). FIG. 13B shows elution fractions analyzed for the presence of hemagglutinin by immunoblotting with anti-H5 (Vietnam) antibodies (for H5). FIG. 13C shows elution fractions analyzed for anti-influenza A antibodies for H1. FIG. 13D shows elution fractions analyzed for anti-influenza A antibodies for soluble H1. FIG. 13E shows elution fractions analyzed for anti-influenza A antibodies for H1 rosette. FIG. 13F shows elution fractions analyzed for anti-influenza A antibodies for H1+M1.

FIG. 14 shows concentration of influenza H5 (A/Indonesia/5/2005 (H5N1)) structures by sucrose gradient centrifugation and electron microscopy examination of hemagglutinin-concentrated fractions.

FIG. 15 C shows isolated H5 VLP enlarged to show details of the structure.

FIG. 16 shows a nucleotide sequence for Influenza A virus (A/New Caledonia/20/99(H1N1)) hemagglutinin (HA) gene, complete cds. GenBank Accession No. AY289929 (SEQ ID NO: 33)

FIG. 17 shows a nucleotide sequence for *Medicago sativa* mRNA for protein disulfide isomerase. GenBank Accession No. Z11499 (SEQ ID NO: 34).

FIG. 18 shows a nucleotide sequence for Influenza A virus (A/Puerto Rico/8/34(H1N1)) segment 7, complete sequence. GenBank Accession No. NC 002016.1 (SEQ ID NO: 35).

FIG. 20 shows induction of serum antibody responses 14 days after boost in Balb/c mice vaccinated with plant-made influenza H5 VLP (A/Indonesia/5/2005 (H5N1)) or recombinant soluble F15 (A/Indonesia/5/2005 (H5N1)).

FIG. 21 shows hemagglutination inhibition antibody response (HAI) 14 days after boost in Balb/c mice vaccinated with plant-made influenza H5 VLP (A/Indonesia/5/2005 (H5N1)) or recombinant soluble H5 (A/Indonesia/5/2005 (H5N1)).

FIG. 22 shows the effect of adjuvant on immunogenicity of the VLPs in Balb/c mice.

FIG. 23**(B) Antibody titers against whole inactivated viruses (A/Indonesia/5/2005 (H5N1) and (A/Vietnam/1194/04 (H5N1))). All groups are statistically different to negative control.

FIG. 25 shows in vitro cross-reactivity of serum antibodies from Balb/c mice immunized with H5 VLP (A/Indonesia/5/2005 (H5N1)) 30 days after boost. (A) Antibody titers whole inactivated viruses. (B) Hemagglutination-inhibition titers against various whole inactivated viruses. Values are the GMT (ln) of reciprocal end-point titers of five mice per group. Bars represent mean deviation. All groups are statistically different to negative control. *p<0.05 compared to the corresponding recombinant soluble H5. All values less than 10 were given an arbitrary value of 5 (1.6 for ln) and are considered negative.

FIG. 28 shows the sequence spanning from DraIII to SacI sites of clone 774-nucleotide sequence of A/Brisbane/59/2007 (H1N1) (SEQ ID NO: 36). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 29 shows the sequence spanning from DraIII to SacI sites of clone 775-nucleotide sequence of A/Solomon Islands 3/2006 (H1N1) (SEQ ID NO: 37). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 30 shows the sequence spanning from DraIII to SacI sites of clone 776-nucleotide sequence of A/Brisbane 10/2007 (H3N2) (SEQ ID NO: 38). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 31 shows the sequence spanning from DraIII to SacI sites of clone 777-nucleotide sequence of A/Wisconsin/67/2005 (H3N2) (SEQ ID NO: 39). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 32 shows the sequence spanning from DraIII to SacI sites of clone 778-nucleotide sequence of B/Malaysia/2506/2004 (SEQ ID NO: 40). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 33 shows the sequence spanning from DraIII to SacI sites of clone 779-nucleotide sequence of B/Florida/4/2006 (SEQ ID NO: 41). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 34 shows the sequence spanning from DraIII to SacI sites of clone 780-nucleotide sequence of A/Singapore/1/57 (H2N2) (SEQ ID NO: 42). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 35 shows the sequence spanning from DraIII to SacI sites of clone 781-nucleotide sequence of A/Anhui/1/2005 (H5N1) (SEQ ID NO: 43). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 36 shows the sequence spanning from DraIII to SacI sites of clone 782-nucleotide sequence of A/Vietnam/1194/2004 (H5N1) (SEQ ID NO: 44). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 37 shows the sequence spanning from DraIII to SacI sites of clone 783-nucleotide sequence of A/Teal/HongKong/W312/97 (H6N1) (SEQ ID NO: 45). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 38 shows the sequence spanning from DraIII to SacI sites of clone 784-nucleotide sequence of A/Equine/Prague/56 (H7N7) (SEQ ID NO: 46). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 39 shows the sequence spanning from DraIII to SacI sites of clone 785-nucleotide sequence of A/HongKong/1073/99 (H9N2) (SEQ ID NO: 47). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 40A shows the amino acid sequence (SEQ ID NO: 48) of the polypeptide translated from clone 774 (A/Brisbane/59/2007 (H1N1)). The open reading frame of clone 774 starts with the ATG indicated in FIG. 28. FIG. 40B shows the amino acid sequence (SEQ ID NO: 49) of the polypeptide translated from clone 775 (A/Solomon Islands 3/2006 (H1N1)). The open reading frame of clone 775 starts with the ATG indicated in FIG. 29.

FIG. 41A shows the amino acid sequence (SEQ ID NO: 50) of the polypeptide translated from clone 776 (A/Brisbane/10/2007 (H3N2)). The open reading frame of clone 776 starts with the ATG indicated in FIG. 30. FIG. 41B shows the amino acid sequence (SEQ ID NO: 51) of the polypeptide translated from clone 777 (A/Wisconsin/67/2005 (H3N2)). The open reading frame of clone 777 starts with the ATG indicated in FIG. 31.

FIG. 42A shows the amino acid sequence (SEQ ID NO: 52) of the polypeptide translated from clone 778 (B/Malaysia/2506/2004). The open reading frame of clone 778 starts with the ATG indicated in FIG. 32. FIG. 42B shows the amino acid sequence (SEQ ID NO: 53) of the polypeptide translated from clone 779 (B/Florida/4/2006). The open reading frame of clone 779 starts with the ATG indicated in FIG. 33.

FIG. 43A shows the amino acid sequence (SEQ ID NO: 54) of the polypeptide translated from clone 780 (A/Singapore/1/57 (H2N2)). The open reading frame of clone 780 starts with the ATG indicated in FIG. 34. FIG. 43B shows the amino acid sequence (SEQ ID NO: 55) of the polypeptide translated from clone 781 (A/Anhui/1/2005 (H5N1)). The open reading frame of clone 781 starts with the ATG indicated in FIG. 35.

FIG. 44A shows the amino acid sequence (SEQ ID NO: 56) of the polypeptide translated from clone 782 (A/Vietnam/1194/2004 (H5N1)). The open reading frame of clone 782 starts with the ATG indicated in FIG. 36. FIG. 44B shows the amino acid sequence (SEQ ID NO: 57) of the polypeptide translated from clone 783 (A/Teal/HongKong/W312/97 (H6N1)). The open reading frame of clone 783 starts with the ATG indicated in FIG. 37.

FIG. 45A shows the amino acid sequence (SEQ ID NO: 58) of the polypeptide translated from clone 784 (A/Equine/Prague/56 (H7N7)). The open reading frame of clone 784 starts with the ATG indicated in FIG. 38. FIG. 45B shows the amino acid sequence (SEQ ID NO: 59) of the polypeptide translated from clone 785 (A/HongKong/1073/99 (H9N2)). The open reading frame of clone 785 starts with the ATG indicated in FIG. 39.

FIG. 51 shows the nucleic acid sequence (SEQ ID NO: 60) of an HA expression cassette comprising alfalfa plastocyanin promoter and 5' UTR, hemagglutinin coding sequence of H5 from A/Indonesia/5/2005 (Construct # 660), alfalfa plastocyanin 3' UTR and terminator sequences FIG. 52 shows the nucleic acid sequence (SEQ ID NO: 61) of an HA expression cassette comprising alfalfa plastocyanin promoter and 5' UTR, hemagglutinin coding sequence of H1 from A/New Caledonia/20/1999 (Construct # 540), alfalfa plastocyanin 3' UTR and terminator sequences FIG. 53 shows the nucleic acid sequence (SEQ ID NO: 62) of an HA expression cassette comprising alfalfa plastocyanin promoter and 5' UTR, hemagglutinin coding sequence of H1 from A/Brisbane/59/2007 (construct #774), alfalfa plastocyanin 3' UTR and terminator sequences.

FIG. 54 shows the nucleic acid sequence (SEQ ID NO: 63) of an HA expression cassette comprising alfalfa plastocyanin promoter and 5' UTR, hemagglutinin coding sequence of H1 from A/Solomon Islands/3/2006 (H1N1) (construct #775), alfalfa plastocyanin 3' UTR and terminator sequences.

FIG. 55 shows the nucleic acid sequence (SEQ ID NO: 64) of an HA expression cassette comprising alfalfa plastocyanin promoter and 5' UTR, hemagglutinin coding sequence of H2 from A/Singapore/1/57 (H2N2) (construct #780), alfalfa plastocyanin 3' UTR and terminator sequences.

FIG. 56 shows the nucleic acid sequence (SEQ ID NO: 65) of an HA expression cassette comprising alfalfa plastocyanin promoter and 5' UTR, hemagglutinin coding sequence of H5 from A/Anhui/1/2005 (H5N1) (Construct#781), alfalfa plastocyanin 3' UTR and terminator sequences.

FIG. 57 shows the nucleic acid sequence (SEQ ID NO: 66) of an HA expression cassette comprising alfalfa plastocyanin promoter and 5' UTR, hemagglutinin coding sequence of H5 from A/Vietnam/1194/2004 (H5N1) (Construct #782), alfalfa plastocyanin 3' UTR and terminator sequences.

FIG. 58 shows the nucleic acid sequence (SEQ ID NO: 67) of an HA expression cassette comprising alfalfa plastocyanin promoter and 5' UTR, hemagglutinin coding sequence of H6 from A/Teal/Hong Kong/W312/97 (H6N1) (Construct #783), alfalfa plastocyanin 3' UTR and terminator sequences.

FIG. 59 shows the nucleic acid sequence (SEQ ID NO: 68) of an HA expression cassette comprising alfalfa plastocyanin promoter and 5' UTR, hemagglutinin coding sequence of H9 from A/Hong Kong/1073/99 (H9N2) (Construct #785), alfalfa plastocyanin 3' UTR and terminator sequences.

FIG. 60 shows the nucleic acid sequence (SEQ ID NO: 69) of an HA expression cassette comprising alfalfa plastocyanin promoter and 5' UTR, hemagglutinin coding sequence of H3 from A/Brisbane/10/2007 (H3N2), alfalfa plastocyanin 3' UTR and terminator sequences.

FIG. 61 shows the nucleic acid sequence (SEQ ID NO: 70) of an HA expression cassette comprising alfalfa plastocyanin promoter and 5' UTR, hemagglutinin coding sequence of H3 from A/Wisconsin/67/2005 (H3N2), alfalfa plastocyanin 3' UTR and terminator sequences.

FIG. 62 shows the nucleic acid sequence (SEQ ID NO: 71) of an HA expression cassette comprising alfalfa plastocyanin promoter and 5' UTR, hemagglutinin coding sequence of H7 from A/Equine/Prague/56 (H7N7), alfalfa plastocyanin 3' UTR and terminator sequences.

FIG. 63 shows the nucleic acid sequence (SEQ ID NO: 72) of an HA expression cassette comprising alfalfa plastocyanin promoter and 5' UTR, hemagglutinin coding sequence of HA from B/Malaysia/2506/2004, alfalfa plastocyanin 3' UTR and terminator sequences.

FIG. 64 shows the nucleic acid sequence (SEQ ID NO: 73) of an HA expression cassette comprising alfalfa plastocyanin promoter and 5' UTR, hemagglutinin coding sequence of HA from B/Florida/4/2006, alfalfa plastocyanin 3' UTR and terminator sequences.

FIG. 65 shows a consensus amino acid sequence (SEQ ID NO: 74) for HA of A/New Caledonia/20/99 (H1N1) (encoded by SEQ ID NO: 33), A/Brisbane/59/2007 (H1N1) (SEQ ID NO: 48), A/Solomon Islands/3/2006 (H1N1) (SEQ ID NO: 49) and SEQ ID NO: 9. X1 (position 3) is A or V; X2 (position 52) is D or N; X3 (position 90) is K or R; X4 (position 99) is K or T; X5 (position 111) is Y or H; X6 (position 145) is V or T; X7 (position 154) is E or K; X8 (position 161) is R or K; X9 (position 181) is V or A; X10 (position 203) is D or N; X11 (position 205) is R or K; X12 (position 210) is T or K; X13 (position 225) is R or K; X14 (position 268) is W or R; X15 (position 283) is T or N; X16 (position 290) is E or K; X17 (position 432) is I or L; X18 (position 489) is N or D.

FIG. 66 shows amino acid sequence (SEQ ID NO: 75) of H1 New Caledonia (AAP34324.1) encoded by SEQ ID NO: 33.

FIG. 67 shows the amino acid sequence (SEQ ID NO: 76) of H1 Puerto Rico (NC_0409878.1) encoded by SEQ ID NO: 35

FIG. 68 shows the nucleic acid sequence of a portion of expression cassette number 828, from PacI (upstream promoter) to AscI (immediately downstream NOS terminator). CPMV HT 5'UTR sequence underlined with mutated ATG. ApaI restriction site (immediately upstream of ATG of protein coding sequence to be express, in this case C5-1 kappa light chain.)

FIG. 69 shows the nucleic acid sequence of a portion of construct number 663, from HindIII (in the multiple cloning site, upstream of the plastocyanin promoter) to EcoRI (immediately downstream of the plastocyanin terminator). H5 (from A/Indonesia/5/2005) coding sequence in fusion with PDI SP is underlined.

FIG. 70 shows the nucleic acid sequence of a portion of construct number 787, from HindIII (in the multiple cloning site, upstream of the plastocyanin promoter) to EcoRI (immediately downstream of the plastocyanin terminator). H1 (from A/Brisbane/59/2007) coding sequence in fusion with PDI SP is underlined.

FIG. 71 shows the nucleic acid sequence of a portion of construct number 790, from HindIII (in the multiple cloning site, upstream of the plastocyanin promoter) to EcoRI (immediately downstream of the plastocyanin terminator). H3 (from A/Brisbane/10/2007) coding sequence in fusion with PDI SP is underlined.

FIG. 72 shows the nucleic acid sequence of a portion of construct number 798, from HindIII (in the multiple cloning site, upstream of the plastocyanin promoter) to EcoRI (immediately downstream of the plastocyanin terminator). HA from B/Florida/4/2006 coding sequence in fusion with PDI SP is underlined.

FIG. 73 shows the nucleic acid sequence of a portion of construct number 580, from PacI (upstream of the 35S promoter) to AscI (immediately downstream of the NOS terminator). Coding sequence of H1 (from A/New Caledonia/20/1999) in fusion with PDI SP is underlined.

FIG. 74 shows the nucleic acid sequence of a portion of construct number 685, from PacI (upstream of the 35S promoter) to AscI (immediately downstream of the NOS terminator). Coding sequence of H5 from A/Indonesia/5/2005 is underlined.

FIG. 75 shows the nucleic acid sequence of a portion of construct number 686, from PacI (upstream of the 35S promoter) to AscI (immediately downstream of the NOS terminator). Coding sequence of H5 from A/Indonesia/5/2005 in fusion with PDI SP is underlined.

FIG. 76 shows the nucleic acid sequence of a portion of construct number 732, from PacI (upstream of the 35S promoter) to AscI (immediately downstream of the NOS terminator). Coding sequence of H1 from A/Brisbane/59/2007 is underlined.

FIG. 77 shows the nucleic acid sequence of a portion of construct number 733, from PacI (upstream of the 35S promoter) to AscI (immediately downstream of the NOS terminator). Coding sequence of H1 from A/Brisbane/59/2007 in fusion with PDI SP is underlined.

FIG. 78 shows the nucleic acid sequence of a portion of construct number 735, from PacI (upstream of the 35S promoter) to AscI (immediately downstream of the NOS terminator). Coding sequence of H3 from A/Brisbane/10/2007 is underlined.

FIG. 79 shows the nucleic acid sequence of a portion of construct number 736, from PacI (upstream of the 35S promoter) to AscI (immediately downstream of the NOS terminator). Coding sequence of H3 from A/Brisbane/10/2007 in fusion with PDI SP is underlined FIG. 80 shows the nucleic acid sequence of a portion of construct number 738, from PacI (upstream of the 35S promoter) to AscI (immediately downstream of the NOS terminator). Coding sequence of HA from B/Florida/4/2006 is underlined.

FIG. 81 shows the nucleic acid sequence of a portion of construct number 739, from PacI (upstream of the 35S promoter) to AscI (immediately downstream of the NOS terminator). Coding sequence of HA from B/Florida/4/2006 in fusion with PDI SP is underlined.

FIG. 82 shows a nucleic acid sequence encoding Msj1 (SEQ ID NO: 114).

FIG. 83 shows the nucleic acid sequence of a portion of construct number R850, from HindIII (in the multiple cloning site, upstream of the promoter) to EcoRI (immediately downstream of the NOS terminator). HSP40 coding sequence is underlined.

FIG. 84 shows the nucleic acid sequence of a portion of construct number R860, from HindIII (in the multiple cloning site, upstream of the promoter) to EcoRI (immediately downstream of the NOS terminator). HSP70 coding sequence is underlined.

FIG. 85 shows the nucleic acid sequence of a portion of construct number R870, from HindIII (in the multiple cloning site, upstream of the promoter) to EcoRI (immediately downstream of the NOS terminator). HSP40 coding sequence is in underlined italic and HSP70 coding sequence is underlined. A) nucleotides 1-5003; B) nucleotides 5004-9493.

FIG. 87 shows an immunoblot analysis of expression of HA using a signal peptide from alfalfa protein disulfide isomerase. Twenty micrograms of leaf protein extract obtained from 3 separate plants were loaded on the SDS-PAGE except for the H1 (A/New Caledonia/20/99 (H1N1)) where five micrograms were used. The indicated controls (whole inactivated virus (WIV) of homologous strain) were spiked in five or twenty micrograms of mock-infiltrated plants. a) Expression of H1 from A/New Caledonia/20/99), b) expression of H1 from A/Brisbane/59/2007, c) expression of H3 from A/Brisbane/10/2007, d) expression of H5 from A/Indonesia/5/2005, e) expression of HA from B/Florida/4/2006. The arrows indicate the immunoband corresponding to HA0. SP WT: native signal peptide, PS PDI: alfalfa PDI signal peptide.

FIG. 92A shows the nucleotide sequence (SEQ ID NO: 127) of the CPMV-HT-based expression cassette for H1 from A/California/04/09 (cassette number 560). Alfalfa protein disulfide isomerase signal peptide coding sequence is underlined and mature H1 coding sequence is highlighted in bold. FIG. 92B shows amino acid sequence (SEQ ID NO: 128) of the H1 from A/California/04/09 (as encoded by SEQ ID NO: 127). Alfalfa protein disulfide isomerase signal peptide is underlined.

FIG. 93 shows the nucloetide sequence of the 2X35S promoter (SEQ ID NO:129).

FIG. 94 shows the nucleotide sequence of intermediary expression cassette number 972 (SEQ ID NO:134), from PacI (upstream promoter) to AscI (immediately downstream NOS terminator). 2X35S promoter sequence is underlined. Mutated ATG are boxed. ApaI restriction site (immediately downstream ATG for protein coding sequence to be express, in this case HA0 of H5 A/Indonesia), is shaded.

FIG. 95 shows the nucleotide sequence of Native H1 A/California/4/2009 sequence (SEQ ID NO:135). Native H1

Figure 1B:
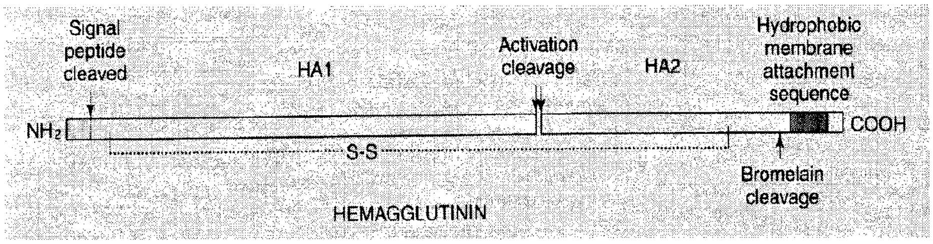
FIG. 1B shows a schematic diagram of functional domains of influenza hemagglutinin. After cleavage of HA0, HA1 and HA2 fragments remain bound together by a disulfide bridge.

A/California/4/2009 signal peptide is underlined. SacI and StuI restriction sites are boxed.

FIG. 96 shows the nucleotide sequences of the final sequence (SEQ ID NO:136) synthesized containing H1 A/California/4/2009 sequence. M protein portion from DraIII to ApaI restriction site is underlined. PDISP is in bold. Mutated SacI and StuI restriction sites are boxed.

FIG. 97 shows the nucleotide sequence of Fragments 1 (SEQ ID NO:137), 2 (SEQ ID NO:138) and 3 (SEQ ID NO:139) used to synthesize the H1 A/California/4/2009 sequence using PCR-based ligation.

FIG. 98 shows the nucleotide sequence of expression cassette number 560 (SEQ ID NO:146), from PacI (upstream promoter) to AscI (immediately downstream NOS terminator). PDISP-HA0 H1 A/California/4/2009 sequence is underlined.

DETAILED DESCRIPTION

The present invention relates to the production of virus-like particles. More specifically, the present invention is directed to the production of virus-like particles comprising influenza antigens.

The following description is of a preferred embodiment.

The present invention provides a nucleic acid comprising a nucleotide sequence encoding an antigen from an enveloped virus, for example, the influenza hemagglutinin (HA), operatively linked to a regulatory region active in a plant.

Furthermore, the present invention provides a method of producing virus like particles (VLPs) in a plant. The method involves introducing a nucleic acid encoding an antigen operatively linked to a regulatory region active in the plant, into the plant, or portion of the plant, and incubating the plant or a portion of the plant under conditions that permit the expression of the nucleic acid, thereby producing the VLPs.

VLPs may be produced from influenza virus, however, VLPs may also be produced from other plasma membrane derived virus including but not limited to Measles, Ebola, Marburg, and HIV.

The invention includes VLPs of all types of influenza virus which may infect humans, including for example, but not limited to the very prevalent A (H1N1) sub-type (e.g. A/New Caledonia/20/99 (H1N1)), the A/Indonesia/5/05 sub-type (H5N1) (SEQ ID NO: 60) and the less common B type (for example SEQ ID NO:26, FIG. 10O), and C type (SEQ ID NO:27, FIG. 10P), and to HAs obtained from other influenza subtypes. VLPs of other influenza subtypes are also included in the present invention, for example, A/Brisbane/59/2007 (H1N1; SEQ ID NO:48), A/Solomon Islands/3/2006 (H1N1; SEQ ID NO:49), A/Singapore/1/57 (H2N2; SEQ ID NO:54), A/Anhui/1/2005 (H5N1; SEQ ID NO:55), A/Vietnam/1194/2004 (H5N1; SEQ ID NO:56), A/Teal/Hong Kong/W312/97 (H6N1; SEQ ID NO:57), A/Hong Kong/1073/99 (H9N2; SEQ ID NO:59), A/Brisbane/10/2007 (H3N2; SEQ ID NO:50), A/Wisconsin/67/2005 (H3N2; SEQ ID NO:51), A/Equine/Prague/56 (H7N7; SEQ ID NO:58), B/Malaysia/2506/2004 (SEQ ID NO:52), B/Florida/4/2006 (SEQ ID NO:53) or A/California/04/09 (H1N1) (SEQ ID NO: 127).

The present invention also pertains to influenza viruses which infect other mammals or host animals, for example humans, primates, horses, pigs, birds, avian water fowl, migratory birds, quail, duck, geese, poultry, chicken, camel, canine, dogs, feline, cats, tiger, leopard, civet, mink, stone marten, ferrets, house pets, livestock, mice, rats, seal, whale and the like.

Non limiting examples of other antigens that may be expressed in plasma membrane derived viruses include, the Capsid protein of HIV-p24; gp120, gp41-envelope proteins, the structural proteins VP30 and VP35; Gp/SGP (a glycosylated integral membrane protein) of Filoviruses, for example Ebola or Marburg, or the H protein, and F protein of Paramyxoviruses, for example, Measles.

The invention also includes, but is not limited to, influenza derived VLPs that obtain a lipid envelope from the plasma membrane of the cell in which the VLP proteins are expressed. For example, if the VLP is expressed in a plant-based system, the VLP may obtain a lipid envelope from the plasma membrane of the cell.

Generally, the term "lipid" refers to a fat-soluble (lipophilic), naturally-occurring molecules. The term is also used more specifically to refer to fatty-acids and their derivatives (including tri-, di-, and monoglycerides and phospholipids), as well as other fat-soluble sterol-containing metabolites or sterols. Phospholipids are a major component of all biological membranes, along with glycolipids, sterols and proteins. Examples of phospholipids include phosphatidylethanolamine, phosphatidylcholine, phosphatidylinositol, phosphatidylserine, phosphatidylglycerol and the like. Examples of sterols include zoosterols (for example, cholesterol) and phytosterols (for example, sitosterol) and steryl-glucoside. Over 200 phytosterols have been identified in various plant species, the most common being campesterol, stigmasterol, ergosterol, brassicasterol, delta-7-stigmasterol, delta-7-avenasterol, daunosterol, sitosterol, 24-methylcholesterol, cholesterol or beta-sitosterol. As one of skill in the art would understand, the lipid composition of the plasma membrane of a cell may vary with the culture or growth conditions of the cell or organism from which the cell is obtained.

Cell membranes generally comprise lipid bilayers, as well as proteins for various functions. Localized concentrations of particular lipids may be found in the lipid bilayer, referred to as 'lipid rafts'. Without wishing to be bound by theory, lipid rafts may have significant roles in endo and exocytosis, entry or egress of viruses or other infectious agents, inter-cell signal transduction, interaction with other structural components of the cell or organism, such as intracellular and extracellular matrices.

With reference to influenza virus, the term "hemagglutinin" or "HA" as used herein refers to a glycoprotein found on the outside of influenza viral particles. HA is a homotrimeric membrane type I glycoprotein, generally comprising a signal peptide, an HA1 domain, and an HA2 domain comprising a membrane-spanning anchor site at the C-terminus and a small cytoplasmic tail (FIG. 1B). Nucleotide sequences encoding HA are well known and are available—see, for example, the BioDefence Public Health base (Influenza Virus; see URL: biohealthbase.org) or National Center for Biotechnology Information (see URL: ncbi.nlm.nih.gov), both of which are incorporated herein by reference.

The term "homotrimer" or "homotrimeric" indicates that an oligomer is formed by three HA protein molecules. Without wishing to be bound by theory, HA protein is synthesized as monomeric precursor protein (HA0) of about 75 kDa, which assembles at the surface into an elongated trimeric protein. Before trimerization occurs, the precursor protein is cleaved at a conserved activation cleavage site (also referred to as fusion peptide) into 2 polypeptide chains, HA1 and HA2 (comprising the transmembrane region), linked by a disulfide bond. The HA1 segment may be 328 amino acids in length, and the HA2 segment may be 221 amino acids in length. Although this cleavage may be important for virus infectivity, it may not be essential for the trimerization of the protein. Insertion of HA within the endoplasmic reticulum (ER) membrane of the host cell, signal peptide cleavage and protein glycosylation are co-translational events. Correct refolding of HA requires glycosylation of the protein and formation of 6 intra-chain disulfide bonds. The HA trimer assembles within the cis- and trans-Golgi complex, the transmembrane domain playing a role in the trimerization process. The crystal structures of bromelain-treated HA proteins, which lack the transmembrane domain, have shown a highly conserved structure amongst influenza strains. It has also been established that HA undergoes major conformational changes during the infection process, which requires the precursor HA0 to be cleaved into the 2 polypeptide chains HA1 and HA2. The HA protein may be processed (i.e., comprise HA1 and HA2 domains), or may be unprocessed (i.e. comprise the HA0 domain).

The present invention pertains to the use of an HA protein comprising the transmembrane domain and includes HA1 and HA2 domains, for example the HA protein may be HA0, or processed HA comprising HA1 and HA2. The HA protein may be used in the production or formation of VLPs using a plant, or plant cell, expression system.

The HA of the present invention may be obtained from any subtype. For example, the HA may be of subtype H1, H2, H3, H4, H5, H6, H7, H8, H9, H10, H11, H12, H13, H14, H15, H16 or of influenza type B. The recombinant HA of the present invention may also comprise an amino acid sequence based on the sequence any hemagglutinin known in the art—see, for example, the BioDefence Public Health base (Influenza Virus; see URL: biohealthbase.org) or National Center for Biotechnology Information (see URL: ncbi.nlm.nih.gov). Furthermore, the HA may be based on the sequence of a hemagglutinin that is isolated from one or more emerging or newly-identified influenza viruses.

The present invention also includes VLPs that comprise HAs obtained from one or more than one influenza subtype. For example, VLPs may comprise one or more than one HA from the subtype H1 (encoded by SEQ ID NO:28), H2 (encoded by SEQ ID NO:12), H3 (encoded by SEQ ID NO:13), H4 (encoded by SEQ ID NO:14), H5 (encoded by SEQ ID NO:15), H6 (encoded by SEQ ID NO:16), H7 (encoded by SEQ ID NO:11), H8 (encoded by SEQ ID NO:17), H9 (encoded by SEQ ID NO:18), H10 (encoded by SEQ ID NO:19), H11 (encoded by SEQ ID NO:20), H12 (encoded by SEQ ID NO:21), H13 (encoded by SEQ ID NO:27), H14 (encoded by SEQ ID NO:23), H15 (encoded by SEQ ID NO:24), H16 (encoded by SEQ ID NO:25), or influenza type B (encoded by SEQ ID NO: 26), or a combination thereof. One or more that one HA from the one or more than one influenza subtypes may be co-expressed within a plant or insect cell to ensure that the synthesis of the one or more than one HA results in the formation of VLPs comprising a combination of HAs obtained from one or more than one influenza subtype. Selection of the combination of HAs may be determined by the intended use of the vaccine prepared from the VLP. For example a vaccine for use in inoculating birds may comprise any combination of HA subtypes, while VLPs useful for inoculating humans may comprise subtypes one or more than one of subtypes H1, H2, H3, H5, H7, H9, H10, N1, N2, N3 and N7. However, other HA subtype combinations may be prepared depending upon the use of the inoculum.

Therefore, the present invention is directed to a VLP comprising one or more than one HA subtype, for example two, three, four, five, six, or more HA subtypes.

The present invention also provides for nucleic acids encoding hemagglutinins that form VLPs when expressed in plants.

Exemplary nucleic acids may comprise nucleotide sequences of hemagglutinin from selected strains of influenza subtypes. For example, an A (H1N1) sub-type such as A/New Caledonia/20/99 (H1N1) (SEQ ID NO: 33), the A/Indonesia/5/05 sub-type (H5N1) (comprising construct #660; SEQ ID NO: 60) and the less common B type (for example SEQ ID NO:26, FIG. 10O), and C type (SEQ ID NO:27, FIG. 10P), and to HAs obtained from other influenza subtypes. VLPs of other influenza subtypes are also included in the present invention, for example, A/Brisbane/59/2007 (H1N1; SEQ ID NO:36), A/Solomon Islands/3/2006 (H1N1; SEQ ID NO:37), A/Singapore/1/57 (H2N2; SEQ ID NO:42), A/Anhui/1/2005 (H5N1; SEQ ID NO:43), A/Vietnam/1194/2004 (H5N1; SEQ ID NO:44), A/Teal/Hong Kong/W312/97 (H6N1; SEQ ID NO:45), A/Hong Kong/1073/99 (H9N2; SEQ ID NO:47), A/Brisbane/10/2007 (H3N2; SEQ ID NO:38), A/Wisconsin/67/2005 (H3N2; SEQ ID NO:39), A/Equine/Prague/56 (H7N7; SEQ ID NO:46), B/Malaysia/2506/2004 (SEQ ID NO:40), B/Florida/4/2006 (SEQ ID NO:41) or A/California/04/09 (H1N1) (SEQ ID NO: 127).

Correct folding of the hemagglutinins may be important for stability of the protein, formation of multimers, formation of VLPs and function of the HA (ability to hemagglutinate), among other characteristics of influenza hemagglutinins. Folding of a protein may be influenced by one or more factors, including, but not limited to, the sequence of the protein, the relative abundance of the protein, the degree of intracellular crowding, the availability of cofactors that may bind or be transiently associated with the folded, partially folded or unfolded protein, the presence of one or more chaperone proteins, or the like.

Heat shock proteins (Hsp) or stress proteins are examples of chaperone proteins, which may participate in various cellular processes including protein synthesis, intracellular trafficking, prevention of misfolding, prevention of protein aggregation, assembly and disassembly of protein complexes, protein folding, and protein disaggregation. Examples of such chaperone proteins include, but are not limited to, Hsp60, Hsp65, Hsp 70, Hsp90, Hsp100, Hsp20-30, Hsp10, Hsp100-200, Hsp100, Hsp90, Lon, TF55, FKBPs, cyclophilins, ClpP, GrpE, ubiquitin, calnexin, and protein disulfide isomerases. See, for example, Macario, A. J. L., *Cold Spring Harbor Laboratory Res.* 25:59-70. 1995; Parsell, D. A. & Lindquist, S. Ann. Rev. Genet. 27:437-496 (1993); U.S. Pat. No. 5,232,833. In some examples, a particular group of chaperone proteins includes Hsp40 and Hsp70.

Examples of Hsp70 include Hsp72 and Hsc73 from mammalian cells, DnaK from bacteria, particularly mycobacteria such as *Mycobacterium leprae, Mycobacterium tuberculosis*, and *Mycobacterium bovis* (such as Bacille-Calmette Guerin: referred to herein as Hsp71). DnaK from *Escherichia coli*, yeast. and other prokaryotes, and BiP and Grp78 from eukaryotes, such as *A. thaliana* (Lin et al. 2001 (Cell Stress and Chaperones 6:201-208). A particular example of an Hsp70 is *A. thaliana* Hsp70 (encoded by SEQ ID NO: 122, or SEQ ID NO: 123). Hsp70 is capable of specifically binding ATP as well as unfolded polypeptides and peptides, thereby participating in protein folding and unfolding as well as in the assembly and disassembly of protein complexes.

Examples of Hsp40 include DnaJ from prokaryotes such as *E. coli* and mycobacteria and HSJ1, HDJ1 and Hsp40 from eukaryotes, such as alfalfa (Frugis et al., 1999. Plant Molecular Biology 40:397-408). A particular example of an Hsp40 is *M. sativa* MsJ1 (encoded by SEQ ID NO: 121, 123 or 114). Hsp40 plays a role as a molecular chaperone in protein folding, thermotolerance and DNA replication, among other cellular activities.

Among Hsps, Hsp70 and its co-chaperone, Hsp40, are involved in the stabilization of translating and newly synthesized polypeptides before the synthesis is complete. Without wishing to be bound by theory, Hsp40 binds to the hydrophobic patches of unfolded (nascent or newly transferred) polypeptides, thus facilitating the interaction of Hsp70-ATP complex with the polypeptide. ATP hydrolysis leads to the formation of a stable complex between the polypeptide, Hsp70 and ADP, and release of Hsp40. The association of Hsp70-ADP complex with the hydrophobic patches of the polypeptide prevents their interaction with other hydrophobic patches, preventing the incorrect folding and the formation of aggregates with other proteins (reviewed in Hartl, F U. 1996. Nature 381:571-579).

Again, without wishing to be bound by theory, as protein production increases in a recombinant protein expression system, the effects of crowding on recombinant protein expression may result in aggregation and/or reduced accumulation of the recombinant protein resulting from degradation of misfolded polypeptide. Native chaperone proteins may be able to facilitate correct folding of low levels of recombinant protein, but as the expression levels increase, native chaperones may become a limiting factor. High levels of expression of hemagglutinin in the agroinfiltrated leaves may lead to the accumulation of hemagglutinin polypeptides in the cytosol, and co-expression of one or more than one chaperone proteins such as Hsp70, Hsp40 or both Hsp70 and Hsp40 may increase stability in the cytosol of the cells expressing the polypeptides cells, thus reducing the level of misfolded or aggregated hemagglutinin polypeptides, and increasing the number of polypeptides accumulate as stable hemagglutinin, exhibiting tertiary and quaternary structural characteristics that allow for hemagglutination and/or formation of virus-like particles.

Therefore, the present invention also provides for a method of producing influenza VLPs in a plant, wherein a first nucleic acid encoding an influenza HA is co-expressed with a second nucleic acid encoding a chaperone. The first and second nucleic acids may be introduced to the plant in the same step, or may be introduced to the plant sequentially. The present invention also provides for a method of producing influenza VLPs in a plant, where the plant comprises the first nucleic acid, and the second nucleic acid is subsequently introduced.

The present invention also provides for a plant comprising a nucleic acid encoding one, or more than one influenza hemagglutinin and a nucleic acid encoding one or more than one chaperones.

Processing of an N-terminal signal peptide (SP) sequence during expression and/or secretion of influenza hemagglutinins has been proposed to have a role in the folding process. The term "signal peptide" refers generally to a short (about 5-30 amino acids) sequence of amino acids, found generally at the N-terminus of a hemagglutinin polypeptide that may direct translocation of the newly-translated polypeptide to a particular organelle, or aid in positioning of specific domains of the polypeptide. The signal peptide of hemagglutinins target the translocation of the protein into the endoplasmic reticulum and have been proposed to aid in positioning of the N-terminus proximal domain relative to a membrane-anchor domain of the nascent hemagglutinin polypeptide to aid in cleavage and folding of the mature hemagglutinin. Removal of a signal peptide (for example, by a signal peptidase), may require precise cleavage and removal of the signal peptide to provide the mature hemagglutinin—this precise cleavage may be dependent on any of several factors, including a portion or all of the signal peptide, amino acid sequence flanking the cleavage site, the length of the signal peptide, or a combination of these, and not all factors may apply to any given sequence.

A signal peptide may be native to the hemagglutinin being expressed, or a recombinant hemagglutinin comprising a signal peptide from a first influenza type, subtype or strain with the balance of the hemagglutinin from a second influenza type, subtype or strain. For example the native SP of HA subtypes H1, H2, H3, H5, H6, H7, H9 or influenza type B may be used to express the HA in a plant system.

A signal peptide may also be non-native, for example, from a structural protein or hemagglutinin of a virus other than influenza, or from a plant, animal or bacterial polypeptide. An exemplary signal peptide is that of alfalfa protein disulfide isomerase (PDISP) (nucleotides 32-103 of Accession No. Z11499; SEQ ID NO: 34; FIG. 17; amino acid sequence MAKNVAIFGLLFSLLLLVPSQIFAEE).

The present invention also provides for an influenza hemagglutinin comprising a native, or a non-native signal peptide, and nucleic acids encoding such hemagglutinins.

Influenza HA proteins exhibit a range of similarities and differences with respect to molecular weight, isoelectric point, size, glycan complement and the like. The physico-chemical properties of the various hemagglutinins may be useful to allow for differentiation between the HAs expressed in a plant, insect cell or yeast system, and may be of particular use when more than one HA is co-expressed in a single system. Examples of such physico-chemical properties are provided in Table 1.

TABLE 1

Physico-chemical properties of influenza hemagglutinins

| Clone | | | AA | | | Glycans | | | Molecular Weight (kDA) | | | | | | Isoelectric point | | |
|---|---|---|---|---|---|---|---|---|---|---|---|---|---|---|---|---|---|
| No | Type | Influenza strains | HA0 | HA1 | HA2 | HA0 | HA1 | HA2 | HA0 | HA0[1] | HA1 | HA1[1] | HA2 | HA2[1] | HA0 | HA1 | HA2 |
| 774 | H1 | A/Brisbane/59/2007 | 548 | 326 | 222 | 9 | 7 | 2 | 61 | 75 | 36 | 47 | 25 | 28 | 6.4 | 7.5 | 5.3 |
| 775 | H1 | A/Solomon Islands/3/2006 | 548 | 326 | 222 | 9 | 7 | 2 | 61 | 75 | 36 | 47 | 25 | 28 | 6.1 | 6.7 | 5.3 |
| 776 | H3 | A/Brisbane/10/2007 | 550 | 329 | 221 | 12 | 11 | 1 | 62 | 80 | 37 | 54 | 25 | 27 | 8.5 | 9.6 | 5.2 |
| 777 | H3 | A/Wisconsin/67/2005 | 550 | 329 | 221 | 11 | 10 | 1 | 62 | 79 | 37 | 52 | 25 | 27 | 8.8 | 9.6 | 5.3 |
| 778 | B | B/Malaysia/2506/2004 | 570 | 347 | 223 | 12 | 8 | 4 | 62 | 80 | 38 | 50 | 24 | 30 | 8.0 | 9.7 | 4.5 |
| 779 | B | B/Florida/4/2006 | 569 | 346 | 223 | 10 | 7 | 3 | 62 | 77 | 38 | 48 | 24 | 29 | 8.0 | 9.7 | 4.5 |
| 780 | H2 | A/Singapore/1/57 | 547 | 325 | 222 | 6 | 4 | 2 | 62 | 71 | 36 | 42 | 25 | 28 | 6.0 | 7.5 | 4.9 |
| 781 | H5 | A/Anhui/1/2005 | 551 | 329 | 222 | 7 | 5 | 2 | 62 | 73 | 37 | 45 | 25 | 28 | 6.2 | 8.9 | 4.7 |
| 782 | H5 | A/Vietnam/1194/2004 | 552 | 330 | 222 | 7 | 5 | 2 | 63 | 74 | 38 | 45 | 25 | 28 | 6.4 | 9.1 | 4.8 |

TABLE 1-continued

Physico-chemical properties of influenza hemagglutinins

| Clone | | | AA | | | Glycans | | | Molecular Weight (kDA) | | | | | | Isoelectric point | | |
|---|---|---|---|---|---|---|---|---|---|---|---|---|---|---|---|---|---|
| No | Type | Influenza strains | HA0 | HA1 | HA2 | HA0 | HA1 | HA2 | HA0 | HA0[1] | HA1 | HA1[1] | HA2 | HA2[1] | HA0 | HA1 | HA2 |
| 783 | H6 | A/Teal/Hong Kong/W312/97 | 550 | 328 | 222 | 8 | 5 | 3 | 62 | 75 | 37 | 45 | 25 | 30 | 5.7 | 5.9 | 5.6 |
| 784 | H7 | A/Equine/Prague/56 | 552 | 331 | 221 | 6 | 4 | 2 | 62 | 71 | 37 | 43 | 25 | 28 | 8.9 | 9.7 | 4.9 |
| 785 | H9 | A/Hong Kong/1073/99 | 542 | 320 | 199 | 9 | 7 | 2 | 61 | 75 | 36 | 46 | 23 | 26 | 8.4 | 9.5 | 5.3 |

The present invention also includes nucleotide sequences SEQ ID NO:28; SEQ ID NO:3; SEQ ID NO:11, encoding HA from H1, H5 or H7, respectively. The present invention also includes a nucleotide sequence that hybridizes under stringent hybridisation conditions to SEQ ID NO:28; SEQ ID NO:3; SEQ ID NO:11. The present invention also includes a nucleotide sequence that hybridizes under stringent hybridisation conditions to a compliment of SEQ ID NO:28; SEQ ID NO:3; SEQ ID NO:1. These nucleotide sequences that hybridize to SEQ ID or a complement of SEQ ID encode a hemagglutinin protein that, when expressed forms a VLP, and the VLP induces production of an antibody when administered to a subject. For example, expression of the nucleotide sequence within a plant cell forms a VLP, and the VLP may be used to produce an antibody that is capable of binding HA, including mature HA, HA0, HA1 or HA2 of one or more influenza types or subtypes. The VLP, when administered to a subject, induces an immune response.

The present invention also includes nucleotide sequences SEQ ID NO:12 SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO:27, SEQ ID NO: 33, SEQ ID NO: 35, SEQ ID NO: 36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO: 127 or SEQ ID NO:47. The present invention also includes a nucleotide sequence that hybridizes under stringent hybridisation conditions to SEQ ID NO:12 SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO:27, SEQ ID NO: 33, SEQ ID NO: 35, SEQ ID NO: 36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO: 127 or SEQ ID NO:47. The present invention also includes a nucleotide sequence that hybridizes under stringent hybridisation conditions to a compliment of SEQ ID NO:12 SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO:27, SEQ ID NO: 33, SEQ ID NO: 35, SEQ ID NO: 36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO: 127 or SEQ ID NO:47. These nucleotide sequences that hybridize to SEQ ID NO:12 SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO:27, SEQ ID NO: 33, SEQ ID NO: 35, SEQ ID NO: 36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO: 127 or SEQ ID NO:47 or a complement of SEQ ID NO:12 SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO:27, SEQ ID NO: 33, SEQ ID NO: 35, SEQ ID NO: 36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO: 127 or SEQ ID NO:47 encode a hemagglutinin protein that, when expressed forms a VLP, and the VLP induces production of an antibody when administered to a subject. For example, expression of the nucleotide sequence within a plant cell forms a VLP, and the VLP may be used to produce an antibody that is capable of binding HA, including mature HA, HA0, HA1, or HA2 of one or more influenza types or subtypes. The VLP, when administered to a subject, induces an immune response.

In some embodiments, the present invention also includes nucleotide sequences SEQ ID NO: 33, SEQ ID NO: 35, SEQ ID NO: 36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO: 127 or SEQ ID NO:47, encoding HA from H1, H2, H3, H5, H7 or H9 subtypes of influenza A, or HA from type B influenza. The present invention also includes a nucleotide sequence that hybridizes under stringent hybridisation conditions to SEQ ID NO: 33, SEQ ID NO: 35, SEQ ID NO: 36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO: 127 or SEQ ID NO:47. The present invention also includes a nucleotide sequence that hybridizes under stringent hybridisation conditions to a compliment of SEQ ID NO: 33, SEQ ID NO: 35, SEQ ID NO: 36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO: 127 or SEQ ID NO:47. These nucleotide sequences that hybridize to SEQ ID NO: 33, SEQ ID NO: 35, SEQ ID NO: 36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO: 127 or SEQ ID NO:47 or a complement of SEQ ID NO: 33, SEQ ID NO: 35, SEQ ID NO: 36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO: 127 or SEQ ID NO:47 encode a hemagglutinin protein that, when expressed forms a VLP, and the VLP induces production of an antibody when administered to a subject. For example, expression of the nucleotide sequence within a plant cell forms a VLP, and the VLP may be used to produce an antibody that is capable of binding HA, including mature HA, HA0, HA1, or HA2 of one or more influenza types or subtypes. The VLP, when administered to a subject, induces an immune response.

Hybridization under stringent hybridization conditions is known in the art (see for example Current Protocols in Molecular Biology, Ausubel et al., eds. 1995 and supplements; Maniatis et al., in Molecular Cloning (A Laboratory Manual), Cold Spring Harbor Laboratory, 1982; Sambrook and Russell, in Molecular Cloning: A Laboratory Manual, $3^{rd}$ edition 2001; each of which is incorporated herein by reference). An example of one such stringent hybridization conditions may be about 16-20 hours hybridization in 4×SSC at 65° C., followed by washing in 0.1×SSC at 65° C. for an hour, or 2 washes in 0.1×SSC at 65° C. each for 20 or 30 minutes. Alternatively, an exemplary stringent hybridization condition could be overnight (16-20 hours) in 50% formamide, 4×SSC at 42° C., followed by washing in 0.1×SSC at 65° C. for an hour, or 2 washes in 0.1×SSC at 65° C. each for 20 or 30 minutes, or overnight (16-20 hours), or hybridization in Church aqueous phosphate buffer (7% SDS; 0.5M $NaPO_4$ buffer pH 7.2; 10 mM EDTA) at 65° C., with 2 washes either at 50° C. in 0.1×SSC, 0.1% SDS for 20 or 30 minutes each, or 2 washes at 65° C. in 2×SSC, 0.1% SDS for 20 or 30 minutes each.

Additionally, the present invention includes nucleotide sequences that are characterized as having about 70, 75, 80, 85, 87, 90, 91, 92, 93 94, 95, 96, 97, 98, 99, 100% or any amount therebetween, sequence identity, or sequence similarity, with the nucleotide sequence encoding HA from H1 (SEQ ID NO:28 or SEQ ID NO:127), H5 (SEQ ID NO:3) or H7 (SEQ ID NO:11), wherein the nucleotide sequence encodes a hemagglutinin protein that when expressed forms a VLP, and that the VLP induces the production of an antibody. For example, expression of the nucleotide sequence within a plant cell forms a VLP, and the VLP may be used to produce an antibody that is capable of binding HA, including mature HA, HA0, HA1 or HA2. The VLP, when administered to a subject, induces an immune response.

Additionally, the present invention includes nucleotide sequences that are characterized as having about 70, 75, 80, 85, 87, 90, 91, 92, 93 94, 95, 96, 97, 98, 99, 100% or any amount therebetween, sequence identity, or sequence similarity, with the nucleotide sequence of SEQ ID NO:12 SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO:27, SEQ ID NO: 33, SEQ ID NO: 35, SEQ ID NO: 36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO: 127 or SEQ ID NO:47, wherein the nucleotide sequence encodes a hemagglutinin protein that when expressed forms a VLP, and that the VLP induces the production of an antibody. For example, expression of the nucleotide sequence within a plant cell forms a VLP, and the VLP may be used to produce an antibody that is capable of binding HA, including mature HA, HA0, HA1 or HA2. The VLP, when administered to a subject, induces an immune response.

Additionally, the present invention includes nucleotide sequences that are characterized as having about 70, 75, 80, 85, 87, 90, 91, 92, 93 94, 95, 96, 97, 98, 99, 100% or any amount therebetween, sequence identity, or sequence similarity, with the nucleotide sequence of SEQ ID NO: 33, SEQ ID NO: 35, SEQ ID NO: 36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO: 127 or SEQ ID NO:47, wherein the nucleotide sequence encodes a hemagglutinin protein that when expressed forms a VLP, and that the VLP induces the production of an antibody. For example, expression of the nucleotide sequence within a plant cell forms a VLP, and the VLP may be used to produce an antibody that is capable of binding HA, including mature HA, HA0, HA1 or HA2. The VLP, when administered to a subject, induces an immune response.

Similarly, the present invention includes HAs associated with the following subtypes H1 (encoded by SEQ ID NO:28 or SEQ ID NO:127), H2 (encoded by SEQ ID NO:12), H3 (encoded by SEQ ID NO:13), H4 (encoded by SEQ ID NO:14), H5 (encoded by SEQ ID NO:15), H6 (encoded by SEQ ID NO:16), H7 (encoded by SEQ ID NO:11), H8 (encoded by SEQ ID NO:17), H9 (encoded by SEQ ID NO:18), H10 (encoded by SEQ ID NO:19), H11 (encoded by SEQ ID NO:20), H12 (encoded by SEQ ID NO:21), H13 (encoded by SEQ ID NO:27), H14 (encoded by SEQ ID NO:23), H15 (encoded by SEQ ID NO:24), H16 (encoded by SEQ ID NO:25), or influenza type B (encoded by SEQ ID NO: 26); see FIGS. 10A to 10O), and nucleotide sequences that are characterized as having from about 70 to 100% or any amount therebetween, 80 to 100% or any amount there between, 90-100% or any amount therebetween, or 95-100% or any amount therebetween, sequence identity with H1 (SEQ ID NO:28 or SEQ ID NO:127), H2 (SEQ ID NO:12), H3 (SEQ ID NO:13), H4 (SEQ ID NO:14), H5 (SEQ ID NO:15), H6 (SEQ ID NO:16), H7 (SEQ ID NO:11), H8 (SEQ ID NO:17), H9 (SEQ ID NO:18), H10 (SEQ ID NO:19), H11 (SEQ ID NO:20), H12 (SEQ ID NO:21), H13 (SEQ ID NO:27), H14 (SEQ ID NO:23), H15 (SEQ ID NO:24), H16 (SEQ ID NO:25), wherein the nucleotide sequence encodes a hemagglutinin protein that when expressed forms a VLP, and that the VLP induces the production of an antibody. For example, expression of the nucleotide sequence within a plant cell forms a VLP, and the VLP may be used to produce an antibody that is capable of binding HA, including mature HA, HA0, HA1 or HA2. The VLP, when administered to a subject, induces an immune response.

An "immune response" generally refers to a response of the adaptive immune system. The adaptive immune system generally comprises a humoral response, and a cell-mediated response. The humoral response is the aspect of immunity that is mediated by secreted antibodies, produced in the cells of the B lymphocyte lineage (B cell). Secreted antibodies bind to antigens on the surfaces of invading microbes (such as viruses or bacteria), which flags them for destruction. Humoral immunity is used generally to refer to antibody production and the processes that accompany it, as well as the effector functions of antibodies, including Th2 cell activation and cytokine production, memory cell generation, opsonin promotion of phagocytosis, pathogen elimination and the like. The terms "modulate" or "modulation" or the like refer to an increase or decrease in a particular response or parameter, as determined by any of several assays generally known or used, some of which are exemplified herein.

A cell-mediated response is an immune response that does not involve antibodies but rather involves the activation of macrophages, natural killer cells (NK), antigen-specific cytotoxic T-lymphocytes, and the release of various cytokines in response to an antigen. Cell-mediated immunity is used generally to refer to some Th cell activation, Tc cell activation and T-cell mediated responses. Cell mediated immunity is of particular importance in responding to viral infections.

For example, the induction of antigen specific CD8 positive T lymphocytes may be measured using an ELISPOT assay; stimulation of CD4 positive T-lymphocytes may be measured using a proliferation assay. Anti-influenza antibody titres may be quantified using an ELISA assay; isotypes of antigen-specific or cross reactive antibodies may also be measured using anti-isotype antibodies (e.g. anti-IgG, IgA, IgE or IgM). Methods and techniques for performing such assays are well-known in the art.

A hemagglutination inhibition (HI, or HAI) assay may also be used to demonstrate the efficacy of antibodies induced by a vaccine, or vaccine composition can inhibit the agglutination of red blood cells (RBC) by recombinant HA. Hemagglutination inhibitory antibody titers of serum samples may be evaluated by microtiter HAI (Aymard et al 1973). Erythrocytes from any of several species may be used—e.g. horse, turkey, chicken or the like. This assay gives indirect information on assembly of the HA trimer on the surface of VLP, confirming the proper presentation of antigenic sites on HAs.

Cross-reactivity HAI titres may also be used to demonstrate the efficacy of an immune response to other strains of virus related to the vaccine subtype. For example, serum from a subject immunized with a vaccine composition of a first strain (e.g. VLPs of A/Indonesia 5/05) may be used in an HAI assay with a second strain of whole virus or virus particles (e.g. A/Vietnam/1194/2004), and the HAI titer determined Cytokine presence or levels may also be quantified. For example a T-helper cell response (Th1/Th2) will be characterized by the measurement of IFN-γ and IL-4 secreting cells using by ELISA (e.g. BD Biosciences OptEIA kits). Peripheral blood mononuclear cells (PBMC) or splenocytes obtained from a subject may be cultured, and the supernatant analyzed. T lymphocytes may also be quantified by fluorescence-activated cell sorting (FACS), using marker specific fluorescent labels and methods as are known in the art.

A microneutralization assay may also be conducted to characterize an immune response in a subject, see for example the methods of Rowe et al., 1973. Virus neutralization titers may be obtained several ways, including: 1) enumeration of lysis plaques (plaque assay) following crystal violet fixation/coloration of cells; 2) microscopic observation of cell lysis in culture; 3) ELISA and spectrophotometric detection of NP virus protein (correlate with virus infection of host cells)

Sequence identity or sequence similarity may be determined using a nucleotide sequence comparison program, such as that provided within DNASIS (for example, using, but not limited to, the following parameters: GAP penalty 5, # of top diagonals 5, fixed GAP penalty 10, k-tuple 2, floating gap 10, and window size 5). However, other methods of alignment of sequences for comparison are well-known in the art for example the algorithms of Smith & Waterman (1981, Adv. Appl. Math. 2:482), Needleman & Wunsch (J. Mol. Biol. 48:443, 1970), Pearson & Lipman (1988, Proc. Nat'l. Acad. Sci. USA 85:2444), and by computerized implementations of these algorithms (e.g. GAP, BESTFIT, FASTA, and BLAST), or by manual alignment and visual inspection.

The term "hemagglutinin domain" refers to a peptide comprising either the HA0 domain, or the HA1 and HA2 domains (alternately referred to as HA1 and HA2 fragments). HA0 is a precursor of the HA1 and HA2 fragments. The HA monomer may be generally subdivided in 2 functional domains—the stem domain and the globular head, or head domain. The stem domain is involved in infectivity and pathogenicity of the virus via the conformational change it may undergo when exposed to acidic pH. The stem domain may be be further subdivided into 4 subdomains or fragments—the fusion sub-domain or peptide (a hydrophobic stretch of amino acids involved in fusion with the host membrane in the acidic pH conformational state); the stem sub-domain (may accommodate the two or more conformations), the transmembrane domain or sub-domain (TmD) (involved in the affinity of the HA for lipid rafts), and the cytoplasmic tail (cytoplasmic tail sub-domain) (Ctail) (involved in secretion of HA). The globular head is divided in 2 subdomains, the RB subdomain and the vestigial esterase domain (E). The E subdomain may be partially or fully buried and not exposed at the surface of the globular head, thus some antibodies raised against HA bind to the RB subdomain.

The term "virus like particle" (VLP), or "virus-like particles" or "VLPs" refers to structures that self-assemble and comprise structural proteins such as influenza HA protein. VLPs are generally morphologically and antigenically similar to virions produced in an infection, but lack genetic information sufficient to replicate and thus are non-infectious. In some examples, VLPs may comprise a single protein species, or more than one protein species. For VLPs comprising more than one protein species, the protein species may be from the same species of virus, or may comprise a protein from a different species, genus, subfamily or family of virus (as designated by the ICTV nomenclature). In other examples, one or more of the protein species comprising a VLP may be modified from the naturally occurring sequence. VLPs may be produced in suitable host cells including plant and insect host cells. Following extraction from the host cell and upon isolation and further purification under suitable conditions, VLPs may be purified as intact structures.

The VLPs produced from influenza derived proteins, in accordance with the present invention do not comprise M1 protein. The M1 protein is known to bind RNA (Wakefield and Brownlee, 1989) which is a contaminant of the VLP preparation. The presence of RNA is undesired when obtaining regulatory approval for the VLP product, therefore a VLP preparation lacking RNA may be advantageous.

The VLPs of the present invention may be produced in a host cell that is characterized by lacking the ability to sialylate proteins, for example a plant cell, an insect cell, fungi, and other organisms including sponge, coelenterara, annelida, arthoropoda, mollusca, nemathelminthea, trochelmintes, plathelminthes, chaetognatha, tentaculate, chlamydia, spirochetes, gram-positive bacteria, cyanobacteria, archaebacteria, or the like. See, for example Glycoforum (URL: glycoforum.grjp/science/word/evolution/ES-A03E.html) or Gupta et al., 1999. Nucleic Acids Research 27:370-372; or Toukach et al., 2007. Nucleic Acids Research 35:D280-D286; or URL:glycostructures.jp (Nakahara et al., 2008. Nucleic Acids Research 36:D368-D371; published online Oct. 11, 2007 doi:10.1093/NAR/gkm833). The VLPs produced as described herein do not typically comprise neuramindase (NA). However, NA may be co-expressed with HA should VLPs comprising HA and NA be desired.

A VLP produced in a plant according to some aspects of the invention may be complexed with plant-derived lipids. The VLP may comprise an HA0, HA1 or HA2 peptide. The plant-derived lipids may be in the form of a lipid bilayer, and may further comprise an envelope surrounding the VLP. The plant derived lipids may comprise lipid components of the plasma membrane of the plant where the VLP is produced, including, but not limited to, phosphatidylcholine (PC), phosphatidylethanolamine (PE), glycosphingolipids, phytosterols or a combination thereof. A plant-derived lipid may alternately be referred to as a 'plant lipid'. Examples of phytosterols are known in the art, and include, for example, stigmasterol, sitosterol, 24-methylcholesterol and cholesterol—see, for example, Mongrand et al., 2004.

VLPs may be assessed for structure and size by, for example, hemagglutination assay, electron microscopy, or by size exclusion chromatography.

For size exclusion chromatography, total soluble proteins may be extracted from plant tissue by homogenizing (Polytron) sample of frozen-crushed plant material in extraction buffer, and insoluble material removed by centrifugation. Precipitation with PEG may also be of benefit. The soluble protein is quantified, and the extract passed through a Sephacryl™ column. Blue Dextran 2000 may be used as a calibration standard. Following chromatography, fractions may be further analyzed by immunoblot to determine the protein complement of the fraction.

Without wishing to be bound by theory, the capacity of HA to bind to RBC from different animals is driven by the affinity of HA for sialic acids α2,3 or α2,3 and the presence of these sialic acids on the surface of RBC. Equine and avian HA from influenza viruses agglutinate erythrocytes from all several species, including turkeys, chickens, ducks, guinea pigs, humans, sheep, horses and cows; whereas human HAs will bind to erythrocytes of turkey, chickens, ducks, guina pigs, humans and sheep (see also Ito T. et al, 1997, Virology, vol 227, p 493-499; and Medeiros R et al, 2001, Virology, vol 289 p. 74-85). Examples of the species reactivity of HAs of different influenza strains is shown in Tables 2A and 2B.

TABLE 2A

Species of RBC bound by HAs of selected seasonal influenza strains.

| Seasonal | Strain | No | Origin | Horse | Turkey |
|---|---|---|---|---|---|
| H1 | A/Brisbane/59/2007 (H1N1) | 774 | Human | + | ++ |
| | A/Solomon Islands/3/2006 (H1N1) | 775 | Human | + | ++ |
| H3 | A/Brisbane/10/2007 (H3N2) | 776 | Human | + | ++ |
| | A/Wisconsin/67/2005 (H3N2) | 777 | Human | + | ++ |
| B | B/Malaysia/2506/2004 | 778 | Human | + | ++ |
| | B/Florida/4/2006 | 779 | Human | + | ++ |

TABLE 2B

Species of RBC bound by HAs of selected pandemic influenza strains

| Pandemic | Strain | No | Origin | Horse | Turkey |
|---|---|---|---|---|---|
| H2 | A/Singapore/1/57 (H2N2) | 780 | Human | + | ++ |
| H5 | A/Anhui/1/2005 (H5N1) | 781 | Hu-Av | ++ | + |
| | A/Vietnam/1194/2004 (H5N1) | 782 | Hu-Av | ++ | + |
| H6 | A/Teal/Hong Kong/W312/97 (H6N1) | 783 | Avian | ++ | + |

TABLE 2B-continued

Species of RBC bound by HAs of selected pandemic influenza strains

| Pandemic | Strain | No | Origin | Horse | Turkey |
|---|---|---|---|---|---|
| H7 | A/Equine/Prague/56 (H7N7) | 784 | Equine | ++ | ++ |
| H9 | A/Hong Kong/1073/99 (H9N2) | 785 | Human | ++ | + |

A fragment or portion of a protein, fusion protein or polypeptide includes a peptide or polypeptide comprising a subset of the amino acid complement of a particular protein or polypeptide, provided that the fragment can form a VLP when expressed. The fragment may, for example, comprise an antigenic region, a stress-response-inducing region, or a region comprising a functional domain of the protein or polypeptide. The fragment may also comprise a region or domain common to proteins of the same general family, or the fragment may include sufficient amino acid sequence to specifically identify the full-length protein from which it is derived.

For example, a fragment or portion may comprise from about 60% to about 100%, of the length of the full length of the protein, or any amount therebetween, provided that the fragment can form a VLP when expressed. For example, from about 60% to about 100%, from about 70% to about 100%, from about 80% to about 100%, from about 90% to about 100%, from about 95% to about 100%, of the length of the full length of the protein, or any amount therebetween. Alternately, a fragment or portion may be from about 150 to about 500 amino acids, or any amount therebetween, depending upon the HA, and provided that the fragment can form a VLP when expressed. For example, a fragment may be from 150 to about 500 amino acids, or any amount therebetween, from about 200 to about 500 amino acids, or any amount therebetween, from about 250 to about 500 amino acids, or any amount therebetween, from about 300 to about 500 or any amount therebetween, from about 350 to about 500 amino acids, or any amount therebetween, from about 400 to about 500 or any amount therebetween, from about 450 to about 500 or any amount therebetween, depending upon the HA, and provided that the fragment can form a VLP when expressed. For example, about 5, 10, 20, 30, 40 or 50 amino acids, or any amount therebetween may be removed from the C terminus, the N terminus or both the N and C terminus of an HA protein, provided that the fragment can form a VLP when expressed.

Numbering of amino acids in any given sequence are relative to the particular sequence, however one of skill can readily determine the 'equivalency' of a particular amino acid in a sequence based on structure and/or sequence. For example, if 6 N terminal amino acids were removed when constructing a clone for crystallography, this would change the specific numerical identity of the amino acid (e.g. relative to the full length of the protein), but would not alter the relative position of the amino acid in the structure.

Comparisons of a sequence or sequences may be done using a BLAST algorithm (Altschul et al., 1990. J. Mol Biol 215:403-410). A BLAST search allows for comparison of a query sequence with a specific sequence or group of sequences, or with a larger library or database (e.g. GenBank or GenPept) of sequences, and identify not only sequences that exhibit 100% identity, but also those with lesser degrees of identity. Nucleic acid or amino acid sequences may be compared using a BLAST algorithm. Furthermore the identity between two or more sequences may be determined by aligning the sequences together and determining the % identity between the sequences. Alignment may be carried out using the BLAST Algorithm (for example as available through GenBank; URL: ncbi.nlm.nih.gov/cgi-bin/BLAST/ using default parameters: Program: blastn; Database: nr; Expect 10; filter: default; Alignment: pairwise; Query genetic Codes: Standard(1)), or BLAST2 through EMBL URL: embl-heidelberg.de/Services/index.html using default parameters: Matrix BLOSUM62; Filter: default, echofilter: on, Expect: 10, cutoff: default; Strand: both; Descriptions: 50, Alignments: 50; or FASTA, using default parameters), or by manually comparing the sequences and calculating the % identity.

The present invention describes, but is not limited to, the cloning of a nucleic acid encoding HA into a plant expression vector, and the production of influenza VLPs from the plant, suitable for vaccine production. Examples of such nucleic acids include, for example, but are not limited to, an influenza A/New Caledonia/20/99 (H1N1) virus HA (e.g. SEQ ID NO: 61), an HA from A/California/04/09 (SEQ ID NO: 127), an HA from A/Indonesia/5/05 sub-type (H5N1) (e.g. SEQ ID NO: 60), A/Brisbane/59/2007 (H1N1) (e.g. SEQ ID NO: 36, 48, 62), A/Solomon Islands/3/2006 (H1N1) (e.g. SEQ ID NO: 37, 49, 63), A/Singapore/1/57 (H2N2) (e.g. SEQ ID NO: 42, 54, 64), A/Anhui/1/2005 (H5N1) (e.g. SEQ ID NO: 43, 55, 65), A/Vietnam/1194/2004 (H5N1) (e.g. SEQ ID NO: 44, 56, 66), A/Teal/Hong Kong/W312/97 (H6N1) (e.g. SEQ ID NO: 45, 57, 67), A/Hong Kong/1073/99 (H9N2) (e.g. SEQ ID NO: 47, 59, 68), A/Brisbane/10/2007 (H3N2) (e.g. SEQ ID NO: 38, 50, 69), A/Wisconsin/67/2005 (H3N2) (e.g. SEQ ID NO: 39, 51, 70), A/Equine/Prague/56 (H7N7) (e.g. SEQ ID NO: 46, 58, 71), B/Malaysia/2506/2004 (e.g. SEQ ID NO: 40, 52, 72), B/Florida/4/2006 (e.g. SEQ ID NO: 41, 53, 73). The corresponding clone or construct numbers for these strains is provided in Table 1. Nucleic acid sequences corresponding to SEQ ID NOs: 36-47 comprise a plastocyanin upstream and operatively linked to the coding sequence of the HA for each of the types or subtypes, as illustrated in FIGS. 28-39. Nucleic acid sequences corresponding to SEQ ID NO: 60-73 comprise an HA expression cassette comprising alfalfa plastocyanin promoter and 5' UTR, hemagglutinin coding sequence of an HA, alfalfa plastocyanin 3' UTR and terminator sequences, as illustrated in FIGS. 51-64.

The VLPs may also be used to produce reagents comprised of recombinant influenza structural proteins that self-assemble into functional and immunogenic homotypic macromolecular protein structures, including subviral influenza particles and influenza VLP, in transformed hosts cells, for example plant cells or insect cells.

Therefore, the invention provides for VLPs, and a method for producing viral VLPs in a plant expression system, from the expression of a single envelope protein. The VLPs may be influenza VLPs, or VLPs produced from other plasma membrane-derived virus including, but not limited to, Measles, Ebola, Marburg, and HIV.

Proteins from other enveloped viruses, for example but not limited to Filoviridae (e.g. Ebola virus, Marburg virus, or the like), Paramyxoviridae (e.g. Measles virus, Mumps virus, Respiratory syncytial virus, pneumoviruses, or the like), Retroviridae (e.g. Human Immunodeficiency Virus-1, Human Immunodeficiency Virus-2, Human T-Cell Leukemia Virus-1, or the like), Flaviviridae (e.g. West Nile Encephalitis, Dengue virus, Hepatitis C virus, yellow fever virus, or the like), Bunyaviridae (e.g. Hantavirus or the like), Coronaviridae (e.g. coronavirus, SARS, or the like), as would be known to those of skill in the art, may also be used.

Non limiting examples of antigens that may be expressed in plasma membrane derived viruses include, the capsid protein of HIV-p24; HIV glycoproteins gp120 or gp41, Filovirus proteins including VP30 or VP35 of Ebolavirus or Gp/SGP of Marburg virus or the H protein or F protein of the Measles paramyxovirus. For example, P24 of HIV (e.g. GenBank reference gi:19172948) is the protein obtained by translation and cleavage of the gag sequence of the HIV virus genome (e.g. GenBank reference gi:9629357); gp120 and gp41 of HIV are glycoproteins obtained by translation and cleavage of the gp160 protein (e.g. GenBank reference gi:9629363), encoded by env of the HIV virus genome. VP30 of Ebolavirus (GenPept Reference gi: 55770813) is the protein obtained by translation of the vp30 sequence of the Ebolavirus genome (e.g. GenBank Reference gi:55770807); VP35 of Ebolavirus (GenPept Reference gi:55770809) is the protein obtained by translation of the vp35 sequence of the Ebolavirus genome. Gp/SGP of Marburg virus (GenPept Reference gi:296965) is the protein obtained by translation of the (sequence) of the Marburg virus genome (GenBank Reference gi:158539108). H protein (GenPept Reference gi: 9626951) is the protein of the H sequence of the Measles virus genome (GenBank Reference gi: 9626945); F protein (GenPept reference gi: 9626950) is the protein of the F sequence of the Measles virus genome.

However, other envelope proteins may be used within the methods of the present invention as would be know to one of skill in the art.

The invention, therefore, provides for a nucleic acid molecule comprising a sequence encoding HIV-p24, HIV-120, HIV-gp41, Ebolavirus-VP30, Ebolavirus-VP35, Marburg virus Gp/SGP, Measles virus-H protein or -F protein. The nucleic acid molecule may be operatively linked to a regulatory region active in an insect, yeast or plant cell, or in a particular plant tissue.

The present invention further provides the cloning of a nucleic acid encoding an HA, for example but not limited to, human influenza A/Indonesia/5/05 virus HA (H5N1) or an HA from influenza strain A/California/04/09 into a plant or insect expression vector (e.g. baculovirus expression vector) and production of influenza vaccine candidates or reagents comprised of recombinant influenza structural proteins that self-assemble into functional and immunogenic homotypic macromolecular protein structures, including subviral influenza particles and influenza VLP, in transformed plant cells or transformed insect cells.

The nucleic acid encoding the HA of influenza subtypes, for example but not limited to, A/New Caledonia/20/99 (H1N1), A/California/04/09 (H1N1) A/Indonesia/5/05 subtype (H5N1), A/Brisbane/59/2007 (H1N1), A/Solomon Islands/3/2006 (H1N1), A/Singapore/1/57 (H2N2), A/Anhui/1/2005 (H5N1), A/Vietnam/1194/2004 (H5N1), A/Teal/Hong Kong/W312/97 (H6N1), A/Hong Kong/1073/99 (H9N2), A/Brisbane/10/2007 (H3N2), A/Wisconsin/67/2005 (H3N2), A/Equine/Prague/56 (H7N7), B/Malaysia/2506/2004, B/Florida/4/2006 may be expressed, for example, using a Baculovirus Expression System in an appropriate cell line, for example, *Spodoptera frugiperda* cells (e.g. Sf-9 cell line; ATCC PTA-4047). Other insect cell lines may also be used.

The nucleic acid encoding the HA may, alternately, be expressed in a plant cell, or in a plant. The nucleic acid encoding HA may be synthesized by reverse transcription and polymerase chain reaction (PCR) using HA RNA. As an example, the RNA may be isolated from human influenza A/New Caledonia/20/99 (H1N1) virus or human influenza A/Indonesia/5/05 (H5N1) virus, or other influenza viruses e.g. A/California/04/09 (H1N1), A/Brisbane/59/2007 (H1N1), A/Solomon Islands/3/2006 (H1N1), A/Singapore/1/57 (H2N2), A/Anhui/1/2005 (H5N1), A/Vietnam/1194/2004 (H5N1), A/Teal/Hong Kong/W312/97 (H6N1), A/Hong Kong/1073/99 (H9N2), A/Brisbane/10/2007 (H3N2), A/Wisconsin/67/2005 (H3N2), A/Equine/Prague/56 (H7N7), B/Malaysia/2506/2004, B/Florida/4/2006, or from cells infected with an influenza virus. For reverse transcription and PCR, oligonucleotide primers specific for HA RNA, for example but not limited to, human influenza A/New Caledonia/20/99 (H1N1) virus HA sequences or human influenza A/Indonesia/5/05 (H5N1) virus HA0 sequences, or HA sequences from influenza subtypes A/California/04/09 (H1N1), A/Brisbane/59/2007 (H1N1), A/Solomon Islands/3/2006 (H1N1), A/Singapore/1/57 (H2N2), A/Anhui/1/2005 (H5N1), A/Vietnam/1194/2004 (H5N1), A/Teal/Hong Kong/W312/97 (H6N1), A/Hong Kong/1073/99 (H9N2), A/Brisbane/10/2007 (H3N2), A/Wisconsin/67/2005 (H3N2), A/Equine/Prague/56 (H7N7), B/Malaysia/2506/2004, B/Florida/4/2006 may be used. Additionally, a nucleic acid encoding HA may be chemically synthesized using methods as would known to one of skill in the art.

The resulting cDNA copies of these genes may be cloned in a suitable expression vector as required by the host expression system. Examples of appropriate expression vectors for plants are described below, alternatively, baculovirus expression vector, for example, pFastBac1 (InVitrogen), resulting in pFastBac1-based plasmids, using known methods, and information provided by the manufacturer's instructions nay be used.

The present invention is further directed to a gene construct comprising a nucleic acid encoding HA, as described above, operatively linked to a regulatory element that is operative in a plant. Examples of regulatory elements operative in a plant cell and that may be used in accordance with the present invention include but are not limited to a plastocyanin regulatory region (U.S. Pat. No. 7,125,978; which is incorporated herein by reference), or a regulatory region of Ribulose 1,5-bisphosphate carboxylase/oxygenase (RuBisCO; U.S. Pat. No. 4,962,028; which is incorporated herein by reference), chlorophyll a/b binding protein (CAB; Leutwiler et al; 1986; which is incorporated herein by reference), ST-LS1 (associated with the oxygen-evolving complex of photosystem II and described by Stockhaus et al. 1987, 1989; which is incorporated herein by reference). An example of a plastocyanin regulatory region is a sequence comprising nucleotides 10-85 of SEQ ID NO: 36, or a similar region of any one of SEQ ID NOS: 37-47. A regulatory element or regulatory region may enhance translation of a nucleotide sequence to which is it operatively linked—the nucleotide sequence may encode a protein or polypeptide. Another example of a regulatory region is that derived from the untranslated regions of the Cowpea Mosaic Virus (CPMV), which may be used to preferentially translate the nucleotide sequence to which it is operatively linked. This CPMV regulatory region comprises a CMPV-HT system—see, for example, Sainsbury et al, 2008, Plant Physiology 148: 1212-1218.

If the construct is expressed in an insect cell, examples of regulatory elements operative in an insect cell include but are not limited to the polyhedrin promoter (Possee and Howard 1987. Nucleic Acids Research 15:10233-10248), the gp64 promoter (Kogan et al, 1995. J Virology 69:1452-1461) and the like.

Therefore, an aspect of the invention provides for a nucleic acid comprising a regulatory region and a sequence encoding an influenza HA. The regulatory region may be a plastocyanin regulatory element, and the influenza HA may be selected from a group of influenza strains or subtypes, comprising A/California/04/09 (H1N1), A/New Caledonia/20/99 (H1N1), A/Indonesia/5/05 sub-type (H5N1), A/Brisbane/59/2007 (H1N1), A/Solomon Islands/3/2006 (H1N1), A/Singapore/1/57 (H2N2), A/Anhui/1/2005 (H5N1), A/Vietnam/1194/2004 (H5N1), A/Teal/Hong Kong/W312/97 (H6N1), A/Hong Kong/1073/99 (H9N2), A/Brisbane/10/2007 (H3N2), A/Wisconsin/67/2005 (H3N2), A/Equine/Prague/56 (H7N7), B/Malaysia/2506/2004, B/Florida/4/2006. Nucleic acid sequences comprising a plastocyanin regulatory element and an influenza HA are exemplified herein by SEQ ID NOs: 36-47.

It is known that there may be sequence differences in the sequence of influenza hemagglutinin amino acids sequences, or the nucleic acids encoding them, when influenza virus is cultured in eggs, or mammalian cells, (e.g. MDCK cells) or when isolated from an infected subject. Non-limiting examples of such differences are illustrated herein, including Example 18. Furthermore, as one of skill in the art would realize, additional variation may be observed within influenza hemagglutinins obtained from new strains as additional mutations continue to occur. Due to the known sequence variability between different influenza hemagglutinins, the present invention includes VLPs that may be made using any influenza hemagglutin provided that when expressed in a host as described herein, the influenza hemagglutin forms a VLP.

Sequence alignments and consensus sequences may be determined using any of several software packages known in the art, for example MULTALIN (F. CORPET, 1988, Nucl. Acids Res., 16 (22), 10881-10890), or sequences may be aligned manually and similarities and differences between the sequences determined.

The structure of hemagglutinins is well-studied and the structures are known to be highly conserved. When hemagglutinin structures are superimposed, a high degree of structural conservation is observed (rmsd<2A). This structural conservation is observed even though the amino acid sequence may vary in some positions (see, for example, Skehel and Wiley, 2000 Ann Rev Biochem 69:531-69; Vaccaro et al 2005). Regions of hemagglutinins are also well-conserved, for example:

Structural domains: The HA0 polyprotein is cleaved to provide mature HA. HA is a homotrimer with each monomer comprising a receptor binding domain (HA1) and a membrane-anchoring domain (HA2) linked by a single disulphide bond; the N-terminal 20 residues of the HA2 subunit may also be referred to as the HA fusion domain or sequence. A 'tail' region (internal to the membrane envelope) is also present. Each hemagglutinin comprises these regions or domains. Individual regions or domains are typically conserved in length.

All hemagglutinins contain the same number and position of intra- and inter-molecular disulfide bridges. The quantity and position on the amino acid sequence of the cysteines that participate in disulfide bridge network is conserved among the HAs. Examples of structures illustrating the characteristic intra- and intermolecular disulfide bridges and other conserved amino acids and their relative positions are described in, for example, Gamblin et al 2004 (Science 303:1838-1842). Exemplary structures and sequences include 1RVZ, 1RVX, 1RVT, 1RV0, 1RUY, 1RU7, available from the Protein Data Bank (Berman et al. 2003. Nature Structural Biology 10:980; URL: rcsb.org)

Cytoplasmic tail—the majority of hemagglutinins comprise 3 cysteines at conserved positions. One or more of these cysteines may be palmitoylated as a post-translational modification.

Amino acid variation is tolerated in hemagglutinins of influenza viruses. This variation provides for new strains that are continually identified. Infectivity between the new strains may vary. However, formation of hemagglutinin trimers, which subsequently form VLPs is maintained. The present invention, therefore, provides for a hemagglutinin amino acid sequence, or a nucleic acid encoding a hemagglutinin amino acid sequence, that forms VLPs in a plant, and includes known sequences and variant sequences that may develop.

FIG. 65 illustrates an example of such known variation. This figure shows a consensus amino acid sequence (SEQ ID NO: 74) for HA of the following H1N1 strains:

A/New Caledonia/20/99 (H1N1) (encoded by SEQ ID NO: 33),

A/Brisbane/59/2007 (H1N1) (SEQ ID NO: 48),

A/Solomon Islands/3/2006 (H1N1) (SEQ ID NO: 49) and

SEQ ID NO: 9. X1 (position 3) is A or V; X2 (position 52) is D or N; X3 (position 90) is K or R; X4 (position 99) is K or T; X5 (position 111) is Y or H; X6 (position 145) is V or T; X7 (position 154) is E or K; X8 (position 161) is R or K; X9 (position 181) is V or A; X10 (position 203) is D or N; X11 (position 205) is R or K; X12 (position 210) is T or K; X13 (position 225) is R or K; X14 (position 268) is W or R; X15 (position 283) is T or N; X16 (position 290) is E or K; X17 (position 432) is I or L; X18 (position 489) is N or D.

As another example of such variation, a sequence alignment and consensus sequence for HA of A/New Caledonia/20/99 (H1N1) (encoded by SEQ ID NO: 33), A/Brisbane/59/2007 (H1N1) (SEQ ID NO: 48), A/Solomon Islands/3/2006 (H1N1) (SEQ ID NO: 49), A/PuertoRico/8/34 (H1N1) and SEQ ID NO: 9 is shown below in Table 3.

TABLE 3

Sequence alignment and consensus sequence for HA of selected H1N1 strains

| SEQ ID NO. | Sequence |
|---|---|
| | 1 50 |
| 75 | MKAKLLVLLC TFTATYADTI CIGYHANNST DTVDTVLEKN VTVTHSVNLL |
| 9 | MKAKLLVLLC TFTATYADTI CIGYHANNST DTVDTVLEKN VTVTHSVNLL |
| 48 | MKVKLLVLLC TFTATYADTI CIGYHANNST DTVDTVLEKN VTVTHSVNLL |
| 49 | MKVKLLVLLC TFTATYADTI CIGYHANNST DTVDTVLEKN VTVTHSVNLL |
| 76 | .......... .......... .......... .......... .......... |
| Consensus | mkxkllvllc tftatyadti cigyhannst dtvdtvlekn vtvthsvnll |
| | 51 100 |
| 75 | EDSHNGKLCL LKGIAPLQLG NCSVAGWILG NPECELLISK ESWSYIVETP |
| 9 | EDSHNGKLCL LKGIAPLQLG NCSVAGWILG NPECELLISK ESWSYIVETP |
| 48 | ENSHNGKLCL LKGIAPLQLG NCSVAGWILG NPECELLISK ESWSYIVEKP |
| 49 | EDSHNGKLCL LKGIAPLQLG NCSVAGWILG NPECELLISR ESWSYIVEKP |
| 76 | .......... .......... .......... .......... .......... |
| Consensus | exshngklcl lkgiaplqlg ncsvagwilg npecellis. eswsyive.p |
| | 101 150 |
| 75 | NPENGTCYPG YFADYEELRE QLSSVSSFER FEIFPKESSW PNHTVTGVSA |
| 9 | NPENGTCYPG YFADYEELRE QLSSVSSFER FEIFPKESSW PNHTVTGVSA |
| 48 | NPENGTCYPG HFADYEELRE QLSSVSSFER FEIFPKESSW PNHTVTGVSA |
| 49 | NPENGTCYPG HFADYEELRE QLSSVSSFER FEIFPKESSW PNHTTTGVSA |
| 76 | .......... .......... .......... .......... .......... |
| Consensus | npengtcypg xfadyeelre qlssyssfer feifpkessw pnhtxtgvsa |
| | 151 200 |
| 75 | SCSHNGKSSF YRNLLWLTGK NGLYPNLSKS YVNNKEKEVL VLWGVHHPPN |
| 9 | SCSHNGKSSF YRNLLWLTGK NGLYPNLSKS YVNNKEKEVL VLWGVHHPPN |
| 48 | SCSHNGESSF YRNLLWLTGK NGLYPNLSKS YANNKEKEVL VLWGVHHPPN |
| 49 | SCSHNGESSF YKNLLWLTGK NGLYPNLSKS YANNKEKEVL VLWGVHHPPN |
| 76 | .......... .......... .......... .......... .......... |
| Consensus | scshngxssf yxnllwltgk nglypnlsks yxnnkekevl vlwgvhhppn |

TABLE 3-continued

Sequence alignment and consensus sequence for HA of selected H1N1 strains

| SEQ ID NO. | Sequence |
|---|---|
| | 201 250 |
| 75 | IGNQRALYHT ENAYVSVVSS HYSRRFTPEI AKRPKVRDQE GRINYYWTLL |
| 9 | IGNQRALYHT ENAYVSVVSS HYSRRFTPEI AKRPKVRDQE GRINYYWTLL |
| 48 | IGDQKALYHT ENAYVSVVSS HYSRKFTPEI AKRPKVRDQE GRINYYWTLL |
| 49 | IGDQRALYHK ENAYVSVVSS HYSRKFTPEI AKRPKVRDQE GRINYYWTLL |
| 76 | .......... .....MSLLT EVETYVLSII PSGPLKAEIA QRLEDVFAGK |
| Consensus | igxqxalyhx enayvsvvss hysrxftpeI akrPkvr#qe gRi#yywtll |
| | 251 300 |
| 75 | EPGDTIIFEA NGNLIAPWYA FALSRGFGSG IITSNAPMDE CDAKCQTPQG |
| 9 | EPGDTIIFEA NGNLIAPWYA FALSRGFGSG IITSNAPMDE CDAKCQTPQG |
| 48 | EPGDTIIFEA NGNLIAPRYA FALSRGFGSG IINSNAPMDK CDAKCQTPQG |
| 49 | EPGDTIIFEA NGNLIAPRYA FALSRGFGSG IINSNAPMDE CDAKCQTPQG |
| 76 | NTDLEVLMEW ...LKTRPIL SPLTKGILGF VFTLTVPSER GLQRRRFVQN |
| Consensus | #pgdt!ifEa ngnLiapxya faLsrGfgsg !itsnaPm#x cdakcqtpQg |
| | 301 350 |
| 75 | AINSSLPFQN VHPVTIGECP KYVRSAKLRM VT.GLRNIPS IQSRGLFGAI |
| 9 | AINSSLPFQN VHPVTIGECP KYVRSAKLRM VT.GLRNIPS IQSRGLFGAI |
| 48 | AINSSLPFQN VHPVTIGECP KYVRSAKLRM VT.GLRNIPS IQSRGLFGAI |
| 49 | AINSSLPFQN VHPVTIGECP KYVRSAKLRM VT.GLRNIPS IQSRGLFGAI |
| 76 | ALNG.....N GDPNNMDKAV KLYRKLKREI TFHGAKEISL SYSAGALASC |
| Consensus | AiNsslpfqN vhPvtigecp KyvRsaKlrm vtxGlr#Ips igSrGlfgai |
| | 351 400 |
| 75 | AGFIEGGWTG MVDGWYGYHH QNEQGSGYAA DQKSTQNAIN GITNKVNSVI |
| 9 | AGFIEGGWTG MVDGWYGYHH QNEQGSGYAA DQKSTQNAIN GITNKVNSVI |
| 48 | AGFIEGGWTG MVDGWYGYHH QNEQGSGYAA DQKSTQNAIN GITNKVNSVI |
| 49 | AGFIEGGWTG MVDGWYGYHH QNEQGSGYAA DQKSTQNAIN GITNKVNSVI |
| 76 | MGLIYNRM.G AVTTEVAFGL VCATCEQIAD SQHRSHRQMV TTTNPLIRHE |
| Consensus | aGfIeggwtG mVdgwyg%hh gneqgsgyAa dQkstqnain giTNkvnsvi |
| | 401 450 |
| 75 | EKMNTQFTAV GKEFNKLERR MENLNKKVDD GFLDIWTYNA ELLVLLENER |
| 9 | EKMNTQFTAV GKEFNKLERR MENLNKKVDD GFLDIWTYNA ELLVLLENER |
| 48 | EKMNTQFTAV GKEFNKLERR MENLNKKVDD GFIDIWTYNA ELLVLLENER |
| 49 | EKMNTQFTAV GKEFNKLERR MENLNKKVDD GFIDIWTYNA ELLVLLENER |
| 76 | NRMVLASTTA .KAMEQMAGS SEQAAEAMEV A........S QARQMVQAMR |
| Consensus | #kMntqfTav gKef#k$err mE#lnkkv#d gfxdiwtyna #llv$l#neR |
| | 451 500 |
| 75 | TLDFHDSNVK NLYEKVKSQL KNNAKEIGNG CFEFYHKCNN ECMESVKNGT |
| 9 | TLDFHDSNVK NLYEKVKSQL KNNAKEIGNG CFEFYHKCNN ECMESVKNGT |
| 48 | TLDFHDSNVK NLYEKVKSQL KNNAKEIGNG CFEFYHKCND ECMESVKNGT |

TABLE 3-continued

Sequence alignment and consensus sequence for HA of selected H1N1 strains

| SEQ ID NO. | Sequence |
|---|---|
| 49 | TLDFHDSNVK NLYEKVKSQL KNNAKEIGNG CFEFYHKCND ECMESVKNGT |
| 76 | TIGTHPSSSA GLKNDLLENL QAYQKRMGVQ MQRFK..... .......... |
| Consensus | TldfHdSnvk nLy#kvks#L knnaKeiGng cfeFyhkcnx ecmesvkngt |
| | 501 550 |
| 75 | YDYPKYSEES KLNREKIDGV KLESMGVYQI LAIYSTVASS LVLLVSLGAI |
| 9 | YDYPKYSEES KLNREKIDGV KLESMGVYQI LAIYSTVASS LVLLVSLGAI |
| 48 | YDYPKYSEES KLNREKIDGV KLESMGVYQI LAIYSTVASS LVLLVSLGAI |
| 49 | YDYPKYSEES KLNREKIDGV KLESMGVYQI LAIYSTVASS LVLLVSLGAI |
| 76 | .......... .......... .......... .......... .......... |
| Consensus | ydypkysees klnrekidgv klesmgvyqi laiystvass lvllvslgai |
| | 551 566 |
| 75 | SFWMCSNGSL QCRICI |
| 9 | SFWMCSNGSL QCRICI |
| 48 | SFWMCSNGSL QCRICI |
| 49 | SFWMCSNGSL QCRICI |
| 76 | .......... ...... |
| Consensus | sfwmcsngsl qcrici |

The consensus sequence indicates in upper case letters amino acids common to all sequences at a designated position; lower case letters indicate amino acids common to at least half, or a majority of the sequences; the symbol ! is any one of I or V; the symbol $ is any one of L or M; the symbol % is any one of F or Y; the symbol # is any one of N, D, Q, E, B or Z; the symbol "." is no amino acid (e.g. a deletion); X at position 3 is any one of A or V; X at position 52 is any one of E or N; X at position 90 is K or R; X at position 99 is T or K; X at position 111 is any one of Y or H; X at position 145 is any one of V or T; X at position 157 is K or E; X at position 162 is R or K; X at position 182 is V or A; X at position 203 is N or D; X at position 205 is R or K; X at position 210 is T or K; X at position 225 is K or Y; X at position 333 is H or a deletion; X at position 433 is I or L; X at position 49) is N or D.

As another example of such variation, a sequence alignment and consensus sequence for HA of A/Anhui/1/2005 (H5N1) (SEQ ID NO: 55), A/Vietnam/1194/2004 (H5N1) and A/Indonesia/5/2006 (H5N1) (SEQ ID NO: 10) is shown below in Table 4.

TABLE 4

Sequence alignment and consensus sequence for HA of selected H1N1 strains

| SEQ ID NO. | Sequence |
|---|---|
| | 1 50 |
| 10 | MEKIVLLLAI VSLVKSDQIC IGYHANNSTE QVDTIMEKNV TVTHAQDILE |
| 56 | MEKIVLLLAI VSLVKSDQIC IGYHANNSTE QVDTIMEKNV TVTHAQDILE |
| 55 | MEKIVLLLAI VSLVKSDQIC IGYHANNSTE QVDTIMEKNV TVTHAQDILE |
| Consensus | MEKIVLLlAI VSLVKSDQIC IGYHANNSTE QVDTIMEKNV TVTHAQDILE |

TABLE 4-continued

Sequence alignment and consensus sequence for HA of selected H1N1 strains

| SEQ ID NO. | Sequence |
|---|---|
| | 51 100 |
| 10 | KTHNGKLCDL DGVKPLILRD CSVAGWLLGN PMCDEFINVP EWSYIVEKAN |
| 56 | KTHNGKLCDL DGVKPLILRD CSVAGWLLGN PMCDEFINVP EWSYIVEKAN |
| 55 | KTHNGKLCDL DGVKPLILRD CSVAGWLLGN PMCDEFINVP EWSYIVEKAN |
| Consensus | KTHNGKLCDL DGVKPLILRD CSVAGWLLGN PMCDEFINVP EWSYIVEKAN |
| | 101 150 |
| 10 | PTNDLCYPGS FNDYEELKHL LSRINHFEKI QIIPKSSWSD HEASSGVSSA |
| 56 | PVNDLCYPGD FNDYEELKHL LSRINHFEKI QIIPKSSWSS HEASLGVSSA |
| 55 | PANDLCYPGN FNDYEELKHL LSRINHFEKI QIIPKSSWSD HEASSGVSSA |
| Consensus | PxNDLCYPGx FNDYEELKHL LSRINHFEKI QIIPKSSWSd HEASsGVSSA |
| | 151 200 |
| 10 | CPYLGSPSFF RNVVWLIKKN STYPTIKKSY NNTNQEDLLV LWGIHHPNDA |
| 56 | CPYQGKSSFF RNVVWLIKKN STYPTIKRSY NNTNQEDLLV LWGIHHPNDA |
| 55 | CPYQGTPSFF RNVVWLIKKN NTYPTIKRSY NNTNQEDLLI LWGIHHSNDA |
| Consensus | CPYqGxpSFF RNVVWLIKKN sTYPTIKrSY NNTNQEDLL! LWGIHHpNDA |
| | 201 250 |
| 10 | AEQTRLYQNP TTYISIGTST LNQRLVPKIA TRSKVNGQSG RMEFFWTILK |
| 56 | AEQTKLYQNP TTYISVGTST LNQRLVPRIA TRSKVNGQSG RMEFFWTILK |
| 55 | AEQTKLYQNP TTYISVGTST LNQRLVPKIA TRSKVNGQSG RMDFFWTILK |
| Consensus | AEQTkLYQNP TTYIS!GTST LNQRLVPkIA TRSKVNGQSG RM#FFWTILK |
| | 251 300 |
| 10 | PNDAINFESN GNFIAPEYAY KIVKKGDSAI MKSELEYGNC NTKCQTPMGA |
| 56 | PNDAINFESN GNFIAPEYAY KIVKKGDSTI MKSELEYGNC NTKCQTPMGA |
| 55 | PNDAINFESN GNFIAPEYAY KIVKKGDSAI VKSEVEYGNC NTKCQTPIGA |
| Consensus | PNDAINFESN GNFIAPEYAY KIVKKGDSaI mKSElEYGNC NTKCQTPmGA |
| | 301 350 |
| 10 | INSSMPFHNI HPLTIGECPK YVKSNRLVLA TGLRNSPQRE SRRKKRGLFG |
| 56 | INSSMPFHNI HPLTIGECPK YVKSNRLVLA TGLRNSPQRE RRRKKRGLFG |
| 55 | INSSMPFHNI HPLTIGECPK YVKSNKLVLA TGLRNSPLRE RRRK.RGLFG |
| Consensus | INSSMPFHNI HPLTIGECPK YVKSNrLVLA TGLRNSPqRE rRRKkRGLFG |
| | 351 400 |
| 10 | AIAGFIEGGW QGMVDGWYGY HHSNEQGSGY AADKESTQKA IDGVTNKVNS |
| 56 | AIAGFIEGGW QGMVDGWYGY HHSNEQGSGY AADKESTQKA IDGVTNKVNS |
| 55 | AIAGFIEGGW QGMVDGWYGY HHSNEQGSGY AADKESTQKA IDGVTNKVNS |
| Consensus | AIAGFIEGGW QGMVDGWYGY HHSNEQGSGY AADKESTQKA IDGVTNKVNS |
| | 401 450 |
| 10 | IIDKMNTQFE AVGREFNNLE RRIENLNKKM EDGFLDVWTY NAELLVLMEN |
| 56 | IIDKMNTQFE AVGREFNNLE RRIENLNKKM EDGFLDVWTY NAELLVLMEN |
| 55 | IIDKMNTQFE AVGREFNNLE RRIENLNKKM EDGFLDVWTY NAELLVLMEN |
| Consensus | IIDKMNTQFE AVGREFNNLE RRIENLNKKM EDGFLDVWTY NAELLVLMEN |

TABLE 4-continued

Sequence alignment and consensus sequence for HA of selected H1N1 strains

| SEQ ID NO. | Sequence |
|---|---|
| | 451 500 |
| 10 | ERTLDFHDSN VKNLYDKVRL QLRDNAKELG NGCFEFYHKC DNECMESIRN |
| 56 | ERTLDFHDSN VKNLYDKVRL QLRDNAKELG NGCFEFYHKC DNECMESVRN |
| 55 | ERTLDFHDSN VKNLYDKVRL QLRDNAKELG NGCFEFYHKC DNECMESVRN |
| Consensus | ERTLDFHDSN VKNLYDKVRL QLRDNAKELG NGCFEFYHKC DNECMES!RN |
| | 501 550 |
| 10 | GTYNYPQYSE EARLKREEIS GVKLESIGTY QILSIYSTVA SSLALAIMMA |
| 56 | GTYDYPQYSE EARLKREEIS GVKLESIGTY QILSIYSTVA SSLALAIMVA |
| 55 | GTYDYPQYSE EARLKREEIS GVKLESIGTY QILSIYSTVA SSLALAIMVA |
| Consensus | GTY#YPQYSE EARLKREEIS GVKLESIGtY QILSIYSTVA SSLALAIMvA |
| | 551 568 |
| 10 | GLSLWMCSNG SLQCRICI |
| 56 | GLSLWMCSNG SLQCRICI |
| 55 | GLSLWMCSNG SLQCRICI |
| Consensus | GLSLWMCSNG SLQCRICI |

The consensus sequence indicates in upper case letters amino acids common to all sequences at a designated position; lower case letters indicate amino acids common to at least half, or a majority of the sequences; the symbol ! is any one of I or V; the symbol $ is any one of L or M; the symbol % is any one of F or Y; the symbol # is any one of N, D, Q, E, B or Z; X at position 102 is any of T, V or A; X t position 110 is any of S, D or N; X at position 156 is any of S, K or T.

The above-illustrated and described alignments and consensus sequences are non-limiting examples of variants in hemagglutinin amino acid sequences that may be used in various embodiments of the invention for the production of VLPs in a plant.

A nucleic acid encoding an amino acid sequence may be easily determined, as the codons for each amino acid are known in the art. Provision of an amino acid sequence, therefore, teaches the degenerate nucleic acid sequences that encode it. The present invention, therefore, provides for a nucleic acid sequence encoding the hemagglutinin of those influenza strains and subtypes disclosed herein (e.g. A/California/04/09 (H1N1), A/New Caledonia/20/99 (H1N1)A/Indonesia/5/2006 (H5N1), A/chicken/New York/1995, A/herring gull/DE/677/88 (H2N8), A/Texas/32/2003, A/mallard/MN/33/00, A/duck/Shanghai/1/2000, A/northern pintail/TX/828189/02, A/Turkey/Ontario/6118/68(H8N4), A/shoveler/Iran/G54/03, A/chicken/Germany/N/1949 (H10N7), A/duck/England/56(H11N6), A/duck/Alberta/60/76(H12N5), A/Gull/Maryland/704/77(H13N6), A/Mallard/Gurjev/263/82, A/duck/Australia/341/83 (H15N8), A/black-headed gull/Sweden/5/99(H16N3), B/Lee/40, C/Johannesburg/66, A/PuertoRico/8/34 (H1N1), A/Brisbane/59/2007 (H1N1), A/Solomon Islands 3/2006 (H1N1), A/Brisbane 10/2007 (H3N2), A/Wisconsin/67/2005 (H3N2), B/Malaysia/2506/2004, B/Florida/4/2006, A/Singapore/1/57 (H2N2), A/Anhui/1/2005 (H5N1), A/Vietnam/1194/2004 (H5N1), A/Teal/HongKong/W312/97 (H6N1), A/Equine/Prague/56 (H7N7), A/HongKong/1073/99 (H9N2)), as well as the degenerate sequences that encode the above hemagglutinins.

Further, an amino acid sequence encoded by a nucleic acid may be easily determined, as the codon or codons for each amino acid are known. Provision of a nucleic acid, therefore, teaches an amino acid sequence encoded by it. The invention, therefore, provides for amino acid sequences of the hemagglutinin of those influenza strains and subtypes disclosed herein those disclosed herein (e.g. A/California/04/09 (H1N1), A/New Caledonia/20/99 (H1N1)A/Indonesia/5/2006 (H5N1), A/chicken/New York/1995, A/herring gull/DE/677/88 (H2N8), A/Texas/32/2003, A/mallard/MN/33/00, A/duck/Shanghai/1/2000, A/northern pintail/TX/828189/02, A/Turkey/Ontario/6118/68(H8N4), A/shoveler/Iran/G54/03, A/chicken/Germany/N/1949(H10N7), A/duck/England/56(H11N6), A/duck/Alberta/60/76(H12N5), A/Gull/Maryland/704/77(H13N6), A/Mallard/Gurjev/263/82, A/duck/Australia/341/83 (H15N8), A/black-headed gull/Sweden/5/99(H16N3), B/Lee/40, C/Johannesburg/66, A/PuertoRico/8/34 (H1N1), A/Brisbane/59/2007 (H1N1), A/Solomon Islands 3/2006 (H1N1), A/Brisbane 10/2007 (H3N2), A/Wisconsin/67/2005 (H3N2), B/Malaysia/2506/2004, B/Florida/4/2006, A/Singapore/1/57 (H2N2), A/Anhui/1/2005 (H5N1), A/Vietnam/1194/2004 (H5N1), A/Teal/HongKong/W312/97 (H6N1), A/Equine/Prague/56 (H7N7), A/HongKong/1073/99 (H9N2)).

In plants, influenza VLPs bud from the plasma membrane (see Example 5, and FIG. 19) therefore the lipid composition of the VLPs reflects their origin. The VLPs produced according to the present invention comprise HA of one or more than one type or subtype of influenza, complexed with plant derived lipids. Plant lipids can stimulate specific immune cells and enhance the immune response induced. Plant membranes are made of lipids, phosphatidylcholine (PC)

and phosphatidylethanolamine (PE), and also contain glycosphingolipids, saponins, and phytosterols. Additionally, lipid rafts are also found in plant plasma membranes—these microdomains are enriched in sphingolipids and sterols. In plants, a variety of phytosterols are known to occur, including stigmasterol, sitosterol, 24-methylcholesterol and cholesterol (Mongrand et al., 2004).

PC and PE, as well as glycosphingolipids can bind to CD1 molecules expressed by mammalian immune cells such as antigen-presenting cells (APCs) like dendritic cells and macrophages and other cells including B and T lymphocytes in the thymus and liver (Tsuji M., 2006). CD1 molecules are structurally similar to major histocompatibility complex (MHC) molecules of class I and their role is to present glycolipid antigens to NKT cells (Natural Killer T cells). Upon activation, NKT cells activate innate immune cells such as NK cells and dendritic cells and also activate adaptive immune cells like the antibody-producing B cells and T-cells.

A variety of phytosterols may be found in a plasma membrane—the specific complement may vary depending on the species, growth conditions, nutrient resources or pathogen state, to name a few factors. Generally, beta-sitosterol is the most abundant phytosterol.

The phytosterols present in an influenza VLP complexed with a lipid bilayer, such as an plasma-membrane derived envelope may provide for an advantageous vaccine composition. Without wishing to be bound by theory, plant-made VLPs complexed with a lipid bilayer, such as a plasma-membrane derived envelope, may induce a stronger immune reaction than VLPs made in other expression systems, and may be similar to the immune reaction induced by live or attenuated whole virus vaccines.

Therefore, in some embodiments, the invention provides for a VLP complexed with a plant-derived lipid bilayer. In some embodiments the plant-derived lipid bilayer may comprise the envelope of the VLP.

The VLP produced within a plant may include an HA comprising plant-specific N-glycans. Therefore, this invention also provides for a VLP comprising HA having plant specific N-glycans.

Furthermore, modification of N-glycan in plants is known (see for example U.S. 60/944,344; which is incorporated herein by reference) and HA having modified N-glycans may be produced. HA comprising a modified glycosylation pattern, for example with reduced fucosylated, xylosylated, or both, fucosylated and xylosylated, N-glycans may be obtained, or HA having a modified glycosylation pattern may be obtained, wherein the protein lacks fucosylation, xylosylation, or both, and comprises increased galatosylation. Furthermore, modulation of post-translational modifications, for example, the addition of terminal galactose may result in a reduction of fucosylation and xylosylation of the expressed HA when compared to a wild-type plant expressing HA.

For example, which is not to be considered limiting, the synthesis of HA having a modified glycosylation pattern may be achieved by co-expressing the protein of interest along with a nucleotide sequence encoding beta-1.4galactosyltransferase (GalT), for example, but not limited to mammalian GalT, or human GalT however GalT from another sources may also be used. The catalytic domain of GalT may also be fused to a CTS domain (i.e. the cytoplasmic tail, transmembrane domain, stem region) of N-acetylglucosaminyl transferase (GNT1), to produce a GNT1-GalT hybrid enzyme, and the hybrid enzyme may be co-expressed with HA. The HA may also be co-expressed along with a nucleotide sequence encoding N-acetylglucosaminyltrasnferase III (GnT-III), for example but not limited to mammalian GnT-III or human GnT-III, GnT-III from other sources may also be used. Additionally, a GNT1-GnT-III hybrid enzyme, comprising the CTS of GNT1 fused to GnT-III may also be used.

Therefore the present invention also includes VLP's comprising HA having modified N-glycans.

Without wishing to be bound by theory, the presence of plant N-glycans on HA may stimulate the immune response by promoting the binding of HA by antigen presenting cells. Stimulation of the immune response using plant N glycan has been proposed by Saint-Jore-Dupas et al. (2007). Furthermore, the conformation of the VLP may be advantageous for the presentation of the antigen, and enhance the adjuvant effect of VLP when complexed with a plant derived lipid layer.

By "regulatory region", "regulatory element" or "promoter" it is meant a portion of nucleic acid typically, but not always, upstream of the protein coding region of a gene, which may be comprised of either DNA or RNA, or both DNA and RNA. When a regulatory region is active, and in operative association, or operatively linked, with a gene of interest, this may result in expression of the gene of interest. A regulatory element may be capable of mediating organ specificity, or controlling developmental or temporal gene activation. A "regulatory region" includes promoter elements, core promoter elements exhibiting a basal promoter activity, elements that are inducible in response to an external stimulus, elements that mediate promoter activity such as negative regulatory elements or transcriptional enhancers. "Regulatory region", as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element comprises a basal promoter element, responsible for the initiation of transcription, as well as other regulatory elements (as listed above) that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well. Examples of tissue-specific regulatory regions, for example see-specific a regulatory region, include the napin promoter, and the cruciferin promoter (Rask et al., 1998, J. Plant Physiol. 152: 595-599; Bilodeau et al., 1994, Plant Cell 14: 125-130). An example of a leaf-specific promoter includes the plastocyanin promoter (FIG. 1*b*; U.S. Pat. No. 7,125,978, which is incorporated herein by reference).

An inducible regulatory region is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory region to activate transcription may be present in an inactive form, which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory region may be exposed to an inducer by externally applying the inducer to the cell or plant such as by spraying, watering, heating or similar methods. Inducible regulatory elements may be derived from either plant or non-plant genes (e.g. Gatz, C. and Lenk, I. R. P., 1998, Trends Plant Sci. 3, 352-358; which is incorporated by reference). Examples, of potential inducible promoters include, but not limited to, tetracycline-inducible promoter (Gatz, C., 1997, Ann. Rev. Plant Physiol. Plant Mol. Biol. 48, 89-108; which is incorporated by reference), steroid inducible promoter (Aoyama, T. and Chua, N. H., 1997, Plant J. 2, 397-404; which is incorporated by reference) and ethanol-inducible promoter (Salter, M. G., et al, 1998, Plant Journal 16, 127-132; Caddick, M. X., et al, 1998, Nature Biotech. 16, 177-180, which are incorporated by reference) cytokinin inducible IB6 and CKI1 genes (Brandstatter, I. and Kieber, J. J., 1998, Plant Cell 10, 1009-1019; Kakimoto, T., 1996, Science 274, 982-985; which are incorporated by reference) and the auxin inducible element, DR5 (Ulmasov, T., et al., 1997, Plant Cell 9, 1963-1971; which is incorporated by reference).

A constitutive regulatory region directs the expression of a gene throughout the various parts of a plant and continuously throughout plant development. Examples of known constitutive regulatory elements include promoters associated with the CaMV 35S transcript. (Odell et al., 1985, Nature, 313: 810-812), the rice actin 1 (Zhang et al, 1991, Plant Cell, 3: 1155-1165), actin 2 (An et al., 1996, Plant J., 10: 107-121), or tms 2 (U.S. Pat. No. 5,428,147, which is incorporated herein by reference), and triosephosphate isomerase 1 (Xu et. al., 1994, Plant Physiol. 106: 459-467) genes, the maize ubiquitin 1 gene (Cornejo et al, 1993, Plant Mol. Biol. 29: 637-646), the *Arabidopsis* ubiquitin 1 and 6 genes (Holtorf et al, 1995, Plant Mol. Biol. 29: 637-646), and the tobacco translational initiation factor 4A gene (Mandel et al, 1995 Plant Mol. Biol. 29: 995-1004). The term "constitutive" as used herein does not necessarily indicate that a gene under control of the constitutive regulatory region is expressed at the same level in all cell types, but that the gene is expressed in a wide range of cell types even though variation in abundance is often observed. Constitutive regulatory elements may be coupled with other sequences to further enhance the transcription and/or translation of the nucleotide sequence to which they are operatively linked. For example, the CMPV-HT system (Sainsbury et al, 2008, Plant Physiology 148: 1212-1218) is derived from the untranslated regions of the Cowpea mosaic virus (COMV) and demonstrates enhanced translation of the associated coding sequence.

By "native" it is meant that the nucleic acid or amino acid sequence is naturally occurring, or "wild type".

By "operatively linked" it is meant that the particular sequences, for example a regulatory element and a coding region of interest, interact either directly or indirectly to carry out an intended function, such as mediation or modulation of gene expression. The interaction of operatively linked sequences may, for example, be mediated by proteins that interact with the operatively linked sequences.

The one or more than one nucleotide sequence of the present invention may be expressed in any suitable plant host that is transformed by the nucleotide sequence, or constructs, or vectors of the present invention. Examples of suitable hosts include, but are not limited to, agricultural crops including alfalfa, canola, *Brassica* spp., maize, *Nicotiana* spp., alfalfa, potato, ginseng, pea, oat, rice, soybean, wheat, barley, sunflower, cotton and the like.

The one or more chimeric genetic constructs of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon. One or more of the chimeric genetic constructs of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence.

Non-limiting examples of suitable 3' regions are the 3' transcribed non-translated regions containing a polyadenylation signal of *Agrobacterium* tumor inducing (Ti) plasmid genes, such as the nopaline synthase (Nos gene) and plant genes such as the soybean storage protein genes, the small subunit of the ribulose-1,5-bisphosphate carboxylase (ssRUBISCO; U.S. Pat. No. 4,962,028; which is incorporated herein by reference) gene, the promoter used in regulating plastocyanin expression (Pwee and Gray 1993; which is incorporated herein by reference). An example of a plastocyanin promoter is described in U.S. Pat. No. 7,125, 978 (which is incorporated herein by reference)

As described herein, promoters comprising enhancer sequences with demonstrated efficiency in leaf expression, have been found to be effective in transient expression. Without wishing to be bound by theory, attachment of upstream regulatory elements of a photosynthetic gene by attachment to the nuclear matrix may mediate strong expression. For example up to −784 from the translation start site of the pea plastocyanin gene may be used mediate strong reporter gene expression.

To aid in identification of transformed plant cells, the constructs of this invention may be further manipulated to include plant selectable markers. Useful selectable markers include enzymes that provide for resistance to chemicals such as an antibiotic for example, gentamycin, hygromycin, kanamycin, or herbicides such as phosphinothrycin, glyphosate, chlorosulfuron, and the like. Similarly, enzymes providing for production of a compound identifiable by colour change such as GUS (beta-glucuronidase), or luminescence, such as luciferase or GFP, may be used.

Also considered part of this invention are transgenic plants, plant cells or seeds containing the chimeric gene construct of the present invention. Methods of regenerating whole plants from plant cells are also known in the art. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Transgenic plants can also be generated without using tissue cultures.

Also considered part of this invention are transgenic plants, trees, yeast, bacteria, fungi, insect and animal cells containing the chimeric gene construct comprising a nucleic acid encoding recombinant HA0 for VLP production, in accordance with the present invention.

The regulatory elements of the present invention may also be combined with coding region of interest for expression within a range of host organisms that are amenable to transformation, or transient expression. Such organisms include, but are not limited to plants, both monocots and dicots, for example but not limited to corn, cereal plants, wheat, barley, oat, *Nicotiana* spp, *Brassica* spp, soybean, bean, pea, alfalfa, potato, tomato, ginseng, and *Arabidopsis*.

Methods for stable transformation, and regeneration of these organisms are established in the art and known to one of skill in the art. The method of obtaining transformed and regenerated plants is not critical to the present invention.

By "transformation" it is meant the stable interspecific transfer of genetic information (nucleotide sequence) that is manifested genotypically, phenotypically or both. The interspecific transfer of genetic information from a chimeric construct to a host may be heritable and the transfer of genetic information considered stable, or the transfer may be transient and the transfer of genetic information is not inheritable.

By the term "plant matter", it is meant any material derived from a plant. Plant matter may comprise an entire plant, tissue, cells, or any fraction thereof. Further, plant matter may comprise intracellular plant components, extracellular plant components, liquid or solid extracts of plants, or a combination thereof. Further, plant matter may comprise plants, plant cells, tissue, a liquid extract, or a combination thereof, from plant leaves, stems, fruit, roots or a combination thereof. Plant matter may comprise a plant or portion thereof which has not been subjected to any processing steps. A portion of a plant may comprise plant matter. However, it is also contemplated that the plant material may be subjected to minimal processing steps as defined below, or more rigorous processing, including partial or substantial protein purification using techniques commonly known within the art including, but not limited to chromatography, electrophoresis and the like.

By the term "minimal processing" it is meant plant matter, for example, a plant or portion thereof comprising a protein of interest which is partially purified to yield a plant extract, homogenate, fraction of plant homogenate or the like (i.e. minimally processed). Partial purification may comprise, but is not limited to disrupting plant cellular structures thereby creating a composition comprising soluble plant components, and insoluble plant components which may be separated for example, but not limited to, by centrifugation, filtration or a combination thereof. In this regard, proteins secreted within the extracellular space of leaf or other tissues could be readily obtained using vacuum or centrifugal extraction, or tissues could be extracted under pressure by passage through rollers or grinding or the like to squeeze or liberate the protein free from within the extracellular space. Minimal processing could also involve preparation of crude extracts of soluble proteins, since these preparations would have negligible contamination from secondary plant products. Further, minimal processing may involve aqueous extraction of soluble protein from leaves, followed by precipitation with any suitable salt. Other methods may include large scale maceration and juice extraction in order to permit the direct use of the extract.

The plant matter, in the form of plant material or tissue may be orally delivered to a subject. The plant matter may be administered as part of a dietary supplement, along with other foods, or encapsulated. The plant matter or tissue may also be concentrated to improve or increase palatability, or provided along with other materials, ingredients, or pharmaceutical excipients, as required.

Examples of a subject or target organism that the VLPs of the present invention may be administered to include, but are not limited to, humans, primates, birds, water fowl, migratory birds, quail, duck, geese, poultry, chicken, swine, sheep, equine, horse, camel, canine, dogs, feline, cats, tiger, leopard, civet, mink, stone marten, ferrets, house pets, livestock, rabbits, mice, rats, guinea pigs or other rodents, seal, whale and the like. Such target organisms are exemplary, and are not to be considered limiting to the applications and uses of the present invention.

It is contemplated that a plant comprising the protein of interest, or expressing the VLP comprising the protein of interest may be administered to a subject or target organism, in a variety of ways depending upon the need and the situation. For example, the protein of interest obtained from the plant may be extracted prior to its use in either a crude, partially purified, or purified form. If the protein is to be purified, then it may be produced in either edible or non-edible plants. Furthermore, if the protein is orally administered, the plant tissue may be harvested and directly feed to the subject, or the harvested tissue may be dried prior to feeding, or an animal may be permitted to graze on the plant with no prior harvest taking place. It is also considered within the scope of this invention for the harvested plant tissues to be provided as a food supplement within animal feed. If the plant tissue is being feed to an animal with little or not further processing it is preferred that the plant tissue being administered is edible.

Post-transcriptional gene silencing (PTGS) may be involved in limiting expression of transgenes in plants, and co-expression of a suppressor of silencing from the potato virus Y (HcPro) may be used to counteract the specific degradation of transgene mRNAs (Brigneti et al., 1998). Alternate suppressors of silencing are well known in the art and may be used as described herein (Chiba et al., 2006, Virology 346:7-14; which is incorporated herein by reference), for example but not limited to, TEV-p1/HC-Pro (Tobacco etch virus-p1/HC-Pro), BYV-p21, p19 of Tomato bushy stunt virus (TBSV p19), capsid protein of Tomato crinkle virus (TCV-CP), 2b of Cucumber mosaic virus;

CMV-2b), p25 of Potato virus X (PVX-p25), p11 of Potato virus M (PVM-p11), p11 of Potato virus S (PVS-p11), p16 of Blueberry scorch virus, (BScV-p16), p23 of Citrus tristeza virus (CTV-p23), p24 of Grapevine leafroll-associated virus-2, (GLRaV-2 p24), p10 of Grapevine virus A, (GVA-p10), p14 of Grapevine virus B (GVB-p14), p10 of Heracleum latent virus (HLV-p10), or p16 of Garlic common latent virus (GCLV-p16). Therefore, a suppressor of silencing, for example, but not limited to, HcPro, TEV-p1/HC-Pro, BYV-p21, TBSV p19, TCV-CP, CMV-2b, PVX-p25, PVM-p11, PVS-p11, BScV-p16, CTV-p23, GLRaV-2 p24, GBV-p14, HLV-p10, GCLV-p16 or GVA-p10, may be co-expressed along with the nucleic acid sequence encoding the protein of interest to further ensure high levels of protein production within a plant.

Furthermore, VLPs may be produced that comprise a combination of HA subtypes. For example, VLPs may comprise one or more than one HA from the subtype H1, H2, H3, H4, H5, H6, H7, H8, H9, H10, H11, H12, H13, H14, H15, H16, type B, or a combination thereof. Selection of the combination of HAs may be determined by the intended use of the vaccine prepared from the VLP. For example a vaccine for use in inoculating birds may comprise any combination of HA subtypes, while VLPs useful for inoculating humans may comprise subtypes one or more than one of subtypes H1, H2, H3, H5, H6, H7, H9 or B. However, other HA subtype combinations may be prepared depending upon the use of the VLP. In order to produce VLPs comprising combinations of HA subtypes, the desired HA subtype may be co-expressed within the same cell, for example a plant cell.

Furthermore, VLPs produced as described herein do not comprise neuraminidase (NA). However, NA may be co-expressed with HA should VLPs comprising HA and NA be desired.

Therefore, the present invention further includes a suitable vector comprising the chimeric construct suitable for use with either stable or transient expression systems. The genetic information may be also provided within one or more than one construct. For example, a nucleotide sequence encoding a protein of interest may be introduced in one construct, and a second nucleotide sequence encoding a protein that modifies glycosylation of the protein of interest may be introduced using a separate construct. These nucleotide sequences may then be co-expressed within a plant. However, a construct comprising a nucleotide sequence encoding both the protein of interest and the protein that modifies glycosylation profile of the protein of interest may also be used. In this case the nucleotide sequence would comprise a first sequence comprising a first nucleic acid sequence encoding the protein of interest operatively linked to a promoter or regulatory region, and a second sequence comprising a second nucleic acid sequence encoding the protein that modifies the glycosylation profile of the protein of interest, the second sequence operatively linked to a promoter or regulatory region.

By "co-expressed" it is meant that two, or more than two, nucleotide sequences are expressed at about the same time within the plant, and within the same tissue of the plant. However, the nucleotide sequences need not be expressed at exactly the same time. Rather, the two or more nucleotide sequences are expressed in a manner such that the encoded products have a chance to interact. For example, the protein that modifies glycosylation of the protein of interest may be expressed either before or during the period when the protein of interest is expressed so that modification of the glycosylation of the protein of interest takes place. The two or more than two nucleotide sequences can be co-expressed using a transient expression system, where the two or more sequences are introduced within the plant at about the same time under conditions that both sequences are expressed. Alternatively, a platform plant comprising one of the nucleotide sequences, for example the sequence encoding the protein that modifies the glycosylation profile of the protein of interest, may be transformed, either transiently or in a stable manner, with an additional sequence encoding the protein of interest. In this case, the sequence encoding the protein that modifies the glycosylation profile of the protein of interest may be expressed within a desired tissue, during a desired stage of development, or its expression may be induced using an inducible promoter, and the additional sequence encoding the protein of interest may be expressed under similar conditions and in the same tissue, to ensure that the nucleotide sequences are co-expressed.

The constructs of the present invention can be introduced into plant cells using Ti plasmids, Ri plasmids, plant virus vectors, direct DNA transformation, micro-injection, electroporation, infiltration, and the like. For reviews of such techniques see for example Weissbach and Weissbach, *Methods for Plant Molecular Biology*, Academy Press, New York VIII, pp. 421-463 (1988); Geierson and Corey, *Plant Molecular Biology,* 2d Ed. (1988); and Miki and Iyer, Fundamentals of Gene Transfer in Plants. In *Plant Metabolism,* 2d Ed. D T. Dennis, D H Turpin, D D Lefebrve, D B Layzell (eds), Addison-Wesley, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (Gene 100: 247-250 (1991), Scheid et al. (Mol. Gen. Genet. 228: 104-112, 1991), Guerche et al. (Plant Science 52: 111-116, 1987), Neuhause et al. (Theor. Appl Genet. 75: 30-36, 1987), Klein et al., Nature 327: 70-73 (1987); Howell et al. (Science 208: 1265, 1980), Horsch et al. (Science 227: 1229-1231, 1985), DeBlock et al., Plant Physiology 91: 694-701, 1989), Methods for Plant Molecular Biology (Weissbach and Weissbach, eds., Academic Press Inc., 1988), Methods in Plant Molecular Biology (Schuler and Zielinski, eds., Academic Press Inc., 1989), Liu and Lomonossoff (J. Virol Meth, 105:343-348, 2002), U.S. Pat. Nos. 4,945,050; 5,036,006; 5,100,792; 6,403,865; 5,625,136, (all of which are hereby incorporated by reference).

Transient expression methods may be used to express the constructs of the present invention (see Liu and Lomonossoff, 2002, Journal of Virological Methods, 105:343-348; which is incorporated herein by reference). Alternatively, a vacuum-based transient expression method, as described by Kapila et al. 1997 (incorporated herein by reference) may be used. These methods may include, for example, but are not limited to, a method of Agro-inoculation or Agro-infiltration, however, other transient methods may also be used as noted above. With either Agro-inoculation or Agro-infiltration, a mixture of *Agrobacteria* comprising the desired nucleic acid enter the intercellular spaces of a tissue, for example the leaves, aerial portion of the plant (including stem, leaves and flower), other portion of the plant (stem, root, flower), or the whole plant. After crossing the epidermis the *Agrobacterium* infect and transfer t-DNA copies into the cells. The t-DNA is episomally transcribed and the mRNA translated, leading to the production of the protein of interest in infected cells, however, the passage of t-DNA inside the nucleus is transient.

If the nucleotide sequence of interest encodes a product that is directly or indirectly toxic to the plant, then by using the method of the present invention, such toxicity may be reduced throughout the plant by selectively expressing the nucleotide sequence of interest within a desired tissue or at a desired stage of plant development. In addition, the limited period of expression resulting from transient expression may reduce the effect when producing a toxic product in the plant. An inducible promoter, a tissue-specific promoter, or a cell specific promoter, may be used to selectively direct expression of the sequence of interest.

The recombinant HA VLPs of the present invention can be used in conjunction with existing influenza vaccines, to supplement the vaccines, render them more efficacious, and to reduce the administration dosages necessary. As would be known to a person of skill in the art, the vaccine may be directed against one or more than one influenza virus. Examples of suitable vaccines include, but are not limited to, those commercially available from Sanofi-Pasteur, ID Biomedical, Merial, Sinovac, Chiron, Roche, Medlmmune, GlaxoSmithKline, Novartis, Sanofi-Aventis, Serono, Shire Pharmaceuticals and the like.

If desired, the VLPs of the present invention may be admixed with a suitable adjuvant as would be known to one of skill in the art. Furthermore, the VLP may be used in a vaccine composition comprising an effective dose of the VLP for the treatment of a target organism, as defined above. Furthermore, the VLP produced according to the present invention may be combined with VLPs obtained using different influenza proteins, for example, neuraminidase (NA).

Therefore, the present invention provides a method for inducing immunity to influenza virus infection in an animal or target organism comprising administering an effective dose of a vaccine comprising one or more than one VLP. The vaccine may be administered orally, intradermally, intranasally, intramuscularly, intraperitoneally, intravenously, or subcutaneously.

Administration of VLPs produced according to the present invention is described in Example 6. Administration of plant-made H5 VLP resulted in a significantly higher response when compared to administration of soluble HA (see FIGS. 21A and 21B).

Figure 26A:
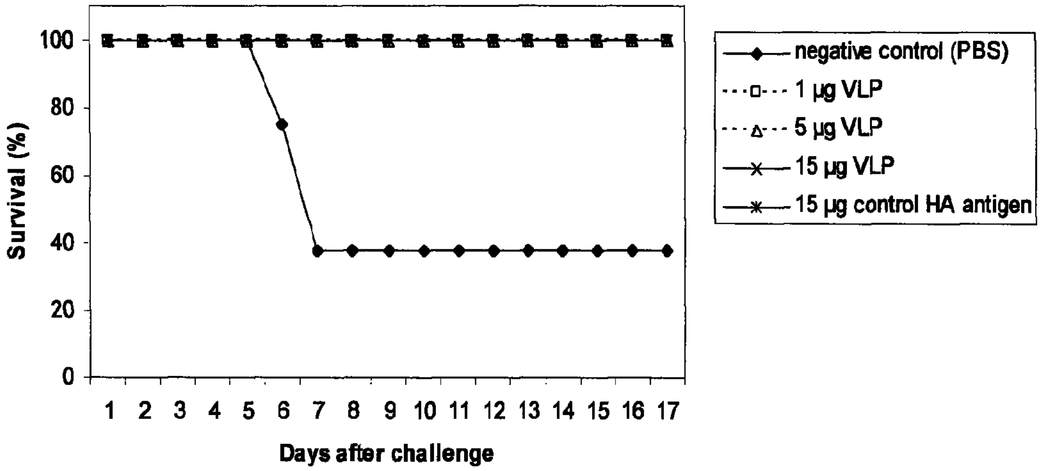
FIG. 26 shows efficacy of the plant made H5 VLP (A/Indonesia/5/2005 (H5N1)). (A) Survival rate of mice after challenge with 1000 $LD_{50}$ ($4.09\times10^6$ $CCID_{50}$) of the influenza strain A/Turkey/582/06 (H5N1) (B) Body weight of immunised mice after challenge. Values are the mean body weight of surviving mice

As shown in FIGS. 26A and 26 B a subject administered A/Indonesia/5/05 H5 VLPs is provided cross-protection to a challenge with influenza A/Turkey/582/06 (H5N1; "Turkey H5N1"). Administration of Indonesia H5 VLPs before challenge did not result in any loss of body mass. However in subject not administered H5 VLPs, but challenged with Turkey H5N1, exhibited significant loss of body mass, and several subject died.

These data, therefore, demonstrate that plant-made influenza VLPs comprising the H5 hemagglutinin viral protein induce an immune response specific for pathogenic influenza strains, and that virus-like particles may bud from a plant plasma membrane.

Therefore, the present invention provides a composition comprising an effective dose of a VLP comprising an influenza virus HA protein, one or more than one plant lipid, and a pharmaceutically acceptable carrier. The influenza virus HA protein may be H5 Indonesia/5/2006, A/Brisbane/50/2007, A/Solomon Islands 3/2006, A/Brisbane/10/2007, A/Wisconsin/67/2005, B/Malaysia/2506/2005, B/Florida/4/2006, A/Singapore/1/57, A/Anhui/1/2005, A/Vietnam/1194/2004, A/Teal/HongKong/W312/97, A/Equine/Prague/56, A/California/04/09 (H1N1) or A/HongKong/1073/99. Also provided is a method of inducing immunity to an influenza virus infection in a subject. The method comprising administering the virus like particle comprising an influenza virus HA protein, one or more than one plant lipid, and a pharmaceutically acceptable carrier. The virus like particle may be administered to a subject orally, intradermally, intranasally, intramusclarly, intraperitoneally, intravenously, or subcutaneously.

Compositions according to various embodiments of the invention may comprise VLPs of two or more influenza strains or subtypes. "Two or more" refers to two, three, four, five, six, seven, eight, nine, 10 or more strains or subtypes. The strains or subtypes represented may be of a single subtype (e.g. all H1N1, or all H5N1), or may be a combination of subtypes. Exemplary subtype and strains include, but are not limited to, those disclosed herein (e.g. A/New Caledonia/20/99 (H1N1)A/Indonesia/5/2006 (H5N1), A/chicken/New York/1995, A/herring gull/DE/677/88 (H2N8), A/Texas/32/2003, A/mallard/MN/33/00, A/duck/Shanghai/1/2000, A/northern pintail/TX/828189/02, A/Turkey/Ontario/6118/68(H8N4), A/shoveler/Iran/G54/03, A/chicken/Germany/N/1949(H10N7), A/duck/England/56 (H11N6), A/duck/Alberta/60/76(H12N5), A/Gull/Maryland/704/77(H13N6), A/Mallard/Gurjev/263/82, A/duck/Australia/341/83 (H15N8), A/black-headed gull/Sweden/5/99 (H16N3), B/Lee/40, C/Johannesburg/66, A/PuertoRico/8/34 (H1N1), A/Brisbane/59/2007 (H1N1), A/Solomon Islands 3/2006 (H1N1), A/Brisbane 10/2007 (H3N2), A/Wisconsin/67/2005 (H3N2), B/Malaysia/2506/2004, B/Florida/4/2006, A/Singapore/1/57 (H2N2), A/Anhui/1/2005 (H5N1), A/Vietnam/1194/2004 (H5N1), A/Teal/HongKong/W312/97 (H6N1), A/Equine/Prague/56 (H7N7), A/California/04/09 (H1N1) or A/HongKong/1073/99 (H9N2)).

The choice of combination of strains and subtypes may depend on the geographical area of the subjects likely to be exposed to influenza, proximity of animal species to a human population to be immunized (e.g. species of waterfowl, agricultural animals such as swine, etc) and the strains they carry, are exposed to or are likely to be exposed to, predictions of antigenic drift within subtypes or strains, or combinations of these factors. Examples of combinations used in past years are available (see URL: who.int/csr/dieease/influenza/vaccine recommendations1/en). Some or all of these strains may be employed in the combinations shown, or in other combinations, in the production of a vaccine composition.

More particularly, exemplary combinations may include VLPs from two or more strains or subtypes selected from the group comprising: A/California/04/09 (H1N1), A/Brisbane/59/2007 (H1N1), an A/Brisbane/59/2007 (H1N1)-like virus, A/Brisbane/10/2007 (H3N2), an A/Brisbane/10/2007 (H3N2)-like virus, B/Florida/4/2006 or an B/Florida/4/2006-like virus.

Another exemplary combination may include VLPs from two or more strains or subtypes selected from the group comprising A/Indonesia/5/2005, an A/Indonesia/5/2005-like virus, A/Vietnam/1194/2004, an A/Vietnam/1194/2004-like virus, A/Anhui/1/05, an A/Anhui/1/05-like virus, A/goose/Guiyang/337/2006, A/goose/Guiyang/337/2006-like virus, A/chicken/Shanxi/2/2006, A/chicken/Shanxi/2/2006-like virus, A/California/04/09 (H1N1) or A/California/04/09 (H1N1)-like virus.

Another exemplary combination may include VLPs of A/Chicken/Italy/13474/99 (H7 type) or A/Chicken/British Columbia/04 (H7N3) strains of influenza.

Another exemplary combination may include VLPs of A/Chicken/HongKong/G9/97 or A/HongKong/1073/99. Another exemplary combination may comprise VLPs of A/Solomon Islands/3/2006. Another exemplary combination may comprise VLPs of A/Brisbane/10/2007. Another exemplary combination may comprise VLPs of A/Wisconsin/67/2005. Another exemplary combination may comprise VLPs of the B/Malaysia/2506/2004, B/Florida/4/2006 or B/Brisbane/3/2007 strains or subtypes.

The two or more VLPs may be expressed individually, and the purified or semi-purified VLPs subsequently combined. Alternately, the VLPs may be co-expressed in the same host, for example a plant. The VLPs may be combined or produced in a desired ratio, for example about equivalent ratios, or may be combined in such a manner that one subtype or strain comprises the majority of the VLPs in the composition.

Therefore, the invention provides for compositions comprising VLPs of two or more strains or subtypes.

Figure 22A:
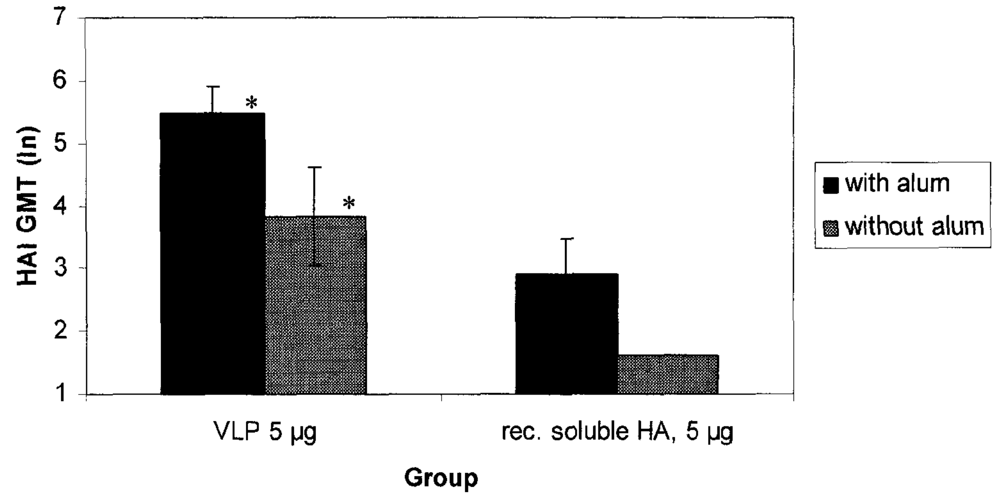
FIG. 22(A) Effect of alum on mice immunized through intramuscular injection.
Figure 22B:
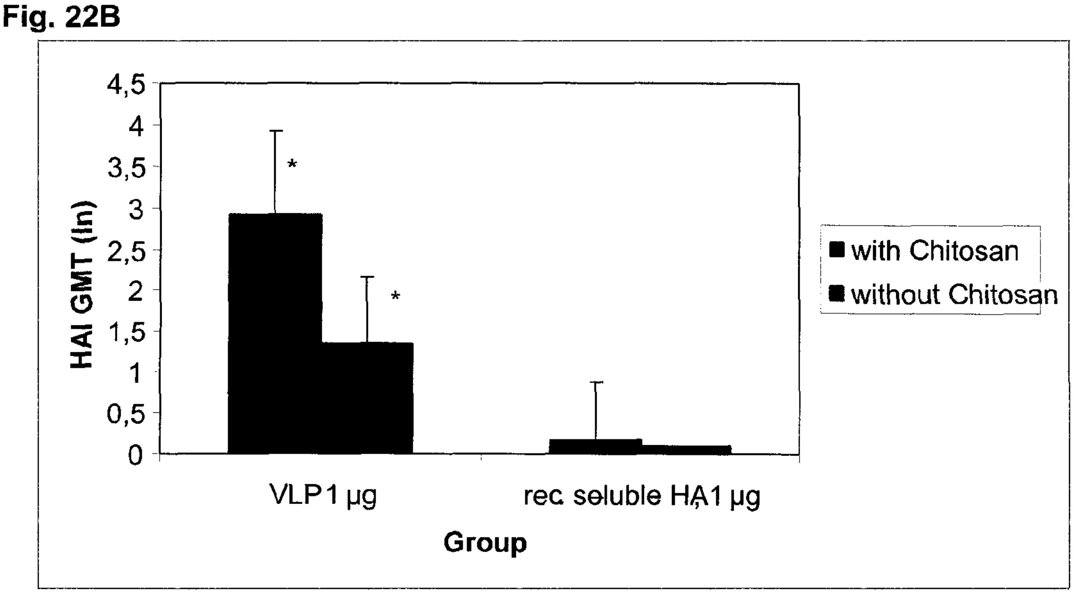
FIG. 22(B) Effect of Chitosan on mice immunized through intranasal administration. HAI antibody responses were measured using inactivated whole H5N1 viruses (A/Indonesia/5/05). GMT: geometric mean titer. Values are the GMT (ln) of reciprocal end-point titers of five mice per group. Bars represent mean deviation. *p<0.05 compared to the corresponding recombinant soluble H5.
Figure 23A:
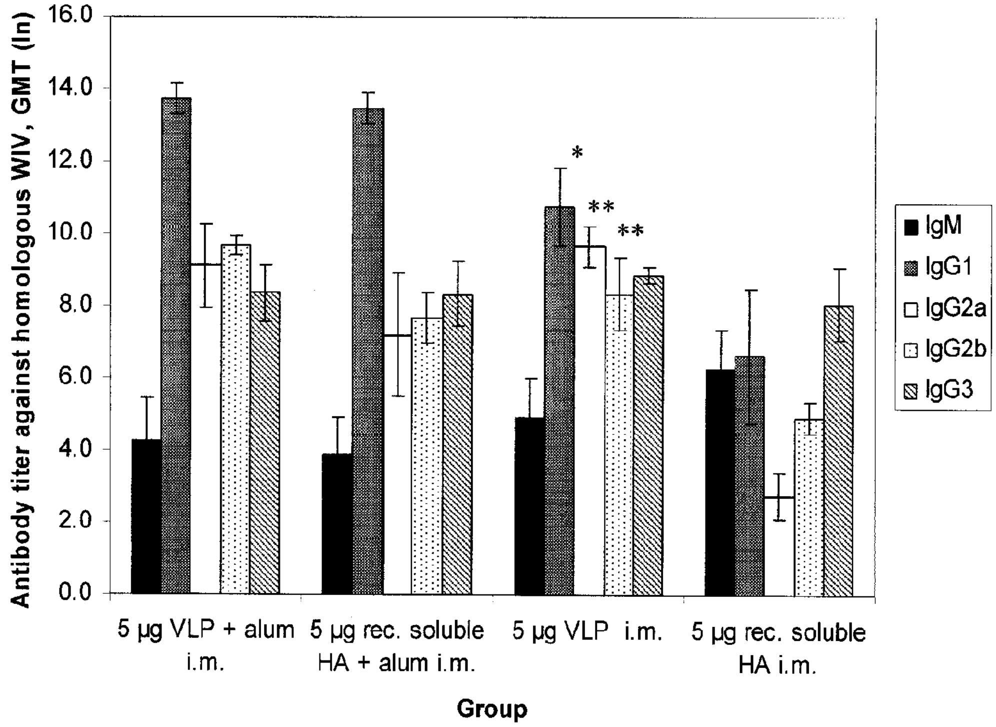
FIG. 23(A) Anti-Indonesia/5/05 immunoglobulin isotype in mice immunized through intramuscular administration, 30 days after boost. Values are the GMT ($log_2$) of reciprocal end-point titers of five mice per group. ELISA performed using whole inactivated H5N1 (A/Indonesia/5/2005) viruses as the coating agent. Bars represent mean deviation. *p<0.05, p<0.001 compared to the corresponding recombinant soluble H5 (A/Indonesia/5/2005 (H5N1)).

VLPs of enveloped viruses generally acquire their envelope from the membrane they bud through. Plant plasma membranes have a phytosterol complement that may have immunostimulatory effects. To investigate this possibility, plant-made H5 VLPs were administered to animals in the presence or absence of an adjuvant, and the HAI (hemagglutination inhibition antibody response) determined (FIGS. 22A, 22B). In the absence of an added adjuvant plant-made H5 VLPs demonstrate a significant HAI, indicative of a systemic immune response to administration of the antigen. Furthermore, the antibody isotype profiles of VLPs administered in the present or absence of adjuvant are similar (FIG. 23A).

Table 5 lists sequences provided in various embodiments of the invention.

TABLE 5

Sequence description for sequence identifiers.

| SEQ ID No | Sequence Description | In Disclosure |
|---|---|---|
| 1 | N terminal H1 fragment | FIG. 4a |
| 2 | C terminal H1 fragment | FIG. 4b |
| 3 | H5 coding sequence | FIG. 6 |
| 4 | primer Plato-443c | FIG. 7a |
| 5 | primer SpHA(Ind)-Plasto.r | FIG. 7b |
| 6 | primer Plasto-SpHA(Ind).c | FIG. 7c |
| 7 | primer HA(Ind)-Sac.r | FIG. 7d |
| 8 | Sequence of the alfalfa plastocyanin-based expression cassette used for the expression of H1 | FIG. 1 |
| 9 | HA1 peptide sequence (A/New Caledonia/20/99) | FIG. 8a |
| 10 | HA5 peptide sequence (A/Indonesia/5/2006) | FIG. 8b |
| 11 | Influenza A Subtype H7 coding sequence (A/chicken/New York/1995) | FIG. 9 |
| 12 | Influenza A Subtype H2 coding sequence (A/herring gull/DE/677/88 (H2N8)) | FIG. 10a |
| 13 | Influenza A Subtype H3 coding sequence (A/Texas/32/2003) | FIG. 10b |

TABLE 5-continued

Sequence description for sequence identifiers.

| SEQ ID No | Sequence Description | In Disclosure |
|---|---|---|
| 14 | Influenza A Subtype H4 coding sequence (A/mallard/MN/33/00) | FIG. 10c |
| 15 | Influenza A Subtype H5 coding sequence (A/duck/Shanghai/1/2000) | FIG. 10d |
| 16 | Influenza A Subtype H6 coding sequence (A/northern pintail/TX/828189/02) | FIG. 10e |
| 17 | Influenza A Subtype H8 coding sequence (A/Turkey/Ontario/6118/68 (H8N4)) | FIG. 10f |
| 18 | Influenza A Subtype H9 coding sequence (A/shoveler/Iran/G54/03) | FIG. 10g |
| 19 | Influenza A Subtype H10 coding sequence (A/chicken/Germany/N/1949 (H10 N7)) | FIG. 10h |
| 20 | Influenza A Subtype H11 coding sequence (A/duck/England/56(H11N6)) | FIG. 10i |
| 21 | Influenza A Subtype H12 coding sequence (A/duck/Alberta/60/76(H12N5)) | FIG. 10j |
| 22 | Influenza A Subtype H13 coding sequence (A/Gull/Maryland/704/77 (H13N6)) | FIG. 10k |
| 23 | Influenza A Subtype H14 coding sequence (A/Mallard/Gurjev/263/82) | FIG. 10l |
| 24 | Influenza A Subtype H15 coding sequence (A/duck/Australia/341/83 (H15N8)) | FIG. 10m |
| 25 | Influenza A Subtype H16 coding sequence (A/black-headed gull/Sweden/5/99 (H16N3)) | FIG. 10n |
| 26 | Influenza B HA coding sequence (B/Lee/40) | FIG. 10o |
| 27 | Influenza C HA coding sequence (C/Johannesburg/66) | FIG. 10p |
| 28 | Complete HA0 H1 sequence | FIG. 5 |
| 29 | Primer XmaI-pPlas.c | FIG. 10q |
| 30 | Primer SacI-ATG-pPlas.r | FIG. 10r |
| 31 | Primer SacI-PlasTer.c | FIG. 10s |
| 32 | Primer EcoRI-PlasTer.r | FIG. 10t |
| 33 | A/New Caledonia/20/99 (H1N1) GenBank Accession No. AY289929 | FIG. 16 |

TABLE 5-continued

Sequence description for sequence identifiers.

| SEQ ID No | Sequence Description | In Disclosure |
|---|---|---|
| 34 | *M. Sativa* protein disulfide isomerase GenBank Accession No. Z11499 | FIG. 17 |
| 35 | A/.PuertoRico/8/34 (H1N1) GenBank Accession No. NC_002016.1 | FIG. 18 |
| 36 | Clone 774: DNA from DraIII to SacI comprising plastocyanin regulatory region operatively linked to sequence encoding HA of A/Brisbane/59/2007 (H1N1) | FIG. 28 |
| 37 | Clone 775: DNA from DraIII to Sacl comprising plastocyanin regulatory region operatively linked to sequence encoding HA of A/Solomon Islands 3/2006 (H1N1) | FIG. 29 |
| 38 | Clone 776: DNA from DraIII to Sacl comprising plastocyanin regulatory region operatively linked to sequence encoding HA of A/Brisbane 10/2007 (H3N2) | FIG. 30 |
| 39 | Clone 777: DNA from DraIII to Sacl comprising plastocyanin regulatory region operatively linked to sequence encoding HA of A/Wisconsin/67/2005 (H3N2) | FIG. 31 |
| 40 | Clone 778: DNA from DraIII to Sacl comprising plastocyanin regulatory region operatively linked to sequence encoding HA of B/Malaysia/2506/2004 | FIG. 32 |
| 41 | Clone 779: DNA from DraIII to Sacl comprising plastocyanin regulatory region operatively linked to sequence encoding HA of B/Florida/4/2006 | FIG. 33 |
| 42 | Clone 780: DNA from DraIII to Sacl comprising plastocyanin regulatory region operatively linked to sequence encoding HA of A/Singapore/1/57 (H2N2) | FIG. 34 |
| 43 | Clone 781: DNA from DraIII to Sacl comprising plastocyanin regulatory region operatively linked to sequence encoding HA of A/Anhui/1/2005 (H5N1) | FIG. 35 |
| 44 | Clone 782: DNA from DraIII to Sacl comprising plastocyanin regulatory region operatively linked to sequence encoding HA of A/Vietnam/1194/2004 (H5N1) | FIG. 36 |
| 45 | Clone 783: DNA from DraIII to Sacl comprising plastocyanin regulatory region operatively linked to sequence encoding HA of A/Teal/HongKong/W312/97 (H6N1) | FIG. 37 |
| 46 | Clone 784: DNA from DraIII to Sacl comprising plastocyanin regulatory region operatively linked to sequence encoding HA of A/Equine/Prague/56 (H7N7) | FIG. 38 |
| 47 | Clone 785: DNA from DraIII to Sacl comprising plastocyanin regulatory region operatively linked to sequence encoding HA of A/HongKong/1073/99 (H9N2) | FIG. 39 |
| 48 | Clone 774 HA amino acid sequence A/Brisbane/59/2007 (H1N1) | FIG. 40A |
| 49 | Clone 775 HA amino acid sequence A/Solomon Islands 3/2006 (H1N1) | FIG. 40B |
| 50 | Clone 776 HA amino acid sequence A/Brisbane 10/2007 (H3N2) | FIG. 41A |
| 51 | Clone 777 HA amino acid sequence A/Wisconsin/67/2005 (H3N2) | FIG. 41B |
| 52 | Clone 778 HA amino acid sequence B/Malaysia/2506/2004 | FIG. 42A |
| 53 | Clone 779 HA amino acid sequence B/Florida/4/2006 | FIG. 42B |
| 54 | Clone 780 HA amino acid sequence A/Singapore/1/57 (H2N2) | FIG. 43A |
| 55 | Clone 781 HA amino acid sequence A/Anhui/1/2005 (H5N1) | FIG. 43B |
| 56 | Clone 782 HA amino acid sequence A/Vietnam/1194/2004 (H5N1) | FIG. 44A |
| 57 | Clone 783 HA amino acid sequence A/Teal/HongKong/W312/97 (H6N1) | FIG. 44B |
| 58 | Clone 784 HA amino acid sequence A/Equine/Prague/56 (H7N7) | FIG. 45A |
| 59 | Clone 785 HA amino acid sequence A/HongKong/1073/99 (H9N2) | FIG. 45B |
| 60 | HA expression cassette comprising alfalfa plastocyanin promoter and 5' UTR, hemagglutinin coding sequence of H5 from A/Indonesia/5/2005 (Construct # 660), alfalfa plastocyanin 3' UTR and terminator sequences | FIG. 51 |
| 61 | HA expression cassette comprising alfalfa plastocyanin promoter and 5' UTR, hemagglutinin coding sequence of H1 from A/New Caledonia/20/1999 (Construct # 540), alfalfa plastocyanin 3' UTR and terminator sequences | FIG. 52 |

TABLE 5-continued

Sequence description for sequence identifiers.

| SEQ ID No | Sequence Description | In Disclosure |
|---|---|---|
| 62 | HA expression cassette comprising alfalfa plastocyanin promoter and 5' UTR, hemagglutinin coding sequence of H1 from A/Brisbane/59/2007 (construct #774), alfalfa plastocyanin 3' UTR and terminator sequences | FIG. 53 |
| 63 | HA expression cassette comprising alfalfa plastocyanin promoter and 5' UTR, hemagglutinin coding sequence of H1 from A/Solomon Islands/3/2006 (H1N1) (construct #775), alfalfa plastocyanin 3' UTR and terminator sequences | FIG. 54 |
| 64 | HA expression cassette comprising alfalfa plastocyanin promoter and 5' UTR, hemagglutinin coding sequence of H2 from A/Singapore/1/57 (H2N2) (construct # 780), alfalfa plastocyanin 3' UTR and terminator sequences | FIG. 55 |
| 65 | HA expression cassette comprising alfalfa plastocyanin promoter and 5' UTR, hemagglutinin coding sequence of H5 from A/Anhui/1/2005 (H5N1) (Construct# 781), alfalfa plastocyanin 3' UTR and terminator sequences | FIG. 56 |
| 66 | HA expression cassette comprising alfalfa plastocyanin promoter and 5' UTR, hemagglutinin coding sequence of H5 from A/Vietnam/1194/2004 (H5N1) (Construct # 782), alfalfa plastocyanin 3' UTR and terminator sequences | FIG. 57 |
| 67 | HA expression cassette comprising alfalfa plastocyanin promoter and 5' UTR, hemagglutinin coding sequence of H6 from A/Teal/Hong Kong/W312/97 (H6N1) (Construct # 783), alfalfa plastocyanin 3' UTR and terminator sequences | FIG. 58 |
| 68 | HA expression cassette comprising alfalfa plastocyanin promoter and 5' UTR, hemagglutinin coding sequence of H9 from A/Hong Kong/1073/99 (H9N2) (Construct # 785), alfalfa plastocyanin 3' UTR and terminator sequences | FIG. 59 |
| 69 | HA expression cassette comprising alfalfa plastocyanin promoter and 5' UTR, hemagglutinin coding sequence of H3 from A/Brisbane/10/2007 (H3N2), alfalfa plastocyanin 3' UTR and terminator sequences | FIG. 60 |
| 70 | HA expression cassette comprising alfalfa plastocyanin promoter and 5' UTR, hemagglutinin coding sequence of H3 from A/Wisconsin/67/2005 (H3N2), alfalfa plastocyanin 3' UTR and terminator sequences | FIG. 61 |
| 71 | HA expression cassette comprising alfalfa plastocyanin promoter and 5' UTR, hemagglutinin coding sequence of H7 from A/Equine/Prague/56 (H7N7), alfalfa plastocyanin 3' UTR and terminator sequences | FIG. 62 |
| 72 | HA expression cassette comprising alfalfa plastocyanin promoter and 5' UTR, hemagglutinin coding sequence of HA from B/Malaysia/2506/2004, alfalfa plastocyanin 3' UTR and terminator sequences | FIG. 63 |
| 73 | HA expression cassette comprising alfalfa plastocyanin promoter and 5' UTR, hemagglutinin coding sequence of HA from B/Florida/4/2006, alfalfa plastocyanin 3' UTR and terminator sequences | FIG. 64 |
| 74 | Consensus amino acid sequence of SEQ ID NO: 49, 48, 33 and 9 | FIG. 65 |
| 75 | Amino acid sequence of H1 New Caledonia (AAP34324.1) encoded by SEQ ID NO: 33 | FIG. 66 |
| 76 | Amino acid sequence of H1 Puerto Rico (NC_0409878.1) encoded by SEQ ID NO: 35 | FIG. 67 |
| 77 | pBinPlus.2613c | AGGAAGGGAAGAAAGCGAAAGGAG |
| 78 | Mut-ATG115.r | GTGCCGAAGCACGATCTGACAACGTTGAAGATCGCT**CAC**GCAAGAAAGACAAGAGA |
| 79 | Mut-ATG161.c | GTTGTCAGATCGTGCTTCGGCACCAGTACA**ACG**TTTTCTTTCACTGAAGCGA |
| 80 | LC-05-1.110r | TCTCCTGGAGTCACAGACAGGGTGG |

TABLE 5-continued

Sequence description for sequence identifiers.

| SEQ ID No | Sequence Description | In Disclosure |
|---|---|---|
| 81 | Expression cassette number 828, from PacI upstream promoter) to AscI (immediately down-stream NOS terminator). | FIG. 68 |
| 82 | SpPDI-HA(Ind).c | GTTCCTTCTCAGATCTTCGCTGATCAGATTTGCATTGGTTACCATGCA |
| 83 | Construct number 663, from HindIII (in the multiple clon-ing site, upstream Plastocyanine promoter) to EcoRI (immediately downstream Plastocynine terminator). | FIG. 69 |
| 84 | SpPDI-H1B.c | TTCTCAGATCTTCGCTGACACAATATGTATAGGCTACCATGCTAACAAC |
| 85 | SacI-H1B.r | CTTA**GAGCTC**TTAGATGCATATTCTACACTGTAAAGACCCATTGGAA |
| 86 | Construct number 787, from HindIII (in the multiple clon-ing site, upstream Plastocyanine promoter) to EcoRI (immediately downstream Plastocynine terminator) | FIG. 70 |
| 87 | H3B-SpPDI.r | TGTCATTTCCGGGAAGTTTTTG**AGCGAAGATCTGAGAAGGAACCA** |
| 88 | SpPDI-H3B.c | **TCTCAGATCTTCGCT**CAAAAACTTCCCGGAAATGACAACAGCACG |
| 89 | H3(A-Bri).982r | TTGCTTAACATATCTGGGACAGG |
| 90 | Construct number 790, from HindIII (in the multiple clon-ing site, upstream Plastocyanine promoter) to EcoRI (immediately downstream Plastocynine terminator). | FIG. 7 |
| 91 | HBF-SpPDI.r | GTTATTCCAGTGCAGATTCGATCAGCGAAGATCTGAGAAGGAACCAACAC |
| 92 | SpPDI-HBF.c | CAGATCTTCGCTGATCGAATCTGCACTGGAATAACATCTTCAAACTCACC |
| 93 | Plaster80r | CAAATAGTATTTCATAACAACAACGATT |
| 94 | Construct number 798, from HindIII (in the multiple clon-ing site, upstream Plastocyanine promoter) to EcoRI (immediately downstream Plastocynine terminator). | FIG. 72 |
| 95 | ApaI-SpPDI.c | TTGTC**GGGCCC**ATGGCGAAAAACGTTGCGATTTTCGGCTTATTGT |
| 96 | StuI-H1(A-NC).r | AAAAT**AGGCCT**TTAGATGCATATTCTACACTGCAAAGACCCA |
| 97 | Construct number 580, from PacI (upstream 35S promoter) to AscI (immediately downstream NOS terminator). | FIG. 73 |
| 98 | ApaI-H5 (A-Indo).1c | TGTC**GGGCCC**ATGGAGAAAATAGTGCTTCTTCTTGCAAT |
| 99 | H5 (A-Indo)-StuI.1707r | AAAT**AGGCCT**TTAAATGCAAATTCTGCATTGTAACGA |
| 100 | Construct number 685, from PacI (upstream 35S promoter) to AscI (immediately downstream NOS terminator). | FIG. 74 |
| 101 | Construct number 686, from PacI (upstream 35S promoter) to AscI (immediately downstream NOS terminator) | FIG. 75 |
| 102 | ApaI-H1B.c | TGTC**GGGCCC**ATGAAAGTAAAACTACTGGTCCTGTTATGCACATT |
| 103 | StuI-H2B.r | AAAT**AGGCCT**TTAGATGCATATTCTACACTGTAAAGACCCATTGGA |
| 104 | Construct 732, from PacI (upstream 35S promoter) to AscI (immediately downstream NOS terminator). | FIG. 76 |
| 105 | Construct number 733, from PacI (upstream 35S promoter) to AscI (immediately downstream NOS terminator). | FIG. 77 |
| 106 | ApaI-H3B.c | TTGTC**GGGCCC**ATGAAGACTATCATTGCTTTGAGCTACATTCTATGTC |
| 107 | StuI-H3B.r | AAAAT**AGGCCT**TCAAATGCAAATGTTGCACCTAATGTTGCCTTT |

TABLE 5-continued

Sequence description for sequence identifiers.

| SEQ ID No | Sequence Description | In Disclosure |
| --- | --- | --- |
| 108 | Construct number 735, from PacI (upstream 35S promoter) to AscI (immediately downstream NOS terminator). | FIG. 78 |
| 109 | Construct number 736, from PacI (upstream 35S promoter) to AscI (immediately downstream NOS terminator). | FIG. 79 |
| 110 | ApI-HBF.c | TTGTC**GGGCCC**AT GAAGGCAATAATTG TACTACTCATGGTA GTAAC |
| 111 | StuI-HBF.r | AAAAT**AGGCCT**TT ATAGACAGATGGA GCATGAAACGTTGT CTCTGG |
| 112 | Construct number 738, from PacI (upstream 35S promoter) to AscI (immediately downstream NOS terminator). | FIG. 80 |
| 113 | Construct number 739, from PacI (upstream 35S promoter) to AscI (immediately downstream NOS terminator). | FIG. 81 |
| 114 | *M. sativa* Msj1 coding sequence | FIG. 82 |
| 115 | Hsp-40Luz.1c | ATGTTTGGGCGCGG ACCAAC |
| 116 | Hsp40Luz-SacI.1272r | AGCT***GAGCTC***CTAC TGTTGAGCGCATTG CAC |
| 117 | Hsp40Luz-Plasto.r | GTTGGTCCGCGCCC AAACATTTTCTCTC AAGATGAT |
| 118 | Hsp70Ara.1c | ATGTCGGGTAAAGG AGAAGGA |
| 119 | Hsp70Ara-SacI.1956r | AGCT***GAGCTC***TTAG TCGACCTCCTCGAT CTTAG |
| 120 | Hsp70Ara-Plasto.r | TCCTTCTCCTTTACC CGACATTTTCTCTC AAGATGAT |
| 121 | Construct number R850, from HindIII (in the multiple cloning site, upstream promoter) to EcoRI (immediately downstream NOS terminator). | FIG. 83 |
| 122 | Construct number R860, from HindIII (in the multiple cloning site, upstream promoter) to EcoRI (immediately downstream NOS terminator) | FIG. 84 |
| 123 | Construct number R870, from HindIII (in the multiple cloning site, upstream promoter) to EcoRI (immediately downstream NOS terminator). | FIG. 85 |
| 124 | supP19-plasto.r | CCTTGTATAGCTCG TTCCATTTTCTCTCA AGATG |
| 125 | supP19-1c | ATGGAACGAGCTAT ACAAGG |
| 126 | SupP19-SacI.r | AGTCGAGCTCTTAC TCGCTTTCTTTTTCG AAG |
| 127 | Nucleotide sequence of the CPMV-HT-based expression cassette for H1 A/California/04/09 (cassette number 560). | FIG. 92A |
| 128 | Amino acid sequence of H1 A/California/04/09 | FIG. 92B |
| 129 | 2x35S promomter | FIG. 93 |
| 130 | primer PacI-MCS-2X35S.c | AATTGTTAATTAAG TCGACAAGCTTGCA TGCCTGCAGGTCAA C |
| 131 | primer CPMV 5'UTR-2X35S.r | TCAAAACCTATTAA GATTTTAATACCTC TCCAAATGAAATGA ACTTCC |
| 132 | primer 2X35S-CPMV 5'UTR.c | TTGGAGAGGTATTA AAATCTTAATAGGT TTTGATAAAAGCGA ACGTGGG |
| 133 | primer ApaI-M prot.r | TCTCCATGGGCCCG ACAAATTTGGGCAG AATATACAGAAGCT TA |
| 134 | intermediary vector 972 | FIG. 94 |
| 135 | H1 A/California/4/2009 | FIG. 95 |
| 136 | portion of CPMV M (from DraIII to ApaI restriction site), signal peptide of alfalfa PDISP, HA0 of A/California/4/2009 hemagglutinin with mutated SacI and StuI restriction site | FIG. 96 |
| 137 | Fragment 1 | FIG. 97 |
| 138 | Fragment 2 | FIG. 97 |
| 139 | Fragment 3 | FIG. 97 |
| 140 | primer DraIII-MProt#2.c | ATGCTAATATCACG TAGTGCGGCGCCAT TAAATAACGTGTAC TTGTCC |
| 141 | primer H1 Cal.390r | GCTTAATTGCTCTC TTAGCTCCTCATAA TCGATGAAATCTCC |
| 142 | primer H1 Cal.310c | TGGAAACACCTAGT TCAGACAATGGAAC GTGTTACCCAGGAG |

TABLE 5-continued

Sequence description for sequence identifiers.

| SEQ ID No | Sequence Description | In Disclosure |
|---|---|---|
| 143 | primer H1 Cal.1159r | CTGCATATCCTGAC CCCTGCTCATTTTG ATGGTGATAACCGT |
| 144 | primer H1 Cal.1081c | TTGAAGGGGGGTG GACAGGGATGGTA GATGGATGGTACGG TT |
| 145 | primer StuI-H1 Cal.r | TATTAGGCCTTTAA ATACATATTCTACA CTGTAGAGACCCAT TAG |
| 146 | SpPDI-H1 A/California/4/2009 (in 2X35S/CPMV-HT expression cassette) construct 560 | FIG. 98 |

The invention will now be described in detail by way of reference only to the following non-limiting examples.

Methods and Materials

1. Assembly of Plastocyanin-Based Expression Cassettes for Native HA

All manipulations were done using the general molecular biology protocols of Sambrook and Russell (2001; which is incorporated herein by reference). The first cloning step consisted in assembling a receptor plasmid containing upstream and downstream regulatory elements of the alfalfa plastocyanin gene. The plastocyanin promoter and 5'UTR sequences were amplified from alfalfa genomic DNA using oligonucleotide primers XmaI-pPlas.c (SEQ ID NO: 29; FIG. 10Q) and SacI-ATG-pPlas.r (SEQ ID NO: 30; FIG. 10R). The resulting amplification product was digested with XmaI and SacI and ligated into pCAMBIA2300 (Cambia, Canberra, Australia), previously digested with the same enzymes, to create pCAMBIApromo Plasto. Similarly, the 3'UTR sequences and terminator of the plastocyanin gene was amplified from alfalfa genomic DNA using the following primers: SacI-PlasTer.c (SEQ ID NO: 31; FIG. 10S) and EcoRI-PlasTer.r (SEQ ID NO: 32; FIG. 10T), and the product was digested with SacI and EcoRI before being inserted into the same sites of pCAMBIApromoPlasto to create pCAMBIAPlasto.

Figure 2A:
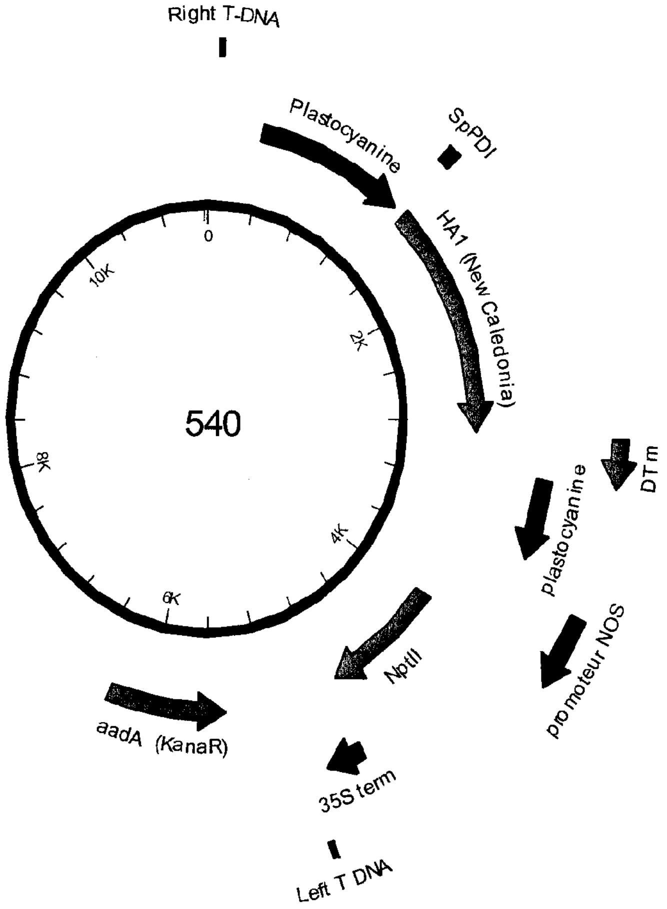
FIG. 2A shows a representation of plasmid 540 assembled for the expression of HA subtype H1 from strain A/New Caledonia/20/99 (H1N1).
Figure 2B:
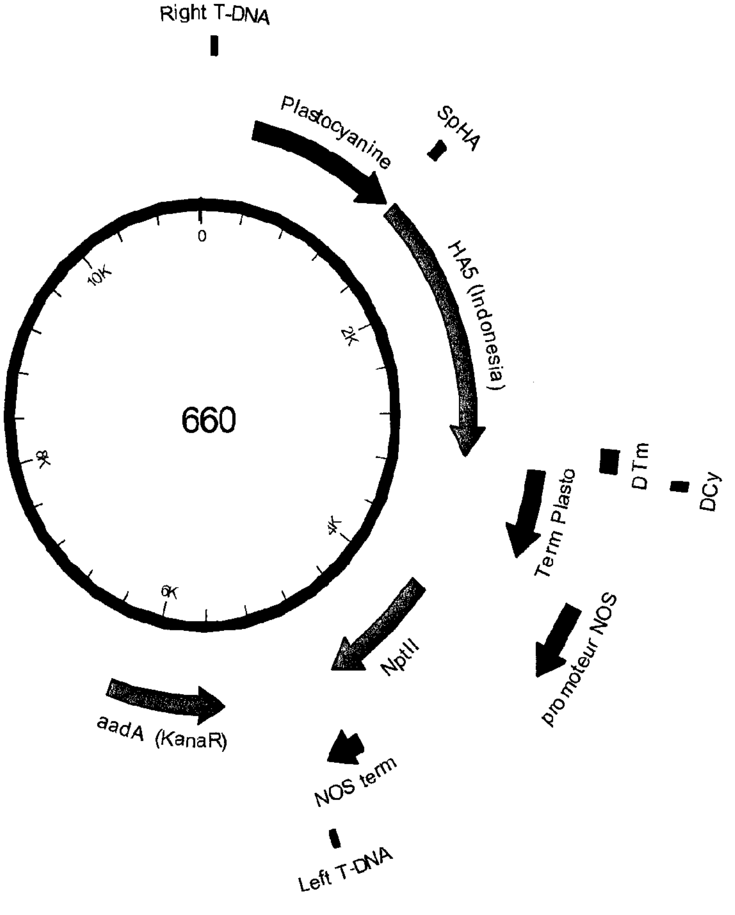
FIG. 2B shows a representation of plasmid 660 assembled for the expression of HA subtype H5 from strain A/Indonesia/5/2005 (H5N1).
Figure 3A:
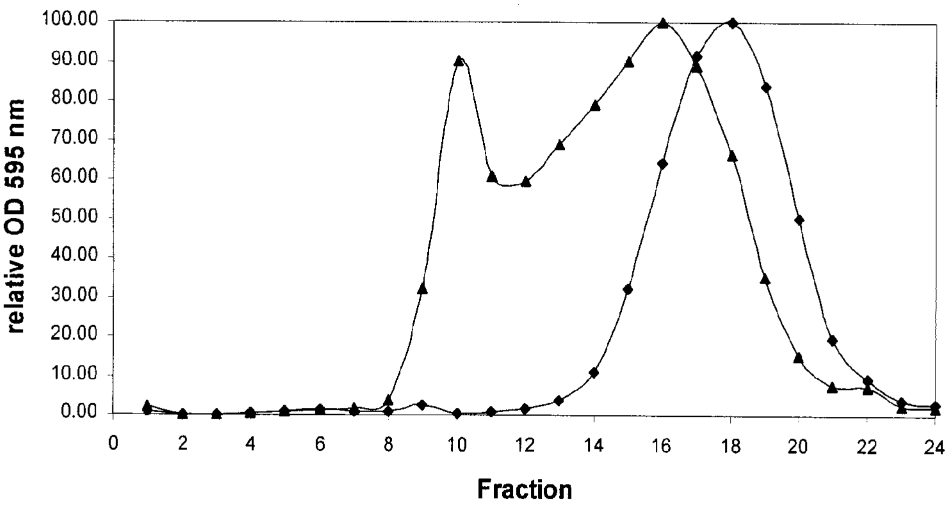
FIG. 3A show the elution profile of Blue Dextran 2000 (triangles) and proteins (diamonds).
Figure 3B:
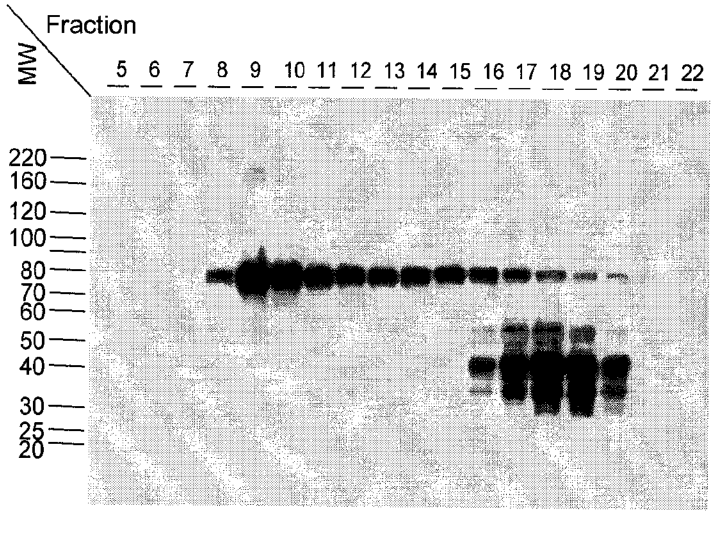
FIG. 3B shows immunodetection (western blot; anti H1) of H1 (A/New Caledonia/20/99 (H1N1)) elution fractions following size exclusion chromatography (S500HR beads).
Figure 3C:
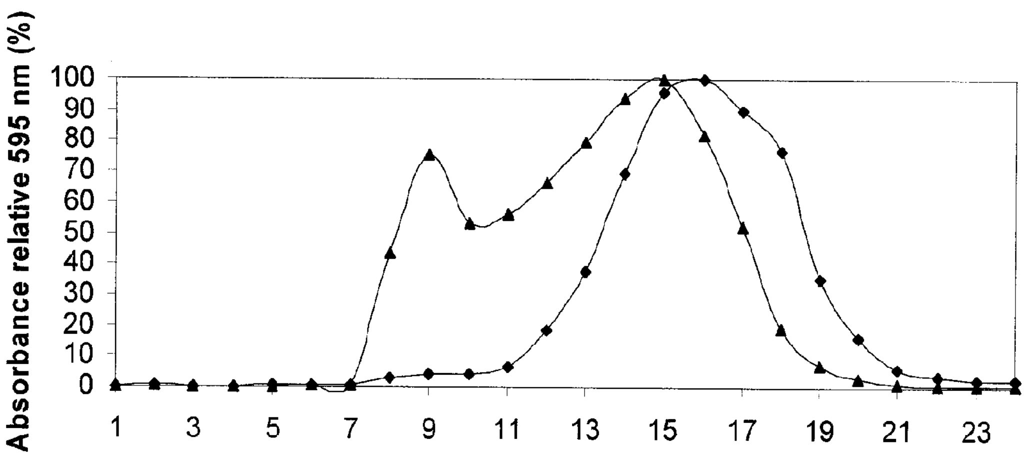
FIG. 3C show the elution profile of H5; Blue Dextran 2000 (triangles) and proteins (diamonds).
Figure 3D:
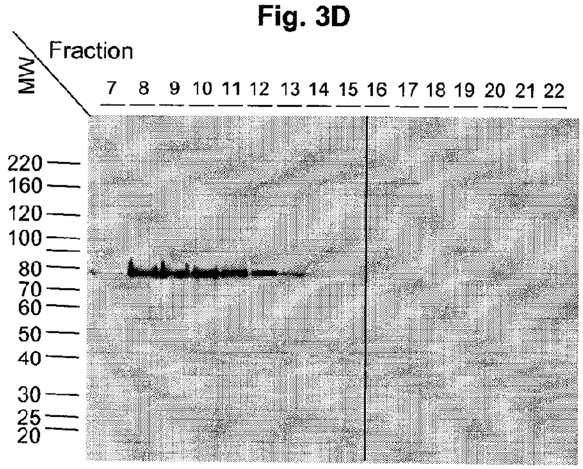
FIG. 3D shows immunodetection (western blot; anti H5) of H5 (A/Indonesia/5/2005 (H5N1)) elution fractions following size exclusion chromatography (S500HR beads).

A fragment encoding hemagglutinin from influenza strain A/Indonesia/5/05 (H5N1; Acc. No. LANL ISDN125873) was synthesized by Epoch Biolabs (Sugar Land, Tex., USA). The fragment produced, containing the complete H5 coding region including the native signal peptide flanked by a HindIII site immediately upstream of the initial ATG, and a SacI site immediately downstream of the stop (TAA) codon, is presented in SEQ ID NO: 3 (FIG. 6). The H5 coding region was cloned into a plastocyanin-based expression cassette by the PCR-based ligation method presented in Darveau et al. (1995). Briefly, a first PCR amplification was obtained using primers Plato-443c (SEQ ID NO: 4; FIG. 7A) and SpHA(Ind)-Plasto.r (SEQ ID NO:5; FIG. 7B) and pCAMBIA promoPlasto as template. In parallel, a second amplification was performed with primers Plasto-SpHA (Ind).c (SEQ ID NO: 6; FIG. 7C) and HA(Ind)-Sacs (SEQ ID NO:7; FIG. 7D) with H5 coding fragment as template. The amplification obtained from both reactions were mixed together and the mixture served as template for a third reaction (assembling reaction) using Plato-443c (SEQ ID NO: 4; FIG. 7A) and HA(Ind)-Sac.r (SEQ ID NO: 7; FIG. 7D) as primers. The resulting fragment was digested with BamHI (in the plastocyanin promoter) and SacI (at the 3' end of the fragment) and cloned into pCAMBIAPlasto previously digested with the same enzymes. The resulting plasmid, named 660, is presented in FIG. 2B (also see FIG. 11).

Hemagglutinin expression cassettes number 774 to 785 were assembled as follows. A synthetic fragment was synthesized comprising the complete hemagglutinin coding sequence (from ATG to stop) flanked in 3' by alfalfa plastocyanin gene sequences corresponding to the first 84 nucleotides upstream of the plastocyanin ATG and ending with a DraIII restriction site. The synthetic fragments also comprised a SacI site immediately after the stop codon.

Synthetic hemagglutinin fragments were synthesized by Top Gene Technologies (Montreal, QC, Canada), Epoch Biolabs (Sugar Land, Tex., USA). The fragment synthesized are presented in FIGS. 28 to 39 and correspond to SEQ ID NO:36 to SEQ ID NO:47. For the assembly of the complete expression cassettes, the synthetic fragments were digested with DraIII and SacI and cloned into pCAMBIAPlasto previously digested with the same enzymes. Table 6 presents the cassettes produced with the corresponding HA and other references in the text.

TABLE 6

Hemagglutinin expression cassettes assembled from DraIII-SacI synthetic fragments.

| | | Synthetic fragment | | Complete cassette | |
|---|---|---|---|---|---|
| Cassette number | Corresponding HA | FIG. | Synthetic fragment SEQ ID NO | FIG. | Final cassette SEQ ID NO |
| 774 | HA of A/Brisbane/59/2007 (H1N1) | 28 | 36 | 53 | 62 |
| 775 | HA of A/Solomon Islands 3/2006 (H1N1) | 29 | 37 | 54 | 63 |
| 776 | HA of A/Brisbane 10/2007 (H3N2) | 30 | 38 | 60 | 69 |
| 777 | HA of A/Wisconsin/67/2005 (H3N2) | 31 | 39 | 61 | 70 |
| 778 | HA of B/Malaysia/2506/2004 | 32 | 40 | 63 | 72 |
| 779 | HA of B/Florida/4/2006 | 33 | 41 | 64 | 73 |
| 780 | HA of A/Singapore/1/57 (H2N2) | 34 | 42 | 55 | 64 |
| 781 | HA of A/Anhui/1/2005 (H5N1) | 35 | 43 | 56 | 65 |
| 782 | HA of A/Vietnam/1194/2004 (H5N1) | 36 | 44 | 57 | 66 |
| 783 | HA of A/Teal/HongKong/W312/97 (H6N1) | 37 | 45 | 58 | 67 |
| 784 | HA of A/Equine/Prague/56 (H7N7) | 38 | 46 | 62 | 71 |
| 785 | HA of A/HongKong/1073/99 (H9N2) | 39 | 47 | 59 | 68 |

Assembly of Plastocyanin-Based PDISP/HA-Fusion Expression Cassettes

H1 A/New Caledonia/20/99 (Construct Number 540)

The open reading frame from the H1 gene of influenza strain A/New Caledonia/20/99 (H1N1) was synthesized in two fragments (Plant Biotechnology Institute, National Research Council, Saskatoon, Canada). A first fragment synthesized corresponds to the wild-type H1 coding sequence (GenBank acc. No. AY289929; SEQ ID NO: 33; FIG. 16) lacking the signal peptide coding sequence at the 5' end and the transmembrane domain coding sequence at the 3' end. A BglII restriction site was added at the 5' end of the coding sequence and a dual SacI/StuI site was added immediately downstream of the stop codon at the 3' terminal end of the fragment, to yield SEQ ID NO: 1 (FIG. 5A). A second fragment encoding the C-terminal end of the H1 protein (comprising a transmembrane domain and cytoplasmic tail) from the KpnI site to the stop codon, and flanked in 3' by SacI and StuI restriction sites was also synthesized (SEQ ID NO. 2; FIG. 5B).

The first H1 fragment was digested with BglII and SacI and cloned into the same sites of a binary vector (pCAMBIAPlasto) containing the plastocyanin promoter and 5'UTR fused to the signal peptide of alfalfa protein disulfide isomerase (PDI) gene (nucleotides 32-103; Accession No. Z11499; SEQ ID NO: 34; FIG. 17) resulting in a PDI-H1 chimeric gene downstream of the plastocyanin regulatory elements. The sequence of the plastocyanin-based cassette containing the PDI signal peptide is presented in FIG. 1 (SEQ ID NO:8). The resulting plasmid contained H1 coding region fused to the PDI signal peptide and flanked by plastocyanin regulatory elements. The addition of the C-terminal end coding region (encoding the transmembrane domain and the cytoplasmic tail) was obtained by inserting the synthesized fragment (SEQ ID NO: 2; FIG. 5B) previously digested with KpnI and SacI, into the H1 expression plasmid. The resulting plasmid, named 540, is presented in FIG. 11 (also see FIG. 2A).

H5 A/Indonesia/5/2005 (Construct Number 663)

The signal peptide of alfalfa protein disulfide isomerase (PDISP) (nucleotides 32-103; Accession No. Z11499; SEQ ID NO: 34; FIG. 17) was linked to the HA0 coding sequence of H5 from A/Indonesia/5/2005 as follows. The H5 coding sequence was amplified with primers SpPDI-HA(Ind).c (SEQ ID NO:82) and HA(Ind)-<u>SacI</u>.r (SEQ ID NO: 7; FIG. 7D) using construct number 660 (SEQ ID NO:60; FIG. 51) as template. The resulting fragment consisted in the H5 coding sequence flanked, in 5', by the last nucleotides encoding PDISP (including a BglII restriction site) and, in 3', by a SacI restriction site. The fragment was digested with BglII and SacI and cloned into construct number 540 (SEQ ID NO:61; FIG. 52) previously digested with the same restriction enzymes. The final cassette, named construct number 663 (SEQ ID NO:83), is presented in FIG. 69.

H1 A/Brisbane/59/2007 (Construct 787)

The signal peptide of alfalfa protein disulfide isomerase (PDISP) (nucleotides 32-103; Accession No. Z11499; SEQ ID NO: 34; FIG. 17) was linked to the HA0 coding sequence of H1 from A/Brisbane/59/2007 as follows. The H1 coding sequence was amplified with primers <u>SpPDI</u>-H1B.c (SEQ ID NO: 84) and <u>SacI</u>-H1B.r (SEQ ID NO:85) using construct 774 (SEQ ID NO:62; FIG. 53) as template. The resulting fragment consisted in the H1 coding sequence flanked, in 5', by the last nucleotides encoding PDISP (including a BglII restriction site) and, in 3', by a SacI restriction site. The fragment was digested with BglII and SacI and cloned into construct number 540 (SEQ ID NO:61; FIG. 52) previously digested with the same restriction enzymes. The final cassette, named construct number 787 (SEQ ID NO:86), is presented in FIG. 70.

H3 A/Brisbane/10/2007 (Construct Number 790)

The signal peptide of alfalfa protein disulfide isomerase (PDISP) (nucleotides 32-103; Accession No. Z11499; SEQ ID NO: 34; FIG. 17) was linked to the HA0 coding sequence of H3 from A/Brisbane/10/2007 as follows. PDISP was linked to the H3 coding sequence by the PCR-based ligation method presented in Darveau et al. (Methods in Neuroscience 26: 77-85 (1995)). In a first round of PCR, a segment of the plastocyanine promoter fused to PDISP was amplified using primers Plasto-443c (SEQ ID NO: 4; FIG. 7A) and H3B-<u>SpPDI</u>.r (SEQ ID NO:87) with construct 540 (SEQ ID NO:61; FIG. 52) as template. In parallel, another fragment containing a portion of the coding sequence of H3 A/Brisbane/10/2007 (from codon 17 to the SpeI restriction site) was amplified with primers <u>SpPDI</u>-H3B.c (SEQ ID NO:88) and H3(A-Bri).982r (SEQ ID NO:89) using construct 776 (SEQ ID NO:69; FIG. 60) as template. Amplification products were then mixed and used as template for a second round of amplification (assembling reaction) with primers Plasto-443c (SEQ ID NO: 4; FIG. 7A) and H3(A-Bri).982r (SEQ ID NO:89). The resulting fragment was digested with BamHI (in the plastocyanin promoter) and SpeI (in the H3 coding sequence) and cloned into construct number 776 (SEQ ID NO:69; FIG. 60), previously digested with the same restriction enzymes to give construct number 790 (SEQ ID NO:90). The construct is presented in FIG. 71.

HA B/Florida/4/2006 (Construct Number 798)

The signal peptide of alfalfa protein disulfide isomerase (PDISP) (nucleotides 32-103; Accession No. Z11499; SEQ ID NO: 34; FIG. 17) was linked to the HA0 coding sequence of HA from HA B/Florida/4/2006 by the PCR-based ligation method presented in Darveau et al. (Methods in Neuroscience 26: 77-85 (1995)). In a first round of amplification, a portion of the plastocyanin promoter fused to the PDISP was amplified using primers Plasto-443c (SEQ ID NO: 4; FIG. 7A) and HBF-<u>SpPDI</u>.r (SEQ ID NO:91) with construct number 540 (SEQ ID NO:61; FIG. 52) as template. In parallel, another fragment containing a portion of the coding sequence of HB B/Flo fused to the plastocyanin terminator was amplified with primers <u>SpPDI</u>-HBF.c (SEQ ID NO:92) and Plaster80r (SEQ ID NO:93) using construct number 779 (SEQ ID NO:73; FIG. 64) as template. PCR products were then mixed and used as template for a second round of amplification (assembling reaction) with primers Plasto-443c (SEQ ID NO: 4; FIG. 7A) and Plaster80r (SEQ ID NO:93). The resulting fragment was digested with BamHI (in the plastocyanin promoter) and AflII (in the HA B/Florida/4/2006 coding sequence) and cloned into construct number 779 (SEQ ID NO:73; FIG. 64), previously digested with the same restriction enzymes to give construct number 798 (SEQ ID NO:94). The resulting expression cassette is presented in FIG. 72.

Assembly of CPMV-HT-Based Expression Cassettes

CPMV-HT expression cassettes use the 35S promoter to control the expression of an mRNA comprising a coding sequence of interest flanked, in 5' by nucleotides 1-512 from the Cowpea mosaic virus (CPMV) RNA2 with mutated ATG at positions 115 and 161 and in 3', by nucleotides 3330-3481 from the CPMV RNA2 (corresponding to the 3' UTR) followed by the NOS terminator. Plasmid pBD-05-1LC, (Sainsbury et al. 2008; Plant Biotechnology Journal 6: 82-92 and PCT Publication WO 2007/135480), was used for the assembly of CPMV-HT-based hemagglutinin expression cassettes. The mutation of ATGs at position 115 and 161 of the CPMV RNA2 was done using a PCR-based ligation method presented in Darveau et al. (Methods in Neuroscience 26: 77-85 (1995)). Two separate PCRs were performed using pBD-05-1LC as template. The primers for the first amplification are pBinPlus.2613c (SEQ ID NO: 77) and Mut-ATG115.r (SEQ ID NO: 78). The primers for the second amplification were Mut-ATG161.c (SEQ ID NO: 79) and LC-05-1.110r (SEQ ID NO: 80). The two obtained fragments are then mixed and used as template for a third amplification using pBinPlus.2613c (SEQ ID NO: 77) and LC-05-1.110r (SEQ ID NO: 80) as primers. Resulting fragment is digested with PacI and ApaI and cloned into pBD-05-1LC digested with the same enzyme. The sequence of the expression cassette generated, named 828, is presented in FIG. 68 (SEQ ID NO: 81).

Assembly of SpPD1-H1 A/New Caledonia/20/99 in CPMV-HT expression cassette (construct number 580).

A sequence encoding alfalfa PDI signal peptide fused to HA0 from H1 A/New Caledonia/20/99 was cloned into CPMV-HT as follows. Restriction sites ApaI (immediately upstream of intial ATG) and StuI (immediately downstream stop codon) were added to the hemagglutinin coding sequence by performing a PCR amplification with primers ApaI-SpPDI.c (SEQ ID NO: 95) and StuI-H1(A-NC).r (SEQ ID NO: 96) using construct number 540 (SEQ ID NO:61; FIG. 52) as template. Resulting fragment was digested with ApaI and StuI restriction enzymes and cloned into construct number 828 (SEQ ID NO: 81) digested with the same enzymes. Resulting cassette was named construct number 580 (SEQ ID NO: 97).

Assembly of SpPDI-H1 A/California/4/2009 in 2X35S/CPMV-HT Expression Cassette (Construct Number 560)

A fragment encoding alfalfa PDI signal peptide fused to HA0 from H1 A/California/4/2009 was cloned into 2X35S-CPMV-HT as follows.

We first created an intermediary vector containing the 2X35S promoter in the CPMV-HT expression cassette in replacement of the 35S promoter previously used. The change of promoter was performed using the PCR-based ligation method presented in Darveau et al. (Methods in Neuroscience 26: 77-85 (1995)). A first fragment containing 2X35S promoter SEQ ID NO: 129 (FIG. 93) was amplified by PCR with primers:

```
PacI-MCS-2X35S.c (SEQ ID NO 130):
AATTGTTAATTAAGTCGACAAGCTTGCATGCCTGCAGGTCAAC
and

CPMV 5'UTR-2X35S.r: (SEQ ID NO 131):
TCAAAACCTATTAAGATTTTAATACCTCTCCAAATGAAATGAACTTCC
```

using a plasmid containing 2X35S promoter as template. In parallel, a second PCR was performed with primers:

```
2X35S-CPMV 5'UTR.c (SEQ ID NO 132):
TTGGAGAGGTATTAAAATCTTAATAGGTTTTGATAAAAGCGAACGTGGG
and

ApaI-M prot.r (SEQ ID NO: 133):
TCTCCATGGGCCCGACAAATTTGGGCAGAATATACAGAAGCTTA
```

using construct 685 (SEQ ID NO 100; FIG. 74) as template. The two fragments obtained were then mixed and used as template for a second round of PCR (assembling reaction) using primers PacI-MCS-2X35S.c (SEQ ID NO:130) and ApaI-M prot.r (SEQ ID NO:133). The resulting fragment was then digested with PacI and ApaI and cloned into construct 685 (SEQ ID NO 100; FIG. 74) digested with the same restriction enzymes. The sequence of the intermediary vector, named 972 (SEQ ID NO:134), is presented in FIG. 94.

Native H1 A/California/4/2009 sequence was obtained from GISAID database (accession number EPI176470) and is presented in FIG. 95 (SEQ ID NO:135). A nucleotide sequence comprising a portion of the CPMV M protein (in the CPMV-HT expression cassette) from DraIII to ApaI restriction site along with the signal peptide of alfalfa protein disulfide isomerase (PDISP) (nucleotides 32-103; Accession No. Z11499; SEQ ID NO: 34; FIG. 17) and HA0 of A/California/4/2009 hemagglutinin with mutated SacI and StuI restriction site is presented in FIG. 96 (SEQ ID NO:136). The sequence was synthesized by DNA2.0 (Menlo Park, Calif., USA) in three different fragments. Fragment 1 (SEQ ID NO:137; FIG. 97), 2 (SEQ ID NO:138; FIG. 97) and 3 (SEQ ID NO:139; FIG. 97) were assembled using the PCR-based ligation method presented in Darveau et al. (Methods in Neuroscience 26: 77-85 (1995)). In a first round of amplification, three different PCR were done. The first fragment was amplified using primer:

```
DraIII-MProt#2.c
                                        (SEQ ID NO: 140)
ATGCTAATATCACGTAGTGCGGCGCCATTAAATAACGTGTACTTGTCC
and

H1 Cal.390r
                                        (SEQ ID NO: 141)
GCTTAATTGCTCTCTTAGCTCCTCATAATCGATGAAATCTCC
```

using pJ201 vector (DNA2.0 proprietary vector) containing Fragment 1 (SEQ ID NO: 139) as template. The second fragment was amplified using primers:

```
H1 Cal.310c
                                        (SEQ ID NO: 142)
TGGAAACACCTAGTTCAGACAATGGAACGTGTTACCCAGGAG
and

H1 Cal.1159r
                                        (SEQ ID NO: 143)
CTGCATATCCTGACCCCTGCTCATTTTGATGGTGATAACCGT
```

using pJ201 vector (DNA2.0 proprietary vector) containing Fragment 2 (SEQ ID NO:138) as template. Finally, the last fragment was amplified using primers:

```
H1 Cal.1081c
                                        (SEQ ID NO: 144)
TTGAAGGGGGGTGGACAGGGATGGTAGATGGATGGTACGGTT
and

StuI-H1 Cal.r
                                        (SEQ ID NO: 145)
TATTAGGCCTTTAAATACATATTCTACACTGTAGAGACCCATTAG
```

using pJ201 vector (DNA2.0 proprietary vector) containing Fragment 3 (SEQ ID NO139) as template. In a second round of PCR (assembly reaction), the three amplification fragments were then mixed and used as template with primers DraIII-MProt#2.c (SEQ ID NO:140) and StuI-H1Cal.r (SEQ ID NO:145). The resulting fragment was digested with DraIII and StuI and inserted into construct 972 (SEQ ID NO:134) digested with the same restriction enzymes. The nucleotide sequence of the resulting construct was named 560 (SEQ ID NO:146; FIG. 98).

Assembly of H5 A/Indonesia/5/2005 in CPMV-HT Expression Cassette (Construct Number 685).

The coding sequence of H5 from A/Indonesia/5/2005 was cloned into CPMV-HT as follows. Restriction sites ApaI (immediately upstream ATG) and StuI (immediately downstream stop codon) were added to the hemagglutinin coding sequence by performing a PCR amplification with primers ApaI-H5 (A-Indo).1c (SEQ ID NO: 98) and H5 (A-Indo)-StuI.1707r (SEQ ID NO: 99) using construct number 660 (SEQ ID NO:60; FIG. 51) as template. Resulting fragment was digested with ApaI and StuI restriction enzymes and cloned into construct number 828 (SEQ ID NO: 81) digested with the same enzymes. Resulting cassette was named construct number 685 (SEQ ID NO:100).

Assembly of SpPDI-H5 A/Indonesia/5/2005 in CPMV-HT Expression Cassette (Construct Number 686).

A sequence encoding alfalfa PDI signal peptide fused to HA0 from H5 A/Indonesia/5/2005 was cloned into CPMV-HT as follows. Restriction sites ApaI (immediately upstream ATG) and StuI (immediately downstream stop codon) were added to the hemagglutinin coding sequence by performing a PCR amplification with primers ApaI-SpPDI.c (SEQ ID NO: 95) and H5 (A-Indo)-StuI.1707r (SEQ ID NO: 99) using construct number 663 (SEQ ID NO: 83) as template. Resulting fragment was digested with ApaI and StuI restriction enzymes and cloned into construct number 828 (SEQ ID NO: 81) digested with the same enzymes. Resulting cassette was named construct number 686 (SEQ ID NO: 101).

Assembly of H1 A/Brisbane/59/2007 in CPMV-HT Expression Cassette (Construct Number 732).

The coding sequence of HA from H1 A/Brisbane/59/2007 was cloned into CPMV-HT as follows. Restriction sites ApaI (immediately upstream ATG) and StuI (immediately downstream stop codon) were added to the hemagglutinin coding sequence by performing a PCR amplification with primers ApaI-H1B.c (SEQ ID NO: 102) and StuI-H1B.r (SEQ ID NO: 103) using construct number 774 (SEQ ID NO:62; FIG. 53) as template. Resulting fragment was digested with ApaI and StuI restriction enzymes and cloned into construct number 828 (SEQ ID NO: 81) digested with the same enzymes. Resulting cassette was named construct number 732 (SEQ ID NO: 104).

Assembly of SpPDI-H1 A/Brisbane/59/2007 in CPMV-HT Expression Cassette (Construct Number 733).

A sequence encoding alfalfa PDI signal peptide fused to HA0 from H1 A/Brisbane/59/2007 was cloned into CPMV-HT as follows. Restriction sites ApaI (immediately upstream ATG) and StuI (immediately downstream stop codon) were added to the hemagglutinin coding sequence by performing a PCR amplification with primers ApaI-SpPDI.c (SEQ ID NO: 95) and StuI-H1B.r (SEQ ID NO: 103) using construct number 787 (SEQ ID NO: 86) as template. Resulting fragment was digested with ApaI and StuI restriction enzymes and cloned into construct number 828 (SEQ ID NO: 81) digested with the same enzymes. Resulting cassette was named construct number 733 (SEQ ID NO: 105).

Assembly of H3 A/Brisbane/10/2007 in CPMV-HT Expression Cassette (Construct Number 735).

The coding sequence of HA from H3 A/Brisbane/10/2007 was cloned into CPMV-HT as follows. Restriction sites ApaI (immediately upstream ATG) and StuI (immediately downstream stop codon) were added to the hemagglutinin coding sequence by performing a PCR amplification with primers ApaI-H3B.c (SEQ ID NO:106) and StuI-H3B.r (SEQ ID NO: 107) using construct number 776 (SEQ ID NO:69) as template. Resulting fragment was digested with ApaI and StuI restriction enzymes and cloned into construct number 828 (SEQ ID NO: 81) digested with the same enzymes. Resulting cassette was named construct number 735 (SEQ ID NO: 108).

Assembly of SpPDI-H3 A/Brisbane/10/2007 in CPMV-HT Expression Cassette (Construct Number 736).

A sequence encoding alfalfa PDI signal peptide fused to HA0 from H3 A/Brisbane/10/2007 was cloned into CPMV-HT as follows. Restriction sites ApaI (immediately upstream ATG) and StuI (immediately downstream stop codon) were added to the hemagglutinin coding sequence by performing a PCR amplification with primers ApaI-SpPDI.c (SEQ ID NO:95) and StuI-H3B.r (SEQ ID NO: 107) using construct number 790 (SEQ ID NO:90) as template. Resulting fragment was digested with ApaI and StuI restriction enzymes and cloned into construct number 828 (SEQ ID NO: 81) digested with the same enzymes. Resulting cassette was named construct number 736 (SEQ ID NO:109).

Assembly of HA B/Florida/4/2006 in CPMV-HT Expression Cassette (Construct Number 738).

The coding sequence of HA from B/Florida/4/2006 was cloned into CPMV-HT as follows. Restriction sites ApaI (immediately upstream ATG) and StuI (immediately downstream stop codon) were added to the hemagglutinin coding sequence by performing a PCR amplification with primers ApaI-HBF.c (SEQ ID NO: 110) and StuI-HBF.r (SEQ ID NO: 111) using construct number 779 (SEQ ID NO:73; FIG. 64) as template. Resulting fragment was digested with ApaI and StuI restriction enzymes and cloned into construct number 828 (SEQ ID NO: 81) digested with the same enzymes. Resulting cassette was named construct number 738 (SEQ ID NO: 112).

Assembly of SpPDI-HA B/Florida/4/2006 in CPMV-HT Expression Cassette (Construct Number 739).

A sequence encoding alfalfa PDI signal peptide fused to HA0 from B/Florida/4/2006 was cloned into CPMV-HT as follows. Restriction sites ApaI (immediately upstream ATG) and StuI (immediately downstream stop codon) were added to the hemagglutinin coding sequence by performing a PCR amplification with primers ApaI-SpPDI.c (SEQ ID NO: 95) and StuI-HBF.r (SEQ ID NO: 111) using construct number 798 (SEQ ID NO: 94) as template. Resulting fragment was digested with ApaI and StuI restriction enzymes and cloned into construct number 828 (SEQ ID NO: 81) digested with the same enzymes. Resulting cassette was named construct number 739 (SEQ ID NO: 113).

Assembly of Chaperone Expression Cassettes

Two heat shock protein (Hsp) expression cassettes were assembled. In a first cassette, expression of the *Arabidopsis thaliana* (ecotype Columbia) cytosolic HSP70 (Athsp70-1 in Lin et al. (2001) Cell Stress and Chaperones 6: 201-208) is controlled by a chimeric promoter combining elments of the alfalfa Nitrite reductase (Nir) and alfalfa Plastocyanin promoters (Nir/Plasto). A second cassette comprising the coding region of the alfalfa cytosolic HSP40 (MsJ1; Frugis et al. (1999) Plant Molecular Biology 40: 397-408) under the control of the chimeric Nir/Plasto promoter was also assembled.

An acceptor plasmid containing the alfalfa Nitrite reductase promoter (Nir), the GUS reporter gene and NOS terminator in plant binary vector was first assembled. Plasmid pNir3K51 (previously described in U.S. Pat. No. 6,420,548) was digested with HindIII and EcoRI. The resulting fragment was cloned into pCAMBIA2300 (Cambia, Canberra, Australia) digested by the same restriction enzyme to give pCAMBIA-Nir3K51.

Coding sequences for Hsp70 and Hsp40 were cloned separately in the acceptor plasmid pCAMBIANir3K51 by the PCR-based ligation method presented in Darveau et al. (Methods in Neuroscience 26:77-85 (1995)).

For Hsp40, Msj1 coding sequence (SEQ ID NO: 114) was amplified by RT-PCR from alfalfa (ecotype Rangelander) leaf total RNA using primers Hsp40Luz.1c (SEQ ID NO: 115) and Hsp40Luz-SacI.1272r (SEQ ID NO: 116). A second amplification was performed with primers Plasto-443c (SEQ ID NO: 4; FIG. 7A) and Hsp40Luz-Plasto.r (SEQ ID NO: 117) with construct 660 (SEQ ID NO: 60; FIG. 51) as template. PCR products were then mixed and used as template for a third amplification (assembling reaction) with primers Plasto-443c (SEQ ID NO: 4; FIG. 7A) and Hsp40Luz-SacI.1272r (SEQ ID NO: 116). The resulting fragment was digested with HpaI (in the plastocyanin promoter) and cloned into pCAMBIANir3K51, previously digested with HpaI (in the Nir promoter) and SacI, and filed with T4 DNA polymerase to generate blunt ends. Clones obtained were screened for correct orientation and sequenced for sequence integrity. The resulting plasmid, named R850, is presented in FIG. 83 (SEQ ID NO: 121). The coding region of the Athsp70-1 was amplified by RT-PCR from *Arabidopsis* leaf RNA using primers Hsp70Ara.1c (SEQ ID NO: 118) and Hsp70Ara-SacI.1956r (SEQ ID NO: 119). A second amplification was performed with primers Plato-443c (SEQ ID NO: 4; FIG. 7A) and Hsp70Ara-Plasto.r (SEQ ID NO: 120) with construct 660 (SEQ ID NO: 60; FIG. 51) as template. PCR products were then mixed and used as template for a third amplification (assembling reaction) with primers Plasto-443c (SEQ ID NO: 4; FIG. 7A) and Hsp70ARA-SacI.1956r (SEQ ID NO: 119). The resulting fragment was digested with HpaI (in the plastocyanin promoter) and cloned into pCAMBIANir3K51 digested with HpaI (in the Nir promoter) and SacI and filed with T4 DNA polymerase to generate blunt ends. Clones obtained were screened for correct orientation and sequenced for sequence integrity. The resulting plasmid, named R860, is presented in FIG. 84 (SEQ ID NO: 122).

A dual Hsp expression plasmid was assembled as follows. R860 was digested with BsrBI (downstream the NOS terminator), treated with T4 DNA polymerase to generate a blunt end, and digested with SbfI (upstream the chimeric NIR/Plasto promoter). The resulting fragment (Chimeric Nir/Plasto promoter-HSP70 coding sequence-Nos terminator) was cloned into R850 previously digested with SbfI and SmaI (both located in the multiple cloning site upstream chimeric Nir/Plasto promoter). The resulting plasmid, named R870, is presented in FIG. 85 (SEQ ID NO: 123).

Assembly of Other Expression Cassettes

Soluble H1 Expression Cassette

Figure 11:
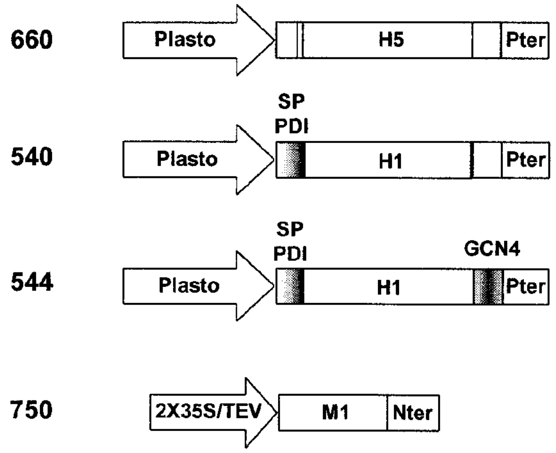
FIG. 11 shows a schematic representation of several constructs as used herein. Construct 660 comprises the nucleotide sequence to encode the HA subtype H5 (A/Indonesia/5/2005 (H5N1)) under operatively linked to the plastocyanin promoter (plasto) and terminator (Pter); construct 540 comprises the nucleotide sequence to encode the HA subtype H1 (A/New Caledonia/20/99 (H1N1) in combination with an alfalfa protein disulfide isomerase signal peptide (SP PDI), and is operatively linked to a plastocyanin promoter (Plasto) and terminator (Pter); construct 544 assembled for the expression of HA subtype H1 (A/New Caledonia/20/99 (H1N1)), the nucleotide sequence encoding H1 is combined with an alfalfa protein disulfide isomerase signal peptide (SP PDI) and an GCN4pII leucine zipper (in place of the transmembrane domain and cytoplasmic tail of HI) and operatively linked to the plastocyanin promoter (Plasto) and terminator (Pter); and construct 750 for the expression of M1 coding region from influenza A/PR/8/34 is combined to the tobacco etch virus (TEV) 5'UTR, and operatively linked with the double 35S promoter and Nos terminator.

The cassette encoding the soluble form of H1 was prepared by replacing the region coding for the transmembrane domain and the cytoplasmic tail in 540 by a fragment encoding the leucine zipper GCN4 pII variant (Harbury et al, 1993, Science 1993; 262: 1401-1407). This fragment was synthesized with flanking KpnI and SacI sites to facilitate cloning. The plasmid resulting from this replacement was named 544 and the expression cassette is illustrated in FIG. 11.

M1 A/Puerto Rico/8/34 Expression Cassette

A fusion between the tobacco etch virus (TEV) 5'UTR and the open reading frame of the influenza A/PR/8/34 M1 gene (Acc. # NC_002016) was synthesized with a flanking SacI site added downstream of the stop codon. The fragment was digested with SwaI (in the TEV 5'UTR) and SacI, and cloned into a 2X35S/TEV based expression cassette in a pCAMBIA binary plasmid. The resulting plasmid bore the M1 coding region under the control of a 2X35S/TEV promoter and 5'UTR and the NOS terminator (construct 750; FIG. 11).

HcPro Expression Cassette

An HcPro construct (35HcPro) was prepared as described in Hamilton et al. (2002). All clones were sequenced to confirm the integrity of the constructs. The plasmids were used to transform *Agrobacteium tumefaciens* (AGL1; ATCC, Manassas, Va. 20108, USA) by electroporation (Mattanovich et al., 1989). The integrity of all *A. tumefaciens* strains were confirmed by restriction mapping.

P19 Expression Cassette

Figure 86:
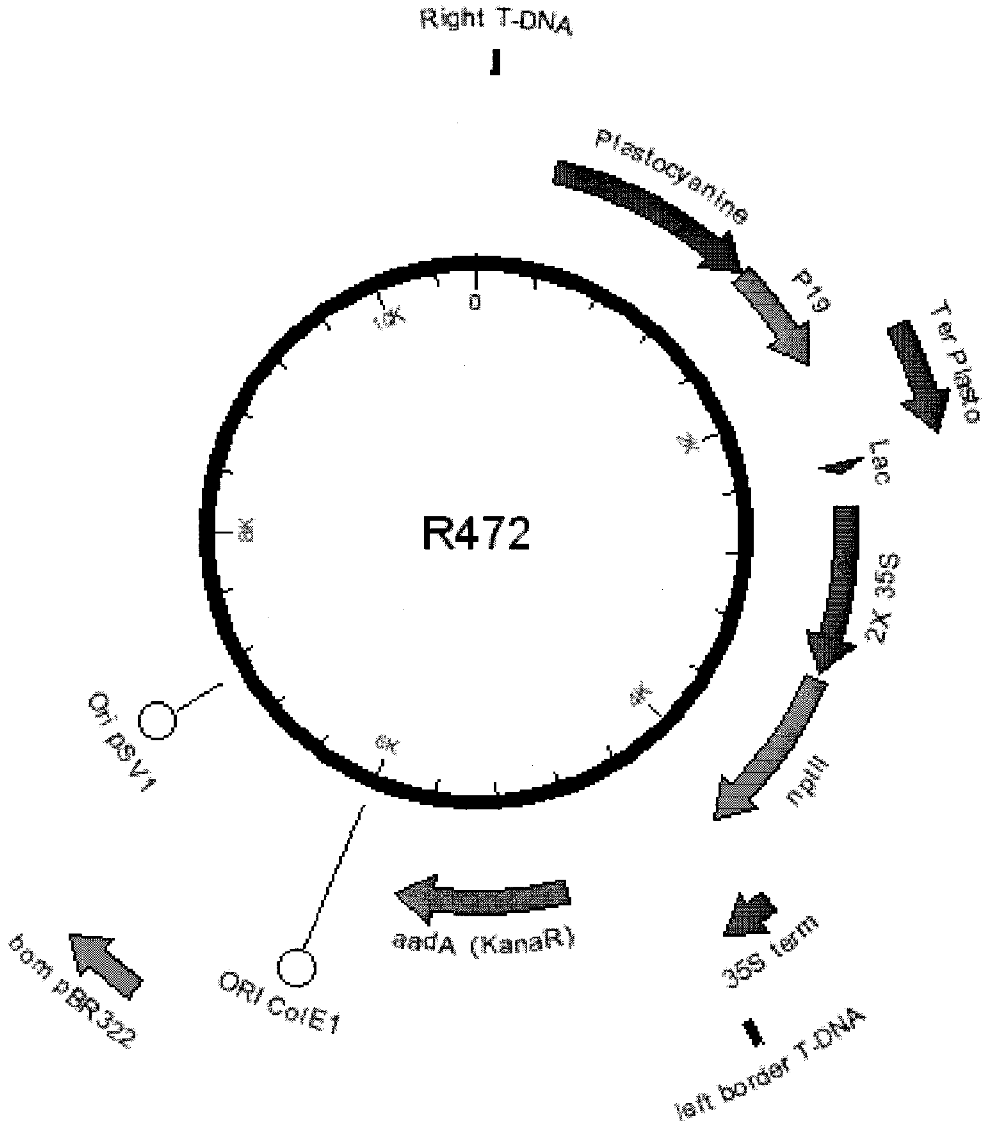
FIG. 86 shows a schematic representation of construct R472.

The coding sequence of p19 protein of tomato bushy stunt virus (TBSV) was linked to the alfalfa plastocyanin expression cassette by the PCR-based ligation method presented in Darveau et al. (Methods in Neuroscience 26: 77-85 (1995)). In a first round of PCR, a segment of the plastocyanin promoter was amplified using primers Plasto-443c (SEQ ID NO: 4; FIG. 7A) and supP19-plasto.r (SEQ ID NO:124) with construct 660 (SEQ ID NO:60; FIG. 51) as template. In parallel, another fragment containing the coding sequence of p19 was amplified with primers supP19-1c (SEQ ID NO:125) and SupP19-SacI.r (SEQ ID NO: 126) using construct 35S:p19 as described in Voinnet et al. (The Plant Journal 33: 949-956 (2003)) as template. Amplification products were then mixed and used as template for a second round of amplification (assembling reaction) with primers Plasto-443c (SEQ ID NO: 4; FIG. 7A) and SupP19-SacI.r (SEQ ID NO: 126). The resulting fragment was digested with BamHI (in the plastocyanin promoter) and SacI (at the end of the p19 coding sequence) and cloned into construct number 660 (SEQ ID NO:60; FIG. 51), previously digested with the same restriction enzymes to give construct number R472. Plasmid R472 is presented in FIG. 86.

3. Preparation of Plant Biomass, Inoculum, Agroinfiltration, and Harvesting

*Nicotiana benthamiana* or *Nicotiana tabacum* plants were grown from seeds in flats filled with a commercial peat moss substrate. The plants were allowed to grow in the greenhouse under a 16/8 photoperiod and a temperature regime of 25° C. day/20° C. night. Three weeks after seeding, individual plantlets were picked out, transplanted in pots and left to grow in the greenhouse for three additional weeks under the same environmental conditions. Prior to transformation, apical and axillary buds were removed at various times as indicated below, either by pinching the buds from the plant, or by chemically treating the plant *Agrobacteria* transfected with each construct were grown in a YEB medium supplemented with 10 mM 2-[N-morpholino]ethanesulfonic acid (MES), 20 μM acetosyringone, 50 μg/mlkanamycin and 25 μg/ml of carbenicillin pH5.6 until they reached an $OD_{600}$ between 0.6 and 1.6. *Agrobacterium* suspensions were centrifuged before use and resuspended in infiltration medium (10 mM $MgCl_2$ and 10 mM MES pH 5.6). Syringe-infiltration was performed as described by Liu and Lomonossoff (2002, Journal of *Virological Methods,* 105:343-348). For vacuum-infiltration, *A. tumefaciens* suspensions were centrifuged, resuspended in the infiltration medium and stored overnight at 4° C. On the day of infiltration, culture batches were diluted in 2.5 culture volumes and allowed to warm before use. Whole plants of *N. benthamiana* or *N. tabacum* were placed upside down in the bacterial suspension in an air-tight stainless steel tank under a vacuum of 20-40 Torr for 2-min. Following syringe or vacuum infiltration, plants were returned to the greenhouse for a 2-6 day incubation period until harvest. Unless otherwise specified, all infiltrations were performed as co-infiltration with AGL1/35S-HcPro in a 1:1 ratio, except for CPMV-HT cassette-bearing strains which were co-infiltrated with strain AGL1/R472 in a 1:1 ratio.

4. Leaf Sampling and Total Protein Extraction

Following incubation, the aerial part of plants was harvested, frozen at −80° C., crushed into pieces. Total soluble proteins were extracted by homogenizing (Polytron) each sample of frozen-crushed plant material in 3 volumes of cold 50 mM Tris pH 7.4, 0.15 M NaCl, and 1 mM phenylmethanesulfonyl fluoride. After homogenization, the slurries were centrifuged at 20,000 g for 20 min at 4° C. and these clarified crude extracts (supernatant) kept for analyses. The total protein content of clarified crude extracts was determined by the Bradford assay (Bio-Rad, Hercules, Calif.) using bovine serum albumin as the reference standard.

5. Size Exclusion Chromatography of Protein Extract

Size exclusion chromatography (SEC) columns of 32 ml Sephacryl™ S-500 high resolution beads (S-500 HR: GE Healthcare, Uppsala, Sweden, Cat. No. 17-0613-10) were packed and equilibrated with equilibration/elution buffer (50 mM Tris pH8, 150 mM NaCl). One and a half millilitre of crude protein extract was loaded onto the column followed by an elution step with 45 mL of equilibration/elution buffer. The elution was collected in fractions of 1.5 mL relative protein content of eluted fractions was monitored by mixing 10 μL of the fraction with 200 μL of diluted Bio-Rad protein dye reagent (Bio-Rad, Hercules, Calif. The column was washed with 2 column volumes of 0.2N NaOH followed by 10 column volumes of 50 mM Tris pH8, 150 mM NaCl, 20% ethanol. Each separation was followed by a calibration of the column with Blue Dextran 2000 (GE Healthcare Bio-Science Corp., Piscataway, N.J., USA). Elution profiles of Blue Dextran 2000 and host soluble proteins were compared between each separation to ensure uniformity of the elution profiles between the columns used.

6. Protein Analysis and Immunoblotting

Protein concentrations were determined by the BCA protein assay (Pierce Biochemicals, Rockport Ill.). Proteins were separated by SDS-PAGE under reducing conditions and stained with Coomassie Blue. Stained gels were scanned and densitometry analysis performed using ImageJ Software (NIH).

Proteins from elution fraction from SEC were precipitated with acetone (Bollag et al., 1996), resuspended in ⅕ volume in equilibration/elution buffer and separated by SDS-PAGE under reducing conditions and electrotransferred onto polyvinylene difluoride (PVDF) membranes (Roche Diagnostics Corporation, Indianapolis, Ind.) for immunodetection. Prior to immunoblotting, the membranes were blocked with 5% skim milk and 0.1% Tween-20 in Tris-buffered saline (TBS-T) for 16-18 h at 4° C.

Immunoblotting was performed by incubation with a suitable antibody (Table 6), in 2 μg/ml in 2% skim milk in TBS-Tween 20 0.1%. Secondary antibodies used for chemiluminescence detection were as indicated in Table 4, diluted as indicated in 2% skim milk in TBS-Tween 20 0.1%. Immunoreactive complexes were detected by chemiluminescence using luminol as the substrate (Roche Diagnostics Corporation). Horseradish peroxidase-enzyme conjugation of human IgG antibody was carried out by using the EZ-Link Plus® Activated Peroxidase conjugation kit (Pierce, Rockford, Ill.). Whole, inactivated virus (WIV), used as controls of detection for H1, H3 and B subtypes, were purchased from National Institute for Biological Standards and Control (NIBSC).

TABLE 6

Electrophoresis conditions, antibodies, and dilutions for immunoblotting of expressed proteins.

| HA subtype | Influenza strain | Electrophoresis condition | Primary antibody | Dilution | Secondary antibody | Dilution |
|---|---|---|---|---|---|---|
| H1 | A/California/04/09 (H1N1) | Reducing | FII 10-I50F | 4 μg/ml | Goat anti-mouse (JIR 115-035-146) | 1:10 000 |
| H1 | A/Brisbane/59/2007 (H1N1) | Reducing | FII 10-I50 | 4 μg/ml | Goat anti-mouse (JIR 115-035-146) | 1:10 000 |
| H1 | A/Solomon Islands/3/2006 (H1N1) | Reducing | NIBSC 07/104 | 1:2000 | Rabbit anti-sheep (JIR 313-035-045) | 1:10 000 |
| H1 | A/New Caledonia/20/99 (H1N1) | Reducing | FII 10-I50 | 4 μg/ml | Goat anti-mouse (JIR 115-035-146) | 1:10 000 |
| H2 | A/Singapore/1/57 (H2N2) | Non-reducing | NIBSC 00/440 | 1:1000 | Rabbit anti-sheep (JIR 313-035-045) | 1:10 000 |
| H3 | A/Brisbane/10/2007 (H3N2) | Non-Reducing | TGA AS393 | 1:4000 | Rabbit anti-sheep (JIR 313-035-045) | 1:10 000 |
| H3 | A/Brisbane/10/2007 (H3N2) | Non-Reducing | NIBSC 08/136 | 1:1000 | Rabbit anti-sheep (JIR 313-035-045) | 1:10 000 |
| H3 | A/Wisconsin/67/2005 (H3N2) | Non-Reducing | NIBSC 05/236 | 1:1000 | Rabbit anti-sheep (JIR 313-035-045) | 1:10 000 |

TABLE 6-continued

Electrophoresis conditions, antibodies, and dilutions for immunoblotting of expressed proteins.

| HA subtype | Influenza strain | Electrophoresis condition | Primary antibody | Dilution | Secondary antibody | Dilution |
|---|---|---|---|---|---|---|
| H5 | A/Indonesia/5/2005 (H5N1) | Reducing | ITC IT-003-005V | 1:4000 | Goat anti-rabbit (JIR 111-035-144) | 1:10 000 |
| H5 | A/Anhui/1/2005 (H5N1) | Reducing | NIBSC 07/338 | 1:750 | Rabbit anti-sheep (JIR 313-035-045) | 1:10 000 |
| H5 | A/Vietnam/1194/2004 (H5N1) | Non-reducing | ITC IT-003-005 | 1:2000 | Goat anti-rabbit (JIR 111-035-144) | 1:10 000 |
| H6 | A/Teal/Hong Kong/W312/97 (H6N1) | Non-reducing | BEI NR 663 | 1:500 | Rabbit anti-sheep (JIR 313-035-045) | 1:10 000 |
| H7 | A/Equine/Prague/56 (H7N7) | Non-reducing | NIBSC 02/294 | 1:1000 | Rabbit anti-sheep (JIR 313-035-045) | 1:10 000 |
| H9 | A/Hong Kong/1073/99 (H9N2) | Reducing | NIBSC 07/146 | 1:1000 | Rabbit anti-sheep (JIR 313-035-045) | 1:10 000 |
| B | B/Malaysia/2506/2004 | Non-Reducing | NIBSC 07/184 | 1:2000 | Rabbit anti-sheep (JIR 313-035-045) | 1:10 000 |
| B | B/Florida/4/2006 | Non-Reducing | NIBSC 07/356 | 1:2000 | Rabbit anti-sheep (JIR 313-035-045) | 1:10 000 |

FII: Fitzgerald Industries International, Concord, MA, USA;
NIBSC: National Institute for Biological Standards and Control;
JIR: Jackson ImmunoResearch, West Grove, PA, USA;
BEI NR: Biodefense and emerging infections research resources repository;
ITC: Immune Technology Corporation, Woodside, NY, USA;
TGA: Therapeutic Goods Administration, Australia.

Hemagglutination assay for H5 was based on a method described by Nayak and Reichl (2004). Briefly, serial double dilutions of the test samples (100 μL) were made in V-bottomed 96-well microtiter plates containing 100 μL PBS, leaving 100 μL of diluted sample per well. One hundred microliters of a 0.25% turkey red blood cells suspension (Bio Link Inc., Syracuse, N.Y.) were added to each well, and plates were incubated for 2 h at room temperature. The reciprocal of the highest dilution showing complete hemagglutination was recorded as HA activity. In parallel, a recombinant HA standard was diluted in PBS and run as a control on each plate.

7. Sucrose Gradient Ultracentrifugation

One milliliter of fractions 9, 10 and 11 eluted from the gel filtration chromatography on H5-containing biomass were pooled, loaded onto a 20-60% (w/v) discontinuous sucrose density gradient, and centrifuged 17.5 h at 125 000 g (4° C.). The gradient was fractionated in 19 3-mL fractions starting from the top, and dialyzed to remove sucrose prior to immunological analysis and hemagglutination assays.

8. Electron Microscopy

One hundred microliters of the samples to be examined were placed in an Airfuge ultracentrifugation tube (Beckman Instruments, Palo Alto, Calif., USA). A grid was placed at the bottom of the tube which was then centrifuged 5 min at 120 000 g. The grid was removed, gently dried, and placed on a drop of 3% phosphotungstic acid at pH 6 for staining. Grids were examined on a Hitachi 7100 transmission electron microscope (TEM) (for images in FIGS. 14B, 15B and 15C).

Figure 19:
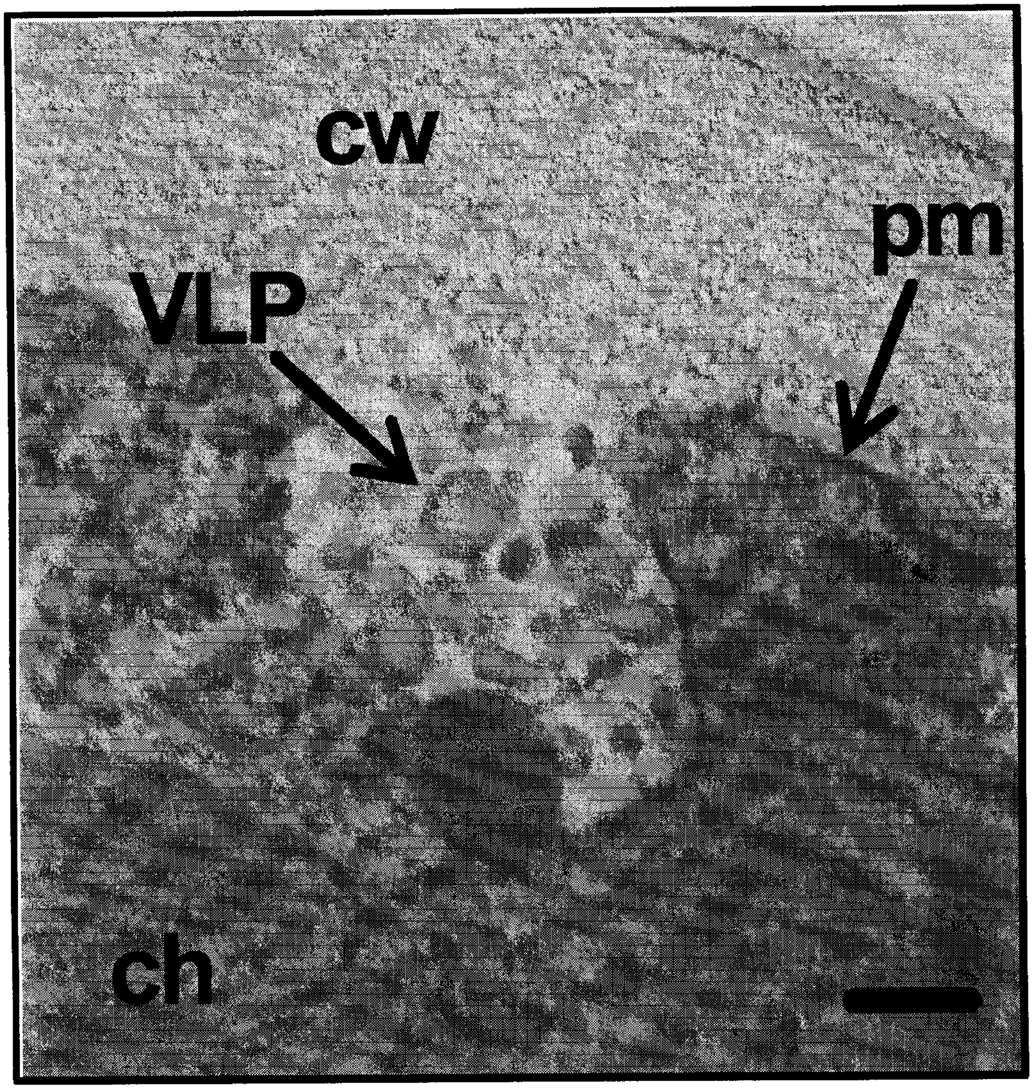
FIG. 19 shows localization of VLP accumulation by positive staining transmission electron microscopy observation of H5 producing tissue. CW: cell wall, ch: chloroplast, pm: plasma membrane, VLP: virus-like particle. The bar represents 100 nm.

For images in FIG. 19, Leaf blocks of approximately 1 $mm^3$ were fixed in PBS containing 2.5% glutaraldehyde and washed in PBS containing 3% sucrose before a post-fixation step in 1.33% osmium tetroxide. Fixed samples were imbedded in Spurr resin and ultrathin layers were laid on a grid. Samples were positively stained with 5% uranyl acetate and 0.2% lead citrate before observation. Grids were examined on a Hitachi 7100 transmission electron microscope (TEM).

9. Plasma Membrane Lipid Analysis

Plasma membranes (PM) were obtained from tobacco leaves and cultured BY2 cells after cell fractionation according to Mongrand et al. by partitioning in an aqueous polymer two-phase system with polyethylene glycol 3350/dextran T-500 (6.6% each). All steps were performed at 4° C.

Lipids were extracted and purified from the different fractions according to Bligh and Dyer. Polar and neutral lipids were separated by mono-dimensional HP-TLC using the solvent systems described in Lefebvre et al. Lipids of PM fractions were detected after staining with copper acetate as described by Macala et al. Lipids were identified by comparison of their migration time with those of standards (all standards were obtained from Sigma-Aldrich, St-Louis, Mo., USA, except for SG which was obtained from Matreya, Pleasant Gap, Pa., USA).

10. H5 VLP (A/Indonesia/5/2005) Purification

Frozen 660-infiltrated leaves of *N. benthamiana* were homogenized in 1.5 volumes of 50 mM Tris pH 8, NaCl 150 mM and 0.04% sodium meta-bisulfite using a commercial blender. The resulting extract was supplemented with 1 mM PMSF and adjusted to pH 6 with 1 M acetic acid before being heated at 42° C. for 5 min. Diatomaceous earth (DE) was added to the heat-treated extract to adsorb the contaminants precipitated by the pH shift and heat treatment, and the slurry was filtered through a Whatman paper filter. The resulting clarified extract was centrifuged at 10,000×g for 10 minutes at RT to remove residual DE, passed through 0.8/0.2 μm Acropack 20 filters and loaded onto a fetuin-agarose affinity column (Sigma-Aldrich, St-Louis, Mo., USA). Following a wash step in 400 mM NaCl, 25 mM Tris pH 6, bound proteins were eluted with 1.5 M NaCl, 50 mM MES pH 6. Eluted VLP were supplemented with Tween-80 to a final concentration of 0.0005% (v/v). VLP were concentrated on a 100 kDa MWCO Amicon membrane, centrifuged at 10,000×g for 30 minutes at 4° C. and resuspended in PBS pH 7.4 with 0.01% Tween-80 and 0.01% thimerosal. Suspended VLPs were filter-sterilized before use.

11. Animal Studies

Mice

Studies on the immune response to influenza VLP administration were performed with 6-8 week old female BALB/c mice (Charles River Laboratories). Seventy mice were randomly divided into fourteen groups of five animals. Eight groups were used for intramuscular immunization and six groups were used to test intranasal route of administration. All groups were immunized in a two-dose regiment, the boost immunization being done 3 weeks following the first immunization.

For intramuscular administration in hind legs, unanaesthetized mice were immunized with either the plant-made H5 VLP (A/Indonesia/5/2005 (H5N1) vaccine (0.1, 1, 5 or 12 μg), or a control hemagglutinin (H5) antigen. The control H5 comprised recombinant soluble hemagglutinin produced based on strain A/Indonesia/5/05 H5N1 and purified from 293 cell culture (Immune Technology Corp., New York, USA) (used at 5 μg per injection unless otherwise indicated). Buffer control was PBS. This antigen consists of amino acids 18-530 of the HA protein, and has a His-tag and a modified cleavage site. Electron microscopy confirmed that this commercial product is not in the form of VLPs.

To measure the effect of adjuvant, two groups of animals were immunized with 5 μg plant-made VLP H5 vaccine plus one volume Alhydrogel 2% (alum, Accurate Chemical & Scientific Corporation, Westbury, N.Y., US) or with 5 μg recombinant hemagglutinin purified from 293 cell culture plus 1 volume alum. Seventy mice were randomly divided into fourteen groups of five animals. Eight groups were used for intramuscular immunization and six groups were used to test intranasal route of administration. All groups were immunized according to a prime-boost regimen, the boost immunization performed 3 weeks following the first immunization.

For intramuscular administration in hind legs, unanaesthetized mice were immunized with the plant-made H5 VLP (0.1, 1, 5 or 12 μg), or the control hemagglutinin (HA) antigen (5 μg) or PBS. All antigen preparations were mixed with Alhydrogel 1% (alum, Accurate Chemical & Scientific Corporation, Westbury, N.Y., US) in a 1:1 volume ratio prior to immunizations. To measure the effect of adjuvant, two groups of animals were immunized with either 5 μg plant-made VLP H5 vaccine or with 5 μg of control HA antigen without any adjuvant.

For intranasal administration, mice were briefly anaesthetized by inhalation of isoflurane using an automated induction chamber. They were then immunized by addition of 4 μl drop/nostril with the plant-made VLP vaccine (0.1 or 1 μg), or with control HA antigen (1 μg) or with PBS. All antigen preparations were mixed with chitosan glutamate 1% (Protosan, Novamatrix/FMC BioPolymer, Norway) prior to immunizations. The mice then breathed in the solutions. To verify the effect of adjuvant with the intranasal route of administration, two groups of animals were immunized with 1 μg plant-made VLP H5 vaccine or with 1 μg control HA antigen.

Ferrets

Ten groups of 5 ferrets (male, 18-24 weeks old, mass of approx 1 kg) were used. Treatment for each group is as described in Table 7. The adjuvant used was Alhydrogel (alum) (Superfos Biosector, Denmark) 2% (final=1%). Vaccine composition was membrane-associated A/Indonesia/5/05 (H5N1) VLPs produced as described. The vaccine control (positive control) was a fully glycosylated membrane-bound recombinant H5 from Indonesia strain produced using adenovirus in 293 cell culture by Immune Technology Corporation (ITC).

TABLE 7

Treatment groups

| Group | n | Product injected to animals | Route of administration | Adjuvant |
|---|---|---|---|---|
| 1 | 5 | PBS (negative control) | i.m.* | — |
| 2 | 5 | Vaccine-plant, 1 μg | i.m. | — |
| 3 | 5 | Vaccine-plant, 1 μg | i.m. | Alum |
| 4 | 5 | Vaccine-plant, 5 μg | i.m. | — |
| 5 | 5 | Vaccine-plant, 5 μg | i.m. | Alum |
| 6 | 5 | Vaccine-plant, 7.5 μg | i.m. | — |
| 7 | 5 | Vaccine-plant, 15 μg | i.m. | — |
| 8 | 5 | Vaccine-plant, 15 μg | i.m. | Alum |
| 9 | 5 | Vaccine-plant, 30 μg | i.m. | — |
| 10 | 5 | Vaccine-control, 5 μg | i.m. | — |

*i.m.: intramuscular

Ferrets were assessed for overall health and appearance (body weight, rectal temperature, posture, fur, movement patterns, breathing, excrement) regularly during the study. Animals were immunized by intramuscular injection (0.5-1.0 total volume) in quadriceps at day 0, 14 and 28; for protocols incorporating adjuvant, the vaccine composition was combined with Alhydrogel immediately prior to immunization in a 1:1 volume ratio). Serum samples were obtained on day 0 before immunizing, and on day 21 and 35. Animals were sacrificed (exsanguination/cardiac puncture) on days 40-45, and, spleens were collected and necropsy performed.

Anti-influenza antibody titres may be quantified in ELISA assays using homologous or heterologous inactivated H5N1 viruses.

Hemagglutination inhibitory antibody titers of serum samples (pre-immune, day 21 and day 35) were evaluated by microtiter HAI as described (Aymard et al 1973). Briefly, sera were pretreated with receptor-destroying enzyme, heat-inactivated and mixed with a suspension of erythrocytes (washed red blood cells-RBC). Horse washed RBC (10%) from Lampire are recommended and considering that the assay may vary depending of the source of the RBC (horse-dependant), washed RBCs from 10 horses have been tested to select the most sensitive batch. Alternately, turkey RBC may be used. Antibody titer was expressed as the reciprocal of the highest dilution which completely inhibits hemagglutination.

Cross-reactive HAI titers: HAI titers of ferrets immunized with a vaccine for the A/Indonesia/5/05 (clade 2.1) were measured using inactivated H5N1 influenza strains from another subclade or clade such as the clade 1 Vietnam strains A/Vietnam/1203/2004 and A/Vietnam/1194/2004 or the A/Anhui/01/2005 (subclade 2.3) or the A/turkey/Turkey/1/05 (subclade 2.2). All analyses were performed on individual samples.

Data analysis: Statistical analysis (ANOVA) were performed on all data to establish if differences between groups are statistically significant.

Experimental Design for Lethal Challenge (Mice)

One hundred twenty eight mice were randomly divided into sixteen groups of eight animals, one group being unimmunized and not challenged (negative control). All groups were immunized via intramuscular administration in a two-dose regimen, the second immunization being done 2 weeks following the first immunization.

For intramuscular administration in hind legs, unanaesthetized mice were immunized with the plant-made H5 VLP (1, 5 or 15 μg), or 15 μg of control HA antigen or PBS. All antigen preparations were mixed with one volume of Alhydrogel 1% prior to immunizations (alum, Accurate Chemical & Scientific Corporation, Westbury, N.Y., US).

During the immunization period, mice were weighted once a week and observation and monitored for local reactions at the injection site.

Twenty two days following the second immunization, anesthetized mice were challenged intranasally (i.n.) into a BL4 containment laboratory (P4-Jean Mérieux-INSERM, Lyon, France) with $4.09\times10^6$ 50% cell culture infective dose (CCID50) of influenza A/Turkey/582/06 virus (kindly provided by Dr. Bruno Lina, Lyon University, Lyon, France). Following challenge, mice were observed for ill clinical symptoms and weighed daily, over a fourteen day period. Mice with severe infection symptoms and weight loss of ≥25% were euthanized after anaesthesia.

Blood Collection, Lung and Nasal Washes and Spleen Collection

Lateral saphenous vein blood collection was performed fourteen days after the first immunization and fourteen days after second immunization on unanaesthetized animal. Serum was collected by centrifugation at 8000 g for 10 min.

Four weeks after second immunisation, mice were anaesthetized with $CO_2$ gas and immediately upon termination, cardiac puncture was used to collect blood.

After final bleeding, a catheter was inserted into the trachea towards the lungs and one ml of cold PBS-protease inhibitor cocktail solution was put into a 1 cc syringe attached to the catheter and injected into the lungs and then removed for analysis. This wash procedure was performed two times. The lung washes were centrifuged to remove cellular debris. For nasal washes, a catheter was inserted towards the nasal area and 0.5 ml of the PBS-protease inhibitor cocktail solution was pushed through the catheter into the nasal passages and then collected. The nasal washes were centrifuged to remove cellular debris. Spleen collection was performed on mice immunized intramuscularly with 5 μg of adjuvanted plant-made vaccine or 5 μg adjuvanted recombinant H5 antigen as well as on mice immunized intranasaly with 1 μg of adjuvanted plant-made vaccine or 1 μg adjuvanted recombinant H5 antigen. Collected spleens were placed in RPMI supplemented with gentamycin and mashed in a 50 ml conical tube with plunger from a 10 ml syringe. Mashed spleens were rinsed 2 times and centrifuged at 2000 rpm for 5 min and resuspended in ACK lysing buffer for 5 min at room temperature. The splenocytes were washed in PBS-gentamycin, resuspended in 5% RPMI and counted. Splenocytes were used for proliferation assay.

Antibody Titers

Anti-influenza antibody titers of sera were measured at 14 days after the first immunization as well as 14 and 28 days after the second immunisation. The titer were determined by enzyme-linked immunosorbent assay (ELISA) using the inactivated virus A/Indonesia/5/05 as the coating antigen. The end-point titers were expressed as the reciprocal value of the highest dilution that reached an OD value of at least 0.1 higher than that of negative control samples.

For antibody class determination (IgG1, IgG2a, IgG2b, IgG3, IgM), the titers were evaluated by ELISA as previously described.

Hemagglutination Inhibition (HI) Titers

Hemagglutination inhibition (HI) titers of sera were measured at 14 and 28 days after the second immunisation as previously described (WHO 2002; Kendal 1982). Inactivated virus preparations from strains A/Indonesia/5/05 or A/Vietnam/1203/2004 were used to test mouse serum samples for HI activity. Sera were pre-treated with receptor-destroying enzyme II (RDE II) (Denka Seiken Co., Tokyo, Japan) prepared from *Vibrio cholerae* (Kendal 1982). HI assays were performed with 0.5% turkey red blood cells. HI antibody titres were defined as the reciprocal of the highest dilution causing complete inhibition of agglutination.

EXAMPLES

Example 1

Transient Expression of Influenza Virus A/Indonesia/5/05 (H5N1) Hemagglutinin by Agroinfiltration in *N. benthamiana* Plants The ability of the transient expression system to produce influenza hemagglutinin was determined through the expression of the H5 subtype from strain A/Indonesia/5/05 (H5N1). As presented in FIG. 11, the hemagglutinin gene coding sequence (GenBank Accession No. EF541394), with its native signal peptide and transmembrane domain, was first assembled in the plastocyanin expression cassette—promoter, 5'UTR, 3'UTR and transcription termination sequences from the alfalfa plastocyanin gene—and the assembled cassette (660) was inserted into to a pCAMBIA binary plasmid. This plasmid was then transfected into *Agrobacterium* (AGL1), creating the recombinant strain AGL1/660, which was used for transient expression.

Figure 12:
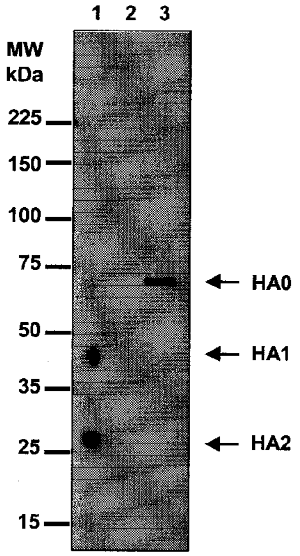
FIG. 12 shows immunodetection of H5 (A/Indonesia/5/2005 (H5N1)), using anti-H5 (Vietnam) antibodies, in protein extracts from *N. benthamiana* leaves transformed with construct 660 (lane 3). Commercial H5 from influenza A/Vietnam/1203/2004 was used as positive control of detection (lane 1), and a protein extract from leaves transformed with an empty vector were used as negative control (lane 2).

*N. benthamiana* plants were infiltrated with AGL1/660, and the leaves were harvested after a six-day incubation period. To determine whether H5 accumulated in the agroinfiltrated leaves, protein were first extracted from infiltrated leaf tissue and analyzed by Western blotting using anti-H5 (Vietnam) polyclonal antibodies. A unique band of approximately 72 kDa was detected in extracts (FIG. 12), corresponding in size to the uncleaved HA0 form of influenza hemagglutinin. The commercial H5 used as positive control (A/Vietnam/1203/2004; Protein Science Corp., Meriden, Conn., USA) was detected as two bands of approximately 48 and 28 kDa, corresponding to the molecular weight of HA1 and HA2 fragments, respectively. This demonstrated that expression of H5 in infiltrated leaves results in the accumulation of the uncleaved translation product.

The formation of active HA trimers was demonstrated by the capacity of crude protein extracts from AGL1/660-transformed leaves to agglutinate turkey red blood cells (data not shown).

Example 2

Figure 13A:
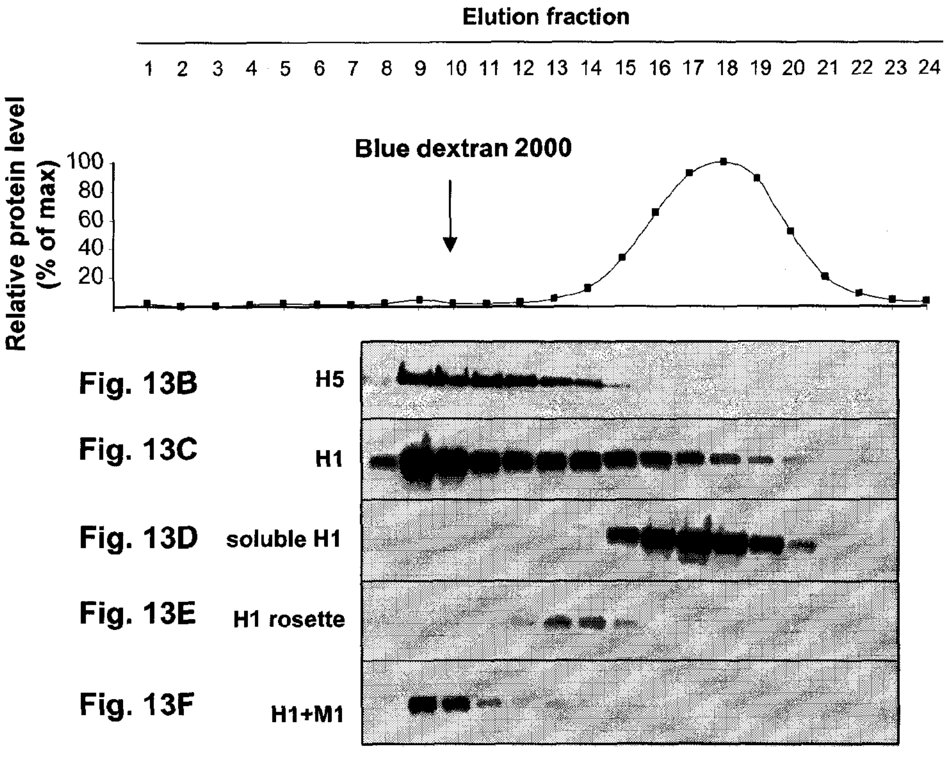
FIG. 13A shows elution fractions analyzed for relative protein content (Relative Protein Level—a standard protein elution profile of a biomass fractionation is shown). Blue Dextran 2000 (2 MDa reference standard) elution peak is indicated.

Characterization of Hemagglutinin-containing Structures in Plant Extracts Using Size Exclusion Chromatography The assembly of plant-produced influenza hemagglutinin into high molecular weight structures was assessed by gel filtration. Crude protein extracts from AGL1/660-infiltrated plants (1.5 mL) were fractionated by size exclusion chromatography (SEC) on Sephacryl™ S-500 HR columns (GE Healthcare Bio-Science Corp., Piscataway, N.J., USA). Elution fractions were assayed for their total protein content and for HA abundance using immunodetection with anti-HA antibodies (FIG. 13A). As shown in FIG. 13A, Blue Dextran (2 MDa) elution peaked early in fraction 10 while the bulk of host proteins was retained in the column and eluted between fractions 14 and 22. When proteins from 200 μL of each SEC elution fraction were concentrated (5-fold) by acetone-precipitation and analyzed by Western blotting (FIG. 15A, H5), hemagglutinin (H5) was primarily found in fractions 9 to 14 (FIG. 13B). Without wishing to be bound by theory, this suggests that the HA protein had either assembled into a large superstructure or that it has attached to a high molecular weight structure.

A second expression cassette was assembled with the H1 nucleic acid sequence from A/New Caledonia/20/99 (H1N1) (SEQ ID NO: 33; FIG. 16; GenBank Accession No. AY289929) to produce construct 540 (FIG. 11). A chimeric gene construct was designed so as to produce a soluble trimeric form of H1 in which the signal peptide originated from a plant protein disulfide isomerase gene, and the transmembrane domain of H1 was replaced by the pII variant of the GCN4 leucine zipper, a peptide shown to self-assemble into trimers (Harbury et al., 1993) (cassette 544, FIG. 11). Although lacking the transmembrane domain, this soluble trimeric form was capable of hemagglutination (data not shown).

Protein extracts from plants infiltrated with AGL1/540 or AGL1/544 were fractionated by SEC and the presence of H1 eluted fractions was examined by Western blotting with anti-influenza A antibodies (Fitzgerald, Concord, Mass., USA). In AGL1/540-infiltrated leaves, H1 accumulated mainly as a very high molecular weight structure, with the peak was skewed toward smaller size structures (H1; FIG. 13C). In AGL1/544-infiltrated leaves, the soluble form of H1 accumulated as isolated trimers as demonstrated by the elution pattern from gel filtration which parallels the host protein elution profile (soluble H1; FIG. 13D). In comparison, H1 rosettes (Protein Science Corp., Meriden, Conn., USA), consisting in micelles of 5-6 trimers of hemagglutinin eluted at fractions 12 to 16 (FIG. 13E), earlier than the soluble form of H1 (FIG. 13D) and later than the native H1 (FIG. 13C).

To evaluate the impact of M1 co-expression on hemagglutinin assembly into structure, a M1 expression cassette was assembled using the nucleic acid corresponding to the coding sequence of the A/PR/8/34 (H1N1) M1 (SEQ ID NO: 35; FIG. 18; GenBank Accession No. NC_002016). The construct was named 750 and is presented in FIG. 11. For the co-expression of M1 and H1, suspensions of AGL1/540 and AGL1/750 were mixed in equal volume before infiltration. Co-infiltration of multiple *Agrobacterium* suspensions permits co-expression of multiple transgenes. The Western blot analysis of SEC elution fractions shows that the co-expression of M1 did not modify the elution profile of the H1 structures, but resulted in a decrease in H1 accumulation in the agroinfiltrated leaves (see FIG. 13F).

Example 3

Figure 14A:
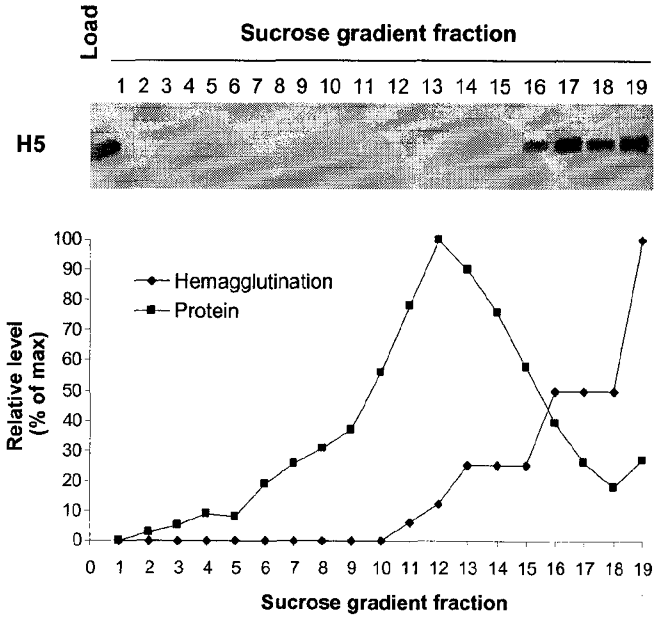
FIG. 14A shows characterization of fractions from sucrose density gradient centrifugation. Each fraction was analyzed for the presence of H5 by immunoblotting using anti-H5 (Vietnam) antibodies (upper panel), and for their relative protein content and hemagglutination capacity (graph).
Figure 14B:
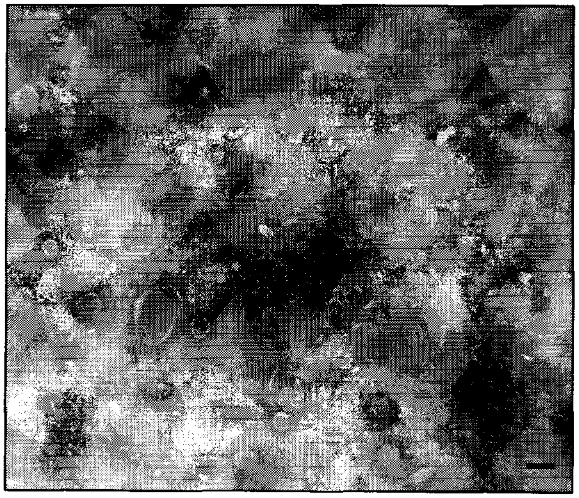
FIG. 14B shows negative staining transmission electron microscopy examination of pooled fractions 17, 18 and 19 from sucrose gradient centrifugation. The bar represents 100 nm.

Isolation of H5 Structures by Centrifugation in Sucrose Gradient and Observation Under Electron Microscopy The observation of hemagglutinin structure under electron microscopy (EM) required a higher concentration and purity level than that obtained from SEC on crude leaf protein extracts. To allow EM observation of H5 structures, a crude leaf protein extract was first concentrated by PEG precipitation (20% PEG) followed by resuspension in 1/10 volumes of extraction buffer. The concentrated protein extract was fractionated by S-500 HR gel filtration and elution fractions 9, 10, and 11 (corresponding to the void volume of the column) were pooled and further isolated from host proteins by ultracentrifugation on a 20-60% sucrose density gradient. The sucrose gradient was fractionated starting from the top and the fractions were dialysed and concentrated on a 100 NMWL centrifugal filter unit prior to analysis. As shown on the Western blots and hemagglutination results (FIG. 14A), H5 accumulated mainly in fractions 16 to 19 which contained ≈60% sucrose, whereas most of the host proteins peaked at fraction 13. Fractions 17, 18, and 19 were pooled, negatively stained, and observed under EM. Examination of the sample clearly demonstrated the presence of spiked spheric structures ranging in size from 80 to 300 nm which matched the morphological characteristics of influenza VLPs (FIG. 14B).

Example 4

Purification of Influenza H5 VLPs from Plant Biomass

Figure 15A:
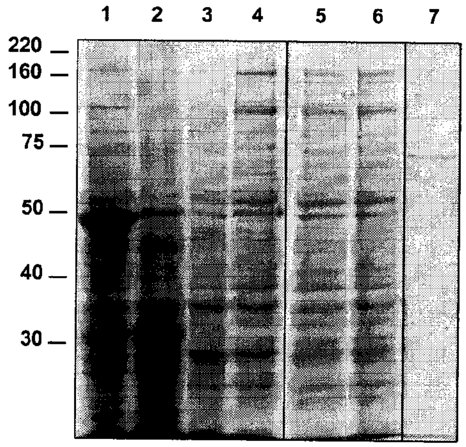
FIG. 15A shows Coomassie Blue stained SDS-PAGE analysis of protein content in the clarification steps—lane 1, crude extract; lane 2, pH 6-adjusted extract; lane 3, heat-treated extract; lane 4, DE-filtrated extract; the fetuin affinity purification steps: lane 5, load; lane 6, flowthrough; lane 7, elution (10× concentrated).

In addition to an abundant content of soluble proteins, plant leaf extracts contain a complex mixture of soluble sugars, nucleic acids and lipids. The crude extract was clarified by a pH shift and heat treatment followed by filtration on diatomaceous earth (see Material and method section for a detailed description of the clarification method). FIG. 15A (lanes 1-4) presents a Coomassie Blue stained gel comparing protein content at the various steps of clarification. A comparison of protein content in the crude extract (lane 1) and in the clarified extract (lane 4) reveals the capacity of the clarification steps to reduce the global protein content and remove most of the major contaminant visible at 50 kDa in crude leaf extracts. The 50 kDa band corresponds to the RuBisCO large subunit, representing up to 30% of total leaf proteins.

Influenza H5 VLPs were purified from these clarified extracts by affinity chromatography on a fetuin column. A comparison of the load fraction (FIG. 15A, lane 5) with the flowthrough (FIG. 15A, lane 6) and the eluted VLPs (FIG. 15A, lane 7) demonstrates the specificity of the fetuin affinity column for influenza H5 VLPs in plant clarified extract.

Figure 15B:
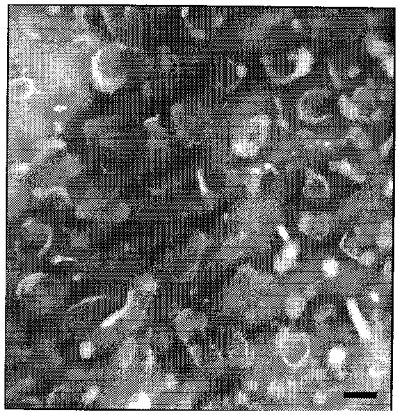
FIG. 15B shows negative staining transmission electron microscopy examination of the purified H5 VLP sample. The bar represents 100 nm.
Figure 15C:
FIG. 15 shows purification of influenza H5 VLPs.
FIG. 15D shows the H5 VLP product on a Coomassie-stained reducing SDS-PAGE (lane A) and Western blot (lane B) using rabbit polyclonal antibody raised against HA from strain A/Vietnam/1203/2004 (H5N1).

The purification procedure resulted in over 75% purity in H5, as determined by densitometry on the Coomassie Blue stained SDS-PAGE gel (FIG. 15A, lane 7). In order to assess the structural quality of the purified product, the purified H5 was concentrated on a 100 NMWL (nominal molecular weight limit) centrifugal filter unit and examined under EM after negative staining. FIG. 15B shows a representative sector showing the presence of profuse VLPs. A closer examination confirmed the presence of spikes on the VLPs (FIG. 15C).

Figure 15D:
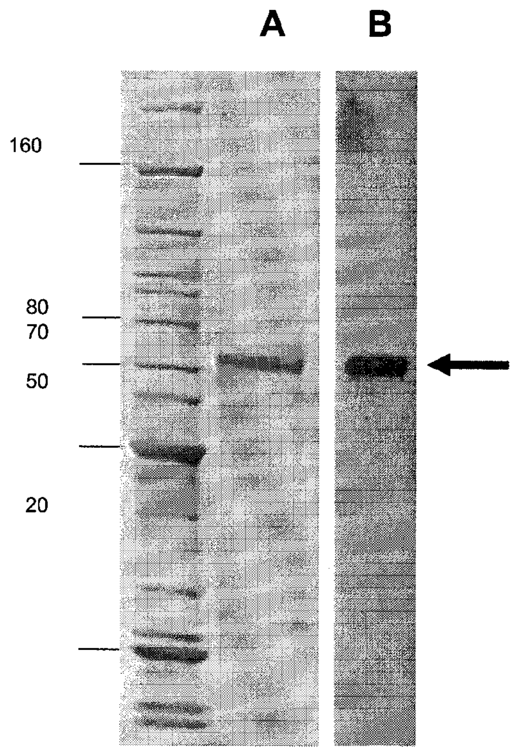

As shown in FIG. 15D, H5 VLPs were purified to approx. 89% purity from clarified leaf extract by affinity chromatography on a fetuin column, based on the density of the Coomassie Blue stained H5 hemagglutinin and on total protein content determination by the BCA method.

The bioactivity of HA VLPs was confirmed by their capacity to agglutinate turkey red blood cells (data not shown).

FIG. 15D also confirms the identity of the purified VLP visualized by Western blotting and immunodetection with an anti-H5 polyclonal serum (A/Vietnam/1203/2004). A unique band of approximately 72 kDa is detected and corresponds in size to the uncleaved HA0 form of influenza hemagglutinin. FIG. 15*c* shows the VLP structure of the vaccine with the hemagglutinin spikes covering its structure.

VLPs were formulated for immunization of mice by filtering through a 0.22 μm filter; endotoxin content was measured using the endotoxin LAL (*Limulus Amebocyte* Lysate) detection kit (Lonza, Walkserville, Miss., USA). The filtered vaccine contained 105.8±11.6% EU/ml (endotoxin units/ml).

Example 5

Localization of Influenza VLPs in Plants

To localize the VLPs and confirm their plasma membrane origin, thin leaf sections of H5-producing plants were fixed and examined under TEM after positive staining. Observation of leaf cells indicated the presence of VLPs in extracellular cavities formed by the invagination of the plasma membrane (FIG. 19). The shape and position of the VLPs observed demonstrated that despite the apposition of their plasma membranes on the cell wall, plant cells have the plasticity required to produce influenza VLPs derived from their plasma membrane and accumulate them in the apoplastic space.

Example 6

Plasma Membrane Lipid Analysis

Figure 27A:
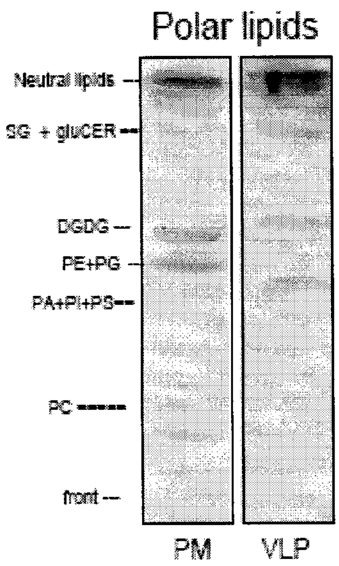
FIG. 27 shows origin of plant-derived influenza VLPs. (A) Polar lipid composition of purified influenza VLPs. Lipids contained in an equivalent of 40 μg of proteins, were extracted from VLP as described, separated by HP-TLC, and compared to the migration profile of lipids isolated from highly purified tobacco plasma membrane (PM). Lipid abbreviations are as following: DGDG, Digalactosyldiacylglycerol; gluCER, glucosyl-ceramide; PA, phosphatic acid; PC, phosphatidylcholine; PE, phosphatidylethanolamine; PG, phosphatidylglycerol; PI, phosphatidylinositol; PS, phosphatidylserine; SG, Steryl-glycoside. (B) Neutral lipid composition of purified influenza VLPs. Lipids contained in an equivalent of 20 μg of proteins were extracted from VLP as described, separated by HP-TLC and compared to the migration of sitosterol. (C) Immunodetection of the plasma membrane marker proton pump ATPase (PMA) in purified VLPs and highly-purified PM from tobacco leaves ($PM_L$) and BY2 tobacco cells ($PM_{BY2}$). Eighteen micrograms of protein were loaded in each lane.
Figure 27B:
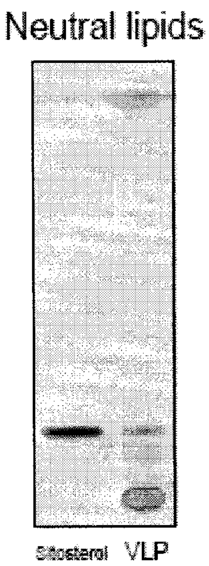
Figure 27C:
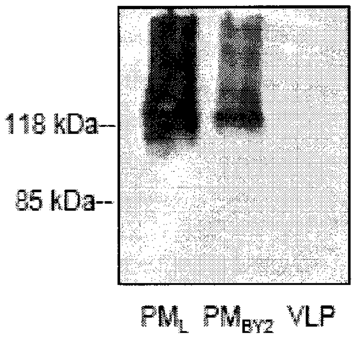

Further confirmation of the composition and origin of the plant influenza VLPs was obtained from analyses of the lipid content. Lipids were extracted from purified VLPs and their composition was compared to that of highly purified tobacco plasma membranes by high performance thin layer chromatography (HP-TLC). The migration patterns of polar and neutral lipids from VLPs and control plasma membranes were similar. Purified VLPs contained the major phospholipids (phosphatidylcholine and phosphatidylethanolamine) and sphingolipids (glucosyl-ceramide) found in the plasma membrane (FIG. 27A), and both contained free sterols as the sole neutral lipids (FIG. 27B). However, immunodetection of a plasma membrane protein marker (ATPase) in purified VLP extracts showed that the VLP lipid bilayer does not contain one of the major proteins associated with plant plasma membranes, suggesting that host proteins may have been excluded from the membranes during the process of VLPs budding from the plant cells (FIG. 27C).

Example 7

Immunogenicity of the 115 VLPs and Effect of Route of Administration

Figure 20A:
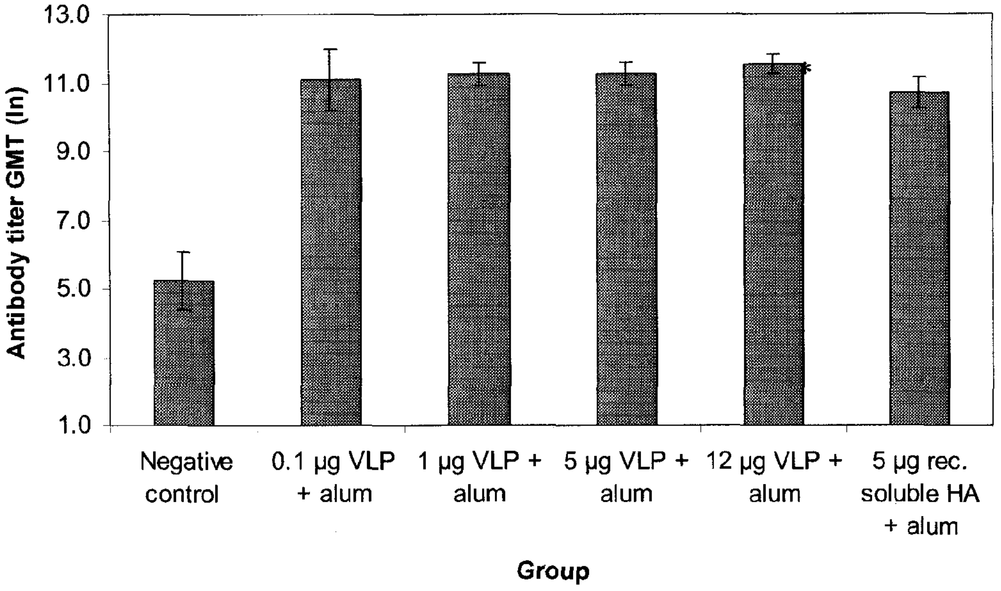
FIG. 20(A) Antibody responses of mice immunized through intramuscular injection.

Mice were administered plant-made H5 VLPs by intramuscular injection, or intranasal (inhalation). 0.1 to 12 ug of VLPs were injected intramuscularly into mice, with alum as an adjuvant, according to the described methods. Peak antibody titers were observed with the lowest antigen quantity, in a similar magnitude to that of 5 ug recombinant, soluble hemagglutinin (H5) (FIG. 20A).

Figure 20B:
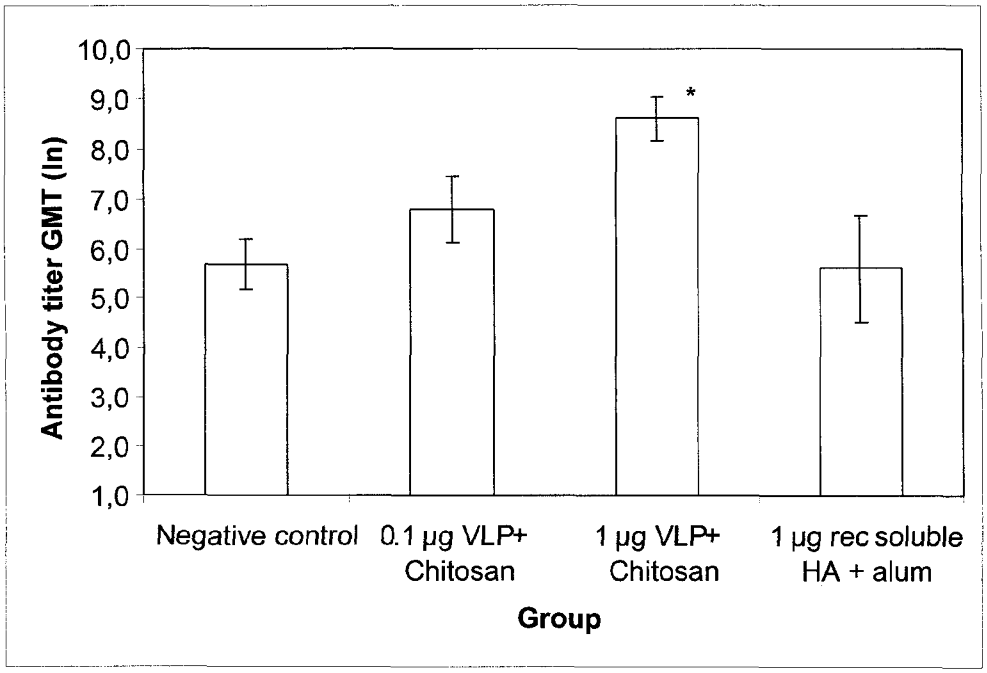
FIG. 20(B) Antibody responses of mice immunized through intranasal administration. Antibody responses were measured against inactivated whole H5N1 viruses (A/Indonesia/5/05). GMT: geometric mean titer. Values are the GMT (ln) of reciprocal end-point titers of five mice per group. Bars represent mean deviation. *p<0.05 compared to recombinant soluble H5.

0.1 to 1 ug plant-made H5 VLPs were administered intranasally with a chitosan adjuvant provided for an antibody response greater than that of the recombinant soluble H5 with an alum adjuvant (FIG. 20B).

For both administration routes, and over a range of antigen quantities, seroconversion was observed in all of the mice tested. Recombinant H5 soluble antigen conferred low (<1/40) or negligible (1<1/10 for the non-adjuvanted recombinant H5) HI titres.

Example 8

Hemagglutination-inhibition Antibody Titer (HAI) H5 VLP

Figure 21A:
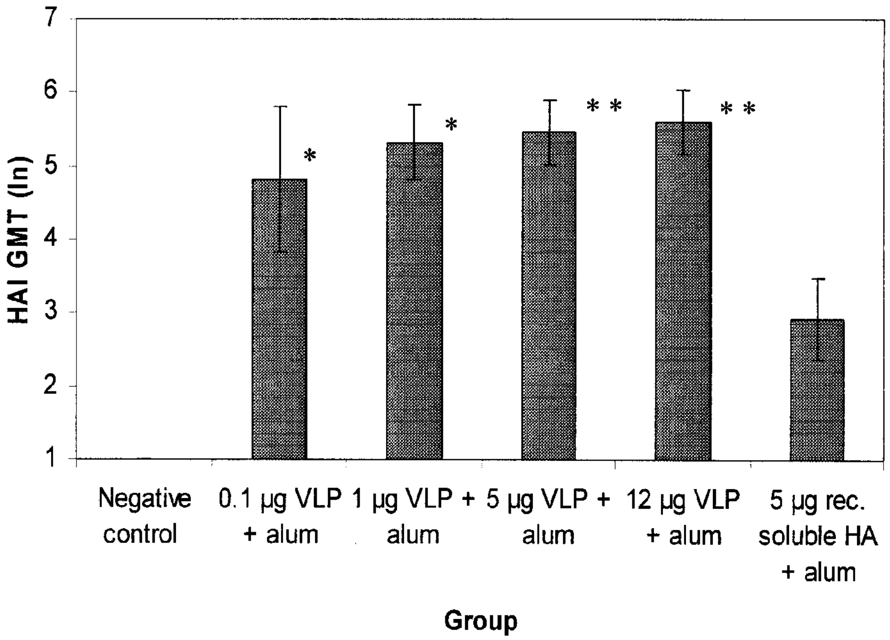
FIG. 21(A) Antibody responses of mice immunized through intramuscular injection.

FIG. 21A, B illustrates the hemagglutination inhibition (HAI) antibody response 14 days following a “boost” with plant-made H5 VLP, or recombinant soluble H5. The lowest dose of antigen (0.1 ug) when administered intramuscularly produced a superior HAI response to a 10-fold greater administration (5 ug) of recombinant soluble H5. Increasing doses of H5 VLP provided a modest increase in HAI over the lowest dose.

Figure 21B:
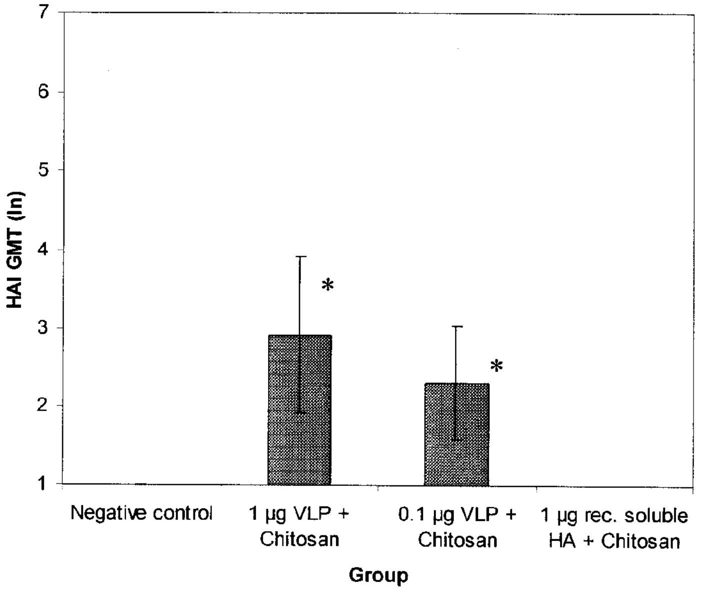
FIG. 21(B) Antibody responses of mice immunized through intranasal administration. HAI antibody responses were measured using inactivated whole H5N1 viruses (A/Indonesia/5/05). GMT: geometric mean titer. Values are the GMT (ln) of reciprocal end-point titers of five mice per group. Bars represent mean deviation. *p<0.05 and **p<0.01 compared to recombinant soluble H5.

HAI response following intranasal administration was significantly increased in mice administered plant-made H5 VLPs (1.0 or 0.1 ug) compared to those administered 1 ug recombinant soluble H5, which was similar to the negative control. All mice immunized by intramuscular injection of H5 VLPs (from 0.1 to 12 μg) had higher HAI titers than mice immunised with the control H5 antigen (FIG. 21A). For the same dose of 5 VLPs induced HAI titers 20 times higher than the corresponding dose of the control H5 antigen. VLPs also induced significantly higher HAI titers than the control HA antigen when delivered through the intranasal route (FIG. 21*b*). For a given dose of H5 VLP the levels of HAI titers were lower in mice immunised intranasally than for mice immunised intramuscularly; 1 μg VLP induced a mean HAI titer of 210 when administered i.m. while the same dose induced a mean HAI titer of 34 administered i.n.

Figure 24:
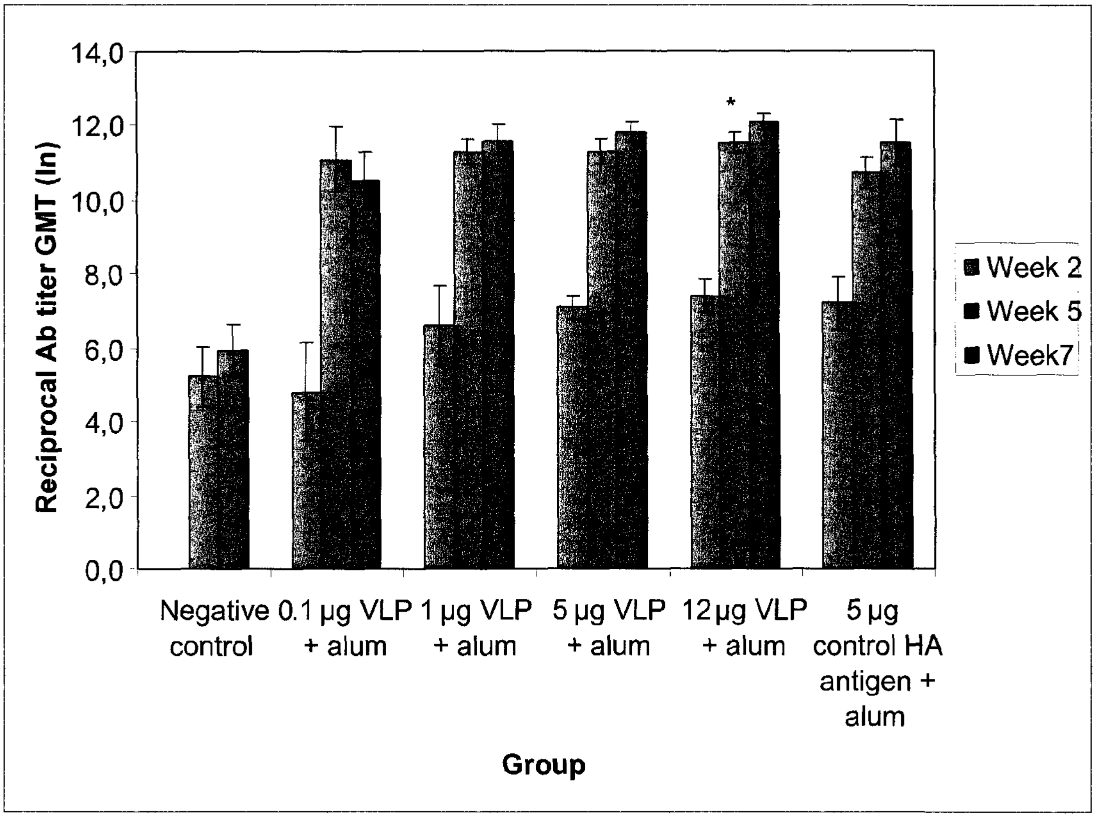
FIG. 24 shows antibody titer against homologous whole inactivated viruses (A/Indonesia/5/05), 14 days weeks after first dose (week 2), 14 days after boost (week 5) or 30 days after boost (week 7) from Balb/c mice immunized with H5 VLP (A/Indonesia/5/2005 (H5N1)). GMT: geometric mean titer. Values are the GMT (ln) of reciprocal end-point titers of five mice per group. *p<0.05 compared to recombinant soluble H5.

When administered intramuscularly, all doses of VLPs induced high level of antibodies capable of binding homologous whole inactivated viruses (FIGS. 20*a* and 24). No significant difference was found between the plant-made VLP vaccine and the control H5 antigen (except the 12 μg VLP group 14 days after boost), as both antigen preparations induce high binding antibody titers against the homologous strain. However, when administered intranasally, VLPs induced higher binding antibody titers in than did the control H5 antigen (FIG. 20*b*). When mixed with Chitosan, immunization with one microgram VLP induced a reciprocal mean Ab titer of 5 500, 8.6 times higher than the level found in mice immunized with 1 μg of the control HA antigen (reciprocal mean Ab titer of 920).

The immunogenicity of the plant-derived influenza VLPs was then investigated through a dose-ranging study in mice. Groups of five BALB/c mice were immunized intramuscularly twice at 3-week intervals with 0.1 μg to 12 μg of VLPs containing HA from influenza A/Indonesia/5/05 (H5N1) formulated in alum (1:1 ratio). Hemagglutination-inhibition titers (HI or HAI), using whole inactivated virus antigen (A/Indonesia/5/05 (H5N1)), were measured on sera collected 14 days after the second immunization with doses of VLP as low as 0.1 μg induced the production of antibodies that inhibited viruses from agglutinating erythrocytes at high dilutions (FIG. 21A). Parallel immunization of mice with 5 μg of non-VLP alum-adjuvanted control H5 antigen (also from A/Indonesia/5/05) induce an HI response that was 2-3 logs lower than that achieved with the lowest VLP dose.

For both administration routes, and over a range of antigen quantities, the HAI response is superior in mice administered VLPs.

Example 9

Effect of Adjuvant on Immunogenicity of H5 VLPs

Plant-made H5 VLPs have a plasma membrane origin (FIG. 19, Example 5).

Without wishing to be bound by theory, enveloped viruses or VLPs of enveloped viruses generally acquire their envelope from the membrane they bud through. Plant plasma membranes have a phytosterol complement that is rarely, if ever found in animal cells, and several of these sterols have been demonstrated to exhibit immunostimulatory effects.

Plant-made H5 VLPs were administered intramuscularly (FIG. 22A) or intranasally (FIG. 22B) to mice in the presence or absence of an adjuvant, and the HAI (hemagglutination inhibition antibody response) determined. VLPs, in the presence or absence of an added adjuvant (alum or chitosan, as in these examples) in either system of administration demonstrated a significantly greater HAI hemagglutinin inhibition than recombinant soluble H5. Even in the absence of an added adjuvant (i.e. alum or chitosan), plant-made H5 VLPs demonstrate a significant HAI, indicative of a systemic immune response to administration of the antigen.

Alum enhanced the mean level of HAI titers by a factor of 5 for intramuscular administration of VLP (FIG. 22*a*) and by a factor of 3.7 for the control H5 antigen. When administered i.m., 5 μg VLPs induced a mean HAI titer 12 times higher than the corresponding dose of control H5 antigen. Chitosan did not boost the mean HAI level of the control H5 antigen (FIG. 22*b*) while it increased the mean HAI level of mice immunised with 1 μg VLP administered i.n. by a factor of 5-fold.

Example 10

Antibody Isotypes

Mice administered plant-made H5 VLPs or recombinant soluble H5 in the presence or absence of alum as an added adjuvant demonstrate a variety of immunoglobulin isotypes (FIG. 23A).

In the presence of an added adjuvant, the antibody isotype profiles of VLPs and the recombinant H5 are similar, with IgG1 being the dominant isotype. When VLPs or recombinant H5 are administered without an added adjuvant, IgG1 response is reduced, but remains the dominant isotype response to VLPs, with IgM, IgG2a, IgG2B and IgG3 maintaining similar titers as in the presence of an added adjuvant. IgG1, IgG2a, and IgG2b titers are markedly reduced when recombinant H5 is administered without an added adjuvant (FIG. 23A).

These data, therefore, demonstrate that plant-made VLPs do not require an added adjuvant to elicit a antibody response in a host.

Figure 23B:
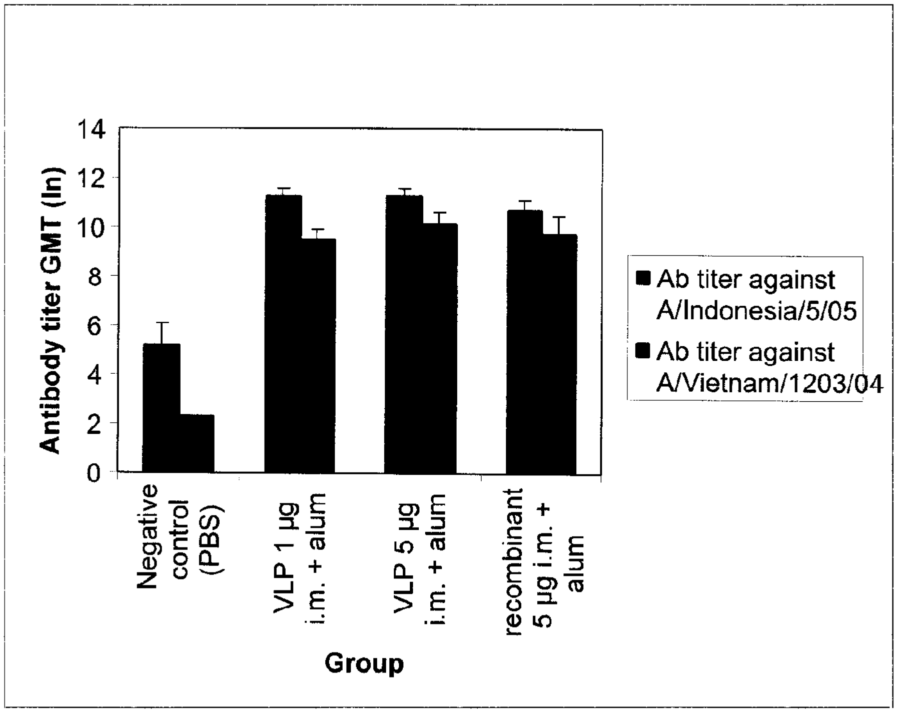
FIG. 23 shows antibody response toH5 VLP (A/Indonesia/5/2005 (H5N1)) administration.

Antibody titers against whole inactivated influenza virus strains (A/Indonesia/5/05; A/Vietnam/1203/04)I in mice administered plant-made VLPs or soluble recombinant HA intramuscularly in the presence of an added antigen are illustrated in FIG. 23B. No significant difference is observed in the antibody titers for these influenza strains in mice administered 1 ug or 5 ug of VLPs or 5 ug of soluble HA.

Example 11

Cross-reactivity of Serum Antibodies Induced by the H5 VLP Vaccine

Cross-reactivity of serum antibodies induced by H5 VLP was assessed against whole inactivated influenza viruses of different strains. All VLP doses (from 0.1 to 12 μg) as well as 5 μg of control HA antigen induced high binding antibody titers against a clade 1 strain (A/Vietnam/1194/04), the homologous strain A/Indonesia/5/05 of clade 2.1, and a clade 2.2 strain A/turkey/Turkey/1/05 (FIG. 25A).

However, only the plant-made VLP induced HAI titer against the A/turkey/Turkey/1/05 strain (FIG. 25*b*). HAI titers for the A/Indonesia/5/05 were high for VLPs.

Example 12

Cross-protection Conferred by Immunization with Plant-made H5 VLP

Mice that previously had been administered a two-dose regimen of A/Indonesia/5/05 H5 VLPs as described, were subsequently challenged intranasally with influenza A/Turkey/582/06 (H5N1) ("Turkey H5N1") infectious virus, and observed. The dose administered, per animal, was 10 $LD_{50}$ ($4.09\times10^5$ $CCID_{50}$).

By 7 days post-challenge, only 37.5% of the mice administered the PBS vaccine control had survived exposure to Turkey H5N1 (FIG. 26A). 100% of animals administered the control antigen (HA) or 1, 5 or 15 ug of Indonesia H5 VLPs survived up to 17 days post-challenge, when the experiment was terminated.

Figure 26B:
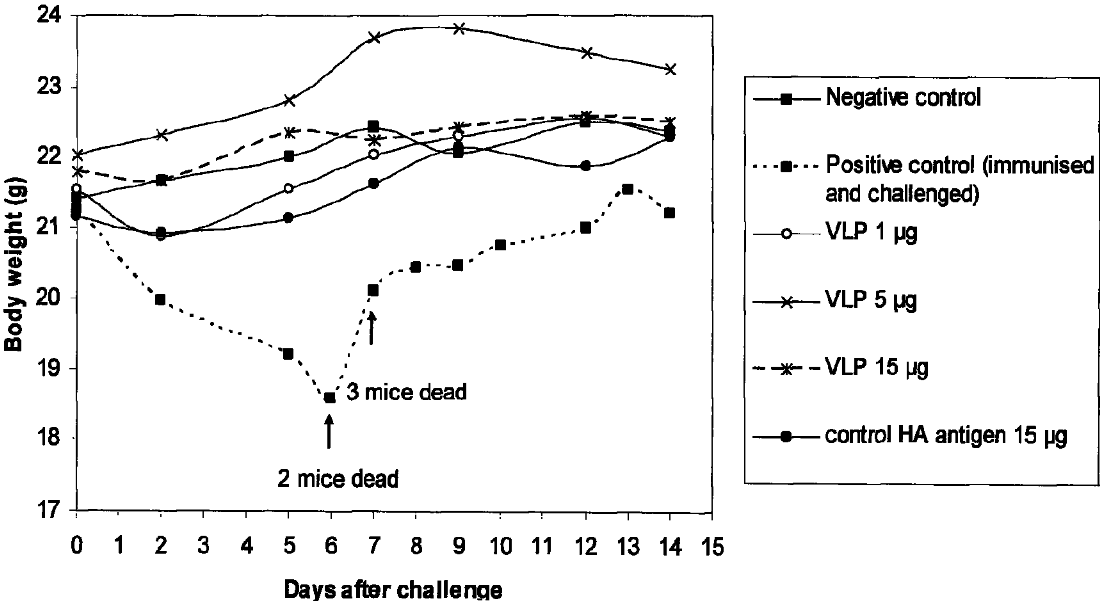

Body mass of the mice was also monitored during the experiment, and the average mass of the surviving mice plotted (FIG. 26B). Mice administered 1, 5 or 15 ug of the Indonesia H5 VLPs before challenge did not lose any appreciable mass during the course of the experiment, and in particular mice administered 5 ug of the VLPs appear to have gained significant mass. Negative control mice (no Turkey H5N1 challenge) did not appreciably gain or lose body mass. Positive control mice (not administered VLPs, but challenged with Turkey H5N1) exhibited significant loss of body mass during the course of the experiment, and three of these mice died. As body mass is an average of all mice in the cohort, removal of the 'sickest' mice (the 3 that died) may lead to an apparent overall increase in mass, however note that the average body mass of the positive control cohort is still significantly below that of the negative or the VLP-treated cohorts.

These data, therefore, demonstrate that plant-made influenza VLPs comprising the H5 hemagglutinin viral protein induce an immune response specific for pathogenic influenza strains, and that virus-like particles may bud from a plant plasma membrane.

These data, therefore, demonstrate that plants are capable of producing influenza virus-like particles, and also for the first time, that virus-like particles can bud from a plant plasma membrane.

Further, using the current transient expression technology, a first antigen lot was produced only 16 days after the sequence of the target HA was obtained. Under the current yields for H5 VLPs, and at an exemplary dose of 5 µg per subject, each kg of infiltrated leaf may produce ~20,000 vaccine doses. This unique combination of platform simplicity, surge capacity and powerful immunogenicity provides for, among other embodiments, a new method response in the context of a pandemic.

Example 13

Figure 46:
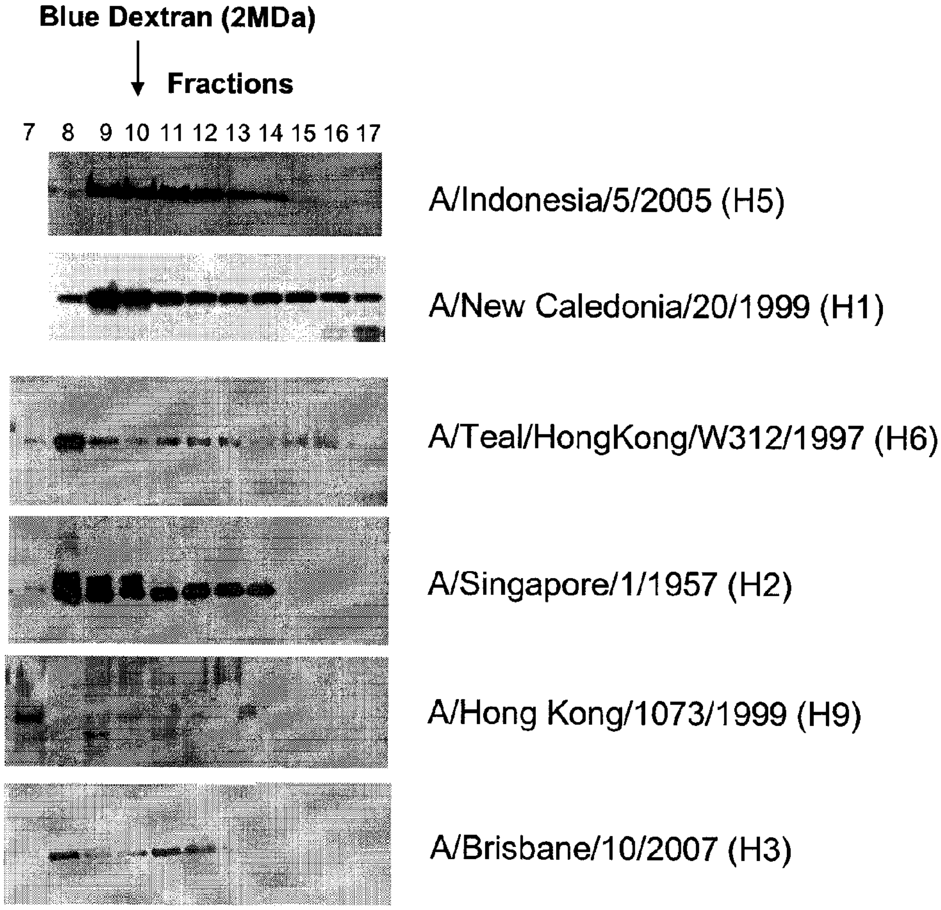
FIG. 46 shows immunodetection (western blot) of elution fractions 7-17 of plant-produced VLPs, following size exclusion chromatography. The elution peak (fraction 10) of BlueDextran is indicated by the arrow. Hemagglutinin subtypes H1, H2, H3, H5, H6 and H9 are shown. Hemagglutinin is detected in fractions 7-14, corresponding to the elution of VLPs.

Characterization of Hemagglutinin-containing (H1, H2, H3, H5, H6 and H9) Structures in Plant Extracts Using Size Exclusion Chromatography The assembly of plant-produced influenza hemagglutinin of different subtypes into high molecular weight structures was assessed by gel filtration. Crude or concentrated protein extracts from AGL1/660-, AGL1/540-, AGL1/783-, AGL1/780-, AGL1/785- and AGL1/790-infiltrated plants (1.5 mL) were fractionated by size exclusion chromatography (SEC) on Sephacryl™ S-500 HR columns (GE Healthcare Bio-Science Corp., Piscataway, N.J., USA). As shown in FIG. 46, Blue Dextran (2 MDa) elution peaked early in fraction 10. When proteins from 200 µL of each SEC elution fraction were concentrated (5-fold) by acetone-precipitation and analyzed by Western blotting (FIG. 46), hemagglutinins were primarily found in fractions 7 to 14, indicating the incorporation of HA into VLPs. Without wishing to be bound by theory, this suggests that the HA protein had either assembled into a large superstructure or that it has attached to a high molecular weight structure, irrespectively of the subtype produced. In FIG. 46, H1 from strain A/New Caledonia/20/1999 and H3 from strain A/Brisbane/10/2007 were produced using PDI signal peptide-containing cassettes. The results obtained indicate that replacement of the native signal peptide by that of alfalfa PDI does not affect the abiity of HA to assemble into particles.

Example 14

Transient Expression of Seasonal Influenza Virus Hemagglutinin by Agroinfiltration in *N. benthamiana* Plants Using the Wild-type Nucleotide Sequence The ability of the transient expression system to produce seasonal influenza hemagglutinins was determined through the expression of the H1 subtype from strains A/Brisbane/59/2007 (H1N1) (plasmid #774), A/New Caledonia/20/1999 (H1N1) (plasmid #540) and A/Solomon Islands/3/2006 (H1N1) (plasmid #775), of the H3 subtype from strains A/Brisbane/10/2007 (plasmid #776) and A/Wisconsin/67/2005 (plasmid #777) and of the B type from strains B/Malaysia/2506/2004 (Victoria lineage) (plasmid #778) and B/Florida/4/2006 (Yamagata lineage) (plasmid #779). The hemagglutinin gene coding sequences were first assembled in the plastocyanin expression cassette—promoter, 5'UTR, 3'UTR and transcription termination sequences from the alfalfa plastocyanin gene—and the assembled cassettes were inserted into to a pCAMBIA binary plasmid. The plasmids were then transfected into *Agrobacterium* (AGL1), producing *Agrobacterium* strains AGL1/774, AGL1/540, AGL1/775, AGL1/776, AGL1/777, AGL1/778 and AGL1/779, respectively.

Figure 47:
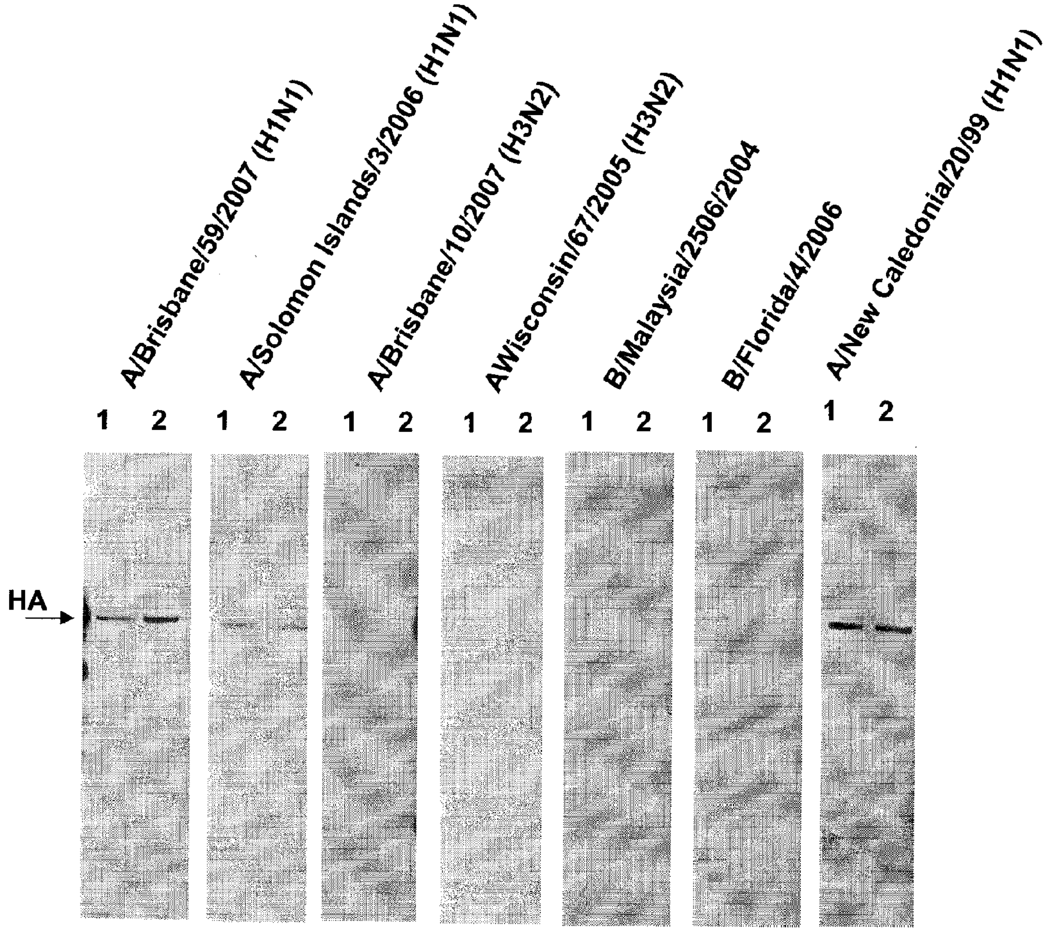
FIG. 47 shows an immunoblot analysis of expression of a series of hemagglutinin from annual epidemic strains. Ten and twenty micrograms of leaf protein extracts were loaded in lanes 1 and 2, respectively, for plants expressing HA from various influenza strains (indicated at the top of the immunoblots).

*N. benthamiana* plants were infiltrated with AGL1/774, AGL1/540, AGL1/775, AGL1/776, AGL1/777, AGL1/778 and AGL1/779 and the leaves were harvested after a six-day incubation period. To determine whether H1 accumulated in the agroinfiltrated leaves, protein was first extracted from infiltrated leaf tissue and analyzed by Western blotting using anti-HA antibodies (see Table 6 for the antibodies and conditions used for the detection of each HA subtype). For the HA from H1 strains, a unique band of approximately 72 kDa was detected in extracts (FIG. 47), corresponding in size to the uncleaved HA0 form of influenza hemagglutinin. This demonstrated that expression of different annual epidemic strains of hemagglutinin in infiltrated leaves results in the accumulation of the uncleaved translation product. Using these expression and immunodetection strategies, the expression of influenza HA from H3 subtype or B type was not detected in the crude protein extracts (FIG. 47).

Example 15

Transient Expression of Potential Pandemic Influenza Virus Hemagglutinin by Agroinfiltration in *N. benthamiana* Plants Using the Wild-type Nucleotide Sequence The ability of the transient expression system to produce potential influenza hemagglutinins was determined through the expression of the H5 subtype from strains A/Anhui/1/2005 (H5N1) (plasmid #781), A/Indonesia/5/2005 (H5N1) (plasmid #660) and A/Vietnam/1194/2004 (H5N1) (plasmid #782), the H2 subtype from strain A/Singapore/1/1957 (H2N2) (plasmid #780), the H6 from strain A/Teal/Hong Kong/W312/1997 (H6N1) (plasmid #783), the H7 for strain A/Equipe/Prague/1956 (H7N7) (plasmid #784) and finally H9 from strain A/Hong Kong/1073/1999 (H9N2) (plasmid #785). The hemagglutinin gene coding sequences were first assembled in the plastocyanin expression cassette—promoter, 5'UTR, 3'UTR and transcription termination sequences from the alfalfa plastocyanin gene—and the assembled cassettes were inserted into to a pCAMBIA binary plasmid. The plasmids were then transfected into *Agrobacterium* (AGL1), producing *Agrobacterium* strains AGL1/781, AGL1/660, AGL1/782, AGL1/780, AGL1/783, AGL1/784 and AGL1/785.

Figure 48A:
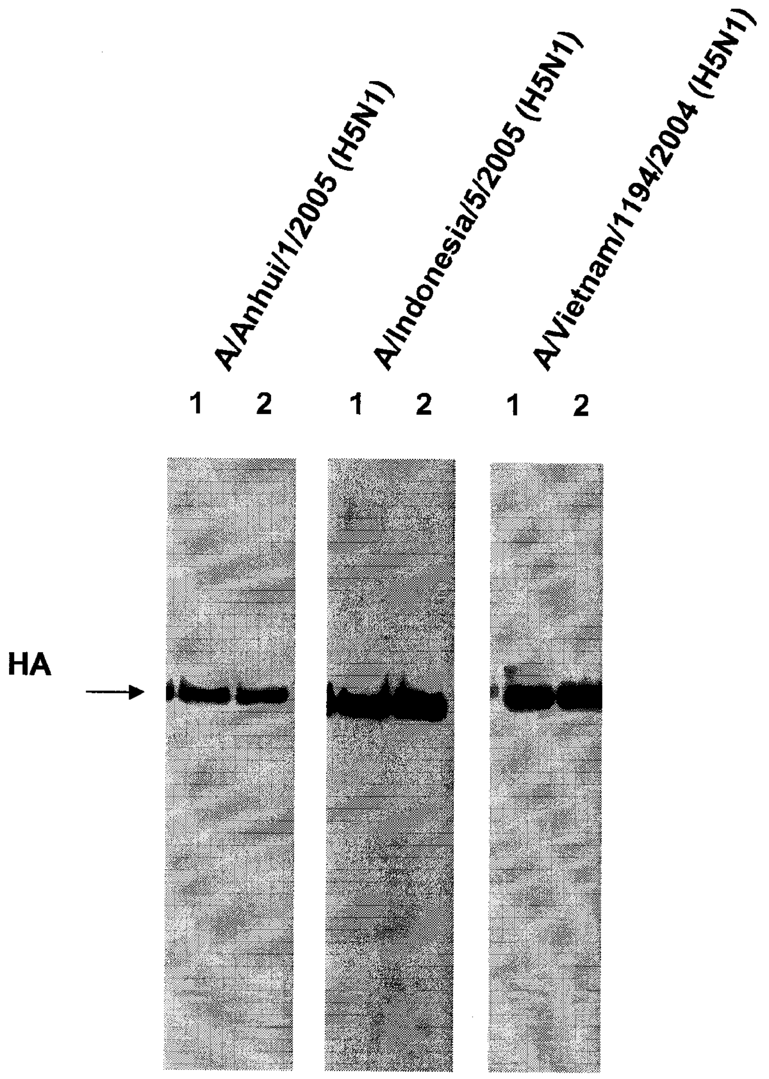
FIG. 48A shows an immunoblot analysis of expression of a series of H5 hemagglutinins from potential pandemic strains. Ten and twenty micrograms of protein extracts were loaded in lanes 1 and 2, respectively.
Figure 48B:
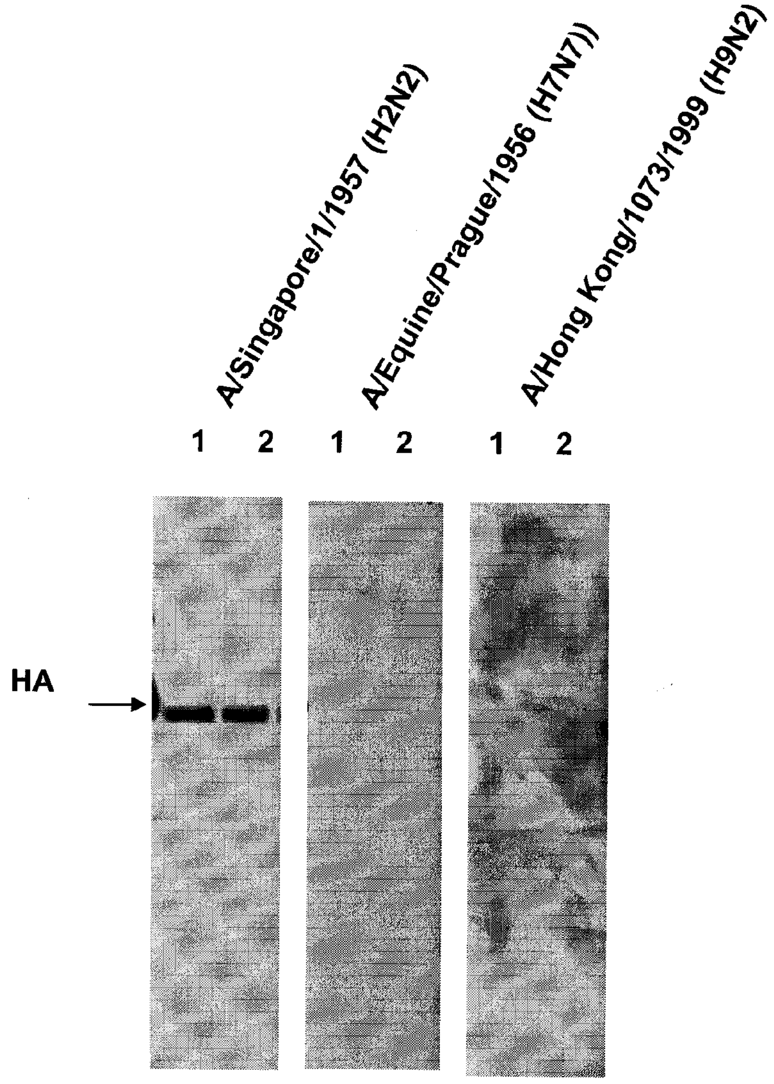
FIG. 48B shows an immunoblot analysis of expression of H2, H7 and H9 hemagglutinin from selected influenza strains. Ten and twenty micrograms of protein extracts were loaded in lanes 1 and 2, respectively.

*N. benthamiana* plants were infiltrated with AGL1/781, AGL1/660, AGL1/782, AGL1/780, AGL1/784 and AGL1/785, and the leaves were harvested after a six-day incubation period. To determine whether H5 accumulated in the agroinfiltrated leaves, protein was first extracted from infiltrated leaf tissue and analyzed by Western blotting using appropriate anti-HA antibodies (see Table 6 for the antibodies and conditions used for the detection of each HA subtype). A unique band of approximately 72 kDa was detected in extracts of plants transformed with H5 and H2 expression constructs (FIGS. 48*a* and *b*), corresponding in size to the uncleaved HA0 form of influenza hemagglutinin. This demonstrated that expression of different potential pandemic strains of hemagglutinin in infiltrated leaves results in the accumulation of the uncleaved translation product. Using these expression and immunodetection strategies, the expression of influenza HA from H7 and H9 was not detected in the crude protein extracts (FIG. 48*b*).

Example 16

Transient Expression of 115 by Agroinfiltration in *N. tabacum* Plants

The ability of the transient expression system to produce influenza hemagglutinin in leaves of *Nicotiana tabacum* was analysed through the expression of the H5 subtype from strain A/Indonesia/5/2005 (H5N1) (plasmid #660). The hemagglutinin gene coding sequences were first assembled in the plastocyanin expression cassette—promoter, 5'UTR, 3'UTR and transcription termination sequences from the alfalfa plastocyanin gene—and the assembled cassettes were inserted into to a pCAMBIA binary plasmid. The plasmids was then transfected into *Agrobacterium* (AGL1), producing strain AGL1/660.

Figure 49:
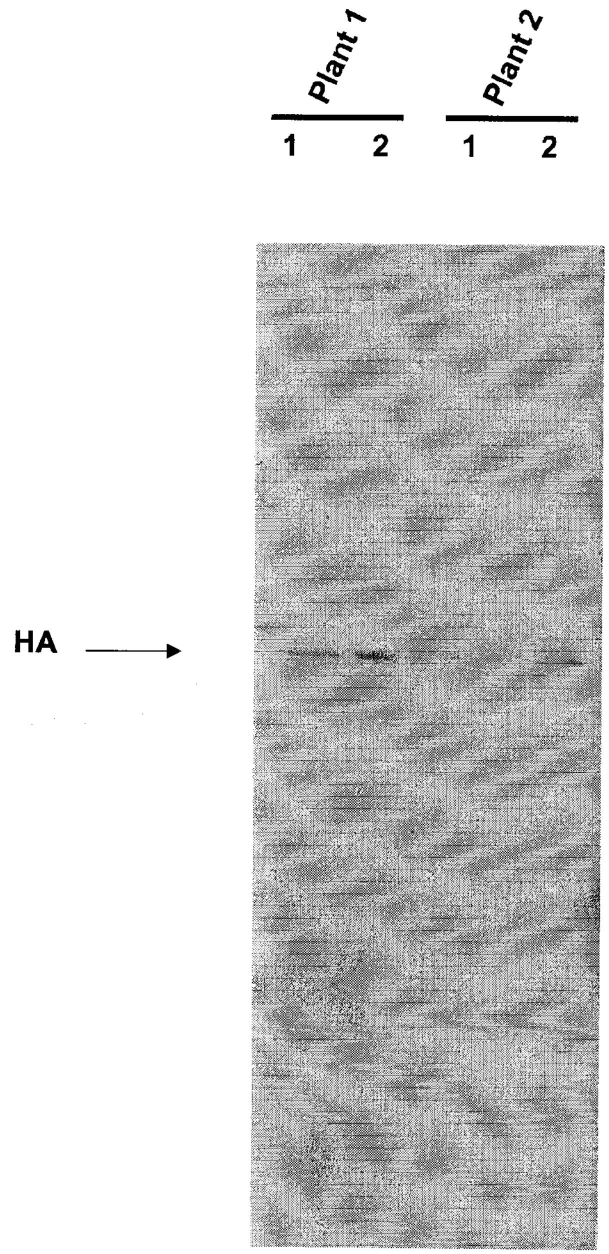
FIG. 49 shows an immunoblot of H5 from strain A/Indonesia/5/2005 in protein extracts from *Nicotiana tabacum* leaves, agroinfiltrated with AGL1/660. Two plants (plant 1 and plant 2) were infiltrated and 10 and 20 μg of soluble protein extracted from each plant were loaded in lanes 1 and 2, respectively.

*N. tabacum* plants were infiltrated with AGL1/660 and the leaves were harvested after a six-day incubation period. To determine whether H5 accumulated in the agroinfiltrated leaves, proteins were first extracted from infiltrated leaves and analyzed by Western blot using anti-H5 antibodies. A unique band of approximately 72 kDa was detected in extracts (FIG. 49), corresponding in size to the uncleaved HA0 form of influenza hemagglutinin. This demonstrated that expression of hemagglutinin in infiltrated *N. tabacum* leaves results in the accumulation of the uncleaved HA0 precursor.

Example 17

Figure 50A:
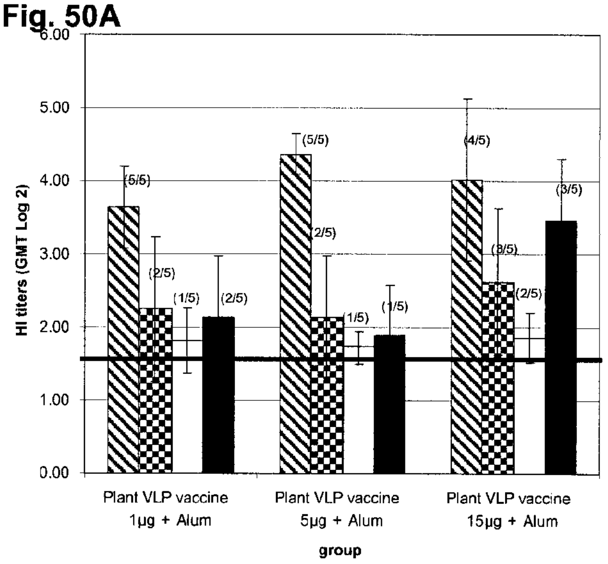
FIG. 50 shows the in vitro cross-reactivity of serum antibodies. Hemagglutination-inhibition (HI) titers in ferret sera, 14 days (A) after 1$^{st}$ immunization and (B) after 2nd boost with plant-made influenza H5 VLP (A/Indonesia/5/2005 (H5N1)). HAI antibody responses were measured using the following inactivated whole H5N1 viruses: A/turkey/Turkey/1/05, A/Vietnam/1194/04, A/Anhui/5/05 and the homologous strain A/Indonesia/5/05. Values are the GMT ($log_2$) of reciprocal end-point titers of five ferrets per group. Diagonal stripe—A/Indonesia/6/06 (clade 2.1.3); checked—A/turkey/Turkey/1/05 (clade 2.2); white bar—A/Vietnam/1194/04 (clade 1); black bar A/Anhui/5/05. Responders are indicated. Bars represent mean deviation.
Figure 50B:
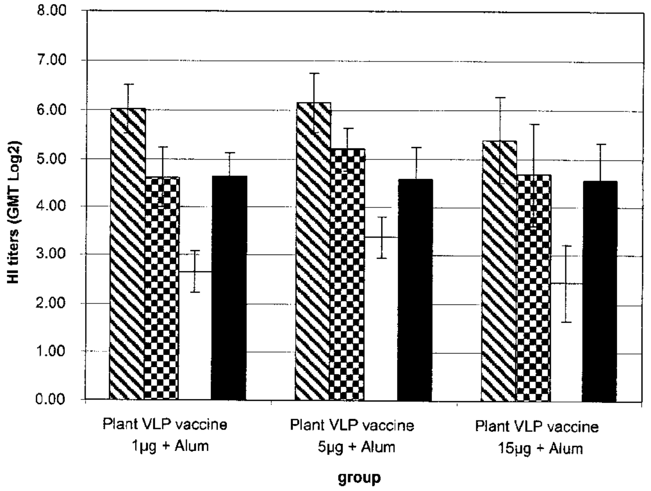

Immunogenicity of Plant-made H5N1 VLP Vaccine from A/Indonesia/5/05 (H5N1) in Ferrets A dose escalation study in ferrets was performed to evaluate the immunogenicity of plant derived VLPs. In vitro cross-reactivity of serum antibody induced by the H5 VLP vaccine at 3 doses (1, 5 and 15 ug) was assessed by hemagglutination inhibition of three other H5N1 strains—A/turkey/Turkey/1/05 (clade 2.2), A/Vietnam/1194/04 (clade 1) and A/Anhui/5/05 (all whole, inactivated virus), using serum taken 14 days after the first dose of vaccine (FIG. 50A), and 14 days after the $2^{nd}$ dose (FIG. 50 B). For all 3 dose concentrations, cross-reactivity is observed Example 18

Analysis of the Immunogenicity Results According to CHMP Criteria

The EMEA's Committee for Medicinal Products for Human Use (CHMP) (http://www.emea.europa.eu/htms/general/contacts/CHMP/CHMP.html) sets out three criteria (applied following the second dose) for vaccine efficacy: 1—Number of seroconversion or significant increase in HI titers (4-fold)>40%; 2—Mean geometric increase of at least 2.5; 3-proportion of subjects achieving an HI titer of 1/40 should be at least 70%. Analysis of these criteria in the ferret model is shown in Tables 8-11. (*) is indicative of meeting or exceeding the CHMP criteria. A summary of cross-immunogenicity analysis in relation to CHMP criteria for licensure is shown in Table 12.

Animals were assessed daily for body weight, temperature and overall condition. No sign of sickness or discomfort was recorded during the study. Body weight and temperature was within normal ranges during the study. The vaccine was safe and tolerated by the animals.

TABLE 8

Data for homologous strain (A/Indonesia/5/05)

| | | Study group | | | | | | | | |
|---|---|---|---|---|---|---|---|---|---|---|
| Day | Criteria | 1 µg | 1 µg adjuvanted | 5 µg | 5 µg adjuvanted | 7.5 µg | 15 µg | 15 µg adjuvanted | 30 µg | 5 µg ITC |
| 14 (post 1st inj.) | % 4-fold increase in HI titer | 0% | 100% | 0% | 100%* | 20% | 20% | 80%* | 0% | 0% |
| | Mean geometric increase | 0% | 7.6 | 0% | 15.6* | 1.3 | 1.2 | 11.2* | 0% | 0% |
| | % of HI titer of 1/40 | 0% | 60% | 0% | 100%* | 20% | 0% | 80%* | 0% | 0% |
| | Mean HI titer | | 38 | | 78 | | | 56 | | |
| 35 (14 days post boost) | % 4-fold increase in HI titer | 0% | 100%* | 0% | 60%* | 0% | 0% | 40%* | 0% | 0% |
| | Mean geometric increase | 0% | 10.8* | 0% | 5.9* | 0.7 | 0% | 4* | 0% | 0% |
| | % of HI titer of 1/40 | 0% | 100%* | 0% | 100%* | 0% | 0% | 100%* | 0% | 0% |
| | Mean HI titer | | 411 | | 465 | | | 217 | | |

TABLE 9

Data for heterologous strain (A/Vietnam/1194/04)

| | | Study group | | | | | | | | |
|---|---|---|---|---|---|---|---|---|---|---|
| Day | Criteria | 1 µg | 1 µg adjuvanted | 5 µg | 5 µg adjuvanted | 7.5 µg | 15 µg | 15 µg adjuvanted | 30 µg | 5 µg ITC |
| 14 (post 1st inj.) | % 4-fold increase in HI titer | | 0% | | 0% | | | 0% | | |
| | Mean geometric increase | | 1.2 | | 1.2 | | | 1.3 | | |
| | % of HI titer of 1/40 | | 0% | | 0% | | | 0% | | |
| 35 (post boost) | % 4-fold increase in HI titer | | 60% | | 80%* | | | 60% | | |
| | Mean geometric increase | | 2.3 | | 5.1* | | | 1.78 | | |
| | % of HI titer of 1/40 | | 0% | | 80%* | | | 20% | | |

TABLE 10

| Data for heterologous strain (A/turkey/Turkey/1/05) | | | | | | | | | | |
|---|---|---|---|---|---|---|---|---|---|---|
| | | Study group | | | | | | | | |
| Day | Criteria | 1 μg | 1 μg adjuvanted | 5 μg | 5 μg adjuvanted | 7.5 μg | 15 μg | 15 μg adjuvanted | 30 μg | 5 μg ITC |
| 14 (post 1st inj.) | % 4-fold increase in HI titer | | 40% | | 20% | | | 60% | | |
| | Mean geometric increase | | 1.9 | | 1.7 | | | 2.8 | | |
| | % of HI titer of 1/40 | | 40% | | 20% | | | 40% | | |
| 35 (post boost) | % 4-fold increase in HI titer | | 80%* | | 100%* | | | 80%* | | |
| | Mean geometric increase | | 10.6* | | 20.8* | | | 7.7* | | |
| | % of HI titer of 1/40 | | 100%* | | 100%* | | | 100%* | | |

TABLE 11

| Data for heterologous strain (A/Anhui/5/05) | | | | | | | | | | |
|---|---|---|---|---|---|---|---|---|---|---|
| | | Study group | | | | | | | | |
| Day | Criteria | 1 μg | 1 μg adjuvanted | 5 μg | 5 μg adjuvanted | 7.5 μg | 15 μg | 15 μg adjuvanted | 30 μg | 5 μg ITC |
| 14 (post 1st inj.) | % 4-fold increase in HI titer | | 40% | | 20% | | | 80%* | | |
| | Mean geometric increase | | 1.8 | | 1.3 | | | 6.4* | | |
| | % of HI titer of 1/40 | | 20% | | 20% | | | 80%* | | |
| 35 (post boost) | % 4-fold increase in HI titer | | 100%* | | 100%* | | | 60%* | | |
| | Mean geometric increase | | 11.8* | | 14.4* | | | 3* | | |
| | % of HI titer of 1/40 | | 100%* | | 80%* | | | 80%* | | |

TABLE 12

| Summary of cross-immunogenicity analysis in relation to CHMP criteria for licensure. | | | | |
|---|---|---|---|---|
| | | Study group | | |
| Strain | Criteria | 1 μg adjuvanted | 5 μg adjuvanted | 15 μg adjuvanted |
| A/turkey/Turkey/ | % 4-fold increase in HI titer | 80%* | 100%* | 80%* |
| 1/05 | Mean geometric increase | 10.6* | 20.8* | 7.7* |
| (clade 2.2 | % of HI titer of 1/40 | 100%* | 100%* | 100%* |
| A/Anhui/1/05 | % 4-fold increase in HI titer | 100%* | 100%* | 60%* |
| (clade 2.3) | Mean geometric increase | 11.8* | 14.4* | 3* |
| | % of HI titer of 1/40 | 100%* | 80%* | 80%* |
| A/Vietnam/ | % 4-fold increase in HI titer | 60% | 80%* | 60% |
| 1194/04 | Mean geometric increase | 2.3 | 7.1* | 1.78 |
| (clade 1) | % of HI titer of 1/40 | 0% | 80%* | 20% |

Example 19

Selection of Hemagglutinin Nucleotide Sequences

The nucleotide sequences of the HA were retrieved from an influenza sequence database (see URL: flu.lanl.gov), or the NCBI influenza virus resource (Bao et al., 2008. J. Virology 82(2): 596-601; see URL: ncbi.nlm.nih.gov/genomes/FLU/FLU.html). For several of the HA nucleic acid sequences, multiple entries are listed in the databases (Table 13). Some variation is associated primarily with the culture system (Origin—MDCK, egg, unknown, viral RNA/clinical isolate); for example, the glycosylation site at position 194 (mature protein numbering) of the HA is absent when type B influenza virus is expressed in allantoic fluid of eggs (see also Chen et al., 2008). For some sequences, domains may be lacking (e.g. incomplete clones, sequencing artifacts, etc.). Domains and sub-domains of influenza hemagglutinin are discussed generally in the Descrition. Domains or sub-domains of a first sequence may be combined with a domain from a second existing sequence e.g. the signal peptide of a first strain sequence may be combined with the balance of the hemagglutinin coding sequence from a second strain to provide a complete coding sequence.

TABLE 13

| Variation in Influenza subtypes for selected HA coding sequences | | | | | | | | |
|---|---|---|---|---|---|---|---|---|
| | Strain | Sequence database reference No. | Origin | SP | HA1 | HA2 | DTm | Divergence |
| H1 | A/Solomon Islands/3/2006 | ISDN231558 (Vaccine rec.) | MDCK | Y | Y | Y | Y | 189: R ou G, 220: K (MDCK) T(Egg), 249: Q (MDCK) R(Egg), 550: L (MDCK) R (Egg) |

TABLE 13-continued

Variation in Influenza subtypes for selected HA coding sequences

| | Strain | Sequence database reference No. | Origin | SP | HA1 | HA2 | DTm | Divergence |
|---|---|---|---|---|---|---|---|---|
| | A/Solomon Islands/3/2006 | ISDN238190 | Egg | Y | Y | Y | Y | 189: R ou G, 220: K (MDCK) T(Egg), 249: Q (MDCK) R(Egg), 550: L (MDCK) R (Egg) |
| | A/Solomon Islands/3/2006 | EU100724 | ? | Y | Y | Y | Y | 189: R ou G, 220: K (MDCK) T(Egg), 249: Q (MDCK) R(Egg), 550: L (MDCK) R (Egg) |
| | A/Solomon Islands/3/2006 | ISDN220951 | MDCK | Y | Y | N | N | 189: R ou G, 220: K (MDCK) T(Egg), 249: Q (MDCK) R(Egg), 550: L (MDCK) R (Egg) |
| | A/Solomon Islands/3/2006 | ISDN220953 | Egg | Y | Y | N | N | 189: R ou G, 220: K (MDCK) T(Egg), 249: Q (MDCK) R(Egg), 550: L (MDCK) R (Egg) |
| | A/Solomon Islands/3/2006 | EU124137 | Egg | Y | Y | N | N | 189: R ou G, 220: K (MDCK) T(Egg), 249: Q (MDCK) R(Egg), 550: L (MDCK) R (Egg) |
| | A/Solomon Islands/3/2006 | EU124135 | MDCK | Y | Y | N | N | 189: R ou G, 220: K (MDCK) T(Egg), 249: Q (MDCK) R(Egg), 550: L (MDCK) R (Egg) |
| | A/Solomon Islands/3/2006 | EU124177 | MDCK | Y | Y | Y | Y | 189: R ou G, 220: K (MDCK) T(Egg), 249: Q (MDCK) R(Egg), 550: L (MDCK) R (Egg) |
| H1 | A/Brisbane/59/2007 | ISDN282676 | MDCK | Y | Y | Y | | 203: D/I/N D est le plus abondant chez les H1 |
| | A/Brisbane/59/2007 | ISDN285101 | Egg | Y | Y | N | N | 203: D/I/N D est le plus abondant chez les H1 |
| | A/Brisbane/59/2007 | ISDN285777 | Egg | Y | Y | Y | Y | 203: D/I/N D est le plus abondant chez les H1 |
| | A/Brisbane/59/2007 | ISDN282677 | Egg | Y | Y | Y | Y | 203: D/I/N D est le plus abondant chez les H1 |
| H3 | A/Brisbane/10/2007 | ISDN274893 | Egg | Y | Y | Y | Y | 202: V/G, 210: L/P, 215: del Ala, 242: S/I |
| | A/Brisbane/10/2007 | ISDN257648 | MDCK | N | Y | Y | Y | 202: V/G, 210: L/P, 215: del Ala, 242: S/I |
| | A/Brisbane/10/2007 | ISDN256751 | Egg | Y | Y | Y | Y | 202: V/G, 210: L/P, 215: del Ala, 242: S/I |
| | A/Brisbane/10/2007 | ISDN273757 | Egg | Y | Y | Y | Y | 202: V/G, 210: L/P, 215: del Ala, 242: S/I |
| | A/Brisbane/10/2007 | ISDN273759 | Egg | Y | Y | Y | Y | 202: V/G, 210: L/P, 215: del Ala, 242: S/I |
| | A/Brisbane/10/2007 | EU199248 | Egg | N | Y | Y | Y | 202: V/G, 210: L/P, 215: del Ala, 242: S/I |
| | A/Brisbane/10/2007 | EU199366 | Egg | Y | Y | Y | Y | 202: V/G, 210: L/P, 215: del Ala, 242: S/I |
| | A/Brisbane/10/2007 | ISDN257043 | Egg | N | Y | Y | Y | 202: V/G, 210: L/P, 215: del Ala, 242: S/I |
| | A/Brisbane/10/2007 | EU199250 | MDCK | N | Y | Y | Y | 202: V/G, 210: L/P, 215: del Ala, 242: S/I |
| | A/Brisbane/10/2007 | ISDN275357 | Egg | N | Y | N | N | 202: V/G, 210: L/P, 215: del Ala, 242: S/I |
| | A/Brisbane/10/2007 | ISDN260430 | Egg | N | Y | Y | Y | 202: V/G, 210: L/P, 215: del Ala, 242: S/I |
| H3 | A/Wisconsin/67/2005 | ISDN131464 (vaccine rec.) | ? | N | Y | Y | N | 138: A/S<br>156: H/Q<br>186: G/V<br>196: H/Y |
| | A/Wisconsin/67/2005 | DQ865947 | ? | N | Y | partiel | N | 138: A/S<br>156: H/Q<br>186: G/V<br>196: H/Y |
| | A/Wisconsin/67/2005 | EF473424 | ? | N | Y | Y | N | 138: A/S<br>156: H/Q<br>186: G/V<br>196: H/Y |

TABLE 13-continued

Variation in Influenza subtypes for selected HA coding sequences

| | Strain | Sequence database reference No. | Origin | SP | HA1 | HA2 | DTm | Divergence |
|---|---|---|---|---|---|---|---|---|
| | A/Wisconsin/67/2005 | ISDN138723 | Egg | N | Y | Y | Y | 138: A/S<br>156: H/Q<br>186: G/V<br>196: H/Y |
| | A/Wisconsin/67/2005 | EF473455 | Egg | N | Y | Y | Y | 138: A/S<br>156: H/Q<br>186: G/V<br>196: H/Y |
| | A/Wisconsin/67/2005 | ISDN138724 | ? | N | Y | Y | Y | 138: A/S<br>156: H/Q<br>186: G/V<br>196: H/Y |
| B | B/Malaysia/2506/2004 | ISDN126672 (vaccine rec.) | Egg | Y | Y | N | N | 120 K/N<br>210 T/A |
| | B/Malaysia/2506/2004 | EF566433 | Egg | Y | Y | N | N | 120 K/N<br>210 T/A |
| | B/Malaysia/2506/2004 | ISDN231265 | Egg | Y | Y | Y | Y | 120 K/N<br>210 T/A |
| | B/Malaysia/2506/2004 | ISDN231557 | MDCK | Y | Y | Y | Y | 120 K/N<br>210 T/A |
| | B/Malaysia/2506/2004 | EF566394 | MDCK | Y | Y | N | N | 120 K/N<br>210 T/A |
| | B/Malaysia/2506/2004 | EU124274 | Egg | Y | Y | Y | Y | 120 K/N<br>210 T/A |
| | B/Malaysia/2506/2004 | EU124275 | MDCK | Y | Y | Y | Y | 120 K/N<br>210 T/A |
| | B/Malaysia/2506/2004 | ISDN124776 | MDCK | Y | Y | N | N | 120 K/N<br>210 T/A |
| B | B/Florida/4/2006 | ISDN261649 | Egg | Y | Y | Y | N | lacking glycosylation site at position 211; 10 amino acids of DTm/cytoplasmic tail |
| | B/Florida/4/2006 | EU100604 | MDCK | N | Y | N | N | |
| | B/Florida/4/2006 | ISDN218061 | MDCK | N | Y | N | N | |
| | B/Florida/4/2006 | ISDN285778 | Egg | Y | Y | Y | Y | Includes cytoplasmic tail |
| B | B/Brisbane/3/2007 | ISDN256628 | Egg | N | Y | N | N | lacking glycosylation site at position 211 |
| | B/Brisbane/3/2007 | ISDN263782 | Egg | Y | Y | Y | Y | lacking glycosylation site at position 211 |
| | B/Brisbane/3/2007 | ISDN263783 | MDCK | Y | Y | Y | Y | |
| H5 | A/Viet Nam/1194/2004 | ISDN38686 (Vaccine rec.) | ? | Y | Y | Y | Y | |
| | A/Viet Nam/1194/2004 | AY651333 | ? | Y | Y | Y | Y | |
| | A/Viet Nam/1194/2004 | EF541402 | ? | Y | Y | Y | Y | |
| H5 | A/Anhui1/1/2005 | DQ37928 (vaccine rec.) | ? | Y | Y | Y | Y | |
| | A/Anhui1/1/2005 | ISDN131465 | Egg | Y | Y | Y | Y | |
| H7 | A/Chicken/Italy/13474/1999 | AJ91720 | ARN gen | Y | Y | Y | Y | |
| H7 | A/Equine/Prague/56 | AB298277 (Lab reassortant) | ? | Y | Y | Y | Y | 152 (R/G)<br>169 (T/I)<br>208 (N/D) (glycosylation site abolished) |
| | A/Equine/Prague/56 | X62552 | ? | Y | Y | Y | Y | |
| H9 | A/Hong Kong/1073/1999 | AJ404626 | ? | Y | Y | Y | Y | |
| | A/Hong Kong/1073/1999 | AB080226 | ? | N | Y | N | N | |
| H2 | A/Singapore/1/1957 | AB296074 | ? | Y | Y | Y | Y | |

TABLE 13-continued

Variation in Influenza subtypes for selected HA coding sequences

| | Strain | Sequence database reference No. | Origin | SP | HA1 | HA2 | DTm | Divergence |
|---|---|---|---|---|---|---|---|---|
| | A/Singapore/1/1957 | L20410 | RNA | Y | Y | Y | Y | |
| | A/Singapore/1/1957 | L11142 | ? | Y | Y | Y | Y | |
| H2 | A/Japan/305/1957 | L20406 | ? | Y | Y | Y | Y | |
| | A/Japan/305/1957 | L20407 | ? | Y | Y | Y | Y | |
| | A/Japan/305/1957 | CY014976 | ? | Y | Y | Y | Y | |
| | A/Japan/305/1957 | AY209953 | ? | Y | Y | N | N | |
| | A/Japan/305/1957 | J02127 | ? | Y | Y | Y | Y | |
| | A/Japan/305/1957 | DQ508841 | ? | Y | Y | Y | Y | |
| | A/Japan/305/1957 | AY643086 | ? | Y | Y | Y | N | |
| | A/Japan/305/1957 | AB289337 | ? | Y | Y | Y | Y | |
| | A/Japan/305/1957 | AY643085 | ? | Y | Y | Y | Y | |
| | A/Japan/305/1957 | AY643087 | Drug resistant | Y | Y | Y | N | |
| H6 | A/Teal/Hong Kong/W312/1997 (H6N1) | AF250479 | Egg | Y | Y | Y | Y | |

Y, N - Yes, No, respectively
SP - presence of signal peptide sequence Y/N
HA1 - complete HA1 domain Y/N
HA2 - complete HA2 domain Y/N
DTm - complete transmembrane domain Y/N Strain: H1 from A/Solomon Islands/3/2006

Eight amino acid sequences were compared, and variations identified. (Table 14). Position 171 exhibited a variation of glycine (G) or arginine (R) in some sequences.

TABLE 14

A/Solomon Islands/3/2006 amino acid variation

| Amino acid #* | MDCK | Egg |
|---|---|---|
| 212 | K | T |
| 241 | Q | R |
| 542 | L | R |

Numbering from the starting M

Strain: H1 from A/Brisbane/59/2007

Position 203 exhibited a variation of aspartic acid (D), isoleucine (I) or asparagine (N).

Strain: H3 from A/Brisbane/10/2007

Sequence variations were observed at 5 positions (Table 15). In position 215, a deletion is observed in two sampled sequences.

TABLE 15

H3 from A/Brisbane/10/2007 amino acid variation

| | Origin | 202, | 210, | 215, | 235 | 242* |
|---|---|---|---|---|---|---|
| ISDN274893 | Egg | V | L | — | Y | I |
| ISDN273759 | Egg | G | P | A | S | I |
| EU199248 | Egg | G | P | A | S | I |
| EU199366 | Egg | G | P | A | S | I |

TABLE 15-continued

H3 from A/Brisbane/10/2007 amino acid variation

| | Origin | 202, | 210, | 215, | 235 | 242* |
|---|---|---|---|---|---|---|
| ISDN273757 | Egg | V | L | — | S | S |
| ISDN257043 | Egg | G | P | A | S | I |
| EU199250 | MDCK | G | L | A | S | I |
| ISDN375357 | Egg | G | P | A | S | I |
| ISDN260430 | Egg | G | P | A | S | I |
| ISDN256751 | Egg | G | P | A | S | I |
| ISDN257648 | MDCK | G | L | A | S | I |

*Numbering from the starting M

Strain: H3 from A/Wisconsin/67/2005

Sequence variations in this strain were observed at 4 positions (Table 16).

TABLE 16

H3 from A/Wisconsin/67/2005 amino acid variation

| | Origin | 138, | 156, | 186, | 196 |
|---|---|---|---|---|---|
| ISDN138724 | Unknown | A | H | G | H |
| DQ865947 | Unknown | S | H | V | Y |
| EF473424 | Unknown | A | H | G | H |
| ISDN138723 | Egg | S | Q | V | Y |
| ISDN131464 | Unknown | A | H | G | H |
| EF473455 | Egg | A | H | G | H |

*Numbering from the mature protein

Strain: B from B/Malaysia/2506/2004

Variation at two positions is observed (Table 17). Position 120 is not a glycosylation site; position 210 is involved in glycosylation; this glycosylation is abolished following culture in eggs.

TABLE 17

Hemagglutinin from B/Malaysia/2506/2004 amino acid variation

| Amino acid #* | MDCK | Egg |
|---|---|---|
| 120 | K | N |
| 210 | T | A |

*Numbering from the middle of SP

Strain: Hemagglutinin from B/Florida/4/2006; ISDN261649

Obseved variations include amino acid sequence variation at position 211, depending on the culture system. Asparatine (N) is found in sequences isolated from MDCK cells, while glutamic acid (D) is found in sequence isolated from eggs. Position 211 is a glycosylation site, and is abolished following culture in eggs.

Strain: H2 from A/Singapore/1/1957

Sequence variations were observed in 6 position s (Table 18).

TABLE 18

H2 from A/Singapore/1/1957 amino acid variation

| | | Amino acid No. | | | | | |
|---|---|---|---|---|---|---|---|
| | Origin | 166 | 168 | 199\ | 236 | 238 | 358 |
| L20410 | Viral RNA | K | E | T | L | S | V |
| L11142 | Unknown | E | G | K | L | S | I |
| AB296074 | Unknown | K | G | T | Q | G | V |
| Consensus A/Japan/305/1957 | | K | G | T | Q/L | G | V |

[1]Numbering from the mature protein

Strains: H5 from A/Vietnam/1194/2004 and H5 from A/Anhui/1/2005

There were no variations observed in the amino acid sequence upon aligning the primary sequences of either of these H5 strains.

Strain: H6 from A/Teal/Hong Kong/W312/1997

Only one entry was available for strain (AF250179).

Strain: H7 from A/Equine/Prague/56

A total of 2 sequence entries were found in the databases. The entry AB298877 was excluded as it is a laboratory reassortant.

Strain: H9 from A/Hong Kong/1073/1999; AJ404626

A total of 2 sequence entries were found in the databases. Only one was complete.

Example 20

Transient Expression of Influenza Virus Hemagglutinin Fused to a Signal Peptide from a Plant Secreted Protein The effect of signal peptide modification on HA accumulation level for other hemagglutinins was also investigated through the expression of the A subtype HAs from strains A/Brisbane/59/2007 (H1N1) (plasmid #787), A/New Caledonia/20/1999 (H1N1) (plasmid #540), from strains A/Brisbane/10/2007 (H3N2) (plasmid 790) and A/Indonesia/5/2005 (H5N1) (plasmid #663) and of the B type from strains B/Florida/4/2006 (plasmid #798) fused to the signal peptide (SP; nucleotides 32-103) from of alfalfa protein disulfide isomerase (PDI; accession No. Z11499; SEQ. ID. NO: 34; FIG. 17). The PDI SP-hemagglutinin gene fusions were assembled in the plastocyanin expression cassette—promoter, 5'UTR, 3'UTR and transcription termination sequences from the alfalfa plastocyanin gene—and the assembled cassettes were inserted into to a pCAMBIA binary plasmid. The plasmids were then transfected into *Agrobacterium* (AGL1), producing *Agrobacterium* strains AGL1/787, AGL1/540, AGL1/790, AGL1/663 and AGL1/798, respectively.

*N. benthamiana* plants were infiltrated with AGL1/787, AGL1/540, AGL1/790, AGL1/663 and AGL1/798. In parallel, a series of plants was infiltrated with AGL1/774, AGL776, AGL1/660 and AGL1/779 for comparison purposes. Leaves were harvested after a six-day incubation period and proteins were extracted from infiltrated leaves and analyzed by Western blot using the appropriate anti-HA antibodies. The expression of HA from H1/Brisbane and H3/Brisbane were considerably improved using the SP from PDI compared to the expression observed for the same HAs with their native signal peptide (FIGS. 87*b* and *c*, respectively). The expression of a third HA from subtype H1 (strain A/New Caledonia/20/1999) was confirmed using this SP replacement strategy (FIG. 87*a*). The modification of sognal peptide did not lead to substantial increase in HA accumulation for H5 (A/Indonesia/5/2005) (FIG. 87*d*), and no signal was detected for HA from strain B/Florida/4/2006, irrespectively of the signal peptide used for expression (FIG. 87*e*). For all the conditions where the expression of HA was detected, a unique immunoreactive band was observed at a molecular weight of approximately 72 kDa (FIG. 87*a* to *d*), corresponding in size to the uncleaved HA0 precursor.

Example 21

HA Expression Under the Control of CPMV-HT Expression Cassette

Figure 88:
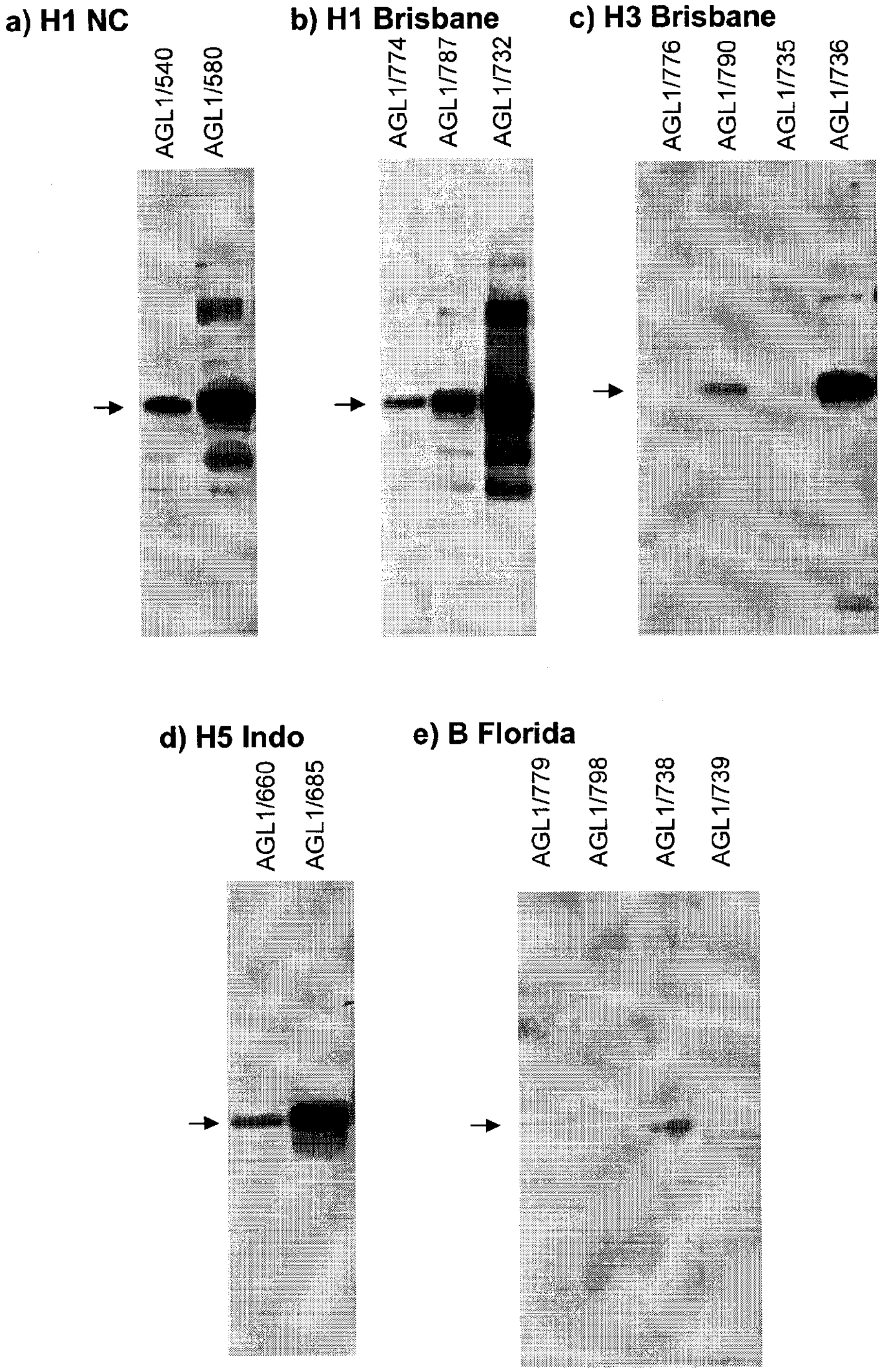
FIG. 88 shows a comparison of HA expression strategies by immunoblot analysis of leaf protein extracts. HA was produced using plastocyanin- or CPMV-HT-based cassettes. For CPMV-HT, the wild-type HA signal peptide and the signal peptide from alfalfa PDI were also compared. Twenty micrograms of protein extract were loaded on the SDS-PAGE for HA subtype analyzed except for the H1 New Caledonia for which five micrograms of proteins were loaded. a) Expression of H1 from A/New Caledonia/20/1999, b) expression of H1 from A/Brisbane/59/2007, c) expression of H3 from A/Brisbane/10/2007, d) expression of H5 from A/Indonesia/5/2005, and e) expression of B from B/Florida/4/2006. The arrows indicate the immunoband corresponding to HA0; specific *Agrobacterium* strains comprising the specific vectors used for HA expression are indicated at the top of the lanes.

An expression cassette CPMV-HT (Sainsbury et al. 2008 Plant Physiology 148: 1212-1218; see also WO 2007/135480) comprising untranslated sequences from the Cowpea mosaic virus (CPMV) RNA2 was used for expression of some hemagglutinins in transgenic plants. HA from A/New Caledonia/20/1999 (H1), A/Brisbane/59/2007 (H1), A/Brisbane/10/2007 (H3), A/Indonesia/5/2005 (H5) and B/Florida/4/2006 (B) were expressed under the control of CPMV-HT in *N. benthamiana* plants, agroinfiltrated as described. After incubation, leaves were harvested, extracted and HA contents in protein extracts were compared by Western blot. As shown in FIG. 88, the CPMV-HT expression cassette led to higher HA expression level than the plastocyanin cassette, irrespectively of the signal peptide used. Furthermore, for strain B from B/Florida/4/2006, the use of CPMV-HT expression cassette allowed the detection of HA accumulation which remained undetectable under these immunodetection conditions when expressed under the plastocyanin cassette.

TABLE 19

| Expression cassette used for expression of influenza hemagglutinins with native or PDI signal peptides. | | | |
|---|---|---|---|
| Agro strain | HA expressed | Signal Peptide | Expression Cassette |
| AGL1/560 | H1 (A/California/04/09) | PDI | 2X35S/CPMV-HT |
| AGL1/540 | H1 (A/New Caledonia/20/99) | PDI | Plastocyanin |
| AGL1/580 | H1 (A/New Caledonia/20/99) | PDI | CPMV-HT |
| AGL1/774 | H1 (A/Brisbane/59/2007) | native | Plastocyanin |
| AGL1/787 | H1 (A/Brisbane/59/2007) | PDI | Plastocyanin |
| AGL1/732 | H1 (A/Brisbane/59/2007) | native | CPMV-HT |
| AGL1/776 | H3 (A/Brisbane/10/2007) | native | Plastocyanin |
| AGL1/790 | H3 (A/Brisbane/10/2007) | PDI | Plastocyanin |
| AGL1/735 | H3 (A/Brisbane/10/2007) | native | CPMV-HT |
| AGL1/736 | H3 (A/Brisbane/10/2007) | PDI | CPMV-HT |
| AGL1/660 | H5 (A/Indonesia/5/2005) | native | Plastocyanin |
| AGL1/685 | H5 (A/Indonesia/5/2005) | native | CPMV-HT |
| AGL1/779 | B (B/Florida/4/2006) | native | Plastocyanin |
| AGL1/798 | B (B/Florida/4/2006) | PDI | Plastocyanin |
| AGL1/738 | B (B/Florida/4/2006) | native | CPMV-HT |
| AGL1/739 | B (B/Florida/4/2006) | PDI | CPMV-HT |

Example 22

Figure 89:
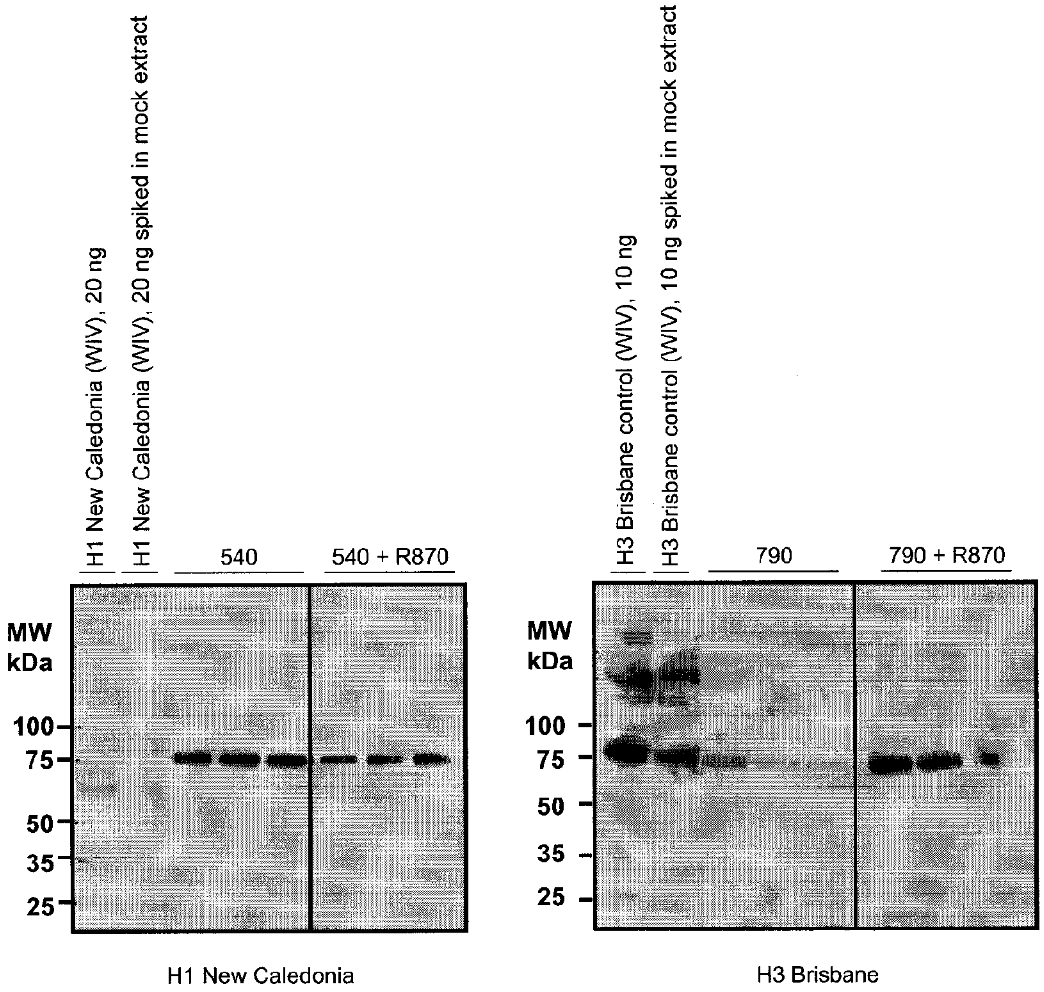
FIG. 89 shows an immunoblot of HA accumulation when co-expressed with Hsp 40 and Hsp70. H1 New Caledonia (AGL1/540) and H3 Brisbane (AGL1/790) were expressed alone or co-expressed with AGL1/R870. HA accumulation level was evaluated by immunoblot analysis of protein extracts from infiltrated leaves. Whole inactivated virus (WIV) of strain A/New Caledonia/20/99 or Brisbane/10/2007 were used as controls.

Co-expression with Hsp70 and Hsp40 in Combination with Signal Peptide Modification Cytosolic Hsp70 and Hsp40 (construct number R870) of plant origin were co-expressed with H1 New Caledonia (construct number 540) or H3Brisbane (construct number 790), both bearing a signal peptide of plant origin (alfalfa PDI signal peptide). The co-expression was performed by agroinfiltration of *N. benthamiana* plants with a bacterial suspension containing a mixture (1:1:1 ratio) of AGL1/540, AGL1/R870, AGL1/35SHcPro (For H1) or AGL1/790, AGL1/R870 and AGL1/35SHcPro (for H3). Control plants were agroinfiltrated with a mixture (1:2 ratio) of AGL1/540, AGL1/35SHcPro (for H1) or AGL1/790, AGL1/35SHcPro (for H3). After incubation, leaves were harvest, extracted and HA contents in protein extracts were compared by Western blot (FIG. 89). In the conditions tested the results obtained indicate that the co-expression of Hsp70 and Hsp40 did not increase hemagglutinin accumulation level for H1 New Caledonia. However, for H3 Brisbane, the Western blot clearly indicated that the co-expression of cytosolic Hsp70 and Hsp40 resulted in a significant increase in hemagglutinin accumulation level.

Example 23

Figure 90:
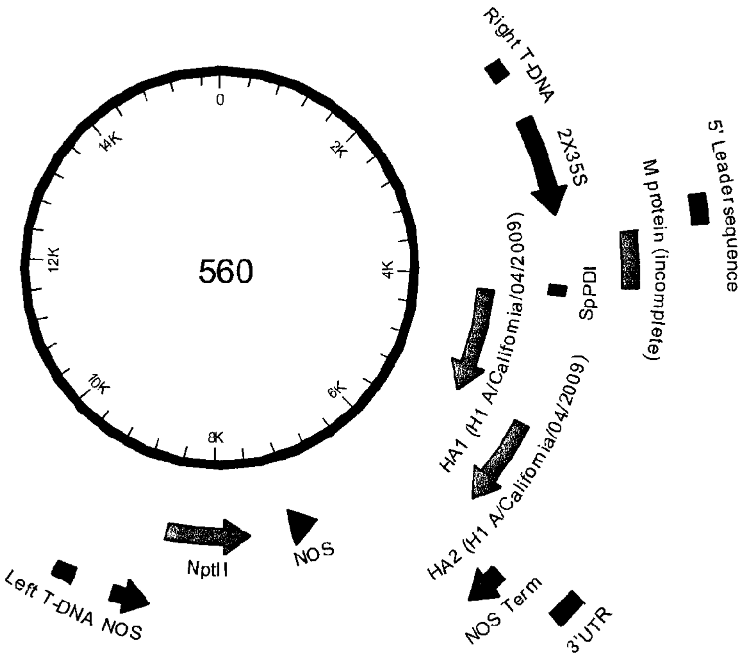
FIG. 90 shows a CPMV-HT based expression cassette for H1 from A/California/04/09 (construct #560).
Figure 91:
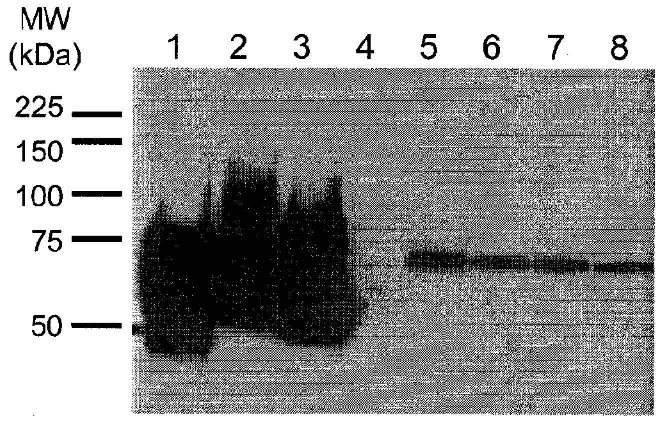
FIG. 91 shows Western blot analysis of H1 from A/California/04/09 in protein extracts from agroinfiltrated plants 2 days post infiltration. Samples run in each lane are laid out in Table 20.

Expression of H1 A/California 04/09 Under Control of 2X35S/CPMV-HT Expression Cassette A CPMV-HT expression cassette was also used for expression of H1 A/California 04/09 (construct #560, FIGS. 90, 98) in *N. benthamiana* plants, agroinfiltrated as described. After 2 days of incubation, leaves were harvested, extracted and HA contents in protein extracts were compared by Western blot. As shown in FIG. 91, the CPMV-HT expression cassette led to significant expression of HA at 2 days post infiltration. VLPs produced form expression of HA in plants demonstrate agglutination of red blood cells.

TABLE 20

| samples for eachlane of the Western blot illustrated in FIG. 91. | | |
|---|---|---|
| Lane # | Description | |
| 1 | 10 ng H1 (A/Bri/59/07) | Positive control (ITC, IT-003-0052p) |
| 2 | 40 ng H1N1 (A/NC/20/99) | Positive control (NISBC, 06/170) |
| 3 | 40 ng H1 (A/Bri/59/07) | Positive control (NISBC, 08/100) |
| 4 | Mock infiltrated plant | Negative control |
| 5 | BW09-I001-560-1 | 2X35S-CPMV HT H1 A/California/4/09 |
| 6 | BW09-I001-560-2 | 2X35S-CPMV HT H1 A/California/4/09 |
| 7 | BW09-I001-560-3 | 2X35S-CPMV HT H1 A/California/4/09 |
| 8 | BW09-I001-560-6 | 2X35S-CPMV HT H1 A/California/4/09 |

All citations are hereby incorporated by reference.

The present invention has been described with regard to one or more embodiments. However, it will be apparent to persons skilled in the art that a number of variations and modifications can be made without departing from the scope of the invention as defined in the claims.

REFERENCES

Aymard, H. M., M. T. Coleman, W. R. Dowdle, W. G. Layer, G. C. Schild, and R. G. Webster. 1973. Influenza virus neuraminidase-inhibition test procedures. Bull. W.H.O. 48: 199-202

Bollag, D. M., Rozycki, M. D., and Edelstein, S. J. (1996) *Protein methods* (*2nd edition*). Wiley-Liss, New York, USA.

Bligh, E. G., & Dyer, W. J. *Can. J. Med. Sci.* 37, 911-917 (1959).

Chen, B. J., Leser, G. P., Morita, E., and Lamb R. A. (2007) Influenza virus hemagglutinin and neuraminidase, but not the matrix protein, are required for assembly and budding of plasmid-derived virus-like particles. J. Virol. 81, 7111-7123.

Chen Z, Aspelund A, Jin H. 2008 Stabilizing the glycosylation pattern of influenza B hemagglutinin following adaptation to growth in eggs. Vaccine vol 26 p 361-371

Crawford, J., Wilkinson, B., Vosnesensky, A., Smith, G., Garcia, M., Stone, H., and Perdue, M. L. (1999). Baculovirus-derived hemagglutinin vaccines protect against lethal influenza infections by avian H5 and H7 subtypes. Vaccine 17, 2265-2274.

Darveau, A., Pelletier, A. & Perreault, J. PCR-mediated synthesis of chimeric molecules. *Methods Neurosc.* 26, 77-85 (1995).

Grgacic E V L, Anderson D A. Virus-like particles: passport to immune recognition. Methods 2006; 40: 60-65.

Gillim-Ross, L., and Subbarao, K. (2006) Emerging respiratory viruses: chanllenges and vaccine strategies. Clin. Microbiol. Rev. 19, 614-636.

Gomez-Puertas, P., Mena, I., Castillo, M., Vivo, A., Perez-Pastrana, E. and Portela, A. (1999) Efficient formation of influenza virus-like particles: dependence on the expression level of viral proteins. J. Gen. Virol. 80, 1635-1645.

Gomez-Puertas, P., Albo, C., Perez-Pastrana, E., Vivo, A., and Portela, A. (2000) Influenza Virus protein is the major driving force in virus budding. J. Virol. 74, 11538-11547.

Hamilton, A., Voinnet, O., Chappell, L. & Baulcombe, D. Two classes of short interfering RNA in RNA silencing. *EMBO J.* 21, 4671-4679 (2002).

Höfgen, R. & Willmitzer, L. Storage of competent cells for *Agrobacterium* transformation. *Nucleic Acid Res.* 16, 9877 (1988).

Harbury P B, Zhang T, Kim P S, Alber T. (1993) A switch between two-, three-, and four-stranded coiled coils in GCN4 leucine zipper mutants. Science; 262: 1401-1407)

Horimoto T., Kawaoka Y. Strategies for developing vaccines against h5N1 influenza a viruses. Trends in Mol. Med. 2006; 12(11):506-514.

Huang Z, Elkin G, Maloney B J, Beuhner N, Arntzen C J, Thanavala Y, Mason H S. Virus-like particle expression and assembly in plants: hepatitis B and Norwalk viruses. Vaccine. 2005 Mar. 7; 23(15):1851-8.

Johansson, B. E. (1999). Immunization with influenza A virus hemagglutinin and neuraminidase produced in recombinant baculovirus results in a balanced and broadened immune response superior to conventional vaccine. Vaccine 17, 2073-2080.

Latham, T., and Galarza, J. M. (2001). Formation of wild-type and chimeric influenza virus-like particles following simultaneous expression of only four structural proteins. J. Virol. 75, 6154-6165.

Lefebvre, B. et al. *Plant Physiol.* 144, 402-418 (2007).

Leutwiler L S et al 1986. Nucleic Acid Sresearch 14910): 4051-64

Liu, L & Lomonossoff, G. P. Agroinfection as a rapid method for propagating Cowpea mosaic virus-based constructs. *J. Virol. Methods* 105, 343-348 (2002).

Macala, L. J., Yo, R. K. & Ando, S. *J Lipid Res.* 24, 1243-1250 (1983)

Mattanovich, D., Rüker, F., da Câmara Machado, A., Laimer, M., Regner, F., Steinkellner, H., Himmler, G., and Katinger, H. (1989) Efficient transformation of *Agrobacterium* spp. By electroporation. *Nucl. Ac. Res.* 17, 6747.

Mena, I., Vivo, A., Perez, E., and Portela, A. (1996) Rescue of synthetic chloramphenicol acetyltransferase RNA into influenza virus-like particles obtained from recombinant plasmids. J. Virol. 70, 5016-5024.

Mongrand S, Morel J, Laroche J, Clayerol S, Carde J P, Hartmann M A et al. Lipid rafts in higher plant cells. The Journal of Biological Chemistry 2004; 279(35): 36277-36286.

Neumann, G., Watanabe, T., and Kawaoka, Y. (2000) Plasmid-driven formation of virus-like particles. J. Virol. 74, 547-551.

Nayak D P, Reichl U. (2004) Neuraminidase activity assays for monitoring MDCK cell culture derived influenza virus. J Virol Methods 122(1):9-15.

Olsen, C. W., McGregor, M. W., Dybdahl-Sissoko, N., Schram, B. R., Nelson, K. M., Lunn, D., Macklin, M. D., and Swain, W. F. (1997). Immunogenicity and efficacy of baculovirus-expressed and DNA-based equine influenza virus hemagglutinin vaccines in mice. Vaccine 15, 1149-1156.

Quan F S, Huang C, Compans R W, Kang S M. Virus-like particle vaccine induces protective immunity against homologous and heterologous strains of influenza virus. Journal of Virology 2007; 81(7): 3514-3524.

Rowe, T. et al. 1999. Detection of antibody to avian influenza a (h5N1) virus in human serum by using a cmbiation of serologic assays. J. Clin Microbiol 37(4):937-43

Saint-Jore-Dupas C et al. 2007. From planta to pharma with glycosylation in the toolbox. Trends in Biotechnology 25(7):317-23

Sambrook J, and Russell D W. Molecular cloning: a laboratory manual. Cold Spring Harbor, N.Y. Cold Spring Harbor Laboratory Press, 2001.

Stockhaus J et at 1987. Analysis of cis-active sequences involved in the leaf-specific expression of a potato gene in transgenic plants. Proceedings of the National Academy of Sciences U.S.S. 84(22):7943-7947.

Stockhaus J et al 1989. Identification of enhancer elements in the upstream region of the nuclear photosynthetic gene ST-LS1. Plant Cell. 1(8):805-13.

Suzuki, Y. (2005) Sialobiology of influenza. Molecular mechanism of host range variation of influenza viruses. Biol. Pharm. Bull 28, 399-408.

Tsuji M., Cell. Mol. Life. Sci., 63 (2006); 1889-1898

Wakefield L., G. G. Brownlee Nuc Acid Res. 17 (1989); 8569-8580.

Kendal, A P, Pereira M S, Skehel J. Concepts and procedures for laboratory-based influenza surveillance. Atlanta:CDC; 1982. p. B17-B35

WHO. Manual on animal influenza diagnosis and surveillance. Department of communicable disease surveillance and response. World Health Organisation Global Influenza Program. 2002.

Skehel J J and Wildy D C Ann Rev Biochem 2000 69:531-69

Vaccaro L et al 2005. Biophysical J. 88:25-36.

Gamblin, S. J., Haire, L. F., Russell, R. J., Stevens, D. J., Xiao, B., Ha, Y., Vasisht, N., Steinhauer, D. A., Daniels, R. S., Elliot, A., Wiley, D. C., Skehel, J. J. (2004) The structure and receptor binding properties of the 1918 influenza hemagglutinin. Science 303: 1838-1842

What is claimed is:

1. A method of producing influenza virus like particles (VLPs) in a plant comprising:

a) introducing by agroinfiltration a nucleic acid comprising a nucleotide sequence encoding an influenza hemagglutinin (HA) and having at least 80% sequence identity to the sequence of HA of type A/California/04/09 as defined by nucleotides 52 to 1701 of SEQ ID NO:135, the nucleotide sequence operatively linked to a regulatory region active in a plant, the regulatory region comprising Cowpea Mosaic Virus (CPMV)-HT, and the HA comprising a native HA signal peptide or a non-native HA signal peptide into the plant, or portion of the plant, the HA having hemagglutinin activity as determined by using a hemagglutination assay;

b) incubating the plant or portion of the plant under conditions that permit the expression of the nucleic acid, thereby producing the VLPs, wherein the nucleic acid is transiently expressed in the plant or portion of the plant; and c) harvesting the plant and purifying the VLPs.

2. The method of claim 1, wherein, in the step of introducing (step a), a second nucleic acid comprising a nucleotide sequence encoding one or more than one chaperone proteins is introduced into the plant.

3. The method of claim 2, wherein the one or more than one chaperone proteins is selected from the group consisting of Hsp40 and Hsp70.

4. A method of producing influenza virus like particles (VLPs) in a plant said method comprising:

a) providing a plant, or a portion of a plant, comprising a nucleic acid introduced by agroinfiltration, the nucleic acid comprising a nucleotide sequence encoding an influenza hemagglutinin (HA) and having at least 80% sequence identity to the sequence of HA of type A/California/04/09 as defined by nucleotides 52 to 1701 of SEQ ID NO:135, the nucleotide sequence operatively linked to a regulatory region active in a plant, the regulatory region comprising Cowpea Mosaic Virus (CPMV)-HT, and the HA comprising a native HA signal peptide or a non-native HA signal peptide, the HA having hemagglutinin activity as determined by using a hemagglutination assay;

b) incubating the plant or portion of the plant under conditions that permit the expression of the nucleic acid, thereby producing the VLPs, wherein the nucleic acid is transiently expressed in the plant or portion of the plant; and c) harvesting the plant and purifying the VLPs.

5. A plant produced by the method of claim 1.

6. The plant of claim 5, further comprising a nucleic acid comprising a nucleotide sequence encoding one or more than one chaperone proteins operatively linked to a regulatory region active in a plant.

7. The plant of claim 6, wherein the one or more than one chaperone proteins is selected from the group consisting of Hsp40 and Hsp70.

8. A virus like particle (VLP) produced in a plant according to the method of claim 1, the VLP comprising one or more than one lipid derived from a plant.

9. A composition comprising an effective dose of the VLP of claim 8 for inducing an immune response and a pharmaceutically acceptable carrier.

10. A method of inducing immunity to an influenza virus infection in a subject, said method comprising administering the virus like particle of claim 8.

11. The method of claim 10, wherein the virus like particle is administered to a subject orally, intradermally, intranasally, intramuscularly, intraperitoneally, intravenously, or subcutaneously.

12. A virus like particle (VLP) produced in a plant according to the method of claim 1, wherein the HA bears plant-specific N-glycans or modified N-glycans.

13. A composition comprising an effective dose of the VLP of claim 12 for inducing an immune response and a pharmaceutically acceptable carrier.

14. A method of inducing immunity to an influenza virus infection in a subject, said method comprising administering the composition of claim 13.

15. The method of claim 14, wherein the composition is administered to a subject orally, intradermally, intranasally, intramuscularly, intraperitoneally, intravenously, or subcutaneously.

16. The method of claim 1, wherein the HA is of influenza type A/California/04/09.

17. The VLP of claim 8, wherein the HA is of type A/California/04/09.

18. The VLP of claim 12, wherein the HA is of type A/California/04/09.

19. The method of claim 1, wherein the influenza hemagglutinin sequence is selected from the group consisting of SEQ ID NO: 127 and 135.

20. The VLP of claim 8, wherein the influenza hemagglutinin sequence is selected from the group consisting of SEQ ID NO: 127 and 135.

21. The VLP of claim 12, wherein the influenza hemagglutinin sequence is selected from the group consisting of SEQ ID NO: 127 and 135.

22. A virus like particle (VLP) produced by the method of claim 1.

23. A virus like particle (VLP) produced by the method of claim 4.

24. The method of claim 1, wherein the non-native HA signal peptide is a protein disulfide isomerase signal peptide.

25. The method of claim 4, wherein the non-native HA signal peptide is a protein disulfide isomerase signal peptide.

26. The method of claim 1, wherein the VLPs range in size from 80-300 nm.

27. The method of claim 4, wherein the VLPs range in size from 80-300 nm.

28. The method of claim 1, wherein the VLP does not comprise neuraminidase (NA).

29. The method of claim 4, wherein the VLP does not comprise neuraminidase (NA).

30. The VLP of claim 23, wherein the VLP comprises HA and one or more than one lipid derived from a plant.

31. The VLP of claim 23, wherein the HA bears plant-specific N-glycans or modified N-glycans.

* * * * *

SEQUENCE LISTING

```
<160> NUMBER OF SEQ ID NOS: 146

<210> SEQ ID NO 1
<211> LENGTH: 1556
<212> TYPE: DNA
<213> ORGANISM: Influenza virus

<400> SEQUENCE: 1

agatcttcgc tgacacaata tgtataggct accatgccaa caactcaacc gacactgttg      60

acacagtact tgagaagaat gtgacagtga cacactctgt caacctactt gaggacagtc     120

acaatggaaa actatgtcta ctaaaaggaa tagccccact acaattgggt aattgcagcg     180

ttgccggatg gatcttagga aacccagaat gcgaattact gatttccaag gaatcatggt     240
```

```
cctacattgt agaaacacca aatcctgaga atggaacatg ttacccaggg tatttcgccg    300

actatgagga actgagggag caattgagtt cagtatcttc atttgagaga ttcgaaatat    360

tccccaaaga aagctcatgg cccaaccaca ccgtaaccgg agtatcagca tcatgctccc    420

ataatgggaa aagcagtttt tacagaaatt tgctatggct gacggggaag aatggtttgt    480

acccaaacct gagcaagtcc tatgtaaaca acaaagagaa agaagtcctt gtactatggg    540

gtgttcatca cccgcctaac atagggaacc aaagggcact ctatcataca gaaaatgctt    600

atgtctctgt agtgtcttca cattatagca gaagattcac cccagaaata gccaaaagac    660

ccaaagtaag agatcaggaa ggaagaatca actactactg gactctgctg gaacctgggg    720

atacaataat atttgaggca aatggaaatc taatagcgcc atggtatgct tttgcactga    780

gtagaggctt tggatcagga atcatcacct caaatgcacc aatggatgaa tgtgatgcga    840

agtgtcaaac acctcaggga gctataaaca gcagtcttcc tttccagaat gtacacccag    900

tcacaatagg agagtgtcca aagtatgtca ggagtgcaaa attaaggatg gttacaggac    960

taaggaacat cccatccatt caatccagag gtttgtttgg agccattgcc ggtttcattg   1020

aagggggtg gactggaatg gtagatgggt ggtatggtta tcatcatcag aatgagcaag   1080

gatctggcta tgctgcagat caaaaaagta cacaaaatgc cattaacggg attacaaaca   1140

aggtcaattc tgtaattgag aaaatgaaca ctcaattcac agctgtgggc aaagagttca   1200

acaaattgga aagaaggatg gaaaacttaa ataaaaaagt tgatgatggg tttctagaca   1260

tttggacata taatgcagaa ttgttggttc tactggaaaa tgaaaggact ttggatttcc   1320

atgactccaa tgtgaagaat ctgtatgaga aagtaaaaag ccaattaaag aataatgcca   1380

aagaaatagg aaacgggtgt tttgagttct atcacaagtg taacaatgaa tgcatggaga   1440

gtgtgaaaaa tggtacctat gactatccaa aatattccga agaatcaaag ttaaacaggg   1500

agaaaattga tggagtgaaa ttggaatcaa tgggagtata ctaagagctc aggcct       1556
```

<210> SEQ ID NO 2
<211> LENGTH: 219
<212> TYPE: DNA
<213> ORGANISM: Influenza virus

<400> SEQUENCE: 2

```
ggtacctatg actatccaaa atattccgaa gaatcaaagt taaacaggga gaaaattgat     60

ggagtgaaat tggaatcaat gggagtatac cagattctgg cgatctactc aactgtcgcc    120

agttccctgg ttcttttggt ctccctgggg gcaatcagct tctggatgtg ttccaatggg    180

tctttgcagt gtagaatatg catctaagag ctcaggcct                           219
```

<210> SEQ ID NO 3
<211> LENGTH: 1719
<212> TYPE: DNA
<213> ORGANISM: Influenza virus

<400> SEQUENCE: 3

```
aagcttatgg agaaaatagt gcttcttctt gcaatagtca gtcttgttaa aagtgatcag     60

atttgcattg gttaccatgc aaacaattca acagagcagg ttgacacaat catggaaaag    120

aacgttactg ttacacatgc ccaagacata ctggaaaaga cacacaacgg gaagctctgc    180

gatctagatg gagtgaagcc tctaatttta agagattgta gtgtagctgg atggctcctc    240

gggaacccaa tgtgtgacga attcatcaat gtaccggaat ggtcttacat agtggagaag    300

gccaatccaa ccaatgacct ctgttaccca gggagtttca acgactatga agaactgaaa    360
```

```
cacctattga gcagaataaa ccattttgag aaaattcaaa tcatccccaa aagttcttgg    420

tccgatcatg aagcctcatc aggagttagc tcagcatgtc catacctggg aagtccctcc    480

ttttttagaa atgtggtatg gcttatcaaa aagaacagta catacccaac aataaagaaa    540

agctacaata ataccaacca agaggatctt ttggtactgt ggggaattca ccatcctaat    600

gatgcggcag agcagacaag gctatatcaa aacccaacca cctatatttc cattgggaca    660

tcaacactaa accagagatt ggtaccaaaa atagctacta gatccaaagt aaacgggcaa    720

agtggaagga tggagttctt ctggacaatt ttaaaaccta atgatgcaat caacttcgag    780

agtaatggaa atttcattgc tccagaatat gcatacaaaa ttgtcaagaa aggggactca    840

gcaattatga aaagtgaatt ggaatatggt aactgcaaca ccaagtgtca aactccaatg    900

ggggcgataa actctagtat gccattccac aacatacacc ctctcaccat cggggaatgc    960

cccaaatatg tgaaatcaaa cagattagtc cttgcaacag ggctcagaaa tagccctcaa   1020

agagagagca gaagaaaaaa gagaggacta tttggagcta tagcaggttt tatagaggga   1080

ggatggcagg gaatggtaga tggttggtat gggtaccacc atagcaatga gcaggggagt   1140

gggtacgctg cagacaaaga atccactcaa aaggcaatag atggagtcac caataaggtc   1200

aactcaatca ttgacaaaat gaacactcag tttgaggccg ttggaaggga atttaataac   1260

ttagaaagga gaatagagaa tttaaacaag aagatggaag acgggtttct agatgtctgg   1320

acttataatg ccgaacttct ggttctcatg gaaaatgaga gaactctaga ctttcatgac   1380

tcaaatgtta agaacctcta cgacaaggtc cgactacagc ttagggataa tgcaaaggag   1440

ctgggtaacg gttgtttcga gttctatcac aaatgtgata atgaatgtat ggaaagtata   1500

agaaacggaa cgtacaacta tccgcagtat tcagaagaag caagattaaa aagagaggaa   1560

ataagtgggg taaaattgga atcaatagga acttaccaaa tactgtcaat ttattcaaca   1620

gtggcgagtt ccctagcact ggcaatcatg atggctggtc tatctttatg gatgtgctcc   1680

aatggatcgt tacaatgcag aatttgcatt taagagctc                          1719
```

```
<210> SEQ ID NO 4
<211> LENGTH: 25
<212> TYPE: DNA
<213> ORGANISM: Artificial sequence
<220> FEATURE:
<223> OTHER INFORMATION: primer Plasto-443c

<400> SEQUENCE: 4

gtattagtaa ttagaatttg gtgtc                                           25


<210> SEQ ID NO 5
<211> LENGTH: 44
<212> TYPE: DNA
<213> ORGANISM: Artificial sequence
<220> FEATURE:
<223> OTHER INFORMATION: primer SpHA(Ind)-Plasto.r

<400> SEQUENCE: 5

gcaagaagaa gcactatttt ctccattttc tctcaagatg atta                      44


<210> SEQ ID NO 6
<211> LENGTH: 45
<212> TYPE: DNA
<213> ORGANISM: Artificial sequence
<220> FEATURE:
<223> OTHER INFORMATION: primer SpHA(Ind)-Plasto.r
```

<400> SEQUENCE: 6
ttaatcatct tgagagaaaa tggagaaaat agtgcttctt cttgc 45

<210> SEQ ID NO 7
<211> LENGTH: 38
<212> TYPE: DNA
<213> ORGANISM: Artificial sequence
<220> FEATURE:
<223> OTHER INFORMATION: primer HA(Ind)-Sac.r

<400> SEQUENCE: 7
actttgagct cttaaatgca aattctgcat tgtaacga 38

<210> SEQ ID NO 8
<211> LENGTH: 1471
<212> TYPE: DNA
<213> ORGANISM: Artificial sequence
<220> FEATURE:
<223> OTHER INFORMATION: alfalfa plastocyanin-based expression cassette

<400> SEQUENCE: 8
agaggtaccc cgggctggta tatttatatg ttgtcaaata actcaaaaac cataaaagtt 60
taagttagca agtgtgtaca tttttacttg aacaaaaata ttcacctact actgttataa 120
atcattatta aacattagag taaagaaata tggatgataa gaacaagagt agtgatattt 180
tgacaacaat tttgttgcaa catttgagaa aattttgttg ttctctcttt tcattggtca 240
aaaacaatag agagagaaaa aggaagaggg agaataaaaa cataatgtga gtatgagaga 300
gaaagttgta caaaagttgt accaaaatag ttgtacaaat atcattgagg aatttgacaa 360
aagctacaca aataagggtt aattgctgta aataaataag gatgacgcat tagagagatg 420
taccattaga gaatttttgg caagtcatta aaaagaaaga ataaattatt tttaaaatta 480
aaagttgagt catttgatta aacatgtgat tatttaatga attgatgaaa gagttggatt 540
aaagttgtat tagtaattag aatttggtgt caaatttaat ttgacatttg atcttttcct 600
atatattgcc ccatagagtc agttaactca tttttatatt tcatagatca aataagagaa 660
ataacggtat attaatccct ccaaaaaaaa aaaacggtat atttactaaa aaatctaagc 720
cacgtaggag gataacagga tccccgtagg aggataacat ccaatccaac caatcacaac 780
aatcctgatg agataaccca ctttaagccc acgcatctgt ggcacatcta cattatctaa 840
atcacacatt cttccacaca tctgagccac acaaaaacca atccacatct ttatcaccca 900
ttctataaaa aatcacactt tgtgagtcta cactttgatt cccttcaaac acatacaaag 960
agaagagact aattaattaa ttaatcatct tgagagaaaa tggcgaaaaa cgttgcgatt 1020
ttcggcttat tgttttctct tcttgtgttg gttccttctc agatctgagc tctaagttaa 1080
aatgcttctt cgtctcctat ttataatatg gtttgttatt gttaattttg ttcttgtaga 1140
agagcttaat taatcgttgt tgttatgaaa tactatttgt atgagatgaa ctggtgtaat 1200
gtaattcatt tacataagtg gagtcagaat cagaatgttt cctccataac taactagaca 1260
tgaagacctg ccgcgtacaa ttgtcttata tttgaacaac taaaattgaa catcttttgc 1320
cacaacttta taagtggtta atatagctca aatatatggt caagttcaat agattaataa 1380
tggaaatatc agttatcgaa attcattaac aatcaactta acgttattaa ctactaattt 1440
tatatcatcc cctttgataa atgatagtac a 1471

<210> SEQ ID NO 9
<211> LENGTH: 565

<212> TYPE: PRT
<213> ORGANISM: Influenza virus

<400> SEQUENCE: 9

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Pro Asn Ile Gly Asn Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400
```

```
Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565
```

<210> SEQ ID NO 10
<211> LENGTH: 568
<212> TYPE: PRT
<213> ORGANISM: Influenza virus

<400> SEQUENCE: 10

```
Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
```

```
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565
```

<210> SEQ ID NO 11
<211> LENGTH: 1629
<212> TYPE: DNA
<213> ORGANISM: Influenza virus

<400> SEQUENCE: 11

-continued

```
gacaaaatat gtcttgggca ccatgctgtg gcaaatggaa caaaagtgaa cacattaaca     60
gagaggggga ttgaagtagt gaacgccaca gagacggtgg aaactgcgaa tatcaagaaa    120
atatgtattc aagggaaaag gccaacagat ctgggacaat gtggacttct aggaacccta    180
ataggacctc cccaatgtga tcaattcctg gagttttact ctgatttgat aattgagcga    240
agagaaggaa ccgatgtgtg ctatcccggt aaattcacaa atgaagaatc actgaggcag    300
atccttcgag ggtcaggagg aattgataag gagtcaatgg gtttcaccta tagtggaata    360
agaaccaatg gagcgacaag tgcctgcaaa agatcaggtt cttctttcta tgcagagatg    420
aagtggttgc tgtcgaattc agacaatgcg gcattccctc aaatgacaaa gtcgtataga    480
aatcccagaa acaaaccagc tctgataatt tggggagttc atcactctgg atcggttagc    540
gagcagacca aactctatgg aagtggaaac aagttgataa cagtaggaag ctcaaaatac    600
cagcaatcat tcaccccaag tccgggagca cggccacaag tgaatggaca atcagggaga    660
atcgattttc actggctact ccttgatccc aatgacacag tgaccttcac tttcaatggg    720
gcattcatag cccctgacag ggcaagtttc tttagaggag aatcactagg agtccagagt    780
gatgttcctc tggattctag ttgtggaggg gattgctttc acagtggggg tacgatagtc    840
agttccctgc cattccaaaa catcaaccct agaactgtgg ggagatgccc tcggtatgtc    900
aaacagacaa gcctcctttt ggctacagga atgagaaatg ttccagagaa tccaaagccc    960
agaggccttt ttggagcaat tgctggattc atagagaatg gatgggaggg tctcatcgat   1020
ggatggtatg gtttcagaca tcaaaatgca caaggggaag gaactgcagc tgactacaaa   1080
agcacccaat ctgcaataga tcagatcaca ggcaaattga atcgtctgat tgacaaaaca   1140
aatcagcagt ttgagctgat agacaatgag ttcaatgaga tagaacaaca aataggaaat   1200
gtcattaatt ggacacgaga cgcaatgact gaggtatggt cgtataatgc tgagctgttg   1260
gtggcaatgg aaaatcagca tacaatagat cttgcggact cagaaatgaa caaactttat   1320
gagcgtgtca gaaaacaact aagggagaat gctgaagaag atggaactgg atgttttgag   1380
atattccata agtgtgatga tcagtgcatg gagagcataa ggaacaacac ttatgaccat   1440
actcaataca gaacagagtc attgcagaat agaatacaga tagacccagt gaaattgagt   1500
agtggataca aagacataat cttatggttt agcttcgggg catcatgttt tcttcttcta   1560
gccgttgtaa tgggattggt tttcatttgc ataaagaatg gaaacatgcg gtgcaccatt   1620
tgtatataa                                                           1629
```

<210> SEQ ID NO 12
<211> LENGTH: 1773
<212> TYPE: DNA
<213> ORGANISM: Influenza virus

<400> SEQUENCE: 12

```
agcaaaagca ggggttatac catagacaac caaaggcaag acaatggcca tcatttatct     60
aattcttctg ttcacagcag tgagagggga ccaaatatgc attggatacc attccaacaa    120
ttccacagaa aaggttgaca caatcctaga gagaaatgtc actgtgactc acgctgagga    180
cattcttgag aagactcaca atgggaagtt atgcaaacta aatggaatcc ctccacttga    240
attaagggat tgcagcattg ccggatggct ccttgggaat ccagaatgtg atatacttct    300
aactgtgcca gaatggtcat acataataga aaaagaaaat ccaaggaacg gcttgtgcta    360
cccaggcagt ttcaatgatt atgaagaatt gaagcatctt atcagcagcg tgacacattt    420
tgagaaagta aagattctgc ccagaaatga atggacacag catacaacaa ctggaggttc    480
```

```
acaggcttgc gcagactatg gtggtccgtc attcttccgg aacatggtct ggttgacaaa    540

gaaagggtcg aattatccaa ttgccaaaag atcttacaac aatacaagtg gggaacaaat    600

gctgatcatt tgggggatac atcaccccaa tgatgaaagt gaacaaagag cattgtatca    660

gaatgtgggg acctatgtgt cagtaggaac atcaacactg aacaaaagat catccccaga    720

aatagcaaca agacctaaag tgaatggaca aggaggcaga atggaattct cgtggactat    780

cttagatata tgggacacaa taaattttga gagtactggc aatctaattg caccagaata    840

tggtttcaaa atatccaaac gaggtagttc agggatcatg aaaacagaag gaaaacttga    900

aaactgcgag accaagtgcc aaactccttt gggagcaata aatacaacat tacccttca     960

caatatccac ccactgacca ttggtgagtg ccccaaatat gtaaaatcgg aaagattagt   1020

cttagcaaca ggactaagaa acgtccctca gattgagtca aggggattgt ttggggcaat   1080

agctggtttt atagagggtg gatggcaagg aatggttgat ggttggtatg ggtatcatca   1140

cagcaatgac cagggatctg ggtatgcagc agacaaagaa tccactcaaa aggcaattga   1200

tggaatcacc aacaaggtaa attctgtgat cgaaaagatg aacacccaat tcggagctgt   1260

tggaaaagaa ttcagtaact tggagagaag actggagaac ttgaataaaa agatggagga   1320

cggatttcta gatgtgtgga catacaatgc cgagctccta gttctaatgg aaaatgagag   1380

gacacttgac tttcatgatt ctaatgtcaa gaatctatat gataaagtca gaatgcaact   1440

gagagacaat gcaaaagaac tagggaatgg atgttttgaa ttttatcaca aatgtgatga   1500

tgaatgcatg aacagtgtga agaatgggac atatgattat tccaagtatg aagaggagtc   1560

taaactaaac aggactgaaa tcaaaggggt taaattgagc aatatggggg tttatcaaat   1620

ccttgccatc tatgctacag tagcaggttc cctgtcactg gcaatcatga tagctgggat   1680

ttctatatgg atgtgctcca acgggtctct gcaatgcaga atctgcatat gatcatcagt   1740

cattttgtaa ttaaaaacac ccttgtttct act                                1773
```

<210> SEQ ID NO 13
<211> LENGTH: 1086
<212> TYPE: DNA
<213> ORGANISM: Influenza virus

<400> SEQUENCE: 13

```
caaaaacttc ccggaaatga caacagcacg gcaacgctgt gccttgggca ccatgcagta     60

ccaaacggaa cgatagtgaa aacaatcacg aatgaccaaa ttgaagttac taatgctact    120

gagctggtac agagttcctc aacaggtgga atatgcgaca gtcctcatca gatccttgat    180

ggagaaaact gcacactaat agatgctcta ttgggagacc ctcagtgtga tggcttccaa    240

aataagaaat gggacctttt tgttgaacgc agcaaagcct acagcaactg ttacccttat    300

gatgtgccgg attatgcctc ccttaggtca ctagttgcct catccggcac actggagttt    360

aacaatgaaa gcttcgattg gactggagtc actcagaatg gaacaagctc tgcttgcaaa    420

aggagatcta ataaaagttt ctttagtaga ttgaattggt tgacccactt aaaatacaaa    480

tacccagcat tgaacgtgac tatgccaaac aatgaaaaat ttgacaaatt gtacatttgg    540

ggggttcacc acccgggtac ggacagtgac caaatcagcc tatatgctca agcatcagga    600

agaatcacag tctctaccaa aagaagccaa caaactgtaa tcccgaatat cggatctaga    660

cccagggtaa gggatgtctc cagccgaata agcatctatt ggacaatagt aaaaccggga    720

gacatacttt tgattaacag cacagggaat ctaattgctc ctcggggtta cttcaaaata    780
```

-continued cgaagtggga aaagctcaat aatgagatca gatgcaccca ttggcaaatg caattccgaa 840
tgcatcactc caaatggaag cattcccaat gacaaaccat ttcaaaatgt aaacaggatc 900
acatatgggg cctgtcccag atatgttaag caaaacactc tgaaattggc aacagggatg 960
cgaaatgtac cagagaaaca aactagaggc atatttggcg caatcgcggg tttcatagaa 1020
aatggttggg agggaatggt ggacggttgg tacggtttca ggcatcaaaa ttctgagggc 1080
acagga 1086

<210> SEQ ID NO 14
<211> LENGTH: 1048
<212> TYPE: DNA
<213> ORGANISM: Influenza virus

<400> SEQUENCE: 14
atgctatcaa tcacgattct gtttctgctc atagcagagg gttcctctca gaattacaca 60
gggaatcccg tgatatgcct gggacatcat gccgtatcca atgggacaat ggtgaaaacc 120
ctgactgatg accaagtaga agttgtcact gcccaagaat tagtggaatc gcaacatcta 180
ccggagttgt gtcctagccc tttaagatta gtagatggac aaacttgtga catcgtcaat 240
ggtgccttgg ggagtccagg ctgtgatcac ttgaatggtg cagaatggga tgtcttcata 300
gaacgaccca ctgctgtgga cacttgttat ccatttgatg tgccggatta ccagagccta 360
cggagtatcc tagcaaacaa tgggaaattt gagttcattg ctgaggaatt ccaatggaac 420
acagtcaaac aaaatgggaa atccggagca tgcaaaagag caaatgtgaa tgactttttc 480
aacagattga actggctgac caaatctgat gggaatgcat acccacttca aaacctgaca 540
aaggttaaca acggggacta tgcaagactt tacatatggg gagttcatca tccttcaact 600
gacacagaac aaaccaactt gtataagaac aaccctggga gagtaactgt ttccaccaaa 660
accagtcaaa caagtgtggt accaaacatt ggcagtagac catgggtaag aggccaaagc 720
ggcaggatta gcttctattg gacaattgtg gagccaggag acctcatagt cttcaacacc 780
atagggaatt taattgctcc gagaggtcat tacaagctta acagtcaaaa gaagagcaca 840
attctgaata ctgcaattcc cataggatct tgtgttagta aatgtcacac agataggggt 900
tcaatctcta caaccaaacc ctttcagaac atctcaagaa tatcaattgg ggactgtccc 960
aagtatgtca aacagggatc cttgaaacta gctacaggaa tgaggaatat ccctgagaaa 1020
gcaaccagag gcctgtttgg tgcaattg 1048

<210> SEQ ID NO 15
<211> LENGTH: 1707
<212> TYPE: DNA
<213> ORGANISM: Influenza virus

<400> SEQUENCE: 15
atggagaaaa tagtgcttct tcttgcaata gtcagtcttg ttaaaagtga tcagatttgc 60
attggttacc atgcaaacaa ctcgacagag caggttgaca caataatgga aaagaacgtt 120
actgttacac atgcccaaga catactggaa aagacacaca acgggaaact ctgcgatcta 180
gatggagtga agcctctaat tttgagagat tgtagtgtag ctggatggct cctcggaaac 240
cctatgtgtg acgaattcat caatgtgccg gaatggtctt acatagtgga gaaggccagt 300
ccagccaatg acctctgtta cccaggggat ttcaacgact atgaagaact gaaacaccta 360
ttgagcagaa taaaccactt tgagaaaatt cagatcatcc ccaaaagttc ttggtccaat 420
catgaagcct catcaggggt gagcgcagca tgtccatacc atgggaagcc ctcctttttc 480
agaaatgtgg tatggcttat caaaaagaac agtgcatacc caacaataaa gaggagctac 540
aataatacca accaagaaga tcttttggta ctgtggggga ttcaccatcc taatgatgcg 600
gcagagcaga caaagctcta tcaaaaccca accacctata tttccgttgg aacatcaaca 660
ctaaaccaga gattggtccc aaaaatagct actagatcca aagtaaacgg gcaaagtgga 720
agaatggagt tcttctggac aattttaaag ccgaatgatg ccataaattt cgagagtaat 780
ggaaatttca ttgctccaga atatgcatac aaaattgtca agaaagggga ctcagcaatt 840
atgaaaagtg aattggaata tggtaactgc aacaccaagt gtcaaactcc aatgggggcg 900
ataaactcta gtatgccatt ccacaacata caccctctca caatcgggga atgccccaaa 960
tatgtgaaat caaacagatt agtccttgcg actggactca gaaatacccc tcaaagagat 1020
agaagaagaa aaaagagagg actatttgga gctatagcag gttttataga gggaggatgg 1080
caaggaatgg tagatggttg gtatgggtac caccatagca atgagcaggg gagtggatac 1140
gctgcagaca aagaatccac tcaaaaggca atagatggag tcaccaataa ggtcaactcg 1200
atcattgaca aaatgaacac tcagtttgag gccgttggaa gggaatttaa taacttagaa 1260
aggaggatag aaaatttaaa caagaagatg gaagacggat tcctagatgt ctggacttat 1320
aatgctgaac ttctggttct catggaaaat gagagaactc tagactttca tgattcaaat 1380
gtcaagaacc tttacaacaa ggtccgacta cagcttaggg ataatgcaaa ggagctgggt 1440
aatggttgtt tcgagttcta tcacaaatgt gataatgaat gtatggaaag tgtaaaaaac 1500
gggacgtatg actacccgca gtattcagaa gaagcaagac taaacagaga ggaaataagt 1560
ggagtaaaat tggaatcaat gggaacttac caaatactgt caatttattc aacagtggcg 1620
agttccctag cactggcaat catggtagct ggtctatctt tatggatgtg ctccaatggg 1680
tcgttacaat gcagaatttg catttaa 1707

<210> SEQ ID NO 16
<211> LENGTH: 1050
<212> TYPE: DNA
<213> ORGANISM: Influenza virus

<400> SEQUENCE: 16
atgattgcaa tcattgtaat agcgatactg gcagcagccg gaaagtcaga caagatctgc 60
attgggtatc atgccaacaa ttcaacaaca caggtggata cgatacttga gaagaatgta 120
accgtcacac actcagttga attgctggag aatcagaagg aagaaagatt ctgcaagatc 180
ttgaacaagg cccctctcga cctaaaggga tgcaccatag agggttggat cttggggaat 240
ccccaatgcg atctgttgct tggtgaccaa agctggtcat atatagtgga aagacctact 300
gcccaaaatg ggatatgcta cccaggagct ttgaatgagg tagaagaact gaaagcattt 360
atcggatcag gagaaagggt agagagattt gagatgtttc ccaaaagcac atgggcaggg 420
gtagacacca gcagtggggt aacaaaagct tgtccttata atagtggttc atctttctac 480
agaaacctcc tatggataat aaagaccaag tcagcagcgt atccagtaat taagggaact 540
tacagcaaca ctggaaacca gccaatcctc tatttctggg gtgtgcacca tcctcctgac 600
accaatgagc aaaatactct gtatggctct ggcgatcggt atgttaggat gggaactgag 660
agcatgaatt ttgccaagag cccagaaatt gcggcaagac ccgctgtgaa tggccaaaga 720
ggtcgaattg attattactg gtctgtttta aaaccaggag aaaccttgaa tgtggaatct 780
aatggaaatc taatcgctcc ttggtatgca tacaaatttg tcaacacaaa taataaggga 840

-continued

```
gccgtcttca agtcaaattt accaatcgag aattgcgatg ccacatgcca gactattgca    900

ggagtcctaa ggaccaataa aacatttcag aatgtgagcc ctctgtggat aggagaatgc    960

cccaagtatg tgaaaagtga aagtctaagg cttgctactg gactaagaaa tgttccacag   1020

attgaaacca gagggctttt cggagctatc                                    1050
```

<210> SEQ ID NO 17
<211> LENGTH: 1698
<212> TYPE: DNA
<213> ORGANISM: Influenza virus

<400> SEQUENCE: 17

```
atggaaaaat tcatcgcaat agcaaccttg gcgagcacaa atgcatacga taggatatgc     60

attgggtacc aatcaaacaa ctccacagac acagtgaaca ctctcataga acagaatgta    120

ccagtcaccc aaacaatgga gctcgtggaa acagagaaac atcccgctta ttgtaacact    180

gatttaggtg ccccattgga actgcgagac tgcaagattg aggcagtaat ctatgggaac    240

cccaagtgtg acatccatct gaaggatcaa ggttggtcat acatagtgga gaggcccagc    300

gcaccagaag ggatgtgtta ccctggatct gtggaaaatc tagaagaact gaggtttgtc    360

ttctccagtg ctgcatctta caagagaata agactatttg actattccag gtggaatgtg    420

actagatctg gaacgagtaa agcatgcaat gcatcaacag gtggccaatc cttctatagg    480

agcatcaatt ggttgaccaa aaaggaacca gacacttatg acttcaatga aggagcttat    540

gttaataatg aagatggaga catcattttc ttatggggga tccatcatcc gccggacaca    600

aaagagcaga caacactata taaaaatgca aacactttga gtagtgttac tactaacact    660

ataaacagaa gctttcaacc aaatattggt cccagaccat tagtaagagg acagcaaggg    720

aggatggatt actattgggg cattctgaaa agaggggaga ctctgaagat caggaccaac    780

ggaaatttaa tcgcacctga atttggctat ctgctcaaag gtgaaagcta cggcagaata    840

attcaaaatg aggatatacc catcgggaac tgtaacacaa aatgtcaaac atatgcggga    900

gcaatcaata gcagcaaacc ctttcagaat gcaagtaggc attacatggg agaatgtccc    960

aaatatgtga agaaggcaag cttgcgactt gcagttgggc ttaggaatac gccttctgtt   1020

gaacccagag gactgtttgg agccattgct ggtttcattg aaggaggatg gtctggaatg   1080

attgatgggt ggtatggatt tcatcacagc aattcagagg gaacaggaat ggcagctgac   1140

cagaaatcaa cacaagaagc catcgataag atcaccaata aagtcaacaa tatagttgac   1200

aagatgaaca gggagtttga agttgtgaat catgagttct ctgaagttga aaaaagaata   1260

aacatgataa acgataaaat agatgaccaa attgaagatc tttgggctta caatgcagag   1320

ctccttgtgc tcttagagaa ccagaaaacg ctagacgaac atgattccaa tgtcaaaaac   1380

ctttttgatg aagtgaaaag gagactgtca gccaatgcaa tagatgctgg gaacggttgc   1440

tttgacatac ttcacaaatg cgacaatgag tgtatggaaa ctataaagaa cggaacttac   1500

gatcataagg aatatgaaga ggaggctaaa ctagaaagga gcaagataaa tggagtaaaa   1560

ctagaagaga acaccactta caaaattctt agcatttaca gtacagtggc ggccagtctt   1620

tgcttggcaa tcctgattgc tggaggttta atcctgggca tgcaaaatgg atcttgtaga   1680

tgcatgttct gtatttga                                                 1698
```

<210> SEQ ID NO 18
<211> LENGTH: 1363
<212> TYPE: DNA
<213> ORGANISM: Influenza virus

<400> SEQUENCE: 18

```
atggaaacag tatcactaat gactatacta ctagtagcaa cagcaagcaa tgcagacaaa     60
atctgcatcg gccaccagtc aacaaactcc acagaaactg tggacacgct aacagaaacc    120
aatgttcctg tgacacatgc caaagaattg ctccacacag agcacaatgg aatgctgtgt    180
gcaacaaatc tgggacatcc cctaatctta gacacgtgca ctattgaagg actgatctat    240
ggtaaccctt cttgtgactt gctgttggga ggaagagaat ggtcctacat cgtcgaaagg    300
tcatcagctg taaatggaac gtgttaccct gggaatgtag agaacctaga ggaactcagg    360
acacttttta gttccgctag ttcctaccga agaatccaaa tcttcccaga cacaatctgg    420
aatgtgactt acactggaac aagcaaagca tgttcagatt cattctacag gagtatgaga    480
tggctgactc aaaaaagcgg gtcttaccct gttcaagacg ctcaatacac aaataatatg    540
ggaaagagca ttcttttcgt gtggggcata catcacccac ccactgaagc tgcacagaca    600
aatttgtaca caagaaccga cacaacaaca agcgtgacaa cagaagactt aaataggatc    660
ttcaaaccga tggtagggcc aaggcccctt gtcaatggtc tgcagggaag aattaattat    720
tattggtcgg tactaaaacc aggccagaca ctgcgagtaa gatccaatgg gaatctaatt    780
gctccatggt atggacacat tctttcggga gggagccatg gaagaatcct gaagactgat    840
ttaaaaagta gtaattgcgt agtgcaatgt cagactgaaa aaggcggctt aaacagtaca    900
ttgccgttcc acaatatcag taaatatgca tttggaaact gtcccaaata tgttagagtt    960
aaaagtctca aactggcagt agggttgagg aacgtgcctg ctagatcaag tagaggacta   1020
ttcggagcca tagctggatt catagaagga ggttggccag gactagtcgc tggttggtat   1080
ggtttccagc attcaaatga tcaaggggtt ggtattgcgg cagataggga ttcaactcaa   1140
aaggcaattg atagaataac aaccaaggtg aataatatag tcgacaaaat gaacaaacaa   1200
tatgaaataa ttgatcatga attcagtgag gttgaaacta ggctcaacat gatcaataat   1260
aagattgatg accaaataca agacatatgg gcatataatg cagagttgct agtactactt   1320
gaaaaccaga aaacactcga tgagcatgac gcaaatgtga aga                     1363
```

<210> SEQ ID NO 19
<211> LENGTH: 1727
<212> TYPE: DNA
<213> ORGANISM: Influenza virus

<400> SEQUENCE: 19

```
agcaaaagca ggggtcacaa tgtacaaagt agtagtaata attgcgctcc ttggagcagt     60
gaaaggtctt gacagaatct gcctaggaca ccatgcggtt gccaatggaa ccattgtgaa    120
gacccttaca aatgaacaag aggaagtgac caatgctact gagacggtag agagcacaaa    180
tttgaataaa ttgtgtatga aaggaagaag ctacaaggac ttgggcaatt gtcacccggt    240
aggaatgttg ataggaacac ctgtttgtga tccgcacttg accgggacct gggacactct    300
cattgagcga gagaatgcca ttgcccactg ttatccaggg gcaaccataa atgaagaagc    360
attgaggcag aaaataatgg aaagtggagg aatcagcaag atgagcactg gcttcactta    420
tgggtcttcc atcacctcag ctgggaccac taaggcatgc atgagaaatg gaggagatag    480
tttctatgca gagctcaaat ggctagtgtc aaagacaaag ggacaaaatt tccctcagac    540
aacaaacacc tatcggaata cggacacagc agaacatctc ataatatggg gaattcatca    600
cccttccagc acacaggaaa agaatgactt atacggaact cagtcactat ctatatcagt    660
```

```
tgagagttct acatatcaga acaactttgt tccagttgtt ggggcaagac ctcaggtcaa     720

tggacaaagt gggcgaattg actttcactg gacactagta cagccgggtg acaacataac     780

cttctcagac aatggaggtc taatagcacc aagtcgagtt agcaaattaa ctggaaggga     840

tttgggaatc caatcagaag cgttgataga caacagttgt gaatccaaat gcttttggag     900

agggggttct ataaatacaa agctcccttt tcaaaatctg tcacccagaa cagtaggtca     960

atgccccaaa tacgtaaatc agaggagttt actgcttgca acagggatga ggaatgtgcc    1020

agaagtggtg cagggaaggg gtctgtttgg tgcaatagca gggttcatag aaaacggatg    1080

ggaaggaatg gtagacggct ggtatggttt cagacaccaa aatgcccagg gcacaggcca    1140

agctgctgat tacaagagta ctcaagcagc tattgaccaa atcacaggga aactgaacag    1200

gttgattgag aagaccaaca ctgagtttga gtcaatagaa tctgaattca gtgagactga    1260

gcatcaaatt ggtaacgtca ttaattggac caaagattca ataaccgaca tttggactta    1320

caacgcagag ctattagtgg caatggagaa tcagcacaca attgacatgg ctgattcaga    1380

gatgctaaat ctgtatgaaa gggtaagaaa gcaactcaga cagaatgcag aagaagacgg    1440

aaagggatgt tttgagatat atcatacttg tgatgattcg tgcatggaga gtataaggaa    1500

caatacttat gaccattcac aatacagaga ggaggctctt ctgaatagac tgaacatcaa    1560

cccagtgaaa ctttcttcgg ggtacaaaga catcatactt tggtttagct tcggggaatc    1620

atgctttgtt cttctagccg ttgttatggg tcttgttttc ttctgcctga aaaatggaaa    1680

catgcgatgc acaatctgta tttagttaaa aacaccttgt ttctact                  1727
```

<210> SEQ ID NO 20
<211> LENGTH: 1698
<212> TYPE: DNA
<213> ORGANISM: Influenza virus

<400> SEQUENCE: 20

```
atggagaaaa cactgctatt tgcagctatt ttcctttgtg tgaaagcaga tgagatctgt      60

atcgggtatt taagcaacaa ctcgacagac aaagttgaca caataattga gaacaatgtc     120

acggtcacta gctcagtgga actggttgag acagaacaca ctggatcatt ctgttcaatc     180

aatggaaaac aaccaataag ccttggagat tgttcatttg ctggatggat attaggaaac     240

cctatgtgtg atgaactaat tggaaagact tcatggtctt acattgtgga aaaacccaat     300

ccaacaaatg gaatctgtta cccaggaact ttagagagtg aagaagaact aagactgaaa     360

ttcagtggag ttttagaatt taacaaattc gaagtattca catcaaatgg atggggtgct     420

gtaaattcag gagtaggagt aaccgctgca tgcaaattcg gggttctaa ttctttcttt      480

cgaaacatgg tatggctgat acaccaatca ggaacatatc ctgtaataaa gagaaccttt     540

aacaacacca aagggagaga tgtactgatt gtttggggaa ttcatcatcc tgctacactg     600

acagaacatc aagatctgta taaaaaggac agctcctatg tagcagtggg ttcagagacc     660

tacaacagaa gattcactcc agaaatcaac actaggccca gagtcaatgg acaggccgga     720

cggatgacat tctactggaa gatagtcaaa ccaggagaat caataacatt cgaatctaat     780

ggggcgttcc tagctcctag atatgctttt gagattgtct ctgttggaaa tgggaaactg     840

ttcaggagcg aactgaacat tgaatcatgc tctaccaaat gtcaaacaga aataggagga     900

attaatacga acaaaagctt ccacaatgtt cacagaaaca ctatcgggga ttgccccaag     960

tatgtgaatg tcaaatcctt aaagcttgca acaggaccta gaaatgtccc agcaatagca    1020

tcgagaggct tgtttggagc aatagctgga ttcatagaag gggatggcc tggactgatc     1080
```

aatggatggt atgggttcca acacagggac gaagaaggaa caggcattgc agcagacaag 1140
gagtcaactc aaaaggcaat agaccagata acatccaagg taaataacat cgttgacagg 1200
atgaatacaa actttgagtc tgtgcaacac gaattcagtg aaatagagga aagaataaat 1260
caattatcaa aacacgtaga tgattctgtg gttgacatct ggtcatataa tgcacagctt 1320
ctcgttttac ttgaaaatga gaagacactg gacctccatg actcaaatgt caggaacctc 1380
catgagaaag tcagaagaat gctaaaggac aatgccaaag atgaggggaa cggatgcttc 1440 acctttttacc ataagtgtga caataaatgc attgaacgag ttagaaacgg aacatatgat 1500
cataaagaat tcgaggagga atcaaaaatc aatcgccagg agattgaagg ggtgaaacta 1560
gattctagtg ggaatgtgta taaaatactg tcaatttaca gctgcattgc aagcagtctt 1620
gtattggcag cactcatcat ggggttcatg ttttgggcat gcagtaatgg atcatgtaga 1680
tgtaccattt gcatttag 1698

<210> SEQ ID NO 21
<211> LENGTH: 1695
<212> TYPE: DNA
<213> ORGANISM: Influenza virus

<400> SEQUENCE: 21
atggaaaaat tcatcatttt gagtactgtc ttggcagcaa gctttgcata tgacaaaatt 60
tgcattggat accaaacaaa caactcgact gaaacggtaa acacactaag tgaacaaaac 120
gttccggtga cgcaggtgga agaacttgta catcgtggga ttgatccgat cctgtgtgga 180
acggaactag gatcaccact agtgcttgat gactgttcat tagagggtct aatcctaggc 240
aatcccaaat gtgatcttta tttgaatggc agggaatggt catacatagt agagaggccc 300
aaagagatgg aaggagtttg ctatccaggg tcaattgaaa accaggaaga gctaagatct 360
ctgttttctt ccatcaaaaa atatgaaaga gtgaagatgt ttgatttcac caaatggaat 420
gtcacataca ctgggaccag caaggcctgc aataatacat caaaccaagg ctcattctat 480
aggagcatga gatggttgac cttaaaatca ggacaatttc cagtccaaac agatgagtac 540
aagaacacca gagattcaga cattgtattc acctgggcca ttcaccaccc accaacatct 600
gatgaacaag taaaattata caaaaatcct gatactctct cttcagtcac caccgtagaa 660
atcaatagga gcttcaagcc taatataggg ccaagaccac tcgtgagagg acaacaaggg 720
agaatggatt actactgggc tgttcttaaa cctggacaaa cagtcaaaat acaaaccaat 780
ggtaatctta ttgcacctga atatggtcac ttaatcacag ggaaatcaca tggcaggata 840
ctcaagaata atttgcccat gggacagtgt gtgactgaat gtcaattgaa cgagggtgta 900
atgaacacaa gcaaaccttt ccagaacact agtaagcact atattgggaa atgccccaaa 960
tacataccat cagggagttt aaaattggca atagggctca ggaatgtccc acaagttcaa 1020
gatcgggggc tctttggagc aattgcaggt ttcatagaag gcggatggcc agggctagtg 1080
gctggttggt acggatttca gcatcaaaat gcggaggggga caggcatagc tgcagacaga 1140
gacagcaccc aaagggcaat agacaatatg caaaacaaac tcaacaatgt catcgacaaa 1200
atgaataaac aatttgaagt ggtgaatcat gagttttcag aagtggaaag cagaataaac 1260
atgattaatt ccaaaattga tgatcagata actgacatat gggcatacaa tgctgaattg 1320
cttgtcctat tggaaaatca gaagacatta gatgagcatg acgctaatgt aaggaatcta 1380
catgatcggg tcagaagagt cctgagggaa aatgcaattg acacaggaga cggctgcttt 1440

```
gagattttac ataaatgtga caacaattgt atggacacga ttagaaacgg gacatacaat   1500

cacaaagagt atgaggaaga aagcaaaatc gaacgacaga aagtcaatgg tgtgaaactt   1560

gaggagaatt ctacatataa aattctgagc atctacagca gtgttgcctc aagcttagtt   1620

ctactgctca tgattattgg gggtttcatt ttcgggtgtc aaaatggaaa tgttcgttgt   1680

actttctgta tttaa                                                    1695
```

<210> SEQ ID NO 22
<211> LENGTH: 1701
<212> TYPE: DNA
<213> ORGANISM: Influenza virus

<400> SEQUENCE: 22

```
atggctctaa atgtcattgc aactttgaca cttataagtg tatgtgtaca tgcagacaga     60

atatgcgtgg ggtatctgag caccaattca tcagaaaggg tcgacacgct ccttgaaaat    120

ggggtcccag tcaccagctc cattgatctg attgagacaa accacacagg aacatactgt    180

tctctaaatg gagtcagtcc agtgcatttg ggagattgca gctttgaagg atggattgta    240

ggaaacccag cctgcaccag caactttggg atcagagagt ggtcatacct gattgaggac    300

cccgcggccc ctcatgggct ttgctaccct ggagaattaa acaacaatgg tgaactcaga    360

cacttgttca gtggaatcag gtcattcagt agaacggaat tgatcccacc tacctcctgg    420

ggggaagtac ttgacggtac aacatctgct tgcagagata acacgggaac caacagcttc    480

tatcgaaatt tagtttggtt tataaagaag aatactagat atccagttat cagtaagacc    540

tacaacaata caacgggaag ggatgtttta gttttatggg gaatacatca cccagtgtct    600

gtggatgaga caaagactct gtatgtcaat agtgatccat acacactggt ttccaccaag    660

tcttggagcg agaaatataa actagaaacg ggagtccgac ctggctataa tggacagagg    720

agctggatga aaatttattg gtctttgata catccagggg agatgattac tttcgagagt    780

aatggtggat tttagcccc aagatatggg tacataattg aagaatatgg aaaaggaagg    840

attttccaga gtcgcatcag aatgtctagg tgcaacacca agtgccagac ttcggttgga    900

gggataaaca caaacagaac gttccaaaac atcgataaga atgctcttgg tgactgtccc    960

aaatacataa agtctggcca actcaagcta gccactggac tcagaaatgt gccagctata   1020

tcgaatagag gattgttcgg agcaattgca gggttcatag aaggaggctg gccaggttta   1080

atcaatggtt ggtacggttt tcagcatcaa aatgaacagg gaacaggaat agctgcagac   1140

aaagaatcaa cacagaaagc tatagaccag ataacaacca aaataaataa cattattgat   1200

aaaatgaatg ggaactatga ttcaattagg ggtgaattca atcaagttga gaagcgtata   1260

aacatgcttg cagacagaat agatgatgcc gtgacggaca tttggtcata caatgccaaa   1320

cttcttgtat tgctggaaaa tgataaaact ttagatatgc atgatgctaa tgtaaagaat   1380

ttacatgagc aagtacgaag agaattgaag gacaatgcaa ttgacgaagg aaatggctgt   1440

tttgaactcc ttcataaatg caatgactcc tgcatggaaa ctataagaaa tggaacgtat   1500

gaccacactg agtatgcaga ggagtcaaag ttaaagaggc aagaaatcga tgggatcaaa   1560

ctcaaatcag aagacaacgt ttacaaagca ttatcaatat acagttgcat tgcaagtagt   1620

gttgtactag taggactcat actctctttc atcatgtggg cctgtagtag tgggaattgc   1680

cgattcaatg tttgtatata a                                             1701
```

<210> SEQ ID NO 23
<211> LENGTH: 1749

<212> TYPE: DNA
<213> ORGANISM: Influenza virus

<400> SEQUENCE: 23
agcaaaagca ggggaaaatg attgcactca tattggttgc actggctctg agccacactg 60
cttattctca gatcacaaat gggacaacag gaaaccccat tatatgcttg gggcatcatg 120
cagtggaaaa cggcacatct gttaaaacac taacagacaa tcacgtagaa gttgtgtcag 180
ctaaagaatt agttgagacg aaccacactg atgaactgtg cccaagcccc ttgaagcttg 240
tcgacgggca agactgccac ctcatcaatg gtgcattggg gagtccaggc tgtgaccgtt 300
tgcaggacac cacttgggat gtcttcattg aaaggcccac tgcagtagac acatgttatc 360
cattcgacgt cccagattac cagagtctca gaagcatcct agcaagcagt gggagtttgg 420
agttcatcgc cgaacaattc acctggaatg gtgtcaaagt tgacggatca agcagtgctt 480
gtttgagggg cggtcgcaac agcttcttct cccgactaaa ctggctaacc aaagcaacaa 540
atggaaacta tggacctatt aacgtcacta aagaaaatac gggctcttat gtcaggctct 600
atctctgggg agtgcatcac ccatcaagcg ataatgagca aacggatctc tacaaggtgg 660
caacagggag agtaacagta tctacccgct cggaccaaat cagtattgtt cccaatatag 720
gaagtagacc gagggtaagg aatcagagcg gcaggataag catctactgg accctagtaa 780
acccagggga ctccatcatt ttcaacagta ttgggaattt gattgcacca agaggccact 840
acaaaataag caaatctact aagagcacag tgcttaaaag tgacaaaagg attgggtcat 900
gcacaagccc ttgcttaact gataaaggtt cgatccaaag tgacaaacct tttcagaatg 960
tatcaaggat tgctatagga aactgcccga aatatgtaaa gcaagggtcc ctgatgttag 1020
caactggaat gcgcaacatc cctggcaaac aggcaaaggg cttatttggg gcaattgctg 1080
gattcattga aaatggttgg caaggcctga ttgatgggtg gtatggattc aggcaccaaa 1140
atgctgaagg aacaggaact gctgcagacc tgaagtcaac tcaggcagcc attgatcaga 1200
taaatggcaa gctgaacaga ttgatagaga agacaaatga aaaatatcac caaatagaaa 1260
aggaattcga acaggtggaa ggaagaatac aagaccttga gaagtacgtt gaggacacta 1320
agattgattt gtggtcatac aatgctgaat tgctagtagc actagagaat cagcacacaa 1380
tagatgtcac agactccgaa atgaacaagc tttttgaaag agtaagaagg caattaagag 1440
agaatgcaga agatcaaggc aacggttgtt tcgagatatt ccatcagtgt gacaacaatt 1500
gtatagaaag cattagaaac ggaacttatg accacaacat ctacagggat gaagccatca 1560
acaatcgaat caaaataaat cctgtcactt tgacgatggg gtacaaggac ataatcctgt 1620
ggatttcttt ctccatgtca tgctttgtct tcgtggcact gattctggga tttgttctat 1680
gggcttgtca aaacgggaat atccgatgcc aaatctgtat ataaagaaaa aacacccttg 1740
tttctactc 1749

<210> SEQ ID NO 24
<211> LENGTH: 1762
<212> TYPE: DNA
<213> ORGANISM: Influenza virus

<400> SEQUENCE: 24
agcaaaagca ggggatacaa aatgaacact caaatcatcg tcattctagt cctcggactg 60
tcgatggtga gatctgacaa gatttgtctc gggcaccatg ccgtagcaaa tgggacaaaa 120
gtcaacacac taactgagaa aggagtggaa gtggtcaatg ccacggagac agtggagatt 180

-continued

```
acaggaataa ataaagtgtg cacaaaaggg aagaaagcgg tggacttggg atcttgtgga    240

atactgggaa ctatcattgg gcctccacaa tgtgactctc atcttaaatt caaagctgat    300

ctgataatag aaagaagaaa ttcaagtgac atctgttacc cagggaaatt cactaatgag    360

gaagcactga gacaaataat cagagaatct ggtggaattg acaaagagcc aatgggattt    420

agatattcag gaataaaaac agacggggca accagtgcgt gtaagagaac agtgtcctct    480

ttctactcag aaatgaaatg gcttttatcc agcaaggcta accaggtgtt cccacaactg    540

aatcagacat acaggaacaa cagaaaagaa ccagccctaa ttgtttgggg agtacatcat    600

tcaagttcct tggatgagca aaataagcta tatggagctg ggaacaagct gataacagta    660

ggaagctcaa aataccaaca atcgttttca ccaagtccag gggacaggcc caaagtgaat    720

ggtcaggccg ggaggatcga ctttcattgg atgctattgg acccagggga tacagtcact    780

tttaccttca atggtgcatt catagcccca gatagagcca cctttctccg ctctaatgcc    840

ccatcgggag ttgagtacaa tgggaagtca ctgggaatac agagtgatgc acaaattgat    900

gaatcatgtg aaggggaatg cttctacagt ggagggacaa taaacagccc tttgccattt    960

caaaacatcg atagttgggc tgtcggaagg tgccccagat atgtaaagca atcaagcctg   1020

ccgctggcct taggaatgaa aaatgtacca gagaaaatac atactagggg actgttcggt   1080

gcaattgcag gattcatcga gaatggatgg gaaggactca ttgatggatg gtatggattt   1140

aggcatcaaa atgcacaggg gcagggaaca gctgctgact acaagagtac tcaggctgca   1200

attgaccaga taacagggaa acttaataga ttaattgaaa aaaccaacac acagtttgaa   1260

ctcatagaca atgagttcac tgaagtggag cagcagatag gcaatgtaat aaactggaca   1320

agggactcct tgactgagat ctggtcatac aatgctgaac ttctagtagc aatggaaaat   1380

cagcatacaa ttgaccttgc agattctgaa atgaacaaac tctatgagag agtgagaaga   1440

cagctaaggg agaatgccga ggaggatgga actggatgtt ttgagatttt ccaccgatgt   1500

gacgatcaat gtatggagag catacgaaat aatacttaca atcacactga atatcgacag   1560

gaagccttac agaataggat aatgatcaat ccggtaaagc ttagtggtgg gtacaaagat   1620

gtgatactat ggtttagctt cggggcatca tgtgtaatgc ttctagccat tgctatgggt   1680

cttattttca tgtgtgtgaa aaacgggaat ctgcggtgca ctatctgtat ataattattt   1740

gaaaaacacc cttgtttcta ct                                            1762


<210> SEQ ID NO 25
<211> LENGTH: 1760
<212> TYPE: DNA
<213> ORGANISM: Influenza virus

<400> SEQUENCE: 25

agcaaaagca ggggatattg tcaaaacaac agaatggtga tcaaagtgct ctactttctc     60

atcgtattgt taagtaggta ttcgaaagca gacaaaatat gcataggata tctaagcaac    120

aacgccacag acacagtaga cacactgaca gagaacggag ttccagtgac cagctcagtt    180

gatctcgttg aaacaaacca cacaggaaca tactgctcac tgaatggaat cagcccaatt    240

catcttggtg actgcagctt tgagggatgg atcgtaggaa acccttcctg tgccaccaac    300

atcaacatca gagagtggtc gtatctaatt gaggaccccca atgcccccaa caaactctgc    360

ttcccaggag agttagataa taatggagaa ttacgacatc tcttcagcgg agtgaactct    420

tttagcagaa cagaattaat aagtcccaac aaatggggag acattctgga tggagtcacc    480

gcttcttgcc gcgataatgg ggcaagcagt ttttacagaa atttggtctg gatagtgaag    540
```

aataaaaatg gaaaataccc tgtcataaag ggggattaca ataacacaac aggcagagat 600
gttctagtac tctggggcat tcaccatccg gatacagaaa caacagccat aaacttgtac 660
gcaagcaaaa acccctacac attagtatca acaaaggaat ggagcaaaag atatgaacta 720
gaaattggca ccagaatagg tgatggacag agaagttgga tgaaactata ttggcacctc 780
atgcgccctg gagagaggat aatgtttgaa agcaacgggg gccttatagc gcccagatac 840
ggatacatca ttgagaagta cggtacagga cgaattttcc aaagtggagt gagaatggcc 900
aaatgcaaca caaagtgtca aacatcatta ggtgggataa acaccaacaa aactttccaa 960
aacatagaga gaaatgctct tggagattgc ccaaagtaca taaagtctgg acagctgaag 1020
cttgcaactg ggctgagaaa tgtcccatcc gttggtgaaa gaggtttgtt tggtgcaatt 1080
gcaggcttca tagaaggagg gtggcctggg ctaattaatg gatggtatgg tttccagcat 1140
cagaatgaac aggggactgg cattgctgca gacaaagcct ccactcagaa agcgatagat 1200
gaaataacaa caaaaattaa caatataata gagaagatga acggaaacta tgattcaata 1260
agaggggaat tcaatcaagt agaaaagagg atcaacatgc tcgctgatcg agttgatgat 1320
gcagtaactg acatatggtc gtacaatgct aaacttcttg tactgcttga aaatgggaga 1380
acattggact tacacgacgc aaatgtcagg aacttacacg atcaggtcaa gagaatattg 1440
aaaagtaatg ctattgatga aggagatggt tgcttcaatc ttcttcacaa atgtaatgac 1500
tcatgcatgg aaactattag aaatgggacc tacaatcatg aagattacag ggaagaatca 1560
caactgaaaa ggcaggaaat tgagggaata aaattgaagt ctgaagacaa tgtgtataaa 1620
gtactgtcga tttatagctg cattgcaagc agtattgtgc tggtaggtct catacttgcg 1680
ttcataatgt gggcatgcag caatggaaat tgccggttta atgtttgtat atagtcggaa 1740 aaaatacct tgtttctact 1760

<210> SEQ ID NO 26
<211> LENGTH: 1882
<212> TYPE: DNA
<213> ORGANISM: Influenza virus

<400> SEQUENCE: 26
agcagaagcg ttgcattttc taatatccac aaaatgaagg caataattgt actactcatg 60
gtagtaacat ccaatgcaga tcgaatctgc actgggataa catcgtcaaa ctcacctcat 120
gtggttaaaa ctgccactca aggggaagtc aatgtgactg gtgtgatacc actaacaaca 180
acacctacca aatctcattt tgcaaatctc aaaggaacac agaccagagg aaaactatgc 240
ccaaactgtt ttaactgcac agatctggac gtggccctag gcagaccaaa atgcatgggg 300
aacacaccct ccgcaaaagt ctcaatactc catgaagtca aacctgctac atctggatgc 360
tttcctataa tgcacgacag aacaaaaatc agacaactac ctaatcttct cagaggatat 420
gaaaacatca ggttatcaac cagtaatgtt atcaatacag agacggcacc aggaggaccc 480
tacaaggtgg ggacctcagg atcttgccct aacgttgcta atgggaacgg cttcttcaac 540
acaatggctt gggttatccc aaaagacaac aacaagacag caataaatcc agtaacagta 600
gaagtaccat acatttgttc agaaggggaa gaccaaatta ctgtttgggg gttccactct 660
gatgacaaaa cccaaatgga aagactctat ggagactcaa atcctcaaaa gttcacctca 720
tctgccaatg gagtaaccac acattatgtt tctcagattg gtggcttccc aaatcaaaca 780
gaagacgaag ggctaaaaca aagcggcaga attgttgttg attacatggt acaaaaacct 840
ggaaaaacag gaacaattgt ttatcaaaga ggcattttat tgcctcaaaa agtgtggtgc 900
gcaagtggca ggagcaaggt aataaaaggg tccttgcctt taattggtga agcagattgc 960
ctccacgaaa agtacggtgg attaaataaa agcaagcctt actacacagg agagcatgca 1020
aaggccatag gaaattgccc aatatgggtg aaaacaccct tgaagctggc caatggaacc 1080
aaatatagac cgcctgcaaa actattaaag gaaagaggtt tcttcggagc tattgctggt 1140
ttcttggaag gaggatggga aggaatgatt gcaggttggc acggatacac atctcatgga 1200
gcacatggag tggcagtggc agcagacctt aagagtacac aagaagctat aaacaagata 1260
acaaaaaatc tcaactattt aagtgagcta gaagtaaaaa accttcaaag actaagcgga 1320
gcaatgaatg agcttcacga cgaaatactc gagctagacg aaaaagtgga tgatctaaga 1380
gctgatacaa taagctcaca aatagagctt gcagtcttgc tttccaacga agggataata 1440
aacagtgaag atgagcatct cttggcactt gaaagaaaac tgaagaaaat gcttggcccc 1500
tctgctgtag aaatagggaa tgggtgcttt gaaaccaaac acaaatgcaa ccagacttgc 1560
ctagacagga tagctgctgg caccttaat gcaggagatt tttctcttcc cacttttgat 1620
tcattaaaca ttactgctgc atctttaaat gatgatggct tggataatca tactatactg 1680
ctctactact caactgctgc ttctagcttg gctgtaacat taatgatagc tatcttcatt 1740
gtctacatgg tctccagaga caatgtttct tgttccatct gtctgtgagg gagattaagc 1800
cctgtgtttt cctttactgt agtgctcatt tgcttgtcac cattacaaag aaacgttatt 1860
gaaaaatgct cttgttacta ct 1882

<210> SEQ ID NO 27
<211> LENGTH: 2073
<212> TYPE: DNA
<213> ORGANISM: Influenza virus

<400> SEQUENCE: 27
agcagaagca gggggttaat aatgtttttc tcattactct tggtgttggg cctcacagag 60
gctgaaaaaa taaagatatg ccttcaaaag caagtgaaca gtagcttcag cctacacaat 120
ggcttcggag gaaatttgta tgccacagaa gaaaaaagaa tgtttgagct tgttaagccc 180
aaagctggag cctctgtctt gaatcaaagt acatggattg gctttggaga ttcaaggact 240
gacaaaagca attcagcttt tcctaggtct gctgatgttt cagcaaaaac tgctgataag 300
tttcgttttt tgtctggtgg atccttaatg ttgagtatgt ttggcccacc tgggaaggta 360
gactaccttt accaaggatg tggaaaacat aaagtttttt atgaaggagt taactggagt 420
ccacatgctg ctataaattg ttacagaaaa aattggactg atatcaaact gaatttccag 480
aaaaacattt atgaattggc ttcacaatca cattgcatga gcttggtgaa tgccttggac 540
aaaactattc ctttacaagt gactgctggg actgcaggaa attgcaacaa cagcttctta 600
aaaaatccag cattgtacac acaagaagtc aagccttcag aaaacaaatg tgggaaagaa 660
aatcttgctt tcttcacact tccaacccaa tttggaacct atgagtgcaa actgcatctt 720
gtggcttctt gctatttcat ctatgatagt aaagaagtgt acaataaaag aggatgtgac 780
aactactttc aagtgatcta tgattcattt ggaaaagtcg ttggaggact agataacagg 840
gtatcacctt acacagggaa ttctggagac accccaacaa tgcaatgtga catgctccag 900
ctgaaacctg gaagatattc agtaagaagc tctccaagat tccttttaat gcctgaaaga 960
agttattgct ttgacatgaa agaaaaagga ccagtcactg ctgtccaatc catttgggga 1020
aaaggcagag aatctgacta tgcagtggat caagcttgct tgagcactcc agggtgcatg 1080

```
ttgatccaaa agcaaaagcc atacattgga gaagctgatg atcaccatgg agatcaagaa   1140

atgagggagt tgctgtcagg actggactat gaagctagat gcatatcaca atcagggtgg   1200

gtgaatgaaa ccagtccttt tacggagaaa tacctccttc ctcccaaatt tggaagatgc   1260

cctttggctg caaaggaaga atccattcca aaaatcccag atggccttct aattcccacc   1320

agtggaaccg ataccactgt aaccaaacct aagagcagaa tttttggaat cgatgacctc   1380

attattggtg tgctctttgt tgcaatcgtt gaaacaggaa ttggaggcta tctgcttgga   1440

agtagaaaag aatcaggagg aggtgtgaca aaagaatcag ctgaaaaagg gtttgagaaa   1500

attggaaatg acatacaaat ttaaaaatct tctataaata tcgcaataga aaaactaaat   1560

gacagaattt ctcatgatga gcaagccatc agagatctaa ctttagaaat tgaaaatgca   1620

agatctgaag ctttattggg agaattggga ataataagag ccttattggt aggaaatata   1680

agcataggat tacaggaatc tttatgggaa ctagcttcag aaataacaaa tagagcagga   1740

gatctagcag ttgaagtctc cccaggttgc tggataattg acaataacat ttgtgatcaa   1800

agctgtcaaa attttatttt caagttcaac gaaactgcac ctgttccaac cattccccct   1860

cttgacacaa aaattgatct gcaatcagat cctttttact ggggaagcag cttgggctta   1920

gcaataactg ctactatttc attggcagct ttggtgatct ctgggatcgc catctgcaga   1980

actaaatgat tgagacaatt ttgaaaaatg gataatgtgt tggtcaatat tttgtacagt   2040

tttataaaaa acaaaaatcc ccttgctact gct                                 2073
```

```
<210> SEQ ID NO 28
<211> LENGTH: 1670
<212> TYPE: DNA
<213> ORGANISM: Artificial sequence
<220> FEATURE:
<223> OTHER INFORMATION: sequence encoding HA0 of H1 (A/New
      Caledonia/20/99 (H1N1))

<400> SEQUENCE: 28
```

```
agatcttcgc tgacacaata tgtataggct accatgccaa caactcaacc gacactgttg     60

acacagtact tgagaagaat gtgacagtga cacactctgt caacctactt gaggacagtc    120

acaatggaaa actatgtcta ctaaaaggaa tagccccact acaattgggt aattgcagcg    180

ttgccggatg gatcttagga aacccagaat gcgaattact gatttccaag gaatcatggt    240

cctacattgt agaaacacca aatcctgaga atggaacatg ttacccaggg tatttcgccg    300

actatgagga actgagggag caattgagtt cagtatcttc atttgagaga ttcgaaatat    360

tccccaaaga aagctcatgg cccaaccaca ccgtaaccgg agtatcagca tcatgctccc    420

ataatgggaa aagcagtttt tacagaaatt tgctatggct gacggggaag aatggtttgt    480

acccaaacct gagcaagtcc tatgtaaaca acaaagagaa agaagtcctt gtactatggg    540

gtgttcatca cccgcctaac atagggaacc aaagggcact ctatcataca gaaaatgctt    600

atgtctctgt agtgtcttca cattatagca gaagattcac cccagaaata gccaaaagac    660

ccaaagtaag agatcaggaa ggaagaatca actactactg gactctgctg gaacctgggg    720

atacaataat atttgaggca aatggaaatc taatagcgcc atggtatgct tttgcactga    780

gtagaggctt tggatcagga atcatcacct caaatgcacc aatggatgaa tgtgatgcga    840

agtgtcaaac acctcaggga gctataaaca gcagtcttcc tttccagaat gtacacccag    900

tcacaatagg agagtgtcca aagtatgtca ggagtgcaaa attaaggatg gttacaggac    960

taaggaacat cccatccatt caatccagag gtttgtttgg agccattgcc ggtttcattg   1020
```

aagggggggtg gactggaatg gtagatgggt ggtatggtta tcatcatcag aatgagcaag 1080
gatctggcta tgctgcagat caaaaaagta cacaaaatgc cattaacggg attacaaaca 1140
aggtcaattc tgtaattgag aaaatgaaca ctcaattcac agctgtgggc aaagagttca 1200
acaaattgga aagaaggatg gaaaacttaa ataaaaaagt tgatgatggg tttctagaca 1260
tttggacata taatgcagaa ttgttggttc tactggaaaa tgaaaggact ttggatttcc 1320
atgactccaa tgtgaagaat ctgtatgaga aagtaaaaag ccaattaaag aataatgcca 1380
aagaaatagg aaacgggtgt tttgagttct atcacaagtg taacaatgaa tgcatggaga 1440
gtgtgaaaaa tggtacctat gactatccaa aatattccga agaatcaaag ttaaacaggg 1500
agaaaattga tggagtgaaa ttggaatcaa tgggagtata ccagattctg gcgatctact 1560
caactgtcgc cagttccctg gttcttttgg tctccctggg ggcaatcagc ttctggatgt 1620
gttccaatgg gtctttgcag tgtagaatat gcatctaaga gctcaggcct 1670

<210> SEQ ID NO 29
<211> LENGTH: 32
<212> TYPE: DNA
<213> ORGANISM: Artificial sequence
<220> FEATURE:
<223> OTHER INFORMATION: primer XmaI-pPlas.c

<400> SEQUENCE: 29
agttccccgg gctggtatat ttatatgttg tc 32

<210> SEQ ID NO 30
<211> LENGTH: 46
<212> TYPE: DNA
<213> ORGANISM: Artificial sequence
<220> FEATURE:
<223> OTHER INFORMATION: primer SacI-ATG-pPlas.r

<400> SEQUENCE: 30
aatagagctc cattttctct caagatgatt aattaattaa ttagtc 46

<210> SEQ ID NO 31
<211> LENGTH: 46
<212> TYPE: DNA
<213> ORGANISM: Artificial sequence
<220> FEATURE:
<223> OTHER INFORMATION: primer SacI-PlasTer.c

<400> SEQUENCE: 31
aatagagctc gttaaaatgc ttcttcgtct cctatttata atatgg 46

<210> SEQ ID NO 32
<211> LENGTH: 48
<212> TYPE: DNA
<213> ORGANISM: Artificial sequence
<220> FEATURE:
<223> OTHER INFORMATION: primer EcoRI-PlasTer.r

<400> SEQUENCE: 32
ttacgaattc tccttcctaa ttggtgtact atcatttatc aaagggga 48

<210> SEQ ID NO 33
<211> LENGTH: 1711
<212> TYPE: DNA
<213> ORGANISM: Influenza virus

<400> SEQUENCE: 33

-continued atgaaagcaa aactactggt cctgttatgt acatttacag ctacatatgc agacacaata 60
tgtataggct accatgccaa caactcaacc gacactgttg acacagtact tgagaagaat 120
gtgacagtga cacactctgt caacctactt gaggacagtc acaatggaaa actatgtcta 180
ctaaaaggaa tagccccact acaattgggt aattgcagcg ttgccggatg gatcttagga 240
aacccagaat gcgaattact gatttccaag gaatcatggt cctacattgt agaaacacca 300
aatcctgaga atggaacatg ttacccaggg tatttcgccg actatgagga actgagggag 360
caattgagtt cagtatcttc atttgagaga ttcgaaatat tccccaaaga aagctcatgg 420
cccaaccaca ccgtaaccgg agtatcagca tcatgctccc ataatgggaa aagcagtttt 480
tacagaaatt tgctatggct gacggggaag aatggtttgt acccaaacct gagcaagtcc 540
tatgtaaaca acaaagagaa agaagtcctt gtactatggg gtgttcatca cccgcctaac 600
atagggaacc aaagggccct ctatcataca gaaaatgctt atgtctctgt agtgtcttca 660
cattatagca gaagattcac cccagaaata gccaaaagac ccaaagtaag agatcaggaa 720
ggaagaatca actactactg gactctgctg gaacctgggg atacaataat atttgaggca 780
aatggaaatc taatagcgcc atggtatgct tttgcactga gtagaggctt tggatcagga 840
atcatcacct caaatgcacc aatggatgaa tgtgatgcga agtgtcaaac acctcaggga 900
gctataaaca gcagtcttcc tttccagaat gtacacccag tcacaatagg agagtgtcca 960
aagtatgtca ggagtgcaaa attaaggatg gttacaggac taaggaacat cccatccatt 1020
caatccagag gtttgtttgg agccattgcc ggtttcattg aaggggggtg gactggaatg 1080
gtagatgggt ggtatggtta tcatcatcag aatgagcaag gatctggcta tgctgcagat 1140
caaaaaagta cacaaaatgc cattaacggg attacaaaca aggtgaattc tgtaattgag 1200
aaaatgaaca ctcaattcac agctgtgggc aaagaattca acaaattgga aagaaggatg 1260
gaaaacttaa ataaaaaagt tgatgatggg tttctagaca tttggacata taatgcagaa 1320
ttgttggttc tactggaaaa tgaaaggact ttggatttcc atgactccaa tgtgaagaat 1380
ctgtatgaga aagtaaaaag ccaattaaag aataatgcca aagaaatagg aaacgggtgt 1440
tttgaattct atcacaagtg taacaatgaa tgcatggaga gtgtgaaaaa tggaacttat 1500
gactatccaa aatattccga agaatcaaag ttaaacaggg agaaaattga tggagtgaaa 1560
ttggaatcaa tgggagtcta tcagattctg gcgatctact caactgtcgc cagttccctg 1620
gttcttttgg tctccctggg ggcaatcagc ttctggatgt gttccaatgg gtctttgcag 1680
tgtagaatat gcatctgaga ccagaatttc a 1711

<210> SEQ ID NO 34
<211> LENGTH: 1781
<212> TYPE: DNA
<213> ORGANISM: Medicago sativa

<400> SEQUENCE: 34
ccaaatcctt aacattcttt caacaccaac aatggcgaaa aacgttgcga ttttcggttt 60
attgttttct cttcttctgt tggttccttc tcagatcttc gctgaggaat catcaactga 120
cgctaaggaa tttgttctta cattggataa cactaatttc catgacactg ttaagaagca 180
cgatttcatc gtcgttgaat tctacgcacc ttggtgtgga cactgtaaga agctagcccc 240
agagtatgag aaggctgctt ctatcttgag cactcacgag ccaccagttg ttttggctaa 300
agttgatgcc aatgaggagc acaacaaaga cctcgcatcg gaaaatgatg ttaagggatt 360
cccaaccatt aagattttta ggaatggtgg aaagaacatt caagaataca aaggtccccg 420
tgaagctgaa ggtattgttg agtatttgaa aaaacaaagt ggccctgcat ccacagaaat 480
taaatctgct gatgatgcga ccgcttttgt tggtgacaac aaagttgtta ttgtcggagt 540
tttccctaaa ttttctggtg aggagtacga taacttcatt gcattagcag agaagttgcg 600
ttctgactat gactttgctc acactttgaa tgccaaacac cttccaaagg gagactcatc 660
agtgtctggg cctgtggtta ggttatttaa gccatttgac gagctctttg ttgactcaaa 720
ggatttcaat gtagaagctc tagagaaatt cattgaagaa tccagtaccc caattgtgac 780
tgtcttcaac aatgagccta gcaatcaccc ttttgttgtc aaattcttta actctcccaa 840
cgcaaaggct atgttgttca tcaactttac taccgaaggt gctgaatctt tcaaaacaaa 900
ataccatgaa gtggctgagc aatacaaaca acagggagtt agctttcttg ttggagatgt 960
tgagtctagt caaggtgcct tccagtattt tggactgaag gaagaacaag tacctctaat 1020
tattattcag cataatgatg gcaagaagtt tttcaaaccc aatttggaac ttgatcaact 1080
cccaacttgg ttgaaggcat acaaggatgg caaggttgaa ccatttgtca agtctgaacc 1140
tattcctgaa actaacaacg agcctgttaa agtggtggtt gggcaaactc ttgaggacgt 1200
tgttttcaag tctgggaaga atgttttgat agagttttat gctccttggt gtggtcactg 1260
caagcagttg gctccaatct tggatgaagt tgctgtctca ttccaaagcg atgctgatgt 1320
tgttattgca aaactggatg caactgccaa cgatatccca accgacacct ttgatgtcca 1380
aggctatcca accttgtact tcaggtcagc aagtggaaaa ctatcacaat acgacggtgg 1440
taggacaaag gaagacatca tagaattcat tgaaaagaac aaggataaaa ctggtgctgc 1500
tcatcaagaa gtagaacaac caaaagctgc tgctcagcca gaagcagaac aaccaaaaga 1560
tgagctttga aaagttccgc ttggaggata tcggcacaca gtcatctgcg ggctttacaa 1620
ctcttttgta tctcagaatc agaagttagg aaatcttagt gccaatctat ctatttttgc 1680
gtttcatttt atctttttgg tttactctaa tgtattactg aataatgtga gttttggcgg 1740
agtttagtac tggaactttt gtttctgtaa aaaaaaaaaa a 1781

<210> SEQ ID NO 35
<211> LENGTH: 1027
<212> TYPE: DNA
<213> ORGANISM: Influenza virus

<400> SEQUENCE: 35
agcgaaagca ggtagatatt gaaagatgag tcttctaacc gaggtcgaaa cgtacgttct 60
ctctatcatc ccgtcaggcc ccctcaaagc cgagatcgca cagagacttg aagatgtctt 120
tgcagggaag aacaccgatc ttgaggttct catggaatgg ctaaagacaa gaccaatcct 180
gtcacctctg actaagggga ttttaggatt tgtgttcacg ctcaccgtgc ccagtgagcg 240
aggactgcag cgtagacgct ttgtccaaaa tgcccttaat gggaacgggg atccaaataa 300
catggacaaa gcagttaaac tgtataggaa gctcaagagg gagataacat tccatggggc 360
caaagaaatc tcactcagtt attctgctgg tgcacttgcc agttgtatgg gcctcatata 420
caacaggatg gggctgtga ccactgaagt ggcatttggc ctggtatgtg caacctgtga 480
acagattgct gactcccagc atcggtctca taggcaaatg gtgacaacaa ccaacccact 540
aatcagacat gagaacagaa tggttttagc cagcactaca gctaaggcta tggagcaaat 600
ggctggatcg agtgagcaag cagcagaggc catggaggtt gctagtcagg ctaggcaaat 660
ggtgcaagcg atgagaacca ttgggactca tcctagctcc agtgctggtc tgaaaaatga 720

```
tcttcttgaa aatttgcagg cctatcagaa acgaatgggg gtgcagatgc aacggttcaa    780

gtgatcctct cgctattgcc gcaaatatca ttgggatctt gcacttgata ttgtggattc    840

ttgatcgtct ttttttcaaa tgcatttacc gtcgctttaa atacggactg aaaggagggc    900

cttctacgga aggagtgcca aagtctatga gggaagaata tcgaaaggaa cagcagagtg    960

ctgtggatgc tgacgatggt cattttgtca gcatagagct ggagtaaaaa actaccttgt   1020

ttctact                                                             1027


<210> SEQ ID NO 36
<211> LENGTH: 1788
<212> TYPE: DNA
<213> ORGANISM: Artificial sequence
<220> FEATURE:
<223> OTHER INFORMATION: clone 774 - nucleotide sequence of
      A/Brisbane/59/2007 (H1N1)

<400> SEQUENCE: 36

cactttgtga gtctacactt tgattccctt caaacacata caaagagaag agactaatta     60

attaattaat catcttgaga gaaaatgaaa gtaaaactac tggtcctgtt atgcacattt    120

acagctacat atgcagacac aatatgtata ggctaccatg ctaacaactc gaccgacact    180

gttgacacag tacttgaaaa gaatgtgaca gtgacacact ctgtcaacct gcttgagaac    240

agtcacaatg gaaaactatg tctattaaaa ggaatagccc cactacaatt gggtaattgc    300

agcgttgccg ggtggatctt aggaaaccca gaatgcgaat tactgatttc caaggagtca    360

tggtcctaca ttgtagaaaa accaaatcct gagaatggaa catgttaccc agggcatttc    420

gctgactatg aggaactgag ggagcaattg agttcagtat cttcatttga gaggttcgaa    480

atattcccca aagaaagctc atggcccaac cacaccgtaa ccggagtgtc agcatcatgc    540

tcccataatg gggaaagcag tttttacaga aatttgctat ggctgacggg gaagaatggt    600

ttgtacccaa acctgagcaa gtcctatgca aacaacaaag aaaaagaagt ccttgtacta    660

tggggtgttc atcacccgcc aaacataggt gaccaaaagg ccctctatca tacagaaaat    720

gcttatgtct ctgtagtgtc ttcacattat agcagaaaat tcaccccaga aatagccaaa    780

agacccaaag taagagatca agaaggaaga atcaattact actggactct gcttgaaccc    840

ggggatacaa taatatttga ggcaaatgga aatctaatag cgccaagata tgctttcgca    900

ctgagtagag gctttggatc aggaatcatc aactcaaatg caccaatgga taaatgtgat    960

gcgaagtgcc aaacacctca gggagctata aacagcagtc ttcctttcca gaacgtacac   1020

ccagtcacaa taggagagtg tccaaagtat gtcaggagtg caaaattaag gatggttaca   1080

ggactaagga acatcccatc cattcaatcc agaggtttgt ttggagccat tgccggtttc   1140

attgaagggg ggtggactgg aatggtagat ggttggtatg gttatcatca tcagaatgag   1200

caaggatctg gctatgctgc agatcaaaaa agcacacaaa atgccattaa tgggattaca   1260

aacaaggtca attctgtaat tgagaaaatg aacactcaat tcacagcagt gggcaaagag   1320

ttcaacaaat tggaaagaag gatggaaaac ttgaataaaa aagttgatga tgggtttata   1380

gacatttgga catataatgc agaactgttg gttctactgg aaaatgaaag gactttggat   1440

ttccatgact ccaatgtgaa gaatctgtat gagaaagtaa aaagccagtt aaagaataat   1500

gctaaagaaa taggaaatgg gtgttttgag ttctatcaca agtgtaacga tgaatgcatg   1560

gagagtgtaa agaatggaac ttatgactat ccaaaatatt ccgaagaatc aaagttaaac   1620

agggagaaaa ttgatggagt gaaattggaa tcaatgggag tctatcagat tctggcgatc   1680
```

tactcaacag tcgccagttc tctggttctt ttggtctccc tgggggcaat cagcttctgg 1740
atgtgttcca atgggtcttt acagtgtaga atatgcatct aagagctc 1788

<210> SEQ ID NO 37
<211> LENGTH: 1788
<212> TYPE: DNA
<213> ORGANISM: Artificial sequence
<220> FEATURE:
<223> OTHER INFORMATION: clone 775 - nucleotide sequence of A/Solomon Islands 3/2006 (H1N1)

<400> SEQUENCE: 37
cactttgtga gtctacactt tgattccctt caaacacata caaagagaag agactaatta 60
attaattaat catcttgaga gaaaatgaaa gtaaaactac tggtcctgtt atgcacattt 120
acagctacat atgcagacac aatatgtata ggctaccatg ccaacaactc aaccgacact 180
gttgacacag tacttgagaa gaatgtgaca gtgacacact ctgtcaacct gcttgaggac 240
agtcacaatg gaaaattatg tctattaaaa ggaatagccc cactacaatt gggtaattgc 300
agcgttgccg gatggatctt aggaaaccca gaatgcgaat tactgatttc cagggaatca 360
tggtcctaca ttgtagaaaa accaaatcct gagaatggaa catgttaccc agggcatttc 420
gccgactatg aggaactgag ggagcaattg agttcagtat cttcatttga gagattcgaa 480
atattcccca aagaaagctc atggcccaac cacaccacaa ccggagtatc agcatcatgc 540
tcccataatg gggaaagcag tttttacaaa aatttgctat ggctgacggg gaagaatggt 600
ttgtacccaa acctgagcaa gtcctatgca aacaacaaag agaaagaagt ccttgtacta 660
tggggtgttc atcacccgcc taacataggt gaccaaaggg ctctctatca taaagaaaat 720
gcttatgtct ctgtagtgtc ttcacattat agcagaaaat tcaccccaga aatagccaaa 780
agacccaaag taagagatca agaaggaaga atcaactact actggactct acttgaaccc 840
ggggatacaa taatatttga ggcaaatgga aatctaatag cgccaagata tgctttcgca 900
ctgagtagag gctttggatc aggaatcatc aactcaaatg caccaatgga tgaatgtgat 960
gcgaagtgcc aaacacctca gggagctata aacagcagtc ttcctttcca gaatgtacac 1020
cctgtcacaa taggagagtg tccaaagtat gtcaggagtg caaaattaag gatggttaca 1080
ggactaagga acatcccatc cattcaatcc agaggtttgt ttggagccat tgccggtttc 1140
attgaagggg ggtggactgg aatggtagat ggttggtatg gttatcatca tcagaatgag 1200
caaggatctg gctatgctgc agatcaaaaa agcacacaaa atgccattaa tgggattaca 1260
aacaaggtca attctgtaat tgagaaaatg aacactcaat tcacagctgt gggcaaagag 1320
ttcaacaaat tggaaagaag gatggaaaac ttaaataaaa aagttgatga tgggtttata 1380
gacatttgga catataatgc agaattgttg gttctactgg aaaatgaaag gactttggat 1440
ttccatgact ccaatgtgaa gaatctgtat gagaaagtaa aaagccaatt aaagaataat 1500
gccaaagaaa taggaaatgg gtgttttgag ttctatcata agtgtaacga tgaatgcatg 1560
gagagtgtaa aaaatggaac ttatgactat ccaaaatatt ccgaagaatc aaagttaaac 1620
agggagaaaa ttgatggagt gaaattggaa tcaatgggag tctatcagat tctggcgatc 1680
tactcaacag tcgccagttc tctggttctt ttggtctccc tgggggcaat cagcttctgg 1740
atgtgttcca atgggtcttt gcagtgtaga atatgcatct gagagctc 1788

<210> SEQ ID NO 38
<211> LENGTH: 1791
<212> TYPE: DNA

<213> ORGANISM: Artificial sequence
<220> FEATURE:
<223> OTHER INFORMATION: clone 776 - nucleotide sequence of A/Brisbane
      10/2007 (H3N2)

<400> SEQUENCE: 38

```
cactttgtga gtctacactt tgattccctt caaacacata caaagagaag agactaatta     60

attaattaat catcttgaga gaaaatgaag actatcattg ctttgagcta cattctatgt    120

ctggttttca ctcaaaaact tcccggaaat gacaacagca cggcaacgct gtgccttggg    180

caccatgcag taccaaacgg aacgatagtg aaaacaatca cgaatgacca aattgaagtt    240

actaatgcta ctgagctggt tcagagttcc tcaacaggtg aaatatgcga cagtcctcat    300

cagatccttg atggagaaaa ctgcacacta atagatgctc tattgggaga ccctcagtgt    360

gatggcttcc aaaataagaa atgggacctt tttgttgaac gcagcaaagc ctacagcaac    420

tgttaccctt atgatgtgcc ggattatgcc tcccttaggt cactagttgc ctcatccggc    480

acactggagt ttaacaatga aagtttcaat tggactggag tcactcaaaa cggaacaagc    540

tctgcttgca taaggagatc taataacagt ttctttagta gattgaattg gttgacccac    600

ttaaaattca aataccccagc attgaacgtg actatgccaa acaatgaaaa atttgacaaa    660

ttgtacattt gggggggttca ccacccgggt acggacaatg accaaatctt cctgtatgct    720

caagcatcag gaagaatcac agtctctacc aaaagaagcc aacaaactgt aatcccgaat    780

atcggatcta gacccagagt aaggaatatc cccagcagaa taagcatcta ttggacaata    840

gtaaaaccgg gagacatact tttgattaac agcacaggga atctaattgc tcctaggggt    900

tacttcaaaa tacgaagtgg gaaaagctca ataatgagat cagatgcacc cattggcaaa    960

tgcaattctg aatgcatcac tccaaacgga agcattccca atgacaaacc attccaaaat   1020

gtaaacagga tcacatacgg ggcctgtccc agatatgtta agcaaaacac tctgaaattg   1080

gcaacaggga tgcgaaatgt accagagaaa caaactagag gcatatttgg cgcaatcgcg   1140

ggtttcatag aaaatggttg ggagggaatg gtggatggtt ggtatggttt caggcatcaa   1200

aattctgagg gaataggaca agcagcagat ctcaaaagca ctcaagcagc aatcgatcaa   1260

atcaatggga agctgaatag gttgatcggg aaaaccaacg agaaattcca tcagattgaa   1320

aaagagttct cagaagtcga agggagaatc caggaccttg agaaatatgt tgaggacacc   1380

aaaatagatc tctggtcata caacgcggag cttcttgttg ccctggagaa ccaacataca   1440

attgatctaa ctgactcaga aatgaacaaa ctgtttgaaa aaacaaagaa gcaactgagg   1500

gaaaatgctg aggatatggg caatggttgt ttcaaaatat accacaaatg tgacaatgcc   1560

tgcataggat caatcagaaa tggaacttat gaccacgatg tatacagaga tgaagcatta   1620

aacaaccggt tccagatcaa gggcgttgag ctgaagtcag gatacaaaga ttggatacta   1680

tggatttcct ttgccatatc atgtttttttg ctttgtgttg ctttgttggg gttcatcatg   1740

tgggcctgcc aaaaaggcaa cattaggtgc aacatttgca tttgagagct c             1791
```

<210> SEQ ID NO 39
<211> LENGTH: 1791
<212> TYPE: DNA
<213> ORGANISM: Artificial sequence
<220> FEATURE:
<223> OTHER INFORMATION: clone 777 - nucleotide sequence of
      A/Wisconsin/67/2005 (H3N2)

<400> SEQUENCE: 39

```
cactttgtga gtctacactt tgattccctt caaacacata caaagagaag agactaatta     60
```

attaattaat catcttgaga gaaaatgaag actatcattg ctttgagcta cattctatgt 120
ctggttttca ctcaaaaact tcccggaaat gacaacagca cggcaacgct gtgccttggg 180
caccatgcag taccaaacgg aacgatagtg aaaacaatca cgaatgacca aattgaagtt 240
actaatgcta ctgagctggt tcagagttcc tcaacaggtg gaatatgcga cagtcctcat 300
cagatccttg atggagaaaa ctgcacacta atagatgctc tattgggaga ccctcagtgt 360
gatggcttcc aaaataagaa atgggacctt tttgttgaac gcagcaaagc ctacagcaac 420
tgttaccctt atgatgtgcc ggattatgcc tcccttaggt cactagttgc ctcatccggc 480
acactggagt ttaacgatga aagtttcaat tggactggag tcactcaaaa tggaacaagc 540
tctgcttgca aaaggagatc taataacagt ttctttagta gattgaattg gttgacccac 600
ttaaaattca aatacccagc attgaacgtg actatgccaa acaatgaaaa atttgacaaa 660
ttgtacattt ggggggttca ccacccgggt acggacaatg accaaatctt cctgcatgct 720
caagcatcag gaagaatcac agtctctacc aaaagaagcc aacaaactgt aatcccgaat 780
atcggatcta gacccagaat aaggaatatc cccagcagaa taagcatcta ttggacaata 840
gtaaaaccgg gagacatact tttgattaac agcacaggga atctaattgc tcctaggggt 900
tacttcaaaa tacgaagtgg gaaaagctca ataatgagat cagatgcacc cattggcaaa 960
tgcaattctg aatgcatcac tccaaatgga agcattccca atgacaaacc atttcaaaat 1020
gtaaacagga tcacatatgg ggcctgtccc agatatgtta agcaaaacac tctgaaattg 1080
gcaacaggga tgcgaaatgt accagagaaa caaactagag gcatatttgg cgcaatcgcg 1140
ggtttcatag aaaatggttg ggagggaatg gtggatggtt ggtacggttt caggcatcaa 1200
aattctgagg gaataggaca agcagcagat ctcaaaagca ctcaagcagc aatcaatcaa 1260
atcaatggga agctgaatag gttgatcggg aaaaccaacg agaaattcca tcagattgaa 1320
aaagagttct cagaagtaga agggagaatc caggacctcg agaaatatgt tgaggacact 1380
aaaatagatc tctggtcata caacgcggag cttcttgttg ccctggagaa ccaacataca 1440
attgatctaa ctgactcaga aatgaacaaa ctgtttgaaa gaacaaagaa gcaactgagg 1500
gaaaatgctg aggatatggg caatggttgt ttcaaaatat accacaaatg tgacaatgcc 1560
tgcataggat caatcagaaa tggaacttat gaccatgatg tatacagaga tgaagcatta 1620
aacaaccggt tccagatcaa aggcgttgag ctgaagtcag gatacaaaga ttggatacta 1680
tggatttcct ttgccatatc atgttttttg ctttgtgttg ctttgttggg gttcatcatg 1740
tgggcctgcc aaaaaggcaa cattaggtgc aacatttgca tttgagagct c 1791

<210> SEQ ID NO 40
<211> LENGTH: 1848
<212> TYPE: DNA
<213> ORGANISM: Artificial sequence
<220> FEATURE:
<223> OTHER INFORMATION: clone 778 - nucleotide sequence of
B/Malaysia/2506/2004

<400> SEQUENCE: 40
cactttgtga gtctacactt tgattccctt caaacacata caaagagaag agactaatta 60
attaattaat catcttgaga gaaaatgaag gcaataattg tactactcat ggtagtaaca 120
tccaatgcag atcgaatctg cactgggata acatcgtcaa actcaccaca tgttgtcaaa 180
actgctactc aaggggaggt caatgtgact ggtgtaatac cactgacaac aacacccacc 240
aaatctcatt ttgcaaatct caaaggaaca gaaaccagag ggaaactatg cccaaaatgc 300

```
ctcaactgca cagatctgga cgtggccttg ggcagaccaa aatgcacggg gaacataccc    360

tcggcaagag tttcaatact ccatgaagtc agacctgtta catctgggtg ctttcctata    420

atgcacgaca gaacaaaaat tagacagctg cctaaacttc tcagaggata cgaacatatc    480

aggttatcaa ctcataacgt tatcaatgca gaaaatgcac caggaggacc ctacaaaatt    540

ggaacctcag ggtcttgccc taacgttacc aatggaaacg gatttttcgc aacaatggct    600

tgggccgtcc caaaaaacga caacaacaaa acagcaacaa attcattaac aatagaagta    660

ccatacattt gtacagaagg agaagaccaa attaccgttt gggggttcca ctctgataac    720

gaaacccaaa tggcaaagct ctatggggac tcaaagcccc agaagttcac ctcatctgcc    780

aacggagtga ccacacatta cgtttcacag attggtggct tcccaaatca aacagaagac    840

ggaggactac cacaaagcgg tagaattgtt gttgattaca tggtgcaaaa atctgggaaa    900

acaggaacaa ttacctatca aagaggtatt ttattgcctc aaaaagtgtg gtgcgcaagt    960

ggcaggagca aggtaataaa aggatcgttg cctttaattg gagaagcaga ttgcctccac   1020

gaaaaatacg gtggattaaa caaaagcaag ccttactaca caggggaaca tgcaaaggcc   1080

ataggaaatt gcccaatatg ggtgaaaaca cccttgaagc tggccaatgg aaccaaatat   1140

agacctcctg caaaactatt aaaggaaagg ggtttcttcg gagctattgc tggtttctta   1200

gaaggaggat gggaaggaat gattgcaggt tggcacggat acacatccca tggggcacat   1260

ggagtagcgg tggcagcaga ccttaagagc actcaagagg ccataaacaa gataacaaaa   1320

aatctcaact ctttgagtga gctggaagta aagaatcttc aaagactaag cggtgccatg   1380

gatgaactcc acaacgaaat actagaacta gacgagaaag tggatgatct cagagctgat   1440

acaataagct cacaaataga actcgcagtc ctgctttcca atgaaggaat aataaacagt   1500

gaagatgagc atctcttggc gcttgaaaga aagctgaaga aaatgctggg cccctctgct   1560

gtagagatag ggaatggatg ctttgaaacc aaacacaagt gcaaccagac ctgtctcgac   1620

agaatagctg ctggtacctt tgatgcagga gaattttctc tccccacttt tgattcactg   1680

aatattactg ctgcatcttt aaatgacgat ggattggata atcatactat actgctttac   1740

tactcaactg ctgcctccag tttggctgta acattgatga tagctatctt tgttgtttat   1800

atggtctcca gagacaatgt ttcttgctcc atctgtctat aagagctc                1848
```

<210> SEQ ID NO 41
<211> LENGTH: 1845
<212> TYPE: DNA
<213> ORGANISM: Artificial sequence
<220> FEATURE:
<223> OTHER INFORMATION: clone 779 - nucleotide sequence of B/Florida/4/2006

<400> SEQUENCE: 41

```
cactttgtga gtctacactt tgattccctt caaacacata caaagagaag agactaatta     60

attaattaat catcttgaga gaaaatgaag gcaataattg tactactcat ggtagtaaca    120

tccaatgcag atcgaatctg cactggaata acatcttcaa actcacctca tgtggtcaaa    180

acagccactc aaggggaggt caatgtgact ggtgtgatac cactaacaac aacaccaaca    240

aaatcttatt ttgcaaatct caaaggaaca aggaccagag ggaaactatg cccagactgt    300

ctcaactgca cagatctgga tgtggctttg ggcagaccaa tgtgtgtggg gaccacacct    360

tcggcgaagg cttcaatact ccacgaagtc aaacctgtta catccgggtg ctttcctata    420

atgcacgaca gaacaaaaat caggcaacta cccaatcttc tcagaggata tgaaaatatc    480
```

```
aggctatcaa cccaaaacgt catcgatgcg gaaaaggcac caggaggacc ctacagactt    540
ggaacctcag gatcttgccc taacgctacc agtaagagcg gatttttcgc aacaatggct    600
tgggctgtcc caaaggacaa caacaaaaat gcaacgaacc cactaacagt agaagtacca    660
tacatttgta cagaagggga agaccaaatc actgtttggg ggttccattc agataacaaa    720
acccaaatga agaacctcta tggagactca aatcctcaaa agttcacctc atctgctaat    780
ggagtaacca cacactatgt ttctcagatt ggcagcttcc cagatcaaac agaagacgga    840
ggactaccac aaagcggcag gattgttgtt gattacatga tgcaaaaacc tgggaaaaca    900
ggaacaattg tctaccaaag aggtgttttg ttgcctcaaa aggtgtggtg cgcgagtggc    960
aggagcaaag taataaaagg gtccttgcct ttaattggtg aagcagattg ccttcatgaa   1020
aaatacggtg gattaaacaa aagcaagcct tactacacag gagaacatgc aaaagccata   1080
ggaaattgcc caatatgggt gaaaacacct ttgaagctcg ccaatggaac caaatataga   1140
cctcctgcaa aactattaaa ggaaaggggt ttcttcggag ctattgctgg tttcctagaa   1200
ggaggatggg aaggaatgat tgcaggctgg cacggataca catctcacgg agcacatgga   1260
gtggcagtgg cggcggacct taagagtacg caagaagcta taaacaagat aacaaaaaat   1320
ctcaattctt tgagtgagct agaagtaaag aatcttcaaa gactaagtgg tgccatggat   1380
gaactccaca acgaaatact cgagctggat gagaaagtgg atgatctcag agctgacact   1440
ataagctcgc aaatagaact tgcagtcttg ctttccaacg aaggaataat aaacagtgaa   1500
gatgagcatc tattggcact tgagagaaaa ctaaagaaaa tgctgggtcc ctctgctgta   1560
gagataggaa atggatgctt cgaaaccaaa cacaagtgca accagacctg cttagacagg   1620
atagctgctg gcacctttaa tgcaggagaa ttttctctcc ccacttttga ttcactgaac   1680
attactgctg catctttaaa tgatgatgga ttggataacc atactatact gctctattac   1740
tcaactgctg cttctagttt ggctgtaaca ttgatgctag ctatttttat tgtttatatg   1800
gtctccagag acaacgtttc atgctccatc tgtctataag agctc                    1845
```

<210> SEQ ID NO 42
<211> LENGTH: 1779
<212> TYPE: DNA
<213> ORGANISM: Artificial sequence
<220> FEATURE:
<223> OTHER INFORMATION: clone 780 - nucleotide sequence of A/Singapore/1/57 (H2N2)

<400> SEQUENCE: 42

```
cactttgtga gtctacactt tgattccctt caaacacata caaagagaag agactaatta     60
attaattaat catcttgaga gaaaatggcc atcatttatc taattctcct gttcacagca    120
gtgagagggg accaaatatg cattggatac catgccaata attccacaga gaaggtcgac    180
acaattctag agcggaacgt cactgtgact catgccaagg acattcttga gaagacccat    240
aacggaaagt tatgcaaact aaacggaatc cctccacttg aactagggga ctgtagcatt    300
gccggatggc tccttggaaa tccagaatgt gataggcttc taagtgtgcc agaatggtcc    360
tatataatgg agaaagaaaa cccgagagac ggtttgtgtt atccaggcag cttcaatgat    420
tatgaagaat tgaaacatct cctcagcagc gtgaaacatt tcgagaaagt aaagattctg    480
cccaaagata gatggacaca gcatacaaca actggaggtt cacgggcctg cgcggtgtct    540
ggtaatccat cattcttcag gaacatggtc tggctgacaa agaaagaatc aaattatccg    600
gttgccaaag gatcgtacaa caatacaagc ggagaacaaa tgctaataat ttggggggtg    660
```

```
caccatccca atgatgagac agaacaaaga acattgtacc agaatgtggg aacctatgtt    720
tccgtaggca catcaacatt gaacaaaagg tcaaccccag acatagcaac aaggcctaaa    780
gtgaatggac taggaagtag aatggagttc tcttggaccc tattggatat gtgggacacc    840
ataaattttg agagtactgg taatctaatt gcaccagagt atggattcaa aatatcgaaa    900
agaggtagtt cagggatcat gaaaacagaa ggaacacttg agaactgtga gaccaaatgc    960
caaactcctt tgggagcaat aaatacaaca ttgccttttc acaatgtcca cccactgaca   1020
ataggtgagt gccccaaata tgtaaaatcg gagaagttgg tcttagcaac aggactaagg   1080
aatgttcccc agattgaatc aagaggattg tttggggcaa tagctggttt tatagaagga   1140
ggatggcaag gaatggttga tggttggtat ggataccatc acagcaatga ccagggatca   1200
gggtatgcag cagacaaaga atccactcaa aaggcatttg atggaatcac caacaaggta   1260
aattctgtga ttgaaaagat gaacacccaa tttgaagctg ttgggaaaga gttcagtaac   1320
ttagagagaa gactggagaa cttgaacaaa aagatggaag acgggtttct agatgtgtgg   1380
acatacaatg ctgagcttct agttctgatg gaaaatgaga ggacacttga ctttcatgat   1440
tctaatgtca agaatctgta tgataaagtc agaatgcagc tgagagacaa cgtcaaagaa   1500
ctaggaaatg gatgttttga attttatcac aaatgtgatg atgaatgcat gaatagtgtg   1560
aaaaacggga cgtatgatta tcccaagtat gaagaagagt ctaaactaaa tagaaatgaa   1620
atcaaagggg taaaattgag cagcatgggg gtttatcaaa tccttgccat ttatgctaca   1680
gtagcaggtt ctctgtcact ggcaatcatg atggctggga tctctttctg gatgtgctcc   1740
aacgggtctc tgcagtgcag gatctgcata tgagagctc                          1779
```

<210> SEQ ID NO 43
<211> LENGTH: 1794
<212> TYPE: DNA
<213> ORGANISM: Artificial sequence
<220> FEATURE:
<223> OTHER INFORMATION: clone 781 - nucleotide sequence of
A/Anhui/1/2005 (H5N1)

<400> SEQUENCE: 43

```
cactttgtga gtctacactt tgattccctt caaacacata caaagagaag agactaatta     60
attaattaat catcttgaga gaaaatggag aaaatagtgc ttcttcttgc aatagtcagc    120
cttgttaaaa gtgatcagat ttgcattggt taccatgcaa acaactcgac agagcaggtt    180
gacacaataa tggaaaagaa cgttactgtt acacatgccc aagacatact ggaaaagaca    240
cacaacggga agctctgcga tctagatgga gtgaagcctc tgattttaag agattgtagt    300
gtagctggat ggctcctcgg aaacccaatg tgtgacgagt tcatcaatgt gccggaatgg    360
tcttacatag tggagaaggc caacccagcc aatgacctct gttacccagg gaatttcaac    420
gactatgaag aactgaaaca cctattgagc agaataaacc attttgagaa aattcagatc    480
atccccaaaa gttcttggtc cgatcatgaa gcctcatcag gggtcagctc agcatgtcca    540
taccagggaa cgccctcctt tttcagaaat gtggtatggc ttatcaaaaa gaacaataca    600
tacccaacaa taaagagaag ctacaataat accaaccagg aagatctttt gatactgtgg    660
gggattcatc attctaatga tgcggcagag cagacaaagc tctatcaaaa cccaaccacc    720
tatatttccg ttgggacatc aacactaaac cagagattgg taccaaaaat agctactaga    780
tccaaagtaa acgggcaaag tggaaggatg gatttcttct ggacaatttt aaaaccgaat    840
gatgcaatca acttcgagag taatggaaat ttcattgctc cagaatatgc atacaaaatt    900
```

```
gtcaagaaag gggactcagc aattgttaaa agtgaagtgg aatatggtaa ctgcaataca    960
aagtgtcaaa ctccaatagg ggcgataaac tctagtatgc cattccacaa catacaccct   1020
ctcaccatcg ggaatgccc caaatatgtg aaatcaaaca aattagtcct tgcgactggg   1080
ctcagaaata gtcctctaag agaaagaaga agaaaaagag gactatttgg agctatagca   1140
gggtttatag agggaggatg gcagggaatg gtagatggtt ggtatgggta ccaccatagc   1200
aatgagcagg ggagtgggta cgctgcagac aaagaatcca ctcaaaaggc aatagatgga   1260
gtcaccaata aggtcaactc gatcattgac aaaatgaaca ctcagtttga ggccgttgga   1320
agggaattta ataacttaga aaggagaata gagaatttaa acaagaaaat ggaagacgga   1380
ttcctagatg tctggactta taatgctgaa cttctggttc tcatggaaaa tgagagaact   1440
ctagacttcc atgattcaaa tgtcaagaac ctttacgaca aggtccgact acagcttagg   1500
gataatgcaa aggagctggg taacggttgt ttcgagttct atcacaaatg tgataatgaa   1560
tgtatggaaa gtgtaagaaa cggaacgtat gactacccgc agtattcaga agaagcaaga   1620
ttaaaaagag aggaaataag tggagtaaaa ttggaatcaa taggaactta ccaaatactg   1680
tcaatttatt caacagttgc gagttctcta gcactggcaa tcatggtggc tggtctatct   1740
ttgtggatgt gctccaatgg gtcgttacaa tgcagaattt gcatttaaga gctc         1794
```

<210> SEQ ID NO 44
<211> LENGTH: 1797
<212> TYPE: DNA
<213> ORGANISM: Artificial sequence
<220> FEATURE:
<223> OTHER INFORMATION: clone 782 - nucleotide sequence of
      A/Vietnam/1194/2004 (H5N1)

<400> SEQUENCE: 44

```
cactttgtga gtctacactt tgattccctt caaacacata caaagagaag agactaatta     60
attaattaat catcttgaga gaaaatggag aaaatagtgc ttctttttgc aatagtcagt    120
cttgttaaaa gtgatcagat ttgcattggt taccatgcaa acaactcgac agagcaggtt    180
gacacaataa tggaaaagaa cgttactgtt acacatgccc aagacatact ggaaaagaca    240
cacaatggga agctctgcga tctagatgga gtgaagcctc taattttgag agattgtagt    300
gtagctggat ggctcctcgg aaacccaatg tgtgacgagt tcatcaatgt gccggaatgg    360
tcttacatag tggagaaggc caatccagtc aatgacctct gttacccagg ggatttcaat    420
gactatgaag aattgaaaca cctattgagc agaataaacc attttgagaa aattcagatc    480
atccccaaaa gttcttggtc cagtcatgaa gcctcattgg gggtcagctc agcatgtcca    540
taccagggaa agtcctcctt tttcagaaat gtggtatggc ttatcaaaaa gaacagtaca    600
tacccaacaa taaagaggag ctacaataat accaaccaag aagatctttt ggtactgtgg    660
gggattcacc atcctaatga tgcggcagag cagacaaagc tctatcaaaa cccaaccacc    720
tatatttccg ttgggacatc tacactaaac cagagattgg taccaagaat agctactaga    780
tccaaagtaa acgggcaaag tggaaggatg gagttcttct ggacaatttt aaaaccgaat    840
gatgcaatca acttcgagag taatggaaat ttcattgctc cagaatatgc atacaaaatt    900
gtcaagaaag gggactcaac aattatgaaa agtgaattgg aatatggtaa ctgcaatacc    960
aagtgtcaaa ctccaatggg ggcgataaac tctagcatgc cattccacaa tatacaccct   1020
ctcaccatcg gggaatgccc caaatatgtg aaatcaaaca gattagtcct tgcgactggg   1080
ctcagaaata gccctcaaag agagagaaga agaaaaaaga gaggattatt tggagctata   1140
```

```
gcaggtttta tagagggagg atggcaggga atggtagatg gttggtatgg gtaccaccat   1200
agcaacgagc aggggagtgg gtacgctgca gacaaagaat ccactcaaaa ggcaatagat   1260
ggagtcacca ataaggtcaa ctcgattatt gacaaaatga acactcagtt tgaggccgtt   1320
ggaagggaat ttaacaactt agaaaggaga atagagaatt taaacaagaa gatggaagac   1380
gggttcctag atgtctggac ttataatgct gaacttctag ttctcatgga aaacgagaga   1440
actctagact ttcatgactc aaatgtcaag aacctttacg acaaggtccg actacagctt   1500
agggataatg caaaggagct gggtaacggt tgtttcgagt tctatcataa atgtgataat   1560
gaatgtatgg aaagtgtaag aaacggaacg tatgactacc cgcagtattc agaagaagca   1620
agactaaaaa gagaggaaat aagtggagta aaattggaat caataggaat ttaccaaata   1680
ttgtcaattt attctacagt ggccagctcc ctagcactgg caatcatggt agctggtcta   1740
tccttatgga tgtgctccaa tgggtcgtta caatgcagaa tttgcattta agagctc      1797
```

```
<210> SEQ ID NO 45
<211> LENGTH: 1791
<212> TYPE: DNA
<213> ORGANISM: Artificial sequence
<220> FEATURE:
<223> OTHER INFORMATION: clone 783 - nucleotide sequence of
      A/Teal/HongKong/W312/97 (H6N1)

<400> SEQUENCE: 45
```

```
cactttgtga gtctacactt tgattccctt caaacacata caaagagaag agactaatta     60
attaattaat catcttgaga gaaaatgatt gcaatcattg taatagcaat actggcagca    120
gccggaaagt cagacaagat ctgcattggg tatcatgcca acaattcaac aacacaggta    180
gatacgatac ttgagaagaa tgtgactgtc acacactcaa ttgaattgct ggaaaatcag    240
aaggaagaaa gattctgcaa gatattgaac aaggcccctc tcgacttaag ggaatgtacc    300
atagagggtt ggatcttggg gaatccccaa tgcgacctat tgcttggtga tcaaagctgg    360
tcatacattg tggaaagacc tactgctcaa aacgggatct gctacccagg aaccttaaat    420
gaggtagaag aactgagggc acttattgga tcaggagaaa gggtagagag atttgagatg    480
tttccccaaa gcacctggca aggagttgac accaacagtg gaacaacaag atcctgccct    540
tattctactg gtgcgtcttt ctacagaaac ctcctatgga taataaaaac caagacagca    600
gaatatccag taattaaggg aatttacaac aacactggaa cccagccaat cctctatttc    660
tggggtgtgc atcatcctcc taacaccgac gagcaagata ctctgtatgg ctctggtgat    720
cgatacgtta gaatgggaac tgaaagcatg aattttgcca agagtccgga aattgcggca    780
aggcctgctg tgaatggaca aagaggcaga attgattatt attggtcggt tttaaaacca    840
ggggaaacct tgaatgtgga atctaatgga aatctaatcg ccccttggta tgcatacaaa    900
tttgtcaaca caaatagtaa aggagccgtc ttcaggtcag atttaccaat cgagaactgc    960
gatgccacat gccagactat tgcaggggtt ctaaggacca ataaaacatt tcagaatgtg   1020
agtcccctgt ggataggaga atgtcccaaa tacgtgaaaa gtgaaagtct gaggcttgca   1080
actggactaa gaaatgttcc acagattgaa actagaggac tcttcggagc tattgcaggg   1140
tttattgaag gaggatggac tgggatgata gatgggtggt atggctatca ccatgaaaat   1200
tctcaagggt caggatatgc agcagacaga gaaagcactc aaaaggctgt aaacagaatt   1260
acaaataagg tcaattccat catcaacaaa atgaacacac aatttgaagc tgtcgatcac   1320
gaattttcaa atctggagag gagaattgac aatctgaaca aaagaatgca agatggattt   1380
```

ctggatgttt ggacatacaa tgctgaactg ttggttcttc ttgaaaacga aagaacacta 1440
gacatgcatg acgcaaatgt gaagaaccta catgaaaagg tcaaatcaca actaagggac 1500
aatgctacga tcttagggaa tggttgcttt gaattttggc ataagtgtga caatgaatgc 1560
atagagtctg tcaaaaatgg tacatatgac tatcccaaat accagactga aagcaaatta 1620
aacaggctaa aaatagaatc agtaaagcta gagaaccttg gtgtgtatca aattcttgcc 1680
atttatagta cggtatcgag cagcctagtg ttggtagggc tgatcatggc aatgggtctt 1740
tggatgtgtt caaatggttc aatgcagtgc aggatatgta tataagagct c 1791

<210> SEQ ID NO 46
<211> LENGTH: 1803
<212> TYPE: DNA
<213> ORGANISM: Artificial sequence
<220> FEATURE:
<223> OTHER INFORMATION: clone 784 - nucleotide sequence of A/Equine/Prague/56 (H7N7)

<400> SEQUENCE: 46
cactttgtga gtctacactt tgattccctt caaacacata caaagagaag agactaatta 60
attaattaat catcttgaga gaaaatgaac actcaaattc taatattagc cacttcggca 120
ttcttctatg tacgtgcaga taaaatctgc ctaggacatc atgctgtgtc taatggaacc 180
aaagtagaca cccttactga aaaaggaata gaagttgtca atgcaacaga aacagttgaa 240
caaacaaaca tccctaagat ctgctcaaaa ggaaaacaga ctgttgacct tggtcaatgt 300
ggattactag ggaccgttat tggtcctccc caatgtgacc aatttcttga gttctctgct 360
aatttaatag ttgaaagaag ggaaggtaat gacatttgtt atccaggcaa atttgacaat 420
gaagaaacat tgagaaaaat actcagaaaa tccggaggaa ttaaaaagga gaatatggga 480
ttcacatata ccggagtgag aaccaatgga gagactagcg catgtagaag gtcaagatct 540
tccttttatg cagagatgaa atggcttcta tccagcacag acaatgggac atttccacaa 600
atgacaaagt cctacaagaa cactaagaag gtaccagctc tgataatctg ggaatccac 660 cactcaggat caactactga acagactaga ttatatggaa gtgggaataa attgataaca 720
gtttggagtt ccaaatacca acaatctttt gtcccaaatc ctggaccaag accgcaaatg 780
aatggtcaat caggaagaat tgactttcac tggctgatgc tagatcccaa tgatactgtc 840
actttcagtt ttaatggggc ctttatagca cctgaccgcg ccagttttct aagaggtaaa 900
tctctaggaa tccaaagtga tgcacaactt gacaataatt gtgaaggtga atgctatcat 960
attggaggta ctataattag caacttgccc tttcaaaaca ttaatagtag ggcaatcgga 1020
aaatgcccca gatacgtgaa gcagaagagc ttaatgctag caacaggaat gaaaaatgtt 1080
cctgaagctc ctgcacataa acaactaact catcacatgc gcaaaaaaag aggtttattt 1140
ggtgcaatag caggattcat tgaaaatggg tgggaaggat taatagacgg atggtatgga 1200
tataagcatc agaatgcaca aggagaaggg actgctgcag actacaaaag tacacaatct 1260
gctatcaacc aaataaccgg aaaattgaac agactaatag aaaaaaccaa ccagcaattc 1320
gaactaatag ataatgagtt caatgaaata gaaaaacaaa ttggcaatgt tattaactgg 1380
actagagatt ctatcatcga agtatggtca tataatgcag agttcctcgt agcagtggag 1440
aatcaacaca ctattgattt aactgactca gaaatgaaca aactatatga aaaggtaaga 1500
agacaactga gagaaaatgc tgaggaagat ggtaatggct gttttgaaat attccaccaa 1560
tgtgacaatg attgcatggc cagcattaga aacaacacat atgaccataa aaaatacaga 1620
aaagaggcaa tacaaaacag aatccagatt gacgcagtaa agttgagcag tggttacaaa 1680
gatataatac tttggtttag cttcggggca tcatgtttct tatttcttgc cattgcaatg 1740
ggtcttgttt tcatatgtat aaaaaatgga aacatgcggt gcactatttg tatataagag 1800
ctc 1803

<210> SEQ ID NO 47
<211> LENGTH: 1773
<212> TYPE: DNA
<213> ORGANISM: Artificial sequence
<220> FEATURE:
<223> OTHER INFORMATION: clone 785 - nucleotide sequence of
A/HongKong/1073/99 (H9N2)

<400> SEQUENCE: 47
cactttgtga gtctacactt tgattccctt caaacacata caaagagaag agactaatta 60
attaattaat catcttgaga gaaaatggaa acaatatcac taataactat actactagta 120
gtaacagcaa gcaatgcaga taaaatctgc atcggccacc agtcaacaaa ctccacagaa 180
actgtggaca cgctaacaga aaccaatgtt cctgtgacac atgccaaaga attgctccac 240
acagagcata atggaatgct gtgtgcaaca agcctgggac atcccctcat tctagacaca 300
tgcactattg aaggactagt ctatggcaac ccttcttgtg acctgctgtt gggaggaaga 360
gaatggtcct acatcgtcga aagatcatca gctgtaaatg gaacgtgtta ccctgggaat 420
gtagaaaacc tagaggaact caggacactt tttagttccg ctagttccta ccaaagaatc 480
caaatcttcc cagacacaac ctggaatgtg acttacactg gaacaagcag agcatgttca 540
ggttcattct acaggagtat gagatggctg actcaaaaga gcggttttta ccctgttcaa 600
gacgcccaat acacaaataa caggggaaag agcattcttt tcgtgtgggg catacatcac 660
ccacccacct ataccgagca aacaaatttg tacataagaa acgacacaac aacaagcgtg 720
acaacagaag atttgaatag gaccttcaaa ccagtgatag ggccaaggcc ccttgtcaat 780
ggtctgcagg gaagaattga ttattattgg tcggtactaa aaccaggcca aacattgcga 840
gtacgatcca atgggaatct aattgctcca tggtatggac acgttctttc aggagggagc 900
catggaagaa tcctgaagac tgatttaaaa ggtggtaatt gtgtagtgca atgtcagact 960
gaaaaaggtg gcttaaacag tacattgcca ttccacaata tcagtaaata tgcatttgga 1020
acctgcccca aatatgtaag agttaatagt ctcaaactgg cagtcggtct gaggaacgtg 1080
cctgctagat caagtagagg actatttgga gccatagctg gattcataga aggaggttgg 1140
ccaggactag tcgctggctg gtatggtttc cagcattcaa atgatcaagg ggttggtatg 1200
gctgcagata gggattcaac tcaaaaggca attgataaaa taacatccaa ggtgaataat 1260
atagtcgaca agatgaacaa gcaatatgaa ataattgatc atgaatttag tgaggttgaa 1320
actagactca atatgatcaa taataagatt gatgaccaaa tacaagacgt atgggcatat 1380
aatgcagaat tgctagtact acttgaaaat caaaaaacac tcgatgagca tgatgcgaac 1440
gtgaacaatc tatataacaa ggtgaagagg gcactgggct ccaatgctat ggaagatggg 1500
aaaggctgtt tcgagctata ccataaatgt gatgatcagt gcatggaaac aattcggaac 1560
gggacctata ataggagaaa gtatagagag gaatcaagac tagaaaggca gaaaatagag 1620
ggggttaagc tggaatctga gggaacttac aaaatcctca ccatttattc gactgtcgcc 1680
tcatctcttg tgcttgcaat ggggtttgct gccttcctgt tctgggccat gtccaatgga 1740
tcttgcagat gcaacatttg tatataagag ctc 1773

<210> SEQ ID NO 48
<211> LENGTH: 565
<212> TYPE: PRT
<213> ORGANISM: Artificial sequence
<220> FEATURE:
<223> OTHER INFORMATION: clone 774 (A/Brisbane/59/2007 (H1N1)

<400> SEQUENCE: 48

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Lys Ala Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365
```

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 49
<211> LENGTH: 565
<212> TYPE: PRT
<213> ORGANISM: Artificial sequence
<220> FEATURE:
<223> OTHER INFORMATION: clone 775 (A/Solomon Islands 3/2006 (H1N1))

<400> SEQUENCE: 49

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Arg Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Thr Thr Gly Val Ser Ala Ser Cys Ser His Asn Gly Glu Ser Ser Phe
145                 150                 155                 160

-continued

```
Tyr Lys Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Lys Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565
```

<210> SEQ ID NO 50
<211> LENGTH: 566
<212> TYPE: PRT
<213> ORGANISM: Artificial sequence
<220> FEATURE:
<223> OTHER INFORMATION: clone 776 (A/Brisbane/10/2007 (H3N2))

<400> SEQUENCE: 50

```
Met Lys Thr Ile Ile Ala Leu Ser Tyr Ile Leu Cys Leu Val Phe Thr
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365
```

```
Phe Arg His Gln Asn Ser Glu Gly Ile Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565


<210> SEQ ID NO 51
<211> LENGTH: 566
<212> TYPE: PRT
<213> ORGANISM: Artificial sequence
<220> FEATURE:
<223> OTHER INFORMATION: clone 777 (A/Wisconsin/67/2005 (H3N2))

<400> SEQUENCE: 51

Met Lys Thr Ile Ile Ala Leu Ser Tyr Ile Leu Cys Leu Val Phe Thr
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asp Glu Ser Phe Asn Trp Thr
    130                 135                 140

Gly Val Thr Gln Asn Gly Thr Ser Ser Ala Cys Lys Arg Arg Ser Asn
145                 150                 155                 160
```

-continued

```
Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
        195                 200                 205

Phe Leu His Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565
```

```
<210> SEQ ID NO 52
<211> LENGTH: 585
<212> TYPE: PRT
<213> ORGANISM: Artificial sequence
<220> FEATURE:
<223> OTHER INFORMATION: clone 778 (B/Malaysia/2506/2004)

<400> SEQUENCE: 52

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Asn Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Lys Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Val Thr Asn Gly Asn Gly Phe Phe Ala Thr Met Ala Trp Ala Val Pro
                165                 170                 175

Lys Asn Asp Asn Asn Lys Thr Ala Thr Asn Ser Leu Thr Ile Glu Val
            180                 185                 190

Pro Tyr Ile Cys Thr Glu Gly Glu Asp Gln Ile Thr Val Trp Gly Phe
        195                 200                 205

His Ser Asp Asn Glu Thr Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
```

```
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
        515                 520                 525

Phe Asp Ser Leu Asn Ile Thr Ala Ala Ser Leu Asn Asp Asp Gly Leu
    530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
            580                 585


<210> SEQ ID NO 53
<211> LENGTH: 584
<212> TYPE: PRT
<213> ORGANISM: Artificial
<220> FEATURE:
<223> OTHER INFORMATION: clone 779 (B/Florida/4/2006)

<400> SEQUENCE: 53

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Lys Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
```

```
145                 150                 155                 160

Ala Thr Ser Lys Ser Gly Phe Phe Ala Thr Met Ala Trp Ala Val Pro
                165                 170                 175

Lys Asp Asn Asn Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
        195                 200                 205

Ser Asp Asn Lys Thr Gln Met Lys Asn Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Ser Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Glu Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
    530                 535                 540

Asn His Thr Ile Leu Leu Tyr Tyr Ser Thr Ala Ala Ser Ser Leu Ala
545                 550                 555                 560

Val Thr Leu Met Leu Ala Ile Phe Ile Val Tyr Met Val Ser Arg Asp
                565                 570                 575
```

```
Asn Val Ser Cys Ser Ile Cys Leu
            580


<210> SEQ ID NO 54
<211> LENGTH: 562
<212> TYPE: PRT
<213> ORGANISM: Artificial sequence
<220> FEATURE:
<223> OTHER INFORMATION: clone 780 (A/Singapore/1/57 (H2N2))

<400> SEQUENCE: 54

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Lys Glu Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Asp Ile Ala Thr Arg Pro Lys Val Asn Gly Leu Gly Ser Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350
```

```
Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Gly Val Lys Leu Ser Ser Met Gly Val Tyr Gln Ile Leu Ala
        515                 520                 525

Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Cys Arg Ile
545                 550                 555                 560

Cys Ile


<210> SEQ ID NO 55
<211> LENGTH: 567
<212> TYPE: PRT
<213> ORGANISM: Artificial sequence
<220> FEATURE:
<223> OTHER INFORMATION: clone 781 (A/Anhui/1/2005 (H5N1))

<400> SEQUENCE: 55

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140
```

-continued

```
Ser Gly Val Ser Ser Ala Cys Pro Tyr Gln Gly Thr Pro Ser Phe Phe
145                 150                 155                 160

Arg Asn Val Val Trp Leu Ile Lys Lys Asn Asn Thr Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Ser Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Asp Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Val Lys Ser Glu Val Glu Tyr Gly
        275                 280                 285

Asn Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Arg Arg Arg Lys Arg Gly Leu Phe Gly Ala Ile Ala
            340                 345                 350

Gly Phe Ile Glu Gly Gly Trp Gln Gly Met Val Asp Gly Trp Tyr Gly
        355                 360                 365

Tyr His His Ser Asn Glu Gln Gly Ser Gly Tyr Ala Ala Asp Lys Glu
    370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
            420                 425                 430

Phe Leu Asp Val Trp Thr Tyr Asn Ala Glu Leu Leu Val Leu Met Glu
        435                 440                 445

Asn Glu Arg Thr Leu Asp Phe His Asp Ser Asn Val Lys Asn Leu Tyr
    450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Gln Tyr Ser Glu Glu Ala Arg
            500                 505                 510

Leu Lys Arg Glu Glu Ile Ser Gly Val Lys Leu Glu Ser Ile Gly Thr
        515                 520                 525

Tyr Gln Ile Leu Ser Ile Tyr Ser Thr Val Ala Ser Ser Leu Ala Leu
    530                 535                 540

Ala Ile Met Val Ala Gly Leu Ser Leu Trp Met Cys Ser Asn Gly Ser
545                 550                 555                 560

Leu Gln Cys Arg Ile Cys Ile
```

565

<210> SEQ ID NO 56
<211> LENGTH: 568
<212> TYPE: PRT
<213> ORGANISM: Artificial sequence
<220> FEATURE:
<223> OTHER INFORMATION: clone 782 (A/Vietnam/1194/2004 (H5N1))

<400> SEQUENCE: 56

```
Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
```

```
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Ile Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565


<210> SEQ ID NO 57
<211> LENGTH: 566
<212> TYPE: PRT
<213> ORGANISM: Artificial sequence
<220> FEATURE:
<223> OTHER INFORMATION: clone 783 (A/Teal/HongKong/W312/97 (H6N1))

<400> SEQUENCE: 57

Met Ile Ala Ile Ile Val Ile Ala Ile Leu Ala Ala Ala Gly Lys Ser
1               5                   10                  15

Asp Lys Ile Cys Ile Gly Tyr His Ala Asn Asn Ser Thr Thr Gln Val
            20                  25                  30

Asp Thr Ile Leu Glu Lys Asn Val Thr Val Thr His Ser Ile Glu Leu
        35                  40                  45

Leu Glu Asn Gln Lys Glu Glu Arg Phe Cys Lys Ile Leu Asn Lys Ala
    50                  55                  60

Pro Leu Asp Leu Arg Glu Cys Thr Ile Glu Gly Trp Ile Leu Gly Asn
65                  70                  75                  80

Pro Gln Cys Asp Leu Leu Leu Gly Asp Gln Ser Trp Ser Tyr Ile Val
                85                  90                  95

Glu Arg Pro Thr Ala Gln Asn Gly Ile Cys Tyr Pro Gly Thr Leu Asn
            100                 105                 110

Glu Val Glu Glu Leu Arg Ala Leu Ile Gly Ser Gly Glu Arg Val Glu
        115                 120                 125

Arg Phe Glu Met Phe Pro Gln Ser Thr Trp Gln Gly Val Asp Thr Asn
    130                 135                 140

Ser Gly Thr Thr Arg Ser Cys Pro Tyr Ser Thr Gly Ala Ser Phe Tyr
```

-continued

```
145                 150                 155                 160

Arg Asn Leu Leu Trp Ile Ile Lys Thr Lys Thr Ala Glu Tyr Pro Val
                165                 170                 175

Ile Lys Gly Ile Tyr Asn Asn Thr Gly Thr Gln Pro Ile Leu Tyr Phe
            180                 185                 190

Trp Gly Val His His Pro Pro Asn Thr Asp Glu Gln Asp Thr Leu Tyr
        195                 200                 205

Gly Ser Gly Asp Arg Tyr Val Arg Met Gly Thr Glu Ser Met Asn Phe
    210                 215                 220

Ala Lys Ser Pro Glu Ile Ala Ala Arg Pro Ala Val Asn Gly Gln Arg
225                 230                 235                 240

Gly Arg Ile Asp Tyr Tyr Trp Ser Val Leu Lys Pro Gly Glu Thr Leu
                245                 250                 255

Asn Val Glu Ser Asn Gly Asn Leu Ile Ala Pro Trp Tyr Ala Tyr Lys
            260                 265                 270

Phe Val Asn Thr Asn Ser Lys Gly Ala Val Phe Arg Ser Asp Leu Pro
        275                 280                 285

Ile Glu Asn Cys Asp Ala Thr Cys Gln Thr Ile Ala Gly Val Leu Arg
    290                 295                 300

Thr Asn Lys Thr Phe Gln Asn Val Ser Pro Leu Trp Ile Gly Glu Cys
305                 310                 315                 320

Pro Lys Tyr Val Lys Ser Glu Ser Leu Arg Leu Ala Thr Gly Leu Arg
                325                 330                 335

Asn Val Pro Gln Ile Glu Thr Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Glu Asn Ser Gln Gly Ser Gly Tyr Ala Ala Asp Arg Glu Ser
    370                 375                 380

Thr Gln Lys Ala Val Asn Arg Ile Thr Asn Lys Val Asn Ser Ile Ile
385                 390                 395                 400

Asn Lys Met Asn Thr Gln Phe Glu Ala Val Asp His Glu Phe Ser Asn
                405                 410                 415

Leu Glu Arg Arg Ile Asp Asn Leu Asn Lys Arg Met Gln Asp Gly Phe
            420                 425                 430

Leu Asp Val Trp Thr Tyr Asn Ala Glu Leu Leu Val Leu Leu Glu Asn
        435                 440                 445

Glu Arg Thr Leu Asp Met His Asp Ala Asn Val Lys Asn Leu His Glu
    450                 455                 460

Lys Val Lys Ser Gln Leu Arg Asp Asn Ala Thr Ile Leu Gly Asn Gly
465                 470                 475                 480

Cys Phe Glu Phe Trp His Lys Cys Asp Asn Glu Cys Ile Glu Ser Val
                485                 490                 495

Lys Asn Gly Thr Tyr Asp Tyr Pro Lys Tyr Gln Thr Glu Ser Lys Leu
            500                 505                 510

Asn Arg Leu Lys Ile Glu Ser Val Lys Leu Glu Asn Leu Gly Val Tyr
        515                 520                 525

Gln Ile Leu Ala Ile Tyr Ser Thr Val Ser Ser Ser Leu Val Leu Val
    530                 535                 540

Gly Leu Ile Met Ala Met Gly Leu Trp Met Cys Ser Asn Gly Ser Met
545                 550                 555                 560

Gln Cys Arg Ile Cys Ile
                565
```

<210> SEQ ID NO 58
<211> LENGTH: 570
<212> TYPE: PRT
<213> ORGANISM: Artificial sequence
<220> FEATURE:
<223> OTHER INFORMATION: clone 784 (A/Equine/Prague/56 (H7N7))

<400> SEQUENCE: 58

Met Asn Thr Gln Ile Leu Ile Leu Ala Thr Ser Ala Phe Phe Tyr Val
1 5 10 15

Arg Ala Asp Lys Ile Cys Leu Gly His His Ala Val Ser Asn Gly Thr
20 25 30

Lys Val Asp Thr Leu Thr Glu Lys Gly Ile Glu Val Val Asn Ala Thr
35 40 45

Glu Thr Val Glu Gln Thr Asn Ile Pro Lys Ile Cys Ser Lys Gly Lys
50 55 60

Gln Thr Val Asp Leu Gly Gln Cys Gly Leu Leu Gly Thr Val Ile Gly
65 70 75 80

Pro Pro Gln Cys Asp Gln Phe Leu Glu Phe Ser Ala Asn Leu Ile Val
85 90 95

Glu Arg Arg Glu Gly Asn Asp Ile Cys Tyr Pro Gly Lys Phe Asp Asn
100 105 110

Glu Glu Thr Leu Arg Lys Ile Leu Arg Lys Ser Gly Gly Ile Lys Lys
115 120 125

Glu Asn Met Gly Phe Thr Tyr Thr Gly Val Arg Thr Asn Gly Glu Thr
130 135 140

Ser Ala Cys Arg Arg Ser Arg Ser Ser Phe Tyr Ala Glu Met Lys Trp
145 150 155 160

Leu Leu Ser Ser Thr Asp Asn Gly Thr Phe Pro Gln Met Thr Lys Ser
165 170 175

Tyr Lys Asn Thr Lys Lys Val Pro Ala Leu Ile Ile Trp Gly Ile His
180 185 190

His Ser Gly Ser Thr Thr Glu Gln Thr Arg Leu Tyr Gly Ser Gly Asn
195 200 205

Lys Leu Ile Thr Val Trp Ser Ser Lys Tyr Gln Gln Ser Phe Val Pro
210 215 220

Asn Pro Gly Pro Arg Pro Gln Met Asn Gly Gln Ser Gly Arg Ile Asp
225 230 235 240

Phe His Trp Leu Met Leu Asp Pro Asn Asp Thr Val Thr Phe Ser Phe
245 250 255

Asn Gly Ala Phe Ile Ala Pro Asp Arg Ala Ser Phe Leu Arg Gly Lys
260 265 270

Ser Leu Gly Ile Gln Ser Asp Ala Gln Leu Asp Asn Asn Cys Glu Gly
275 280 285

Glu Cys Tyr His Ile Gly Gly Thr Ile Ile Ser Asn Leu Pro Phe Gln
290 295 300

Asn Ile Asn Ser Arg Ala Ile Gly Lys Cys Pro Arg Tyr Val Lys Gln
305 310 315 320

Lys Ser Leu Met Leu Ala Thr Gly Met Lys Asn Val Pro Glu Ala Pro
325 330 335

Ala His Lys Gln Leu Thr His His Met Arg Lys Lys Arg Gly Leu Phe
340 345 350

Gly Ala Ile Ala Gly Phe Ile Glu Asn Gly Trp Glu Gly Leu Ile Asp
355 360 365

```
Gly Trp Tyr Gly Tyr Lys His Gln Asn Ala Gln Gly Glu Gly Thr Ala
    370                 375                 380

Ala Asp Tyr Lys Ser Thr Gln Ser Ala Ile Asn Gln Ile Thr Gly Lys
385                 390                 395                 400

Leu Asn Arg Leu Ile Glu Lys Thr Asn Gln Gln Phe Glu Leu Ile Asp
                405                 410                 415

Asn Glu Phe Asn Glu Ile Glu Lys Gln Ile Gly Asn Val Ile Asn Trp
            420                 425                 430

Thr Arg Asp Ser Ile Ile Glu Val Trp Ser Tyr Asn Ala Glu Phe Leu
        435                 440                 445

Val Ala Val Glu Asn Gln His Thr Ile Asp Leu Thr Asp Ser Glu Met
    450                 455                 460

Asn Lys Leu Tyr Glu Lys Val Arg Arg Gln Leu Arg Glu Asn Ala Glu
465                 470                 475                 480

Glu Asp Gly Asn Gly Cys Phe Glu Ile Phe His Gln Cys Asp Asn Asp
                485                 490                 495

Cys Met Ala Ser Ile Arg Asn Asn Thr Tyr Asp His Lys Lys Tyr Arg
            500                 505                 510

Lys Glu Ala Ile Gln Asn Arg Ile Gln Ile Asp Ala Val Lys Leu Ser
        515                 520                 525

Ser Gly Tyr Lys Asp Ile Ile Leu Trp Phe Ser Phe Gly Ala Ser Cys
    530                 535                 540

Phe Leu Phe Leu Ala Ile Ala Met Gly Leu Val Phe Ile Cys Ile Lys
545                 550                 555                 560

Asn Gly Asn Met Arg Cys Thr Ile Cys Ile
                565                 570
```

<210> SEQ ID NO 59
<211> LENGTH: 560
<212> TYPE: PRT
<213> ORGANISM: Artificial sequence
<220> FEATURE:
<223> OTHER INFORMATION: clone 785 (A/HongKong/1073/99 (H9N2))

<400> SEQUENCE: 59

```
Met Glu Thr Ile Ser Leu Ile Thr Ile Leu Leu Val Val Thr Ala Ser
1               5                   10                  15

Asn Ala Asp Lys Ile Cys Ile Gly His Gln Ser Thr Asn Ser Thr Glu
            20                  25                  30

Thr Val Asp Thr Leu Thr Glu Thr Asn Val Pro Val Thr His Ala Lys
        35                  40                  45

Glu Leu Leu His Thr Glu His Asn Gly Met Leu Cys Ala Thr Ser Leu
    50                  55                  60

Gly His Pro Leu Ile Leu Asp Thr Cys Thr Ile Glu Gly Leu Val Tyr
65                  70                  75                  80

Gly Asn Pro Ser Cys Asp Leu Leu Leu Gly Gly Arg Glu Trp Ser Tyr
                85                  90                  95

Ile Val Glu Arg Ser Ser Ala Val Asn Gly Thr Cys Tyr Pro Gly Asn
            100                 105                 110

Val Glu Asn Leu Glu Glu Leu Arg Thr Leu Phe Ser Ser Ala Ser Ser
        115                 120                 125

Tyr Gln Arg Ile Gln Ile Phe Pro Asp Thr Thr Trp Asn Val Thr Tyr
    130                 135                 140

Thr Gly Thr Ser Arg Ala Cys Ser Gly Ser Phe Tyr Arg Ser Met Arg
145                 150                 155                 160
```

```
Trp Leu Thr Gln Lys Ser Gly Phe Tyr Pro Val Gln Asp Ala Gln Tyr
                165                 170                 175

Thr Asn Asn Arg Gly Lys Ser Ile Leu Phe Val Trp Gly Ile His His
            180                 185                 190

Pro Pro Thr Tyr Thr Glu Gln Thr Asn Leu Tyr Ile Arg Asn Asp Thr
        195                 200                 205

Thr Thr Ser Val Thr Thr Glu Asp Leu Asn Arg Thr Phe Lys Pro Val
    210                 215                 220

Ile Gly Pro Arg Pro Leu Val Asn Gly Leu Gln Gly Arg Ile Asp Tyr
225                 230                 235                 240

Tyr Trp Ser Val Leu Lys Pro Gly Gln Thr Leu Arg Val Arg Ser Asn
                245                 250                 255

Gly Asn Leu Ile Ala Pro Trp Tyr Gly His Val Leu Ser Gly Gly Ser
            260                 265                 270

His Gly Arg Ile Leu Lys Thr Asp Leu Lys Gly Gly Asn Cys Val Val
        275                 280                 285

Gln Cys Gln Thr Glu Lys Gly Gly Leu Asn Ser Thr Leu Pro Phe His
    290                 295                 300

Asn Ile Ser Lys Tyr Ala Phe Gly Thr Cys Pro Lys Tyr Val Arg Val
305                 310                 315                 320

Asn Ser Leu Lys Leu Ala Val Gly Leu Arg Asn Val Pro Ala Arg Ser
                325                 330                 335

Ser Arg Gly Leu Phe Gly Ala Ile Ala Gly Phe Ile Glu Gly Gly Trp
            340                 345                 350

Pro Gly Leu Val Ala Gly Trp Tyr Gly Phe Gln His Ser Asn Asp Gln
        355                 360                 365

Gly Val Gly Met Ala Ala Asp Arg Asp Ser Thr Gln Lys Ala Ile Asp
    370                 375                 380

Lys Ile Thr Ser Lys Val Asn Asn Ile Val Asp Lys Met Asn Lys Gln
385                 390                 395                 400

Tyr Glu Ile Ile Asp His Glu Phe Ser Glu Val Glu Thr Arg Leu Asn
                405                 410                 415

Met Ile Asn Asn Lys Ile Asp Asp Gln Ile Gln Asp Val Trp Ala Tyr
            420                 425                 430

Asn Ala Glu Leu Leu Val Leu Leu Glu Asn Gln Lys Thr Leu Asp Glu
        435                 440                 445

His Asp Ala Asn Val Asn Asn Leu Tyr Asn Lys Val Lys Arg Ala Leu
    450                 455                 460

Gly Ser Asn Ala Met Glu Asp Gly Lys Gly Cys Phe Glu Leu Tyr His
465                 470                 475                 480

Lys Cys Asp Asp Gln Cys Met Glu Thr Ile Arg Asn Gly Thr Tyr Asn
                485                 490                 495

Arg Arg Lys Tyr Arg Glu Glu Ser Arg Leu Glu Arg Gln Lys Ile Glu
            500                 505                 510

Gly Val Lys Leu Glu Ser Glu Gly Thr Tyr Lys Ile Leu Thr Ile Tyr
        515                 520                 525

Ser Thr Val Ala Ser Ser Leu Val Leu Ala Met Gly Phe Ala Ala Phe
    530                 535                 540

Leu Phe Trp Ala Met Ser Asn Gly Ser Cys Arg Cys Asn Ile Cys Ile
545                 550                 555                 560
```

<210> SEQ ID NO 60
<211> LENGTH: 3111

<212> TYPE: DNA
<213> ORGANISM: Artificial sequence
<220> FEATURE:
<223> OTHER INFORMATION: H5 from A/Indonesia/5/2005 (Construct #660)

<400> SEQUENCE: 60
agaggtaccc cgggctggta tatttatatg ttgtcaaata actcaaaaac cataaaagtt 60
taagttagca agtgtgtaca tttttacttg aacaaaaata ttcacctact actgttataa 120
atcattatta aacattagag taaagaaata tggatgataa gaacaagagt agtgatattt 180
tgacaacaat tttgttgcaa catttgagaa aattttgttg ttctctcttt tcattggtca 240
aaaacaatag agagagaaaa aggaagaggg agaataaaaa cataatgtga gtatgagaga 300
gaaagttgta caaaagttgt accaaaatag ttgtacaaat atcattgagg aatttgacaa 360
aagctacaca aataagggtt aattgctgta aataaataag gatgacgcat tagagagatg 420
taccattaga gaatttttgg caagtcatta aaaagaaaga ataaattatt tttaaaatta 480
aaagttgagt catttgatta aacatgtgat tatttaatga attgatgaaa gagttggatt 540
aaagttgtat tagtaattag aatttggtgt caaatttaat ttgacatttg atcttttcct 600
atatattgcc ccatagagtc agttaactca tttttatatt tcatagatca aataagagaa 660
ataacggtat attaatccct ccaaaaaaaa aaaacggtat atttactaaa aaatctaagc 720
cacgtaggag gataacagga tccccgtagg aggataacat ccaatccaac caatcacaac 780
aatcctgatg agataaccca ctttaagccc acgcatctgt ggcacatcta cattatctaa 840
atcacacatt cttccacaca tctgagccac acaaaaacca atccacatct ttatcaccca 900
ttctataaaa aatcacactt tgtgagtcta cactttgatt cccttcaaac acatacaaag 960
agaagagact aattaattaa ttaatcatct tgagagaaaa tggagaaaat agtgcttctt 1020
cttgcaatag tcagtcttgt taaaagtgat cagatttgca ttggttacca tgcaaacaat 1080
tcaacagagc aggttgacac aatcatggaa aagaacgtta ctgttacaca tgcccaagac 1140
atactggaaa agacacacaa cgggaagctc tgcgatctag atggagtgaa gcctctaatt 1200
ttaagagatt gtagtgtagc tggatggctc ctcgggaacc caatgtgtga cgaattcatc 1260
aatgtaccgg aatggtctta catagtggag aaggccaatc caaccaatga cctctgttac 1320
ccagggagtt tcaacgacta tgaagaactg aaacacctat tgagcagaat aaaccatttt 1380
gagaaaattc aaatcatccc caaaagttct tggtccgatc atgaagcctc atcaggagtt 1440
agctcagcat gtccatacct gggaagtccc tcctttttta gaaatgtggt atggcttatc 1500
aaaaagaaca gtacataccc aacaataaag aaaagctaca ataataccaa ccaagaggat 1560
cttttggtac tgtggggaat tcaccatcct aatgatgcgg cagagcagac aaggctatat 1620
caaaacccaa ccacctatat ttccattggg acatcaacac taaaccagag attggtacca 1680
aaaatagcta ctagatccaa agtaaacggg caaagtggaa ggatggagtt cttctggaca 1740
attttaaaac ctaatgatgc aatcaacttc gagagtaatg gaaatttcat tgctccagaa 1800
tatgcataca aaattgtcaa gaaaggggac tcagcaatta tgaaaagtga attggaatat 1860
ggtaactgca acaccaagtg tcaaactcca atgggggcga taaactctag tatgccattc 1920
cacaacatac accctctcac catcggggaa tgccccaaat atgtgaaatc aaacagatta 1980
gtccttgcaa cagggctcag aaatagccct caaagagaga gcagaagaaa aaagagagga 2040
ctatttggag ctatagcagg ttttatagag ggaggatggc agggaatggt agatggttgg 2100
tatgggtacc accatagcaa tgagcagggg agtgggtacg ctgcagacaa agaatccact 2160
caaaaggcaa tagatggagt caccaataag gtcaactcaa tcattgacaa aatgaacact 2220
cagtttgagg ccgttggaag ggaatttaat aacttagaaa ggagaataga gaatttaaac 2280
aagaagatgg aagacgggtt tctagatgtc tggacttata atgccgaact tctggttctc 2340
atggaaaatg agagaactct agactttcat gactcaaatg ttaagaacct ctacgacaag 2400
gtccgactac agcttaggga taatgcaaag gagctgggta acggttgttt cgagttctat 2460
cacaaatgtg ataatgaatg tatggaaagt ataagaaacg gaacgtacaa ctatccgcag 2520
tattcagaag aagcaagatt aaaaagagag gaaataagtg gggtaaaatt ggaatcaata 2580
ggaacttacc aaatactgtc aatttattca acagtggcga gttccctagc actggcaatc 2640
atgatggctg gtctatcttt atggatgtgc tccaatggat cgttacaatg cagaatttgc 2700
atttaagagc tctaagttaa aatgcttctt cgtctcctat ttataatatg gtttgttatt 2760
gttaattttg ttcttgtaga agagcttaat taatcgttgt tgttatgaaa tactatttgt 2820
atgagatgaa ctggtgtaat gtaattcatt tacataagtg gagtcagaat cagaatgttt 2880
cctccataac taactagaca tgaagacctg ccgcgtacaa ttgtcttata tttgaacaac 2940
taaaattgaa catcttttgc cacaacttta taagtggtta atatagctca aatatatggt 3000
caagttcaat agattaataa tggaaatatc agttatcgaa attcattaac aatcaactta 3060
acgttattaa ctactaattt tatatcatcc cctttgataa atgatagtac a 3111

<210> SEQ ID NO 61
<211> LENGTH: 3123
<212> TYPE: DNA
<213> ORGANISM: Artificial sequence
<220> FEATURE:
<223> OTHER INFORMATION: H1 from A/New Caledonia/20/1999 (Construct
#540)

<400> SEQUENCE: 61
agaggtaccc cgggctggta tatttatatg ttgtcaaata actcaaaaac cataaaagtt 60
taagttagca agtgtgtaca tttttacttg aacaaaaata ttcacctact actgttataa 120
atcattatta aacattagag taaagaaata tggatgataa gaacaagagt agtgatattt 180
tgacaacaat tttgttgcaa catttgagaa aattttgttg ttctctcttt tcattggtca 240
aaaacaatag agagagaaaa aggaagaggg agaataaaaa cataatgtga gtatgagaga 300
gaaagttgta caaaagttgt accaaaatag ttgtacaaat atcattgagg aatttgacaa 360
aagctacaca aataagggtt aattgctgta aataaataag gatgacgcat tagagagatg 420
taccattaga gaatttttgg caagtcatta aaaagaaaga ataaattatt tttaaaatta 480
aaagttgagt catttgatta aacatgtgat tatttaatga attgatgaaa gagttggatt 540
aaagttgtat tagtaattag aatttggtgt caaatttaat ttgacatttg atcttttcct 600
atatattgcc ccatagagtc agttaactca tttttatatt tcatagatca aataagagaa 660
ataacggtat attaatccct ccaaaaaaaa aaaacggtat atttactaaa aaatctaagc 720
cacgtaggag gataacagga tccccgtagg aggataacat ccaatccaac caatcacaac 780
aatcctgatg agataaccca ctttaagccc acgcatctgt ggcacatcta cattatctaa 840
atcacacatt cttccacaca tctgagccac acaaaaacca atccacatct ttatcaccca 900
ttctataaaa aatcacactt tgtgagtcta cactttgatt cccttcaaac acatacaaag 960
agaagagact aattaattaa ttaatcatct tgagagaaaa tggcgaaaaa cgttgcgatt 1020
ttcggcttat tgttttctct tcttgtgttg gttccttctc agatcttcgc tgacacaata 1080

-continued tgtataggct accatgccaa caactcaacc gacactgttg acacagtact tgagaagaat 1140
gtgacagtga cacactctgt caacctactt gaggacagtc acaatggaaa actatgtcta 1200
ctaaaaggaa tagccccact acaattgggt aattgcagcg ttgccggatg gatcttagga 1260
aacccagaat gcgaattact gatttccaag gaatcatggt cctacattgt agaaacacca 1320
aatcctgaga atggaacatg ttacccaggg tatttcgccg actatgagga actgagggag 1380
caattgagtt cagtatcttc atttgagaga ttcgaaatat tccccaaaga aagctcatgg 1440
cccaaccaca ccgtaaccgg agtatcagca tcatgctccc ataatgggaa aagcagtttt 1500
tacagaaatt tgctatggct gacggggaag aatggtttgt acccaaacct gagcaagtcc 1560
tatgtaaaca acaaagagaa agaagtcctt gtactatggg gtgttcatca cccgcctaac 1620
atagggaacc aaagggcact ctatcataca gaaaatgctt atgtctctgt agtgtcttca 1680
cattatagca gaagattcac cccagaaata gccaaaagac ccaaagtaag agatcaggaa 1740
ggaagaatca actactactg gactctgctg gaacctgggg atacaataat atttgaggca 1800
aatggaaatc taatagcgcc atggtatgct tttgcactga gtagaggctt tggatcagga 1860
atcatcacct caaatgcacc aatggatgaa tgtgatgcga agtgtcaaac acctcaggga 1920
gctataaaca gcagtcttcc tttccagaat gtacacccag tcacaatagg agagtgtcca 1980
aagtatgtca ggagtgcaaa attaaggatg gttacaggac taaggaacat cccatccatt 2040
caatccagag gtttgtttgg agccattgcc ggtttcattg aagggggtg gactggaatg 2100 gtagatgggt ggtatggtta tcatcatcag aatgagcaag gatctggcta tgctgcagat 2160
caaaaaagta cacaaaatgc cattaacggg attacaaaca aggtcaattc tgtaattgag 2220
aaaatgaaca ctcaattcac agctgtgggc aaagagttca acaaattgga aagaaggatg 2280
gaaaacttaa ataaaaaagt tgatgatggg tttctagaca tttggacata taatgcagaa 2340
ttgttggttc tactggaaaa tgaaaggact ttggatttcc atgactccaa tgtgaagaat 2400
ctgtatgaga aagtaaaaag ccaattaaag aataatgcca aagaaatagg aaacgggtgt 2460
tttgagttct atcacaagtg taacaatgaa tgcatggaga gtgtgaaaaa tggtacctat 2520
gactatccaa aatattccga agaatcaaag ttaaacaggg agaaaattga tggagtgaaa 2580
ttggaatcaa tgggagtata ccagattctg gcgatctact caactgtcgc cagttccctg 2640
gttcttttgg tctccctggg ggcaatcagc ttctggatgt gttccaatgg gtctttgcag 2700
tgtagaatat gcatctaaga gctctaagtt aaaatgcttc ttcgtctcct atttataata 2760
tggtttgtta ttgttaattt tgttcttgta gaagagctta attaatcgtt gttgttatga 2820
aatactattt gtatgagatg aactggtgta atgtaattca tttacataag tggagtcaga 2880
atcagaatgt ttcctccata actaactaga catgaagacc tgccgcgtac aattgtctta 2940
tatttgaaca actaaaattg aacatctttt gccacaactt tataagtggt taatatagct 3000
caaatatatg gtcaagttca atagattaat aatggaaata tcagttatcg aaattcatta 3060
acaatcaact taacgttatt aactactaat tttatatcat cccctttgat aaatgatagt 3120
aca 3123

<210> SEQ ID NO 62
<211> LENGTH: 3088
<212> TYPE: DNA
<213> ORGANISM: Artificial
<220> FEATURE:
<223> OTHER INFORMATION: H1 from A/Brisbane/59/2007 (construct #774)

<400> SEQUENCE: 62

```
ctggtatatt tatatgttgt caaataactc aaaaaccata aaagtttaag ttagcaagtg     60
tgtacatttt tacttgaaca aaaatattca cctactactg ttataaatca ttattaaaca    120
ttagagtaaa gaaatatgga tgataagaac aagagtagtg atattttgac aacaattttg    180
ttgcaacatt tgagaaaatt ttgttgttct ctcttttcat tggtcaaaaa caatagagag    240
agaaaaagga agagggagaa taaaaacata atgtgagtat gagagagaaa gttgtacaaa    300
agttgtacca aaatagttgt acaaatatca ttgaggaatt tgacaaaagc tacacaaata    360
agggttaatt gctgtaaata aataaggatg acgcattaga gagatgtacc attagagaat    420
ttttggcaag tcattaaaaa gaaagaataa attattttta aaattaaaag ttgagtcatt    480
tgattaaaca tgtgattatt taatgaattg atgaaagagt tggattaaag ttgtattagt    540
aattagaatt tggtgtcaaa tttaatttga catttgatct tttcctatat attgccccat    600
agagtcagtt aactcatttt tatatttcat agatcaaata agagaaataa cggtatatta    660
atccctccaa aaaaaaaaaa cggtatattt actaaaaaat ctaagccacg taggaggata    720
acaggatccc cgtaggagga taacatccaa tccaaccaat cacaacaatc ctgatgagat    780
aacccacttt aagcccacgc atctgtggca catctacatt atctaaatca cacattcttc    840
cacacatctg agccacacaa aaaccaatcc acatctttat cacccattct ataaaaaatc    900
acactttgtg agtctacact ttgattccct tcaaacacat acaaagagaa gagactaatt    960
aattaattaa tcatcttgag agaaaatgaa agtaaaacta ctggtcctgt tatgcacatt   1020
tacagctaca tatgcagaca caatatgtat aggctaccat gctaacaact cgaccgacac   1080
tgttgacaca gtacttgaaa agaatgtgac agtgacacac tctgtcaacc tgcttgagaa   1140
cagtcacaat ggaaaactat gtctattaaa aggaatagcc ccactacaat tgggtaattg   1200
cagcgttgcc gggtggatct taggaaaccc agaatgcgaa ttactgattt ccaaggagtc   1260
atggtcctac attgtagaaa aaccaaatcc tgagaatgga acatgttacc cagggcattt   1320
cgctgactat gaggaactga gggagcaatt gagttcagta tcttcatttg agaggttcga   1380
aatattcccc aaagaaagct catggcccaa ccacaccgta accggagtgt cagcatcatg   1440
ctcccataat ggggaaagca gtttttacag aaatttgcta tggctgacgg ggaagaatgg   1500
tttgtaccca aacctgagca agtcctatgc aaacaacaaa gaaaaagaag tccttgtact   1560
atggggtgtt catcacccgc caaacatagg tgaccaaaag gccctctatc atacagaaaa   1620
tgcttatgtc tctgtagtgt cttcacatta tagcagaaaa ttcaccccag aaatagccaa   1680
aagacccaaa gtaagagatc aagaaggaag aatcaattac tactggactc tgcttgaacc   1740
cggggataca ataatatttg aggcaaatgg aaatctaata gcgccaagat atgctttcgc   1800
actgagtaga ggctttggat caggaatcat caactcaaat gcaccaatgg ataaatgtga   1860
tgcgaagtgc caaacacctc agggagctat aaacagcagt cttcctttcc agaacgtaca   1920
cccagtcaca ataggagagt gtccaaagta tgtcaggagt gcaaaattaa ggatggttac   1980
aggactaagg aacatcccat ccattcaatc cagaggtttg tttggagcca ttgccggttt   2040
cattgaaggg gggtggactg gaatggtaga tggttggtat ggttatcatc atcagaatga   2100
gcaaggatct ggctatgctg cagatcaaaa aagcacacaa aatgccatta atgggattac   2160
aaacaaggtc aattctgtaa ttgagaaaat gaacactcaa ttcacagcag tgggcaaaga   2220
gttcaacaaa ttggaaagaa ggatggaaaa cttgaataaa aaagttgatg atgggtttat   2280
agacatttgg acatataatg cagaactgtt ggttctactg gaaaatgaaa ggactttgga   2340
```

```
tttccatgac tccaatgtga agaatctgta tgagaaagta aaaagccagt taaagaataa   2400

tgctaaagaa ataggaaatg ggtgttttga gttctatcac aagtgtaacg atgaatgcat   2460

ggagagtgta aagaatggaa cttatgacta tccaaaatat tccgaagaat caaagttaaa   2520

cagggagaaa attgatggag tgaaattgga atcaatggga gtctatcaga ttctggcgat   2580

ctactcaaca gtcgccagtt ctctggttct tttggtctcc ctgggggcaa tcagcttctg   2640

gatgtgttcc aatgggtctt tacagtgtag aatatgcatc taagagctct aagttaaaat   2700

gcttcttcgt ctcctattta taatatggtt tgttattgtt aattttgttc ttgtagaaga   2760

gcttaattaa tcgttgttgt tatgaaatac tatttgtatg agatgaactg gtgtaatgta   2820

attcatttac ataagtggag tcagaatcag aatgtttcct ccataactaa ctagacatga   2880

agacctgccg cgtacaattg tcttatattt gaacaactaa aattgaacat cttttgccac   2940

aactttataa gtggttaata tagctcaaat atatggtcaa gttcaataga ttaataatgg   3000

aaatatcagt tatcgaaatt cattaacaat caacttaacg ttattaacta ctaattttat   3060

atcatcccct ttgataaatg atagtaca                                      3088


<210> SEQ ID NO 63
<211> LENGTH: 3102
<212> TYPE: DNA
<213> ORGANISM: Artificial
<220> FEATURE:
<223> OTHER INFORMATION: H1 from A/Solomon Islands/3/2006 (H1N1)
      (Construct #775)

<400> SEQUENCE: 63

agaggtaccc cgggctggta tatttatatg ttgtcaaata actcaaaaac cataaaagtt     60

taagttagca agtgtgtaca tttttacttg aacaaaaata ttcacctact actgttataa    120

atcattatta aacattagag taaagaaata tggatgataa gaacaagagt agtgatattt    180

tgacaacaat tttgttgcaa catttgagaa aattttgttg ttctctcttt tcattggtca    240

aaaacaatag agagagaaaa aggaagaggg agaataaaaa cataatgtga gtatgagaga    300

gaaagttgta caaaagttgt accaaaatag ttgtacaaat atcattgagg aatttgacaa    360

aagctacaca aataagggtt aattgctgta aataaataag gatgacgcat tagagagatg    420

taccattaga gaatttttgg caagtcatta aaaagaaaga ataaattatt tttaaaatta    480

aaagttgagt catttgatta aacatgtgat tatttaatga attgatgaaa gagttggatt    540

aaagttgtat tagtaattag aatttggtgt caaatttaat ttgacatttg atcttttcct    600

atatattgcc ccatagagtc agttaactca tttttatatt tcatagatca aataagagaa    660

ataacggtat attaatccct ccaaaaaaaa aaaacggtat atttactaaa aaatctaagc    720

cacgtaggag gataacagga tccccgtagg aggataacat ccaatccaac caatcacaac    780

aatcctgatg agataaccca ctttaagccc acgcatctgt ggcacatcta cattatctaa    840

atcacacatt cttccacaca tctgagccac acaaaaacca atccacatct ttatcaccca    900

ttctataaaa aatcacactt tgtgagtcta cactttgatt cccttcaaac acatacaaag    960

agaagagact aattaattaa ttaatcatct tgagagaaaa tgaaagtaaa actactggtc   1020

ctgttatgca catttacagc tacatatgca gacacaatat gtataggcta ccatgccaac   1080

aactcaaccg acactgttga cacagtactt gagaagaatg tgacagtgac acactctgtc   1140

aacctgcttg aggacagtca caatggaaaa ttatgtctat taaaaggaat agccccacta   1200

caattgggta attgcagcgt tgccggatgg atcttaggaa acccagaatg cgaattactg   1260
```

atttccaggg aatcatggtc ctacattgta gaaaaaccaa atcctgagaa tggaacatgt 1320
tacccagggc atttcgccga ctatgaggaa ctgagggagc aattgagttc agtatcttca 1380
tttgagagat tcgaaatatt ccccaaagaa agctcatggc ccaaccacac cacaaccgga 1440
gtatcagcat catgctccca taatggggaa agcagttttt acaaaaattt gctatggctg 1500
acggggaaga atggtttgta cccaaacctg agcaagtcct atgcaaacaa caaagagaaa 1560
gaagtccttg tactatgggg tgttcatcac ccgcctaaca taggtgacca aagggctctc 1620
tatcataaag aaaatgctta tgtctctgta gtgtcttcac attatagcag aaaattcacc 1680
ccagaaatag ccaaaagacc caaagtaaga gatcaagaag gaagaatcaa ctactactgg 1740
actctacttg aacccgggga tacaataata tttgaggcaa atggaaatct aatagcgcca 1800
agatatgctt tcgcactgag tagaggcttt ggatcaggaa tcatcaactc aaatgcacca 1860
atggatgaat gtgatgcgaa gtgccaaaca cctcagggag ctataaacag cagtcttcct 1920
ttccagaatg tacaccctgt cacaatagga gagtgtccaa agtatgtcag gagtgcaaaa 1980
ttaaggatgg ttacaggact aaggaacatc ccatccattc aatccagagg tttgtttgga 2040
gccattgccg gtttcattga aggggggtgg actggaatgg tagatggttg gtatggttat 2100
catcatcaga atgagcaagg atctggctat gctgcagatc aaaaaagcac acaaaatgcc 2160
attaatggga ttacaaacaa ggtcaattct gtaattgaga aaatgaacac tcaattcaca 2220
gctgtgggca aagagttcaa caaattggaa agaaggatgg aaaacttaaa taaaaaagtt 2280
gatgatgggt ttatagacat ttggacatat aatgcagaat tgttggttct actggaaaat 2340
gaaaggactt tggatttcca tgactccaat gtgaagaatc tgtatgagaa agtaaaaagc 2400
caattaaaga ataatgccaa agaaatagga aatgggtgtt ttgagttcta tcataagtgt 2460
aacgatgaat gcatggagag tgtaaaaaat ggaacttatg actatccaaa atattccgaa 2520
gaatcaaagt taaacaggga gaaaattgat ggagtgaaat tggaatcaat gggagtctat 2580
cagattctgg cgatctactc aacagtcgcc agttctctgg ttcttttggt ctccctgggg 2640
gcaatcagct tctggatgtg ttccaatggg tctttgcagt gtagaatatg catctgagag 2700
ctctaagtta aaatgcttct tcgtctccta tttataatat ggtttgttat tgttaatttt 2760
gttcttgtag aagagcttaa ttaatcgttg ttgttatgaa atactatttg tatgagatga 2820
actggtgtaa tgtaattcat ttacataagt ggagtcagaa tcagaatgtt tcctccataa 2880
ctaactagac atgaagacct gccgcgtaca attgtcttat atttgaacaa ctaaaattga 2940
acatcttttg ccacaacttt ataagtggtt aatatagctc aaatatatgg tcaagttcaa 3000
tagattaata atggaaatat cagttatcga aattcattaa caatcaactt aacgttatta 3060
actactaatt ttatatcatc ccctttgata aatgatagta ca 3102

<210> SEQ ID NO 64
<211> LENGTH: 3093
<212> TYPE: DNA
<213> ORGANISM: Artificial sequence
<220> FEATURE:
<223> OTHER INFORMATION: H2 from A/Singapore/1/57 (H2N2) (construct #780)

<400> SEQUENCE: 64
agaggtaccc cgggctggta tatttatatg ttgtcaaata actcaaaaac cataaaagtt 60
taagttagca agtgtgtaca tttttacttg aacaaaaata ttcacctact actgttataa 120
atcattatta aacattagag taaagaaata tggatgataa gaacaagagt agtgatattt 180

-continued

```
tgacaacaat tttgttgcaa catttgagaa aattttgttg ttctctcttt tcattggtca    240
aaaacaatag agagagaaaa aggaagaggg agaataaaaa cataatgtga gtatgagaga    300
gaaagttgta caaaagttgt accaaaatag ttgtacaaat atcattgagg aatttgacaa    360
aagctacaca aataagggtt aattgctgta aataaataag gatgacgcat tagagagatg    420
taccattaga gaatttttgg caagtcatta aaaagaaaga ataaattatt tttaaaatta    480
aaagttgagt catttgatta aacatgtgat tatttaatga attgatgaaa gagttggatt    540
aaagttgtat tagtaattag aatttggtgt caaatttaat ttgacatttg atcttttcct    600
atatattgcc ccatagagtc agttaactca tttttatatt tcatagatca aataagagaa    660
ataacggtat attaatccct ccaaaaaaaa aaaacggtat atttactaaa aaatctaagc    720
cacgtaggag gataacagga tccccgtagg aggataacat ccaatccaac caatcacaac    780
aatcctgatg agataaccca ctttaagccc acgcatctgt ggcacatcta cattatctaa    840
atcacacatt cttccacaca tctgagccac acaaaaacca atccacatct ttatcaccca    900
ttctataaaa aatcacactt tgtgagtcta cactttgatt cccttcaaac acatacaaag    960
agaagagact aattaattaa ttaatcatct tgagagaaaa tggccatcat ttatctaatt   1020
ctcctgttca cagcagtgag aggggaccaa atatgcattg gataccatgc caataattcc   1080
acagagaagg tcgacacaat tctagagcgg aacgtcactg tgactcatgc caaggacatt   1140
cttgagaaga cccataacgg aaagttatgc aaactaaacg gaatccctcc acttgaacta   1200
ggggactgta gcattgccgg atggctcctt ggaaatccag aatgtgatag gcttctaagt   1260
gtgccagaat ggtcctatat aatggagaaa gaaaacccga gagacggttt gtgttatcca   1320
ggcagcttca atgattatga agaattgaaa catctcctca gcagcgtgaa acatttcgag   1380
aaagtaaaga ttctgcccaa agatagatgg acacagcata caacaactgg aggttcacgg   1440
gcctgcgcgg tgtctggtaa tccatcattc ttcaggaaca tggtctggct gacaaagaaa   1500
gaatcaaatt atccggttgc caaaggatcg tacaacaata caagcggaga acaaatgcta   1560
ataatttggg gggtgcacca tcccaatgat gagacagaac aaagaacatt gtaccagaat   1620
gtgggaacct atgtttccgt aggcacatca acattgaaca aaaggtcaac cccagacata   1680
gcaacaaggc ctaaagtgaa tggactagga agtagaatgg agttctcttg gaccctattg   1740
gatatgtggg acaccataaa ttttgagagt actggtaatc taattgcacc agagtatgga   1800
ttcaaaatat cgaaaagagg tagttcaggg atcatgaaaa cagaaggaac acttgagaac   1860
tgtgagacca aatgccaaac tcctttggga gcaataaata caacattgcc ttttcacaat   1920
gtccacccac tgacaatagg tgagtgcccc aaatatgtaa aatcggagaa gttggtctta   1980
gcaacaggac taaggaatgt tccccagatt gaatcaagag gattgtttgg ggcaatagct   2040
ggttttatag aaggaggatg gcaaggaatg gttgatggtt ggtatggata ccatcacagc   2100
aatgaccagg gatcagggta tgcagcagac aaagaatcca ctcaaaaggc atttgatgga   2160
atcaccaaca aggtaaattc tgtgattgaa aagatgaaca cccaatttga agctgttggg   2220
aaagagttca gtaacttaga gagaagactg gagaacttga acaaaaagat ggaagacggg   2280
tttctagatg tgtggacata caatgctgag cttctagttc tgatggaaaa tgagaggaca   2340
cttgactttc atgattctaa tgtcaagaat ctgtatgata aagtcagaat gcagctgaga   2400
gacaacgtca aagaactagg aaatggatgt tttgaatttt atcacaaatg tgatgatgaa   2460
tgcatgaata gtgtgaaaaa cgggacgtat gattatccca agtatgaaga agagtctaaa   2520
ctaaatagaa atgaaatcaa aggggtaaaa ttgagcagca tgggggttta tcaaatcctt   2580
```

gccatttatg ctacagtagc aggttctctg tcactggcaa tcatgatggc tgggatctct 2640
ttctggatgt gctccaacgg gtctctgcag tgcaggatct gcatatgaga gctctaagtt 2700
aaaatgcttc ttcgtctcct atttataata tggtttgtta ttgttaattt tgttcttgta 2760
gaagagctta attaatcgtt gttgttatga aatactattt gtatgagatg aactggtgta 2820
atgtaattca tttacataag tggagtcaga atcagaatgt ttcctccata actaactaga 2880
catgaagacc tgccgcgtac aattgtctta tatttgaaca actaaaattg aacatctttt 2940
gccacaactt tataagtggt taatatagct caaatatatg gtcaagttca atagattaat 3000
aatggaaata tcagttatcg aaattcatta acaatcaact taacgttatt aactactaat 3060
tttatatcat cccctttgat aaatgatagt aca 3093

<210> SEQ ID NO 65
<211> LENGTH: 3108
<212> TYPE: DNA
<213> ORGANISM: Artificial sequence
<220> FEATURE:
<223> OTHER INFORMATION: H5 from A/Anhui/1/2005 (H5N1) (Construct #781)

<400> SEQUENCE: 65
agaggtaccc cgggctggta tatttatatg ttgtcaaata actcaaaaac cataaaagtt 60
taagttagca agtgtgtaca tttttacttg aacaaaaata ttcacctact actgttataa 120
atcattatta aacattagag taaagaaata tggatgataa gaacaagagt agtgatattt 180
tgacaacaat tttgttgcaa catttgagaa aattttgttg ttctctcttt tcattggtca 240
aaaacaatag agagagaaaa aggaagaggg agaataaaaa cataatgtga gtatgagaga 300
gaaagttgta caaaagttgt accaaaatag ttgtacaaat atcattgagg aatttgacaa 360
aagctacaca aataagggtt aattgctgta aataaataag gatgacgcat tagagagatg 420
taccattaga gaatttttgg caagtcatta aaaagaaaga ataaattatt tttaaaatta 480
aaagttgagt catttgatta aacatgtgat tatttaatga attgatgaaa gagttggatt 540
aaagttgtat tagtaattag aatttggtgt caaatttaat ttgacatttg atcttttcct 600
atatattgcc ccatagagtc agttaactca tttttatatt tcatagatca aataagagaa 660
ataacggtat attaatccct ccaaaaaaaa aaaacggtat atttactaaa aaatctaagc 720
cacgtaggag gataacagga tccccgtagg aggataacat ccaatccaac caatcacaac 780
aatcctgatg agataaccca ctttaagccc acgcatctgt ggcacatcta cattatctaa 840
atcacacatt cttccacaca tctgagccac acaaaaacca atccacatct ttatcaccca 900
ttctataaaa aatcacactt tgtgagtcta cactttgatt cccttcaaac acatacaaag 960
agaagagact aattaattaa ttaatcatct tgagagaaaa tggagaaaat agtgcttctt 1020
cttgcaatag tcagccttgt taaaagtgat cagatttgca ttggttacca tgcaaacaac 1080
tcgacagagc aggttgacac aataatggaa aagaacgtta ctgttacaca tgcccaagac 1140
atactggaaa agacacacaa cgggaagctc tgcgatctag atggagtgaa gcctctgatt 1200
ttaagagatt gtagtgtagc tggatggctc ctcggaaacc caatgtgtga cgagttcatc 1260
aatgtgccgg aatggtctta catagtggag aaggccaacc cagccaatga cctctgttac 1320
ccagggaatt tcaacgacta tgaagaactg aaacacctat tgagcagaat aaaccatttt 1380
gagaaaattc agatcatccc caaaagttct tggtccgatc atgaagcctc atcaggggtc 1440
agctcagcat gtccatacca gggaacgccc tcctttttca gaaatgtggt atggcttatc 1500

```
aaaaagaaca atacataccc aacaataaag agaagctaca ataataccaa ccaggaagat   1560
cttttgatac tgtgggggat tcatcattct aatgatgcgg cagagcagac aaagctctat   1620
caaaacccaa ccacctatat ttccgttggg acatcaacac taaaccagag attggtacca   1680
aaaatagcta ctagatccaa agtaaacggg caaagtggaa ggatggattt cttctggaca   1740
attttaaaac cgaatgatgc aatcaacttc gagagtaatg gaaatttcat tgctccagaa   1800
tatgcataca aaattgtcaa gaaaggggac tcagcaattg ttaaaagtga agtggaatat   1860
ggtaactgca atacaaagtg tcaaactcca ataggggcga taaactctag tatgccattc   1920
cacaacatac accctctcac catcggggaa tgccccaaat atgtgaaatc aaacaaatta   1980
gtccttgcga ctgggctcag aaatagtcct ctaagagaaa gaagaagaaa aagaggacta   2040
tttggagcta tagcagggtt tatagaggga ggatggcagg gaatggtaga tggttggtat   2100
gggtaccacc atagcaatga gcaggggagt gggtacgctg cagacaaaga atccactcaa   2160
aaggcaatag atggagtcac caataaggtc aactcgatca ttgacaaaat gaacactcag   2220
tttgaggccg ttggaaggga atttaataac ttagaaagga gaatagagaa tttaaacaag   2280
aaaatggaag acggattcct agatgtctgg acttataatg ctgaacttct ggttctcatg   2340
gaaaatgaga gaactctaga cttccatgat tcaaatgtca agaaccttta cgacaaggtc   2400
cgactacagc ttagggataa tgcaaaggag ctgggtaacg gttgtttcga gttctatcac   2460
aaatgtgata atgaatgtat ggaaagtgta agaaacggaa cgtatgacta cccgcagtat   2520
tcagaagaag caagattaaa aagagaggaa ataagtggag taaaattgga atcaatagga   2580
acttaccaaa tactgtcaat ttattcaaca gttgcgagtt ctctagcact ggcaatcatg   2640
gtggctggtc tatctttgtg gatgtgctcc aatgggtcgt tacaatgcag aatttgcatt   2700
taagagctct aagttaaaat gcttcttcgt ctcctattta taatatggtt tgttattgtt   2760
aattttgttc ttgtagaaga gcttaattaa tcgttgttgt tatgaaatac tatttgtatg   2820
agatgaactg gtgtaatgta attcatttac ataagtggag tcagaatcag aatgtttcct   2880
ccataactaa ctagacatga agacctgccg cgtacaattg tcttatattt gaacaactaa   2940
aattgaacat cttttgccac aactttataa gtggttaata tagctcaaat atatggtcaa   3000
gttcaataga ttaataatgg aaatatcagt tatcgaaatt cattaacaat caacttaacg   3060
ttattaacta ctaattttat atcatcccct ttgataaatg atagtaca                3108
```

<210> SEQ ID NO 66
<211> LENGTH: 3111
<212> TYPE: DNA
<213> ORGANISM: Artificial sequence
<220> FEATURE:
<223> OTHER INFORMATION: H5 from A/Vietnam/1194/2004 (H5N1) (Construct #782)

<400> SEQUENCE: 66

```
agaggtaccc cgggctggta tatttatatg ttgtcaaata actcaaaaac cataaaagtt     60
taagttagca agtgtgtaca tttttacttg aacaaaaata ttcacctact actgttataa    120
atcattatta aacattagag taaagaaata tggatgataa gaacaagagt agtgatattt    180
tgacaacaat tttgttgcaa catttgagaa aattttgttg ttctctcttt tcattggtca    240
aaaacaatag agagagaaaa aggaagaggg agaataaaaa cataatgtga gtatgagaga    300
gaaagttgta caaaagttgt accaaaatag ttgtacaaat atcattgagg aatttgacaa    360
aagctacaca aataagggtt aattgctgta aataaataag gatgacgcat tagagagatg    420
```

-continued

```
taccattaga gaatttttgg caagtcatta aaaagaaaga ataaattatt tttaaaatta    480
aaagttgagt catttgatta aacatgtgat tatttaatga attgatgaaa gagttggatt    540
aaagttgtat tagtaattag aatttggtgt caaatttaat ttgacatttg atcttttcct    600
atatattgcc ccatagagtc agttaactca tttttatatt tcatagatca aataagagaa    660
ataacggtat attaatccct ccaaaaaaaa aaaacggtat atttactaaa aaatctaagc    720
cacgtaggag gataacagga tccccgtagg aggataacat ccaatccaac caatcacaac    780
aatcctgatg agataaccca ctttaagccc acgcatctgt ggcacatcta cattatctaa    840
atcacacatt cttccacaca tctgagccac acaaaaacca atccacatct ttatcaccca    900
ttctataaaa aatcacactt tgtgagtcta cactttgatt cccttcaaac acatacaaag    960
agaagagact aattaattaa ttaatcatct tgagagaaaa tggagaaaat agtgcttctt   1020
tttgcaatag tcagtcttgt taaaagtgat cagatttgca ttggttacca tgcaaacaac   1080
tcgacagagc aggttgacac aataatggaa aagaacgtta ctgttacaca tgcccaagac   1140
atactggaaa agacacacaa tgggaagctc tgcgatctag atggagtgaa gcctctaatt   1200
ttgagagatt gtagtgtagc tggatggctc ctcggaaacc caatgtgtga cgagttcatc   1260
aatgtgccgg aatggtctta catagtggag aaggccaatc cagtcaatga cctctgttac   1320
ccaggggatt tcaatgacta tgaagaattg aaacacctat tgagcagaat aaaccatttt   1380
gagaaaattc agatcatccc caaaagttct tggtccagtc atgaagcctc attgggggtc   1440
agctcagcat gtccatacca gggaaagtcc tcctttttca gaaatgtggt atggcttatc   1500
aaaaagaaca gtacataccc aacaataaag aggagctaca ataataccaa ccaagaagat   1560
cttttggtac tgtgggggat tcaccatcct aatgatgcgg cagagcagac aaagctctat   1620
caaaacccaa ccacctatat ttccgttggg acatctacac taaaccagag attggtacca   1680
agaatagcta ctagatccaa agtaaacggg caaagtggaa ggatggagtt cttctggaca   1740
attttaaaac cgaatgatgc aatcaacttc gagagtaatg gaaatttcat tgctccagaa   1800
tatgcataca aaattgtcaa gaaaggggac tcaacaatta tgaaaagtga attggaatat   1860
ggtaactgca ataccaagtg tcaaactcca atgggggcga taaactctag catgccattc   1920
cacaatatac accctctcac catcggggaa tgccccaaat atgtgaaatc aaacagatta   1980
gtccttgcga ctgggctcag aaatagccct caaagagaga gaagaagaaa aaagagagga   2040
ttatttggag ctatagcagg ttttatagag ggaggatggc agggaatggt agatggttgg   2100
tatgggtacc accatagcaa cgagcagggg agtgggtacg ctgcagacaa agaatccact   2160
caaaaggcaa tagatggagt caccaataag gtcaactcga ttattgacaa aatgaacact   2220
cagtttgagg ccgttggaag ggaatttaac aacttagaaa ggagaataga gaatttaaac   2280
aagaagatgg aagacgggtt cctagatgtc tggacttata atgctgaact tctagttctc   2340
atggaaaacg agagaactct agactttcat gactcaaatg tcaagaacct ttacgacaag   2400
gtccgactac agcttaggga taatgcaaag gagctgggta acggttgttt cgagttctat   2460
cataaatgtg ataatgaatg tatggaaagt gtaagaaacg gaacgtatga ctacccgcag   2520
tattcagaag aagcaagact aaaaagagag gaaataagtg gagtaaaatt ggaatcaata   2580
ggaatttacc aaatattgtc aatttattct acagtggcca gctccctagc actggcaatc   2640
atggtagctg gtctatcctt atggatgtgc tccaatgggt cgttacaatg cagaatttgc   2700
atttaagagc tctaagttaa aatgcttctt cgtctcctat ttataatatg gtttgttatt   2760
gttaattttg ttcttgtaga agagcttaat taatcgttgt tgttatgaaa tactatttgt   2820
```

```
atgagatgaa ctggtgtaat gtaattcatt tacataagtg gagtcagaat cagaatgttt   2880

cctccataac taactagaca tgaagacctg ccgcgtacaa ttgtcttata tttgaacaac   2940

taaaattgaa catcttttgc cacaacttta taagtggtta atatagctca aatatatggt   3000

caagttcaat agattaataa tggaaatatc agttatcgaa attcattaac aatcaactta   3060

acgttattaa ctactaattt tatatcatcc cctttgataa atgatagtac a            3111
```

<210> SEQ ID NO 67
<211> LENGTH: 3105
<212> TYPE: DNA
<213> ORGANISM: Artificial
<220> FEATURE:
<223> OTHER INFORMATION: H6 from A/Teal/Hong Kong/W312/97 (H6N1)
(Construct #783)

<400> SEQUENCE: 67

```
agaggtaccc cgggctggta tatttatatg ttgtcaaata actcaaaaac cataaaagtt     60

taagttagca agtgtgtaca tttttacttg aacaaaaata ttcacctact actgttataa    120

atcattatta aacattagag taaagaaata tggatgataa gaacaagagt agtgatattt    180

tgacaacaat tttgttgcaa catttgagaa aattttgttg ttctctcttt tcattggtca    240

aaaacaatag agagagaaaa aggaagaggg agaataaaaa cataatgtga gtatgagaga    300

gaaagttgta caaaagttgt accaaaatag ttgtacaaat atcattgagg aatttgacaa    360

aagctacaca aataagggtt aattgctgta aataaataag gatgacgcat tagagagatg    420

taccattaga gaatttttgg caagtcatta aaaagaaaga ataaattatt tttaaaatta    480

aaagttgagt catttgatta aacatgtgat tatttaatga attgatgaaa gagttggatt    540

aaagttgtat tagtaattag aatttggtgt caaatttaat ttgacatttg atcttttcct    600

atatattgcc ccatagagtc agttaactca tttttatatt tcatagatca aataagagaa    660

ataacggtat attaatccct ccaaaaaaaa aaaacggtat atttactaaa aaatctaagc    720

cacgtaggag gataacagga tccccgtagg aggataacat ccaatccaac caatcacaac    780

aatcctgatg agataaccca ctttaagccc acgcatctgt ggcacatcta cattatctaa    840

atcacacatt cttccacaca tctgagccac acaaaaacca atccacatct ttatcaccca    900

ttctataaaa aatcacactt tgtgagtcta cactttgatt cccttcaaac acatacaaag    960

agaagagact aattaattaa ttaatcatct tgagagaaaa tgattgcaat cattgtaata   1020

gcaatactgg cagcagccgg aaagtcagac aagatctgca ttgggtatca tgccaacaat   1080

tcaacaacac aggtagatac gatacttgag aagaatgtga ctgtcacaca ctcaattgaa   1140

ttgctggaaa atcagaagga agaaagattc tgcaagatat tgaacaaggc ccctctcgac   1200

ttaagggaat gtaccataga gggttggatc ttggggaatc cccaatgcga cctattgctt   1260

ggtgatcaaa gctggtcata cattgtggaa agacctactg ctcaaaacgg gatctgctac   1320

ccaggaacct taaatgaggt agaagaactg agggcactta ttggatcagg agaaagggta   1380

gagagatttg agatgtttcc ccaaagcacc tggcaaggag ttgacaccaa cagtggaaca   1440

acaagatcct gcccttattc tactggtgcg tctttctaca gaaacctcct atggataata   1500

aaaaccaaga cagcagaata tccagtaatt aagggaattt acaacaacac tggaacccag   1560

ccaatcctct atttctgggg tgtgcatcat cctcctaaca ccgacgagca agatactctg   1620

tatggctctg gtgatcgata cgttagaatg ggaactgaaa gcatgaattt tgccaagagt   1680

ccggaaattg cggcaaggcc tgctgtgaat ggacaaagag gcagaattga ttattattgg   1740
```

```
tcggttttaa aaccagggga aaccttgaat gtggaatcta atggaaatct aatcgcccct   1800
tggtatgcat acaaatttgt caacacaaat agtaaaggag ccgtcttcag gtcagattta   1860
ccaatcgaga actgcgatgc cacatgccag actattgcag ggttctaag gaccaataaa   1920
acatttcaga atgtgagtcc cctgtggata ggagaatgtc ccaaatacgt gaaaagtgaa   1980
agtctgaggc ttgcaactgg actaagaaat gttccacaga ttgaaactag aggactcttc   2040
ggagctattg cagggtttat tgaaggagga tggactggga tgatagatgg gtggtatggc   2100
tatcaccatg aaaattctca agggtcagga tatgcagcag acagagaaag cactcaaaag   2160
gctgtaaaca gaattacaaa taaggtcaat tccatcatca acaaaatgaa cacacaattt   2220
gaagctgtcg atcacgaatt ttcaaatctg gagaggagaa ttgacaatct gaacaaaaga   2280
atgcaagatg gatttctgga tgtttggaca tacaatgctg aactgttggt tcttcttgaa   2340
aacgaaagaa cactagacat gcatgacgca aatgtgaaga acctacatga aaaggtcaaa   2400
tcacaactaa gggacaatgc tacgatctta gggaatggtt gctttgaatt ttggcataag   2460
tgtgacaatg aatgcataga gtctgtcaaa aatggtacat atgactatcc caaataccag   2520
actgaaagca aattaaacag gctaaaaata gaatcagtaa agctagagaa ccttggtgtg   2580
tatcaaattc ttgccattta tagtacggta tcgagcagcc tagtgttggt agggctgatc   2640
atggcaatgg gtctttggat gtgttcaaat ggttcaatgc agtgcaggat atgtatataa   2700
gagctctaag ttaaaatgct tcttcgtctc ctatttataa tatggtttgt tattgttaat   2760
tttgttcttg tagaagagct taattaatcg ttgttgttat gaaatactat ttgtatgaga   2820
tgaactggtg taatgtaatt catttacata agtggagtca gaatcagaat gtttcctcca   2880
taactaacta gacatgaaga cctgccgcgt acaattgtct tatatttgaa caactaaaat   2940
tgaacatctt ttgccacaac tttataagtg gttaatatag ctcaaatata tggtcaagtt   3000
caatagatta ataatggaaa tatcagttat cgaaattcat taacaatcaa cttaacgtta   3060
ttaactacta attttatatc atcccctttg ataaatgata gtaca                    3105
```

<210> SEQ ID NO 68
<211> LENGTH: 3087
<212> TYPE: DNA
<213> ORGANISM: Artificial sequence
<220> FEATURE:
<223> OTHER INFORMATION: H9 from A/Hong Kong/1073/99 (H9N2) (Construct #785)

<400> SEQUENCE: 68

```
agaggtaccc cgggctggta tatttatatg ttgtcaaata actcaaaaac cataaaagtt     60
taagttagca agtgtgtaca tttttacttg aacaaaaata ttcacctact actgttataa    120
atcattatta aacattagag taaagaaata tggatgataa gaacaagagt agtgatattt    180
tgacaacaat tttgttgcaa catttgagaa aattttgttg ttctctcttt tcattggtca    240
aaaacaatag agagagaaaa aggaagaggg agaataaaaa cataatgtga gtatgagaga    300
gaaagttgta caaaagttgt accaaaatag ttgtacaaat atcattgagg aatttgacaa    360
aagctacaca aataagggtt aattgctgta aataaataag gatgacgcat tagagagatg    420
taccattaga gaatttttgg caagtcatta aaaagaaaga ataaattatt tttaaaatta    480
aaagttgagt catttgatta aacatgtgat tatttaatga attgatgaaa gagttggatt    540
aaagttgtat tagtaattag aatttggtgt caaatttaat ttgacatttg atcttttcct    600
atatattgcc ccatagagtc agttaactca tttttatatt tcatagatca aataagagaa    660
```

```
ataacggtat attaatccct ccaaaaaaaa aaaacggtat atttactaaa aaatctaagc    720
cacgtaggag gataacagga tccccgtagg aggataacat ccaatccaac caatcacaac    780
aatcctgatg agataaccca ctttaagccc acgcatctgt ggcacatcta cattatctaa    840
atcacacatt cttccacaca tctgagccac acaaaaacca atccacatct ttatcaccca    900
ttctataaaa aatcacactt tgtgagtcta cactttgatt cccttcaaac acatacaaag    960
agaagagact aattaattaa ttaatcatct tgagagaaaa tggaaacaat atcactaata   1020
actatactac tagtagtaac agcaagcaat gcagataaaa tctgcatcgg ccaccagtca   1080
acaaactcca cagaaactgt ggacacgcta acagaaacca atgttcctgt gacacatgcc   1140
aaagaattgc tccacacaga gcataatgga atgctgtgtg caacaagcct gggacatccc   1200
ctcattctag acacatgcac tattgaagga ctagtctatg gcaacccttc ttgtgacctg   1260
ctgttgggag gaagagaatg gtcctacatc gtcgaaagat catcagctgt aaatggaacg   1320
tgttaccctg ggaatgtaga aaacctagag gaactcagga cactttttag ttccgctagt   1380
tcctaccaaa gaatccaaat cttcccagac acaacctgga atgtgactta cactggaaca   1440
agcagagcat gttcaggttc attctacagg agtatgagat ggctgactca aaagagcggt   1500
ttttaccctg ttcaagacgc ccaatacaca aataacaggg gaaagagcat tcttttcgtg   1560
tggggcatac atcacccacc cacctatacc gagcaaacaa atttgtacat aagaaacgac   1620
acaacaacaa gcgtgacaac agaagatttg aataggacct tcaaaccagt gatagggcca   1680
aggccccttg tcaatggtct gcagggaaga attgattatt attggtcggt actaaaacca   1740
ggccaaacat tgcgagtacg atccaatggg aatctaattg ctccatggta tggacacgtt   1800
ctttcaggag ggagccatgg aagaatcctg aagactgatt taaaaggtgg taattgtgta   1860
gtgcaatgtc agactgaaaa aggtggctta aacagtacat tgccattcca caatatcagt   1920
aaatatgcat ttggaacctg ccccaaatat gtaagagtta atagtctcaa actggcagtc   1980
ggtctgagga acgtgcctgc tagatcaagt agaggactat ttggagccat agctggattc   2040
atagaaggag gttggccagg actagtcgct ggctggtatg gtttccagca ttcaaatgat   2100
caaggggttg gtatggctgc agatagggat tcaactcaaa aggcaattga taaaataaca   2160
tccaaggtga ataatatagt cgacaagatg aacaagcaat atgaaataat tgatcatgaa   2220
tttagtgagg ttgaaactag actcaatatg atcaataata agattgatga ccaaatacaa   2280
gacgtatggg catataatgc agaattgcta gtactacttg aaaatcaaaa aacactcgat   2340
gagcatgatg cgaacgtgaa caatctatat aacaaggtga agagggcact gggctccaat   2400
gctatggaag atgggaaagg ctgtttcgag ctataccata aatgtgatga tcagtgcatg   2460
gaaacaattc ggaacgggac ctataatagg agaaagtata gagaggaatc aagactagaa   2520
aggcagaaaa tagagggggt taagctggaa tctgagggaa cttacaaaat cctcaccatt   2580
tattcgactg tcgcctcatc tcttgtgctt gcaatggggt ttgctgcctt cctgttctgg   2640
gccatgtcca atggatcttg cagatgcaac atttgtatat aagagctcta agttaaaatg   2700
cttcttcgtc tcctatttat aatatggttt gttattgtta attttgttct tgtagaagag   2760
cttaattaat cgttgttgtt atgaaatact atttgtatga gatgaactgg tgtaatgtaa   2820
ttcatttaca taagtggagt cagaatcaga atgtttcctc cataactaac tagacatgaa   2880
gacctgccgc gtacaattgt cttatatttg aacaactaaa attgaacatc ttttgccaca   2940
actttataag tggttaatat agctcaaata tatggtcaag ttcaatagat taataatgga   3000
```

aatatcagtt atcgaaattc attaacaatc aacttaacgt tattaactac taattttata 3060
tcatcccctt tgataaatga tagtaca 3087

<210> SEQ ID NO 69
<211> LENGTH: 3105
<212> TYPE: DNA
<213> ORGANISM: Artificial sequence
<220> FEATURE:
<223> OTHER INFORMATION: H3 from A/Brisbane/10/2007 (H3N2)

<400> SEQUENCE: 69
agaggtaccc cgggctggta tatttatatg ttgtcaaata actcaaaaac cataaaagtt 60
taagttagca agtgtgtaca tttttacttg aacaaaaata ttcacctact actgttataa 120
atcattatta aacattagag taaagaaata tggatgataa gaacaagagt agtgatattt 180
tgacaacaat tttgttgcaa catttgagaa aattttgttg ttctctcttt tcattggtca 240
aaaacaatag agagagaaaa aggaagaggg agaataaaaa cataatgtga gtatgagaga 300
gaaagttgta caaaagttgt accaaaatag ttgtacaaat atcattgagg aatttgacaa 360
aagctacaca aataagggtt aattgctgta aataaataag gatgacgcat tagagagatg 420
taccattaga gaatttttgg caagtcatta aaaagaaaga ataaattatt tttaaaatta 480
aaagttgagt catttgatta aacatgtgat tatttaatga attgatgaaa gagttggatt 540
aaagttgtat tagtaattag aatttggtgt caaatttaat ttgacatttg atcttttcct 600
atatattgcc ccatagagtc agttaactca tttttatatt tcatagatca aataagagaa 660
ataacggtat attaatccct ccaaaaaaaa aaaacggtat atttactaaa aaatctaagc 720
cacgtaggag gataacagga tccccgtagg aggataacat ccaatccaac caatcacaac 780
aatcctgatg agataaccca ctttaagccc acgcatctgt ggcacatcta cattatctaa 840
atcacacatt cttccacaca tctgagccac acaaaaacca atccacatct ttatcaccca 900
ttctataaaa aatcacactt tgtgagtcta cactttgatt cccttcaaac acatacaaag 960
agaagagact aattaattaa ttaatcatct tgagagaaaa tgaagactat cattgctttg 1020
agctacattc tatgtctggt tttcactcaa aaacttcccg gaaatgacaa cagcacggca 1080
acgctgtgcc ttgggcacca tgcagtacca aacggaacga tagtgaaaac aatcacgaat 1140
gaccaaattg aagttactaa tgctactgag ctggttcaga gttcctcaac aggtgaaata 1200
tgcgacagtc ctcatcagat ccttgatgga gaaaactgca cactaataga tgctctattg 1260
ggagaccctc agtgtgatgg cttccaaaat aagaaatggg acctttttgt tgaacgcagc 1320
aaagcctaca gcaactgtta cccttatgat gtgccggatt atgcctccct taggtcacta 1380
gttgcctcat ccggcacact ggagtttaac aatgaaagtt tcaattggac tggagtcact 1440
caaaacggaa caagctctgc ttgcataagg agatctaata acagtttctt tagtagattg 1500
aattggttga cccacttaaa attcaaatac ccagcattga acgtgactat gccaaacaat 1560
gaaaaatttg acaaattgta catttggggg gttcaccacc cgggtacgga caatgaccaa 1620
atcttcctgt atgctcaagc atcaggaaga atcacagtct ctaccaaaag aagccaacaa 1680
actgtaatcc cgaatatcgg atctagaccc agagtaagga atatccccag cagaataagc 1740
atctattgga caatagtaaa accgggagac atacttttga ttaacagcac agggaatcta 1800
attgctccta ggggttactt caaaatacga agtgggaaaa gctcaataat gagatcagat 1860
gcacccattg gcaaatgcaa ttctgaatgc atcactccaa acggaagcat tcccaatgac 1920
aaaccattcc aaaatgtaaa caggatcaca tacggggcct gtcccagata tgttaagcaa 1980
aacactctga aattggcaac agggatgcga aatgtaccag agaaacaaac tagaggcata 2040
tttggcgcaa tcgcgggttt catagaaaat ggttgggagg gaatggtgga tggttggtat 2100
ggtttcaggc atcaaaattc tgagggaata ggacaagcag cagatctcaa aagcactcaa 2160
gcagcaatcg atcaaatcaa tgggaagctg aataggttga tcgggaaaac caacgagaaa 2220
ttccatcaga ttgaaaaaga gttctcagaa gtcgaaggga gaatccagga ccttgagaaa 2280
tatgttgagg acaccaaaat agatctctgg tcatacaacg cggagcttct tgttgccctg 2340
gagaaccaac atacaattga tctaactgac tcagaaatga acaaactgtt tgaaaaaaca 2400
aagaagcaac tgagggaaaa tgctgaggat atgggcaatg gttgtttcaa aatataccac 2460
aaatgtgaca atgcctgcat aggatcaatc agaaatggaa cttatgacca cgatgtatac 2520
agagatgaag cattaaacaa ccggttccag atcaagggcg ttgagctgaa gtcaggatac 2580
aaagattgga tactatggat ttcctttgcc atatcatgtt ttttgctttg tgttgctttg 2640
ttggggttca tcatgtgggc ctgccaaaaa ggcaacatta ggtgcaacat ttgcatttga 2700
gagctctaag ttaaaatgct tcttcgtctc ctatttataa tatggtttgt tattgttaat 2760
tttgttcttg tagaagagct taattaatcg ttgttgttat gaaatactat ttgtatgaga 2820
tgaactggtg taatgtaatt catttacata agtggagtca gaatcagaat gtttcctcca 2880
taactaacta gacatgaaga cctgccgcgt acaattgtct tatatttgaa caactaaaat 2940
tgaacatctt ttgccacaac tttataagtg gttaatatag ctcaaatata tggtcaagtt 3000
caatagatta ataatggaaa tatcagttat cgaaattcat taacaatcaa cttaacgtta 3060
ttaactacta attttatatc atcccctttg ataaatgata gtaca 3105

<210> SEQ ID NO 70
<211> LENGTH: 3105
<212> TYPE: DNA
<213> ORGANISM: Artificial sequence
<220> FEATURE:
<223> OTHER INFORMATION: H3 from A/Wisconsin/67/2005 (H3N2)

<400> SEQUENCE: 70
agaggtaccc cgggctggta tatttatatg ttgtcaaata actcaaaaac cataaaagtt 60
taagttagca agtgtgtaca tttttacttg aacaaaaata ttcacctact actgttataa 120
atcattatta aacattagag taaagaaata tggatgataa gaacaagagt agtgatattt 180
tgacaacaat tttgttgcaa catttgagaa aattttgttg ttctctcttt tcattggtca 240
aaaacaatag agagagaaaa aggaagaggg agaataaaaa cataatgtga gtatgagaga 300
gaaagttgta caaaagttgt accaaaatag ttgtacaaat atcattgagg aatttgacaa 360
aagctacaca aataagggtt aattgctgta aataaataag gatgacgcat tagagagatg 420
taccattaga gaatttttgg caagtcatta aaaagaaaga ataaattatt tttaaaatta 480
aaagttgagt catttgatta aacatgtgat tatttaatga attgatgaaa gagttggatt 540
aaagttgtat tagtaattag aatttggtgt caaatttaat ttgacatttg atcttttcct 600
atatattgcc ccatagagtc agttaactca tttttatatt tcatagatca aataagagaa 660
ataacggtat attaatccct ccaaaaaaaa aaaacggtat atttactaaa aaatctaagc 720
cacgtaggag gataacagga tccccgtagg aggataacat ccaatccaac caatcacaac 780
aatcctgatg agataaccca ctttaagccc acgcatctgt ggcacatcta cattatctaa 840
atcacacatt cttccacaca tctgagccac acaaaaacca atccacatct ttatcaccca 900

```
ttctataaaa aatcacactt tgtgagtcta cactttgatt cccttcaaac acatacaaag    960
agaagagact aattaattaa ttaatcatct tgagagaaaa tgaagactat cattgctttg   1020
agctacattc tatgtctggt tttcactcaa aaacttcccg gaaatgacaa cagcacggca   1080
acgctgtgcc ttgggcacca tgcagtacca aacggaacga tagtgaaaac aatcacgaat   1140
gaccaaattg aagttactaa tgctactgag ctggttcaga gttcctcaac aggtggaata   1200
tgcgacagtc ctcatcagat ccttgatgga gaaaactgca cactaataga tgctctattg   1260
ggagaccctc agtgtgatgg cttccaaaat aagaaatggg accttttttgt tgaacgcagc   1320
aaagcctaca gcaactgtta cccttatgat gtgccggatt atgcctccct taggtcacta   1380
gttgcctcat ccggcacact ggagtttaac gatgaaagtt tcaattggac tggagtcact   1440
caaaatggaa caagctctgc ttgcaaaagg agatctaata acagtttctt tagtagattg   1500
aattggttga cccacttaaa attcaaatac ccagcattga acgtgactat gccaaacaat   1560
gaaaaatttg acaaattgta catttggggg gttcaccacc cgggtacgga caatgaccaa   1620
atcttcctgc atgctcaagc atcaggaaga atcacagtct ctaccaaaag aagccaacaa   1680
actgtaatcc cgaatatcgg atctagaccc agaataagga atatccccag cagaataagc   1740
atctattgga caatagtaaa accgggagac atacttttga ttaacagcac agggaatcta   1800
attgctccta ggggttactt caaaatacga agtgggaaaa gctcaataat gagatcagat   1860
gcacccattg gcaaatgcaa ttctgaatgc atcactccaa atggaagcat tcccaatgac   1920
aaaccatttc aaaatgtaaa caggatcaca tatggggcct gtcccagata tgttaagcaa   1980
aacactctga aattggcaac agggatgcga aatgtaccag agaaacaaac tagaggcata   2040
tttggcgcaa tcgcgggttt catagaaaat ggttgggagg gaatggtgga tggttggtac   2100
ggtttcaggc atcaaaattc tgagggaata ggacaagcag cagatctcaa aagcactcaa   2160
gcagcaatca atcaaatcaa tgggaagctg aataggttga tcgggaaaac caacgagaaa   2220
ttccatcaga ttgaaaaaga gttctcagaa gtagaaggga gaatccagga cctcgagaaa   2280
tatgttgagg acactaaaat agatctctgg tcatacaacg cggagcttct tgttgccctg   2340
gagaaccaac atacaattga tctaactgac tcagaaatga acaaactgtt tgaaagaaca   2400
aagaagcaac tgagggaaaa tgctgaggat atgggcaatg gttgtttcaa aatataccac   2460
aaatgtgaca atgcctgcat aggatcaatc agaaatggaa cttatgacca tgatgtatac   2520
agagatgaag cattaaacaa ccggttccag atcaaaggcg ttgagctgaa gtcaggatac   2580
aaagattgga tactatggat ttcctttgcc atatcatgtt ttttgctttg tgttgctttg   2640
ttggggttca tcatgtgggc ctgccaaaaa ggcaacatta ggtgcaacat ttgcatttga   2700
gagctctaag ttaaaatgct tcttcgtctc ctatttataa tatggtttgt tattgttaat   2760
tttgttcttg tagaagagct taattaatcg ttgttgttat gaaatactat ttgtatgaga   2820
tgaactggtg taatgtaatt catttacata agtggagtca gaatcagaat gtttcctcca   2880
taactaacta gacatgaaga cctgccgcgt acaattgtct tatatttgaa caactaaaat   2940
tgaacatctt ttgccacaac tttataagtg gttaatatag ctcaaatata tggtcaagtt   3000
caatagatta ataatggaaa tatcagttat cgaaattcat taacaatcaa cttaacgtta   3060
ttaactacta attttatatc atcccctttg ataaatgata gtaca                   3105
```

<210> SEQ ID NO 71
<211> LENGTH: 3117
<212> TYPE: DNA
<213> ORGANISM: Artificial sequence
<220> FEATURE:
<223> OTHER INFORMATION: H7 from A/Equine/Prague/56 (H7N7)

<400> SEQUENCE: 71

```
agaggtaccc cgggctggta tatttatatg ttgtcaaata actcaaaaac cataaaagtt     60
taagttagca agtgtgtaca tttttacttg aacaaaaata ttcacctact actgttataa    120
atcattatta aacattagag taaagaaata tggatgataa gaacaagagt agtgatattt    180
tgacaacaat tttgttgcaa catttgagaa aattttgttg ttctctcttt tcattggtca    240
aaaacaatag agagagaaaa aggaagaggg agaataaaaa cataatgtga gtatgagaga    300
gaaagttgta caaaagttgt accaaaatag ttgtacaaat atcattgagg aatttgacaa    360
aagctacaca aataagggtt aattgctgta aataaataag gatgacgcat tagagagatg    420
taccattaga gaatttttgg caagtcatta aaaagaaaga ataaattatt tttaaaatta    480
aaagttgagt catttgatta aacatgtgat tatttaatga attgatgaaa gagttggatt    540
aaagttgtat tagtaattag aatttggtgt caaatttaat ttgacatttg atcttttcct    600
atatattgcc ccatagagtc agttaactca tttttatatt tcatagatca aataagagaa    660
ataacggtat attaatccct ccaaaaaaaa aaaacggtat atttactaaa aaatctaagc    720
cacgtaggag gataacagga tccccgtagg aggataacat ccaatccaac caatcacaac    780
aatcctgatg agataaccca ctttaagccc acgcatctgt ggcacatcta cattatctaa    840
atcacacatt cttccacaca tctgagccac acaaaaacca atccacatct ttatcaccca    900
ttctataaaa aatcacactt tgtgagtcta cactttgatt cccttcaaac acatacaaag    960
agaagagact aattaattaa ttaatcatct tgagagaaaa tgaacactca aattctaata   1020
ttagccactt cggcattctt ctatgtacgt gcagataaaa tctgcctagg acatcatgct   1080
gtgtctaatg gaaccaaagt agacaccctt actgaaaaag gaatagaagt tgtcaatgca   1140
acagaaacag ttgaacaaac aaacatccct aagatctgct caaaaggaaa acagactgtt   1200
gaccttggtc aatgtggatt actagggacc gttattggtc ctccccaatg tgaccaattt   1260
cttgagttct ctgctaattt aatagttgaa agaagggaag gtaatgacat ttgttatcca   1320
ggcaaatttg acaatgaaga aacattgaga aaaatactca gaaaatccgg aggaattaaa   1380
aaggagaata tgggattcac atataccgga gtgagaacca atggagagac tagcgcatgt   1440
agaaggtcaa gatcttcctt ttatgcagag atgaaatggc ttctatccag cacagacaat   1500
gggacatttc cacaaatgac aaagtcctac aagaacacta agaaggtacc agctctgata   1560
atctggggaa tccaccactc aggatcaact actgaacaga ctagattata tggaagtggg   1620
aataaattga taacagtttg gagttccaaa taccaacaat cttttgtccc aaatcctgga   1680
ccaagaccgc aaatgaatgg tcaatcagga agaattgact ttcactggct gatgctagat   1740
cccaatgata ctgtcacttt cagttttaat ggggccttta tagcacctga ccgcgccagt   1800
tttctaagag gtaaatctct aggaatccaa agtgatgcac aacttgacaa taattgtgaa   1860
ggtgaatgct atcatattgg aggtactata attagcaact tgccctttca aaacattaat   1920
agtagggcaa tcggaaaatg ccccagatac gtgaagcaga agagcttaat gctagcaaca   1980
ggaatgaaaa atgttcctga agctcctgca cataaacaac taactcatca catgcgcaaa   2040
aaaagaggtt tatttggtgc aatagcagga ttcattgaaa atgggtggga aggattaata   2100
gacggatggt atggatataa gcatcagaat gcacaaggag aagggactgc tgcagactac   2160
aaaagtacac aatctgctat caaccaaata accggaaaat tgaacagact aatagaaaaa   2220
```

accaaccagc aattcgaact aatagataat gagttcaatg aaatagaaaa acaaattggc 2280
aatgttatta actggactag agattctatc atcgaagtat ggtcatataa tgcagagttc 2340
ctcgtagcag tggagaatca acacactatt gatttaactg actcagaaat gaacaaacta 2400
tatgaaaagg taagaagaca actgagagaa aatgctgagg aagatggtaa tggctgtttt 2460
gaaatattcc accaatgtga caatgattgc atggccagca ttagaaacaa cacatatgac 2520
cataaaaaat acagaaaaga ggcaatacaa aacagaatcc agattgacgc agtaaagttg 2580
agcagtggtt acaaagatat aatactttgg tttagcttcg ggcatcatg tttcttattt 2640 cttgccattg caatgggtct tgttttcata tgtataaaaa atggaaacat gcggtgcact 2700
atttgtatat aagagctcta agttaaaatg cttcttcgtc tcctatttat aatatggttt 2760
gttattgtta attttgttct tgtagaagag cttaattaat cgttgttgtt atgaaatact 2820
atttgtatga gatgaactgg tgtaatgtaa ttcatttaca taagtggagt cagaatcaga 2880
atgtttcctc cataactaac tagacatgaa gacctgccgc gtacaattgt cttatatttg 2940
aacaactaaa attgaacatc ttttgccaca actttataag tggttaatat agctcaaata 3000
tatggtcaag ttcaatagat taataatgga aatatcagtt atcgaaattc attaacaatc 3060
aacttaacgt tattaactac taattttata tcatcccctt tgataaatga tagtaca 3117

<210> SEQ ID NO 72
<211> LENGTH: 3162
<212> TYPE: DNA
<213> ORGANISM: Artificial sequence
<220> FEATURE:
<223> OTHER INFORMATION: HA from B/Malaysia/2506/2004

<400> SEQUENCE: 72
agaggtaccc cgggctggta tatttatatg ttgtcaaata actcaaaaac cataaaagtt 60
taagttagca agtgtgtaca tttttacttg aacaaaaata ttcacctact actgttataa 120
atcattatta aacattagag taaagaaata tggatgataa gaacaagagt agtgatattt 180
tgacaacaat tttgttgcaa catttgagaa aattttgttg ttctctcttt tcattggtca 240
aaaacaatag agagagaaaa aggaagaggg agaataaaaa cataatgtga gtatgagaga 300
gaaagttgta caaaagttgt accaaaatag ttgtacaaat atcattgagg aatttgacaa 360
aagctacaca aataagggtt aattgctgta aataaataag gatgacgcat tagagagatg 420
taccattaga gaatttttgg caagtcatta aaaagaaaga ataaattatt tttaaaatta 480
aaagttgagt catttgatta aacatgtgat tatttaatga attgatgaaa gagttggatt 540
aaagttgtat tagtaattag aatttggtgt caaatttaat ttgacatttg atcttttcct 600
atatattgcc ccatagagtc agttaactca tttttatatt tcatagatca aataagagaa 660
ataacggtat attaatccct ccaaaaaaaa aaaacggtat atttactaaa aaatctaagc 720
cacgtaggag gataacagga tccccgtagg aggataacat ccaatccaac caatcacaac 780
aatcctgatg agataaccca ctttaagccc acgcatctgt ggcacatcta cattatctaa 840
atcacacatt cttccacaca tctgagccac acaaaaacca atccacatct ttatcaccca 900
ttctataaaa aatcacactt tgtgagtcta cactttgatt cccttcaaac acatacaaag 960
agaagagact aattaattaa ttaatcatct tgagagaaaa tgaaggcaat aattgtacta 1020
ctcatggtag taacatccaa tgcagatcga atctgcactg ggataacatc gtcaaactca 1080
ccacatgttg tcaaaactgc tactcaaggg gaggtcaatg tgactggtgt aataccactg 1140
acaacaacac ccaccaaatc tcattttgca aatctcaaag gaacagaaac cagagggaaa 1200
ctatgcccaa aatgcctcaa ctgcacagat ctggacgtgg ccttgggcag accaaaatgc 1260
acggggaaca taccctcggc aagagtttca atactccatg aagtcagacc tgttacatct 1320
gggtgctttc ctataatgca cgacagaaca aaaattagac agctgcctaa acttctcaga 1380
ggatacgaac atatcaggtt atcaactcat aacgttatca atgcagaaaa tgcaccagga 1440
ggaccctaca aaattggaac ctcagggtct tgccctaacg ttaccaatgg aaacggattt 1500
ttcgcaacaa tggcttgggc cgtcccaaaa aacgacaaca acaaaacagc aacaaattca 1560
ttaacaatag aagtaccata catttgtaca gaaggagaag accaaattac cgtttggggg 1620
ttccactctg ataacgaaac ccaaatggca aagctctatg ggactcaaa gccccagaag 1680 ttcacctcat ctgccaacgg agtgaccaca cattacgttt cacagattgg tggcttccca 1740
aatcaaacag aagacggagg actaccacaa agcggtagaa ttgttgttga ttacatggtg 1800
caaaaatctg ggaaaacagg aacaattacc tatcaaagag gtattttatt gcctcaaaaa 1860
gtgtggtgcg caagtggcag gagcaaggta ataaaaggat cgttgccttt aattggagaa 1920
gcagattgcc tccacgaaaa atacggtgga ttaaacaaaa gcaagcctta ctacacaggg 1980
gaacatgcaa aggccatagg aaattgccca atatgggtga aaacaccctt gaagctggcc 2040
aatggaacca aatatagacc tcctgcaaaa ctattaaagg aaaggggttt cttcggagct 2100
attgctggtt tcttagaagg aggatgggaa ggaatgattg caggttggca cggatacaca 2160
tcccatgggg cacatggagt agcggtggca gcagacctta agagcactca agaggccata 2220
aacaagataa caaaaaatct caactctttg agtgagctgg aagtaaagaa tcttcaaaga 2280
ctaagcggtg ccatggatga actccacaac gaaatactag aactagacga gaaagtggat 2340
gatctcagag ctgatacaat aagctcacaa atagaactcg cagtcctgct ttccaatgaa 2400
ggaataataa acagtgaaga tgagcatctc ttggcgcttg aaagaaagct gaagaaaatg 2460
ctgggcccct ctgctgtaga gatagggaat ggatgctttg aaaccaaaca caagtgcaac 2520
cagacctgtc tcgacagaat agctgctggt acctttgatg caggagaatt ttctctcccc 2580
acttttgatt cactgaatat tactgctgca tctttaaatg acgatggatt ggataatcat 2640
actatactgc tttactactc aactgctgcc tccagtttgg ctgtaacatt gatgatagct 2700
atctttgttg tttatatggt ctccagagac aatgtttctt gctccatctg tctataagag 2760
ctctaagtta aaatgcttct tcgtctccta tttataatat ggtttgttat tgttaatttt 2820
gttcttgtag aagagcttaa ttaatcgttg ttgttatgaa atactatttg tatgagatga 2880
actggtgtaa tgtaattcat ttacataagt ggagtcagaa tcagaatgtt tcctccataa 2940
ctaactagac atgaagacct gccgcgtaca attgtcttat atttgaacaa ctaaaattga 3000
acatcttttg ccacaacttt ataagtggtt aatatagctc aaatatatgg tcaagttcaa 3060
tagattaata atggaaatat cagttatcga aattcattaa caatcaactt aacgttatta 3120
actactaatt ttatatcatc ccctttgata aatgatagta ca 3162

<210> SEQ ID NO 73
<211> LENGTH: 3159
<212> TYPE: DNA
<213> ORGANISM: Artificial sequence
<220> FEATURE:
<223> OTHER INFORMATION: HA from B/Florida/4/2006

<400> SEQUENCE: 73
agaggtaccc cgggctggta tatttatatg ttgtcaaata actcaaaaac cataaaagtt 60

-continued

```
taagttagca agtgtgtaca tttttacttg aacaaaaata ttcacctact actgttataa    120
atcattatta aacattagag taaagaaata tggatgataa gaacaagagt agtgatattt    180
tgacaacaat tttgttgcaa catttgagaa aattttgttg ttctctcttt tcattggtca    240
aaaacaatag agagagaaaa aggaagaggg agaataaaaa cataatgtga gtatgagaga    300
gaaagttgta caaaagttgt accaaaatag ttgtacaaat atcattgagg aatttgacaa    360
aagctacaca aataagggtt aattgctgta aataaataag gatgacgcat tagagagatg    420
taccattaga gaatttttgg caagtcatta aaaagaaaga ataaattatt tttaaaatta    480
aaagttgagt catttgatta aacatgtgat tatttaatga attgatgaaa gagttggatt    540
aaagttgtat tagtaattag aatttggtgt caaatttaat ttgacatttg atcttttcct    600
atatattgcc ccatagagtc agttaactca tttttatatt tcatagatca aataagagaa    660
ataacggtat attaatccct ccaaaaaaaa aaaacggtat atttactaaa aaatctaagc    720
cacgtaggag gataacagga tccccgtagg aggataacat ccaatccaac caatcacaac    780
aatcctgatg agataaccca ctttaagccc acgcatctgt ggcacatcta cattatctaa    840
atcacacatt cttccacaca tctgagccac acaaaaacca atccacatct ttatcaccca    900
ttctataaaa aatcacactt tgtgagtcta cactttgatt cccttcaaac acatacaaag    960
agaagagact aattaattaa ttaatcatct tgagagaaaa tgaaggcaat aattgtacta   1020
ctcatggtag taacatccaa tgcagatcga atctgcactg gaataacatc ttcaaactca   1080
cctcatgtgg tcaaaacagc cactcaaggg gaggtcaatg tgactggtgt gataccacta   1140
acaacaacac caacaaaatc ttattttgca aatctcaaag gaacaaggac cagagggaaa   1200
ctatgcccag actgtctcaa ctgcacagat ctggatgtgg ctttgggcag accaatgtgt   1260
gtggggacca caccttcggc gaaggcttca atactccacg aagtcaaacc tgttacatcc   1320
gggtgctttc ctataatgca cgacagaaca aaaatcaggc aactacccaa tcttctcaga   1380
ggatatgaaa atatcaggct atcaacccaa aacgtcatcg atgcggaaaa ggcaccagga   1440
ggaccctaca gacttggaac ctcaggatct tgccctaacg ctaccagtaa gagcggattt   1500
ttcgcaacaa tggcttgggc tgtcccaaag gacaacaaca aaaatgcaac gaacccacta   1560
acagtagaag taccatacat ttgtacagaa ggggaagacc aaatcactgt ttggggggttc   1620
cattcagata acaaaaccca aatgaagaac ctctatggag actcaaatcc tcaaaagttc   1680
acctcatctg ctaatggagt aaccacacac tatgtttctc agattggcag cttcccagat   1740
caaacagaag acggaggact accacaaagc ggcaggattg ttgttgatta catgatgcaa   1800
aaacctggga aaacaggaac aattgtctac caaagaggtg ttttgttgcc tcaaaaggtg   1860
tggtgcgcga gtggcaggag caaagtaata aaagggtcct tgcctttaat tggtgaagca   1920
gattgccttc atgaaaaata cggtggatta aacaaaagca agccttacta cacaggagaa   1980
catgcaaaag ccataggaaa ttgcccaata tgggtgaaaa cacctttgaa gctcgccaat   2040
ggaaccaaat atagacctcc tgcaaaacta ttaaaggaaa ggggtttctt cggagctatt   2100
gctggtttcc tagaaggagg atgggaagga atgattgcag gctggcacgg atacacatct   2160
cacggagcac atggagtggc agtggcggcg gaccttaaga gtacgcaaga agctataaac   2220
aagataacaa aaaatctcaa ttctttgagt gagctagaag taaagaatct tcaaagacta   2280
agtggtgcca tggatgaact ccacaacgaa atactcgagc tggatgagaa agtggatgat   2340
ctcagagctg acactataag ctcgcaaata gaacttgcag tcttgctttc caacgaagga   2400
ataataaaca gtgaagatga gcatctattg gcacttgaga gaaaactaaa gaaaatgctg   2460
```

```
ggtccctctg ctgtagagat aggaaatgga tgcttcgaaa ccaaacacaa gtgcaaccag   2520

acctgcttag acaggatagc tgctggcacc tttaatgcag gagaattttc tctccccact   2580

tttgattcac tgaacattac tgctgcatct ttaaatgatg atggattgga taaccatact   2640

atactgctct attactcaac tgctgcttct agtttggctg taacattgat gctagctatt   2700

tttattgttt atatggtctc cagagacaac gtttcatgct ccatctgtct ataagagctc   2760

taagttaaaa tgcttcttcg tctcctattt ataatatggt ttgttattgt taattttgtt   2820

cttgtagaag agcttaatta atcgttgttg ttatgaaata ctatttgtat gagatgaact   2880

ggtgtaatgt aattcattta cataagtgga gtcagaatca gaatgtttcc tccataacta   2940

actagacatg aagacctgcc gcgtacaatt gtcttatatt tgaacaacta aaattgaaca   3000

tcttttgcca caactttata agtggttaat atagctcaaa tatatggtca agttcaatag   3060

attaataatg gaaatatcag ttatcgaaat tcattaacaa tcaacttaac gttattaact   3120

actaatttta tatcatcccc tttgataaat gatagtaca                          3159
```

<210> SEQ ID NO 74
<211> LENGTH: 565
<212> TYPE: PRT
<213> ORGANISM: Influenza virus
<220> FEATURE:
<221> NAME/KEY: misc_feature
<222> LOCATION: (3)..(3)
<223> OTHER INFORMATION: Xaa can be Ala or Val
<220> FEATURE:
<221> NAME/KEY: misc_feature
<222> LOCATION: (52)..(52)
<223> OTHER INFORMATION: Xaa can be Asp or Asn
<220> FEATURE:
<221> NAME/KEY: misc_feature
<222> LOCATION: (90)..(90)
<223> OTHER INFORMATION: Xaa can be Lys or Arg
<220> FEATURE:
<221> NAME/KEY: misc_feature
<222> LOCATION: (99)..(99)
<223> OTHER INFORMATION: Xaa can be Lys or Thr
<220> FEATURE:
<221> NAME/KEY: misc_feature
<222> LOCATION: (111)..(111)
<223> OTHER INFORMATION: Xaa can be Tyr or His
<220> FEATURE:
<221> NAME/KEY: misc_feature
<222> LOCATION: (145)..(145)
<223> OTHER INFORMATION: Xaa can be Val or Thr
<220> FEATURE:
<221> NAME/KEY: misc_feature
<222> LOCATION: (157)..(157)
<223> OTHER INFORMATION: Xaa can be Glu Lys
<220> FEATURE:
<221> NAME/KEY: misc_feature
<222> LOCATION: (162)..(162)
<223> OTHER INFORMATION: Xaa can be Arg or Lys
<220> FEATURE:
<221> NAME/KEY: misc_feature
<222> LOCATION: (182)..(182)
<223> OTHER INFORMATION: Xaa can be Val or Ala
<220> FEATURE:
<221> NAME/KEY: misc_feature
<222> LOCATION: (203)..(203)
<223> OTHER INFORMATION: Xaa can be Asp or Asn
<220> FEATURE:
<221> NAME/KEY: misc_feature
<222> LOCATION: (205)..(205)
<223> OTHER INFORMATION: Xaa can be Arg or Lys
<220> FEATURE:
<221> NAME/KEY: misc_feature
<222> LOCATION: (210)..(210)
<223> OTHER INFORMATION: Xaa can be Thr or Lys
<220> FEATURE:

```
<221> NAME/KEY: misc_feature
<222> LOCATION: (225)..(225)
<223> OTHER INFORMATION: Xaa can be Arg or Lys
<220> FEATURE:
<221> NAME/KEY: misc_feature
<222> LOCATION: (268)..(268)
<223> OTHER INFORMATION: Xaa can be Trp or Arg
<220> FEATURE:
<221> NAME/KEY: misc_feature
<222> LOCATION: (283)..(283)
<223> OTHER INFORMATION: Xaa can be Thr or Asn
<220> FEATURE:
<221> NAME/KEY: misc_feature
<222> LOCATION: (290)..(290)
<223> OTHER INFORMATION: Xaa can be Glu or Gly
<220> FEATURE:
<221> NAME/KEY: misc_feature
<222> LOCATION: (432)..(432)
<223> OTHER INFORMATION: Xaa can be Ile or Leu
<220> FEATURE:
<221> NAME/KEY: misc_feature
<222> LOCATION: (489)..(489)
<223> OTHER INFORMATION: Xaa can be Asn or Asp

<400> SEQUENCE: 74

Met Lys Xaa Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Xaa Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Xaa Glu Ser Trp Ser Tyr Ile
                85                  90                  95

Val Glu Xaa Pro Asn Pro Glu Asn Gly Thr Cys Tyr Pro Gly Xaa Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Xaa Thr Gly Val Ser Ala Ser Cys Ser His Asn Gly Xaa Ser Ser Phe
145                 150                 155                 160

Tyr Xaa Asn Leu Leu Trp Leu Thr Gly Lys Asn Gly Leu Tyr Pro Asn
                165                 170                 175

Leu Ser Lys Ser Tyr Xaa Asn Asn Lys Glu Lys Glu Val Leu Val Leu
            180                 185                 190

Trp Gly Val His His Pro Pro Asn Ile Gly Xaa Gln Xaa Ala Leu Tyr
        195                 200                 205

His Xaa Glu Asn Ala Tyr Val Ser Val Val Ser Ser His Tyr Ser Arg
    210                 215                 220

Xaa Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Xaa Tyr Ala Phe Ala
            260                 265                 270

Leu Ser Arg Gly Phe Gly Ser Gly Ile Ile Xaa Ser Asn Ala Pro Met
        275                 280                 285
```

```
Asp Xaa Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Xaa
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Xaa Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 75
<211> LENGTH: 565
<212> TYPE: PRT
<213> ORGANISM: Influenza virus

<400> SEQUENCE: 75

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
```

```
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Pro Asn Ile Gly Asn Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510
```

Arg Glu Lys Ile Asp Gly Val Lys Leu Glu Ser Met Gly Val Tyr Gln
515 520 525

Ile Leu Ala Ile Tyr Ser Thr Val Ala Ser Ser Leu Val Leu Leu Val
530 535 540

Ser Leu Gly Ala Ile Ser Phe Trp Met Cys Ser Asn Gly Ser Leu Gln
545 550 555 560

Cys Arg Ile Cys Ile
565

<210> SEQ ID NO 76
<211> LENGTH: 252
<212> TYPE: PRT
<213> ORGANISM: Influenza virus

<400> SEQUENCE: 76

Met Ser Leu Leu Thr Glu Val Glu Thr Tyr Val Leu Ser Ile Ile Pro
1 5 10 15

Ser Gly Pro Leu Lys Ala Glu Ile Ala Gln Arg Leu Glu Asp Val Phe
20 25 30

Ala Gly Lys Asn Thr Asp Leu Glu Val Leu Met Glu Trp Leu Lys Thr
35 40 45

Arg Pro Ile Leu Ser Pro Leu Thr Lys Gly Ile Leu Gly Phe Val Phe
50 55 60

Thr Leu Thr Val Pro Ser Glu Arg Gly Leu Gln Arg Arg Arg Phe Val
65 70 75 80

Gln Asn Ala Leu Asn Gly Asn Gly Asp Pro Asn Asn Met Asp Lys Ala
85 90 95

Val Lys Leu Tyr Arg Lys Leu Lys Arg Glu Ile Thr Phe His Gly Ala
100 105 110

Lys Glu Ile Ser Leu Ser Tyr Ser Ala Gly Ala Leu Ala Ser Cys Met
115 120 125

Gly Leu Ile Tyr Asn Arg Met Gly Ala Val Thr Thr Glu Val Ala Phe
130 135 140

Gly Leu Val Cys Ala Thr Cys Glu Gln Ile Ala Asp Ser Gln His Arg
145 150 155 160

Ser His Arg Gln Met Val Thr Thr Thr Asn Pro Leu Ile Arg His Glu
165 170 175

Asn Arg Met Val Leu Ala Ser Thr Thr Ala Lys Ala Met Glu Gln Met
180 185 190

Ala Gly Ser Ser Glu Gln Ala Ala Glu Ala Met Glu Val Ala Ser Gln
195 200 205

Ala Arg Gln Met Val Gln Ala Met Arg Thr Ile Gly Thr His Pro Ser
210 215 220

Ser Ser Ala Gly Leu Lys Asn Asp Leu Leu Glu Asn Leu Gln Ala Tyr
225 230 235 240

Gln Lys Arg Met Gly Val Gln Met Gln Arg Phe Lys
245 250

<210> SEQ ID NO 77
<211> LENGTH: 24
<212> TYPE: DNA
<213> ORGANISM: Artificial sequence
<220> FEATURE:
<223> OTHER INFORMATION: pBinPlus.2613c

<400> SEQUENCE: 77
aggaagggaa gaaagcgaaa ggag 24

<210> SEQ ID NO 78
<211> LENGTH: 56
<212> TYPE: DNA
<213> ORGANISM: Artificial sequence
<220> FEATURE:
<223> OTHER INFORMATION: Mut-ATG115.r

<400> SEQUENCE: 78
gtgccgaagc acgatctgac aacgttgaag atcgctcacg caagaaagac aagaga 56

<210> SEQ ID NO 79
<211> LENGTH: 52
<212> TYPE: DNA
<213> ORGANISM: Artificial sequence
<220> FEATURE:
<223> OTHER INFORMATION: Mut-ATG161.c

<400> SEQUENCE: 79
gttgtcagat cgtgcttcgg caccagtaca acgttttctt tcactgaagc ga 52

<210> SEQ ID NO 80
<211> LENGTH: 25
<212> TYPE: DNA
<213> ORGANISM: Artificial sequence
<220> FEATURE:
<223> OTHER INFORMATION: LC-C5-1.110r

<400> SEQUENCE: 80
tctcctggag tcacagacag ggtgg 25

<210> SEQ ID NO 81
<211> LENGTH: 2065
<212> TYPE: DNA
<213> ORGANISM: Artificial sequence
<220> FEATURE:
<223> OTHER INFORMATION: Expression cassette number 828

<400> SEQUENCE: 81
ttaattaaga attcgagctc caccgcggaa acctcctcgg attccattgc ccagctatct 60
gtcactttat tgagaagata gtggaaaagg aaggtggctc ctacaaatgc catcattgcg 120
ataaaggaaa ggccatcgtt gaagatgcct ctgccgacag tggtcccaaa gatggacccc 180
cacccacgag gagcatcgtg gaaaaagaag acgttccaac cacgtcttca aagcaagtgg 240
attgatgtga tatctccact gacgtaaggg atgacgcaca atcccactat ccttcgcaag 300
acccttcctc tatataagga agttcatttc atttggagag gtattaaaat cttaataggt 360
tttgataaaa gcgaacgtgg ggaaacccga accaaacctt cttctaaact ctctctcatc 420
tctcttaaag caaacttctc tcttgtcttt cttgcgtgag cgatcttcaa cgttgtcaga 480
tcgtgcttcg gcaccagtac aacgttttct ttcactgaag cgaaatcaaa gatctctttg 540
tggacacgta gtgcggcgcc attaaataac gtgtacttgt cctattcttg tcggtgtggt 600
cttgggaaaa gaaagcttgc tggaggctgc tgttcagccc catacattac ttgttacgat 660
tctgctgact ttcggcgggt gcaatatctc tacttctgct tgacgaggta ttgttgcctg 720
tacttctttc ttcttcttct tgctgattgg ttctataaga aatctagtat tttctttgaa 780
acagagtttt cccgtggttt tcgaacttgg agaaagattg ttaagcttct gtatattctg 840
cccaaatttg tcgggcccat ggttttcaca cctcagatac ttggacttat gctttttttgg 900 atttcagcct ccagaggtga tattgtgcta actcagtctc cagccaccct gtctgtgact 960
ccaggagata gtgtcagtct ttcctgcagg gccagccaaa gtattagcaa caacctacac 1020
tggtttcaac aaaaatcgca tgagtctcca aggcttctca tcaagtatgc ttcccagtcc 1080
atatctggga tcccctccag gttcagtggc agtggatctg ggacagattt cactctcagt 1140
atcaacagtg tgaagactga agattttgga atgtttttct gtcaacagag taacagctgg 1200
cctctcacgt tcggtgatgg gacaaagctg gagctgaaac gggctgatgc tgcaccaact 1260
gtatccatct tcccaccatc cagtgagcag ttaacatctg gaggtgcctc agtcgtgtgc 1320
ttcttgaaca acttctaccc caaagacatc aatgtcaagt ggaagattga tggcagtgaa 1380
cgacaaaatg gcgtcctgaa cagttggact gatcaggaca gcaaagacag cacctacagc 1440
atgagcagca ccctcacgtt gaccaaggac gagtatgaac gacataacag ctatacctgt 1500
gaggccactc acaagacatc aacttcaccc attgtcaaga gcttcaacag gaatgagtgt 1560
tagaggccta ttttctttag tttgaattta ctgttattcg gtgtgcattt ctatgtttgg 1620
tgagcggttt tctgtgctca gagtgtgttt attttatgta atttaatttc tttgtgagct 1680
cctgtttagc aggtcgtccc ttcagcaagg acacaaaaag attttaattt tattaaaaaa 1740
aaaaaaaaaa aagaccggga attcgatatc aagcttatcg acctgcagat cgttcaaaca 1800
tttggcaata aagtttctta agattgaatc ctgttgccgg tcttgcgatg attatcatat 1860
aatttctgtt gaattacgtt aagcatgtaa taattaacat gtaatgcatg acgttattta 1920
tgagatgggt ttttatgatt agagtcccgc aattatacat ttaatacgcg atagaaaaca 1980
aaatatagcg cgcaaactag gataaattat cgcgcgcggt gtcatctatg ttactagatt 2040
ctagagtctc aagcttcggc gcgcc 2065

<210> SEQ ID NO 82
<211> LENGTH: 48
<212> TYPE: DNA
<213> ORGANISM: Artificial sequence
<220> FEATURE:
<223> OTHER INFORMATION: SpPDI-HA(Ind).c

<400> SEQUENCE: 82
gttccttctc agatcttcgc tgatcagatt tgcattggtt accatgca 48

<210> SEQ ID NO 83
<211> LENGTH: 3218
<212> TYPE: DNA
<213> ORGANISM: Artificial sequence
<220> FEATURE:
<223> OTHER INFORMATION: Construct number 663, from HindIII

<400> SEQUENCE: 83
aagcttgcta gcggcctcaa tggccctgca ggtcgactct agaggtaccc cgggctggta 60
tatttatatg ttgtcaaata actcaaaaac cataaaagtt taagttagca agtgtgtaca 120
tttttacttg aacaaaaata ttcacctact actgttataa atcattatta aacattagag 180
taaagaaata tggatgataa gaacaagagt agtgatattt tgacaacaat tttgttgcaa 240
catttgagaa aattttgttg ttctctcttt tcattggtca aaaacaatag agagagaaaa 300
aggaagaggg agaataaaaa cataatgtga gtatgagaga gaaagttgta caaaagttgt 360
accaaaatag ttgtacaaat atcattgagg aatttgacaa aagctacaca aataagggtt 420
aattgctgta aataaataag gatgacgcat tagagagatg taccattaga gaatttttgg 480
caagtcatta aaaagaaaga ataaattatt tttaaaatta aaagttgagt catttgatta 540

-continued

```
aacatgtgat tatttaatga attgatgaaa gagttggatt aaagttgtat tagtaattag    600
aatttggtgt caaatttaat ttgacatttg atcttttcct atatattgcc ccatagagtc    660
agttaactca tttttatatt tcatagatca aataagagaa ataacggtat attaatccct    720
ccaaaaaaaa aaaacggtat atttactaaa aaatctaagc cacgtaggag gataacagga    780
tccccgtagg aggataacat ccaatccaac caatcacaac aatcctgatg agataaccca    840
ctttaagccc acgcatctgt ggcacatcta cattatctaa atcacacatt cttccacaca    900
tctgagccac acaaaaacca atccacatct ttatcaccca ttctataaaa aatcacactt    960
tgtgagtcta cactttgatt cccttcaaac acatacaaag agaagagact aattaattaa   1020
ttaatcatct tgagagaaaa tggcgaaaaa cgttgcgatt ttcggcttat tgttttctct   1080
tcttgtgttg gttccttctc agatcttcgc tgatcagatt tgcattggtt accatgcaaa   1140
caattcaaca gagcaggttg acacaatcat ggaaaagaac gttactgtta cacatgccca   1200
agacatactg gaaaagacac acaacgggaa gctctgcgat ctagatggag tgaagcctct   1260
aattttaaga gattgtagtg tagctggatg gctcctcggg aacccaatgt gtgacgaatt   1320
catcaatgta ccggaatggt cttacatagt ggagaaggcc aatccaacca atgacctctg   1380
ttacccaggg agtttcaacg actatgaaga actgaaacac ctattgagca gaataaacca   1440
ttttgagaaa attcaaatca tccccaaaag ttcttggtcc gatcatgaag cctcatcagg   1500
agttagctca gcatgtccat acctgggaag tccctccttt tttagaaatg tggtatggct   1560
tatcaaaaag aacagtacat acccaacaat aaagaaaagc tacaataata ccaaccaaga   1620
ggatcttttg gtactgtggg gaattcacca tcctaatgat gcggcagagc agacaaggct   1680
atatcaaaac ccaaccacct atatttccat tgggacatca acactaaacc agagattggt   1740
accaaaaata gctactagat ccaaagtaaa cgggcaaagt ggaaggatgg agttcttctg   1800
gacaatttta aaacctaatg atgcaatcaa cttcgagagt aatggaaatt tcattgctcc   1860
agaatatgca tacaaaattg tcaagaaagg ggactcagca attatgaaaa gtgaattgga   1920
atatggtaac tgcaacacca agtgtcaaac tccaatgggg gcgataaact ctagtatgcc   1980
attccacaac atacaccctc tcaccatcgg ggaatgcccc aaatatgtga aatcaaacag   2040
attagtcctt gcaacagggc tcagaaatag ccctcaaaga gagagcagaa gaaaaaagag   2100
aggactattt ggagctatag caggttttat agagggagga tggcagggaa tggtagatgg   2160
ttggtatggg taccaccata gcaatgagca ggggagtggg tacgctgcag acaaagaatc   2220
cactcaaaag gcaatagatg gagtcaccaa taaggtcaac tcaatcattg acaaaatgaa   2280
cactcagttt gaggccgttg gaagggaatt taataactta gaaaggagaa tagagaattt   2340
aaacaagaag atggaagacg ggtttctaga tgtctggact tataatgccg aacttctggt   2400
tctcatggaa aatgagagaa ctctagactt tcatgactca aatgttaaga acctctacga   2460
caaggtccga ctacagctta gggataatgc aaaggagctg ggtaacggtt gtttcgagtt   2520
ctatcacaaa tgtgataatg aatgtatgga aagtataaga aacggaacgt acaactatcc   2580
gcagtattca gaagaagcaa gattaaaaag agaggaaata agtggggtaa aattggaatc   2640
aataggaact taccaaatac tgtcaattta ttcaacagtg gcgagttccc tagcactggc   2700
aatcatgatg gctggtctat ctttatggat gtgctccaat ggatcgttac aatgcagaat   2760
ttgcatttaa gagctctaag ttaaaatgct tcttcgtctc ctatttataa tatggtttgt   2820
tattgttaat tttgttcttg tagaagagct taattaatcg ttgttgttat gaaatactat   2880
ttgtatgaga tgaactggtg taatgtaatt catttacata agtggagtca gaatcagaat   2940
```

gtttcctcca taactaacta gacatgaaga cctgccgcgt acaattgtct tatatttgaa 3000
caactaaaat tgaacatctt ttgccacaac tttataagtg gttaatatag ctcaaatata 3060
tggtcaagtt caatagatta ataatggaaa tatcagttat cgaaattcat taacaatcaa 3120
cttaacgtta ttaactacta attttatatc atcccctttg ataaatgata gtacaccaat 3180
taggaaggag catgctcgag gcctggctgg ccgaattc 3218

<210> SEQ ID NO 84
<211> LENGTH: 49
<212> TYPE: DNA
<213> ORGANISM: Artificial sequence
<220> FEATURE:
<223> OTHER INFORMATION: SpPDI-H1B.c

<400> SEQUENCE: 84
ttctcagatc ttcgctgaca caatatgtat aggctaccat gctaacaac 49

<210> SEQ ID NO 85
<211> LENGTH: 47
<212> TYPE: DNA
<213> ORGANISM: Artificial sequence
<220> FEATURE:
<223> OTHER INFORMATION: SacI-H1B.r

<400> SEQUENCE: 85
cttagagctc ttagatgcat attctacact gtaaagaccc attggaa 47

<210> SEQ ID NO 86
<211> LENGTH: 3206
<212> TYPE: DNA
<213> ORGANISM: Artificial sequence
<220> FEATURE:
<223> OTHER INFORMATION: Construct number 787, from HindIII

<400> SEQUENCE: 86
aagcttgcta gcggcctcaa tggccctgca ggtcgactct agaggtaccc cgggctggta 60
tatttatatg ttgtcaaata actcaaaaac cataaaagtt taagttagca agtgtgtaca 120
tttttacttg aacaaaaata ttcacctact actgttataa atcattatta aacattagag 180
taaagaaata tggatgataa gaacaagagt agtgatattt tgacaacaat tttgttgcaa 240
catttgagaa aattttgttg ttctctcttt tcattggtca aaaacaatag agagagaaaa 300
aggaagaggg agaataaaaa cataatgtga gtatgagaga gaaagttgta caaaagttgt 360
accaaaatag ttgtacaaat atcattgagg aatttgacaa aagctacaca aataagggtt 420
aattgctgta aataaataag gatgacgcat tagagagatg taccattaga gaatttttgg 480
caagtcatta aaaagaaaga ataaattatt tttaaaatta aaagttgagt catttgatta 540
aacatgtgat tatttaatga attgatgaaa gagttggatt aaagttgtat tagtaattag 600
aatttggtgt caaatttaat ttgacatttg atcttttcct atatattgcc ccatagagtc 660
agttaactca tttttatatt tcatagatca aataagagaa ataacggtat attaatccct 720
ccaaaaaaaa aaaacggtat atttactaaa aaatctaagc cacgtaggag gataacagga 780
tccccgtagg aggataacat ccaatccaac caatcacaac aatcctgatg agataaccca 840
ctttaagccc acgcatctgt ggcacatcta cattatctaa atcacacatt cttccacaca 900
tctgagccac acaaaaacca atccacatct ttatcaccca ttctataaaa aatcacactt 960
tgtgagtcta cactttgatt cccttcaaac acatacaaag agaagagact aattaattaa 1020

```
ttaatcatct tgagagaaaa tggcgaaaaa cgttgcgatt ttcggcttat tgttttctct   1080
tcttgtgttg gttccttctc agatcttcgc tgacacaata tgtataggct accatgctaa   1140
caactcgacc gacactgttg acacagtact tgaaaagaat gtgacagtga cacactctgt   1200
caacctgctt gagaacagtc acaatggaaa actatgtcta ttaaaaggaa tagccccact   1260
acaattgggt aattgcagcg ttgccgggtg gatcttagga aacccagaat gcgaattact   1320
gatttccaag gagtcatggt cctacattgt agaaaaacca aatcctgaga atggaacatg   1380
ttacccaggg catttcgctg actatgagga actgagggag caattgagtt cagtatcttc   1440
atttgagagg ttcgaaatat tccccaaaga aagctcatgg cccaaccaca ccgtaaccgg   1500
agtgtcagca tcatgctccc ataatgggga aagcagtttt tacagaaatt tgctatggct   1560
gacggggaag aatggtttgt acccaaacct gagcaagtcc tatgcaaaca acaaagaaaa   1620
agaagtcctt gtactatggg gtgttcatca cccgccaaac ataggtgacc aaaaggccct   1680
ctatcataca gaaaatgctt atgtctctgt agtgtcttca cattatagca gaaaattcac   1740
cccagaaata gccaaaagac ccaaagtaag agatcaagaa ggaagaatca attactactg   1800
gactctgctt gaacccgggg atacaataat atttgaggca aatggaaatc taatagcgcc   1860
aagatatgct ttcgcactga gtagaggctt tggatcagga atcatcaact caaatgcacc   1920
aatggataaa tgtgatgcga agtgccaaac acctcaggga gctataaaca gcagtcttcc   1980
tttccagaac gtacacccag tcacaatagg agagtgtcca aagtatgtca ggagtgcaaa   2040
attaaggatg gttacaggac taaggaacat cccatccatt caatccagag gtttgtttgg   2100
agccattgcc ggtttcattg aaggggggtg gactggaatg gtagatggtt ggtatggtta   2160
tcatcatcag aatgagcaag gatctggcta tgctgcagat caaaaaagca cacaaaatgc   2220
cattaatggg attacaaaca aggtcaattc tgtaattgag aaaatgaaca ctcaattcac   2280
agcagtgggc aaagagttca acaaattgga aagaaggatg gaaaacttga ataaaaaagt   2340
tgatgatggg tttatagaca tttggacata taatgcagaa ctgttggttc tactggaaaa   2400
tgaaaggact ttggatttcc atgactccaa tgtgaagaat ctgtatgaga aagtaaaaag   2460
ccagttaaag aataatgcta aagaaatagg aaatgggtgt tttgagttct atcacaagtg   2520
taacgatgaa tgcatggaga gtgtaaagaa tggaacttat gactatccaa aatattccga   2580
agaatcaaag ttaaacaggg agaaaattga tggagtgaaa ttggaatcaa tgggagtcta   2640
tcagattctg gcgatctact caacagtcgc cagttctctg gttcttttgg tctccctggg   2700
ggcaatcagc ttctggatgt gttccaatgg gtctttacag tgtagaatat gcatctaaga   2760
gctctaagtt aaaatgcttc ttcgtctcct atttataata tggtttgtta ttgttaattt   2820
tgttcttgta gaagagctta attaatcgtt gttgttatga aatactattt gtatgagatg   2880
aactggtgta atgtaattca tttacataag tggagtcaga atcagaatgt ttcctccata   2940
actaactaga catgaagacc tgccgcgtac aattgtctta tatttgaaca actaaaattg   3000
aacatctttt gccacaactt tataagtggt taatatagct caaatatatg gtcaagttca   3060
atagattaat aatggaaata tcagttatcg aaattcatta acaatcaact taacgttatt   3120
aactactaat tttatatcat cccctttgat aaatgatagt acaccaatta ggaaggagca   3180
tgctcgaggc ctggctggcc gaattc                                        3206
```

<210> SEQ ID NO 87
<211> LENGTH: 45
<212> TYPE: DNA
<213> ORGANISM: Artificial sequence
<220> FEATURE:
<223> OTHER INFORMATION: H3B-SpPDI.r

<400> SEQUENCE: 87
tgtcatttcc gggaagtttt tgagcgaaga tctgagaagg aacca 45

<210> SEQ ID NO 88
<211> LENGTH: 45
<212> TYPE: DNA
<213> ORGANISM: Artificial sequence
<220> FEATURE:
<223> OTHER INFORMATION: SpPDI-H3B.c

<400> SEQUENCE: 88
tctcagatct tcgctcaaaa acttcccgga aatgacaaca gcacg 45

<210> SEQ ID NO 89
<211> LENGTH: 23
<212> TYPE: DNA
<213> ORGANISM: Artificial sequence
<220> FEATURE:
<223> OTHER INFORMATION: H3(A-Bri).982r

<400> SEQUENCE: 89
ttgcttaaca tatctgggac agg 23

<210> SEQ ID NO 90
<211> LENGTH: 3212
<212> TYPE: DNA
<213> ORGANISM: Artificial sequence
<220> FEATURE:
<223> OTHER INFORMATION: Construct number 790, from HindIII

<400> SEQUENCE: 90
aagcttgcta gcggcctcaa tggccctgca ggtcgactct agaggtaccc cgggctggta 60
tatttatatg ttgtcaaata actcaaaaac cataaaagtt taagttagca agtgtgtaca 120
tttttacttg aacaaaaata ttcacctact actgttataa atcattatta aacattagag 180
taaagaaata tggatgataa gaacaagagt agtgatattt tgacaacaat tttgttgcaa 240
catttgagaa aattttgttg ttctctcttt tcattggtca aaaacaatag agagagaaaa 300
aggaagaggg agaataaaaa cataatgtga gtatgagaga gaaagttgta caaaagttgt 360
accaaaatag ttgtacaaat atcattgagg aatttgacaa aagctacaca aataagggtt 420
aattgctgta aataaataag gatgacgcat tagagagatg taccattaga gaatttttgg 480
caagtcatta aaaagaaaga ataaattatt tttaaaatta aaagttgagt catttgatta 540
aacatgtgat tatttaatga attgatgaaa gagttggatt aaagttgtat tagtaattag 600
aatttggtgt caaatttaat ttgacatttg atcttttcct atatattgcc ccatagagtc 660
agttaactca tttttatatt tcatagatca aataagagaa ataacggtat attaatccct 720
ccaaaaaaaa aaaacggtat atttactaaa aaatctaagc cacgtaggag gataacagga 780
tccccgtagg aggataacat ccaatccaac caatcacaac aatcctgatg agataaccca 840
ctttaagccc acgcatctgt ggcacatcta cattatctaa atcacacatt cttccacaca 900
tctgagccac acaaaaacca atccacatct ttatcaccca ttctataaaa aatcacactt 960
tgtgagtcta cactttgatt cccttcaaac acatacaaag agaagagact aattaattaa 1020
ttaatcatct tgagagaaaa tggcgaaaaa cgttgcgatt ttcggcttat tgttttctct 1080
tcttgtgttg gttccttctc agatcttcgc tcaaaaactt cccggaaatg acaacagcac 1140

-continued

```
ggcaacgctg tgccttgggc accatgcagt accaaacgga acgatagtga aaacaatcac   1200

gaatgaccaa attgaagtta ctaatgctac tgagctggtt cagagttcct caacaggtga   1260

aatatgcgac agtcctcatc agatccttga tggagaaaac tgcacactaa tagatgctct   1320

attgggagac cctcagtgtg atggcttcca aaataagaaa tgggaccttt ttgttgaacg   1380

cagcaaagcc tacagcaact gttaccctta tgatgtgccg gattatgcct cccttaggtc   1440

actagttgcc tcatccggca cactggagtt taacaatgaa agtttcaatt ggactggagt   1500

cactcaaaac ggaacaagct ctgcttgcat aaggagatct aataacagtt tctttagtag   1560

attgaattgg ttgacccact taaaattcaa atacccagca ttgaacgtga ctatgccaaa   1620

caatgaaaaa tttgacaaat tgtacatttg gggggttcac cacccgggta cggacaatga   1680

ccaaatcttc ctgtatgctc aagcatcagg aagaatcaca gtctctacca aaagaagcca   1740

acaaactgta atcccgaata tcggatctag acccagagta aggaatatcc ccagcagaat   1800

aagcatctat tggacaatag taaaaccggg agacatactt ttgattaaca gcacagggaa   1860

tctaattgct cctaggggtt acttcaaaat acgaagtggg aaaagctcaa taatgagatc   1920

agatgcaccc attggcaaat gcaattctga atgcatcact ccaaacggaa gcattcccaa   1980

tgacaaacca ttccaaaatg taaacaggat cacatacggg gcctgtccca gatatgttaa   2040

gcaaaacact ctgaaattgg caacagggat gcgaaatgta ccagagaaac aaactagagg   2100

catatttggc gcaatcgcgg gtttcataga aaatggttgg gagggaatgg tggatggttg   2160

gtatggtttc aggcatcaaa attctgaggg aataggacaa gcagcagatc tcaaaagcac   2220

tcaagcagca atcgatcaaa tcaatgggaa gctgaatagg ttgatcggga aaaccaacga   2280

gaaattccat cagattgaaa aagagttctc agaagtcgaa gggagaatcc aggaccttga   2340

gaaatatgtt gaggacacca aaatagatct ctggtcatac aacgcggagc ttcttgttgc   2400

cctggagaac caacatacaa ttgatctaac tgactcagaa atgaacaaac tgtttgaaaa   2460

aacaaagaag caactgaggg aaaatgctga ggatatgggc aatggttgtt tcaaaatata   2520

ccacaaatgt gacaatgcct gcataggatc aatcagaaat ggaacttatg accacgatgt   2580

atacagagat gaagcattaa acaaccggtt ccagatcaag ggcgttgagc tgaagtcagg   2640

atacaaagat tggatactat ggatttcctt tgccatatca tgtttttttgc tttgtgttgc   2700

tttgttgggg ttcatcatgt gggcctgcca aaaaggcaac attaggtgca acatttgcat   2760

ttgagagctc taagttaaaa tgcttcttcg tctcctattt ataatatggt ttgttattgt   2820

taattttgtt cttgtagaag agcttaatta atcgttgttg ttatgaaata ctatttgtat   2880

gagatgaact ggtgtaatgt aattcattta cataagtgga gtcagaatca gaatgtttcc   2940

tccataacta actagacatg aagacctgcc gcgtacaatt gtcttatatt tgaacaacta   3000

aaattgaaca tcttttgcca caactttata agtggttaat atagctcaaa tatatggtca   3060

agttcaatag attaataatg gaaatatcag ttatcgaaat tcattaacaa tcaacttaac   3120

gttattaact actaatttta tatcatcccc tttgataaat gatagtacac caattaggaa   3180

ggagcatgct cgaggcctgg ctggccgaat tc                                3212
```

<210> SEQ ID NO 91
<211> LENGTH: 50
<212> TYPE: DNA
<213> ORGANISM: Artificial sequence
<220> FEATURE:
<223> OTHER INFORMATION: HBF-SpPDI.r

<400> SEQUENCE: 91
gttattccag tgcagattcg atcagcgaag atctgagaag gaaccaacac 50

<210> SEQ ID NO 92
<211> LENGTH: 50
<212> TYPE: DNA
<213> ORGANISM: Artificial sequence
<220> FEATURE:
<223> OTHER INFORMATION: SpPDI-HBF.c

<400> SEQUENCE: 92
cagatcttcg ctgatcgaat ctgcactgga ataacatctt caaactcacc 50

<210> SEQ ID NO 93
<211> LENGTH: 28
<212> TYPE: DNA
<213> ORGANISM: Artificial sequence
<220> FEATURE:
<223> OTHER INFORMATION: Plaster80r

<400> SEQUENCE: 93
caaatagtat ttcataacaa caacgatt 28

<210> SEQ ID NO 94
<211> LENGTH: 3269
<212> TYPE: DNA
<213> ORGANISM: Artificial sequence
<220> FEATURE:
<223> OTHER INFORMATION: Construct number 798, from HindIII

<400> SEQUENCE: 94
aagcttgcta gcggcctcaa tggccctgca ggtcgactct agaggtaccc cgggctggta 60
tatttatatg ttgtcaaata actcaaaaac cataaaagtt taagttagca agtgtgtaca 120
tttttacttg aacaaaaata ttcacctact actgttataa atcattatta aacattagag 180
taaagaaata tggatgataa gaacaagagt agtgatattt tgacaacaat tttgttgcaa 240
catttgagaa aattttgttg ttctctcttt tcattggtca aaaacaatag agagagaaaa 300
aggaagaggg agaataaaaa cataatgtga gtatgagaga gaaagttgta caaaagttgt 360
accaaaatag ttgtacaaat atcattgagg aatttgacaa aagctacaca aataagggtt 420
aattgctgta aataaataag gatgacgcat tagagagatg taccattaga gaatttttgg 480
caagtcatta aaaagaaaga ataaattatt tttaaaatta aaagttgagt catttgatta 540
aacatgtgat tatttaatga attgatgaaa gagttggatt aaagttgtat tagtaattag 600
aatttggtgt caaatttaat ttgacatttg atcttttcct atatattgcc ccatagagtc 660
agttaactca tttttatatt tcatagatca aataagagaa ataacggtat attaatccct 720
ccaaaaaaaa aaaacggtat atttactaaa aaatctaagc cacgtaggag gataacagga 780
tccccgtagg aggataacat ccaatccaac caatcacaac aatcctgatg agataaccca 840
ctttaagccc acgcatctgt ggcacatcta cattatctaa atcacacatt cttccacaca 900
tctgagccac acaaaaacca atccacatct ttatcaccca ttctataaaa aatcacactt 960
tgtgagtcta cactttgatt cccttcaaac acatacaaag agaagagact aattaattaa 1020
ttaatcatct tgagagaaaa tggcgaaaaa cgttgcgatt ttcggcttat tgttttctct 1080
tcttgtgttg gttccttctc agatcttcgc tgatcgaatc tgcactggaa taacatcttc 1140
aaactcacct catgtggtca aaacagccac tcaaggggag gtcaatgtga ctggtgtgat 1200
accactaaca acaacaccaa caaaatctta ttttgcaaat ctcaaaggaa caaggaccag 1260

-continued agggaaacta tgcccagact gtctcaactg cacagatctg gatgtggctt tgggcagacc 1320
aatgtgtgtg gggaccacac cttcggcgaa ggcttcaata ctccacgaag tcaaacctgt 1380
tacatccggg tgctttccta taatgcacga cagaacaaaa atcaggcaac tacccaatct 1440
tctcagagga tatgaaaata tcaggctatc aacccaaaac gtcatcgatg cggaaaaggc 1500
accaggagga ccctacagac ttggaacctc aggatcttgc cctaacgcta ccagtaagag 1560
cggatttttc gcaacaatgg cttgggctgt cccaaaggac aacaacaaaa atgcaacgaa 1620
cccactaaca gtagaagtac catacatttg tacagaaggg gaagaccaaa tcactgtttg 1680
ggggttccat tcagataaca aaacccaaat gaagaacctc tatggagact caaatcctca 1740
aaagttcacc tcatctgcta atggagtaac cacacactat gtttctcaga ttggcagctt 1800
cccagatcaa acagaagacg gaggactacc acaaagcggc aggattgttg ttgattacat 1860
gatgcaaaaa cctgggaaaa caggaacaat tgtctaccaa agaggtgttt tgttgcctca 1920
aaaggtgtgg tgcgcgagtg gcaggagcaa agtaataaaa gggtccttgc ctttaattgg 1980
tgaagcagat tgccttcatg aaaaatacgg tggattaaac aaaagcaagc cttactacac 2040
aggagaacat gcaaaagcca taggaaattg cccaatatgg gtgaaaacac ctttgaagct 2100
cgccaatgga accaaatata gacctcctgc aaaactatta aaggaaaggg gtttcttcgg 2160
agctattgct ggtttcctag aaggaggatg ggaaggaatg attgcaggct ggcacggata 2220
cacatctcac ggagcacatg gagtggcagt ggcggcggac cttaagagta cgcaagaagc 2280
tataaacaag ataacaaaaa atctcaattc tttgagtgag ctagaagtaa agaatcttca 2340
aagactaagt ggtgccatgg atgaactcca caacgaaata ctcgagctgg atgagaaagt 2400
ggatgatctc agagctgaca ctataagctc gcaaatagaa cttgcagtct tgctttccaa 2460
cgaaggaata ataaacagtg aagatgagca tctattggca cttgagagaa aactaaagaa 2520
aatgctgggt ccctctgctg tagagatagg aaatggatgc ttcgaaacca aacacaagtg 2580
caaccagacc tgcttagaca ggatagctgc tggcaccttt aatgcaggag aattttctct 2640
ccccactttt gattcactga acattactgc tgcatcttta aatgatgatg gattggataa 2700
ccatactata ctgctctatt actcaactgc tgcttctagt ttggctgtaa cattgatgct 2760
agctattttt attgtttata tggtctccag agacaacgtt tcatgctcca tctgtctata 2820
agagctctaa gttaaaatgc ttcttcgtct cctatttata atatggtttg ttattgttaa 2880
ttttgttctt gtagaagagc ttaattaatc gttgttgtta tgaaatacta tttgtatgag 2940
atgaactggt gtaatgtaat tcatttacat aagtggagtc agaatcagaa tgtttcctcc 3000
ataactaact agacatgaag acctgccgcg tacaattgtc ttatatttga acaactaaaa 3060
ttgaacatct tttgccacaa ctttataagt ggttaatata gctcaaatat atggtcaagt 3120
tcaatagatt aataatggaa atatcagtta tcgaaattca ttaacaatca acttaacgtt 3180
attaactact aattttatat catccccttt gataaatgat agtacaccaa ttaggaagga 3240
gcatgctcga ggcctggctg gccgaattc 3269

<210> SEQ ID NO 95
<211> LENGTH: 45
<212> TYPE: DNA
<213> ORGANISM: Artificial sequence
<220> FEATURE:
<223> OTHER INFORMATION: ApaI-SpPDI.c

<400> SEQUENCE: 95
ttgtcgggcc catggcgaaa aacgttgcga ttttcggctt attgt 45

<210> SEQ ID NO 96
<211> LENGTH: 42
<212> TYPE: DNA
<213> ORGANISM: Artificial sequence
<220> FEATURE:
<223> OTHER INFORMATION: StuI-H1(A-NC).r

<400> SEQUENCE: 96
aaaataggcc tttagatgca tattctacac tgcaaagacc ca 42

<210> SEQ ID NO 97
<211> LENGTH: 3079
<212> TYPE: DNA
<213> ORGANISM: Artificial sequence
<220> FEATURE:
<223> OTHER INFORMATION: Construct number 580, from PacI

<400> SEQUENCE: 97
ttaattaaga attcgagctc caccgcggaa acctcctcgg attccattgc ccagctatct 60
gtcactttat tgagaagata gtggaaaagg aaggtggctc ctacaaatgc catcattgcg 120
ataaaggaaa ggccatcgtt gaagatgcct ctgccgacag tggtcccaaa gatggacccc 180
cacccacgag gagcatcgtg gaaaaagaag acgttccaac cacgtcttca aagcaagtgg 240
attgatgtga tatctccact gacgtaaggg atgacgcaca atcccactat ccttcgcaag 300
acccttcctc tatataagga agttcatttc atttggagag gtattaaaat cttaataggt 360
tttgataaaa gcgaacgtgg ggaaacccga accaaacctt cttctaaact ctctctcatc 420
tctcttaaag caaacttctc tcttgtcttt cttgcgtgag cgatcttcaa cgttgtcaga 480
tcgtgcttcg gcaccagtac aacgttttct ttcactgaag cgaaatcaaa gatctctttg 540
tggacacgta gtgcggcgcc attaaataac gtgtacttgt cctattcttg tcggtgtggt 600
cttgggaaaa gaaagcttgc tggaggctgc tgttcagccc catacattac ttgttacgat 660
tctgctgact ttcggcgggt gcaatatctc tacttctgct tgacgaggta ttgttgcctg 720
tacttctttc ttcttcttct tgctgattgg ttctataaga aatctagtat tttctttgaa 780
acagagtttt cccgtggttt tcgaacttgg agaaagattg ttaagcttct gtatattctg 840
cccaaatttg tcgggcccat ggcgaaaaac gttgcgattt tcggcttatt gttttctctt 900
cttgtgttgg ttccttctca gatcttcgct gacacaatat gtataggcta ccatgccaac 960
aactcaaccg acactgttga cacagtactt gagaagaatg tgacagtgac acactctgtc 1020
aacctacttg aggacagtca caatggaaaa ctatgtctac taaaaggaat agccccacta 1080
caattgggta attgcagcgt tgccggatgg atcttaggaa acccagaatg cgaattactg 1140
atttccaagg aatcatggtc ctacattgta gaaacaccaa atcctgagaa tggaacatgt 1200
tacccagggt atttcgccga ctatgaggaa ctgagggagc aattgagttc agtatcttca 1260
tttgagagat tcgaaatatt ccccaaagaa agctcatggc ccaaccacac cgtaaccgga 1320
gtatcagcat catgctccca taatgggaaa agcagttttt acagaaattt gctatggctg 1380
acggggaaga atggtttgta cccaaacctg agcaagtcct atgtaaacaa caaagagaaa 1440
gaagtccttg tactatgggg tgttcatcac ccgcctaaca tagggaacca aagggcactc 1500
tatcatacag aaaatgctta tgtctctgta gtgtcttcac attatagcag aagattcacc 1560
ccagaaatag ccaaaagacc caaagtaaga gatcaggaag gaagaatcaa ctactactgg 1620
actctgctgg aacctgggga tacaataata tttgaggcaa atggaaatct aatagcgcca 1680

```
tggtatgctt ttgcactgag tagaggcttt ggatcaggaa tcatcacctc aaatgcacca   1740

atggatgaat gtgatgcgaa gtgtcaaaca cctcagggag ctataaacag cagtcttcct   1800

ttccagaatg tacacccagt cacaatagga gagtgtccaa agtatgtcag gagtgcaaaa   1860

ttaaggatgg ttacaggact aaggaacatc ccatccattc aatccagagg tttgtttgga   1920

gccattgccg gtttcattga aggggggtgg actggaatgg tagatgggtg gtatggttat   1980

catcatcaga atgagcaagg atctggctat gctgcagatc aaaaaagtac acaaaatgcc   2040

attaacggga ttacaaacaa ggtcaattct gtaattgaga aaatgaacac tcaattcaca   2100

gctgtgggca aagagttcaa caaattggaa agaaggatgg aaaacttaaa taaaaaagtt   2160

gatgatgggt ttctagacat ttggacatat aatgcagaat tgttggttct actggaaaat   2220

gaaaggactt tggatttcca tgactccaat gtgaagaatc tgtatgagaa agtaaaaagc   2280

caattaaaga ataatgccaa agaaatagga aacgggtgtt ttgagttcta tcacaagtgt   2340

aacaatgaat gcatggagag tgtgaaaaat ggtacctatg actatccaaa atattccgaa   2400

gaatcaaagt taaacaggga gaaaattgat ggagtgaaat tggaatcaat gggagtatac   2460

cagattctgg cgatctactc aactgtcgcc agttccctgg ttcttttggt ctccctgggg   2520

gcaatcagct tctggatgtg ttccaatggg tctttgcagt gtagaatatg catctaaagg   2580

cctattttct ttagtttgaa tttactgtta ttcggtgtgc atttctatgt ttggtgagcg   2640

gttttctgtg ctcagagtgt gtttatttta tgtaatttaa tttctttgtg agctcctgtt   2700

tagcaggtcg tcccttcagc aaggacacaa aaagatttta attttattaa aaaaaaaaaa   2760

aaaaaagacc gggaattcga tatcaagctt atcgacctgc agatcgttca aacatttggc   2820

aataaagttt cttaagattg aatcctgttg ccggtcttgc gatgattatc atataatttc   2880

tgttgaatta cgttaagcat gtaataatta acatgtaatg catgacgtta tttatgagat   2940

gggtttttat gattagagtc ccgcaattat acatttaata cgcgatagaa aacaaaatat   3000

agcgcgcaaa ctaggataaa ttatcgcgcg cggtgtcatc tatgttacta gattctagag   3060

tctcaagctt cggcgcgcc                                                3079
```

<210> SEQ ID NO 98
<211> LENGTH: 39
<212> TYPE: DNA
<213> ORGANISM: Artificial sequence
<220> FEATURE:
<223> OTHER INFORMATION: ApaI-H5 (A-Indo).1c

<400> SEQUENCE: 98

```
tgtcgggccc atggagaaaa tagtgcttct tcttgcaat                            39
```

<210> SEQ ID NO 99
<211> LENGTH: 37
<212> TYPE: DNA
<213> ORGANISM: Artificial sequence
<220> FEATURE:
<223> OTHER INFORMATION: H5 (A-Indo)-StuI.1707r

<400> SEQUENCE: 99

```
aaataggcct ttaaatgcaa attctgcatt gtaacga                              37
```

<210> SEQ ID NO 100
<211> LENGTH: 3067
<212> TYPE: DNA
<213> ORGANISM: Artificial sequence
<220> FEATURE:
<223> OTHER INFORMATION: Construct number 685, from PacI

<400> SEQUENCE: 100
ttaattaaga attcgagctc caccgcggaa acctcctcgg attccattgc ccagctatct 60
gtcactttat tgagaagata gtggaaaagg aaggtggctc ctacaaatgc catcattgcg 120
ataaaggaaa ggccatcgtt gaagatgcct ctgccgacag tggtcccaaa gatggacccc 180
cacccacgag gagcatcgtg gaaaaagaag acgttccaac cacgtcttca aagcaagtgg 240
attgatgtga tatctccact gacgtaaggg atgacgcaca atcccactat ccttcgcaag 300
acccttcctc tatataagga agttcatttc atttggagag gtattaaaat cttaataggt 360
tttgataaaa gcgaacgtgg ggaaacccga accaaacctt cttctaaact ctctctcatc 420
tctcttaaag caaacttctc tcttgtcttt cttgcgtgag cgatcttcaa cgttgtcaga 480
tcgtgcttcg gcaccagtac aacgttttct ttcactgaag cgaaatcaaa gatctctttg 540
tggacacgta gtgcggcgcc attaaataac gtgtacttgt cctattcttg tcggtgtggt 600
cttgggaaaa gaaagcttgc tggaggctgc tgttcagccc catacattac ttgttacgat 660
tctgctgact ttcggcgggt gcaatatctc tacttctgct tgacgaggta ttgttgcctg 720
tacttctttc ttcttcttct tgctgattgg ttctataaga aatctagtat tttctttgaa 780
acagagtttt cccgtggttt tcgaacttgg agaaagattg ttaagcttct gtatattctg 840
cccaaatttg tcgggcccat ggagaaaata gtgcttcttc ttgcaatagt cagtcttgtt 900
aaaagtgatc agatttgcat tggttaccat gcaaacaatt caacagagca ggttgacaca 960
atcatggaaa agaacgttac tgttacacat gcccaagaca tactggaaaa gacacacaac 1020
gggaagctct gcgatctaga tggagtgaag cctctaattt taagagattg tagtgtagct 1080
ggatggctcc tcgggaaccc aatgtgtgac gaattcatca atgtaccgga atggtcttac 1140
atagtggaga aggccaatcc aaccaatgac ctctgttacc cagggagttt caacgactat 1200
gaagaactga aacacctatt gagcagaata aaccattttg agaaaattca aatcatcccc 1260
aaaagttctt ggtccgatca tgaagcctca tcaggagtta gctcagcatg tccatacctg 1320
ggaagtccct cctttttag aaatgtggta tggcttatca aaaagaacag tacataccca 1380
acaataaaga aaagctacaa taataccaac caagaggatc ttttggtact gtggggaatt 1440
caccatccta atgatgcggc agagcagaca aggctatatc aaaacccaac cacctatatt 1500
tccattggga catcaacact aaaccagaga ttggtaccaa aaatagctac tagatccaaa 1560
gtaaacgggc aaagtggaag gatggagttc ttctggacaa ttttaaaacc taatgatgca 1620
atcaacttcg agagtaatgg aaatttcatt gctccagaat atgcatacaa aattgtcaag 1680
aaaggggact cagcaattat gaaaagtgaa ttggaatatg gtaactgcaa caccaagtgt 1740
caaactccaa tgggggcgat aaactctagt atgccattcc acaacataca ccctctcacc 1800
atcggggaat gccccaaata tgtgaaatca aacagattag tccttgcaac agggctcaga 1860
aatagccctc aaagagagag cagaagaaaa aagagaggac tatttggagc tatagcaggt 1920
tttatagagg gaggatggca gggaatggta gatggttggt atgggtacca ccatagcaat 1980
gagcagggga gtgggtacgc tgcagacaaa gaatccactc aaaaggcaat agatggagtc 2040
accaataagg tcaactcaat cattgacaaa atgaacactc agtttgaggc cgttggaagg 2100
gaatttaata acttagaaag gagaatagag aatttaaaca agaagatgga agacgggttt 2160
ctagatgtct ggacttataa tgccgaactt ctggttctca tggaaaatga gagaactcta 2220
gactttcatg actcaaatgt taagaacctc tacgacaagg tccgactaca gcttagggat 2280
aatgcaaagg agctgggtaa cggttgtttc gagttctatc acaaatgtga taatgaatgt 2340
atggaaagta taagaaacgg aacgtacaac tatccgcagt attcagaaga agcaagatta 2400
aaaagagagg aaataagtgg ggtaaaattg gaatcaatag gaacttacca aatactgtca 2460
atttattcaa cagtggcgag ttccctagca ctggcaatca tgatggctgg tctatcttta 2520
tggatgtgct ccaatggatc gttacaatgc agaatttgca tttaaaggcc tattttcttt 2580
agtttgaatt tactgttatt cggtgtgcat ttctatgttt ggtgagcggt tttctgtgct 2640
cagagtgtgt ttattttatg taatttaatt tctttgtgag ctcctgttta gcaggtcgtc 2700
ccttcagcaa ggacacaaaa agattttaat tttattaaaa aaaaaaaaaa aaaagaccgg 2760
gaattcgata tcaagcttat cgacctgcag atcgttcaaa catttggcaa taaagtttct 2820
taagattgaa tcctgttgcc ggtcttgcga tgattatcat ataatttctg ttgaattacg 2880
ttaagcatgt aataattaac atgtaatgca tgacgttatt tatgagatgg gtttttatga 2940
ttagagtccc gcaattatac atttaatacg cgatagaaaa caaaatatag cgcgcaaact 3000
aggataaatt atcgcgcgcg gtgtcatcta tgttactaga ttctagagtc tcaagcttcg 3060
gcgcgcc 3067

<210> SEQ ID NO 101
<211> LENGTH: 3091
<212> TYPE: DNA
<213> ORGANISM: Artificial sequence
<220> FEATURE:
<223> OTHER INFORMATION: Construct number 686, from PacI

<400> SEQUENCE: 101
ttaattaaga attcgagctc caccgcggaa acctcctcgg attccattgc ccagctatct 60
gtcactttat tgagaagata gtggaaaagg aaggtggctc ctacaaatgc catcattgcg 120
ataaaggaaa ggccatcgtt gaagatgcct ctgccgacag tggtcccaaa gatggacccc 180
cacccacgag gagcatcgtg gaaaaagaag acgttccaac cacgtcttca aagcaagtgg 240
attgatgtga tatctccact gacgtaaggg atgacgcaca atcccactat ccttcgcaag 300
acccttcctc tatataagga agttcatttc atttggagag gtattaaaat cttaataggt 360
tttgataaaa gcgaacgtgg ggaaacccga accaaacctt cttctaaact ctctctcatc 420
tctcttaaag caaacttctc tcttgtcttt cttgcgtgag cgatcttcaa cgttgtcaga 480
tcgtgcttcg gcaccagtac aacgttttct ttcactgaag cgaaatcaaa gatctctttg 540
tggacacgta gtgcggcgcc attaaataac gtgtacttgt cctattcttg tcggtgtggt 600
cttgggaaaa gaaagcttgc tggaggctgc tgttcagccc catacattac ttgttacgat 660
tctgctgact ttcggcgggt gcaatatctc tacttctgct tgacgaggta ttgttgcctg 720
tacttctttc ttcttcttct tgctgattgg ttctataaga aatctagtat tttctttgaa 780
acagagtttt cccgtggttt tcgaacttgg agaaagattg ttaagcttct gtatattctg 840
cccaaatttg tcgggcccat ggcgaaaaac gttgcgattt tcggcttatt gttttctctt 900
cttgtgttgg ttccttctca gatcttcgct gatcagattt gcattggtta ccatgcaaac 960
aattcaacag agcaggttga cacaatcatg gaaaagaacg ttactgttac acatgcccaa 1020
gacatactgg aaaagacaca caacgggaag ctctgcgatc tagatggagt gaagcctcta 1080
attttaagag attgtagtgt agctggatgg ctcctcggga acccaatgtg tgacgaattc 1140
atcaatgtac cggaatggtc ttacatagtg gagaaggcca atccaaccaa tgacctctgt 1200
tacccaggga gtttcaacga ctatgaagaa ctgaaacacc tattgagcag aataaaccat 1260

```
tttgagaaaa ttcaaatcat ccccaaaagt tcttggtccg atcatgaagc ctcatcagga   1320
gttagctcag catgtccata cctgggaagt ccctcctttt ttagaaatgt ggtatggctt   1380
atcaaaaaga acagtacata cccaacaata aagaaaagct acaataatac caaccaagag   1440
gatcttttgg tactgtgggg aattcaccat cctaatgatg cggcagagca gacaaggcta   1500
tatcaaaacc caaccaccta tatttccatt gggacatcaa cactaaacca gagattggta   1560
ccaaaaatag ctactagatc caaagtaaac gggcaaagtg gaaggatgga gttcttctgg   1620
acaattttaa aacctaatga tgcaatcaac ttcgagagta atggaaattt cattgctcca   1680
gaatatgcat acaaaattgt caagaaaggg gactcagcaa ttatgaaaag tgaattggaa   1740
tatggtaact gcaacaccaa gtgtcaaact ccaatggggg cgataaactc tagtatgcca   1800
ttccacaaca tacaccctct caccatcggg gaatgcccca aatatgtgaa atcaaacaga   1860
ttagtccttg caacagggct cagaaatagc cctcaaagag agagcagaag aaaaaagaga   1920
ggactatttg gagctatagc aggttttata gagggaggat ggcagggaat ggtagatggt   1980
tggtatgggt accaccatag caatgagcag gggagtgggt acgctgcaga caaagaatcc   2040
actcaaaagg caatagatgg agtcaccaat aaggtcaact caatcattga caaaatgaac   2100
actcagtttg aggccgttgg aagggaattt aataacttag aaaggagaat agagaattta   2160
aacaagaaga tggaagacgg gtttctagat gtctggactt ataatgccga acttctggtt   2220
ctcatggaaa atgagagaac tctagacttt catgactcaa atgttaagaa cctctacgac   2280
aaggtccgac tacagcttag ggataatgca aaggagctgg gtaacggttg tttcgagttc   2340
tatcacaaat gtgataatga atgtatggaa agtataagaa acggaacgta caactatccg   2400
cagtattcag aagaagcaag attaaaaaga gaggaaataa gtggggtaaa attggaatca   2460
ataggaactt accaaatact gtcaatttat tcaacagtgg cgagttccct agcactggca   2520
atcatgatgg ctggtctatc tttatggatg tgctccaatg gatcgttaca atgcagaatt   2580
tgcatttaaa ggcctatttt ctttagtttg aatttactgt tattcggtgt gcatttctat   2640
gtttggtgag cggttttctg tgctcagagt gtgtttattt tatgtaattt aatttctttg   2700
tgagctcctg tttagcaggt cgtcccttca gcaaggacac aaaaagattt taattttatt   2760
aaaaaaaaaa aaaaaaaaga ccgggaattc gatatcaagc ttatcgacct gcagatcgtt   2820
caaacatttg gcaataaagt ttcttaagat tgaatcctgt tgccggtctt gcgatgatta   2880
tcatataatt tctgttgaat tacgttaagc atgtaataat taacatgtaa tgcatgacgt   2940
tatttatgag atgggttttt atgattagag tcccgcaatt atacatttaa tacgcgatag   3000
aaaacaaaat atagcgcgca aactaggata aattatcgcg cgcggtgtca tctatgttac   3060
tagattctag agtctcaagc ttcggcgcgc c                                  3091
```

<210> SEQ ID NO 102
<211> LENGTH: 45
<212> TYPE: DNA
<213> ORGANISM: Artificial sequence
<220> FEATURE:
<223> OTHER INFORMATION: ApaI-H1B.c

<400> SEQUENCE: 102

```
tgtcgggccc atgaaagtaa aactactggt cctgttatgc acatt                     45
```

<210> SEQ ID NO 103
<211> LENGTH: 46
<212> TYPE: DNA

<213> ORGANISM: Artificial sequence
<220> FEATURE:
<223> OTHER INFORMATION: StuI-H2B.r

<400> SEQUENCE: 103
aaataggcct ttagatgcat attctacact gtaaagaccc attgga 46

<210> SEQ ID NO 104
<211> LENGTH: 3058
<212> TYPE: DNA
<213> ORGANISM: Artificial sequence
<220> FEATURE:
<223> OTHER INFORMATION: Construct 732, from PacI

<400> SEQUENCE: 104
ttaattaaga attcgagctc caccgcggaa acctcctcgg attccattgc ccagctatct 60
gtcactttat tgagaagata gtggaaaagg aaggtggctc ctacaaatgc catcattgcg 120
ataaaggaaa ggccatcgtt gaagatgcct ctgccgacag tggtcccaaa gatggacccc 180
cacccacgag gagcatcgtg gaaaaagaag acgttccaac cacgtcttca aagcaagtgg 240
attgatgtga tatctccact gacgtaaggg atgacgcaca atcccactat ccttcgcaag 300
acccttcctc tatataagga agttcatttc atttggagag gtattaaaat cttaataggt 360
tttgataaaa gcgaacgtgg ggaaacccga accaaacctt cttctaaact ctctctcatc 420
tctcttaaag caaacttctc tcttgtcttt cttgcgtgag cgatcttcaa cgttgtcaga 480
tcgtgcttcg gcaccagtac aacgttttct ttcactgaag cgaaatcaaa gatctctttg 540
tggacacgta gtgcggcgcc attaaataac gtgtacttgt cctattcttg tcggtgtggt 600
cttgggaaaa gaaagcttgc tggaggctgc tgttcagccc catacattac ttgttacgat 660
tctgctgact ttcggcgggt gcaatatctc tacttctgct tgacgaggta ttgttgcctg 720
tacttctttc ttcttcttct tgctgattgg ttctataaga aatctagtat tttctttgaa 780
acagagtttt cccgtggttt tcgaacttgg agaaagattg ttaagcttct gtatattctg 840
cccaaatttg tcgggcccat gaaagtaaaa ctactggtcc tgttatgcac atttacagct 900
acatatgcag acacaatatg tataggctac catgctaaca actcgaccga cactgttgac 960
acagtacttg aaaagaatgt gacagtgaca cactctgtca acctgcttga gaacagtcac 1020
aatggaaaac tatgtctatt aaaaggaata gccccactac aattgggtaa ttgcagcgtt 1080
gccgggtgga tcttaggaaa cccagaatgc gaattactga tttccaagga gtcatggtcc 1140
tacattgtag aaaaaccaaa tcctgagaat ggaacatgtt acccagggca tttcgctgac 1200
tatgaggaac tgagggagca attgagttca gtatcttcat ttgagaggtt cgaaatattc 1260
cccaaagaaa gctcatggcc caaccacacc gtaaccggag tgtcagcatc atgctcccat 1320
aatggggaaa gcagtttttta cagaaatttg ctatggctga cggggaagaa tggtttgtac 1380
ccaaacctga gcaagtccta tgcaaacaac aaagaaaaag aagtccttgt actatggggt 1440
gttcatcacc cgccaaacat aggtgaccaa aaggccctct atcatacaga aaatgcttat 1500
gtctctgtag tgtcttcaca ttatagcaga aaattcaccc cagaaatagc caaaagaccc 1560
aaagtaagag atcaagaagg aagaatcaat tactactgga ctctgcttga acccggggat 1620
acaataatat ttgaggcaaa tggaaatcta atagcgccaa gatatgcttt cgcactgagt 1680
agaggctttg gatcaggaat catcaactca aatgcaccaa tggataaatg tgatgcgaag 1740
tgccaaacac ctcagggagc tataaacagc agtcttcctt tccagaacgt acacccagtc 1800
acaataggag agtgtccaaa gtatgtcagg agtgcaaaat taaggatggt tacaggacta 1860
aggaacatcc catccattca atccagaggt ttgtttggag ccattgccgg tttcattgaa 1920
ggggggtgga ctggaatggt agatggttgg tatggttatc atcatcagaa tgagcaagga 1980
tctggctatg ctgcagatca aaaaagcaca caaaatgcca ttaatgggat tacaaacaag 2040
gtcaattctg taattgagaa aatgaacact caattcacag cagtgggcaa agagttcaac 2100
aaattggaaa gaaggatgga aaacttgaat aaaaaagttg atgatgggtt tatagacatt 2160
tggacatata atgcagaact gttggttcta ctggaaaatg aaaggacttt ggatttccat 2220
gactccaatg tgaagaatct gtatgagaaa gtaaaaagcc agttaaagaa taatgctaaa 2280
gaaataggaa atgggtgttt tgagttctat cacaagtgta acgatgaatg catggagagt 2340
gtaaagaatg gaacttatga ctatccaaaa tattccgaag aatcaaagtt aaacagggag 2400
aaaattgatg gagtgaaatt ggaatcaatg ggagtctatc agattctggc gatctactca 2460
acagtcgcca gttctctggt tcttttggtc tccctggggg caatcagctt ctggatgtgt 2520
tccaatgggt ctttacagtg tagaatatgc atctaaaggc ctattttctt tagtttgaat 2580
ttactgttat tcggtgtgca tttctatgtt tggtgagcgg ttttctgtgc tcagagtgtg 2640
tttattttat gtaatttaat ttctttgtga gctcctgttt agcaggtcgt cccttcagca 2700
aggacacaaa aagattttaa ttttattaaa aaaaaaaaaa aaaaagaccg ggaattcgat 2760
atcaagctta tcgacctgca gatcgttcaa acatttggca ataaagtttc ttaagattga 2820
atcctgttgc cggtcttgcg atgattatca tataatttct gttgaattac gttaagcatg 2880
taataattaa catgtaatgc atgacgttat ttatgagatg ggtttttatg attagagtcc 2940
cgcaattata catttaatac gcgatagaaa acaaaatata gcgcgcaaac taggataaat 3000
tatcgcgcgc ggtgtcatct atgttactag attctagagt ctcaagcttc ggcgcgcc 3058

<210> SEQ ID NO 105
<211> LENGTH: 3079
<212> TYPE: DNA
<213> ORGANISM: Artificial sequence
<220> FEATURE:
<223> OTHER INFORMATION: Construct number 733, from PacI

<400> SEQUENCE: 105
ttaattaaga attcgagctc caccgcggaa acctcctcgg attccattgc ccagctatct 60
gtcactttat tgagaagata gtggaaaagg aaggtggctc ctacaaatgc catcattgcg 120
ataaaggaaa ggccatcgtt gaagatgcct ctgccgacag tggtcccaaa gatggacccc 180
cacccacgag gagcatcgtg gaaaaagaag acgttccaac cacgtcttca aagcaagtgg 240
attgatgtga tatctccact gacgtaaggg atgacgcaca atcccactat ccttcgcaag 300
acccttcctc tatataagga agttcatttc atttggagag gtattaaaat cttaataggt 360
tttgataaaa gcgaacgtgg ggaaacccga accaaacctt cttctaaact ctctctcatc 420
tctcttaaag caaacttctc tcttgtcttt cttgcgtgag cgatcttcaa cgttgtcaga 480
tcgtgcttcg gcaccagtac aacgttttct ttcactgaag cgaaatcaaa gatctctttg 540
tggacacgta gtgcggcgcc attaaataac gtgtacttgt cctattcttg tcggtgtggt 600
cttgggaaaa gaaagcttgc tggaggctgc tgttcagccc catacattac ttgttacgat 660
tctgctgact ttcggcgggt gcaatatctc tacttctgct tgacgaggta ttgttgcctg 720
tacttctttc ttcttcttct tgctgattgg ttctataaga aatctagtat tttctttgaa 780
acagagtttt cccgtggttt tcgaacttgg agaaagattg ttaagcttct gtatattctg 840

-continued

```
cccaaatttg tcgggcccat ggcgaaaaac gttgcgattt tcggcttatt gttttctctt    900
cttgtgttgg ttccttctca gatcttcgct gacacaatat gtataggcta ccatgctaac    960
aactcgaccg acactgttga cacagtactt gaaaagaatg tgacagtgac acactctgtc   1020
aacctgcttg agaacagtca caatggaaaa ctatgtctat taaaaggaat agccccacta   1080
caattgggta attgcagcgt tgccgggtgg atcttaggaa acccagaatg cgaattactg   1140
atttccaagg agtcatggtc ctacattgta gaaaaaccaa atcctgagaa tggaacatgt   1200
tacccagggc atttcgctga ctatgaggaa ctgagggagc aattgagttc agtatcttca   1260
tttgagaggt tcgaaatatt ccccaaagaa agctcatggc ccaaccacac cgtaaccgga   1320
gtgtcagcat catgctccca taatggggaa agcagttttt acagaaattt gctatggctg   1380
acggggaaga atggtttgta cccaaacctg agcaagtcct atgcaaacaa caaagaaaaa   1440
gaagtccttg tactatgggg tgttcatcac ccgccaaaca taggtgacca aaaggccctc   1500
tatcatacag aaaatgctta tgtctctgta gtgtcttcac attatagcag aaaattcacc   1560
ccagaaatag ccaaaagacc caaagtaaga gatcaagaag gaagaatcaa ttactactgg   1620
actctgcttg aacccgggga tacaataata tttgaggcaa atggaaatct aatagcgcca   1680
agatatgctt tcgcactgag tagaggcttt ggatcaggaa tcatcaactc aaatgcacca   1740
atggataaat gtgatgcgaa gtgccaaaca cctcagggag ctataaacag cagtcttcct   1800
ttccagaacg tacacccagt cacaatagga gagtgtccaa agtatgtcag gagtgcaaaa   1860
ttaaggatgg ttacaggact aaggaacatc ccatccattc aatccagagg tttgtttgga   1920
gccattgccg gtttcattga agggggggtgg actggaatgg tagatggttg gtatggttat   1980
catcatcaga atgagcaagg atctggctat gctgcagatc aaaaaagcac acaaaatgcc   2040
attaatggga ttacaaacaa ggtcaattct gtaattgaga aaatgaacac tcaattcaca   2100
gcagtgggca aagagttcaa caaattggaa agaaggatgg aaaacttgaa taaaaaagtt   2160
gatgatgggt ttatagacat ttggacatat aatgcagaac tgttggttct actggaaaat   2220
gaaaggactt tggatttcca tgactccaat gtgaagaatc tgtatgagaa agtaaaaagc   2280
cagttaaaga ataatgctaa agaaatagga aatgggtgtt ttgagttcta tcacaagtgt   2340
aacgatgaat gcatggagag tgtaaagaat ggaacttatg actatccaaa atattccgaa   2400
gaatcaaagt taaacaggga gaaaattgat ggagtgaaat tggaatcaat gggagtctat   2460
cagattctgg cgatctactc aacagtcgcc agttctctgg ttcttttggt ctccctgggg   2520
gcaatcagct tctggatgtg ttccaatggg tctttacagt gtagaatatg catctaaagg   2580
cctattttct ttagtttgaa tttactgtta ttcggtgtgc atttctatgt ttggtgagcg   2640
gttttctgtg ctcagagtgt gtttatttta tgtaatttaa tttctttgtg agctcctgtt   2700
tagcaggtcg tcccttcagc aaggacacaa aaagatttta attttattaa aaaaaaaaaa   2760
aaaaaagacc gggaattcga tatcaagctt atcgacctgc agatcgttca aacatttggc   2820
aataaagttt cttaagattg aatcctgttg ccggtcttgc gatgattatc atataatttc   2880
tgttgaatta cgttaagcat gtaataatta acatgtaatg catgacgtta tttatgagat   2940
gggtttttat gattagagtc ccgcaattat acatttaata cgcgatagaa aacaaaatat   3000
agcgcgcaaa ctaggataaa ttatcgcgcg cggtgtcatc tatgttacta gattctagag   3060
tctcaagctt cggcgcgcc                                                3079
```

<210> SEQ ID NO 106
<211> LENGTH: 48

<212> TYPE: DNA
<213> ORGANISM: Artificial sequence
<220> FEATURE:
<223> OTHER INFORMATION: ApaI-H3B.c

<400> SEQUENCE: 106
ttgtcgggcc catgaagact atcattgctt tgagctacat tctatgtc 48

<210> SEQ ID NO 107
<211> LENGTH: 44
<212> TYPE: DNA
<213> ORGANISM: Artificial sequence
<220> FEATURE:
<223> OTHER INFORMATION: StuI-H3B.r

<400> SEQUENCE: 107
aaaataggcc ttcaaatgca aatgttgcac ctaatgttgc cttt 44

<210> SEQ ID NO 108
<211> LENGTH: 3061
<212> TYPE: DNA
<213> ORGANISM: Artificial sequence
<220> FEATURE:
<223> OTHER INFORMATION: Construct number 735, from PacI

<400> SEQUENCE: 108
ttaattaaga attcgagctc caccgcggaa acctcctcgg attccattgc ccagctatct 60
gtcactttat tgagaagata gtggaaaagg aaggtggctc ctacaaatgc catcattgcg 120
ataaaggaaa ggccatcgtt gaagatgcct ctgccgacag tggtcccaaa gatggacccc 180
cacccacgag gagcatcgtg gaaaaagaag acgttccaac cacgtcttca aagcaagtgg 240
attgatgtga tatctccact gacgtaaggg atgacgcaca atcccactat ccttcgcaag 300
acccttcctc tatataagga agttcatttc atttggagag gtattaaaat cttaataggt 360
tttgataaaa gcgaacgtgg ggaaacccga accaaacctt cttctaaact ctctctcatc 420
tctcttaaag caaacttctc tcttgtcttt cttgcgtgag cgatcttcaa cgttgtcaga 480
tcgtgcttcg gcaccagtac aacgttttct ttcactgaag cgaaatcaaa gatctctttg 540
tggacacgta gtgcggcgcc attaaataac gtgtacttgt cctattcttg tcggtgtggt 600
cttgggaaaa gaaagcttgc tggaggctgc tgttcagccc catacattac ttgttacgat 660
tctgctgact ttcggcgggt gcaatatctc tacttctgct tgacgaggta ttgttgcctg 720
tacttctttc ttcttcttct tgctgattgg ttctataaga aatctagtat tttctttgaa 780
acagagtttt cccgtggttt tcgaacttgg agaaagattg ttaagcttct gtatattctg 840
cccaaatttg tcgggcccat gaagactatc attgctttga gctacattct atgtctggtt 900
ttcactcaaa aacttcccgg aaatgacaac agcacggcaa cgctgtgcct tgggcaccat 960
gcagtaccaa acggaacgat agtgaaaaca atcacgaatg accaaattga agttactaat 1020
gctactgagc tggttcagag ttcctcaaca ggtgaaatat gcgacagtcc tcatcagatc 1080
cttgatggag aaaactgcac actaatagat gctctattgg gagaccctca gtgtgatggc 1140
ttccaaaata agaaatggga cctttttgtt gaacgcagca aagcctacag caactgttac 1200
ccttatgatg tgccggatta tgcctccctt aggtcactag ttgcctcatc cggcacactg 1260
gagtttaaca atgaaagttt caattggact ggagtcactc aaaacggaac aagctctgct 1320
tgcataagga gatctaataa cagtttcttt agtagattga attggttgac ccacttaaaa 1380
ttcaaatacc cagcattgaa cgtgactatg ccaaacaatg aaaaatttga caaattgtac 1440
atttgggggg ttcaccaccc gggtacggac aatgaccaaa tcttcctgta tgctcaagca 1500
tcaggaagaa tcacagtctc taccaaaaga agccaacaaa ctgtaatccc gaatatcgga 1560
tctagaccca gagtaaggaa tatccccagc agaataagca tctattggac aatagtaaaa 1620
ccgggagaca tacttttgat taacagcaca gggaatctaa ttgctcctag gggttacttc 1680
aaaatacgaa gtgggaaaag ctcaataatg agatcagatg cacccattgg caaatgcaat 1740
tctgaatgca tcactccaaa cggaagcatt cccaatgaca aaccattcca aaatgtaaac 1800
aggatcacat acggggcctg tcccagatat gttaagcaaa acactctgaa attggcaaca 1860
gggatgcgaa atgtaccaga gaaacaaact agaggcatat ttggcgcaat cgcgggtttc 1920
atagaaaatg gttgggaggg aatggtggat ggttggtatg gtttcaggca tcaaaattct 1980
gagggaatag gacaagcagc agatctcaaa agcactcaag cagcaatcga tcaaatcaat 2040
gggaagctga ataggttgat cgggaaaacc aacgagaaat tccatcagat tgaaaaagag 2100
ttctcagaag tcgaagggag aatccaggac cttgagaaat atgttgagga caccaaaata 2160
gatctctggt catacaacgc ggagcttctt gttgccctgg agaaccaaca tacaattgat 2220
ctaactgact cagaaatgaa caaactgttt gaaaaaacaa agaagcaact gagggaaaat 2280
gctgaggata tgggcaatgg ttgtttcaaa atataccaca aatgtgacaa tgcctgcata 2340
ggatcaatca gaaatggaac ttatgaccac gatgtataca gagatgaagc attaaacaac 2400
cggttccaga tcaagggcgt tgagctgaag tcaggataca aagattggat actatggatt 2460
tcctttgcca tatcatgttt tttgctttgt gttgctttgt tggggttcat catgtgggcc 2520
tgccaaaaag gcaacattag gtgcaacatt tgcatttgaa ggcctatttt ctttagtttg 2580
aatttactgt tattcggtgt gcatttctat gtttggtgag cggttttctg tgctcagagt 2640
gtgtttattt tatgtaattt aatttctttg tgagctcctg tttagcaggt cgtcccttca 2700
gcaaggacac aaaaagattt taattttatt aaaaaaaaaa aaaaaaaaga ccgggaattc 2760
gatatcaagc ttatcgacct gcagatcgtt caaacatttg gcaataaagt ttcttaagat 2820
tgaatcctgt tgccggtctt gcgatgatta tcatataatt tctgttgaat tacgttaagc 2880
atgtaataat taacatgtaa tgcatgacgt tatttatgag atgggttttt atgattagag 2940
tcccgcaatt atacatttaa tacgcgatag aaaacaaaat atagcgcgca aactaggata 3000
aattatcgcg cgcggtgtca tctatgttac tagattctag agtctcaagc ttcggcgcgc 3060
c 3061

<210> SEQ ID NO 109
<211> LENGTH: 3085
<212> TYPE: DNA
<213> ORGANISM: Artificial sequence
<220> FEATURE:
<223> OTHER INFORMATION: Construct number 736, from PacI

<400> SEQUENCE: 109
ttaattaaga attcgagctc caccgcggaa acctcctcgg attccattgc ccagctatct 60
gtcactttat tgagaagata gtggaaaagg aaggtggctc ctacaaatgc catcattgcg 120
ataaaggaaa ggccatcgtt gaagatgcct ctgccgacag tggtcccaaa gatggacccc 180
cacccacgag gagcatcgtg gaaaaagaag acgttccaac cacgtcttca aagcaagtgg 240
attgatgtga tatctccact gacgtaaggg atgacgcaca atcccactat ccttcgcaag 300
acccttcctc tatataagga agttcatttc atttggagag gtattaaaat cttaataggt 360
tttgataaaa gcgaacgtgg ggaaacccga accaaacctt cttctaaact ctctctcatc 420

```
tctcttaaag caaacttctc tcttgtcttt cttgcgtgag cgatcttcaa cgttgtcaga    480
tcgtgcttcg gcaccagtac aacgttttct ttcactgaag cgaaatcaaa gatctctttg    540
tggacacgta gtgcggcgcc attaaataac gtgtacttgt cctattcttg tcggtgtggt    600
cttgggaaaa gaaagcttgc tggaggctgc tgttcagccc catacattac ttgttacgat    660
tctgctgact ttcggcgggt gcaatatctc tacttctgct tgacgaggta ttgttgcctg    720
tacttctttc ttcttcttct tgctgattgg ttctataaga aatctagtat tttctttgaa    780
acagagtttt cccgtggttt tcgaacttgg agaaagattg ttaagcttct gtatattctg    840
cccaaatttg tcgggcccat ggcgaaaaac gttgcgattt tcggcttatt gttttctctt    900
cttgtgttgg ttccttctca gatcttcgct caaaaacttc ccggaaatga caacagcacg    960
gcaacgctgt gccttgggca ccatgcagta ccaaacggaa cgatagtgaa aacaatcacg   1020
aatgaccaaa ttgaagttac taatgctact gagctggttc agagttcctc aacaggtgaa   1080
atatgcgaca gtcctcatca gatccttgat ggagaaaact gcacactaat agatgctcta   1140
ttgggagacc ctcagtgtga tggcttccaa aataagaaat gggacctttt tgttgaacgc   1200
agcaaagcct acagcaactg ttacccttat gatgtgccgg attatgcctc ccttaggtca   1260
ctagttgcct catccggcac actggagttt aacaatgaaa gtttcaattg gactggagtc   1320
actcaaaacg gaacaagctc tgcttgcata aggagatcta ataacagttt ctttagtaga   1380
ttgaattggt tgacccactt aaaattcaaa tacccagcat tgaacgtgac tatgccaaac   1440
aatgaaaaat ttgacaaatt gtacatttgg ggggttcacc acccgggtac ggacaatgac   1500
caaatcttcc tgtatgctca agcatcagga agaatcacag tctctaccaa aagaagccaa   1560
caaactgtaa tcccgaatat cggatctaga cccagagtaa ggaatatccc cagcagaata   1620
agcatctatt ggacaatagt aaaaccggga gacatacttt tgattaacag cacagggaat   1680
ctaattgctc ctaggggtta cttcaaaata cgaagtggga aaagctcaat aatgagatca   1740
gatgcaccca ttggcaaatg caattctgaa tgcatcactc caaacggaag cattcccaat   1800
gacaaaccat tccaaaatgt aaacaggatc acatacgggg cctgtcccag atatgttaag   1860
caaaacactc tgaaattggc aacagggatg cgaaatgtac cagagaaaca aactagaggc   1920
atatttggcg caatcgcggg tttcatagaa aatggttggg agggaatggt ggatggttgg   1980
tatggtttca ggcatcaaaa ttctgaggga ataggacaag cagcagatct caaaagcact   2040
caagcagcaa tcgatcaaat caatgggaag ctgaataggt tgatcgggaa aaccaacgag   2100
aaattccatc agattgaaaa agagttctca gaagtcgaag ggagaatcca ggaccttgag   2160
aaatatgttg aggacaccaa aatagatctc tggtcataca acgcggagct tcttgttgcc   2220
ctggagaacc aacatacaat tgatctaact gactcagaaa tgaacaaact gtttgaaaaa   2280
acaaagaagc aactgaggga aaatgctgag gatatgggca atggttgttt caaaatatac   2340
cacaaatgtg acaatgcctg cataggatca atcagaaatg gaacttatga ccacgatgta   2400
tacagagatg aagcattaaa caaccggttc cagatcaagg gcgttgagct gaagtcagga   2460
tacaaagatt ggatactatg gatttccttt gccatatcat gtttttttgct ttgtgttgct   2520
ttgttggggt tcatcatgtg ggcctgccaa aaaggcaaca ttaggtgcaa catttgcatt   2580
tgaaggccta ttttctttag tttgaattta ctgttattcg gtgtgcattt ctatgtttgg   2640
tgagcggttt tctgtgctca gagtgtgttt attttatgta atttaatttc tttgtgagct   2700
cctgtttagc aggtcgtccc ttcagcaagg acacaaaaag attttaattt tattaaaaaa   2760
```

aaaaaaaaaa aagaccggga attcgatatc aagcttatcg acctgcagat cgttcaaaca 2820
tttggcaata aagtttctta agattgaatc ctgttgccgg tcttgcgatg attatcatat 2880
aatttctgtt gaattacgtt aagcatgtaa taattaacat gtaatgcatg acgttattta 2940
tgagatgggt ttttatgatt agagtcccgc aattatacat ttaatacgcg atagaaaaca 3000
aaatatagcg cgcaaactag gataaattat cgcgcgcggt gtcatctatg ttactagatt 3060
ctagagtctc aagcttcggc gcgcc 3085

<210> SEQ ID NO 110
<211> LENGTH: 46
<212> TYPE: DNA
<213> ORGANISM: Artificial sequence
<220> FEATURE:
<223> OTHER INFORMATION: ApI-HBF.c

<400> SEQUENCE: 110
ttgtcgggcc catgaaggca ataattgtac tactcatggt agtaac 46

<210> SEQ ID NO 111
<211> LENGTH: 46
<212> TYPE: DNA
<213> ORGANISM: Artificial sequence
<220> FEATURE:
<223> OTHER INFORMATION: StuI-HBF.r

<400> SEQUENCE: 111
aaaataggcc tttatagaca gatggagcat gaaacgttgt ctctgg 46

<210> SEQ ID NO 112
<211> LENGTH: 3115
<212> TYPE: DNA
<213> ORGANISM: Artificial sequence
<220> FEATURE:
<223> OTHER INFORMATION: Construct number 738, from PacI

<400> SEQUENCE: 112
ttaattaaga attcgagctc caccgcggaa acctcctcgg attccattgc ccagctatct 60
gtcactttat tgagaagata gtggaaaagg aaggtggctc ctacaaatgc catcattgcg 120
ataaaggaaa ggccatcgtt gaagatgcct ctgccgacag tggtcccaaa gatggacccc 180
cacccacgag gagcatcgtg gaaaaagaag acgttccaac cacgtcttca aagcaagtgg 240
attgatgtga tatctccact gacgtaaggg atgacgcaca atcccactat ccttcgcaag 300
acccttcctc tatataagga agttcatttc atttggagag gtattaaaat cttaataggt 360
tttgataaaa gcgaacgtgg ggaaacccga accaaacctt cttctaaact ctctctcatc 420
tctcttaaag caaacttctc tcttgtcttt cttgcgtgag cgatcttcaa cgttgtcaga 480
tcgtgcttcg gcaccagtac aacgttttct ttcactgaag cgaaatcaaa gatctctttg 540
tggacacgta gtgcggcgcc attaaataac gtgtacttgt cctattcttg tcggtgtggt 600
cttgggaaaa gaaagcttgc tggaggctgc tgttcagccc catacattac ttgttacgat 660
tctgctgact ttcggcgggt gcaatatctc tacttctgct tgacgaggta ttgttgcctg 720
tacttctttc ttcttcttct tgctgattgg ttctataaga aatctagtat tttctttgaa 780
acagagtttt cccgtggttt tcgaacttgg agaaagattg ttaagcttct gtatattctg 840
cccaaatttg tcgggcccat gaaggcaata attgtactac tcatggtagt aacatccaat 900
gcagatcgaa tctgcactgg aataacatct tcaaactcac ctcatgtggt caaaacagcc 960
actcaagggg aggtcaatgt gactggtgtg ataccactaa caacaacacc aacaaaatct 1020
tattttgcaa atctcaaagg aacaaggacc agagggaaac tatgcccaga ctgtctcaac 1080
tgcacagatc tggatgtggc tttgggcaga ccaatgtgtg tggggaccac accttcggcg 1140
aaggcttcaa tactccacga agtcaaacct gttacatccg ggtgctttcc tataatgcac 1200
gacagaacaa aaatcaggca actacccaat cttctcagag gatatgaaaa tatcaggcta 1260
tcaacccaaa acgtcatcga tgcggaaaag gcaccaggag gaccctacag acttggaacc 1320
tcaggatctt gccctaacgc taccagtaag agcggatttt tcgcaacaat ggcttgggct 1380
gtcccaaagg acaacaacaa aaatgcaacg aacccactaa cagtagaagt accatacatt 1440
tgtacagaag gggaagacca aatcactgtt tgggggttcc attcagataa caaaacccaa 1500
atgaagaacc tctatggaga ctcaaatcct caaaagttca cctcatctgc taatggagta 1560
accacacact atgtttctca gattggcagc ttcccagatc aaacagaaga cggaggacta 1620
ccacaaagcg gcaggattgt tgttgattac atgatgcaaa aacctgggaa aacaggaaca 1680
attgtctacc aaagaggtgt tttgttgcct caaaaggtgt ggtgcgcgag tggcaggagc 1740
aaagtaataa aagggtcctt gcctttaatt ggtgaagcag attgccttca tgaaaaatac 1800
ggtggattaa acaaaagcaa gccttactac acaggagaac atgcaaaagc cataggaaat 1860
tgcccaatat gggtgaaaac acctttgaag ctcgccaatg gaaccaaata tagacctcct 1920
gcaaaactat taaaggaaag ggtttcttc ggagctattg ctggtttcct agaaggagga 1980
tgggaaggaa tgattgcagg ctggcacgga tacacatctc acggagcaca tggagtggca 2040
gtggcggcgg accttaagag tacgcaagaa gctataaaca agataacaaa aaatctcaat 2100
tctttgagtg agctagaagt aaagaatctt caaagactaa gtggtgccat ggatgaactc 2160
cacaacgaaa tactcgagct ggatgagaaa gtggatgatc tcagagctga cactataagc 2220
tcgcaaatag aacttgcagt cttgctttcc aacgaaggaa taataaacag tgaagatgag 2280
catctattgg cacttgagag aaaactaaag aaaatgctgg gtccctctgc tgtagagata 2340
ggaaatggat gcttcgaaac caaacacaag tgcaaccaga cctgcttaga caggatagct 2400
gctggcacct ttaatgcagg agaattttct ctccccactt ttgattcact gaacattact 2460
gctgcatctt taaatgatga tggattggat aaccatacta tactgctcta ttactcaact 2520
gctgcttcta gtttggctgt aacattgatg ctagctattt ttattgttta tatggtctcc 2580
agagacaacg tttcatgctc catctgtcta taaaggccta ttttctttag tttgaattta 2640
ctgttattcg gtgtgcattt ctatgtttgg tgagcggttt tctgtgctca gagtgtgttt 2700
attttatgta atttaatttc tttgtgagct cctgtttagc aggtcgtccc ttcagcaagg 2760
acacaaaaag attttaattt tattaaaaaa aaaaaaaaaa aagaccggga attcgatatc 2820
aagcttatcg acctgcagat cgttcaaaca tttggcaata aagtttctta agattgaatc 2880
ctgttgccgg tcttgcgatg attatcatat aatttctgtt gaattacgtt aagcatgtaa 2940
taattaacat gtaatgcatg acgttattta tgagatgggt ttttatgatt agagtcccgc 3000
aattatacat ttaatacgcg atagaaaaca aaatatagcg cgcaaactag gataaattat 3060
cgcgcgcggt gtcatctatg ttactagatt ctagagtctc aagcttcggc gcgcc 3115

<210> SEQ ID NO 113
<211> LENGTH: 3142
<212> TYPE: DNA
<213> ORGANISM: Artificial sequence
<220> FEATURE:
<223> OTHER INFORMATION: Construct number 739, from PacI

<400> SEQUENCE: 113

```
ttaattaaga attcgagctc caccgcggaa acctcctcgg attccattgc ccagctatct     60
gtcactttat tgagaagata gtggaaaagg aaggtggctc ctacaaatgc catcattgcg    120
ataaaggaaa ggccatcgtt gaagatgcct ctgccgacag tggtcccaaa gatggacccc    180
cacccacgag gagcatcgtg gaaaaagaag acgttccaac cacgtcttca aagcaagtgg    240
attgatgtga tatctccact gacgtaaggg atgacgcaca atcccactat ccttcgcaag    300
acccttcctc tatataagga agttcatttc atttggagag gtattaaaat cttaataggt    360
tttgataaaa gcgaacgtgg ggaaacccga accaaacctt cttctaaact ctctctcatc    420
tctcttaaag caaacttctc tcttgtcttt cttgcgtgag cgatcttcaa cgttgtcaga    480
tcgtgcttcg gcaccagtac aacgttttct ttcactgaag cgaaatcaaa gatctctttg    540
tggacacgta gtgcggcgcc attaaataac gtgtacttgt cctattcttg tcggtgtggt    600
cttgggaaaa gaaagcttgc tggaggctgc tgttcagccc catacattac ttgttacgat    660
tctgctgact ttcggcgggt gcaatatctc tacttctgct tgacgaggta ttgttgcctg    720
tacttctttc ttcttcttct tgctgattgg ttctataaga aatctagtat tttctttgaa    780
acagagtttt cccgtggttt tcgaacttgg agaaagattg ttaagcttct gtatattctg    840
cccaaatttg tcgggcccat ggcgaaaaac gttgcgattt tcggcttatt gttttctctt    900
cttgtgttgg ttccttctca gatcttcgct gatcgaatct gcactggaat aacatcttca    960
aactcacctc atgtggtcaa aacagccact caaggggagg tcaatgtgac tggtgtgata   1020
ccactaacaa caacaccaac aaaatcttat tttgcaaatc tcaaaggaac aaggaccaga   1080
gggaaactat gcccagactg tctcaactgc acagatctgg atgtggcttt gggcagacca   1140
atgtgtgtgg ggaccacacc ttcggcgaag gcttcaatac tccacgaagt caaacctgtt   1200
acatccgggt gctttcctat aatgcacgac agaacaaaaa tcaggcaact acccaatctt   1260
ctcagaggat atgaaaatat caggctatca acccaaaacg tcatcgatgc ggaaaaggca   1320
ccaggaggac cctacagact tggaacctca ggatcttgcc ctaacgctac cagtaagagc   1380
ggatttttcg caacaatggc ttgggctgtc ccaaaggaca acaacaaaaa tgcaacgaac   1440
ccactaacag tagaagtacc atacatttgt acagaagggg aagaccaaat cactgtttgg   1500
gggttccatt cagataacaa aacccaaatg aagaacctct atggagactc aaatcctcaa   1560
aagttcacct catctgctaa tggagtaacc acacactatg tttctcagat tggcagcttc   1620
ccagatcaaa cagaagacgg aggactacca caaagcggca ggattgttgt tgattacatg   1680
atgcaaaaac ctgggaaaac aggaacaatt gtctaccaaa gaggtgtttt gttgcctcaa   1740
aaggtgtggt gcgcgagtgg caggagcaaa gtaataaaag ggtccttgcc tttaattggt   1800
gaagcagatt gccttcatga aaaatacggt ggattaaaca aaagcaagcc ttactacaca   1860
ggagaacatg caaaagccat aggaaattgc ccaatatggg tgaaaacacc tttgaagctc   1920
gccaatggaa ccaaatatag acctcctgca aaactattaa aggaaagggg tttcttcgga   1980
gctattgctg gtttcctaga aggaggatgg gaaggaatga ttgcaggctg gcacggatac   2040
acatctcacg gagcacatgg agtggcagtg gcggcggacc ttaagagtac gcaagaagct   2100
ataaacaaga taacaaaaaa tctcaattct ttgagtgagc tagaagtaaa gaatcttcaa   2160
agactaagtg gtgccatgga tgaactccac aacgaaatac tcgagctgga tgagaaagtg   2220
gatgatctca gagctgacac tataagctcg caaatagaac ttgcagtctt gctttccaac   2280
gaaggaataa taaacagtga agatgagcat ctattggcac ttgagagaaa actaaagaaa   2340
```

atgctgggtc cctctgctgt agagatagga aatggatgct tcgaaaccaa acacaagtgc 2400
aaccagacct gcttagacag gatagctgct ggcaccttta atgcaggaga attttctctc 2460
cccacttttg attcactgaa cattactgct gcatctttaa atgatgatgg attggataac 2520
catactatac tgctctatta ctcaactgct gcttctagtt tggctgtaac attgatgcta 2580
gctattttta ttgtttatat ggtctccaga gacaacgttt catgctccat ctgtctataa 2640
aggcctattt tctttagttt gaatttactg ttattcggtg tgcatttcta tgtttggtga 2700
gcggttttct gtgctcagag tgtgtttatt ttatgtaatt taatttcttt gtgagctcct 2760
gtttagcagg tcgtcccttc agcaaggaca caaaaagatt ttaattttat taaaaaaaaa 2820
aaaaaaaaag accgggaatt cgatatcaag cttatcgacc tgcagatcgt tcaaacattt 2880
ggcaataaag tttcttaaga ttgaatcctg ttgccggtct tgcgatgatt atcatataat 2940
ttctgttgaa ttacgttaag catgtaataa ttaacatgta atgcatgacg ttatttatga 3000
gatgggtttt tatgattaga gtcccgcaat tatacattta atacgcgata gaaaacaaaa 3060
tatagcgcgc aaactaggat aaattatcgc gcgcggtgtc atctatgtta ctagattcta 3120
gagtctcaag cttcggcgcg cc 3142

<210> SEQ ID NO 114
<211> LENGTH: 1272
<212> TYPE: DNA
<213> ORGANISM: Medicago sativa

<400> SEQUENCE: 114
atgtttgggc gcggaccaac aaggaagagt gataacacca aatattacga tattcttggt 60
gtttcaaaaa gtgctagtga agatgaaatc aagaaagcct atagaaaggc agcgatgaag 120
aaccatccag ataagggtgg ggatcctgag aagttcaagg agttgggcca agcatatgaa 180
gtgttgagcg atcctgaaaa gaaagaactg tatgatcaat atggtgaaga tgcccttaaa 240
gaaggaatgg ggggaggcgc aggaagctca tttcataatc cgtttgatat tttcgaatca 300
ttttttggtg caggctttgg tggtggtggt ccttcacgcg caagaagaca gaagcaagga 360
gaagatgtgg tgcattctat aaaggtttcc ttggaggatg tgtataacgg cactacaaag 420
aagctatcac tttctaggaa tgcactgtgc tcaaaatgta aagggaaagg ttcaaaaagt 480
ggaactgctg gaaggtgttt tggatgccag ggcacaggta tgaagattac cagaaggcaa 540
attggactgg gcatgattca acaaatgcaa cacgtctgtc ctgactgcaa aggaacaggc 600
gaggtcatta gtgagagaga tagatgccct caatgcaagg gaaacaagat tactcaagaa 660
aagaaggtgc tggaggtgca tgtggaaaag gggatgcagc agggtcacaa gattgtattc 720
gaaggacaag ctgatgaagc tcctgataca atcacaggag acatagtttt tgtcttgcaa 780
gtaaagggac atccgaagtt tcggagggag cgtgatgacc tccacattga acacaatttg 840
agcttaactg aggctctctg tggcttccag tttaatgtca cacatcttga tggaaggcaa 900
ctattggtca aatcgaaccc cggcgaagtc atcaagccag gtcaacataa agctataaat 960
gatgagggaa tgccacaaca tggtaggccg ttcatgaagg gacgcctata catcaagttt 1020
agtgttgatt tcccggattc gggttttctt tccccaagcc aaagcctgga attagaaaag 1080
atattacctc aaaagacaag caagaacttg tcccaaaagg aggtagatga ttgtgaggag 1140
accaccctgc atgatgtcaa tattgcagag gagatgagtc gaaagaagca acaataccgt 1200
gaggcatatg atgacgatga tgatgaagat gatgagcact cgcagcctcg ggtgcaatgc 1260
gctcaacagt ag 1272

<210> SEQ ID NO 115
<211> LENGTH: 20
<212> TYPE: DNA
<213> ORGANISM: Artificial sequence
<220> FEATURE:
<223> OTHER INFORMATION: Hsp-40Luz.1c

<400> SEQUENCE: 115
atgtttgggc gcggaccaac 20

<210> SEQ ID NO 116
<211> LENGTH: 31
<212> TYPE: DNA
<213> ORGANISM: Artificial sequence
<220> FEATURE:
<223> OTHER INFORMATION: Hsp40Luz-SacI.1272r

<400> SEQUENCE: 116
agctgagctc ctactgttga gcgcattgca c 31

<210> SEQ ID NO 117
<211> LENGTH: 36
<212> TYPE: DNA
<213> ORGANISM: Artificial sequence
<220> FEATURE:
<223> OTHER INFORMATION: Hsp40Luz-Plasto.r

<400> SEQUENCE: 117
gttggtccgc gcccaaacat tttctctcaa gatgat 36

<210> SEQ ID NO 118
<211> LENGTH: 21
<212> TYPE: DNA
<213> ORGANISM: Artificial sequence
<220> FEATURE:
<223> OTHER INFORMATION: Hsp70Ara.1c

<400> SEQUENCE: 118
atgtcgggta aaggagaagg a 21

<210> SEQ ID NO 119
<211> LENGTH: 33
<212> TYPE: DNA
<213> ORGANISM: Artificial sequence
<220> FEATURE:
<223> OTHER INFORMATION: Hsp70Ara-SacI.1956r

<400> SEQUENCE: 119
agctgagctc ttagtcgacc tcctcgatct tag 33

<210> SEQ ID NO 120
<211> LENGTH: 37
<212> TYPE: DNA
<213> ORGANISM: Artificial sequence
<220> FEATURE:
<223> OTHER INFORMATION: Hsp70Ara-Plasto.r

<400> SEQUENCE: 120
tccttctcct ttacccgaca ttttctctca agatgat 37

<210> SEQ ID NO 121
<211> LENGTH: 4402
<212> TYPE: DNA
<213> ORGANISM: Artificial sequence

```
<220> FEATURE:
<223> OTHER INFORMATION: Construct number R850, from HindIII

<400> SEQUENCE: 121

aagcttgcat gcctgcaggt cgactctaga ggatccccgg gctggtctgt acattcatct     60

tgccgccttt gcattcactt ggccacaaag agtagagaga aggaagagaa gagcccagac    120

ttcaagaagc gaccttgcaa gtgcactcga gggtcagaaa ctgtatatca tatctatgtg    180

agagaaaggg gaacatttga gatggagtcc atttacttga ggtatactta ttattttgat    240

caataaattt gtatacttct tatttagatc aataaatttg tcattaagct ataatccaaa    300

ataaattacg atcaaatatg caaatgttag ccagtacttg tgttaaactt gatggcatct    360

cttggtttct ttggcaatca catgcctaag aaataaatag tatcatatga ttgtgtttgg    420

tcagacttca gagtcagatg actctgtttg gataaacagc ttaattaagc gcttatagaa    480

tatcatatga ttgtgtttgg tcagacttca gagcatctct tggtttctct ggcaatcata    540

tgcctaagaa ataaatagta tcatatgatt gtgtttggtc agacttcaga gtcagatgac    600

cctgtttggg taaacagctt aattaagtgc ttatagaata agcgcttatc atataagtgc    660

ttttgtacag ttatttctat gaaagtagaa gaaatagtca tattgtttta atataagcta    720

tcctggagag cttgtggaaa taaccagaaa agaacttatg gacacgtcat gagctgttta    780

cataagatct ccctaacagt ctcaaaagtg tttatgccag tagataaatt caaataagtc    840

aatctaaaca gaccctaaat ccattatggt acctatcatt ttagcttatt ccatctttat    900

taagaatgtc atgagataac ataatgataa cacattattt tgacacaaat gggcagatct    960

agcaatttaa ctctggagtc cttcaagact gctgttctta cgaagttcac gtccctgaat   1020

catgttcctg tatggaagcc tgaaagacct caaattctaa aaggtggcga taaattgaag   1080

gtttacaaaa tataccctgc gggcttgaca cagaggcaag ctctttatac cttccagttc   1140

aacggggatg ttgatttcag aagtcacttg gagagcaatc cttgtgccaa gtttgaagta   1200

atttttgtgt agcatatgtt gagctaccta caatttacat gatcacctag cattagctct   1260

ttcacttaac tgagagaatg aagttttagg aatgagtatg accatggagt cggcatggct   1320

ttgtaatgcc taccctactt tggccaactc atcggggatt tacattcaga aaatatacat   1380

gacttcaacc atacttaaac cccttttgt aagataactg aatgttcata tttaatgttg   1440

ggttgtagtg tttttacttg attatatcca gacagttaca agttggacaa caagattgtg   1500

ggtctgtact gttatttatt tatttttttt ttagcagaaa caccttatct tttgtttcgt   1560

ttgaatgtag aatgaaaata aaagaaagaa aatataacat catcggccgc gcttgtctaa   1620

tttcgggcag ttaggatcct ctccggtcac cggaaagttt cagtagaaga aacaaaacac   1680

cgtgactaaa atgatactat tattttattt attgtgtttt tctttttttct accggaactt   1740

tttagaacgg atcccaactc gttccggggc cgctacaact gaaacaaaag aagatatttt   1800

ctctctcttc agaaatgtaa gttttccttt acagataccc attcaccatt tgattcagat   1860

gtggtgacta gagataaagc atactaattt gactcttgga aacccataaa gtttatgtta   1920

tccgtgttct ggaccaatcc acttgggggc ataacctgtg tctatgtgtg gtttggtttc   1980

cattctgatt tatgcggcga cttgtaattt aaaatctagg aggggcagac attgaacaat   2040

cccaatattt taataactta tgcaagattt tttttattaa tgagatgatg tgtttgtgac   2100

tgagattgag tcatacattt cactaagaaa tggttccaag taccaaacta tcatgaccca   2160

gttgcaaaca tgacgttcgg gagtggtcac tttgatagtt caatttcatc ttggcttctt   2220
```

-continued attcctttta taattctaat tcttcttgtg taaactattt catgtattat ttttctttaa 2280
aatttacatg tcatttattt tgcctcacta actcaatttt gcatataaca atgataagtg 2340
atattttgac tcacaaaatt tacatcaaat ttcgacatcg tttattatgt tcattggatg 2400
attaacaaat ataacaaact ttgcaactaa ttaaccacca actgaatata attaactata 2460
actgtgaaag tagttaactc atttttatat ttcatagatc aaataagaga aataacggta 2520
tattaatccc tccaaaaaaa aaaaacggta tatttactaa aaaatctaag ccacgtagga 2580
ggataacagg atccccgtag gaggataaca tccaatccaa ccaatcacaa caatcctgat 2640
gagataaccc actttaagcc cacgcatctg tggcacatct acattatcta aatcacacat 2700
tcttccacac atctgagcca cacaaaaacc aatccacatc tttatcaccc attctataaa 2760
aaatcacact ttgtgagtct acactttgat tcccttcaaa cacatacaaa gagaagagac 2820
taattaatta attaatcatc ttgagagaaa atgtttgggc gcggaccaac aaggaagagt 2880
gataacacca aatattacga tattcttggt gtttcaaaaa gtgctagtga agatgaaatc 2940
aagaaagcct atagaaaggc agcgatgaag aaccatccag ataagggtgg ggatcctgag 3000
aagttcaagg agttgggcca agcatatgaa gtgttgagcg atcctgaaaa gaaagaactg 3060
tatgatcaat atggtgaaga tgcccttaaa gaaggaatgg ggggaggcgc aggaagctca 3120
tttcataatc cgtttgatat tttcgaatca ttttttggtg caggctttgg tggtggtggt 3180
ccttcacgcg caagaagaca gaagcaagga gaagatgtgg tgcattctat aaaggtttcc 3240
ttggaggatg tgtataacgg cactacaaag aagctatcac tttctaggaa tgcactgtgc 3300
tcaaaatgta aagggaaagg ttcaaaaagt ggaactgctg gaaggtgttt tggatgccag 3360
ggcacaggta tgaagattac cagaaggcaa attggactgg gcatgattca acaaatgcaa 3420
cacgtctgtc ctgactgcaa aggaacaggc gaggtcatta gtgagagaga tagatgccct 3480
caatgcaagg gaaacaagat tactcaagaa aagaaggtgc tggaggtgca tgtggaaaag 3540
gggatgcagc agggtcacaa gattgtattc gaaggacaag ctgatgaagc tcctgataca 3600
atcacaggag acatagtttt tgtcttgcaa gtaaagggac atccgaagtt tcggagggag 3660
cgtgatgacc tccacattga acacaatttg agcttaactg aggctctctg tggcttccag 3720
tttaatgtca cacatcttga tggaaggcaa ctattggtca aatcgaaccc cggcgaagtc 3780
atcaagccag gtcaacataa agctataaat gatgagggaa tgccacaaca tggtaggccg 3840
ttcatgaagg gacgcctata catcaagttt agtgttgatt tcccggattc gggttttctt 3900
tccccaagcc aaagcctgga attagaaaag atattacctc aaaagacaag caagaacttg 3960
tcccaaaagg aggtagatga ttgtgaggag accaccctgc atgatgtcaa tattgcagag 4020
gagatgagtc gaaagaagca acaataccgt gaggcatatg atgacgatga tgatgaagat 4080
gatgagcact cgcagcctcg ggtgcaatgc gctcaacagt aggagctcag ctcgaatttc 4140
cccgatcgtt caaacatttg gcaataaagt ttcttaagat tgaatcctgt tgccggtctt 4200
gcgatgatta tcatataatt tctgttgaat tacgttaagc atgtaataat taacatgtaa 4260
tgcatgacgt tatttatgag atgggttttt atgattagag tcccgcaatt atacatttaa 4320
tacgcgatag aaaacaaaat atagcgcgca aactaggata aattatcgcg cgcggtgtca 4380
tctatgttac tagatcgaat tc 4402

<210> SEQ ID NO 122
<211> LENGTH: 5086
<212> TYPE: DNA
<213> ORGANISM: Artificial sequence
<220> FEATURE:
<223> OTHER INFORMATION: Construct number R860, from HindIII

<400> SEQUENCE: 122
aagcttgcat gcctgcaggt cgactctaga ggatccccgg gctggtctgt acattcatct 60
tgccgccttt gcattcactt ggccacaaag agtagagaga aggaagagaa gagcccagac 120
ttcaagaagc gaccttgcaa gtgcactcga gggtcagaaa ctgtatatca tatctatgtg 180
agagaaaggg gaacatttga gatggagtcc atttacttga ggtatactta ttattttgat 240
caataaattt gtatacttct tatttagatc aataaatttg tcattaagct ataatccaaa 300
ataaattacg atcaaatatg caaatgttag ccagtacttg tgttaaactt gatggcatct 360
cttggtttct ttggcaatca catgcctaag aaataaatag tatcatatga ttgtgtttgg 420
tcagacttca gagtcagatg actctgtttg gataaacagc ttaattaagc gcttatagaa 480
tatcatatga ttgtgtttgg tcagacttca gagcatctct tggtttctct ggcaatcata 540
tgcctaagaa ataaatagta tcatatgatt gtgtttggtc agacttcaga gtcagatgac 600
cctgtttggg taaacagctt aattaagtgc ttatagaata agcgcttatc atataagtgc 660
ttttgtacag ttatttctat gaaagtagaa gaaatagtca tattgtttta atataagcta 720
tcctggagag cttgtggaaa taaccagaaa agaacttatg gacacgtcat gagctgttta 780
cataagatct ccctaacagt ctcaaaagtg tttatgccag tagataaatt caaataagtc 840
aatctaaaca gaccctaaat ccattatggt acctatcatt ttagcttatt ccatctttat 900
taagaatgtc atgagataac ataatgataa cacattattt tgacacaaat gggcagatct 960
agcaatttaa ctctggagtc cttcaagact gctgttctta cgaagttcac gtccctgaat 1020
catgttcctg tatggaagcc tgaaagacct caaattctaa aaggtggcga taaattgaag 1080
gtttacaaaa tataccctgc gggcttgaca cagaggcaag ctctttatac cttccagttc 1140
aacggggatg ttgatttcag aagtcacttg gagagcaatc cttgtgccaa gtttgaagta 1200
atttttgtgt agcatatgtt gagctaccta caatttacat gatcacctag cattagctct 1260
ttcacttaac tgagagaatg aagttttagg aatgagtatg accatggagt cggcatggct 1320
ttgtaatgcc taccctactt tggccaactc atcggggatt tacattcaga aaatatacat 1380
gacttcaacc atacttaaac cccttttgt aagataactg aatgttcata tttaatgttg 1440
ggttgtagtg tttttacttg attatatcca gacagttaca agttggacaa caagattgtg 1500
ggtctgtact gttatttatt tatttttttt ttagcagaaa caccttatct tttgtttcgt 1560
ttgaatgtag aatgaaaata aaagaaagaa aatataacat catcggccgc gcttgtctaa 1620
tttcgggcag ttaggatcct ctccggtcac cggaaagttt cagtagaaga aacaaaacac 1680
cgtgactaaa atgatactat tattttattt attgtgtttt tctttttct accggaactt 1740 tttagaacgg atcccaactc gttccggggc cgctacaact gaaacaaaag aagatatttt 1800
ctctctcttc agaaatgtaa gttttccttt acagataccc attcaccatt tgattcagat 1860
gtggtgacta gagataaagc atactaattt gactcttgga aacccataaa gtttatgtta 1920
tccgtgttct ggaccaatcc acttgggggc ataacctgtg tctatgtgtg gtttggtttc 1980
cattctgatt tatgcggcga cttgtaattt aaaatctagg aggggcagac attgaacaat 2040
cccaatattt taataactta tgcaagattt tttttattaa tgagatgatg tgtttgtgac 2100
tgagattgag tcatacattt cactaagaaa tggttccaag taccaaacta tcatgaccca 2160
gttgcaaaca tgacgttcgg gagtggtcac tttgatagtt caatttcatc ttggcttctt 2220

```
attcctttta taattctaat tcttcttgtg taaactattt catgtattat ttttctttaa   2280

aatttacatg tcatttattt tgcctcacta actcaatttt gcatataaca atgataagtg   2340

atattttgac tcacaaaatt tacatcaaat ttcgacatcg tttattatgt tcattggatg   2400

attaacaaat ataacaaact ttgcaactaa ttaaccacca actgaatata attaactata   2460

actgtgaaag tagttaactc atttttatat ttcatagatc aaataagaga aataacggta   2520

tattaatccc tccaaaaaaa aaaaacggta tatttactaa aaaatctaag ccacgtagga   2580

ggataacagg atccccgtag gaggataaca tccaatccaa ccaatcacaa caatcctgat   2640

gagataaccc actttaagcc cacgcatctg tggcacatct acattatcta aatcacacat   2700

tcttccacac atctgagcca cacaaaaacc aatccacatc tttatcaccc attctataaa   2760

aaatcacact ttgtgagtct acactttgat tcccttcaaa cacatacaaa gagaagagac   2820

taattaatta attaatcatc ttgagagaaa atgtcgggta aaggagaagg accagctatc   2880

ggtatcgatc ttggtaccac ttactcttgc gtcggagtat ggcaacacga ccgtgttgag   2940

atcattgcta atgatcaagg aaacagaacc acgccatctt acgttgcttt caccgactcc   3000

gagaggttga tcggtgacgc agctaagaat caggtcgcca tgaaccccgt taacaccgtt   3060

ttcgacgcta agaggttgat cggtcgtcgt ttctctgaca gctctgttca gagtgacatg   3120

aaattgtggc cattcaagat tcaagccgga cctgccgata agccaatgat ctacgtcgaa   3180

tacaagggtg aagagaaaga gttcgcagct gaggagattt cttccatggt tcttattaag   3240

atgcgtgaga ttgctgaggc ttaccttggt gtcacaatca agaacgccgt tgttaccgtt   3300

ccagcttact tcaacgactc tcagcgtcag gctacaaagg atgctggtgt catcgctggt   3360

ttgaacgtta tgcgaatcat caacgagcct acagccgccg ctattgccta cggtcttgac   3420

aaaaaggcta ccagcgttgg agagaagaat gttcttatct tcgatcttgg tggtggcact   3480

tttgatgtct ctcttcttac cattgaagag ggtatctttg aggtgaaggc aactgctggt   3540

gacacccatc ttggtgggga agattttgac aacagaatgg ttaaccactt tgtccaagag   3600

ttcaagagga agagtaagaa ggatatcacc ggtaacccaa gagctcttag gaggttgaga   3660

acttcctgtg agagagcgaa gaggactctt tcttccactg ctcagaccac catcgagatt   3720

gactctctat acgagggtat cgacttctac tccaccatca cccgtgctag atttgaggag   3780

ctcaacatgg atctcttcag gaagtgtatg gagccagttg agaagtgtct tcgtgatgct   3840

aagatggaca agagcactgt tcatgatgtt gtccttgttg gtggttctac ccgtatccct   3900

aaggttcagc aattgctcca ggacttcttc aacggcaaag agctttgcaa gtctattaac   3960

cctgatgagg ctgttgccta cggtgctgct gtccagggag ctattctcag cggtgaagga   4020

aacgagaagg ttcaagatct tctattgctc gatgtcactc ctctctccct tggtttggaa   4080

actgccggtg gtgtcatgac cactttgatc ccaaggaaca caaccatccc aaccaagaag   4140

gaacaagtct tctccaccta ctcagacaac caacccggtg tgttgatcca ggtgtacgaa   4200

ggagagagag ccagaaccaa ggacaacaac cttcttggta aatttgagct ctccggaatt   4260

cctccagctc ctcgtggtgt cccccagatc acagtctgct ttgacattga tgccaatggt   4320

atcctcaatg tctctgctga ggacaagacc accggacaga agaacaagat caccatcacc   4380

aatgacaagg gtcgtctctc caaggatgag attgagaaga tggttcaaga ggctgagaag   4440

tacaagtccg aagacgagga gcacaagaag aaggttgaag ccaagaacgc tctcgagaac   4500

tacgcttaca acatgaggaa caccatccaa gacgagaaga ttggtgagaa gctcccggct   4560

gcagacaaga agaagatcga ggattctatt gagcaggcga ttcaatggct cgagggtaac   4620
```

cagttggctg aggctgatga gttcgaagac aagatgaagg aattggagag catctgcaac 4680
ccaatcattg ccaagatgta ccaaggagct ggtggtgaag ccggtggtcc aggtgcctct 4740
ggtatggacg atgatgctcc ccctgcttca ggcggtgctg gacctaagat cgaggaggtc 4800
gactaagagc tcagctcgaa tttccccgat cgttcaaaca tttggcaata aagtttctta 4860
agattgaatc ctgttgccgg tcttgcgatg attatcatat aatttctgtt gaattacgtt 4920
aagcatgtaa taattaacat gtaatgcatg acgttattta tgagatgggt ttttatgatt 4980
agagtcccgc aattatacat ttaatacgcg atagaaaaca aaatatagcg cgcaaactag 5040
gataaattat cgcgcgcggt gtcatctatg ttactagatc gaattc 5086

<210> SEQ ID NO 123
<211> LENGTH: 9493
<212> TYPE: DNA
<213> ORGANISM: Artificial sequence
<220> FEATURE:
<223> OTHER INFORMATION: Construct number R870, from HindIII

<400> SEQUENCE: 123
aagcttgcat gcctgcaggt cgactctaga ggatccccgg gctggtctgt acattcatct 60
tgccgccttt gcattcactt ggccacaaag agtagagaga aggaagagaa gagcccagac 120
ttcaagaagc gaccttgcaa gtgcactcga gggtcagaaa ctgtatatca tatctatgtg 180
agagaaaggg gaacatttga gatggagtcc atttacttga ggtatactta ttattttgat 240
caataaattt gtatacttct tatttagatc aataaatttg tcattaagct ataatccaaa 300
ataaattacg atcaaatatg caaatgttag ccagtacttg tgttaaactt gatggcatct 360
cttggtttct ttggcaatca catgcctaag aaataaatag tatcatatga ttgtgtttgg 420
tcagacttca gagtcagatg actctgtttg gataaacagc ttaattaagc gcttatagaa 480
tatcatatga ttgtgtttgg tcagacttca gagcatctct tggtttctct ggcaatcata 540
tgcctaagaa ataaatagta tcatatgatt gtgtttggtc agacttcaga gtcagatgac 600
cctgtttggg taaacagctt aattaagtgc ttatagaata agcgcttatc atataagtgc 660
ttttgtacag ttatttctat gaaagtagaa gaaatagtca tattgtttta atataagcta 720
tcctggagag cttgtggaaa taaccagaaa agaacttatg gacacgtcat gagctgttta 780
cataagatct ccctaacagt ctcaaaagtg tttatgccag tagataaatt caaataagtc 840
aatctaaaca gaccctaaat ccattatggt acctatcatt ttagcttatt ccatctttat 900
taagaatgtc atgagataac ataatgataa cacattattt tgacacaaat gggcagatct 960
agcaatttaa ctctggagtc cttcaagact gctgttctta cgaagttcac gtccctgaat 1020
catgttcctg tatggaagcc tgaaagacct caaattctaa aaggtggcga taaattgaag 1080
gtttacaaaa tataccctgc gggcttgaca cagaggcaag ctctttatac cttccagttc 1140
aacggggatg ttgatttcag aagtcacttg gagagcaatc cttgtgccaa gtttgaagta 1200
atttttgtgt agcatatgtt gagctaccta caatttacat gatcacctag cattagctct 1260
ttcacttaac tgagagaatg aagttttagg aatgagtatg accatggagt cggcatggct 1320
ttgtaatgcc taccctactt tggccaactc atcggggatt tacattcaga aaatatacat 1380
gacttcaacc atacttaaac ccctttttgt aagataactg aatgttcata tttaatgttg 1440
ggttgtagtg tttttacttg attatatcca gacagttaca agttggacaa caagattgtg 1500
ggtctgtact gttatttatt tattttttt ttagcagaaa caccttatct tttgtttcgt 1560

-continued

```
ttgaatgtag aatgaaaata aaagaaagaa aatataacat catcggccgc gcttgtctaa   1620
tttcgggcag ttaggatcct ctccggtcac cggaaagttt cagtagaaga aacaaaacac   1680
cgtgactaaa atgatactat tattttattt attgtgtttt tctttttct accggaactt    1740
tttagaacgg atcccaactc gttccggggc cgctacaact gaaacaaaag aagatatttt   1800
ctctctcttc agaaatgtaa gttttccttt acagataccc attcaccatt tgattcagat   1860
gtggtgacta gagataaagc atactaattt gactcttgga aacccataaa gtttatgtta   1920
tccgtgttct ggaccaatcc acttgggggc ataacctgtg tctatgtgtg gtttggtttc   1980
cattctgatt tatgcggcga cttgtaattt aaaatctagg aggggcagac attgaacaat   2040
cccaatattt taataactta tgcaagattt tttttattaa tgagatgatg tgtttgtgac   2100
tgagattgag tcatacattt cactaagaaa tggttccaag taccaaacta tcatgaccca   2160
gttgcaaaca tgacgttcgg gagtggtcac tttgatagtt caatttcatc ttggcttctt   2220
attcctttta taattctaat tcttcttgtg taaactattt catgtattat ttttctttaa   2280
aatttacatg tcatttattt tgcctcacta actcaatttt gcatataaca atgataagtg   2340
atattttgac tcacaaaatt tacatcaaat ttcgacatcg tttattatgt tcattggatg   2400
attaacaaat ataacaaact ttgcaactaa ttaaccacca actgaatata attaactata   2460
actgtgaaag tagttaactc atttttatat ttcatagatc aaataagaga aataacggta   2520
tattaatccc tccaaaaaaa aaaaacggta tatttactaa aaaatctaag ccacgtagga   2580
ggataacagg atccccgtag gaggataaca tccaatccaa ccaatcacaa caatcctgat   2640
gagataaccc actttaagcc cacgcatctg tggcacatct acattatcta aatcacacat   2700
tcttccacac atctgagcca cacaaaaacc aatccacatc tttatcaccc attctataaa   2760
aaatcacact ttgtgagtct acactttgat tcccttcaaa cacatacaaa gagaagagac   2820
taattaatta attaatcatc ttgagagaaa atgtcgggta aaggagaagg accagctatc   2880
ggtatcgatc ttggtaccac ttactcttgc gtcggagtat ggcaacacga ccgtgttgag   2940
atcattgcta atgatcaagg aaacagaacc acgccatctt acgttgcttt caccgactcc   3000
gagaggttga tcggtgacgc agctaagaat caggtcgcca tgaaccccgt taacaccgtt   3060
ttcgacgcta agaggttgat cggtcgtcgt ttctctgaca gctctgttca gagtgacatg   3120
aaattgtggc cattcaagat tcaagccgga cctgccgata agccaatgat ctacgtcgaa   3180
tacaagggtg aagagaaaga gttcgcagct gaggagattt cttccatggt tcttattaag   3240
atgcgtgaga ttgctgaggc ttaccttggt gtcacaatca agaacgccgt tgttaccgtt   3300
ccagcttact tcaacgactc tcagcgtcag gctacaaagg atgctggtgt catcgctggt   3360
ttgaacgtta tgcgaatcat caacgagcct acagccgccg ctattgccta cggtcttgac   3420
aaaaaggcta ccagcgttgg agagaagaat gttcttatct tcgatcttgg tggtggcact   3480
tttgatgtct ctcttcttac cattgaagag ggtatctttg aggtgaaggc aactgctggt   3540
gacacccatc ttggtgggga agattttgac aacagaatgg ttaaccactt tgtccaagag   3600
ttcaagagga agagtaagaa ggatatcacc ggtaacccaa gagctcttag gaggttgaga   3660
acttcctgtg agagagcgaa gaggactctt tcttccactg ctcagaccac catcgagatt   3720
gactctctat acgagggtat cgacttctac tccaccatca cccgtgctag atttgaggag   3780
ctcaacatgg atctcttcag gaagtgtatg gagccagttg agaagtgtct tcgtgatgct   3840
aagatggaca agagcactgt tcatgatgtt gtccttgttg gtggttctac ccgtatccct   3900
aaggttcagc aattgctcca ggacttcttc aacggcaaag agctttgcaa gtctattaac   3960
```

cctgatgagg ctgttgccta cggtgctgct gtccagggag ctattctcag cggtgaagga 4020
aacgagaagg ttcaagatct tctattgctc gatgtcactc ctctctccct tggtttggaa 4080
actgccggtg gtgtcatgac cactttgatc ccaaggaaca caaccatccc aaccaagaag 4140
gaacaagtct tctccaccta ctcagacaac caacccggtg tgttgatcca ggtgtacgaa 4200
ggagagagag ccagaaccaa ggacaacaac cttcttggta aatttgagct ctccggaatt 4260
cctccagctc ctcgtggtgt cccccagatc acagtctgct ttgacattga tgccaatggt 4320
atcctcaatg tctctgctga ggacaagacc accggacaga agaacaagat caccatcacc 4380
aatgacaagg gtcgtctctc caaggatgag attgagaaga tggttcaaga ggctgagaag 4440
tacaagtccg aagacgagga gcacaagaag aaggttgaag ccaagaacgc tctcgagaac 4500
tacgcttaca acatgaggaa caccatccaa gacgagaaga ttggtgagaa gctcccggct 4560
gcagacaaga agaagatcga ggattctatt gagcaggcga ttcaatggct cgagggtaac 4620
cagttggctg aggctgatga gttcgaagac aagatgaagg aattggagag catctgcaac 4680
ccaatcattg ccaagatgta ccaaggagct ggtggtgaag ccggtggtcc aggtgcctct 4740
ggtatggacg atgatgctcc ccctgcttca ggcggtgctg gacctaagat cgaggaggtc 4800
gactaagagc tcagctcgaa tttccccgat cgttcaaaca tttggcaata aagtttctta 4860
agattgaatc ctgttgccgg tcttgcgatg attatcatat aatttctgtt gaattacgtt 4920
aagcatgtaa taattaacat gtaatgcatg acgttattta tgagatgggt ttttatgatt 4980
agagtcccgc aattatacat ttaatacgcg atagaaaaca aaatatagcg cgcaaactag 5040
gataaattat cgcgcgcggt gtcatctatg ttactagatc gaattcgtaa tcatggtcat 5100
agctgtttcc tgtgtgaaat tgttatccgg ggctggtctg tacattcatc ttgccgcctt 5160
tgcattcact tggccacaaa gagtagagag aaggaagaga agagcccaga cttcaagaag 5220
cgaccttgca agtgcactcg agggtcagaa actgtatatc atatctatgt gagagaaagg 5280
ggaacatttg agatggagtc catttacttg aggtatactt attattttga tcaataaatt 5340
tgtatacttc ttatttagat caataaattt gtcattaagc tataatccaa aataaattac 5400
gatcaaatat gcaaatgtta gccagtactt gtgttaaact tgatggcatc tcttggtttc 5460
tttggcaatc acatgcctaa gaaataaata gtatcatatg attgtgtttg gtcagacttc 5520
agagtcagat gactctgttt ggataaacag cttaattaag cgcttataga atatcatatg 5580
attgtgtttg gtcagacttc agagcatctc ttggtttctc tggcaatcat atgcctaaga 5640
aataaatagt atcatatgat tgtgtttggt cagacttcag agtcagatga ccctgtttgg 5700
gtaaacagct taattaagtg cttatagaat aagcgcttat catataagtg cttttgtaca 5760
gttatttcta tgaaagtaga agaaatagtc atattgtttt aatataagct atcctggaga 5820
gcttgtggaa ataaccagaa aagaacttat ggacacgtca tgagctgttt acataagatc 5880
tccctaacag tctcaaaagt gtttatgcca gtagataaat tcaaataagt caatctaaac 5940
agaccctaaa tccattatgg tacctatcat tttagcttat tccatcttta ttaagaatgt 6000
catgagataa cataatgata acacattatt ttgacacaaa tgggcagatc tagcaattta 6060
actctggagt ccttcaagac tgctgttctt acgaagttca cgtccctgaa tcatgttcct 6120
gtatggaagc ctgaaagacc tcaaattcta aaaggtggcg ataaattgaa ggtttacaaa 6180
atataccctg cgggcttgac acagaggcaa gctctttata ccttccagtt caacggggat 6240
gttgatttca gaagtcactt ggagagcaat ccttgtgcca agtttgaagt aatttttgtg 6300
tagcatatgt tgagctacct acaatttaca tgatcaccta gcattagctc tttcacttaa 6360
ctgagagaat gaagttttag gaatgagtat gaccatggag tcggcatggc tttgtaatgc 6420
ctaccctact ttggccaact catcggggat ttacattcag aaaatataca tgacttcaac 6480
catacttaaa cccctttttg taagataact gaatgttcat atttaatgtt gggttgtagt 6540
gtttttactt gattatatcc agacagttac aagttggaca acaagattgt gggtctgtac 6600
tgttatttat ttattttttt tttagcagaa acaccttatc ttttgtttcg tttgaatgta 6660
gaatgaaaat aaaagaaaga aaatataaca tcatcggccg cgcttgtcta atttcgggca 6720
gttaggatcc tctccggtca ccggaaagtt tcagtagaag aaacaaaaca ccgtgactaa 6780
aatgatacta ttattttatt tattgtgttt ttcttttttc taccggaact ttttagaacg 6840
gatcccaact cgttccgggg ccgctacaac tgaaacaaaa gaagatattt tctctctctt 6900
cagaaatgta agttttcctt tacagatacc cattcaccat ttgattcaga tgtggtgact 6960
agagataaag catactaatt tgactcttgg aaacccataa agtttatgtt atccgtgttc 7020
tggaccaatc cacttggggg cataacctgt gtctatgtgt ggtttggttt ccattctgat 7080
ttatgcggcg acttgtaatt taaaatctag gaggggcaga cattgaacaa tcccaatatt 7140
ttaataactt atgcaagatt ttttttatta atgagatgat gtgtttgtga ctgagattga 7200
gtcatacatt tcactaagaa atggttccaa gtaccaaact atcatgaccc agttgcaaac 7260
atgacgttcg ggagtggtca ctttgatagt tcaatttcat cttggcttct tattcctttt 7320
ataattctaa ttcttcttgt gtaaactatt tcatgtatta tttttcttta aaatttacat 7380
gtcatttatt ttgcctcact aactcaattt tgcatataac aatgataagt gatattttga 7440
ctcacaaaat ttacatcaaa tttcgacatc gtttattatg ttcattggat gattaacaaa 7500
tataacaaac tttgcaacta attaaccacc aactgaatat aattaactat aactgtgaaa 7560
gtagttaact catttttata tttcatagat caaataagag aaataacggt atattaatcc 7620
ctccaaaaaa aaaaaacggt atatttacta aaaaatctaa gccacgtagg aggataacag 7680
gatccccgta ggaggataac atccaatcca accaatcaca acaatcctga tgagataacc 7740
cactttaagc ccacgcatct gtggcacatc tacattatct aaatcacaca ttcttccaca 7800
catctgagcc acacaaaaac caatccacat ctttatcacc cattctataa aaaatcacac 7860
tttgtgagtc tacactttga ttcccttcaa acacatacaa agagaagaga ctaattaatt 7920
aattaatcat cttgagagaa aatgtttggg cgcggaccaa caaggaagag tgataacacc 7980
aaatattacg atattcttgg tgtttcaaaa agtgctagtg aagatgaaat caagaaagcc 8040
tatagaaagg cagcgatgaa gaaccatcca gataagggtg gggatcctga gaagttcaag 8100
gagttgggcc aagcatatga agtgttgagc gatcctgaaa agaaagaact gtatgatcaa 8160
tatggtgaag atgcccttaa agaaggaatg gggggaggcg caggaagctc atttcataat 8220
ccgtttgata ttttcgaatc attttttggt gcaggctttg gtggtggtgg tccttcacgc 8280
gcaagaagac agaagcaagg agaagatgtg gtgcattcta taaaggtttc cttggaggat 8340
gtgtataacg gcactacaaa gaagctatca ctttctagga atgcactgtg ctcaaaatgt 8400
aaagggaaag gttcaaaaag tggaactgct ggaaggtgtt ttggatgcca gggcacaggt 8460
atgaagatta ccagaaggca aattggactg ggcatgattc aacaaatgca acacgtctgt 8520
cctgactgca aaggaacagg cgaggtcatt agtgagagag atagatgccc tcaatgcaag 8580
ggaaacaaga ttactcaaga aaagaaggtg ctggaggtgc atgtggaaaa ggggatgcag 8640
cagggtcaca agattgtatt cgaaggacaa gctgatgaag ctcctgatac aatcacagga 8700
gacatagttt ttgtcttgca agtaaaggga catccgaagt ttcggaggga gcgtgatgac 8760
ctccacattg aacacaattt gagcttaact gaggctctct gtggcttcca gtttaatgtc 8820
acacatcttg atggaaggca actattggtc aaatcgaacc ccggcgaagt catcaagcca 8880
ggtcaacata aagctataaa tgatgaggga atgccacaac atggtaggcc gttcatgaag 8940
ggacgcctat acatcaagtt tagtgttgat ttcccggatt cgggttttct ttccccaagc 9000
caaagcctgg aattagaaaa gatattacct caaaagacaa gcaagaactt gtcccaaaag 9060
gaggtagatg attgtgagga gaccaccctg catgatgtca atattgcaga ggagatgagt 9120
cgaaagaagc aacaataccg tgaggcatat gatgacgatg atgatgaaga tgatgagcac 9180
tcgcagcctc gggtgcaatg cgctcaacag taggagctca gctcgaattt ccccgatcgt 9240
tcaaacattt ggcaataaag tttcttaaga ttgaatcctg ttgccggtct tgcgatgatt 9300
atcatataat ttctgttgaa ttacgttaag catgtaataa ttaacatgta atgcatgacg 9360
ttatttatga gatgggtttt tatgattaga gtcccgcaat tatacattta atacgcgata 9420
gaaaacaaaa tatagcgcgc aaactaggat aaattatcgc gcgcggtgtc atctatgtta 9480
ctagatcgaa ttc 9493

<210> SEQ ID NO 124
<211> LENGTH: 34
<212> TYPE: DNA
<213> ORGANISM: Artificial sequence
<220> FEATURE:
<223> OTHER INFORMATION: supP19-plasto.r

<400> SEQUENCE: 124
ccttgtatag ctcgttccat ttctctcaa gatg 34

<210> SEQ ID NO 125
<211> LENGTH: 20
<212> TYPE: DNA
<213> ORGANISM: Artificial sequence
<220> FEATURE:
<223> OTHER INFORMATION: supP19-1c

<400> SEQUENCE: 125
atggaacgag ctatacaagg 20

<210> SEQ ID NO 126
<211> LENGTH: 32
<212> TYPE: DNA
<213> ORGANISM: Artificial sequence
<220> FEATURE:
<223> OTHER INFORMATION: SupP19-SacI.r

<400> SEQUENCE: 126
agtcgagctc ttactcgctt tctttttcga ag 32

<210> SEQ ID NO 127
<211> LENGTH: 3462
<212> TYPE: DNA
<213> ORGANISM: Artificial
<220> FEATURE:
<223> OTHER INFORMATION: A/California/04/09 (cassette number 560)

<400> SEQUENCE: 127
gtcaacatgg tggagcacga cacacttgtc tactccaaaa atatcaaaga tacagtctca 60
gaagaccaaa gggcaattga gacttttcaa caaagggtaa tatccggaaa cctcctcgga 120

-continued

```
ttccattgcc cagctatctg tcactttatt gtgaagatag tggaaaagga aggtggctcc    180
tacaaatgcc atcattgcga taaaggaaag gccatcgttg aagatgcctc tgccgacagt    240
ggtcccaaag atggaccccc acccacgagg agcatcgtgg aaaaagaaga cgttccaacc    300
acgtcttcaa agcaagtgga ttgatgtgat aacatggtgg agcacgacac acttgtctac    360
tccaaaaata tcaaagatac agtctcagaa gaccaaaggg caattgagac ttttcaacaa    420
agggtaatat ccggaaacct cctcggattc cattgcccag ctatctgtca ctttattgtg    480
aagatagtgg aaaaggaagg tggctcctac aaatgccatc attgcgataa aggaaaggcc    540
atcgttgaag atgcctctgc cgacagtggt cccaaagatg gacccccacc cacgaggagc    600
atcgtggaaa aagaagacgt tccaaccacg tcttcaaagc aagtggattg atgtgatatc    660
tccactgacg taagggatga cgcacaatcc cactatcctt cgcaagaccc ttcctctata    720
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaacg ttttctttca ctgaagcgaa atcaaagatc tctttgtgga cacgtagtgc    960
ggcgccatta aataacgtgt acttgtccta ttcttgtcgg tgtggtcttg ggaaaagaaa   1020
gcttgctgga ggctgctgtt cagccccata cattacttgt tacgattctg ctgactttcg   1080
gcgggtgcaa tatctctact tctgcttgac gaggtattgt tgcctgtact tctttcttct   1140
tcttcttgct gattggttct ataagaaatc tagtattttc tttgaaacag agttttcccg   1200
tggttttcga acttggagaa agattgttaa gcttctgtat attctgccca aatttgtcgg   1260
gcccatggcg aaaaacgttg cgattttcgg cttattgttt tctcttcttg tgttggttcc   1320
ttctcagatc ttcgctgaca cattatgtat aggttatcat gcgaacaatt caacagacac   1380
tgtagacaca gtactagaaa agaatgtaac agtaacacac tctgttaacc ttctagaaga   1440
caagcataac gggaaactat gcaaactaag aggggtagcc ccattgcatt tgggtaaatg   1500
taacattgct ggctggatcc tgggaaatcc agagtgtgaa tcactctcca cagcaagctc   1560
atggtcctac attgtggaaa cacctagttc agacaatgga acgtgttacc caggagattt   1620
catcgattat gaggagctaa gagagcaatt aagctcagtg tcatcatttg aaaggtttga   1680
gatattcccc aagacaagtt catggcccaa tcatgactcg aacaaaggtg taacggcagc   1740
atgtcctcat gctggagcaa aaagcttcta caaaaattta atatggctag ttaaaaaagg   1800
aaattcatac ccaaagctca gcaaatccta cattaatgat aaagggaaag aagtcctcgt   1860
gctatggggc attcaccatc catctactag tgctgaccaa caaagtctct atcagaatgc   1920
agatacatat gtttttgtgg ggtcatcaag atacagcaag aagttcaagc cggaaatagc   1980
aataagaccc aaagtgaggg atcaagaagg gagaatgaac tattactgga cactagtaga   2040
gccgggagac aaaataacat tcgaagcaac tggaaatcta gtggtaccga gatatgcatt   2100
cgcaatggaa agaaatgctg gatctggtat tatcatttca gatacaccag tccacgattg   2160
caatacaact tgtcaaacac ccaagggtgc tataaacacc agcctcccat ttcagaatat   2220
acatccgatc acaattggaa aatgtccaaa atatgtaaaa agcacaaaat tgagactggc   2280
cacaggattg aggaatatcc cgtctattca atctagagga ctatttgggg ccattgccgg   2340
tttcattgaa ggggggtgga cagggatggt agatggatgg tacggttatc accatcaaaa   2400
tgagcagggg tcaggatatg cagccgacct gaagagcaca cagaatgcca ttgacgagat   2460
tactaacaaa gtaaattctg ttattgaaaa gatgaataca cagttcacag cagtaggtaa   2520
```

agagttcaac cacctggaaa aaagaataga gaatttaaat aaaaaagttg atgatggttt 2580
cctggacatt tggacttaca atgccgaact gttggttcta ttggaaaatg aaagaacttt 2640
ggactaccac gattcaaatg tgaagaactt atatgaaaag gtaagaagcc agctaaaaaa 2700
caatgccaag gaaattggaa acggctgctt tgaattttac cacaaatgcg ataacacgtg 2760
catggaaagt gtcaaaaatg ggacttatga ctacccaaaa tactcagagg aagcaaaatt 2820
aaacagagaa gaaatagatg gggtaaagct ggaatcaaca aggatttacc agattttggc 2880
gatctattca actgtcgcca gttcattggt actggtagtc tccctggggg caatcagttt 2940
ctggatgtgc tctaatgggt ctctacagtg tagaatatgt atttaaaggc ctattttctt 3000
tagtttgaat ttactgttat tcggtgtgca tttctatgtt tggtgagcgg ttttctgtgc 3060
tcagagtgtg tttattttat gtaatttaat ttctttgtga gctcctgttt agcaggtcgt 3120
cccttcagca aggacacaaa aagattttaa ttttattaaa aaaaaaaaaa aaaaagaccg 3180
ggaattcgat atcaagctta tcgacctgca gatcgttcaa acatttggca ataaagtttc 3240
ttaagattga atcctgttgc cggtcttgcg atgattatca tataatttct gttgaattac 3300
gttaagcatg taataattaa catgtaatgc atgacgttat ttatgagatg ggtttttatg 3360
attagagtcc cgcaattata catttaatac gcgatagaaa acaaaatata gcgcgcaaac 3420
taggataaat tatcgcgcgc ggtgtcatct atgttactag at 3462

<210> SEQ ID NO 128
<211> LENGTH: 573
<212> TYPE: PRT
<213> ORGANISM: Artificial sequence
<220> FEATURE:
<223> OTHER INFORMATION: A/California/04/09

<400> SEQUENCE: 128

Met Ala Lys Asn Val Ala Ile Phe Gly Leu Leu Phe Ser Leu Leu Val
1 5 10 15

Leu Val Pro Ser Gln Ile Phe Ala Asp Thr Leu Cys Ile Gly Tyr His
20 25 30

Ala Asn Asn Ser Thr Asp Thr Val Asp Thr Val Leu Glu Lys Asn Val
35 40 45

Thr Val Thr His Ser Val Asn Leu Leu Glu Asp Lys His Asn Gly Lys
50 55 60

Leu Cys Lys Leu Arg Gly Val Ala Pro Leu His Leu Gly Lys Cys Asn
65 70 75 80

Ile Ala Gly Trp Ile Leu Gly Asn Pro Glu Cys Glu Ser Leu Ser Thr
85 90 95

Ala Ser Ser Trp Ser Tyr Ile Val Glu Thr Pro Ser Ser Asp Asn Gly
100 105 110

Thr Cys Tyr Pro Gly Asp Phe Ile Asp Tyr Glu Glu Leu Arg Glu Gln
115 120 125

Leu Ser Ser Val Ser Ser Phe Glu Arg Phe Glu Ile Phe Pro Lys Thr
130 135 140

Ser Ser Trp Pro Asn His Asp Ser Asn Lys Gly Val Thr Ala Ala Cys
145 150 155 160

Pro His Ala Gly Ala Lys Ser Phe Tyr Lys Asn Leu Ile Trp Leu Val
165 170 175

Lys Lys Gly Asn Ser Tyr Pro Lys Leu Ser Lys Ser Tyr Ile Asn Asp
180 185 190

```
Lys Gly Lys Glu Val Leu Val Leu Trp Gly Ile His His Pro Ser Thr
        195                 200                 205

Ser Ala Asp Gln Gln Ser Leu Tyr Gln Asn Ala Asp Thr Tyr Val Phe
    210                 215                 220

Val Gly Ser Ser Arg Tyr Ser Lys Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Ala Met Glu Arg Asn Ala Gly Ser Gly
        275                 280                 285

Ile Ile Ile Ser Asp Thr Pro Val His Asp Cys Asn Thr Thr Cys Gln
    290                 295                 300

Thr Pro Lys Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Ile Pro Ser Ile Gln Ser Arg Gly
            340                 345                 350

Leu Phe Gly Ala Ile Ala Gly Phe Ile Glu Gly Gly Trp Thr Gly Met
        355                 360                 365

Val Asp Gly Trp Tyr Gly Tyr His His Gln Asn Glu Gln Gly Ser Gly
    370                 375                 380

Tyr Ala Ala Asp Leu Lys Ser Thr Gln Asn Ala Ile Asp Glu Ile Thr
385                 390                 395                 400

Asn Lys Val Asn Ser Val Ile Glu Lys Met Asn Thr Gln Phe Thr Ala
                405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
        435                 440                 445

Leu Leu Val Leu Leu Glu Asn Glu Arg Thr Leu Asp Tyr His Asp Ser
    450                 455                 460

Asn Val Lys Asn Leu Tyr Glu Lys Val Arg Ser Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Glu Ile Asp Gly Val Lys
        515                 520                 525

Leu Glu Ser Thr Arg Ile Tyr Gln Ile Leu Ala Ile Tyr Ser Thr Val
    530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570
```

<210> SEQ ID NO 129
<211> LENGTH: 747
<212> TYPE: DNA
<213> ORGANISM: Artificial sequence
<220> FEATURE:
<223> OTHER INFORMATION: 2X35S promoter

<400> SEQUENCE: 129
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540
atcgttgaag atgcctctgc cgacagtggt cccaaagatg gacccccacc cacgaggagc 600
atcgtggaaa aagaagacgt tccaaccacg tcttcaaagc aagtggattg atgtgatatc 660
tccactgacg taagggatga cgcacaatcc cactatcctt cgcaagaccc ttcctctata 720
taaggaagtt catttcattt ggagagg 747

<210> SEQ ID NO 130
<211> LENGTH: 43
<212> TYPE: DNA
<213> ORGANISM: Artificial sequence
<220> FEATURE:
<223> OTHER INFORMATION: primer PacI-MCS-2X35S.c

<400> SEQUENCE: 130
aattgttaat taagtcgaca agcttgcatg cctgcaggtc aac 43

<210> SEQ ID NO 131
<211> LENGTH: 48
<212> TYPE: DNA
<213> ORGANISM: Artificial sequence
<220> FEATURE:
<223> OTHER INFORMATION: primer CPMV 5'UTR-2X35S.r

<400> SEQUENCE: 131
tcaaaaccta ttaagatttt aatacctctc caaatgaaat gaacttcc 48

<210> SEQ ID NO 132
<211> LENGTH: 49
<212> TYPE: DNA
<213> ORGANISM: Artificial sequence
<220> FEATURE:
<223> OTHER INFORMATION: primer 2X35S-CPMV 5'UTR.c

<400> SEQUENCE: 132
ttggagaggt attaaaatct taataggttt tgataaaagc gaacgtggg 49

<210> SEQ ID NO 133
<211> LENGTH: 44
<212> TYPE: DNA
<213> ORGANISM: Artificial sequence
<220> FEATURE:
<223> OTHER INFORMATION: primer ApaI-M prot.r

<400> SEQUENCE: 133
tctccatggg cccgacaaat ttgggcagaa tatacagaag ctta 44

<210> SEQ ID NO 134

<211> LENGTH: 3505
<212> TYPE: DNA
<213> ORGANISM: Artificial sequence
<220> FEATURE:
<223> OTHER INFORMATION: expression cassette number 972

<400> SEQUENCE: 134

```
ttaattaagt cgacaagctt gcatgcctgc aggtcaacat ggtggagcac gacacacttg     60
tctactccaa aaatatcaaa gatacagtct cagaagacca aagggcaatt gagacttttc    120
aacaaagggt aatatccgga aacctcctcg gattccattg cccagctatc tgtcacttta    180
ttgtgaagat agtggaaaag gaaggtggct cctacaaatg ccatcattgc gataaaggaa    240
aggccatcgt tgaagatgcc tctgccgaca gtggtcccaa agatggaccc ccacccacga    300
ggagcatcgt ggaaaaagaa gacgttccaa ccacgtcttc aaagcaagtg gattgatgtg    360
ataacatggt ggagcacgac acacttgtct actccaaaaa tatcaaagat acagtctcag    420
aagaccaaag ggcaattgag acttttcaac aaagggtaat atccggaaac ctcctcggat    480
tccattgccc agctatctgt cactttattg tgaagatagt ggaaaaggaa ggtggctcct    540
acaaatgcca tcattgcgat aaaggaaagg ccatcgttga agatgcctct gccgacagtg    600
gtcccaaaga tggaccccca cccacgagga gcatcgtgga aaaagaagac gttccaacca    660
cgtcttcaaa gcaagtggat tgatgtgata tctccactga cgtaagggat gacgcacaat    720
cccactatcc ttcgcaagac ccttcctcta tataaggaag ttcatttcat ttggagaggt    780
attaaaatct taataggttt tgataaaagc gaacgtgggg aaacccgaac caaaccttct    840
tctaaactct ctctcatctc tcttaaagca aacttctctc ttgtctttct tgcgtgagcg    900
atcttcaacg ttgtcagatc gtgcttcggc accagtacaa cgttttcttt cactgaagcg    960
aaatcaaaga tctctttgtg gacacgtagt gcggcgccat taaataacgt gtacttgtcc   1020
tattcttgtc ggtgtggtct tgggaaaaga aagcttgctg gaggctgctg ttcagcccca   1080
tacattactt gttacgattc tgctgacttt cggcgggtgc aatatctcta cttctgcttg   1140
acgaggtatt gttgcctgta cttctttctt cttcttcttg ctgattggtt ctataagaaa   1200
tctagtattt tctttgaaac agagttttcc cgtggttttc gaacttggag aaagattgtt   1260
aagcttctgt atattctgcc caaatttgtc gggcccatgg agaaaatagt gcttcttctt   1320
gcaatagtca gtcttgttaa aagtgatcag atttgcattg gttaccatgc aaacaattca   1380
acagagcagg ttgacacaat catggaaaag aacgttactg ttacacatgc ccaagacata   1440
ctggaaaaga cacacaacgg gaagctctgc gatctagatg gagtgaagcc tctaatttta   1500
agagattgta gtgtagctgg atggctcctc gggaacccaa tgtgtgacga attcatcaat   1560
gtaccggaat ggtcttacat agtggagaag gccaatccaa ccaatgacct ctgttaccca   1620
gggagtttca acgactatga agaactgaaa cacctattga gcagaataaa ccattttgag   1680
aaaattcaaa tcatccccaa aagttcttgg tccgatcatg aagcctcatc aggagttagc   1740
tcagcatgtc catacctggg aagtccctcc ttttttagaa atgtggtatg gcttatcaaa   1800
aagaacagta catacccaac aataaagaaa agctacaata ataccaacca agaggatctt   1860
ttggtactgt ggggaattca ccatcctaat gatgcggcag agcagacaag gctatatcaa   1920
aacccaacca cctatatttc cattgggaca tcaacactaa accagagatt ggtaccaaaa   1980
atagctacta gatccaaagt aaacgggcaa agtggaagga tggagttctt ctggacaatt   2040
ttaaaaccta atgatgcaat caacttcgag agtaatggaa atttcattgc tccagaatat   2100
gcatacaaaa ttgtcaagaa aggggactca gcaattatga aaagtgaatt ggaatatggt   2160
```

```
aactgcaaca ccaagtgtca aactccaatg ggggcgataa actctagtat gccattccac   2220
aacatacacc ctctcaccat cggggaatgc cccaaatatg tgaaatcaaa cagattagtc   2280
cttgcaacag ggctcagaaa tagccctcaa agagagagca gaagaaaaaa gagaggacta   2340
tttggagcta tagcaggttt tatagaggga ggatggcagg gaatggtaga tggttggtat   2400
gggtaccacc atagcaatga gcaggggagt gggtacgctg cagacaaaga atccactcaa   2460
aaggcaatag atggagtcac caataaggtc aactcaatca ttgacaaaat gaacactcag   2520
tttgaggccg ttggaaggga atttaataac ttagaaagga gaatagagaa tttaaacaag   2580
aagatggaag acgggtttct agatgtctgg acttataatg ccgaacttct ggttctcatg   2640
gaaaatgaga gaactctaga ctttcatgac tcaaatgtta agaacctcta cgacaaggtc   2700
cgactacagc ttagggataa tgcaaaggag ctgggtaacg gttgtttcga gttctatcac   2760
aaatgtgata atgaatgtat ggaaagtata agaaacggaa cgtacaacta tccgcagtat   2820
tcagaagaag caagattaaa aagagaggaa ataagtgggg taaaattgga atcaatagga   2880
acttaccaaa tactgtcaat ttattcaaca gtggcgagtt ccctagcact ggcaatcatg   2940
atggctggtc tatctttatg gatgtgctcc aatggatcgt tacaatgcag aatttgcatt   3000
taaaggccta ttttctttag tttgaattta ctgttattcg gtgtgcattt ctatgtttgg   3060
tgagcggttt tctgtgctca gagtgtgttt attttatgta atttaatttc tttgtgagct   3120
cctgtttagc aggtcgtccc ttcagcaagg acacaaaaag attttaattt tattaaaaaa   3180
aaaaaaaaaa aagaccggga attcgatatc aagcttatcg acctgcagat cgttcaaaca   3240
tttggcaata aagtttctta agattgaatc ctgttgccgg tcttgcgatg attatcatat   3300
aatttctgtt gaattacgtt aagcatgtaa taattaacat gtaatgcatg acgttattta   3360
tgagatgggt ttttatgatt agagtcccgc aattatacat ttaatacgcg atagaaaaca   3420
aaatatagcg cgcaaactag gataaattat cgcgcgcggt gtcatctatg ttactagatt   3480
ctagagtctc aagcttcggc gcgcc                                         3505
```

<210> SEQ ID NO 135
<211> LENGTH: 1701
<212> TYPE: DNA
<213> ORGANISM: Influenza virus

<400> SEQUENCE: 135

```
atgaaggcaa tactagtagt tctgctatat acatttgcaa ccgcaaatgc agacacatta     60
tgtataggtt atcatgcgaa caattcaaca gacactgtag acacagtact agaaaagaat    120
gtaacagtaa cacactctgt taaccttcta gaagacaagc ataacgggaa actatgcaaa    180
ctaagagggg tagccccatt gcatttgggt aaatgtaaca ttgctggctg gatcctggga    240
aatccagagt gtgaatcact ctccacagca agctcatggt cctacattgt ggaaacacct    300
agttcagaca atggaacgtg ttacccagga gatttcatcg attatgagga gctaagagag    360
caattgagct cagtgtcatc atttgaaagg tttgagatat tccccaagac aagttcatgg    420
cccaatcatg actcgaacaa aggtgtaacg gcagcatgtc ctcatgctgg agcaaaaagc    480
ttctacaaaa atttaatatg gctagttaaa aaaggaaatt catacccaaa gctcagcaaa    540
tcctacatta atgataaagg gaaagaagtc ctcgtgctat ggggcattca ccatccatct    600
actagtgctg accaacaaag tctctatcag aatgcagata catatgtttt tgtggggtca    660
tcaagataca gcaagaagtt caagccggaa atagcaataa gacccaaagt gagggatcaa    720
```

```
gaagggagaa tgaactatta ctggacacta gtagagccgg gagacaaaat aacattcgaa    780

gcaactggaa atctagtggt accgagatat gcattcgcaa tggaaagaaa tgctggatct    840

ggtattatca tttcagatac accagtccac gattgcaata caacttgtca aacacccaag    900

ggtgctataa acaccagcct cccatttcag aatatacatc cgatcacaat tggaaaatgt    960

ccaaaatatg taaaaagcac aaaattgaga ctggccacag gattgaggaa tatcccgtct   1020

attcaatcta gaggcctatt tggggccatt gccggtttca ttgaaggggg gtggacaggg   1080

atggtagatg gatggtacgg ttatcaccat caaaatgagc aggggtcagg atatgcagcc   1140

gacctgaaga gcacacagaa tgccattgac gagattacta acaaagtaaa ttctgttatt   1200

gaaaagatga atacacagtt cacagcagta ggtaaagagt tcaaccacct ggaaaaaaga   1260

atagagaatt taaataaaaa agttgatgat ggtttcctgg acatttggac ttacaatgcc   1320

gaactgttgg ttctattgga aaatgaaaga actttggact accacgattc aaatgtgaag   1380

aacttatatg aaaaggtaag aagccagcta aaaaacaatg ccaaggaaat tggaaacggc   1440

tgctttgaat tttaccacaa atgcgataac acgtgcatgg aaagtgtcaa aaatgggact   1500

tatgactacc caaaatactc agaggaagca aaattaaaca gagaagaaat agatggggta   1560

aagctggaat caacaaggat ttaccagatt ttggcgatct attcaactgt cgccagttca   1620

ttggtactgg tagtctccct gggggcaatc agtttctgga tgtgctctaa tgggtctcta   1680

cagtgtagaa tatgtattta a                                             1701
```

```
<210> SEQ ID NO 136
<211> LENGTH: 2056
<212> TYPE: DNA
<213> ORGANISM: Artificial sequence
<220> FEATURE:
<223> OTHER INFORMATION: to be synthesized containing H1
      A/California/4/2009

<400> SEQUENCE: 136
```

```
atgctaatat cacgtagtgc ggcgccatta aataacgtgt acttgtccta ttcttgtcgg     60

tgtggtcttg ggaaaagaaa gcttgctgga ggctgctgtt cagccccata cattacttgt    120

tacgattctg ctgactttcg gcgggtgcaa tatctctact tctgcttgac gaggtattgt    180

tgcctgtact tctttcttct tcttcttgct gattggttct ataagaaatc tagtattttc    240

tttgaaacag agttttcccg tggttttcga acttggagaa agattgttaa gcttctgtat    300

attctgccca aatttgtcgg gcccatggcg aaaaacgttg cgattttcgg cttattgttt    360

tctcttcttg tgttggttcc ttctcagatc ttcgctgaca cattatgtat aggttatcat    420

gcgaacaatt caacagacac tgtagacaca gtactagaaa agaatgtaac agtaacacac    480

tctgttaacc ttctagaaga caagcataac gggaaactat gcaaactaag aggggtagcc    540

ccattgcatt tgggtaaatg taacattgct ggctggatcc tgggaaatcc agagtgtgaa    600

tcactctcca cagcaagctc atggtcctac attgtggaaa cacctagttc agacaatgga    660

acgtgttacc caggagattt catcgattat gaggagctaa gagagcaatt aagctcagtg    720

tcatcatttg aaaggtttga gatattcccc aagacaagtt catggcccaa tcatgactcg    780

aacaaaggtg taacggcagc atgtcctcat gctggagcaa aaagcttcta caaaaattta    840

atatggctag ttaaaaaagg aaattcatac ccaaagctca gcaaatccta cattaatgat    900

aaagggaaag aagtcctcgt gctatggggc attcaccatc catctactag tgctgaccaa    960

caaagtctct atcagaatgc agatacatat gtttttgtgg ggtcatcaag atacagcaag   1020
```

-continued

```
aagttcaagc cggaaatagc aataagaccc aaagtgaggg atcaagaagg gagaatgaac   1080

tattactgga cactagtaga gccgggagac aaaataacat tcgaagcaac tggaaatcta   1140

gtggtaccga gatatgcatt cgcaatggaa agaaatgctg gatctggtat tatcatttca   1200

gatacaccag tccacgattg caatacaact tgtcaaacac ccaagggtgc tataaacacc   1260

agcctcccat ttcagaatat acatccgatc acaattggaa aatgtccaaa atatgtaaaa   1320

agcacaaaat tgagactggc cacaggattg aggaatatcc cgtctattca atctagagga   1380

ctatttgggg ccattgccgg tttcattgaa ggggggtgga cagggatggt agatggatgg   1440

tacggttatc accatcaaaa tgagcagggg tcaggatatg cagccgacct gaagagcaca   1500

cagaatgcca ttgacgagat tactaacaaa gtaaattctg ttattgaaaa gatgaataca   1560

cagttcacag cagtaggtaa agagttcaac cacctggaaa aaagaataga gaatttaaat   1620

aaaaaagttg atgatggttt cctggacatt tggacttaca atgccgaact gttggttcta   1680

ttggaaaatg aaagaacttt ggactaccac gattcaaatg tgaagaactt atatgaaaag   1740

gtaagaagcc agctaaaaaa caatgccaag gaaattggaa acggctgctt tgaattttac   1800

cacaaatgcg ataacacgtg catggaaagt gtcaaaaatg ggacttatga ctacccaaaa   1860

tactcagagg aagcaaaatt aaacagagaa gaaatagatg gggtaaagct ggaatcaaca   1920

aggatttacc agattttggc gatctattca actgtcgcca gttcattggt actggtagtc   1980

tccctggggg caatcagttt ctggatgtgc tctaatgggt ctctacagtg tagaatatgt   2040

atttaaaggc ctaata                                                   2056
```

<210> SEQ ID NO 137
<211> LENGTH: 714
<212> TYPE: DNA
<213> ORGANISM: Artificial sequence
<220> FEATURE:
<223> OTHER INFORMATION: synthesized fragment 1

<400> SEQUENCE: 137

```
atgctaatat cacgtagtgc ggcgccatta aataacgtgt acttgtccta ttcttgtcgg     60

tgtggtcttg ggaaaagaaa gcttgctgga ggctgctgtt cagccccata cattacttgt    120

tacgattctg ctgactttcg gcgggtgcaa tatctctact tctgcttgac gaggtattgt    180

tgcctgtact tctttcttct tcttcttgct gattggttct ataagaaatc tagtattttc    240

tttgaaacag agttttcccg tggttttcga acttggagaa agattgttaa gcttctgtat    300

attctgccca aatttgtcgg gcccatggcg aaaaacgttg cgatttttcgg cttattgttt    360

tctcttcttg tgttggttcc ttctcagatc ttcgctgaca cattatgtat aggttatcat    420

gcgaacaatt caacagacac tgtagacaca gtactagaaa agaatgtaac agtaacacac    480

tctgttaacc ttctagaaga caagcataac gggaaactat gcaaactaag aggggtagcc    540

ccattgcatt tgggtaaatg taacattgct ggctggatcc tgggaaatcc agagtgtgaa    600

tcactctcca cagcaagctc atggtcctac attgtggaaa cacctagttc agacaatgga    660

acgtgttacc caggagattt catcgattat gaggagctaa gagagcaatt aagc          714
```

<210> SEQ ID NO 138
<211> LENGTH: 849
<212> TYPE: DNA
<213> ORGANISM: Artificial sequence
<220> FEATURE:
<223> OTHER INFORMATION: synthesized fragment 2

<400> SEQUENCE: 138

```
tggaaacacc tagttcagac aatggaacgt gttacccagg agatttcatc gattatgagg     60
agctaagaga gcaattaagc tcagtgtcat catttgaaag gtttgagata ttccccaaga    120
caagttcatg gcccaatcat gactcgaaca aaggtgtaac ggcagcatgt cctcatgctg    180
gagcaaaaag cttctacaaa aatttaatat ggctagttaa aaaaggaaat tcatacccaa    240
agctcagcaa atcctacatt aatgataaag ggaaagaagt cctcgtgcta tggggcattc    300
accatccatc tactagtgct gaccaacaaa gtctctatca gaatgcagat acatatgttt    360
ttgtggggtc atcaagatac agcaagaagt tcaagccgga aatagcaata agacccaaag    420
tgagggatca agaagggaga atgaactatt actggacact agtagagccg ggagacaaaa    480
taacattcga agcaactgga aatctagtgg taccgagata tgcattcgca atggaaagaa    540
atgctggatc tggtattatc atttcagata caccagtcca cgattgcaat acaacttgtc    600
aaacacccaa gggtgctata aacaccagcc tcccatttca gaatatacat ccgatcacaa    660
ttggaaaatg tccaaaatat gtaaaaagca caaaattgag actggccaca ggattgagga    720
atatcccgtc tattcaatct agaggactat ttggggccat tgccggtttc attgaagggg    780
ggtggacagg gatggtagat ggatggtacg gttatcacca tcaaaatgag caggggtcag    840
gatatgcag                                                            849
```

<210> SEQ ID NO 139
<211> LENGTH: 651
<212> TYPE: DNA
<213> ORGANISM: Artificial sequence
<220> FEATURE:
<223> OTHER INFORMATION: synthesized fragment 3

<400> SEQUENCE: 139

```
ttgaaggggg gtggacaggg atggtagatg gatggtacgg ttatcaccat caaaatgagc     60
aggggtcagg atatgcagcc gacctgaaga gcacacagaa tgccattgac gagattacta    120
acaaagtaaa ttctgttatt gaaaagatga atacacagtt cacagcagta ggtaaagagt    180
tcaaccacct ggaaaaaaga atagagaatt taaataaaaa agttgatgat ggtttcctgg    240
acatttggac ttacaatgcc gaactgttgg ttctattgga aaatgaaaga actttggact    300
accacgattc aaatgtgaag aacttatatg aaaaggtaag aagccagcta aaaaacaatg    360
ccaaggaaat tggaaacggc tgctttgaat tttaccacaa atgcgataac acgtgcatgg    420
aaagtgtcaa aaatgggact tatgactacc caaaatactc agaggaagca aaattaaaca    480
gagaagaaat agatggggta aagctggaat caacaaggat ttaccagatt ttggcgatct    540
attcaactgt cgccagttca ttggtactgg tagtctccct gggggcaatc agtttctgga    600
tgtgctctaa tgggtctcta cagtgtagaa tatgtattta aaggcctaat a             651
```

<210> SEQ ID NO 140
<211> LENGTH: 48
<212> TYPE: DNA
<213> ORGANISM: Artificial sequence
<220> FEATURE:
<223> OTHER INFORMATION: primer DraIII-MProt#2.c

<400> SEQUENCE: 140

```
atgctaatat cacgtagtgc ggcgccatta aataacgtgt acttgtcc                  48
```

<210> SEQ ID NO 141
<211> LENGTH: 42
<212> TYPE: DNA
<213> ORGANISM: Artificial sequence
<220> FEATURE:
<223> OTHER INFORMATION: primer H1 Cal.390r

<400> SEQUENCE: 141
gcttaattgc tctcttagct cctcataatc gatgaaatct cc 42

<210> SEQ ID NO 142
<211> LENGTH: 42
<212> TYPE: DNA
<213> ORGANISM: Artificial sequence
<220> FEATURE:
<223> OTHER INFORMATION: primer H1 Cal.310c

<400> SEQUENCE: 142
tggaaacacc tagttcagac aatggaacgt gttacccagg ag 42

<210> SEQ ID NO 143
<211> LENGTH: 42
<212> TYPE: DNA
<213> ORGANISM: Artificial sequence
<220> FEATURE:
<223> OTHER INFORMATION: primer H1 Cal.1159r

<400> SEQUENCE: 143
ctgcatatcc tgacccctgc tcattttgat ggtgataacc gt 42

<210> SEQ ID NO 144
<211> LENGTH: 42
<212> TYPE: DNA
<213> ORGANISM: Artificial sequence
<220> FEATURE:
<223> OTHER INFORMATION: primer H1 Cal.1081c

<400> SEQUENCE: 144
ttgaaggggg gtggacaggg atggtagatg gatggtacgg tt 42

<210> SEQ ID NO 145
<211> LENGTH: 45
<212> TYPE: DNA
<213> ORGANISM: Artificial sequence
<220> FEATURE:
<223> OTHER INFORMATION: primer StuI-H1 Cal.r

<400> SEQUENCE: 145
tattaggcct ttaaatacat attctacact gtagagaccc attag 45

<210> SEQ ID NO 146
<211> LENGTH: 3520
<212> TYPE: DNA
<213> ORGANISM: Artificial sequence
<220> FEATURE:
<223> OTHER INFORMATION: expression cassette number 560

<400> SEQUENCE: 146
ttaattaagt cgacaagctt gcatgcctgc aggtcaacat ggtggagcac gacacacttg 60
tctactccaa aaatatcaaa gatacagtct cagaagacca aagggcaatt gagacttttc 120
aacaaagggt aatatccgga aacctcctcg gattccattg cccagctatc tgtcacttta 180
ttgtgaagat agtggaaaag gaaggtggct cctacaaatg ccatcattgc gataaaggaa 240
aggccatcgt tgaagatgcc tctgccgaca gtggtcccaa agatggaccc ccacccacga 300
ggagcatcgt ggaaaaagaa gacgttccaa ccacgtcttc aaagcaagtg gattgatgtg 360
ataacatggt ggagcacgac acacttgtct actccaaaaa tatcaaagat acagtctcag 420

-continued

```
aagaccaaag ggcaattgag acttttcaac aaagggtaat atccggaaac ctcctcggat    480
tccattgccc agctatctgt cactttattg tgaagatagt ggaaaaggaa ggtggctcct    540
acaaatgcca tcattgcgat aaaggaaagg ccatcgttga agatgcctct gccgacagtg    600
gtcccaaaga tggaccccca cccacgagga gcatcgtgga aaaagaagac gttccaacca    660
cgtcttcaaa gcaagtggat tgatgtgata tctccactga cgtaagggat gacgcacaat    720
cccactatcc ttcgcaagac ccttcctcta tataaggaag ttcatttcat ttggagaggt    780
attaaaatct taataggttt tgataaaagc gaacgtgggg aaacccgaac caaaccttct    840
tctaaactct ctctcatctc tcttaaagca aacttctctc ttgtctttct tgcgtgagcg    900
atcttcaacg ttgtcagatc gtgcttcggc accagtacaa cgttttcttt cactgaagcg    960
aaatcaaaga tctctttgtg gacacgtagt gcggcgccat taaataacgt gtacttgtcc   1020
tattcttgtc ggtgtggtct tgggaaaaga aagcttgctg gaggctgctg ttcagcccca   1080
tacattactt gttacgattc tgctgacttt cggcgggtgc aatatctcta cttctgcttg   1140
acgaggtatt gttgcctgta cttctttctt cttcttcttg ctgattggtt ctataagaaa   1200
tctagtattt tctttgaaac agagttttcc cgtggttttc gaacttggag aaagattgtt   1260
aagcttctgt atattctgcc caaatttgtc gggcccatgg cgaaaaacgt tgcgattttc   1320
ggcttattgt tttctcttct tgtgttggtt ccttctcaga tcttcgctga cacattatgt   1380
ataggttatc atgcgaacaa ttcaacagac actgtagaca cagtactaga aaagaatgta   1440
acagtaacac actctgttaa ccttctagaa gacaagcata acgggaaact atgcaaacta   1500
agaggggtag ccccattgca tttgggtaaa tgtaacattg ctggctggat cctgggaaat   1560
ccagagtgtg aatcactctc cacagcaagc tcatggtcct acattgtgga aacacctagt   1620
tcagacaatg gaacgtgtta cccaggagat ttcatcgatt atgaggagct aagagagcaa   1680
ttaagctcag tgtcatcatt tgaaaggttt gagatattcc ccaagacaag ttcatggccc   1740
aatcatgact cgaacaaagg tgtaacggca gcatgtcctc atgctggagc aaaaagcttc   1800
tacaaaaatt taatatggct agttaaaaaa ggaaattcat acccaaagct cagcaaatcc   1860
tacattaatg ataaagggaa agaagtcctc gtgctatggg gcattcacca tccatctact   1920
agtgctgacc aacaaagtct ctatcagaat gcagatacat atgtttttgt ggggtcatca   1980
agatacagca agaagttcaa gccggaaata gcaataagac ccaaagtgag ggatcaagaa   2040
gggagaatga actattactg gacactagta gagccgggag acaaaataac attcgaagca   2100
actggaaatc tagtggtacc gagatatgca ttcgcaatgg aaagaaatgc tggatctggt   2160
attatcattt cagatacacc agtccacgat tgcaatacaa cttgtcaaac acccaagggt   2220
gctataaaca ccagcctccc atttcagaat atacatccga tcacaattgg aaaatgtcca   2280
aaatatgtaa aaagcacaaa attgagactg gccacaggat tgaggaatat cccgtctatt   2340
caatctagag gactatttgg ggccattgcc ggtttcattg aaggggggtg gacagggatg   2400
gtagatggat ggtacggtta tcaccatcaa aatgagcagg ggtcaggata tgcagccgac   2460
ctgaagagca cacagaatgc cattgacgag attactaaca aagtaaattc tgttattgaa   2520
aagatgaata cacagttcac agcagtaggt aaagagttca accacctgga aaaaagaata   2580
gagaatttaa ataaaaaagt tgatgatggt ttcctggaca tttggactta caatgccgaa   2640
ctgttggttc tattggaaaa tgaaagaact ttggactacc acgattcaaa tgtgaagaac   2700
ttatatgaaa aggtaagaag ccagctaaaa aacaatgcca aggaaattgg aaacggctgc   2760
tttgaatttt accacaaatg cgataacacg tgcatggaaa gtgtcaaaaa tgggacttat   2820
```

-continued

```
gactacccaa aatactcaga ggaagcaaaa ttaaacagag aagaaataga tggggtaaag   2880

ctggaatcaa caaggattta ccagattttg gcgatctatt caactgtcgc cagttcattg   2940

gtactggtag tctccctggg ggcaatcagt ttctggatgt gctctaatgg gtctctacag   3000

tgtagaatat gtatttaaag gcctattttc tttagtttga atttactgtt attcggtgtg   3060

catttctatg tttggtgagc ggttttctgt gctcagagtg tgtttatttt atgtaattta   3120

atttctttgt gagctcctgt ttagcaggtc gtcccttcag caaggacaca aaaagatttt   3180

aattttatta aaaaaaaaaa aaaaaaagac cgggaattcg atatcaagct tatcgacctg   3240

cagatcgttc aaacatttgg caataaagtt tcttaagatt gaatcctgtt gccggtcttg   3300

cgatgattat catataattt ctgttgaatt acgttaagca tgtaataatt aacatgtaat   3360

gcatgacgtt atttatgaga tgggttttta tgattagagt cccgcaatta tacatttaat   3420

acgcgataga aaacaaaata tagcgcgcaa actaggataa attatcgcgc gcggtgtcat   3480

ctatgttact agatctctag agtctcaagc ttggcgcgcc                         3520
```